US012636375B2

(12) United States Patent
Brentjens et al.

(10) Patent No.: US 12,636,375 B2
(45) Date of Patent: May 26, 2026

(54) ANTIBODIES TARGETING Fc RECEPTOR-LIKE 5 AND METHODS OF USE

(71) Applicants: MEMORIAL SLOAN-KETTERING CANCER CENTER, New York, NY (US); EUREKA THERAPEUTICS, INC., Emeryville, CA (US)

(72) Inventors: Renier J. Brentjens, New York, NY (US); Eric L. Smith, New York, NY (US); Cheng Liu, Emeryville, CA (US)

(73) Assignees: MEMORIAL SLOAN-KETTERING CANCER CENTER, New York, NY (US); EUREKA THERAPEUTICS, INC., Emeryville, CA (US)

( * ) Notice: Subject to any disclaimer, the term of this patent is extended or adjusted under 35 U.S.C. 154(b) by 1228 days.

(21) Appl. No.: 17/143,833

(22) Filed: Jan. 7, 2021

(65) Prior Publication Data

US 2021/0388081 A1 Dec. 16, 2021

Related U.S. Application Data

(60) Division of application No. 15/997,155, filed on Jun. 4, 2018, now Pat. No. 10,913,796, which is a continuation of application No. PCT/US2016/064550, filed on Dec. 2, 2016.

(60) Provisional application No. 62/263,586, filed on Dec. 4, 2015.

(51) Int. Cl.

| | |
|---|---|
| *C12N 5/02* | (2006.01) |
| *A61K 39/395* | (2006.01) |
| *A61K 47/64* | (2017.01) |
| *A61P 35/00* | (2006.01) |
| *C07K 16/28* | (2006.01) |
| *C12N 1/20* | (2026.01) |
| *A61K 39/00* | (2006.01) |

(52) U.S. Cl.

CPC .... *C07K 16/2809* (2013.01); *A61K 39/39558* (2013.01); *A61K 47/6415* (2017.08); *A61K 47/6425* (2017.08); *A61P 35/00* (2018.01); *C07K 16/2803* (2013.01); *C07K 16/283* (2013.01); *A61K 2039/572* (2013.01); *A61K 2039/585* (2013.01); *C07K 2317/21* (2013.01); *C07K 2317/31* (2013.01); *C07K 2317/34* (2013.01); *C07K 2317/622* (2013.01)

(58) Field of Classification Search

None

See application file for complete search history.

(56) References Cited

U.S. PATENT DOCUMENTS

| | | | |
|---|---|---|---|
| 4,956,778 A | 9/1990 | Naito | |
| 5,091,513 A | 2/1992 | Huston et al. | |
| 5,132,405 A | 7/1992 | Huston et al. | |
| 5,399,346 A | 3/1995 | Anderson et al. | |
| 5,840,344 A | 11/1998 | Fukushima | |
| 7,129,053 B1 | 10/2006 | Reiter et al. | |
| 7,446,190 B2 | 11/2008 | Sadelain et al. | |
| 7,521,541 B2 | 4/2009 | Eigenbrot et al. | |
| 8,344,111 B2 | 1/2013 | Bachmann et al. | |
| 8,389,282 B2 | 3/2013 | Sadelain et al. | |
| 8,399,645 B2 | 3/2013 | Campana et al. | |
| 8,497,118 B2 | 7/2013 | Jensen | |
| 8,802,374 B2 | 8/2014 | Jensen | |
| 10,913,796 B2 | 2/2021 | Brentjens et al. | |
| 11,059,891 B2 | 7/2021 | Brentjens et al. | |
| 2005/0196754 A1 | 9/2005 | Drmanac et al. | |
| 2010/0228007 A1 | 9/2010 | Hoogenboom et al. | |
| 2010/0260748 A1 | 10/2010 | Elkins et al. | |
| 2011/0171125 A1 | 7/2011 | Elkins et al. | |
| 2014/0243504 A1 | 8/2014 | Davis et al. | |
| 2015/0098900 A1 | 4/2015 | Ebens et al. | |
| 2017/0275362 A1 | 9/2017 | Brentjens et al. | |
| 2018/0371085 A1 | 12/2018 | Brentjens et al. | |

FOREIGN PATENT DOCUMENTS

| | | |
|---|---|---|
| RU | 2412947 C2 | 2/2011 |
| WO | WO 1995/006748 A1 | 3/1995 |
| WO | WO 2002/002641 A2 | 1/2002 |
| WO | WO 2006/034488 A2 | 3/2006 |
| WO | WO 2006/039238 A2 | 4/2006 |
| WO | WO 2006/076691 A2 | 7/2006 |
| WO | WO 2010/114940 A1 | 10/2010 |
| WO | WO 2010/120561 A1 | 10/2010 |
| WO | WO 2014/087010 A1 | 6/2014 |
| WO | WO 2014/134165 A1 | 9/2014 |
| WO | WO 2014/191128 A1 | 12/2014 |
| WO | WO 2014/210064 A1 | 12/2014 |
| WO | WO 2015/142675 A2 | 9/2015 |
| WO | WO 2016/090337 A1 | 6/2016 |
| WO | WO 2017/096120 A1 | 6/2017 |

OTHER PUBLICATIONS

U.S. Appl. No. 17/332,853, filed May 27, 2021, Brentjens et al.

Polson et al., "FcRL5 as a Target of Antibody-Drug Conjugates for the Treatment of Multiple Myeloma," Blood 114(22):3836 2 pgs. (2009).

Wang et al., "Overview of Research on Immunoglobuin Fc Receptors in Newborn Animals," Chinese Journal of Animal Husbandry 42(5):42-44 (2006) [with English abstract].

U.S. Appl. No. 15/997,155 (U.S. Pat. No. 10,913,796), filed Jun. 4, 2018 (Feb. 9, 2021).

U.S. Appl. No. 15/614,108 (US 2017/0275362), filed Jun. 5, 2017 (Sep. 28, 2017).

U.S. Appl. No. 15/997,155, filed Dec. 9, 2020 Issue Fee Payment.

U.S. Appl. No. 15/997,155, filed Sep. 10, 2020 Notice of Allowance.

(Continued)

*Primary Examiner* — Chun W Dahle

(74) *Attorney, Agent, or Firm* — Baker Botts L.L.P.

(57) ABSTRACT

The presently disclosed subject matter provides fully human antibodies or antigen-binding fragments thereof that bind to FcRL5 and methods of using the same.

15 Claims, 33 Drawing Sheets

Specification includes a Sequence Listing.

(56) References Cited

OTHER PUBLICATIONS

U.S. Appl. No. 15/997,155, filed Jun. 26, 2020 Response to Restriction Requirement.
U.S. Appl. No. 15/997,155, filed Mar. 27, 2020 Restriction Requirement.
Allen, "Ligand-Targeted Therapeutics in Anticancer Therapy," Nat. Rev. Cancer 2:750-763 (2002).
Altschul et al., "Basic Local Alignment Search Tool," J. Mol. Biol. 215:403-410 (1990).
Altschul et al., "Gapped Blast and PSI-Blast: a new generation of protein database search programs," Nucleic Acids Res. 25(17):3389-3402 (1997).
An et al., "Chromosome 1q21 gains confer inferior outcomes in multiple myeloma treated with bortezomib but copy number variation and percentage of plasma cells involved have no additional prognostic value," Haematologica 99(2):353-359 (2014).
Anderson, "Prospects for Human Gene Therapy," Science 226(4673):401-409 (1984).
Arnon et al., "Monoclonal Antibodies for Immunotargeting of Drugs in Cancer Therapy," in Monoclonal Antibodies and Cancer Therapy, Reisfeld et al. (eds.), pp. 243-256 Alan R. Liss, Inc. (1985).
Ausubel et al., Current Protocols in Molecular Biology, John Wiley & Sons Inc., New York, 2003.
Azinovic et al., "Survival benefit associated with human anti-mouse antibody (HAMA) in patients with B-cell malignancies," Cancer Immunol. Immunother. 55:1451-1458 (2006).
U.S. Appl. No. 15/614,108, filed Apr. 2, 2020 Restriction Requirement.
U.S. Appl. No. 15/614,108, filed Aug. 3, 2020 Response to Restriction Requirement.
U.S. Appl. No. 15/614,108, filed Oct. 7, 2020 Non-Final Office Action.
U.S. Appl. No. 15/614,108, filed Feb. 5, 2021 Response to Non-Final Office Action.
U.S. Appl. No. 15/614,108, filed Feb. 23, 2021 Notice of Allowance.
Bataille et al., "The phenotype of normal, reactive and malignant plasma cells. Identification of "many and multiple myelomas" and of new targets for myeloma therapy," Haematologica 91:1234-1240 (2006).
Benton et al., "Screening λgt Recombinant Clones by Hybridization to Single Plaques in situ," Science 196(4286):180-182 (1977).
Bertilaccio et al., "Low-Dose Lenalidomide Improves CAR-Based Immunotherapy in CLL by Reverting T-Cell Defects In Vivo," Blood 122:4171 (2013).
Bird et al., "Single-Chain Antigen-Binding Proteins," Science 242(4877):423-426 (1988).
Blömer et al., "Highly Efficient and Sustained Gene Transfer in Adult Neurons with a Lentivirus Vector," Journal of Virology 71(9):6641-6649 (1997).
Boissel et al., "Retargeting NK-92 cells by means of CD19- and CD20-specific chimeric antigen receptors compares favorably with antibody-dependent cellular cytotoxicity," Oncoimmunology, 2(10):e26527 (2013).
Boyd et al., "The Clinical Impact and Molecular Biology of del(17p) in Multiple Myeloma Treated with Conventional or Thalidomide-Based Therapy," Genes, Chromosomes & Cancer 50:765-774 (2011).
Bregni et al., "Human Peripheral Blood Hematopoietic Progenitors are Optimal Targets of Retroviral-Mediated Gene Transfer," Blood 80(6):1418-1422 (1992).
Brennan et al., "Preparation of Bispecific Antibodies by Chemical Recombination of Monoclonal," Science 229(4708):81-83 (1985).
Brentjens et al., "CD19-Targeted T Cells Rapidly Induce Molecular Remissions in Adults with Chemotherapy-Refractory Acute Lymphoblastic Leukemia," Science Translational Medicine 5:177ra38 (2013).

Brentjens et al., "Eradication of systemic B-cell tumors by genetically targeted human T lymphocytes co-stimulated by CD80 and interleukin-15," Nature Medicine 9(3):279-286 (2003).
Brentjens et al., "Genetically Targeted T Cells Eradicate Systemic Acute Lymphoblastic Leukemia Xenografts," Clin Cancer Res 13(18):5426-5435 (2007).
Brentjens et al., "Safety and persistence of adoptively transferred autologous CD19-targeted T cells in patients with relapsed or chemotherapy refractory B-cell leukemias," Blood 118(18):4817-4828 (2011).
Brigham et al., "Rapid Communication: In vivo Transfection of Murine Lungs with a Functioning Prokaryotic Gene Using a Liposome Vehicle," Am. J. Med. Sci. 298(4):278-281 (1989).
Brocks et al., "A TNF receptor antagonistic scFv, which is not secreted in mammalian cells, is expressed as a soluble mono- and bivalent scFv derivative in insect cells," Immunotechnology 3:173-184 (1997).
Brown et al., "Tolerance to single, but not multiple, amino acid replacements in antibody V-H CDR2: A means of mm1mlzmg B cell wastage from somatic hypermutation?" The J Immunol, 156(9):3285-3291 (1996).
Caron et al., "Engineered Humanized Dimeric Forms of IgG are More Effective Antibodies," J. Exp. Med 176:1191-1195 (1992).
Cayouette et al., "Adenovirus-Mediated Gene Transfer of Ciliary Neurotrophic Factor can Prevent Photoreceptor Degeneration in the Retinal Degeneration (rd) Mouse," Human Gene Therapy 8:423-430 (1997).
Colman, "Effects of amino acid sequence changes on antibody-antigen interactions," Research in Immunology, 145(1):33-36 (1994).
Cornetta et al., "Gene Transfer into Primates and Prospects for Gene Therapy in Humans," Progress in Nucleic Acid Research and Molecular Biology 36:311-322 (1987).
Cuesta et al., Multivalent antibodies: when design surpasses evolution, Trends in Biotechnology 28(7):355-362 (2010).
Danos et al., "Safe and efficient generation of recombinant retroviruses with amphotropic and ecotropic host ranges," Proc. Natl. Acad Sci. USA 85:6460-6464 (1988).
Davila et al., "Efficacy and Toxicity Management of 19-28z CAR T Cell Therapy in B Cell Acute Lymphoblastic Leukemia," Science Translational Medicine 6:224ra25 (2014).
Dement-Brown et al., "Fc receptor-like 5 promotes B cell proliferation and drives the development of cells displaying switched isotypes," Journal of Leukocyte Biology 91:59-67 (2012).
Dudley et al., "Adoptive Cell Therapy for Patients with Metastatic Melanoma: Evaluation of Intensive Myeloablative Chemoradiation Preparative Regimens," J Clin Oncol 26(32):5233-5239 (2008).
Dupont et al., "Artificial Antigen-Presenting Cells Transduced with Telomerase Efficiently Expand Epitope-Specific, Human Leukocyte Antigen-Restricted Cytotoxic T Cells," Cancer Res 65(12):5417-5427 (2005).
Eglitis et al., "Retroviral Vectors for Introduction of Genes into Mammalian Cells," BioTechniques 6(7):608-614 (1988).
Elkins et al., "FcRL5 as a Target of Antibody-Drug Conjugates for the Treatment of Multiple Myeloma," Molecular Cancer Therapeutics 11(10):2222-2232 (2012).
Felgner et al., "Lipofection: A highly efficient, lipid-mediated DNA-transfection procedure," Proc. Natl. Acad. Sci. USA 84:7413-7417 (1987).
Fife et al., "Inhibition of T cell activation and autoimmune diabetes using a B cell surface-linked CTLA-4 agonist," J Clin Invest 116(8):2252-2261 (2006).
Flatman et al., "Process analytics for purification of monoclonal antibodies," J. Chromatogr. B 848:79-87 (2007).
Franco et al., "Human Fc Receptor-Like 5 Binds Intact IgG via Mechanisms Distinct from Those of Fc Receptors," Journal of Immunology 190:5739-5746 (2013).
Friedman, "Progress toward Human Gene Therapy," Science 244(4910):1275-1281 (1989).
Frigyesi et al., "Robust isolation of malignant plasma cells in multiple myeloma," Blood 123(9):1336-1340 (2014).
Gade et al., "Targeted Elimination of Prostate Cancer by Genetically Directed Human T Lymphocytes," Cancer Res 65(19):9080-9088 (2005).

(56) References Cited

OTHER PUBLICATIONS

Gahrton et al., "Allogeneic Bone Marrow Transplantation in Multiple Myeloma," Bone Marrow Transplantation in Multiple Myeloma, The New England Journal of Medicine 325(18):1267-1273 (1991).

Garfall et al., "Immunotherapy with Chimeric Antigen Receptors for Multiple Myeloma," Discov Med., 17(91):37-46 (2014).

Gershoni et al., "Epitope mapping—The first step in developing epitope-based vaccines," Biodrugs, 21 (3): 145-156 (2007).

Giomarelli et al., "Inhibition of thrombin-inducedplatelet aggregation using human single-chain Fv antibodies specific for TREM-like transcript-I," Thromb Haemost 97:955-963 (2007).

Glennie et al., "Preparation and performance of bispecific F(ab' gamma)2 antibody containing thioether-linked Fab' gamma fragments," J. Immunol. 139:2367-2375 (1987).

Gong et al., "Cancer Patient T Cells Genetically Targeted to Prostate-Specific Membrane Antigen Specifically Lyse Prostate Cancer Cells and Release Cytokines in Response to Prostate-Specific Membrane Antigen," Neoplasia 1(2):123-127 (1999).

Grunstein et al., "Colony hybridization: A method for the isolation of clofted DNAs that contain a specific gene," Proc. Nat. Acad. Sci., USA 72(10):3961-3965 (1975).

Guide to Molecular Cloning Techniques, Guide to Molecular Cloning Techniques, vol. 152, eds. Berger and Kimmel 1987, Academic Press, New York.

Harris et al., "Crystallographic Structure of an Intact IgG1 Monoclonal Antibody," Journal of Molecular Biology 275:861-872 (1998).

Hatzivassiliou et al., "IRTA1 and IRTA2, Novel Immunoglobulin Superfamily Receptors Expressed in B Cells and Involved in Chromosome 1q21 Abnormalities in B Cell Malignancy," Immunity 14:277-289 (2001).

Hellstrom et al., "Antibodies for Drug Delivery," in Controlled Drug Delivery (2nd Ed.), Robinson et al. (eds.), pp. 623-653 (Marcel Dekker, Inc. 1987).

Ho et al., "Inhibition of Cocaine Binding to the Human Dopamine Transporter by a Single Chain Anti-Idiotypic Antibody: its Cloning, Expression and Functional Properties," BioChim Biophys Acta 1638(3):257-266 (2003).

Hollyman et al., "Manufacturing Validation of Biologically Functional T Cells Targeted to CD19 Antigen for Autologous Adoptive Cell Therapy," J Immunother 32:169-180 (2009).

Hughes et al., "Retroviral Gene Transfer to Primitive Normal and Leukemic Hematopoietic Cells Using Clinically Applicable Procedures," J. Clin. Invest. 89:1817-1824 (1992).

Hunder et al., "Treatment of Metastatic Melanoma with Autologous CD4+ T cells against NY-ESO-1," N Engl J Med 358:2698-2703 (2008).

Huston et al., "Protein engineering of antibody binding sites: Recovery of specific activity in an anti-digoxin single-chain Fv analogue produced in Escherichia coli," Proc. Natl. Acad. Sci. USA 85:5879-5883 (1988).

International Search Report dated Mar. 11, 2016 in International Application No. PCT/US15/64134.

International Search Report mailed May 8, 2017 in International Application No. PCT/US16/64550.

Ise et al. "Sandwich ELISAs for soluble immunoglobulin superfamily receptor translocation-associated 2 (IRTA2)/FcRH5 (CD307) proteins in human sera," Clinical Chemistry and Laboratory Medicine 44(5):594-602 (2006).

Ise et al., "Elevation of Soluble CD307 (IRTA2/FcRH5) Protein in the Blood and Expression on Malignant Cells of Patients with Multiple Myeloma, Chronic Lymphocytic Leukemia, and Mantle Cell Lymphoma," Leukemia 21:169-174 (2007).

Ise et al., "Immunoglobulin Superfamily Receptor Translocation Associated 2 Protein on Lymphoma Cell Lines and Hairy Cell Leukemia Cells Detected by Novel Monoclonal Antibodies," Clinical Cancer Research 11:87-96 (2005).

Johnson, "Gene Therapy for Cystic Fibrosis," Chest 107:77S-83S (1995).

Kabat et al. Sequences of Proteins of Immunological Interest, vol. I, Fifth Edition, U.S. Department of Health and Human Services, NIH Publication No. 91-3242 (1991).

Kabat et al., Sequences of Proteins of Immunological Interest, 4th Edition, U. S. Department of Health and Human Services, National Institutes of Health (1987).

Karpovsky et al., "Production of Target-Specific Effector Cells Using Hetero-Cross-Linked Aggregates Containing Anti-Target Cell and Anti-Fcγ Receptor Antibodies," J. Exp. Med. 160:1686-1701 (1984).

Kershaw et al., "Gene-Engineered T Cells as a Superior Adjuvant Therapy for Metastatic Cancer," J Immunol 173:2143-2150 (2004).

Kido et al., "Use of a retroviral vector with an internal opsin promoter to direct gene expression to retinal photoreceptor cells," Current Eye Research 15:833-844 (1996).

Kimmel, "Identification and Characterization of Specific Clones: Strategy for Confirming the Validity of Presumptive Clones," Methods in Enzymology 152:507-511 (1987).

Klechevsky et al., "Antitumor activity of immunotoxins with T-cell receptor-like specificity against human melanoma xenografts," Cancer Res. 68(15):6360-6367 (2008).

Kochenderfer et al., "Adoptive transfer of syngeneic T cells transduced with a chimeric antigen receptor that recognizes murine CD19 can eradicate lymphoma and normal B cells," Blood, 116(19):3875-3886 (2010).

Koyko et al., "Immunology," translated from English, edited by N.B. Serebryanaya, Mosow, "Akademiya," 2008, p. 37 (in Russian).

Krause et al., "Antigen-dependent CD28 Signaling Selectively Enhances Survival and Proliferation in Genetically Modified Activated Human Primary T Lymphocytes," J. Exp. Med. 188(4):619-626 (1998).

Le Gal La Salle et al., "An Adenovirus Vector for Gene Transfer into Neurons and Glia in the Brain," Science 259(5097):988-990 (1993).

Ledbetter et al., "Agonistic Activity of a CD40-Specific Single-Chain Fv Constructed from the Variable Regions of mAb G28-5," Crit Rev Immunol 17:427-435 (1997).

Liu et al., "Heteroantibody duplexes target cells for lysis by cytotoxic T lymphocytes," PNAS USA 82:8648-8652 (1985).

Long et al., "4-1BB Costimulation Ameliorates T cell Exhaustion Induced by Tonic Signaling of Chimeric Antigen Receptors," Nat Med 21(6):581-590 (2015).

Lyddane et al., "Cutting Edge: CD28 Controls Dominant Regulatory T cell Activity during Active Immunization," J Immunol. 176:3306-3310 (2006).

Maher et al., "Human T-lymphocyte cytotoxicity and proliferation directed by a single chimeric TCRζ/CD28 receptor," Nat. Biotechnol. 20:70-75 (2002).

Mariuzza et al., "The Structural Basis of Antigen-Antibody Recognition," Annual Review of Biophysis and Biophysical Chemistry, 16:139-159 (1987).

Mccafferty et al., "Phage antibodies: filamentous phage displaying antibody variable domains," Nature, 348:552-554 (1990).

Meyers et al., "Optimal alignments in linear space," Cabios 4(1): 11-17 (1988).

Miller et al., "Cloning and Expression of a Yeast Ubiquitin-Protein Cleaving Activity in Escherichia coli," Biotechnology 7:698-704 (1989).

Miller et al., "Generation of Helper-Free Amphotropic Retroviruses That Transduce a Dominant-Acting, Methotrexate-Resistant Dihydrofolate Reductase Gene," Mol Cell Biol. 5(3):431-437 (1985).

Miller et al., "Redesign of Retrovirus Packaging Cell Lines to Avoid Recombination Leading to Helper Virus Production," Mol. Cell. Biol. 6(8):2895-2902 (1986).

Miller, "Retrovirus Packaging Cells," Human Gene Therapy 1:5-14 (1990).

Miyoshi et al., "Stable and efficient gene transfer into the retina using an HIV-based lentiviral vector," Proc. Natl. Acad. Sci. USA 94:10319-10323 (1997).

Moen, "Directions in Gene Therapy," Blood Cells 17:407-416 (1991).

Moosmayer et al., "A single-chain TNF receptor antagonist is an effective inhibitor of TNF mediated cytotoxicity," Therapeutic Immunol 2:31-40 (1995).

(56) References Cited

OTHER PUBLICATIONS

Morgan et al., "Cancer Regression in Patients After Transfer of Genetically Engineered Lymphocytes," Science 314:126-129 (2006).
Morgan et al., "Case Report of a Serious Adverse Event Following the Administration of T cells Transduced with a Chimeric Antigen Receptor Recognizing ERBB2," Molecular Therapy 18(4):843-851 (2010).
Naldini et al., "In Vivo Gene Delivery and Stable Transduction of Nondividing Cells by a Lentiviral Vector," Science 272(5259):263-267 (1996).
Needleman et al., "A General Method Applicable to the Search for Similarities in the Amino Acid Sequence of Two Proteins," J. Mol. Biol. 48:443-453 (1970).
Ono et al., "Plasmid DNAs directly injected into mouse brain with lipofectin can be incorporated and expressed by brain cells," Neuroscience Letters 117:259-263 (1990).
Ozhegov et al. "Dictionary of a Russian Language: 80,000 words and phraseological expressions," 4th ed. Supplemented, Mosow, "OOO 'A Temp'" 2006, p. 375.
Panelli et al., "A Tumor-Infiltrating Lymphocyte from a Melanoma Metastasis with Decreased Expression of Melanoma Differentiation Antigens Recognizes MAGE-12," J Immunol 164:4382-4392 (2000).
Panelli et al., "Expansion of Tumor-T Cell Pairs from Fine Needle Aspirates of Melanoma Metastases," J Immunol 164:495-504 (2000).
Papanicolaou et al., "Rapid expansion of cytomegalovirus-specific cytotoxic T lymphocytes by artificial antigen-presenting cells expressing a single HLA allele," Blood 102:2498-2505 (2003).
Parkman R., "Clonal analysis of murine graft-vs-host disease. I. Phenotypic and functional analysis of T lymphocyte clones," J. Immunol. 136(10):3543-3548 (1986).
Pastan et al., "Overview Immunotoxins in cancer therapy," Curr. Opin. Investig. Drugs 3(7):1089-1091 (2002).
Paulus, "Preparation and Biomedical Applications of Bispecific Antibodies," Behring Inst. Mitt. 78:118-132 (1985).
Payne, "Progress in immunoconjugate cancer therapeutics," Cancer Cell 3:207-212 (2003).
Pegram et al., "Tumor-targeted T cells modified to secrete IL-12 eradicate systemic tumors without need for prior conditioning," Blood 119(18):4133-4141 (2012).
Perez De La Lastra et al., "Epitope mapping of 10 monoclonal antibodies against the pig analogue of human membrane cofactor protein (MCP)," Immunology, 96:663-670 (1999).
Persic et al., "An integrated vector system for the eukaryotic expression of antibodies or their fragments after selection from phage display libraries," Gene 187:9-18 (1997).
Peter et al., "Protective effects of an anti-melanocortin-4 receptor scFv derivative in lipopolysaccharide-induced cachexia in rats," J Cachexia Sarcopenia Muscle 4:79-88 (2013).
Peter et al., "scFv Single Chain Antibody Variable Fragment as Inverse Agonist of the Æ2-Adrenergic Receptor," J Biol. Chem 278(38):36740-36747 (2003).
Riviere et al., "Novel Strategies for Cancer Therapy: The Potential of Genetically Modified T Lymphocytes," Curr Hematol Rep 3:290-297 (2004).
Roberts et al., "Vaccination with CD20 peptides induces a biologically active, specific immune response in mice," Blood 99:3748-3755 (2002).
Roitt et al., Immunology, Moscow, "Mir", pp. 110-111 (2000) (in Russian with an English translation).
Rosenberg et al., "Adoptive cell transfer: a clinical path to effective cancer immunotherapy," Nat. Rev. Cancer 8:299-308 (2008).
Rosenberg et al., "Gene Transfer Into Humans—Immunotherapy of Patients With Advanced Melanoma, Using Tumor-Infiltrating Lymphocytes Modified by Retroviral Gene Transduction," N Engl J Med 323:570-578 (1990).
Rudikoff et al., "Single amino acid substitution altering antigen-binding specificity," Immunology, Proc. Natl. Acad. Sci. USA, 79:1979-1983 (1982).
Sadelain et al., "Targeting Tumours With Genetically Enhanced T Lymphocytes," Nat Rev Cancer 3:35-45 (2003).

Sadelain et al., "The basic principles of chimeric antigen receptor (CAR) design," Cancer Discovery 3(4):388-398 (2013).
Sadelain et al., "The promise and potential pitfalls of chimeric antigen receptors," Curr Opin Immunol 21:215-223 (2009).
Sakahara et al. "Effect of DTPA Conjugation on the Antigen Binding Activity and Biodistribution of Monoclonal Antibodies Against α-Fetoprotein," J Nucl Med, 26:750-755 (1985).
Sambrook, Fritsch and Maniatis, Molecular Cloning: A Laboratory Manual (2d ed.), CSH Press, 1989.
Sharp, "Gene Therapy," The Lancet 337:1277-1278 (1991).
Shaughnessy Jr., et al., "A validated gene expression model of high-risk multiple myeloma is defined by deregulated expression of genes mapping to chromosome 1," Blood 109(6):2276-2284 (2007).
Shen et al., "Engineering Peptide Linkers for scFv Immunosensors," Anal Chem. 80(6):1910-1917 (2008).
Shieh et al., "Transgenic Expression of Single-Chain Anti-CTLA-4 Fv on β Cells Protects Nonobese Diabetic Mice from Autoimmune Diabetes," J Immunol. 183:2277-2285 (2009).
Siegel et al., "Cancer Statistics, 2013," CA Cancer J Clin 63:11-30 (2013).
Singer et al., Genes and Genomes, Moscow, "Mir", pp. 63-64 (1998) (in Russian with an English translation).
Stephan et al., "T cell-encoded CD80 and 4-1BBL induce auto- and transcostimulation, resulting in potent tumor rejection," Nat. Med 13(12):1440-1449 (2007).
Straubinger et al., "Liposomes as Carriers for Intracellular Delivery of Nucleic Acids," Methods in Enzymology 101:512-527 (1983).
Supplementary European Search Report dated Apr. 30, 2018 in Application No. EP 15864773.
Supplementary Partial European Search Report dated Sep. 30, 2019 in EP Application No. 16871553.
Tai et al., "Antibody-Based Therapies in Multiple Myeloma," Bone Marrow Research Article ID: 924058 14 pg. (2011).
Tang et al., "The Foxp3+ regulatory T cell: a jack of all trades, master of regulation," Nat Immunol 9(3):239-244 (2008).
Thorpe et al., "The Preparation and Cytotoxic Properties of Antibody-Toxin Conjugates," Immunol. Rev., 62:119-158 (1982).
Thorpe, "Antibody Carriers of Cytotoxic Agents in Cancer Therapy: A Review," in Monoclonal Antibodies '84: Biological and Clinical Applications, Pinchera et al. (eds.), pp. 475-506 (1985).
Tolstoshev et al., "Gene expression using retroviral vectors," Current Opinion in Biotechnology 1:55-61 (1990).
Tomimatsu et al., "Production of Human Monoclonal Antibodies against FcεRIα by a Method Combining in Vitro Immunization with Phage Display," Biosci Biotechnol Biochem 73(7):1465-1469 (2009).
Trail et al., "Monoclonal antibody drug immunoconjugates for targeted treatment of cancer," Cancer Immunol. Immunother. 52:328-337 (2003).
Wahl et al., "Investigative Nuclear Medicine," J. Nucl Med. 24:316-325 (1983).
Wahl et al., "Molecular Hybridization of Immobilized Nucleic Acids: Theoretical Concepts and Practical Considerations," Methods Enzymol. 152:399-407 (1987).
Ward et al., "Binding activities of a repertoire of single immunoglobulin variable domains secreted from *Escherichia coli*," Nature 341:544-546 (1989).
Wolff et al., "Direct Gene Transfer into Mouse Muscle in Vivo," Science 247(4949):1465-1468 (1990).
Wu et al., "Receptor-mediated Gene Delivery and Expression in Vivo," Journal of Biological Chemistry 263(29):14621-14624 (1988).
Wu et al., "Targeting Genes: Delivery and Persistent Expression of a Foreign Gene Driven by Mammalian Regulatory Elements in Vivo," Journal of Biological Chemistry 264(29):16985-16987 (1989).
Xie et al., "Direct demonstration of MuSK involvement in acetylcholine receptor clustering through identification of agonist ScFv," Nat Biotech 15:768-771 (1997).
Xu et al., "Correction of the enzyme deficiency in hematopoietic cells of Gaucher patients using a clinically acceptable retroviral supernatant transduction protocol," Exp. Hemat. 22:223-230 (1994).
Yasmina et al., "Probing the binding mechanism and affinity of tanezumab, a recombinant humanized anti-NGF monoclonal antibody, using a repertoire of biosensors," Protein Science 17:1326-1335 (2008).

(56)                    References Cited

OTHER PUBLICATIONS

Yeger, L., "Clinical Immunology and Allergology" vol. 1, 219-222 Book (1990).

Zhao et al., "Characteristics of an scFv Antibody Fragment That Binds to Immunoglobulin G of Graves' Disease Patients and Inhibits Autoantibody-Mediated Thyroid-Stimulating Activity," Hybridoma 27(6):445-451 (2008).

Zhong et al., "Chimeric antigen receptors combining 4-1BB and CD28 signaling domains augment PI3kinase/AKT/Bcl-XL activation and CD8+ T cell-mediated tumor eradication," Mol Ther 18(2):413-420 (2010).

3T3 / 3T3-Cocktail (FcRL1,2,3,4,6) / 3T3-FcRL5

| | Sample Name | Median, PE-H |
|---|---|---|
| - - - - | Plate1 E12.fcs | 124 |
| -·-·- | Plate1 E11.fcs | 3.15E4 |
| —— | Plate1 E10.fcs | 216 |

Domain 1–8

Domain 9

TM

Myc3

>MSK_delDOM9_myc_mCD8

MLLWVILLVLAPVSGQFARTPRPIIFLQPPWTTVFQGERVTLTCKGFRFYSPQKTKWYHRYLGKEILRET
PDNILEVQESGEYRCQAQGSPLSSPVHLDFSSASLILQAPLSVFEGDSVVLRCRAKAEVTLNNTIYKNDN
VLAFLNKRTDFHIPHACLKDNGAYRCTGYKESCCPVSSNTVKIQVQEPFTRPVLRASSFQPISGNPVTLT
CETQLSLERSDVPLRFRFFRDDQTLGLGWSLSPNFQITAMWSKDSGFYWCKAATMPHSIISDSPRSWIQV
QIPASHPVLTLSPEKALNFEGTKVTLHCETQEDSLRTLYRFYHEGVPLRHKSVRCERGASISFSLTTENS
GNYYCTADNGLGAKPSKAVSLSVTVPVSHPVLNLSSPEDLIFEGAKVTLHCEAQRGSLPILYQFHHEDAA
LERRSANSAGGVAISFSLTAEHSGNYYCTADNGFGPQRSKAVSLSITVPVSHPVLTLSSAEALTFEGATV
TLHCEVQRGSPQILYQFYHEDMPLWSSSTPSVGRVSFSFSLTEGHSGNYYCTADNGFGPQRSEVVSLFVT
VPVSRPILTLRVPRAQAVVGDLLELHCEAPRGSPPILYWFYHEDVTLGSSSAPSGGEASFNLSLTAEHSG
NYSCEANNGLVAQHSDTISLSVIVPVSRPILTFRAPRAQAVVGDLLELHCEALRGSSPILYWFYHEDVTL
GKISAPSGGGASFNLSLTTEHSGIYSCEADNGLEAQRSEMVTLKVAAAAEQKLISEEDLEQKLISEEDLE
QKLISEEDLTGVAGGLLSIAGLAAGALLLYCWLSRKAGRKPASDPARSPSDSDSQEPTYHNVPAWEELQP
VYTNANPRGENVVYSEVRIIQEKKKHAVASDPRHLRNKGSPIIYSEVKVASTPVSGSLFL
ASSAPHR*

>gi|14278719|gb|AAK50059.2|AF369794_1 B cell crosslinked IgM-activating
sequence protein [Homo sapiens]

MLLWVILLVLAPVSGQFARTPRPIIFLQPPWTTVFQGERVTLTCKGFRFYSPQKTKWYHRYLGKEILRET
PDNILEVQESGEYRCQAQGSPLSSPVHLDFSSASLILQAPLSVFEGDSVVLRCRAKAEVTLNNTIYKNDN
VLAFLNKRTDFHIPHACLKDNGAYRCTGYKESCCPVSSNTVKIQVQEPFTRPVLRASSFQPISGNPVTLT
CETQLSLERSDVPLRFRFFRDDQTLGLGWSLSPNFQITAMWSKDSGFYWCKAATMPHSIISDSPRSWIQV
QIPASHPVLTLSPEKALNFEGTKVTLHCETQEDSLRTLYRFYHEGVPLRHKSVRCERGASISFSLTTENS
GNYYCTADNGLGAKPSKAVSLSVTVPVSHPVLNLSSPEDLIFEGAKVTLHCEAQRGSLPILYQFHHEDAA
LERRSANSAGGVAISFSLTAEHSGNYYCTADNGFGPQRSKAVSLSITVPVSHPVLTLSSAEALTFEGATV
TLHCEVQRGSPQILYQFYHEDMPLWSSSTPSVGRVSFSFSLTEGHSGNYYCTADNGFGPQRSEVVSLFVT
VPVSRPILTLRVPRAQAVVGDLLELHCEAPRGSPPILYWFYHEDVTLGSSSAPSGGEASFNLSLTAEHSG
NYSCEANNGLVAQHSDTISLSVIVPVSRPILTFRAPRAQAVVGDLLELHCEALRGSSPILYWFYHEDVTL
GKISAPSGGGASFNLSLTTEHSGIYSCEADNGPEAQRSEMVTLKVAVPVSRPVLTLRAPGTHAAVGDLLE
LHCEALRGSPLILYRFFHEDVTLGNRSSPSGGASLNLSLTAEHSGNYSCEADNGLGAQRSETVTLYITGL
TANRSGPFATGVAGGLLSIAGLAAGALLLYCWLSRKAGRKPASDPARSPPDSDSQEPTYHNVPAWEELQP
VYTNANPRGENVVYSEVRIIQEKKKHAVASDPRHLRNKGSPIIYSEVKVASTPVSGSLFLASSAPHR

FIG. 3C

MSK_deIDOW9_myc3_mCD8    MLLWVILLVLAPVSGQFARTPRPIIFLQPPWTTVFQGERVTLTCKGFRFYSPQKTKWYHR
gi|14278719|gb|AAK50059.2|AF3697    MLLWVILLVLAPVSGQFARTPRPIIFLQPPWTTVFQGERVTLTCKGFRFYSPQKTKWYHR MSK_deIDOW9_myc3_mCD8    YLGKEILRETPDNILEVQESGEYRCQAQGSPLSSPVHLDFSSASLILQAPLSVFEGDSVV
gi|14278719|gb|AAK50059.2|AF3697    YLGKEILRETPDNILEVQESGEYRCQAQGSPLSSPVHLDFSSASLILQAPLSVFEGDSVV MSK_deIDOW9_myc3_mCD8    LRCRAKAEVTLNNTIYKNDNVLAFLNKRTDFHIPHACLKDNGAYRCTGYKESCCPVSSNT
gi|14278719|gb|AAK50059.2|AF3697    LRCRAKAEVTLNNTIYKNDNVLAFLNKRTDFHIPHACLKDNGAYRCTGYKESCCPVSSNT MSK_deIDOW9_myc3_mCD8    VKIQVQEPFTRPVLRASSFQPISGNPVTLTCETQLSLERSDVPLRFRFFRDDQTLGLGWS
gi|14278719|gb|AAK50059.2|AF3697    VKIQVQEPFTRPVLRASSFQPISGNPVTLTCETQLSLERSDVPLRFRFFRDDQTLGLGWS MSK_deIDOW9_myc3_mCD8    LSPNFQITAMWSKDSGFYWCKAATMPHSIISDSPRSWIQVQIPASHPVLTLSPEKALNFE
gi|14278719|gb|AAK50059.2|AF3697    LSPNFQITAMWSKDSGFYWCKAATMPHSVISDSPRSWIQVQIPASHPVLTLSPEKALNFE MSK_deIDOW9_myc3_mCD8    GTKVTLHCETQEDSLRTLYRFYHEGVPLRHKSVRCERGASISFSLTTENSGNYYCTADNG
gi|14278719|gb|AAK50059.2|AF3697    GTKVTLHCETQEDSLRTLYRFYHEGVPLRHKSVRCERGASISFSLTTENSGNYYCTADNG MSK_deIDOW9_myc3_mCD8    LGAKPSKAVSLSVTVPVSHPVLNLSSPEDLIFEGAKVTLHCEAQRGSLPILYQFHHEDAA
gi|14278719|gb|AAK50059.2|AF3697    LGAKPSKAVSLSVTVPVSHPVLNLSSPEDLIFEGAKVTLHCEAQRGSLPILYQFHHEDAA MSK_deIDOW9_myc3_mCD8    LERRSANSAGGVAISFSLTAEHSGNYYCTADNGFGPQRSKAVSLSITVPVSHPVLTLSSA
gi|14278719|gb|AAK50059.2|AF3697    LERRSANSAGGVAISFSLTAEHSGNYYCTADNGFGPQRSKAVSLSITVPVSHPVLTLSSA

FIG. 3D

Figure 3D:
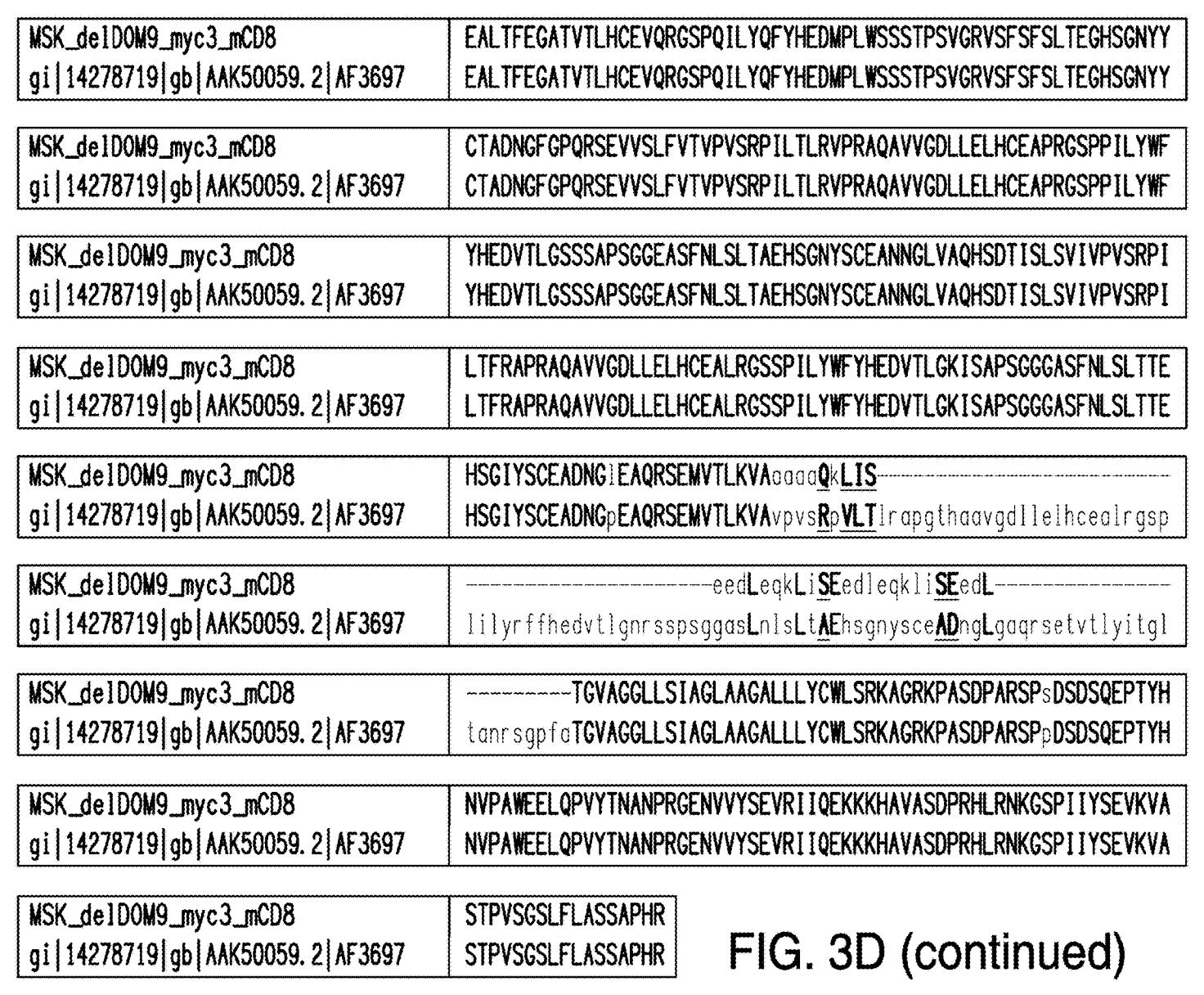

MSK_delDOM9_myc3_mCD8            EALTFEGATVTLHCEVQRGSPQILYQFYHEDMPLWSSTPSVGRVSFSFSLTEGHSGNYY
gi|14278719|gb|AAK50059.2|AF3697  EALTFEGATVTLHCEVQRGSPQILYQFYHEDMPLWSSTPSVGRVSFSFSLTEGHSGNYY MSK_delDOM9_myc3_mCD8            CTADNGFGPQRSEVVSLFVTVPVSRPILTLRVPRAQAVVGDLLELHCEAPRGSPPILYWF
gi|14278719|gb|AAK50059.2|AF3697  CTADNGFGPQRSEVVSLFVTVPVSRPILTLRVPRAQAVVGDLLELHCEAPRGSPPILYWF MSK_delDOM9_myc3_mCD8            YHEDVTLGSSSAPSGGEASFNLSLTAEHSGNYSCEANNGLVAQHSDTISLSVIVPVSRPI
gi|14278719|gb|AAK50059.2|AF3697  YHEDVTLGSSSAPSGGEASFNLSLTAEHSGNYSCEANNGLVAQHSDTISLSVIVPVSRPI MSK_delDOM9_myc3_mCD8            LTFRAPRAQAVVGDLLELHCEALRGSSPILYWFYHEDVTLGKISAPSGGGASFNLSLTTE
gi|14278719|gb|AAK50059.2|AF3697  LTFRAPRAQAVVGDLLELHCEALRGSSPILYWFYHEDVTLGKISAPSGGGASFNLSLTTE MSK_delDOM9_myc3_mCD8            HSGIYSCEADNGiEAQRSEMVTLKVAgggqQkLIS————————————
gi|14278719|gb|AAK50059.2|AF3697  HSGIYSCEADNGpEAQRSEMVTLKVAvpvsRpVLTlrapgthaavgdllelhcealrgsp MSK_delDOM9_myc3_mCD8            ————————eedLeqkLISEedLeqkliSEedL————————
gi|14278719|gb|AAK50059.2|AF3697  lilyrffhedvtlgnrsspsgggasLnlsLtAEhsgnysceADngLggqrsetvtlyitgl MSK_delDOM9_myc3_mCD8            ——————————TGVAGGLLSIAGLAAGALLLYCWLSRKAGRKPASDPARSPsDSDSQEPTYH
gi|14278719|gb|AAK50059.2|AF3697  tanrsgpfoTGVAGGLLSIAGLAAGALLLYCWLSRKAGRKPASDPARSPpDSDSQEPTYH MSK_delDOM9_myc3_mCD8            NVPAWEELQPVYTNANPRGENVVYSEVRIIQEKKKHAVASDPRHLRNKGSPIIYSEVKVA
gi|14278719|gb|AAK50059.2|AF3697  NVPAWEELQPVYTNANPRGENVVYSEVRIIQEKKKHAVASDPRHLRNKGSPIIYSEVKVA MSK_delDOM9_myc3_mCD8            STPVSGSLFLASSAPHR
gi|14278719|gb|AAK50059.2|AF3697  STPVSGSLFLASSAPHR FIG. 3D (continued)

ET200-39

| | Sample Name | Median, PE-A |
|---|---|---|
| —— | D05+Raji-FcRL5.fcs | 1.11E4 |
| —— | A04+Raji-FcRL5.fcs | 82.1 |

| | Sample Name | Median, PE-A |
|---|---|---|
| —— | D05+3T3-FcRL5.fcs | 3.76E4 |
| —— | A04+3T3-FcRL5.fcs | 1137 |

| | Sample Name | Median, PE-A |
|---|---|---|
| —— | D05+3T3-FcRL5-Delta.fcs | 496 |
| —— | A04+3T3-FcRL5-Delta.fcs | 162 |

| | Sample Name | Median, PE-A |
|---|---|---|
| —— | D05+NIH 3T3.fcs | 379 |
| —— | A04+NIH 3t3.fcs | 271 |

—— Negative control phage
—— ET200 phage

ET200-104

| | Sample Name | Median, PE-A |
|---|---|---|
| —— | E11+Raji-FcRL5.fcs | 9165 |
| —— | A04+Raji-FcRL5.fcs | 82.1 |

| | Sample Name | Median, PE-A |
|---|---|---|
| —— | E11+3T3-FcRL5.fcs | 2.91E4 |
| —— | A04+Raji-FcRL5.fcs | 1137 |

| | Sample Name | Median, PE-A |
|---|---|---|
| —— | E11+3T3-FcRL5-Delta.fcs | 387 |
| —— | A04+3T3-FcRL5-Delta.fcs | 162 |

| | Sample Name | Median, PE-A |
|---|---|---|
| —— | E11+NIH 3T3.fcs | 360 |
| —— | A04+NIH 3T3.fcs | 271 |

—— Negative control phage
—— ET200 phage

ET200-105

| | Sample Name | Median, PE-A |
|---|---|---|
| —— | E12+Raji-FcRL5.fcs | 1.80E4 |
| —— | A04+Raji-FcRL5.fcs | 82.1 |

| | Sample Name | Median, PE-A |
|---|---|---|
| —— | E12+3T3-FcRL5.fcs | 3.52E4 |
| —— | A04+3T3-FcRL5.fcs | 1137 |

| | Sample Name | Median, PE-A |
|---|---|---|
| —— | E12+3T3-FcRL5-Delta.fcs | 415 |
| —— | A04+3T3-FcRL5-Delta.fcs | 162 |

| | Sample Name | Median, PE-A |
|---|---|---|
| —— | E12+NIH 3T3.fcs | 309 |
| —— | A04+NIH 3T3.fcs | 271 |

—— Negative control phage  —— ET200 phage

3T3/3T3-FcRL5Δdom9/3T3-FcRL5/Raji-FcRL5

| | Sample Name | Median, PE-A |
|---|---|---|
| – – – | E12+Raji-FcRL5.fcs | 1.80E4 |
| – – – | E12+NIH 3T3.fcs | 309 |
| —— | E12+3T3-FcRL5-Delta.fcs | 415 |
| —— | E12+3T3-FcRL5.fcs | 3.52E4 |

ET200-109

| | Sample Name | Median, PE-A |
|---|---|---|
| —— | F04+Raji—FcRL5.fcs | 6161 |
| —— | A04+Raji—FcRL5.fcs | 82.1 |

| | Sample Name | Median, PE-A |
|---|---|---|
| —— | F04+3T3—FcRL5.fcs | 1.75E4 |
| —— | A04+3T3—FcRL5.fcs | 1137 |

| | Sample Name | Median, PE-A |
|---|---|---|
| —— | F04+3T3—FcRL5—Delta.fcs | 328 |
| —— | A04+3T3—FcRL5—Delta.fcs | 162 |

| | Sample Name | Median, PE-A |
|---|---|---|
| —— | F04+NIH 3T3.fcs | 343 |
| —— | A04+NIH 3T3.fcs | 271 |

—— Negative control phage      —— ET200 phage

ET200-117

| | Sample Name | Median, PE-A |
|---|---|---|
| —— | F12+Raji-FcRL5.fcs | 1.27E4 |
| —— | A04+Raji-FcRL5.fcs | 82.1 |

| | Sample Name | Median, PE-A |
|---|---|---|
| —— | F12+3T3-FcRL5.fcs | 3.23E4 |
| —— | A04+3T3-FcRL5.fcs | 1137 |

| | Sample Name | Median, PE-A |
|---|---|---|
| —— | F12+3T3-FcRL5-Delta.fcs | 260 |
| —— | A04+3T3-FcRL5-Delta.fcs | 162 |

| | Sample Name | Median, PE-A |
|---|---|---|
| —— | F12+NIH 3T3.fcs | 317 |
| —— | A04+NIH 3T3.fcs | 271 |

—— Negative control phage     —— ET200 phage

| Sample Name | Median, APC-A |
|---|---|
| A03 3T3+ ET200-31 L2K.fcs | 50.4 |
| B03 3T3-FcRL5+ ET200-31 L2K.fcs | 1126 |

| Sample Name | Median, APC-A |
|---|---|
| A04 3T3+ ET200-39 L2K.fcs | 35.0 |
| B04 3T3-FcRL5+ ET200-39 L2K.fcs | 493 |

| | Sample Name | Median, APC−A |
|---|---|---|
| —— | A05 3T3+ ET200−69 L2K.fcs | 46.1 |
| —— | B05 3T3−FcRL5+ ET200−69 L2K.fcs | 1231 |

| | Sample Name | Median, APC−A |
|---|---|---|
| —— | A06 3T3+ ET200−104 L2K.fcs | 35.1 |
| —— | B06 3T3−FcRL5+ ET200−104 L2K.fcs | 779 |

| | Sample Name | Median, APC−A |
|---|---|---|
| —— | A07 3T3+ ET200−105 L2K.fcs | 35.6 |
| —— | B07 3T3−FcRL5+ ET200−105 L2K.fcs | 812 |

| | Sample Name | Median, APC−A |
|---|---|---|
| —— | A08 3T3+ ET200−109 L2K.fcs | 51.6 |
| —— | B08 3T3−FcRL5+ ET200−109 L2K.fcs | 1080 |

| | Sample Name | Median, APC-A |
|---|---|---|
| —— | A09 3T3+ ET200-117 L2K.fcs | 63.6 |
| —— | B09 3T3-FcRL5+ ET200-117 L2K.fcs | 495 |

| | Sample Name | Median, APC-A |
|---|---|---|
| — — | A01 3T3.fcs | 33.0 |
| – – | B01 3T3-FcRL5.fcs | 45.1 |
| —— | A02 3T3+ 2nd Ab.fcs | 33.8 |
| —— | B02 3T3-FcRL5+ 2nd Ab.fcs | 44.9 |

Herceptin ,MAT limit:0.74

1

ANTIBODIES TARGETING Fc RECEPTOR-LIKE 5 AND METHODS OF USE

CROSS-REFERENCE TO RELATED APPLICATIONS

This application is a Divisional of U.S. patent application Ser. No. 15/997,155, filed Jun. 4, 2018, which is a Continuation of International Patent Application No. PCT/US16/64550, filed Dec. 2, 2016, which claims priority to U.S. Provisional Patent Application Ser. No. 62/263,586, filed Dec. 4, 2015, the contents of each of which are incorporated by reference in their entirety, and to each of which priority is claimed.

SEQUENCE LISTING

The specification further incorporates by reference the Sequence Listing submitted herewith via EFS on Jan. 7, 2021. Pursuant to 37 C.F.R. § 1.52(e)(5), the Sequence Listing text file, identified as 0727341187_SL.txt, is 951,008 bytes and was created on Jan. 5, 2021. The Sequence Listing electronically filed herewith, does not extend beyond the scope of the specification and thus does not contain new matter.

FIELD OF THE SUBJECT MATTER

The presently disclosed subject matter relates to fully human antibodies that bind to Fc Receptor-like 5 (FcRL5), and methods of using the same. The presently disclosed subject matter further relates to fully human antibodies that bind to domain 9 of FcRL5.

BACKGROUND OF THE SUBJECT MATTER

Fc receptor-like (FcRL) proteins are a family of cellular receptors homologous to FcγRI and are predominantly expressed by B cells. FcRL5 is expressed on both mature B cells and plasma cells, and is induced by Epstein-Barr virus (EBV) proteins (Polson et al., Int. Immunol. 18:1363-1373 (2006); Mohan et al., Blood. 107:4433-4439 (2006)). FcRL5 has been shown to inhibit B cell antigen receptor signaling and the co-stimulation of FcRL5 and the B cell antigen receptor promotes proliferation and differentiation of naive B cells (Dement-Brown et al., J. Leukoc. Biol. 91:59-67 (2012)). FcRL5 has been implicated in human diseases, including cancer and autoimmune conditions (Kochi et al. Nat. Genet. 37:478-485 (2005); Li et al. Blood. 112(1):179-87 (2008)). In particular, FcRL5 has been shown to be overexpressed on malignant B cells of hairy cell leukemia, chronic lymphocytic leukemia, mantle cell lymphoma and multiple myeloma patients (Polson et al., Int. Immunol. 18(9):1363-73 (2006); Li et al. (2008)). In addition, serum levels of soluble FcRL5 are elevated in patients with several types of B cell tumors (Ise et al., Leukemia. 21:169-174 (2007)). Given the significant association between FcRL5 and B cell cancers, therapeutics targeting FcRL5 are desired.

SUMMARY OF THE SUBJECT MATTER

The presently disclosed subject matter provides fully human antibodies that bind to Fc Receptor-like 5 (FcRL5), and methods of using the same. The presently disclosed subject matter further provides fully human antibodies that specifically bind domain 7, 8 or 9 of FcRL5. It is based, at least in part, on the discovery of 76 clones from a human phage display library that specifically bind to FcRL5.

In various non-limiting embodiments, the presently disclosed subject matter provides for antibodies, and particularly variable regions of antibodies, that bind specifically to human FcRL5, as well as nucleic acids encoding said antibodies and variable regions, vectors comprising said nucleic acids and methods of producing said antibodies. The presently disclosed subject matter further provides pharmaceutical compositions comprising the disclosed anti-FcRL5 antibodies and methods of treatment. 76 species of antibodies, as well as competitively binding antibodies, are provided.

BRIEF DESCRIPTION OF THE FIGURES

FIGS. 3A-3D. (FIG. 3A) A representation of the domains of FcRL5 and the soluble, glycosylphosphatidylinositol (GPI)-anchored and transmembrane forms of FcRL5. (FIG. 3B) A representation of the vector used to express a mutated form of FcRL5 that lacks domain 9 (also referred to herein as FcRL5Δdom9). (FIG. 3C) The nucleotide sequences of full length FcRL5 and the form of FcRL5 that lacks domain 9. (FIG. 3D) A representation of the differences in the nucleotide sequences of full length FcRL5 and the mutated form of FcRL5 in which domain 9 is deleted (referred to herein as "FcRL5Δdom9").

(FIG. 13A) Table of combined peptides, with two sub-sequences indicated as "Loop 1" and "Loop 2. " (FIG. 13B) Data from A displayed as a matrix. (FIG. 13C) Color bar indication of the heat map representation. (FIG. 13D) Heat map visualization of data from FIG. 13A.

DETAILED DESCRIPTION OF THE SUBJECT MATTER

Figure 1:
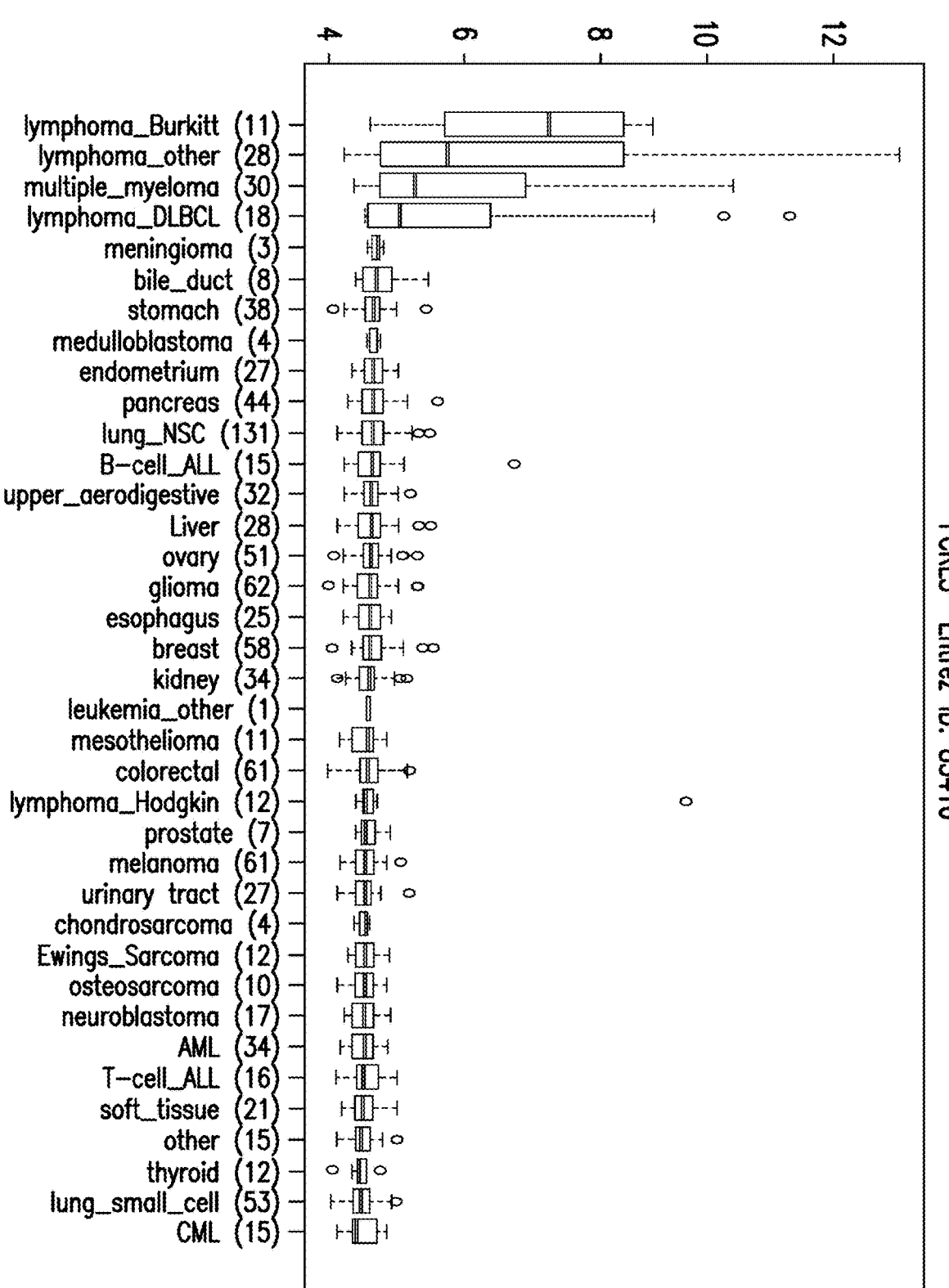
FIG. 1 depicts the FcRL5 expression in various normal tissues and human cancer cell lines.
Figure 1:
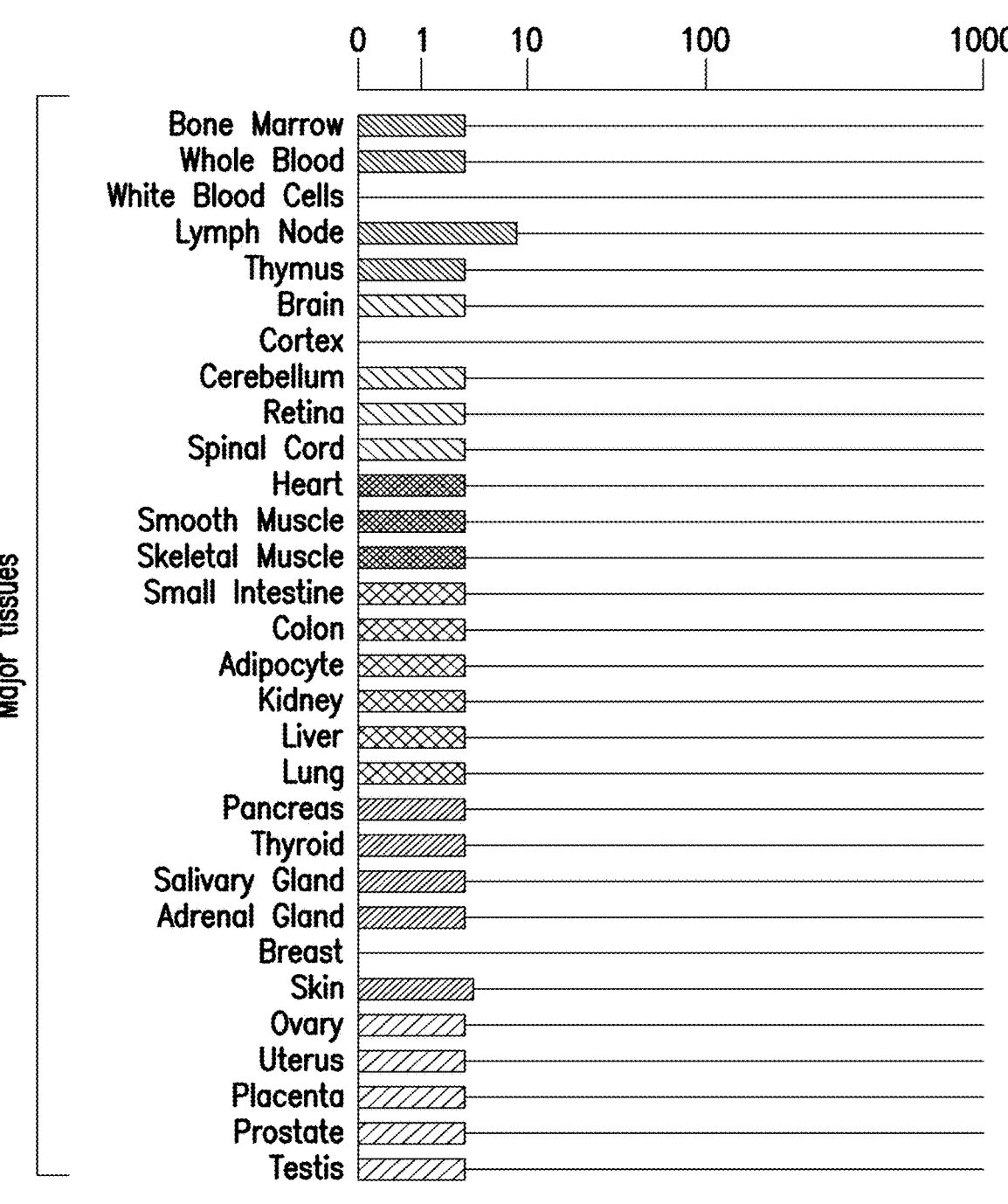
Figure 1:
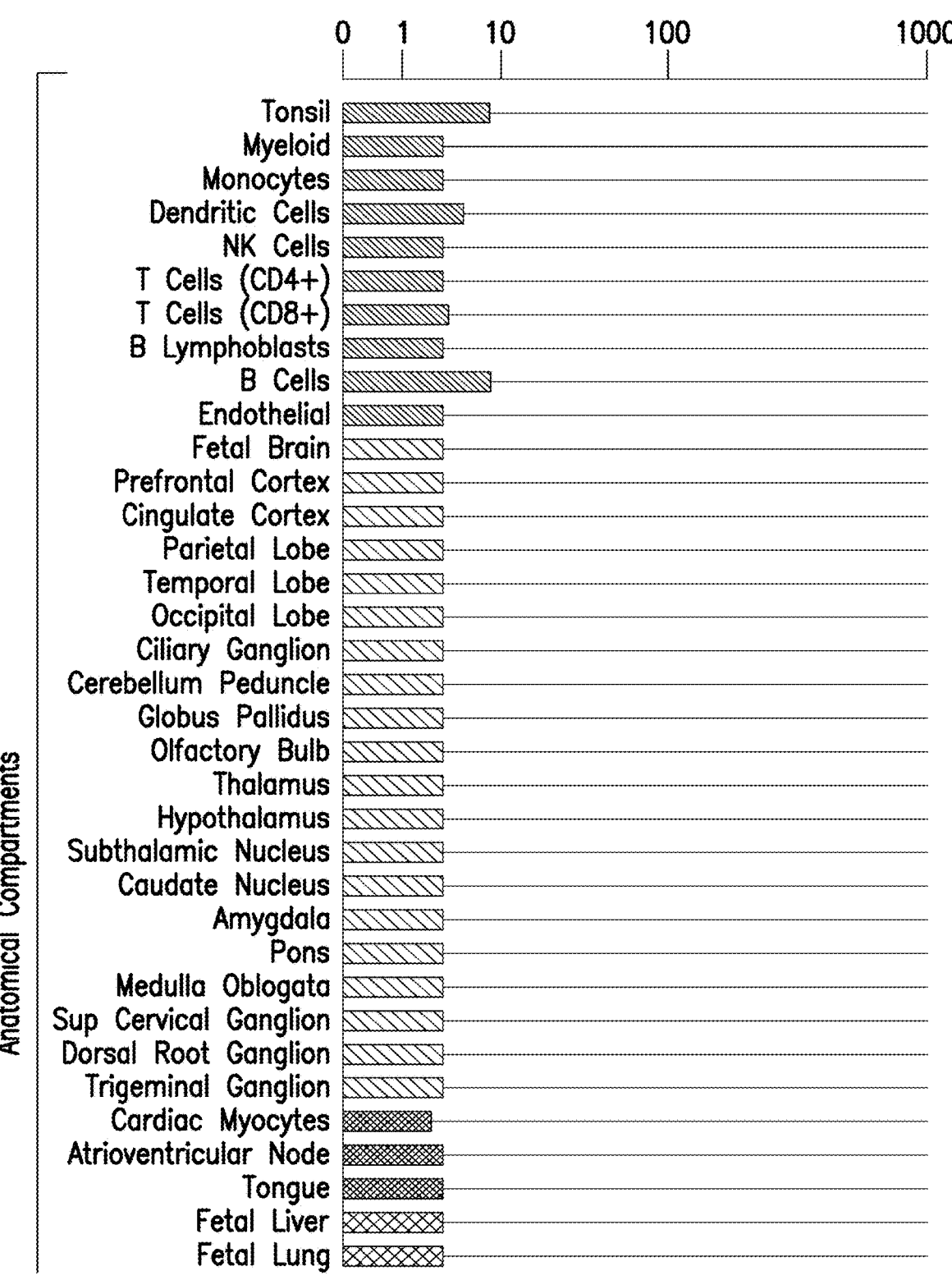
Figure 1:
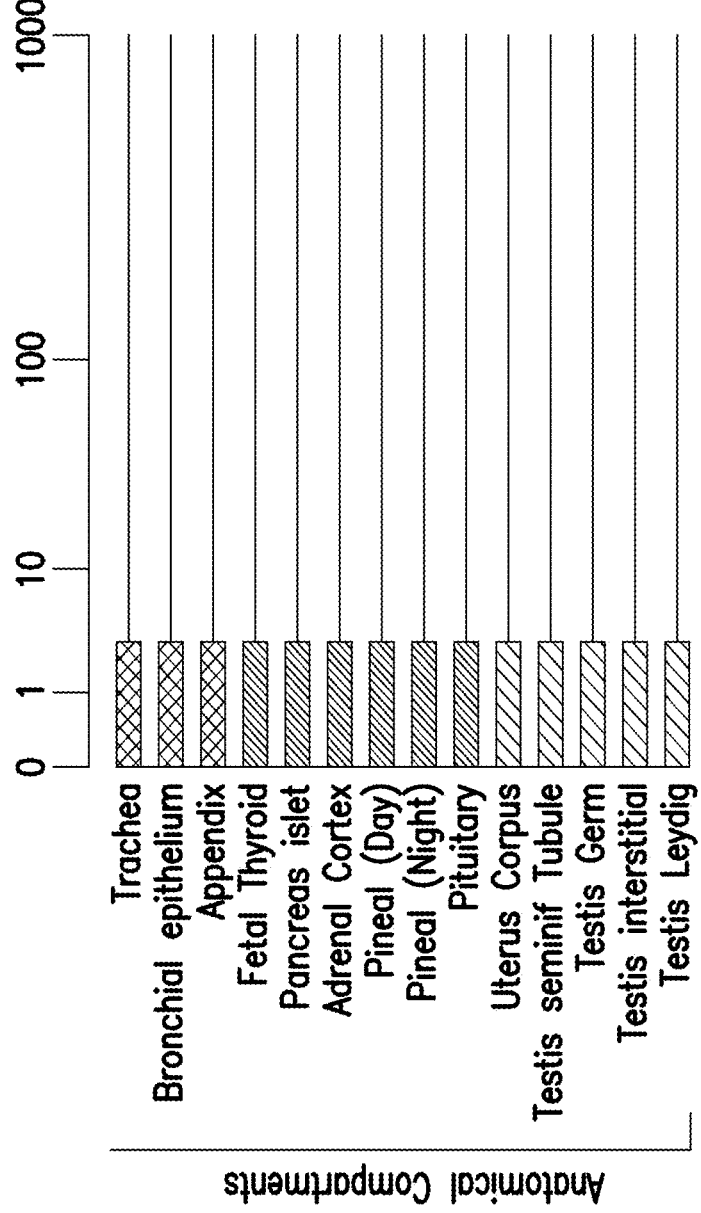

All publications, patents and other references cited herein are incorporated by reference in their entirety into the present disclosure.

In practicing the presently disclosed subject matter, many conventional techniques in molecular biology, microbiology, cell biology, biochemistry, and immunology are used, which are within the skill of the art. These techniques are described in greater detail in, for example, Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction," (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the present disclosure.

Definitions

In the description that follows, certain conventions will be followed as regards the usage of terminology. Generally, terms used herein are intended to be interpreted consistently with the meaning of those terms as they are known to those of skill in the art.

An "antigen-binding protein" is a protein or polypeptide that comprises an antigen-binding region or antigen-binding fragment, that is, has a strong affinity to another molecule to which it binds. Antigen-binding proteins encompass antibodies, chimeric antigen receptors (CARs) and fusion proteins.

"Antibody" and "antibodies," as those terms are known in the art, refer to antigen binding-proteins of the immune system. The term "antibody," as referred to herein, includes whole, full length antibodies having an antigen-binding region, and any fragment thereof in which the "antigen-binding portion," "antigen-binding fragment" or "antigen-binding region" is retained, or single chains, for example, single chain variable fragment (scFv), thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant (CH) region. The heavy chain constant region is comprised of three domains, CH1, CH2 and CH3. Each light chain is comprised of a light chain variable region (abbreviated herein as $V_L$) and a light chain constant $C_L$ region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1 q) of the classical complement system.

The term "human antibody," as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the presently disclosed subject matter may include amino acid residues not encoded by human germline immunoglobulin sequences (e.g., mutations introduced by random or site-specific mutagenesis in vitro or by somatic mutation in vivo).

The term "monoclonal antibody," as used herein, refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the presently disclosed subject matter may be made by a variety of techniques, including, but not limited to, the hybridoma method, recombinant DNA methods, phage-display methods, and methods utilizing transgenic animals containing all or part of the human immunoglobulin loci, such methods and other exemplary methods for making monoclonal antibodies being described herein.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, an antibody that "specifically binds to human FcRL5" is intended to refer to an antibody that binds to human FcRL5 with a $K_d$ of $5 \times 10^{-7}$ M or less, $1 \times 10^{-7}$ M or less, $5 \times 10^{-8}$ M or less, $1 \times 10^{-8}$ M or less, $5 \times 10^{-9}$ M or less, $1 \times 10^{-9}$ M or less, $5 \times 10^{-10}$ M or less, $1 \times 10^{-10}$ M or less, $5 \times 10^{-11}$ M or less or $1 \times 10^{-11}$ M or less.

An "antibody that competes for binding" or "antibody that cross-competes for binding" with a reference antibody for binding to an antigen, e.g., FcRL5, refers to an antibody that blocks binding of the reference antibody to the antigen (e.g., FcRL5) in a competition assay by about 50% or more, e.g., about 55% or more, about 60% or more, about 65% or more, about 70% or more, about 75% or more, about 80% or more, about 85% or more, about 90% or more, about 95% or more, about 98% or more or about 99% or more, and conversely, the reference antibody blocks binding of the antibody to the antigen (e.g., FcRL5) in a competition assay by about 50% or more, e.g., about 55% or more, about 60% or more, about 65% or more, about 70% or more, about 75% or more, about 80% or more, about 85% or more, about 90% or more, about 95% or more, about 98% or more or about 99% or more. An exemplary competition assay is described in "Antibodies," Harlow and Lane (Cold Spring Harbor Press, Cold Spring Harbor, NY) (1988).

As used herein, "isotype" refers to the antibody class (e.g., IgM or IgG1) that is encoded by the heavy chain constant region genes.

The phrases "an antibody recognizing an antigen" and "an antibody specific for an antigen" are used interchangeably herein with the term "an antibody which binds specifically to an antigen" (e.g., a FcRL5 polypeptide).

The term "antigen-binding portion," "antigen-binding fragment" or "antigen-binding region" of an antibody, as used herein, refers to that region or portion of the antibody that binds to the antigen and which confers antigen specificity to the antibody, for example, antibodies includes one or more fragments of an antibody that retain the ability to specifically bind to an antigen (e.g., a FcRL5 polypeptide). It has been shown that the antigen-binding function of an antibody can be performed by fragments of a full-length antibody. Examples of antigen-binding fragments encompassed within the term "antibody fragments" of an antibody include a Fab or Fab' fragment, a monovalent fragment consisting of the $V_L$, $V_H$, $C_L$ and CH1 domains; a F(ab')$_2$ fragment; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989, Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules. These are known as single chain Fvs (scFvs); see, e.g., Bird et al., 1988 Science 242:423-426; and Huston et al., 1988 Proc. Natl. Acad. Sci. 85:5879-5883. These antibody fragments are obtained using conventional techniques known to those of skill in the art, and the fragments are screened for utility in the same manner as are intact antibodies.

An "isolated antibody" or "isolated antigen-binding fragment" is one which has been identified and separated and/or recovered from a component of its natural environment. "Synthetic antibodies" or "recombinant antibodies" are generally generated using recombinant technology or using peptide synthetic techniques known to those of skill in the art.

The terms "FcRL5" and "FC Receptor-Like 5" are used interchangeably herein, and include variants, isoforms, species homologs of human FcRL5, and analogs having at least one common epitope with FcRL5 (e.g., human FcRL5). Non-limiting examples of human FcRL5 sequences can be found under GenBank Protein Accession Nos: AAI01070.1; XP_011508332.1; XP_011508334.1; XP_011508333.1; XP_011508332.1; and NP_001182317.1. In certain non-limiting embodiments, FcRL5 is a human FcRL5 having the amino acid sequence set forth in SEQ ID NO:899, or fragments thereof. SEQ ID NO:899 is provided below:

[SEQ ID NO: 899]

MLLWVILLVLAPVSGQFARTPRPIIFLQPPWTTVFQGERVTLTCKGFRFYS

PQKTKWYHRYLGKEILRETPDNILEVQESGEYRCQAQGSPLSSPVHLDFSS

ASLILQAPLSVFEGDSVVLRCRAKAEVTLNNTIYKNDNVLAFLNKRTDFHI

PHACLKDNGAYRCTGYKESCCPVSSNTVKIQVQEPFTRPVLRASSFQPISG

NPVTLTCETQLSLERSDVPLRFRFFRDDQTLGLGWSLSPNFQITAMWSKDS

GFYWCKAATMPHSIISDSPRSWIQVQIPASHPVLTLSPEKALNFEGTKVTL

HCETQEDSLRTLYRFYHEGVPLRHKSVRCERGASISFSLTTENSGNYYCTA

DNGLGAKPSKAVSLSVTVPVSHPVLNLSSPEDLIFEGAKVTLHCEAQRGSL

PILYQFHHEDAALERRSANSAGGVAISFSLTAEHSGNYYCTADNGFGPQRS

KAVSLSITVPVSHPVLTLSSAEALTFEGATVTLHCEVQRGSPQILYQFYHE

DMPLWSSSTPSVGRVSFSFSLTEGHSGNYYCTADNGFGPQRSEVVSLFVTV

PVSRPILTLRVPRAQAVVGDLLELHCEAPRGSPPILYWFYHEDVTLGSSSA

PSGGEASFNLSLTAEHSGNYSCEANNGLVAQHSDTISLSVIVPVSRPILTF

RAPRAQAVVGDLLELHCEALRGSSPILYWFYHEDVTLGKISAPSGGGASFN

LSLTTEHSGIYSCEADNGLEAQRSEMVTLKVAVPVSRPVLTLRAPGTHAAV

GDLLELHCEALRGSPLILYRFFHEDVTLGNRSSPSGGASLNLSLTAEHSGN

-continued

YSCEADNGLGAQRSETVTLYITGLTANRSGPFATGVAGGLLSIAGLAAGAL

LLYCWLSRKAGRKPASDPARSPSDSDSQEPTYHNVPAWEELQPVYTNANPR

GENVVYSEVRIIQEKKKHAVASDPRHLRNKGSPHYSEVKVASTPVSGSLFL

ASSAPHR.

Figure 3A:
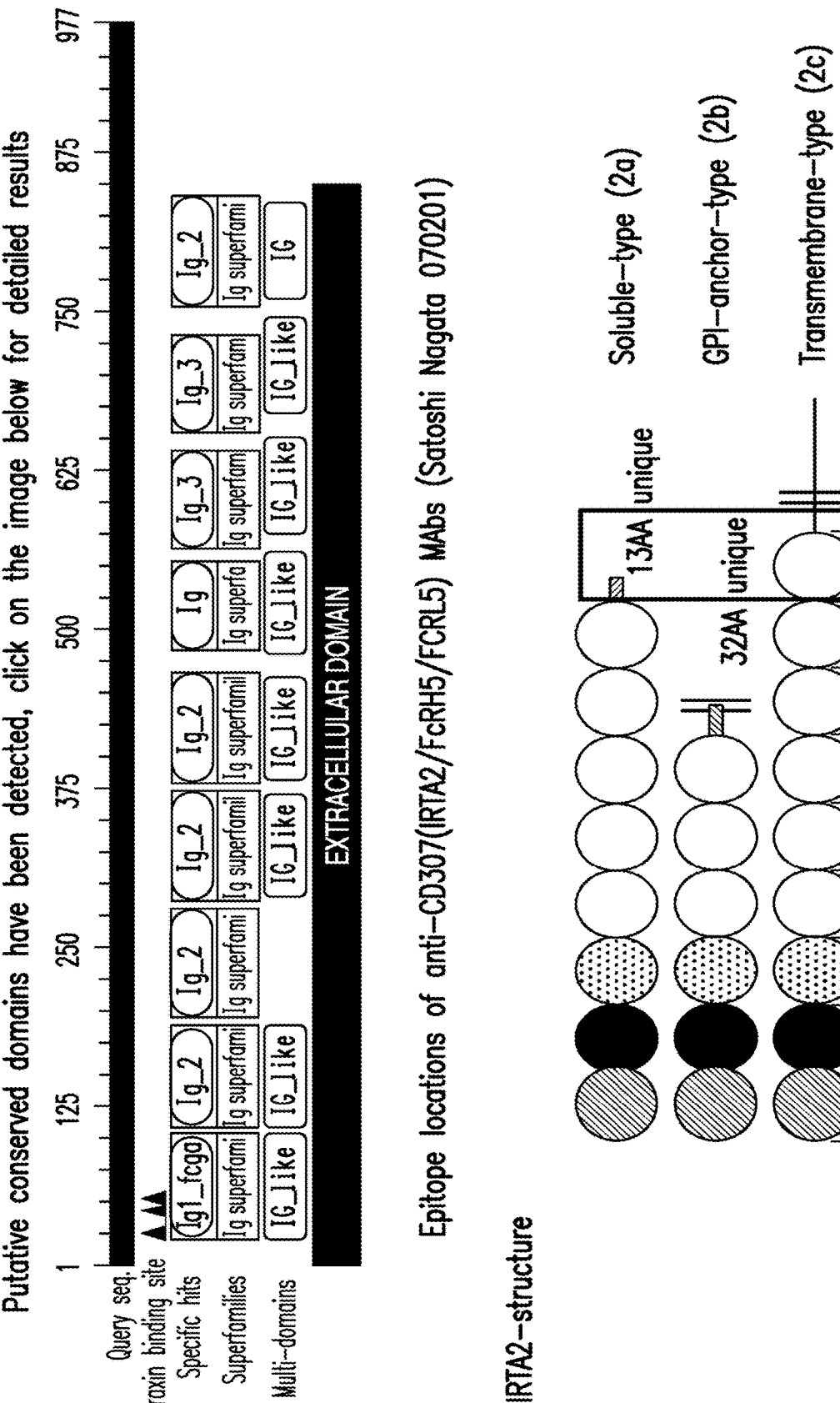
Figure 3B:
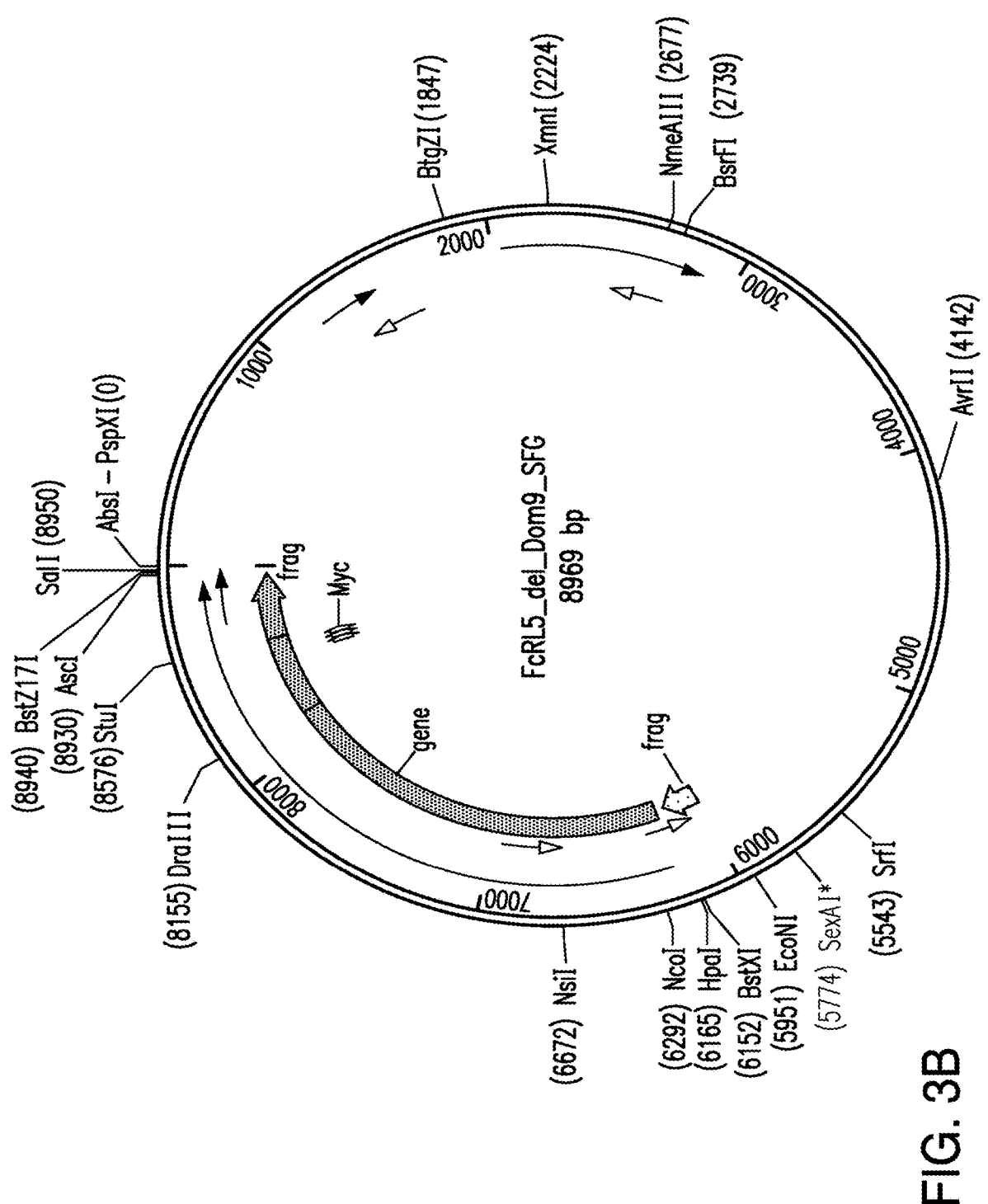
Figure 4:
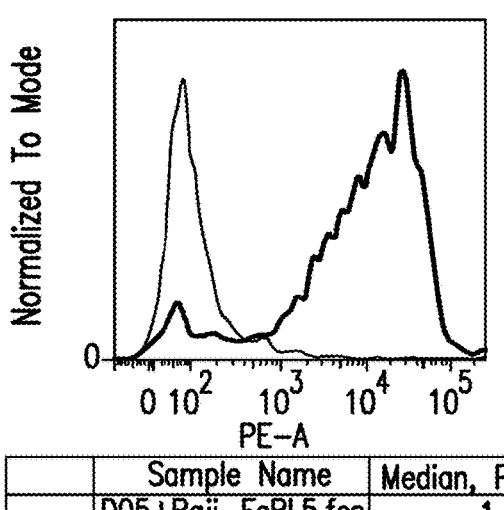
FIG. 4 depicts the screening of anti-FcRL5 scFv ET200-39 on 3T3 cells expressing FcRL5Δdom9.
Figure 4:
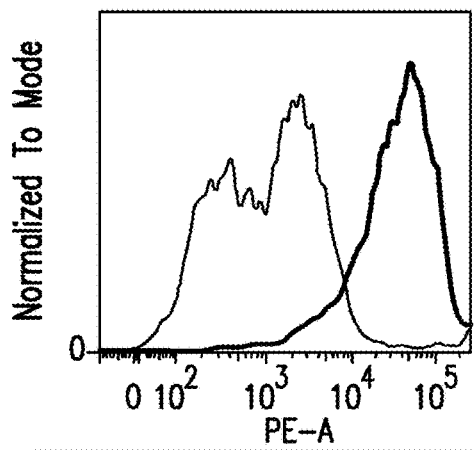
Figure 4:
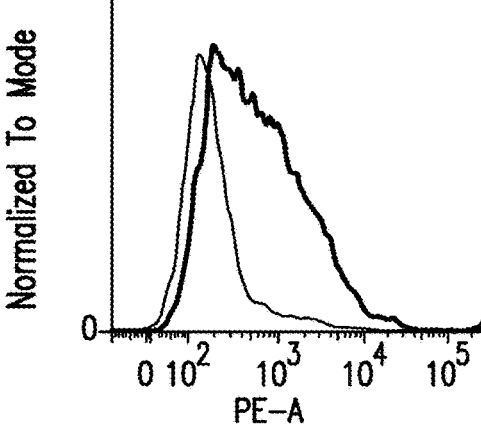
Figure 5:
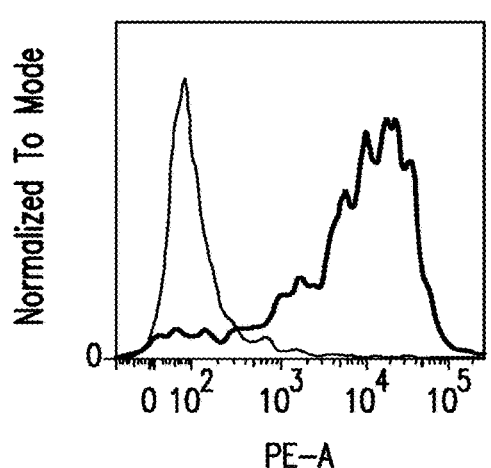
FIG. 5 depicts the screening of anti-FcRL5 scFv ET200-104 on 3T3 cells expressing FcRL5Δdom9.
Figure 5:
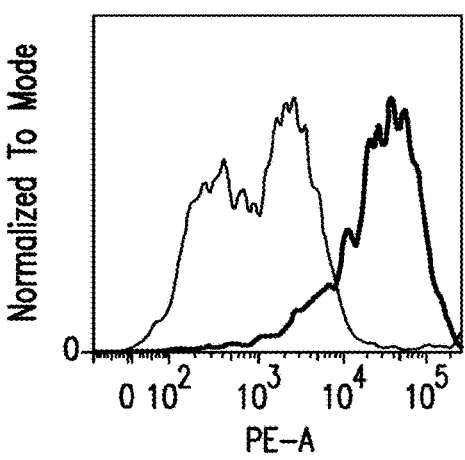
Figure 5:
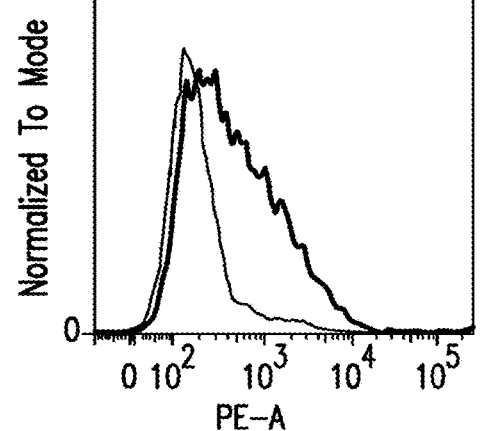
Figure 6:
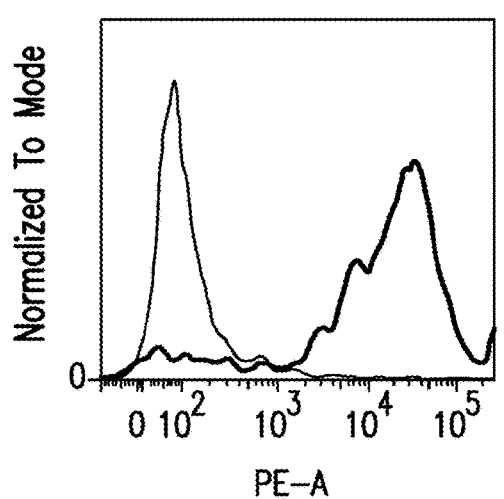
FIG. 6 depicts the screening of anti-FcRL5 scFv ET200-105 on 3T3 cells expressing FcRL5Δdom9.
Figure 6:
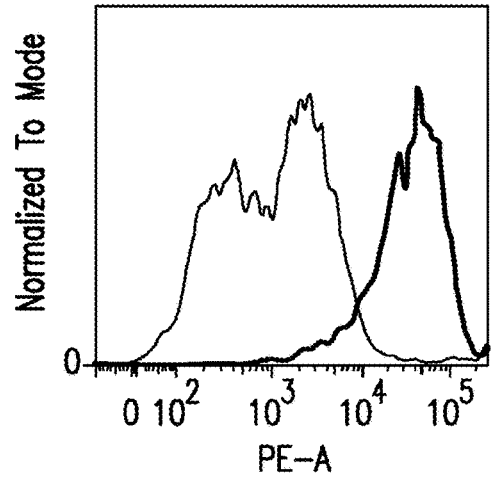
Figure 6:
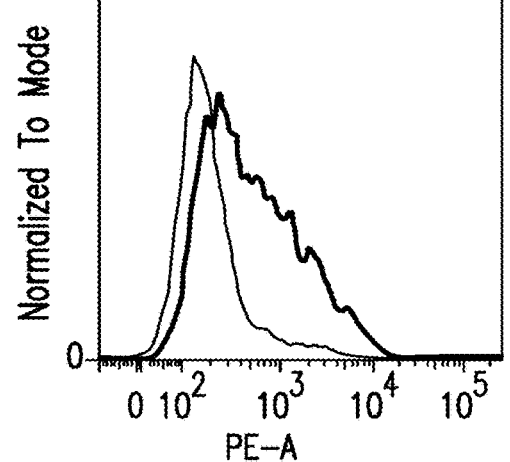
Figure 6:
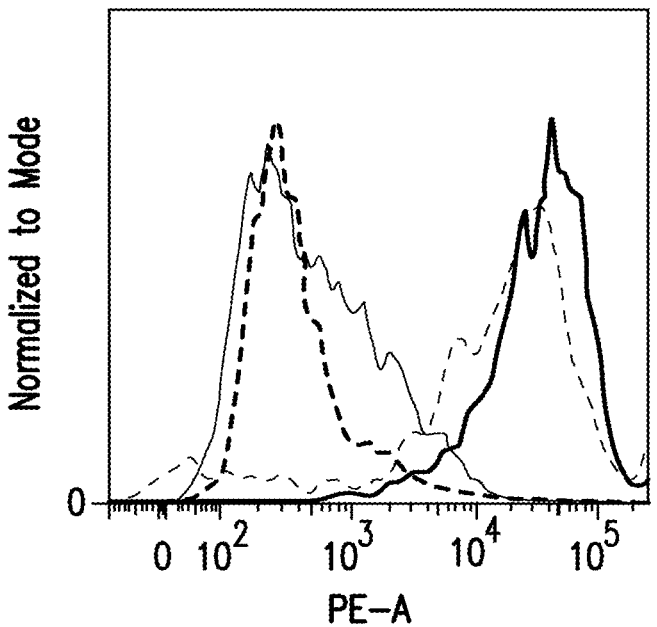
Figure 7:
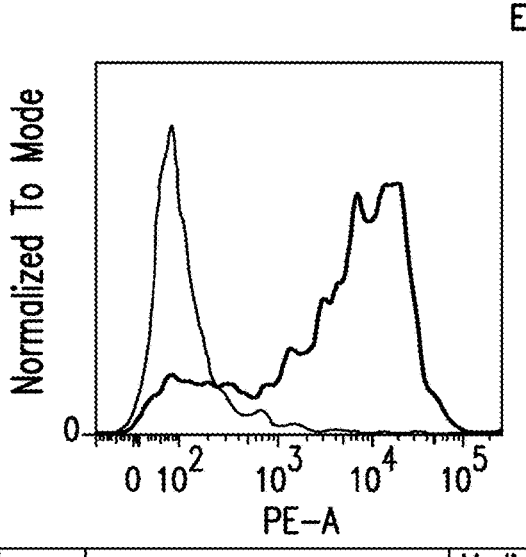
FIG. 7 depicts the screening of anti-FcRL5 scFv ET200-109 on 3T3 cells expressing FcRL5Δdom9.
Figure 7:
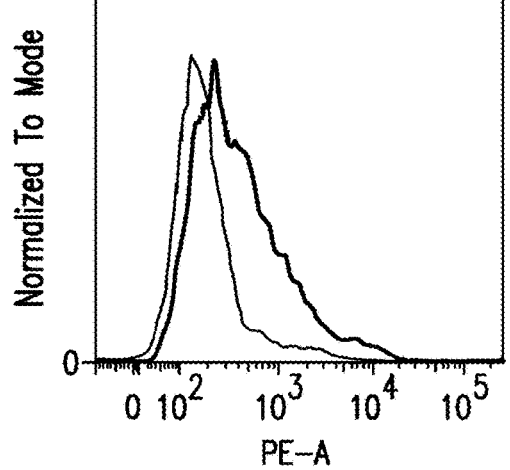
Figure 8:
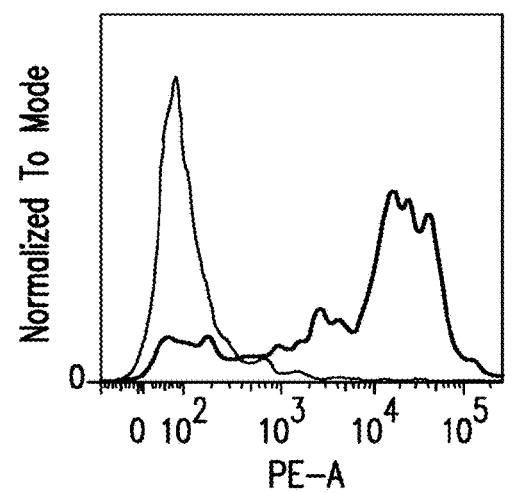
FIG. 8 depicts the screening of anti-FcRL5 scFv ET200-117 on 3T3 cells expressing FcRL5Δdom9.
Figure 8:
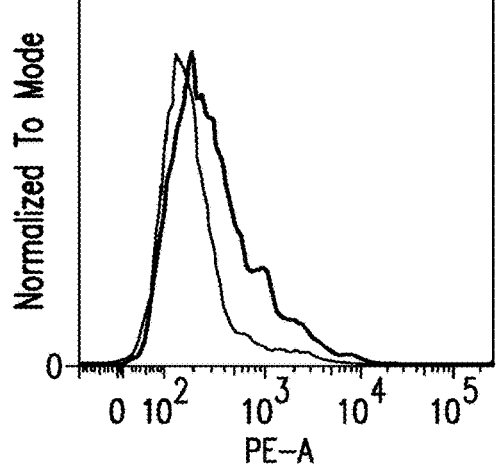

In certain embodiments, FcRL5 has 9 transmembrane Ig-like domains, i.e., domain 1, domain 2, domain 3, domain 4, domain 5, domain 6, domain 7, domain 8 and domain 9 (see FIGS. 3A and 3B). For example, and not by way of limitation, domain 1 can comprise amino acids 23-100 of SEQ ID NO:899; domain 2 can comprise amino acids 105-185 of SEQ ID NO:899; domain 3 can comprise amino acids 191-273 of SEQ ID NO:899; domain 4 can comprise amino acids 287-373 of SEQ ID NO:899; domain 5 can comprise amino acids 380-466 of SEQ ID NO:899; domain 6 can comprise amino acids 490-555 of SEQ ID NO:899; domain 7 can comprise amino acids 565-638 of SEQ ID NO:899; domain 8 can comprise amino acids 658-731 of SEQ ID NO:899; and domain 9 can comprise amino acids 754-835 of SEQ ID NO:899.

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H::V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. The linker can link the heavy chain variable region and the light chain variable region of the antigen-binding domain. Non-limiting examples of linkers are disclosed in Shen et al., Anal. Chem. 80(6):1910-1917 (2008) and WO 2014/087010, the contents of which are hereby incorporated by reference in their entireties. In certain embodiments, the linker is a G4S linker.

In one non-limiting embodiment, the linker comprises amino acids having the sequence set forth in SEQ ID NO:897 as provided below:

[SEQ ID NO: 897]
GGGGSGGGGSGGGGS.

In one embodiment, the nucleic acid sequence encoding the amino acid sequence of SEQ ID NO:897 is set forth in SEQ ID NO:898, which is provided below:

[SEQ ID NO: 898]
GGTGGAGGTGGATCAGGTGGAGG

TGGATCTGGTGGAGGTGGATCT.

In certain embodiments, the linker comprises amino acids having the sequence set forth in SEQ ID NO:307 as provided below:

[SEQ ID NO: 307]
SRGGGGSGGGGSGGGGSLEMA.

In one embodiment, the nucleic acid sequence encoding the amino acid sequence of SEQ ID NO:307 is set forth in SEQ ID NO:305, which is provided below:

[SEQ ID NO: 305]
TCTAGAGGTGGTGGTGGTAGCGGCGGCGGCGG

CTCTGGTGGTGGTGGATCCCTCGAGAT

GGCC.

In certain embodiments, the linker comprises amino acids having the following sequence GGGGS [SEQ ID NO:901].

In certain embodiments, the linker comprises amino acids having the following sequence SGGSGGS [SEQ ID NO:902].

In certain embodiments, the linker comprises amino acids having the following sequence GGGGSGGGS [SEQ ID NO:903].

In certain embodiments, the linker comprises amino acids having the following sequence GGGGSGGGGS [SEQ ID NO:904].

In certain embodiments, the linker comprises amino acids having the following sequence GGGGSGGGGSGGGGGGGS [SEQ ID NO:905].

In certain embodiments, the linker comprises amino acids having the following sequence GGGGSGGGGSGGGGSGGGGS [SEQ ID NO:906].

In certain embodiments, the linker comprises amino acids having the following sequence GGGGSGGGGSGGGGSGGGGSGGGGS [SEQ ID NO:907].

In certain embodiments, the linker comprises amino acids having the following sequence GGGGSGGGGSGGGGSGGGGSGGGGSGGGGS [SEQ ID NO:908].

In certain embodiments, the linker comprises amino acids having the following sequence GGGGSGGGGSGGGGSGGGGSGGGGSGGGGSGGGGS [SEQ ID NO:909].

In certain embodiments, the linker comprises amino acids having the following sequence EPKSCDKTHTCPPCP [SEQ ID NO:910].

In certain embodiments, the linker comprises amino acids having the following sequence GGGGSGGGSEPKSCDKTHTCPPCP [SEQ ID NO:911].

In certain embodiments, the linker comprises amino acids having the following sequence ELKTPLGDTTHTCPRC-PEPKSCDTPPPCPRCPEPKSCDTPPPCPRC-PEPKSCDTPPPCPRCP [SEQ ID NO:912].

In certain embodiments, the linker comprises amino acids having the following sequence GSGSGS [SEQ ID NO:913].

In certain embodiments, the linker comprises amino acids having the following sequence AAA [SEQ ID NO:914].

Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther. Immunol. 1995 2(10:31-40). Agonistic scFvs having stimulatory activity have been described (see, e.g., Peter et al., J Bio. Chem. 2003 25278(38):36740-7; Xie et al., Nat Biotech 1997 15(8):768-71; Ledbetter et al., Crit Rev. Immunol. 1997 17(5-6):427-55; Ho et al., BioChim Biophys Acta 2003 1638(3):257-66).

As used herein, "F(ab)" or "Fab" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')$_2$" fragment can be split into two individual Fab' fragments.

As used herein, the term "vector" refers to any genetic element, such as a plasmid, phage, transposon, cosmid, chromosome, virus, virion, etc., which is capable of replication when associated with the proper control elements and which can transfer gene sequences into cells. Thus, the term includes cloning and expression vehicles, as well as viral vectors and plasmid vectors.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th U.S. Department of Health and Human Services, National Institutes of Health (1987). The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise three heavy chain and three light chain CDRs or CDR regions in the variable region. CDRs provide the majority of contact residues for the binding of the antibody to the antigen or epitope.

An "isolated antibody" is one which has been separated from a component of its natural environment. In certain embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated nucleic acid" refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

An "isolated nucleic acid encoding an antibody" (including references to a specific antibody, e.g., an anti-FcRL5 antibody) refers to one or more nucleic acid molecules encoding antibody heavy and light chains (or fragments thereof), including such nucleic acid molecule(s) in a single vector separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

An "immunoconjugate" is an antibody conjugated to one or more heterologous molecule(s), including, but not limited to, a cytotoxic agent.

An "effective amount" of an agent, e.g., an anti-FcRL5 antibody or an antigen-binding fragment thereof, refers to an amount effective, at dosages and for periods of time necessary, to achieve the desired therapeutic or prophylactic result, e.g., treating a cancer (or a tumor of the cancer) (e.g., multiple myeloma).

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In certain embodiments, antibodies of the presently disclosed subject matter are used to delay development of a disease or to slow the progression of a disease, e.g., a tumor (multiple myeloma).

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

As described herein, any concentration range, percentage range, ratio range or integer range is to be understood to include the value of any integer within the recited range and, when appropriate, fractions thereof (such as one tenth and one hundredth of an integer), unless otherwise indicated.

Anti-FcRL5 Antibodies

The presently disclosed subject matter provides fully human antibodies or antigen binding fragments that are specific to FcRL5. The anti-FcRL5 antibodies or antigen binding fragments thereof of the present disclosure are based on the identification and selection of single chain variable fragments (scFvs) using phage display, the amino acid sequences of which confer the molecules' specificity for a FcRL5 polypeptide of interest and forms the basis of all FcRL5 antibodies or antigen binding fragments thereof of the disclosure. The scFvs, therefore, can be used to design a diverse array of "antibody" molecules, including, for example, full length antibodies, fragments thereof, such as Fab, Fab' and F(ab')$_2$, minibodies, fusion proteins, including scFv-Fc fusions, multivalent antibodies, that is, antibodies that have more than one specificity for the same antigen or different antigens, for example, bispecific antibodies, tribodies, etc. (see Cuesta et al., Multivalent antibodies: when design surpasses evolution. Trends in Biotechnology 28:355-362 2010).

The antibodies of the presently disclosed subject matter are characterized by particular functional features or properties of the antibodies. For example, the antibodies of the present disclosure bind specifically to FcRL5 (e.g., bind to human FcRL5 and may cross-react with FcRL5 from other species, such as mouse) with high affinity. In certain embodiments, antibodies of the present disclosure can bind to at least a portion of an FcRL5 polypeptide comprising the amino acid sequence set forth in SEQ ID NO:899 with high affinity. In certain embodiments, an antibody or antigen-binding fragment thereof of the present disclosure binds to at least a portion of the domain 8 of FcRL5 with high affinity. In certain embodiments, an antibody or antigen-binding fragment thereof of the present disclosure binds to at least a portion of the domain 7 of FcRL5 with high affinity. In certain embodiments, an antibody or antigen-binding fragment thereof of the present disclosure binds to at least a portion of the domain 8 of FcRL5 with high affinity. In certain embodiments, an antibody or antigen-binding fragment thereof of the present disclosure specifically binds to domain 9 of FcRL5 with high affinity. For example, and not by way of limitation, domain 9 of FcRL5 can have the amino acid sequence set forth in SEQ ID NO:900, or fragments thereof. SEQ ID NO:900 is provided below:

[SEQ ID NO: 900]
RPVLTLRAPGTHAAVGDLLELHCEALRGSPLIL

YRFFHEDVTLGNRSSPSGGASLNLSLTAEHSGN

YSCEADNGLGAQRSETVTLYI.

In certain embodiments, domain 9 of FcRL5 can have the amino acid sequence set forth in SEQ ID NO:917, or fragments thereof. SEQ ID NO:917 is provided below:

[SEQ ID NO: 917]
GTHAAVGDLLELHCEALRGSPLILYRFFHEDVT

LGNRSSPSGGASLNLSLTAEHSGNYSCEADNGL

GAQRSETVTLYI.

In certain embodiments, domain 9 of FcRL5 comprises an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence of SEQ ID NO:900 or 917. In certain embodiments, an antibody of the presently disclosed subject matter binds to FcRL5 or a portion thereof, e.g., domain 9 of FcRL5, with a $K_d$ of $1\times10^{-7}$ M or less, e.g., about $1\times10^{-8}$ M or less, about $1\times10^{-9}$ M or less, about $1\times10^{-10}$ M or less or about $1\times10^{-11}$ M or less. In certain embodiments, a presently disclosed anti-FcRL5 antibody binds to FcRL5 (e.g., human FcRL5) with a $K_d$ of from about $1\times10^{-11}$M to about $1\times10^{-7}$ M, e.g., from about $1\times10^{-11}$ M to about $1\times10^{-10}$ M, from about $1\times10^{-10}$ M to about $1\times10^{-9}$M, from $1\times10^{-9}$M to about $1\times10^{-8}$M, or from about $1\times10^{-8}$M to about $1\times10^{-7}$ M.

The heavy and light chains of an anti-FcRL5 antibody of the present disclosure can be full-length (e.g., an antibody including at least one (e.g., one or two) complete heavy chains, and at least one (e.g., one or two) complete light chains) or can include an antigen-binding portion (e.g., a Fab, Fab', F(ab')$_2$, Fv or a single chain Fv fragment ("scFv")). In certain embodiments, an anti-FcRL5 antibody of the present disclosure can include a one or more constant regions. In certain embodiments, the heavy chain constant region of a disclosed antibody is chosen from, e.g., IgG1, IgG2, IgG3, IgG4, IgM, IgA1, IgA2, IgD, and IgE. In certain embodiments, the immunoglobulin isotype is selected from IgG1, IgG2, IgG3, and IgG4, more particularly, IgG1 (e.g., human IgG1). In another non-limiting embodiment, the antibody light chain constant region is chosen from, e.g., kappa or lambda, particularly kappa. The choice of antibody isotype can depend on the immune effector function that the antibody is designed to elicit. In constructing a recombinant immunoglobulin, appropriate amino acid sequences for constant regions of various immunoglobulin isotypes and methods for the production of a wide array of antibodies are known to those of skill in the art.

1. Single-Chain Variable Fragments (scFvs)

In certain embodiments, the presently disclosed subject matter includes antibodies that have the scFv sequence fused to one or more constant domains to form an antibody with an Fc region of a human immunoglobulin to yield a bivalent protein, increasing the overall avidity and stability of the antibody. In addition, the Fc portion allows the direct conjugation of other molecules, including, but not limited to, fluorescent dyes, cytotoxins, radioisotopes etc. to the antibody for example, for use in antigen quantitation studies, to immobilize the antibody for affinity measurements, for targeted delivery of a therapeutic agent, to test for Fc-mediated cytotoxicity using immune effector cells and many other applications.

The presently disclosure subject matter provides scFvs that specifically bind to an FcRL5 polypeptide. In certain embodiments, an anti-FcRL5 scFv antibody of the present disclosure comprises a light chain variable region comprising an amino acid sequence selected from the group consisting of SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303, wherein the scFv antibody binds to an FcRL5 polypeptide.

In certain embodiments, an anti-FcRL5 scFv antibody of the present disclosure comprises a heavy chain variable region comprising an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, wherein the scFv antibody binds to an FcRL5 polypeptide.

In certain embodiments, an anti-FcRL5 scFv antibody comprises (a) a light chain variable region comprising an amino acid sequence selected from the group consisting of SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303 and (b) a heavy chain variable region comprising an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, wherein the scFv antibody binds to an FcRL5 polypeptide.

In certain embodiments, the anti-FcRL5 scFv antibody, optionally comprises (c) a linker sequence, for example a linker peptide, between the heavy chain variable region and the light chain variable region. In one non-limiting embodiment, the linker comprises amino acids having the sequence set forth in SEQ ID NO:307. In certain embodiments, the linker comprises the amino acid sequence set forth in SEQ ID NO:897.

In certain embodiments, an anti-FcRL5 scFv antibody comprises (a) a light chain variable region comprising amino acids having a sequence set forth in SEQ ID NO:3, and (b) a heavy chain variable region comprising amino acids having a sequence set forth in SEQ ID NO:4.

In certain embodiments, an anti-FcRL5 scFv antibody comprises (a) a light chain variable region comprising amino acids having a sequence set forth in SEQ ID NO:7, and (b) a heavy chain variable region comprising amino acids having a sequence set forth in SEQ ID NO:8.

In certain embodiments, an anti-FcRL5 scFv antibody comprises (a) a light chain variable region comprising amino acids having a sequence set forth in SEQ ID NO:11, and (b) a heavy chain variable region comprising amino acids having a sequence set forth in SEQ ID NO:12.

In certain embodiments, an anti-FcRL5 scFv antibody comprises (a) a light chain variable region comprising amino acids having a sequence set forth in SEQ ID NO:15, and (b) a heavy chain variable region comprising amino acids having a sequence set forth in SEQ ID NO:16.

In certain embodiments, an anti-FcRL5 scFv antibody comprises (a) a light chain variable region comprising amino acids having a sequence set forth in SEQ ID NO:19, and (b) a heavy chain variable region comprising amino acids having a sequence set forth in SEQ ID NO:20.

In certain embodiments, an anti-FcRL5 scFv antibody comprises (a) a light chain variable region comprising amino acids having a sequence set forth in SEQ ID NO:23, and (b) a heavy chain variable region comprising amino acids having a sequence set forth in SEQ ID NO:24.

In certain embodiments, an anti-FcRL5 scFv antibody comprises (a) a light chain variable region comprising amino acids having a sequence set forth in SEQ ID NO:27, and (b) a heavy chain variable region comprising amino acids having a sequence set forth in SEQ ID NO:28.

In certain embodiments, an anti-FcRL5 scFv antibody comprises (a) a light chain variable region comprising amino acids having a sequence set forth in SEQ ID NO:31, and (b) a heavy chain variable region comprising amino acids having a sequence set forth in SEQ ID NO:32.

In certain embodiments, an anti-FcRL5 scFv antibody comprises (a) a light chain variable region comprising amino acids having a sequence set forth in SEQ ID NO:35, and (b)

a heavy chain variable region comprising amino acids having a sequence set forth in SEQ ID NO:36.

In certain embodiments, an anti-FcRL5 scFv antibody comprises (a) a light chain variable region comprising amino acids having a sequence set forth in SEQ ID NO:39, and (b) a heavy chain variable region comprising amino acids having a sequence set forth in SEQ ID NO:40.

In certain embodiments, an anti-FcRL5 scFv antibody comprises (a) a light chain variable region comprising amino acids having a sequence set forth in SEQ ID NO:43, and (b) a heavy chain variable region comprising amino acids having a sequence set forth in SEQ ID NO:44.

In certain embodiments, an anti-FcRL5 scFv antibody comprises (a) a light chain variable region comprising amino acids having a sequence set forth in SEQ ID NO:47, and (b) a heavy chain variable region comprising amino acids having a sequence set forth in SEQ ID NO:48.

In certain embodiments, an anti-FcRL5 scFv antibody comprises (a) a light chain variable region comprising amino acids having a sequence set forth in SEQ ID NO:51, and (b) a heavy chain variable region comprising amino acids having a sequence set forth in SEQ ID NO:52.

In certain embodiments, an anti-FcRL5 scFv antibody comprises (a) a light chain variable region comprising amino acids having a sequence set forth in SEQ ID NO:55, and (b) a heavy chain variable region comprising amino acids having a sequence set forth in SEQ ID NO:56.

In certain embodiments, an anti-FcRL5 scFv antibody comprises (a) a light chain variable region comprising amino acids having a sequence set forth in SEQ ID NO:59, and (b) a heavy chain variable region comprising amino acids having a sequence set forth in SEQ ID NO:60.

In certain embodiments, an anti-FcRL5 scFv antibody comprises (a) a light chain variable region comprising amino acids having a sequence set forth in SEQ ID NO:63, and (b) a heavy chain variable region comprising amino acids having a sequence set forth in SEQ ID NO:64.

In certain embodiments, an anti-FcRL5 scFv antibody comprises (a) a light chain variable region comprising amino acids having a sequence set forth in SEQ ID NO:67, and (b) a heavy chain variable region comprising amino acids having a sequence set forth in SEQ ID NO:68.

In certain embodiments, an anti-FcRL5 scFv antibody comprises (a) a light chain variable region comprising amino acids having a sequence set forth in SEQ ID NO:71, and (b) a heavy chain variable region comprising amino acids having a sequence set forth in SEQ ID NO:72.

In certain embodiments, an anti-FcRL5 scFv antibody comprises (a) a light chain variable region comprising amino acids having a sequence set forth in SEQ ID NO:75, and (b) a heavy chain variable region comprising amino acids having a sequence set forth in SEQ ID NO:76.

In certain embodiments, an anti-FcRL5 scFv antibody comprises (a) a light chain variable region comprising amino acids having a sequence set forth in SEQ ID NO:79, and (b) a heavy chain variable region comprising amino acids having a sequence set forth in SEQ ID NO:80.

In certain embodiments, an anti-FcRL5 scFv antibody comprises (a) a light chain variable region comprising amino acids having a sequence set forth in SEQ ID NO:83, and (b) a heavy chain variable region comprising amino acids having a sequence set forth in SEQ ID NO:84.

In certain embodiments, an anti-FcRL5 scFv antibody comprises (a) a light chain variable region comprising amino acids having a sequence set forth in SEQ ID NO:87, and (b) a heavy chain variable region comprising amino acids having a sequence set forth in SEQ ID NO:88.

In certain embodiments, an anti-FcRL5 scFv antibody comprises (a) a light chain variable region comprising amino acids having a sequence set forth in SEQ ID NO:91, and (b) a heavy chain variable region comprising amino acids having a sequence set forth in SEQ ID NO:92.

In certain embodiments, an anti-FcRL5 scFv antibody comprises (a) a light chain variable region comprising amino acids having a sequence set forth in SEQ ID NO:95, and (b) a heavy chain variable region comprising amino acids having a sequence set forth in SEQ ID NO:96.

In certain embodiments, an anti-FcRL5 scFv antibody comprises (a) a light chain variable region comprising amino acids having a sequence set forth in SEQ ID NO:99, and (b) a heavy chain variable region comprising amino acids having a sequence set forth in SEQ ID NO:100.

In certain embodiments, an anti-FcRL5 scFv antibody comprises (a) a light chain variable region comprising amino acids having a sequence set forth in SEQ ID NO:103, and (b) a heavy chain variable region comprising amino acids having a sequence set forth in SEQ ID NO:104.

In certain embodiments, an anti-FcRL5 scFv antibody comprises (a) a light chain variable region comprising amino acids having a sequence set forth in SEQ ID NO:107, and (b) a heavy chain variable region comprising amino acids having a sequence set forth in SEQ ID NO:108.

In certain embodiments, an anti-FcRL5 scFv antibody comprises (a) a light chain variable region comprising amino acids having a sequence set forth in SEQ ID NO:111, and (b) a heavy chain variable region comprising amino acids having a sequence set forth in SEQ ID NO:112.

In certain embodiments, an anti-FcRL5 scFv antibody comprises (a) a light chain variable region comprising amino acids having a sequence set forth in SEQ ID NO:115, and (b) a heavy chain variable region comprising amino acids having a sequence set forth in SEQ ID NO:116.

In certain embodiments, an anti-FcRL5 scFv antibody comprises (a) a light chain variable region comprising amino acids having a sequence set forth in SEQ ID NO:119, and (b) a heavy chain variable region comprising amino acids having a sequence set forth in SEQ ID NO:120.

In certain embodiments, an anti-FcRL5 scFv antibody comprises (a) a light chain variable region comprising amino acids having a sequence set forth in SEQ ID NO:123, and (b) a heavy chain variable region comprising amino acids having a sequence set forth in SEQ ID NO:124.

In certain embodiments, an anti-FcRL5 scFv antibody comprises (a) a light chain variable region comprising amino acids having a sequence set forth in SEQ ID NO:127, and (b) a heavy chain variable region comprising amino acids having a sequence set forth in SEQ ID NO:128.

In certain embodiments, an anti-FcRL5 scFv antibody comprises (a) a light chain variable region comprising amino acids having a sequence set forth in SEQ ID NO:131, and (b) a heavy chain variable region comprising amino acids having a sequence set forth in SEQ ID NO:132.

In certain embodiments, an anti-FcRL5 scFv antibody comprises (a) a light chain variable region comprising amino acids having a sequence set forth in SEQ ID NO:135, and (b) a heavy chain variable region comprising amino acids having a sequence set forth in SEQ ID NO:136.

In certain embodiments, an anti-FcRL5 scFv antibody comprises (a) a light chain variable region comprising amino acids having a sequence set forth in SEQ ID NO:139, and (b) a heavy chain variable region comprising amino acids having a sequence set forth in SEQ ID NO:140.

In certain embodiments, an anti-FcRL5 scFv antibody comprises (a) a light chain variable region comprising amino acids having a sequence set forth in SEQ ID NO:143, and (b) a heavy chain variable region comprising amino acids having a sequence set forth in SEQ ID NO:144.

In certain embodiments, an anti-FcRL5 scFv antibody comprises (a) a light chain variable region comprising amino acids having a sequence set forth in SEQ ID NO:147, and (b) a heavy chain variable region comprising amino acids having a sequence set forth in SEQ ID NO:148.

In certain embodiments, an anti-FcRL5 scFv antibody comprises (a) a light chain variable region comprising amino acids having a sequence set forth in SEQ ID NO:151, and (b) a heavy chain variable region comprising amino acids having a sequence set forth in SEQ ID NO:152.

In certain embodiments, an anti-FcRL5 scFv antibody comprises (a) a light chain variable region comprising amino acids having a sequence set forth in SEQ ID NO:155, and (b) a heavy chain variable region comprising amino acids having a sequence set forth in SEQ ID NO:156.

In certain embodiments, an anti-FcRL5 scFv antibody comprises (a) a light chain variable region comprising amino acids having a sequence set forth in SEQ ID NO:159, and (b) a heavy chain variable region comprising amino acids having a sequence set forth in SEQ ID NO:160.

In certain embodiments, an anti-FcRL5 scFv antibody comprises (a) a light chain variable region comprising amino acids having a sequence set forth in SEQ ID NO:163, and (b) a heavy chain variable region comprising amino acids having a sequence set forth in SEQ ID NO:164.

In certain embodiments, an anti-FcRL5 scFv antibody comprises (a) a light chain variable region comprising amino acids having a sequence set forth in SEQ ID NO:167, and (b) a heavy chain variable region comprising amino acids having a sequence set forth in SEQ ID NO:168.

In certain embodiments, an anti-FcRL5 scFv antibody comprises (a) a light chain variable region comprising amino acids having a sequence set forth in SEQ ID NO:171, and (b) a heavy chain variable region comprising amino acids having a sequence set forth in SEQ ID NO:172.

In certain embodiments, an anti-FcRL5 scFv antibody comprises (a) a light chain variable region comprising amino acids having a sequence set forth in SEQ ID NO:175, and (b) a heavy chain variable region comprising amino acids having a sequence set forth in SEQ ID NO:176.

In certain embodiments, an anti-FcRL5 scFv antibody comprises (a) a light chain variable region comprising amino acids having a sequence set forth in SEQ ID NO:179, and (b) a heavy chain variable region comprising amino acids having a sequence set forth in SEQ ID NO:180.

In certain embodiments, an anti-FcRL5 scFv antibody comprises (a) a light chain variable region comprising amino acids having a sequence set forth in SEQ ID NO:183, and (b) a heavy chain variable region comprising amino acids having a sequence set forth in SEQ ID NO:184.

In certain embodiments, an anti-FcRL5 scFv antibody comprises (a) a light chain variable region comprising amino acids having a sequence set forth in SEQ ID NO:187, and (b) a heavy chain variable region comprising amino acids having a sequence set forth in SEQ ID NO:188.

In certain embodiments, an anti-FcRL5 scFv antibody comprises (a) a light chain variable region comprising amino acids having a sequence set forth in SEQ ID NO:191, and (b) a heavy chain variable region comprising amino acids having a sequence set forth in SEQ ID NO:192.

In certain embodiments, an anti-FcRL5 scFv antibody comprises (a) a light chain variable region comprising amino acids having a sequence set forth in SEQ ID NO:195, and (b)

a heavy chain variable region comprising amino acids having a sequence set forth in SEQ ID NO:196.

In certain embodiments, an anti-FcRL5 scFv antibody comprises (a) a light chain variable region comprising amino acids having a sequence set forth in SEQ ID NO:199, and (b) a heavy chain variable region comprising amino acids having a sequence set forth in SEQ ID NO:200.

In certain embodiments, an anti-FcRL5 scFv antibody comprises (a) a light chain variable region comprising amino acids having a sequence set forth in SEQ ID NO:203, and (b) a heavy chain variable region comprising amino acids having a sequence set forth in SEQ ID NO:204.

In certain embodiments, an anti-FcRL5 scFv antibody comprises (a) a light chain variable region comprising amino acids having a sequence set forth in SEQ ID NO:207, and (b) a heavy chain variable region comprising amino acids having a sequence set forth in SEQ ID NO:208.

In certain embodiments, an anti-FcRL5 scFv antibody comprises (a) a light chain variable region comprising amino acids having a sequence set forth in SEQ ID NO:211, and (b) a heavy chain variable region comprising amino acids having a sequence set forth in SEQ ID NO:212.

In certain embodiments, an anti-FcRL5 scFv antibody comprises (a) a light chain variable region comprising amino acids having a sequence set forth in SEQ ID NO:215, and (b) a heavy chain variable region comprising amino acids having a sequence set forth in SEQ ID NO:216.

In certain embodiments, an anti-FcRL5 scFv antibody comprises (a) a light chain variable region comprising amino acids having a sequence set forth in SEQ ID NO:219, and (b) a heavy chain variable region comprising amino acids having a sequence set forth in SEQ ID NO:220.

In certain embodiments, an anti-FcRL5 scFv antibody comprises (a) a light chain variable region comprising amino acids having a sequence set forth in SEQ ID NO:223, and (b) a heavy chain variable region comprising amino acids having a sequence set forth in SEQ ID NO:224.

In certain embodiments, an anti-FcRL5 scFv antibody comprises (a) a light chain variable region comprising amino acids having a sequence set forth in SEQ ID NO:227, and (b) a heavy chain variable region comprising amino acids having a sequence set forth in SEQ ID NO:228.

In certain embodiments, an anti-FcRL5 scFv antibody comprises (a) a light chain variable region comprising amino acids having a sequence set forth in SEQ ID NO:231, and (b) a heavy chain variable region comprising amino acids having a sequence set forth in SEQ ID NO:232.

In certain embodiments, an anti-FcRL5 scFv antibody comprises (a) a light chain variable region comprising amino acids having a sequence set forth in SEQ ID NO:235, and (b) a heavy chain variable region comprising amino acids having a sequence set forth in SEQ ID NO:236.

In certain embodiments, an anti-FcRL5 scFv antibody comprises (a) a light chain variable region comprising amino acids having a sequence set forth in SEQ ID NO:239, and (b) a heavy chain variable region comprising amino acids having a sequence set forth in SEQ ID NO:240.

In certain embodiments, an anti-FcRL5 scFv antibody comprises (a) a light chain variable region comprising amino acids having a sequence set forth in SEQ ID NO:243, and (b) a heavy chain variable region comprising amino acids having a sequence set forth in SEQ ID NO:244.

In certain embodiments, an anti-FcRL5 scFv antibody comprises (a) a light chain variable region comprising amino acids having a sequence set forth in SEQ ID NO:247, and (b) a heavy chain variable region comprising amino acids having a sequence set forth in SEQ ID NO:248.

In certain embodiments, an anti-FcRL5 scFv antibody comprises (a) a light chain variable region comprising amino acids having a sequence set forth in SEQ ID NO:251, and (b) a heavy chain variable region comprising amino acids having a sequence set forth in SEQ ID NO:252.

In certain embodiments, an anti-FcRL5 scFv antibody comprises (a) a light chain variable region comprising amino acids having a sequence set forth in SEQ ID NO:255, and (b) a heavy chain variable region comprising amino acids having a sequence set forth in SEQ ID NO:256.

In certain embodiments, an anti-FcRL5 scFv antibody comprises (a) a light chain variable region comprising amino acids having a sequence set forth in SEQ ID NO:259, and (b) a heavy chain variable region comprising amino acids having a sequence set forth in SEQ ID NO:260.

In certain embodiments, an anti-FcRL5 scFv antibody comprises (a) a light chain variable region comprising amino acids having a sequence set forth in SEQ ID NO:263, and (b) a heavy chain variable region comprising amino acids having a sequence set forth in SEQ ID NO:264.

In certain embodiments, an anti-FcRL5 scFv antibody comprises (a) a light chain variable region comprising amino acids having a sequence set forth in SEQ ID NO:267, and (b) a heavy chain variable region comprising amino acids having a sequence set forth in SEQ ID NO:268.

In certain embodiments, an anti-FcRL5 scFv antibody comprises (a) a light chain variable region comprising amino acids having a sequence set forth in SEQ ID NO:271, and (b) a heavy chain variable region comprising amino acids having a sequence set forth in SEQ ID NO:272.

In certain embodiments, an anti-FcRL5 scFv antibody comprises (a) a light chain variable region comprising amino acids having a sequence set forth in SEQ ID NO:275, and (b) a heavy chain variable region comprising amino acids having a sequence set forth in SEQ ID NO:276.

In certain embodiments, an anti-FcRL5 scFv antibody comprises (a) a light chain variable region comprising amino acids having a sequence set forth in SEQ ID NO:279, and (b) a heavy chain variable region comprising amino acids having a sequence set forth in SEQ ID NO:280.

In certain embodiments, an anti-FcRL5 scFv antibody comprises (a) a light chain variable region comprising amino acids having a sequence set forth in SEQ ID NO:283, and (b) a heavy chain variable region comprising amino acids having a sequence set forth in SEQ ID NO:284.

In certain embodiments, an anti-FcRL5 scFv antibody comprises (a) a light chain variable region comprising amino acids having a sequence set forth in SEQ ID NO:287, and (b) a heavy chain variable region comprising amino acids having a sequence set forth in SEQ ID NO:288.

In certain embodiments, an anti-FcRL5 scFv antibody comprises (a) a light chain variable region comprising amino acids having a sequence set forth in SEQ ID NO:291, and (b) a heavy chain variable region comprising amino acids having a sequence set forth in SEQ ID NO:292.

In certain embodiments, an anti-FcRL5 scFv antibody comprises (a) a light chain variable region comprising amino acids having a sequence set forth in SEQ ID NO:279, and (b) a heavy chain variable region comprising amino acids having a sequence set forth in SEQ ID NO:280.

In certain embodiments, an anti-FcRL5 scFv antibody comprises (a) a light chain variable region comprising amino acids having a sequence set forth in SEQ ID NO:283, and (b) a heavy chain variable region comprising amino acids having a sequence set forth in SEQ ID NO:284.

In certain embodiments, an anti-FcRL5 scFv antibody comprises (a) a light chain variable region comprising amino acids having a sequence set forth in SEQ ID NO:287, and (b) a heavy chain variable region comprising amino acids having a sequence set forth in SEQ ID NO:288.

In certain embodiments, an anti-FcRL5 scFv antibody comprises (a) a light chain variable region comprising amino acids having a sequence set forth in SEQ ID NO:291, and (b) a heavy chain variable region comprising amino acids having a sequence set forth in SEQ ID NO:292.

In certain embodiments, an anti-FcRL5 scFv antibody comprises (a) a light chain variable region comprising amino acids having a sequence set forth in SEQ ID NO:295, and (b) a heavy chain variable region comprising amino acids having a sequence set forth in SEQ ID NO:296.

In certain embodiments, an anti-FcRL5 scFv antibody comprises (a) a light chain variable region comprising amino acids having a sequence set forth in SEQ ID NO:299, and (b) a heavy chain variable region comprising amino acids having a sequence set forth in SEQ ID NO:300.

In certain embodiments, an anti-FcRL5 scFv antibody comprises (a) a light chain variable region comprising amino acids having a sequence set forth in SEQ ID NO:303, and (b) a heavy chain variable region comprising amino acids having a sequence set forth in SEQ ID NO:304.

The presently disclosed subject matter further provides anti-FcRL5 scFv antibodies that comprise heavy chain variable region and light chain variable region CDRs, e.g., CDR1s, CDR2s and CDR3s, as disclosed herein in Table 229. The CDR regions are delineated using the Kabat system (Kabat, E. A., et al. (1991) Sequences of Proteins of Immunological Interest, Fifth Edition, U.S. Department of Health and Human Services, NIH Publication No. 91-3242).

In certain embodiments, an anti-FcRL5 scFv antibody comprises a light chain variable region, wherein the light chain variable region comprises: (a) a CDR1 comprising an amino acid sequence selected from the group consisting of SEQ ID NOs: 312, 318, 324, 329, 338, 343, 348, 352, 357, 363, 369, 381, 390, 397, 401, 406, 416, 423, 428, 433, 447, 460, 468, 474, 477, 483, 490, 498, 503, 508, 518, 533, 540, 544, 547, 556, 562, 568, 571, 580, 585 and 588; (b) a CDR2 comprising an amino acid sequence selected from the group consisting of SEQ ID NOs:313, 319, 330, 344, 349, 358, 364, 370, 382, 385, 391, 398, 409, 417, 429, 434, 438, 448, 454, 461, 469, 478, 484, 487, 504, 513, 523, 534, 429, 448, 548, 557, 563, 572, 575 and 586; and (c) a CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592; wherein the antibody specifically binds FcRL5.

In certain embodiments, an anti-FcRL5 scFv antibody comprises a heavy chain variable region, wherein the heavy chain variable region comprises: (a) a CDR1 comprising an amino acid sequence selected from the group consisting of SEQ ID NOs: 309, 315, 321, 326, 332, 335, 340, 346, 354, 360, 366, 372, 378, 387, 393, 403, 411, 420, 425, 436, 440, 444, 471, 480, 500, 510, 515, 520, 525, 537, 551, 559, 565, 582 and 589; (b) a CDR2 comprising an amino acid sequence selected from the group consisting of SEQ ID NOs: 310, 316, 322, 327, 333, 336, 341, 355, 361, 367, 373, 379, 388, 404, 412, 421, 426, 431, 441, 445, 450, 466, 472, 475, 481, 496, 501, 506, 511, 516, 521, 526, 538, 552, 560, 566, 583 and 590; and (c) a CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591; wherein the anti-FcRL5 scFv antibody specifically binds FcRL5.

In certain embodiments, the presently disclosed subject matter provides an anti-FcRL5 scFv antibody comprising: (a) a heavy chain variable region CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591; and (b) a light chain variable region CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592; wherein the anti-FcRL5 scFv antibody specifically binds FcRL5.

In certain embodiments, an anti-FcRL5 scFv antibody of the present disclosure comprises a heavy chain variable region CDR1, a heavy chain variable region CDR2, a heavy chain variable region CDR3, a light chain variable region CDR1, a light chain variable region CDR2 and a light chain variable region CDR3 selected from Table 229. For example, and not by way of limitation, an anti-FcRL5 scFv antibody comprises: (a) a heavy chain variable region CDR1 comprising an amino acid sequence selected from the group consisting of SEQ ID NOs: 309, 315, 321, 326, 332, 335, 340, 346, 354, 360, 366, 372, 378, 387, 393, 403, 411, 420, 425, 436, 440, 444, 471, 480, 500, 510, 515, 520, 525, 537, 551, 559, 565, 582 and 589; (b) a heavy chain variable region CDR2 comprising an amino acid sequence selected from the group consisting of SEQ ID NOs: 310, 316, 322, 327, 333, 336, 341, 355, 361, 367, 373, 379, 388, 404, 412, 421, 426, 431, 441, 445, 450, 466, 472, 475, 481, 496, 501, 506, 511, 516, 521, 526, 538, 552, 560, 566, 583 and 590; (c) a heavy chain variable region CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591; (d) a light chain variable region CDR1 comprising an amino acid sequence selected from the group consisting of SEQ ID NOs: 312, 318, 324, 329, 338, 343, 348, 352, 357, 363, 369, 381, 390, 397, 401, 406, 416, 423, 428, 433, 447, 460, 468, 474, 477, 483, 490, 498, 503, 508, 518, 533, 540, 544, 547, 556, 562, 568, 571, 580, 585 and 588; (e) a light chain variable region CDR2 comprising an amino acid sequence selected from the group consisting of SEQ ID NOs:313, 319, 330, 344, 349, 358, 364, 370, 382, 385, 391, 398, 409, 417, 429, 434, 438, 448, 454, 461, 469, 478, 484, 487, 504, 513, 523, 534, 429, 448, 548, 557, 563, 572, 575 and 586; and (f) a light chain variable region CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592; wherein the antibody specifically binds FcRL5.

In certain embodiments, an anti-FcRL5 scFv antibody comprises: (a) a heavy chain variable region CDR1 comprising the amino acid sequence of SEQ ID NO:411; (b) a heavy chain variable region CDR2 comprising the amino acid sequence of SEQ ID NO:412; (c) a heavy chain variable region CDR3 comprising the amino acid sequence of SEQ ID NO:463; (d) a light chain variable region CDR1 comprising the amino acid sequence of SEQ ID NO:318; (e) a light chain variable region CDR2 comprising the amino acid sequence of SEQ ID NO:319; and (f) a light chain variable region CDR3 comprising the amino acid sequence of SEQ ID NO:419.

In certain embodiments, an anti-FcRL5 scFv antibody comprises: (a) a heavy chain variable region CDR1 comprising the amino acid sequence of SEQ ID NO:515; (b) a heavy chain variable region CDR2 comprising the amino acid sequence of SEQ ID NO:516; (c) a heavy chain variable region CDR3 comprising the amino acid sequence of SEQ ID NO:517; (d) a light chain variable region CDR1 comprising the amino acid sequence of SEQ ID NO:318; (e) a light chain variable region CDR2 comprising the amino acid sequence of SEQ ID NO:319; and (f) a light chain variable region CDR3 comprising the amino acid sequence of SEQ ID NO:531.

In certain embodiments, an anti-FcRL5 scFv antibody comprises: (a) a heavy chain variable region CDR1 comprising the amino acid sequence of SEQ ID NO:403; (b) a heavy chain variable region CDR2 comprising the amino acid sequence of SEQ ID NO:404; (c) a heavy chain variable region CDR3 comprising the amino acid sequence of SEQ ID NO:532; (d) a light chain variable region CDR1 comprising the amino acid sequence of SEQ ID NO:533; (e) a light chain variable region CDR2 comprising the amino acid sequence of SEQ ID NO:534; and (f) a light chain variable region CDR3 comprising the amino acid sequence of SEQ ID NO:535.

In certain embodiments, an anti-FcRL5 scFv antibody comprises: (a) a heavy chain variable region CDR1 comprising the amino acid sequence of SEQ ID NO:411; (b) a heavy chain variable region CDR2 comprising the amino acid sequence of SEQ ID NO:412; (c) a heavy chain variable region CDR3 comprising the amino acid sequence of SEQ ID NO:543; (d) a light chain variable region CDR1 comprising the amino acid sequence of SEQ ID NO:544; (e) a light chain variable region CDR2 comprising the amino acid sequence of SEQ ID NO:448; and (f) a light chain variable region CDR3 comprising the amino acid sequence of SEQ ID NO:545.

In certain embodiments, an anti-FcRL5 scFv antibody comprises: (a) a heavy chain variable region CDR1 comprising the amino acid sequence of SEQ ID NO:372; (b) a heavy chain variable region CDR2 comprising the amino acid sequence of SEQ ID NO:475; (c) a heavy chain variable region CDR3 comprising the amino acid sequence of SEQ ID NO:570; (d) a light chain variable region CDR1 comprising the amino acid sequence of SEQ ID NO:571; (e) a light chain variable region CDR2 comprising the amino acid sequence of SEQ ID NO:572; and (f) a light chain variable region CDR3 comprising the amino acid sequence of SEQ ID NO:573.

In certain embodiments, an anti-FcRL5 scFv antibody comprises: (a) a heavy chain variable region CDR1 comprising the amino acid sequence of SEQ ID NO:440; (b) a heavy chain variable region CDR2 comprising the amino acid sequence of SEQ ID NO:441; (c) a heavy chain variable region CDR3 comprising the amino acid sequence of SEQ ID NO:442; (d) a light chain variable region CDR1 comprising the amino acid sequence of SEQ ID NO:329; (e) a light chain variable region CDR2 comprising the amino acid sequence of SEQ ID NO:330; and (f) a light chain variable region CDR3 comprising the amino acid sequence of SEQ ID NO:443.

In certain embodiments, an anti-FcRL5 scFv antibody comprises: (a) a heavy chain variable region CDR1 comprising the amino acid sequence of SEQ ID NO:309; (b) a heavy chain variable region CDR2 comprising the amino acid sequence of SEQ ID NO:310; (c) a heavy chain variable region CDR3 comprising the amino acid sequence of SEQ ID NO:489; (d) a light chain variable region CDR1 comprising the amino acid sequence of SEQ ID NO:490; (e) a light chain variable region CDR2 comprising the amino acid sequence of SEQ ID NO:313; and (f) a light chain variable region CDR3 comprising the amino acid sequence of SEQ ID NO:491.

The presently disclosed subject matter further provides anti-FcRL5 scFv antibodies comprising a heavy chain variable region, a light chain variable region and a linker peptide between the heavy chain variable region and the light chain variable region. In certain embodiments, the linker peptide comprises the amino acid sequence set forth in SEQ ID NO: 308 or 897. Non-limiting examples of anti-FcRL5 scFv antibodies of the present disclosure that comprise a heavy chain variable region, a light chain variable region and a linker peptide are disclosed in Tables 77-152. For example, and not by way of limitation, an anti-FcRL5 scFv antibody having a heavy chain variable region, a light chain variable region and a linker peptide of the present disclosure comprises an amino acid sequence selected from the group consisting of SEQ ID NO:594, SEQ ID NO:596, SEQ ID NO:598, SEQ ID NO:600, SEQ ID NO:602, SEQ ID NO:604, SEQ ID NO:606, SEQ ID NO:608, SEQ ID NO:610, SEQ ID NO:612, SEQ ID NO:614, SEQ ID NO:616, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:644, SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:680, SEQ ID NO:682, SEQ ID NO:684, SEQ ID NO:686, SEQ ID NO:688, SEQ ID NO:690, SEQ ID NO:692, SEQ ID NO:694, SEQ ID NO:696, SEQ ID NO:698, SEQ ID NO:700, SEQ ID NO:702, SEQ ID NO:704, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:722, SEQ ID NO:724, SEQ ID NO:726, SEQ ID NO:728, SEQ ID NO:730, SEQ ID NO:732, SEQ ID NO:734, SEQ ID NO:736, SEQ ID NO:738, SEQ ID NO:740, SEQ ID NO:742 and SEQ ID NO:744 (as shown in Tables 77-152).

In certain embodiments, an anti-FcRL5 scFv antibody having a heavy chain variable region, a light chain variable region and a linker peptide comprises the amino acid sequence of SEQ ID NO:664.

In certain embodiments, an anti-FcRL5 scFv antibody having a heavy chain variable region, a light chain variable region and a linker peptide comprises the amino acid sequence of SEQ ID NO:700.

In certain embodiments, an anti-FcRL5 scFv antibody having a heavy chain variable region, a light chain variable region and a linker peptide comprises the amino acid sequence of SEQ ID NO:702.

In certain embodiments, an anti-FcRL5 scFv antibody having a heavy chain variable region, a light chain variable region and a linker peptide comprises the amino acid sequence of SEQ ID NO:710.

In certain embodiments, an anti-FcRL5 scFv antibody having a heavy chain variable region, a light chain variable region and a linker peptide comprises the amino acid sequence of SEQ ID NO:726.

In certain embodiments, an anti-FcRL5 scFv antibody having a heavy chain variable region, a light chain variable region and a linker peptide comprises the amino acid sequence of SEQ ID NO:650.

In certain embodiments, an anti-FcRL5 scFv antibody having a heavy chain variable region, a light chain variable region and a linker peptide comprises the amino acid sequence of SEQ ID NO:678.

The presently disclosed subject matter further provides anti-FcRL5 scFv antibodies comprising a heavy chain variable region, a light chain variable region, a linker peptide between the heavy chain variable region and the light chain variable region, and a His-tag and a HA-tag. In certain embodiments, the amino acid sequence of the His-tag and HA-tag comprises the amino acid sequence of SEQ ID NO:308. The nucleotide sequence encoding SEQ ID NO: 308 is SEQ ID NO: 306. Non-limiting examples of anti-FcRL5 scFv antibodies of the present disclosure that comprise a His-tag and a HA-tag are disclosed in Tables 153-228.

In certain embodiments, an anti-FcRL5 scFv antibody having a heavy chain variable region, a light chain variable region, a linker peptide and a His-tag and a HA-tag comprises the amino acid sequence of SEQ ID NO:816.

In certain embodiments, an anti-FcRL5 scFv antibody having a heavy chain variable region, a light chain variable region, a linker peptide and a His-tag and a HA-tag comprises the amino acid sequence of SEQ ID NO:852.

In certain embodiments, an anti-FcRL5 scFv antibody having a heavy chain variable region, a light chain variable region, a linker peptide and a His-tag and a HA-tag comprises the amino acid sequence of SEQ ID NO:854.

In certain embodiments, an anti-FcRL5 scFv antibody having a heavy chain variable region, a light chain variable region, a linker peptide and a His-tag and a HA-tag comprises the amino acid sequence of SEQ ID NO:862.

In certain embodiments, an anti-FcRL5 scFv antibody having a heavy chain variable region, a light chain variable region, a linker peptide and a His-tag and a HA-tag comprises the amino acid sequence of SEQ ID NO:878.

In certain embodiments, an anti-FcRL5 scFv antibody having a heavy chain variable region, a light chain variable region, a linker peptide and a His-tag and a HA-tag comprises the amino acid sequence of SEQ ID NO:802.

In certain embodiments, an anti-FcRL5 scFv antibody having a heavy chain variable region, a light chain variable region, a linker peptide and a His-tag and a HA-tag comprises the amino acid sequence of SEQ ID NO:830.

2. Monoclonal Antibodies

The presently disclosed subject matter further provides antibodies (e.g., human monoclonal antibodies) that specifically bind to FcRL5 (e.g., human FcRL5) and were isolated and structurally characterized as described in Examples 1 and 2.

The $V_H$ amino acid sequences of human anti-FcRL5 antibodies ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 disclosed herein are set forth in SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, respectively, and are shown in Tables 1-76.

The $V_L$ amino acid sequences of human anti-FcRL5 antibodies ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 disclosed herein are set forth in SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303, respectively, and are shown in Tables 1-76.

Given that each of the disclosed anti-FcRL5 antibodies ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 antibodies can bind to FcRL5, the $V_H$ and $V_L$ sequences (shown in Tables 1-76) can be "mixed and matched" to create other anti-FcRL5 binding molecules. FcRL5 binding of such "mixed and matched" antibodies can be tested using the binding assays known in the art, including for example, ELISAs, Western blots, RIAs and Biacore analysis. In certain embodiments, when $V_H$ and $V_L$ chains are mixed and matched, a $V_H$ sequence from a particular $V_H$/$V_L$ pairing is replaced with a structurally similar $V_H$ sequence. Likewise, a $V_L$ sequence from a particular $V_H$/$V_L$ pairing is replaced with a structurally similar $V_L$ sequence.

In certain embodiments, the presently disclosed subject matter provides an isolated anti-FcRL5 antibody or antigen-binding fragment thereof comprising a light chain variable region, wherein the light chain variable region comprises an amino acid sequence selected from the group consisting of SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:3 5, SEQ ID NO:3 9, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303.

In certain embodiments, an isolated anti-FcRL5 antibody or antigen-binding fragment thereof comprises a heavy chain variable region, wherein the heavy chain variable region comprises an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, wherein the antibody or antigen-binding fragment thereof binds to an FcRL5 polypeptide.

In certain embodiments, the presently disclosed subject matter provides an isolated anti-FcRL5 antibody or antigen-binding fragment thereof comprising: (a) a light chain variable region comprising an amino acid sequence selected from the group consisting of SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303; and (b) a heavy chain variable region comprising an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, wherein the antibody or antigen-binding fragment thereof binds to an FcRL5 polypeptide.

In certain embodiments, an isolated anti-FcRL5 antibody or antigen-binding fragment thereof comprises (a) a light chain variable region comprising amino acids having a sequence set forth in SEQ ID NO:3, and (b) a heavy chain variable region comprising amino acids having a sequence set forth in SEQ ID NO:4.

In certain embodiments, an isolated anti-FcRL5 antibody or antigen-binding fragment thereof comprises (a) a light chain variable region comprising amino acids having a sequence set forth in SEQ ID NO:7, and (b) a heavy chain variable region comprising amino acids having a sequence set forth in SEQ ID NO:8.

In certain embodiments, an isolated anti-FcRL5 antibody or antigen-binding fragment thereof comprises (a) a light chain variable region comprising amino acids having a sequence set forth in SEQ ID NO:11, and (b) a heavy chain variable region comprising amino acids having a sequence set forth in SEQ ID NO:12.

In certain embodiments, an isolated anti-FcRL5 antibody or antigen-binding fragment thereof comprises (a) a light chain variable region comprising amino acids having a sequence set forth in SEQ ID NO:15, and (b) a heavy chain variable region comprising amino acids having a sequence set forth in SEQ ID NO:16.

In certain embodiments, an isolated anti-FcRL5 antibody or antigen-binding fragment thereof comprises (a) a light chain variable region comprising amino acids having a sequence set forth in SEQ ID NO:19, and (b) a heavy chain variable region comprising amino acids having a sequence set forth in SEQ ID NO:20.

In certain embodiments, an isolated anti-FcRL5 antibody or antigen-binding fragment thereof comprises (a) a light chain variable region comprising amino acids having a sequence set forth in SEQ ID NO:23, and (b) a heavy chain variable region comprising amino acids having a sequence set forth in SEQ ID NO:24.

In certain embodiments, an isolated anti-FcRL5 antibody or antigen-binding fragment thereof comprises (a) a light chain variable region comprising amino acids having a sequence set forth in SEQ ID NO:27, and (b) a heavy chain variable region comprising amino acids having a sequence set forth in SEQ ID NO:28.

In certain embodiments, an isolated anti-FcRL5 antibody or antigen-binding fragment thereof comprises (a) a light chain variable region comprising amino acids having a sequence set forth in SEQ ID NO:31, and (b) a heavy chain variable region comprising amino acids having a sequence set forth in SEQ ID NO:32.

In certain embodiments, an isolated anti-FcRL5 antibody or antigen-binding fragment thereof comprises (a) a light chain variable region comprising amino acids having a sequence set forth in SEQ ID NO:35, and (b) a heavy chain variable region comprising amino acids having a sequence set forth in SEQ ID NO:36.

In certain embodiments, an isolated anti-FcRL5 antibody or antigen-binding fragment thereof comprises (a) a light chain variable region comprising amino acids having a sequence set forth in SEQ ID NO:39, and (b) a heavy chain variable region comprising amino acids having a sequence set forth in SEQ ID NO:40.

In certain embodiments, an isolated anti-FcRL5 antibody or antigen-binding fragment thereof comprises (a) a light chain variable region comprising amino acids having a sequence set forth in SEQ ID NO:43, and (b) a heavy chain variable region comprising amino acids having a sequence set forth in SEQ ID NO:44.

In certain embodiments, an isolated anti-FcRL5 antibody or antigen-binding fragment thereof comprises (a) a light chain variable region comprising amino acids having a sequence set forth in SEQ ID NO:47, and (b) a heavy chain variable region comprising amino acids having a sequence set forth in SEQ ID NO:48.

In certain embodiments, an isolated anti-FcRL5 antibody or antigen-binding fragment thereof comprises (a) a light chain variable region comprising amino acids having a sequence set forth in SEQ ID NO:51, and (b) a heavy chain variable region comprising amino acids having a sequence set forth in SEQ ID NO:52.

In certain embodiments, an isolated anti-FcRL5 antibody or antigen-binding fragment thereof comprises (a) a light chain variable region comprising amino acids having a sequence set forth in SEQ ID NO:55, and (b) a heavy chain variable region comprising amino acids having a sequence set forth in SEQ ID NO:56.

In certain embodiments, an isolated anti-FcRL5 antibody or antigen-binding fragment thereof comprises (a) a light chain variable region comprising amino acids having a sequence set forth in SEQ ID NO:59, and (b) a heavy chain variable region comprising amino acids having a sequence set forth in SEQ ID NO:60.

In certain embodiments, an isolated anti-FcRL5 antibody or antigen-binding fragment thereof comprises (a) a light chain variable region comprising amino acids having a sequence set forth in SEQ ID NO:63, and (b) a heavy chain variable region comprising amino acids having a sequence set forth in SEQ ID NO:64.

In certain embodiments, an isolated anti-FcRL5 antibody or antigen-binding fragment thereof comprises (a) a light chain variable region comprising amino acids having a sequence set forth in SEQ ID NO:67, and (b) a heavy chain variable region comprising amino acids having a sequence set forth in SEQ ID NO:68.

In certain embodiments, an isolated anti-FcRL5 antibody or antigen-binding fragment thereof comprises (a) a light chain variable region comprising amino acids having a sequence set forth in SEQ ID NO:71, and (b) a heavy chain variable region comprising amino acids having a sequence set forth in SEQ ID NO:72.

In certain embodiments, an isolated anti-FcRL5 antibody or antigen-binding fragment thereof comprises (a) a light chain variable region comprising amino acids having a sequence set forth in SEQ ID NO:75, and (b) a heavy chain variable region comprising amino acids having a sequence set forth in SEQ ID NO:76.

In certain embodiments, an isolated anti-FcRL5 antibody or antigen-binding fragment thereof comprises (a) a light chain variable region comprising amino acids having a sequence set forth in SEQ ID NO:79, and (b) a heavy chain variable region comprising amino acids having a sequence set forth in SEQ ID NO:80.

In certain embodiments, an isolated anti-FcRL5 antibody or antigen-binding fragment thereof comprises (a) a light chain variable region comprising amino acids having a sequence set forth in SEQ ID NO:83, and (b) a heavy chain variable region comprising amino acids having a sequence set forth in SEQ ID NO:84.

In certain embodiments, an isolated anti-FcRL5 antibody or antigen-binding fragment thereof comprises (a) a light chain variable region comprising amino acids having a sequence set forth in SEQ ID NO:87, and (b) a heavy chain variable region comprising amino acids having a sequence set forth in SEQ ID NO:88.

In certain embodiments, an isolated anti-FcRL5 antibody or antigen-binding fragment thereof comprises (a) a light chain variable region comprising amino acids having a sequence set forth in SEQ ID NO:91, and (b) a heavy chain variable region comprising amino acids having a sequence set forth in SEQ ID NO:92.

In certain embodiments, an isolated anti-FcRL5 antibody or antigen-binding fragment thereof comprises (a) a light chain variable region comprising amino acids having a sequence set forth in SEQ ID NO:95, and (b) a heavy chain variable region comprising amino acids having a sequence set forth in SEQ ID NO:96.

In certain embodiments, an isolated anti-FcRL5 antibody or antigen-binding fragment thereof comprises (a) a light chain variable region comprising amino acids having a sequence set forth in SEQ ID NO:99, and (b) a heavy chain variable region comprising amino acids having a sequence set forth in SEQ ID NO:100.

In certain embodiments, an isolated anti-FcRL5 antibody or antigen-binding fragment thereof comprises (a) a light chain variable region comprising amino acids having a sequence set forth in SEQ ID NO:103, and (b) a heavy chain variable region comprising amino acids having a sequence set forth in SEQ ID NO:104.

In certain embodiments, an isolated anti-FcRL5 antibody or antigen-binding fragment thereof comprises (a) a light chain variable region comprising amino acids having a sequence set forth in SEQ ID NO:107, and (b) a heavy chain variable region comprising amino acids having a sequence set forth in SEQ ID NO:108.

In certain embodiments, an isolated anti-FcRL5 antibody or antigen-binding fragment thereof comprises (a) a light chain variable region comprising amino acids having a sequence set forth in SEQ ID NO:111, and (b) a heavy chain variable region comprising amino acids having a sequence set forth in SEQ ID NO:112.

In certain embodiments, an isolated anti-FcRL5 antibody or antigen-binding fragment thereof comprises (a) a light chain variable region comprising amino acids having a sequence set forth in SEQ ID NO:115, and (b) a heavy chain variable region comprising amino acids having a sequence set forth in SEQ ID NO:116.

In certain embodiments, an isolated anti-FcRL5 antibody or antigen-binding fragment thereof comprises (a) a light chain variable region comprising amino acids having a sequence set forth in SEQ ID NO:119, and (b) a heavy chain variable region comprising amino acids having a sequence set forth in SEQ ID NO:120.

In certain embodiments, an isolated anti-FcRL5 antibody or antigen-binding fragment thereof comprises (a) a light chain variable region comprising amino acids having a sequence set forth in SEQ ID NO:123, and (b) a heavy chain variable region comprising amino acids having a sequence set forth in SEQ ID NO:124.

In certain embodiments, an isolated anti-FcRL5 antibody or antigen-binding fragment thereof comprises (a) a light chain variable region comprising amino acids having a sequence set forth in SEQ ID NO:127, and (b) a heavy chain variable region comprising amino acids having a sequence set forth in SEQ ID NO:128.

In certain embodiments, an isolated anti-FcRL5 antibody or antigen-binding fragment thereof comprises (a) a light chain variable region comprising amino acids having a sequence set forth in SEQ ID NO:131, and (b) a heavy chain variable region comprising amino acids having a sequence set forth in SEQ ID NO:132.

In certain embodiments, an isolated anti-FcRL5 antibody or antigen-binding fragment thereof comprises (a) a light chain variable region comprising amino acids having a sequence set forth in SEQ ID NO:135, and (b) a heavy chain variable region comprising amino acids having a sequence set forth in SEQ ID NO:136.

In certain embodiments, an isolated anti-FcRL5 antibody or antigen-binding fragment thereof comprises (a) a light chain variable region comprising amino acids having a sequence set forth in SEQ ID NO:139, and (b) a heavy chain variable region comprising amino acids having a sequence set forth in SEQ ID NO:140.

In certain embodiments, an isolated anti-FcRL5 antibody or antigen-binding fragment thereof comprises (a) a light chain variable region comprising amino acids having a sequence set forth in SEQ ID NO:143, and (b) a heavy chain variable region comprising amino acids having a sequence set forth in SEQ ID NO:144.

In certain embodiments, an isolated anti-FcRL5 antibody or antigen-binding fragment thereof comprises (a) a light chain variable region comprising amino acids having a sequence set forth in SEQ ID NO:147, and (b) a heavy chain variable region comprising amino acids having a sequence set forth in SEQ ID NO:148.

In certain embodiments, an isolated anti-FcRL5 antibody or antigen-binding fragment thereof comprises (a) a light chain variable region comprising amino acids having a sequence set forth in SEQ ID NO:151, and (b) a heavy chain variable region comprising amino acids having a sequence set forth in SEQ ID NO:152.

In certain embodiments, an isolated anti-FcRL5 antibody or antigen-binding fragment thereof comprises (a) a light chain variable region comprising amino acids having a sequence set forth in SEQ ID NO:155, and (b) a heavy chain variable region comprising amino acids having a sequence set forth in SEQ ID NO:156.

In certain embodiments, an isolated anti-FcRL5 antibody or antigen-binding fragment thereof comprises (a) a light chain variable region comprising amino acids having a sequence set forth in SEQ ID NO:159, and (b) a heavy chain variable region comprising amino acids having a sequence set forth in SEQ ID NO:160.

In certain embodiments, an isolated anti-FcRL5 antibody or antigen-binding fragment thereof comprises (a) a light chain variable region comprising amino acids having a sequence set forth in SEQ ID NO:163, and (b) a heavy chain variable region comprising amino acids having a sequence set forth in SEQ ID NO:164.

In certain embodiments, an isolated anti-FcRL5 antibody or antigen-binding fragment thereof comprises (a) a light chain variable region comprising amino acids having a sequence set forth in SEQ ID NO:167, and (b) a heavy chain variable region comprising amino acids having a sequence set forth in SEQ ID NO:168.

In certain embodiments, an isolated anti-FcRL5 antibody or antigen-binding fragment thereof comprises (a) a light chain variable region comprising amino acids having a sequence set forth in SEQ ID NO:171, and (b) a heavy chain variable region comprising amino acids having a sequence set forth in SEQ ID NO:172.

In certain embodiments, an isolated anti-FcRL5 antibody or antigen-binding fragment thereof comprises (a) a light chain variable region comprising amino acids having a sequence set forth in SEQ ID NO:175, and (b) a heavy chain variable region comprising amino acids having a sequence set forth in SEQ ID NO:176.

In certain embodiments, an isolated anti-FcRL5 antibody or antigen-binding fragment thereof comprises (a) a light chain variable region comprising amino acids having a sequence set forth in SEQ ID NO:179, and (b) a heavy chain variable region comprising amino acids having a sequence set forth in SEQ ID NO:180.

In certain embodiments, an isolated anti-FcRL5 antibody or antigen-binding fragment thereof comprises (a) a light chain variable region comprising amino acids having a sequence set forth in SEQ ID NO:183, and (b) a heavy chain variable region comprising amino acids having a sequence set forth in SEQ ID NO:184.

In certain embodiments, an isolated anti-FcRL5 antibody or antigen-binding fragment thereof comprises (a) a light chain variable region comprising amino acids having a sequence set forth in SEQ ID NO:187, and (b) a heavy chain variable region comprising amino acids having a sequence set forth in SEQ ID NO:188.

In certain embodiments, an isolated anti-FcRL5 antibody or antigen-binding fragment thereof comprises (a) a light chain variable region comprising amino acids having a sequence set forth in SEQ ID NO:191, and (b) a heavy chain variable region comprising amino acids having a sequence set forth in SEQ ID NO:192.

In certain embodiments, an isolated anti-FcRL5 antibody or antigen-binding fragment thereof comprises (a) a light chain variable region comprising amino acids having a sequence set forth in SEQ ID NO:195, and (b) a heavy chain variable region comprising amino acids having a sequence set forth in SEQ ID NO:196.

In certain embodiments, an isolated anti-FcRL5 antibody or antigen-binding fragment thereof comprises (a) a light chain variable region comprising amino acids having a sequence set forth in SEQ ID NO:199, and (b) a heavy chain variable region comprising amino acids having a sequence set forth in SEQ ID NO:200.

In certain embodiments, an isolated anti-FcRL5 antibody or antigen-binding fragment thereof comprises (a) a light chain variable region comprising amino acids having a sequence set forth in SEQ ID NO:203, and (b) a heavy chain variable region comprising amino acids having a sequence set forth in SEQ ID NO:204.

In certain embodiments, an isolated anti-FcRL5 antibody or antigen-binding fragment thereof comprises (a) a light chain variable region comprising amino acids having a sequence set forth in SEQ ID NO:207, and (b) a heavy chain variable region comprising amino acids having a sequence set forth in SEQ ID NO:208.

In certain embodiments, an isolated anti-FcRL5 antibody or antigen-binding fragment thereof comprises (a) a light chain variable region comprising amino acids having a sequence set forth in SEQ ID NO:211, and (b) a heavy chain variable region comprising amino acids having a sequence set forth in SEQ ID NO:212.

In certain embodiments, an isolated anti-FcRL5 antibody or antigen-binding fragment thereof comprises (a) a light chain variable region comprising amino acids having a sequence set forth in SEQ ID NO:215, and (b) a heavy chain variable region comprising amino acids having a sequence set forth in SEQ ID NO:216.

In certain embodiments, an isolated anti-FcRL5 antibody or antigen-binding fragment thereof comprises (a) a light chain variable region comprising amino acids having a sequence set forth in SEQ ID NO:219, and (b) a heavy chain variable region comprising amino acids having a sequence set forth in SEQ ID NO:220.

In certain embodiments, an isolated anti-FcRL5 antibody or antigen-binding fragment thereof comprises (a) a light chain variable region comprising amino acids having a sequence set forth in SEQ ID NO:223, and (b) a heavy chain variable region comprising amino acids having a sequence set forth in SEQ ID NO:224.

In certain embodiments, an isolated anti-FcRL5 antibody or antigen-binding fragment thereof comprises (a) a light chain variable region comprising amino acids having a sequence set forth in SEQ ID NO:227, and (b) a heavy chain variable region comprising amino acids having a sequence set forth in SEQ ID NO:228.

In certain embodiments, an isolated anti-FcRL5 antibody or antigen-binding fragment thereof comprises (a) a light chain variable region comprising amino acids having a sequence set forth in SEQ ID NO:231, and (b) a heavy chain variable region comprising amino acids having a sequence set forth in SEQ ID NO:232.

In certain embodiments, an isolated anti-FcRL5 antibody or antigen-binding fragment thereof comprises (a) a light chain variable region comprising amino acids having a sequence set forth in SEQ ID NO:235, and (b) a heavy chain variable region comprising amino acids having a sequence set forth in SEQ ID NO:236.

In certain embodiments, an isolated anti-FcRL5 antibody or antigen-binding fragment thereof comprises (a) a light chain variable region comprising amino acids having a sequence set forth in SEQ ID NO:239, and (b) a heavy chain variable region comprising amino acids having a sequence set forth in SEQ ID NO:240.

In certain embodiments, an isolated anti-FcRL5 antibody or antigen-binding fragment thereof comprises (a) a light chain variable region comprising amino acids having a sequence set forth in SEQ ID NO:243, and (b) a heavy chain variable region comprising amino acids having a sequence set forth in SEQ ID NO:244.

In certain embodiments, an isolated anti-FcRL5 antibody or antigen-binding fragment thereof comprises (a) a light chain variable region comprising amino acids having a sequence set forth in SEQ ID NO:247, and (b) a heavy chain variable region comprising amino acids having a sequence set forth in SEQ ID NO:248.

In certain embodiments, an isolated anti-FcRL5 antibody or antigen-binding fragment thereof comprises (a) a light chain variable region comprising amino acids having a sequence set forth in SEQ ID NO:251, and (b) a heavy chain variable region comprising amino acids having a sequence set forth in SEQ ID NO:252.

In certain embodiments, an isolated anti-FcRL5 antibody or antigen-binding fragment thereof comprises (a) a light chain variable region comprising amino acids having a sequence set forth in SEQ ID NO:255, and (b) a heavy chain variable region comprising amino acids having a sequence set forth in SEQ ID NO:256.

In certain embodiments, an isolated anti-FcRL5 antibody or antigen-binding fragment thereof comprises (a) a light chain variable region comprising amino acids having a sequence set forth in SEQ ID NO:259, and (b) a heavy chain variable region comprising amino acids having a sequence set forth in SEQ ID NO:260.

In certain embodiments, an isolated anti-FcRL5 antibody or antigen-binding fragment thereof comprises (a) a light chain variable region comprising amino acids having a sequence set forth in SEQ ID NO:263, and (b) a heavy chain variable region comprising amino acids having a sequence set forth in SEQ ID NO:264.

In certain embodiments, an isolated anti-FcRL5 antibody or antigen-binding fragment thereof comprises (a) a light chain variable region comprising amino acids having a sequence set forth in SEQ ID NO:267, and (b) a heavy chain variable region comprising amino acids having a sequence set forth in SEQ ID NO:268.

In certain embodiments, an isolated anti-FcRL5 antibody or antigen-binding fragment thereof comprises (a) a light chain variable region comprising amino acids having a sequence set forth in SEQ ID NO:271, and (b) a heavy chain variable region comprising amino acids having a sequence set forth in SEQ ID NO:272.

In certain embodiments, an isolated anti-FcRL5 antibody or antigen-binding fragment thereof comprises (a) a light chain variable region comprising amino acids having a sequence set forth in SEQ ID NO:275, and (b) a heavy chain variable region comprising amino acids having a sequence set forth in SEQ ID NO:276.

In certain embodiments, an isolated anti-FcRL5 antibody or antigen-binding fragment thereof comprises (a) a light chain variable region comprising amino acids having a sequence set forth in SEQ ID NO:279, and (b) a heavy chain variable region comprising amino acids having a sequence set forth in SEQ ID NO:280.

In certain embodiments, an isolated anti-FcRL5 antibody or antigen-binding fragment thereof comprises (a) a light chain variable region comprising amino acids having a sequence set forth in SEQ ID NO:283, and (b) a heavy chain variable region comprising amino acids having a sequence set forth in SEQ ID NO:284.

In certain embodiments, an isolated anti-FcRL5 antibody or antigen-binding fragment thereof comprises (a) a light chain variable region comprising amino acids having a sequence set forth in SEQ ID NO:287, and (b) a heavy chain variable region comprising amino acids having a sequence set forth in SEQ ID NO:288.

In certain embodiments, an isolated anti-FcRL5 antibody or antigen-binding fragment thereof comprises (a) a light chain variable region comprising amino acids having a sequence set forth in SEQ ID NO:291, and (b) a heavy chain variable region comprising amino acids having a sequence set forth in SEQ ID NO:292.

In certain embodiments, an isolated anti-FcRL5 antibody or antigen-binding fragment thereof comprises (a) a light chain variable region comprising amino acids having a sequence set forth in SEQ ID NO:279, and (b) a heavy chain variable region comprising amino acids having a sequence set forth in SEQ ID NO:280.

In certain embodiments, an isolated anti-FcRL5 antibody or antigen-binding fragment thereof comprises (a) a light chain variable region comprising amino acids having a sequence set forth in SEQ ID NO:283, and (b) a heavy chain variable region comprising amino acids having a sequence set forth in SEQ ID NO:284.

In certain embodiments, an isolated anti-FcRL5 antibody or antigen-binding fragment thereof comprises (a) a light chain variable region comprising amino acids having a sequence set forth in SEQ ID NO:287, and (b) a heavy chain variable region comprising amino acids having a sequence set forth in SEQ ID NO:288.

In certain embodiments, an isolated anti-FcRL5 antibody or antigen-binding fragment thereof comprises (a) a light chain variable region comprising amino acids having a sequence set forth in SEQ ID NO:291, and (b) a heavy chain variable region comprising amino acids having a sequence set forth in SEQ ID NO:292.

In certain embodiments, an isolated anti-FcRL5 antibody or antigen-binding fragment thereof comprises (a) a light chain variable region comprising amino acids having a sequence set forth in SEQ ID NO:295, and (b) a heavy chain variable region comprising amino acids having a sequence set forth in SEQ ID NO:296.

In certain embodiments, an isolated anti-FcRL5 antibody or antigen-binding fragment thereof comprises (a) a light chain variable region comprising amino acids having a sequence set forth in SEQ ID NO:299, and (b) a heavy chain variable region comprising amino acids having a sequence set forth in SEQ ID NO:300.

In certain embodiments, an isolated anti-FcRL5 antibody or antigen-binding fragment thereof comprises (a) a light chain variable region comprising amino acids having a sequence set forth in SEQ ID NO:303, and (b) a heavy chain variable region comprising amino acids having a sequence set forth in SEQ ID NO:304.

In certain embodiments, the presently disclosed subject matter provides antibodies that comprise the heavy chain variable region and light chain variable region CDR1s, CDR2s and CDR3s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 shown in Table 229.

The amino acid sequences of the $V_H$ CDR1s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 are shown in Table 229.

The amino acid sequences of the $V_H$ CDR2s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 are shown in Table 229.

The amino acid sequences of the $V_H$ CDR3s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 are shown in Table 229.

The amino acid sequences of the $V_L$ CDR1s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 are shown in Table 229.

The amino acid sequences of the $V_L$ CDR2s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 are shown in Table 229.

The amino acid sequences of the $V_L$ CDR3s of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 are shown in Table 229.

Given that each of the disclosed antibodies can bind to FcRL5 and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and match, although each antibody must contain a $V_H$ CDR1, CDR2, and CDR3 and a $V_L$ CDR1, CDR2, and CDR3) to create other anti-FcRL5 binding molecules. FcRL5 binding of such "mixed and matched" antibodies can be tested using the binding assays described above. When $V_H$ CDR sequences are mixed and matched, the CDR1, CDR2 and/or CDR3 sequence from a particular $V_H$ sequence is replaced with a structurally similar CDR sequence(s). Likewise, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences of the antibodies ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 disclosed herein. See Table 229.

For example, and not by way of limitation, an isolated anti-FcRL5 antibody or antigen-binding fragment thereof comprises a light chain variable region, wherein the light chain variable region comprises: (a) a CDR1 comprising an amino acid sequence selected from the group consisting of SEQ ID NOs: 312, 318, 324, 329, 338, 343, 348, 352, 357, 363, 369, 381, 390, 397, 401, 406, 416, 423, 428, 433, 447, 460, 468, 474, 477, 483, 490, 498, 503, 508, 518, 533, 540, 544, 547, 556, 562, 568, 571, 580, 585 and 588; (b) a CDR2 comprising an amino acid sequence selected from the group consisting of SEQ ID NOs:313, 319, 330, 344, 349, 358, 364, 370, 382, 385, 391, 398, 409, 417, 429, 434, 438, 448, 454, 461, 469, 478, 484, 487, 504, 513, 523, 534, 429, 448, 548, 557, 563, 572, 575 and 586; and (c) a CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592, and wherein the antibody or antigen-binding fragment thereof specifically binds FcRL5.

In certain embodiments, the presently disclosed subject matter provides an isolated anti-FcRL5 antibody or antigen-binding fragment thereof, comprising a heavy chain variable region, wherein the heavy chain variable region comprises: (a) a CDR1 comprising an amino acid sequence selected from the group consisting of SEQ ID NOs: 309, 315, 321, 326, 332, 335, 340, 346, 354, 360, 366, 372, 378, 387, 393, 403, 411, 420, 425, 436, 440, 444, 471, 480, 500, 510, 515, 520, 525, 537, 551, 559, 565, 582 and 589; (b) a CDR2 comprising an amino acid sequence selected from the group consisting of SEQ ID NOs: 310, 316, 322, 327, 333, 336, 341, 355, 361, 367, 373, 379, 388, 404, 412, 421, 426, 431, 441, 445, 450, 466, 472, 475, 481, 496, 501, 506, 511, 516, 521, 526, 538, 552, 560, 566, 583 and 590; and (c) a CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591, and wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591; and (b) a light chain variable region CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592, wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:463; and (b) a light chain variable region CDR3 comprising the amino acid sequence of SEQ ID NO:419; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:517; and (b) a light chain variable region CDR3 comprising the amino acid sequence of SEQ ID NO:531; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:532; and (b) a light chain variable region CDR3 comprising the amino acid sequence of SEQ ID NO:535; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:543; and (b) a light chain variable region CDR3 comprising the amino acid sequence of SEQ ID NO:545; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:570; and (b) a light chain variable region CDR3 comprising the amino acid sequence of SEQ ID NO:573; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:442; and (b) a light chain variable region CDR3 comprising the amino acid sequence of SEQ ID NO:443; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR3 comprising the amino acid sequence of SEQ ID NO:489; and (b) a light chain variable region CDR3 comprising the amino acid sequence of SEQ ID NO:491; wherein the antibody or antigen-binding fragment thereof specifically binds FcRL5.

In certain embodiments, the presently disclosed subject matter provides an isolated anti-FcRL5 antibody or antigen-binding fragment thereof comprising: (a) a heavy chain variable region CDR1 comprising an amino acid sequence selected from the group consisting of SEQ ID NOs: 309, 315, 321, 326, 332, 335, 340, 346, 354, 360, 366, 372, 378, 387, 393, 403, 411, 420, 425, 436, 440, 444, 471, 480, 500, 510, 515, 520, 525, 537, 551, 559, 565, 582 and 589; (b) a heavy chain variable region CDR2 comprising an amino acid sequence selected from the group consisting of SEQ ID NOs: 310, 316, 322, 327, 333, 336, 341, 355, 361, 367, 373, 379, 388, 404, 412, 421, 426, 431, 441, 445, 450, 466, 472, 475, 481, 496, 501, 506, 511, 516, 521, 526, 538, 552, 560, 566, 583 and 590; (c) a heavy chain variable region CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591; (d) a light chain variable region CDR1 comprising an amino acid sequence selected from the group consisting of SEQ ID NOs: 312, 318, 324, 329, 338, 343, 348, 352, 357, 363, 369, 381, 390, 397, 401, 406, 416, 423, 428, 433, 447, 460, 468, 474, 477, 483, 490, 498, 503, 508, 518, 533, 540, 544, 547, 556, 562, 568, 571, 580, 585 and 588; (e) a light chain variable region CDR2 comprising an amino acid sequence selected from the group consisting of SEQ ID NOs:313, 319, 330, 344, 349, 358, 364, 370, 382, 385, 391, 398, 409, 417, 429, 434, 438, 448, 454, 461, 469, 478, 484, 487, 504, 513, 523, 534, 429, 448, 548, 557, 563, 572, 575 and 586; and (f) a light chain variable region CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592; wherein the anti-FcRL5 antibody or antigen-binding fragment thereof binds to FcRL5.

In certain embodiments, a presently disclosed anti-FcRL5 antibody or antigen-binding fragment thereof comprises: (a) a heavy chain variable region CDR1 comprising the amino acid sequence of SEQ ID NO:411; (b) a heavy chain variable region CDR2 comprising the amino acid sequence of SEQ ID NO:412; (c) a heavy chain variable region CDR3 comprising the amino acid sequence of SEQ ID NO:463; (d) a light chain variable region CDR1 comprising the amino acid sequence of SEQ ID NO:318; (e) a light chain variable region CDR2 comprising the amino acid sequence of SEQ ID NO:319; and (f) a light chain variable region CDR3 comprising the amino acid sequence of SEQ ID NO:419.

In certain embodiments, a presently disclosed anti-FcRL5 antibody or antigen-binding fragment thereof comprises: (a) a heavy chain variable region CDR1 comprising the amino acid sequence of SEQ ID NO:515; (b) a heavy chain variable region CDR2 comprising the amino acid sequence of SEQ ID NO:516; (c) a heavy chain variable region CDR3 comprising the amino acid sequence of SEQ ID NO:517; (d) a light chain variable region CDR1 comprising the amino acid sequence of SEQ ID NO:318; (e) a light chain variable region CDR2 comprising the amino acid sequence of SEQ ID NO:319; and (f) a light chain variable region CDR3 comprising the amino acid sequence of SEQ ID NO:531.

In certain embodiments, a presently disclosed anti-FcRL5 antibody or antigen-binding fragment thereof comprises: (a) a heavy chain variable region CDR1 comprising the amino acid sequence of SEQ ID NO:403; (b) a heavy chain variable region CDR2 comprising the amino acid sequence of SEQ ID NO:404; (c) a heavy chain variable region CDR3 comprising the amino acid sequence of SEQ ID NO:532; (d) a light chain variable region CDR1 comprising the amino acid sequence of SEQ ID NO:533; (e) a light chain variable region CDR2 comprising the amino acid sequence of SEQ ID NO:534; and (f) a light chain variable region CDR3 comprising the amino acid sequence of SEQ ID NO:535.

In certain embodiments, a presently disclosed anti-FcRL5 antibody or antigen-binding fragment thereof comprises: (a) a heavy chain variable region CDR1 comprising the amino acid sequence of SEQ ID NO:411; (b) a heavy chain variable region CDR2 comprising the amino acid sequence of SEQ ID NO:412; (c) a heavy chain variable region CDR3 comprising the amino acid sequence of SEQ ID NO:543; (d) a light chain variable region CDR1 comprising the amino acid sequence of SEQ ID NO:544; (e) a light chain variable region CDR2 comprising the amino acid sequence of SEQ ID NO:448; and (f) a light chain variable region CDR3 comprising the amino acid sequence of SEQ ID NO:545.

In certain embodiments, a presently disclosed anti-FcRL5 antibody or antigen-binding fragment thereof comprises: (a) a heavy chain variable region CDR1 comprising the amino acid sequence of SEQ ID NO:372; (b) a heavy chain variable region CDR2 comprising the amino acid sequence of SEQ ID NO:475; (c) a heavy chain variable region CDR3 comprising the amino acid sequence of SEQ ID NO:570; (d) a light chain variable region CDR1 comprising the amino acid sequence of SEQ ID NO:571; (e) a light chain variable region CDR2 comprising the amino acid sequence of SEQ ID NO:572; and (f) a light chain variable region CDR3 comprising the amino acid sequence of SEQ ID NO:573.

In certain embodiments, a presently disclosed anti-FcRL5 antibody or antigen-binding fragment thereof comprises: (a) a heavy chain variable region CDR1 comprising the amino acid sequence of SEQ ID NO:440; (b) a heavy chain variable region CDR2 comprising the amino acid sequence of SEQ ID NO:441; (c) a heavy chain variable region CDR3 comprising the amino acid sequence of SEQ ID NO:442; (d) a light chain variable region CDR1 comprising the amino acid sequence of SEQ ID NO:329; (e) a light chain variable region CDR2 comprising the amino acid sequence of SEQ ID NO:330; and (f) a light chain variable region CDR3 comprising the amino acid sequence of SEQ ID NO:443.

In certain embodiments, a presently disclosed anti-FcRL5 antibody or antigen-binding fragment thereof comprises: (a) a heavy chain variable region CDR1 comprising the amino acid sequence of SEQ ID NO:309; (b) a heavy chain variable region CDR2 comprising the amino acid sequence of SEQ ID NO:310; (c) a heavy chain variable region CDR3 comprising the amino acid sequence of SEQ ID NO:489; (d) a light chain variable region CDR1 comprising the amino acid sequence of SEQ ID NO:490; (e) a light chain variable region CDR2 comprising the amino acid sequence of SEQ ID NO:313; and (f) a light chain variable region CDR3 comprising the amino acid sequence of SEQ ID NO:491.

In certain embodiments, the extracellular antigen-binding domain, e.g., the human scFv, comprises a heavy chain variable region, a light chain variable region, a linker peptide between the heavy chain variable region and the light chain variable region, and an His-tag and an HA-tag. In certain embodiments, the amino acid sequence of the His-tag and HA-tag comprises the amino acid sequence of SEQ ID NO:308. The nucleotide sequence encoding SEQ ID NO: 308 is SEQ ID NO: 306.

In certain embodiments, a presently disclosed anti-FcRL5 antibody is a fully-human antibody, e.g., any one of ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124. Fully-human mAbs are preferred for therapeutic use in humans because murine antibodies cause an immunogenicity reaction, known as the HAMA (human anti-mouse antibodies) response (Azinovic, et al. Survival benefit associated with human anti-mouse antibody (HAMA) in patients with B-cell malignancies. Cancer Immunol. Immunother. 2006; 55(12): 1451-8; Tjandra, et al. Development of human anti-murine antibody (HAMA) response in patients. Immunol. Cell Biol. 1990; 68(6):367-76), when administered to humans, causing serious side effects, including anaphylaxis and hypersensitivity reactions. This immunogenicity reaction is triggered by the human immune system recognizing the murine antibodies as foreign because of slightly different amino acid sequences from natural human antibodies.

The use of fully human phage display libraries has made it possible to select large numbers of antibody (Ab) repertoires for unique and rare Abs against very defined epitopes (for more details on phage display see McCafferty et al., Phage antibodies: filamentous phage displaying antibody variable domains. Nature, 348: 552-554 (1990)). The rapid identification of human Fab, Fab' or single chain Fv (scFV) fragments highly specific for tumor antigen-derived peptide-MHC complex molecules has thus become possible. Recently, immuno-toxins, generated by fusing TCR-like Fab specific for melanoma Ag MART-1 26-35/A2 or gp100

280-288/A2 to a truncated form of Pseudomonas endotoxin, have been shown to inhibit human melanoma growth both in vitro and in vivo (Klechevsky, et al. Antitumor activity of immunotoxins with T-cell receptor-like specificity against human melanoma xenografts. Cancer Res 2008; 68 (15): 6360-6367). In addition, by engineering full-length mAb using the Fab fragments, it is possible to directly generate a therapeutic human mAb, bypassing months of time-consuming work, normally needed for developing therapeutic mAbs.

The presently disclosed subject matter involves the development of a fully human mAb that recognizes, for example, a human FcRL5 polypeptide (e.g., one having the amino acid sequence set forth in SEQ ID NO:899) for cancer therapy. The presently disclosed subject matter further involves the development of a fully human mAb that recognizes at least a part of domain 9 of a human FcRL5 polypeptide (e.g., a polypeptide having the amino acid sequence set forth in SEQ ID NO:900 or 917) for cancer therapy. The presently disclosed subject matter further involves the development of a fully human mAb that recognizes at least a part of domain 8 of a human FcRL5 polypeptide for cancer therapy. The presently disclosed subject matter further involves the development of a fully human mAb that recognizes at least a part of domain 7 of a human FcRL5 polypeptide for cancer therapy. In certain embodiments, the presently disclosed subject provides fully human mAbs that are specific for domain 7, domain 8 or domain 9 of FcRL5 for cancer therapy.

3. Homologous Antibodies

In certain embodiments, an antibody of the presently disclosed subject matter comprises heavy and light chain variable regions comprising amino acid sequences that are homologous to the amino acid sequences of the antibodies described herein and as disclosed in Tables 1-76 (e.g., ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 antibodies), and wherein the antibodies retain the desired functional properties of the anti-FcRL5 antibodies of the presently disclosed subject matter.

For example, and not by way of limitation, the presently disclosed subject matter provides an isolated anti-FcRL5 antibody or antigen-binding fragment thereof comprising a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303, wherein the anti-FcRL5 antibody or antigen-binding fragment thereof binds to an FcRL5 polypeptide.

In certain embodiments, an isolated anti-FcRL5 antibody or antigen-binding fragment thereof, comprises a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, wherein the anti-FcRL5 antibody or antigen-binding fragment thereof binds to an FcRL5 polypeptide.

In certain embodiments, an isolated anti-FcRL5 antibody or antigen-binding fragment thereof, comprises (a) a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NO:3, SEQ ID NO:7, SEQ ID NO:11, SEQ ID NO:15, SEQ ID NO:19, SEQ ID NO:23, SEQ ID NO:27, SEQ ID NO:31, SEQ ID NO:35, SEQ ID NO:39, SEQ ID NO:43, SEQ ID NO:47, SEQ ID NO:51, SEQ ID NO:55, SEQ ID NO:59, SEQ ID NO:63, SEQ ID NO:67, SEQ ID NO:71, SEQ ID NO:75, SEQ ID NO:79, SEQ ID NO:83, SEQ ID NO:87, SEQ ID NO:91, SEQ ID NO:95, SEQ ID NO:99, SEQ ID NO:103, SEQ ID NO:107, SEQ ID NO:111, SEQ ID NO:115, SEQ ID NO:119, SEQ ID NO:123, SEQ ID NO:127, SEQ ID NO:131, SEQ ID NO:135, SEQ ID NO:139, SEQ ID NO:143, SEQ ID NO:147, SEQ ID NO:151, SEQ ID NO:155, SEQ ID NO:159, SEQ ID NO:163, SEQ ID NO:167, SEQ ID NO:171, SEQ ID NO:175, SEQ ID NO:179, SEQ ID NO:183, SEQ ID NO:187, SEQ ID NO:191, SEQ ID NO:195, SEQ ID NO:199, SEQ ID NO:203, SEQ ID NO:207, SEQ ID NO:211, SEQ ID NO:215, SEQ ID NO:219, SEQ ID NO:223, SEQ ID NO:227, SEQ ID NO:231, SEQ ID NO:235, SEQ ID NO:239, SEQ ID NO:243, SEQ ID NO:247, SEQ ID NO:251, SEQ ID NO:255, SEQ ID NO:259, SEQ ID NO:263, SEQ ID NO:267, SEQ ID NO:271, SEQ ID NO:275, SEQ ID NO:279, SEQ ID NO:283, SEQ ID NO:287, SEQ ID NO:291, SEQ ID NO:295, SEQ ID NO:299 and SEQ ID NO:303; and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to an amino acid sequence selected from the group consisting of SEQ ID NO:4, SEQ ID NO:8, SEQ ID NO:12, SEQ ID NO:16, SEQ ID NO:20, SEQ ID NO:24, SEQ ID NO:28, SEQ ID NO:32, SEQ ID NO:36, SEQ ID NO:40, SEQ ID NO:44, SEQ ID NO:48, SEQ ID NO:52, SEQ ID NO:56, SEQ ID NO:60, SEQ ID NO:64, SEQ ID NO:68, SEQ ID NO:72, SEQ ID NO:76, SEQ ID NO:80, SEQ ID NO:84, SEQ ID NO:88, SEQ ID NO:92, SEQ ID NO:96, SEQ ID NO:100, SEQ ID NO:104, SEQ ID NO:108, SEQ ID NO:112, SEQ ID NO:116, SEQ ID NO:120, SEQ ID NO:124, SEQ ID NO:128, SEQ ID NO:132, SEQ ID NO:136, SEQ ID NO:140, SEQ ID NO:144, SEQ ID NO:148, SEQ ID NO:152, SEQ ID NO:156, SEQ ID NO:160, SEQ ID NO:164, SEQ ID NO:168, SEQ ID NO:172, SEQ ID NO:176, SEQ ID NO:180, SEQ ID NO:184, SEQ ID NO:188, SEQ ID NO:192, SEQ ID NO:196, SEQ ID NO:200, SEQ ID NO:204, SEQ ID NO:208, SEQ ID NO:212, SEQ ID NO:216, SEQ ID NO:220, SEQ ID NO:224, SEQ ID NO:228, SEQ ID NO:232, SEQ ID NO:236, SEQ ID NO:240, SEQ ID NO:244, SEQ ID NO:248, SEQ ID NO:252, SEQ ID NO:256, SEQ ID NO:260, SEQ ID NO:264, SEQ ID NO:268, SEQ ID NO:272, SEQ ID NO:276, SEQ ID NO:280, SEQ ID NO:284, SEQ ID NO:288, SEQ ID NO:292, SEQ ID NO:296, SEQ ID NO:300 and SEQ ID NO:304, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:143, and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:144, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:215, and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:216, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:219, and (b) a heavy chain variable comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:220, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:235, and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:236, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:267, and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:268, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:115, and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:116, wherein the anti-FcRL5 antibody or antigen-binding fragment thereof binds to an FcRL5 polypeptide.

In certain embodiments, an isolated anti-FcRL5 antibody or antigen-binding fragment thereof comprises (a) a light chain variable comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:171, and (b) a heavy chain variable region comprising an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% homologous to the amino acid sequence set forth in SEQ ID NO:172, wherein the anti-FcRL5 antibody or antigen-binding fragment thereof binds to an FcRL5 polypeptide.

An anti-FcRL5 antibody or antigen-binding fragment thereof comprising $V_H$ and/or $V_L$ regions having high (i.e., 80% or greater) homology to the $V_H$ and $V_L$ regions of the sequences set forth above, can be obtained by mutagenesis (e.g., site-directed or PCR-mediated mutagenesis), followed by testing of the encoded altered antibody for retained function (i.e., the binding affinity) using the binding assays described herein. In certain embodiments, a $V_L$ sequence having at least 90%, 91%, 92%, 93%, 94%, 95%, 96%, 97%, 98% or 99% identity contains substitutions (e.g., conservative substitutions to generate conservative modifications of a sequence), insertions or deletions relative to the reference sequence, but an anti-FcRL5 antibody or antigen-binding fragment thereof comprising that sequence retains the ability to bind to FcRL5. In certain embodiments, a $V_H$ sequence having at least 90%, 91%, 92%, 93%, 94%, 95%, 96%, 97%, 98%, or 99% identity contains substitutions (e.g., conservative substitutions), insertions or deletions relative to the reference sequence, but an anti-FcRL5 antibody or antigen-binding fragment thereof comprising that sequence retains the ability to bind to FcRL5. In certain embodiments, a total of about 1 to about 10 amino acids have been substituted, inserted and/or deleted in the disclosed sequences. Non-limiting examples of conservative modifications are provided below, e.g., within Table 230.

As used herein, the percent homology between two amino acid sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent homology between two amino acid sequences can be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent homology between two amino acid sequences can be determined using the Needleman and Wunsch (J. Mol. Biol. 48:444-453 (1970)) algorithm which has been incorporated into the GAP program in the GCG software package (available at www.gcg.com), using either a Blossum 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the presently disclosed subject matter can further be used as a "query sequence" to perform a search against public databases to, for example, identify related sequences. Such searches can be performed using the XBLAST program (version 2.0) of Altschul, et al. (1990) J. Mol. Biol. 215: 403-10. BLAST protein searches can be performed with the)(BLAST program, score=50, wordlength=3 to obtain amino acid sequences homologous to the antibody molecules of the invention. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g.,)(BLAST and NBLAST) can be used. (See www.ncbi.nlm.nih.gov).

4. Antibodies with Conservative Modifications

The present disclosure further provides antibodies and antigen-binding fragments thereof that comprise conservative modifications of the antibody sequences disclosed herein. For example, and not by way of limitation, an antibody or antigen-binding fragment thereof of the presently disclosed subject matter comprises a heavy chain variable region comprising CDR1, CDR2 and CDR3 sequences and a light chain variable region comprising CDR1, CDR2 and CDR3 sequences, wherein one or more of these CDR sequences comprise specified amino acid sequences based on the antibodies described herein (e.g., ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 antibodies), or conservative modifications thereof, and wherein the antibodies retain the desired functional properties of the anti-FcRL5 antibodies of the presently disclosed subject matter. See Table 229.

In certain embodiments, the presently disclosed subject matter provides an isolated anti-FcRL5 antibody or antigen-binding fragment thereof comprising a light chain variable region, wherein the light chain variable region comprises: (a) a CDR1 comprising an amino acid sequence selected from the group consisting of SEQ ID NOs: 312, 318, 324, 329, 338, 343, 348, 352, 357, 363, 369, 381, 390, 397, 401, 406, 416, 423, 428, 433, 447, 460, 468, 474, 477, 483, 490, 498, 503, 508, 518, 533, 540, 544, 547, 556, 562, 568, 571, 580, 585 and 588, and conservative modifications thereof; (b) a CDR2 comprising an amino acid sequence selected from the group consisting of SEQ ID NOs:313, 319, 330, 344, 349, 358, 364, 370, 382, 385, 391, 398, 409, 417, 429, 434, 438, 448, 454, 461, 469, 478, 484, 487, 504, 513, 523, 534, 429, 448, 548, 557, 563, 572, 575 and 586, and conservative modifications thereof; and (c) a CDR3 comprising an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592, and conservative modifications thereof; wherein the antibody or antigen-binding fragment thereof specifically binds FcRL5.

In certain embodiments, the presently disclosed subject matter provides an isolated anti-FcRL5 antibody or antigen-binding fragment thereof comprising a heavy chain variable region, wherein the heavy chain variable region comprises: (a) a CDR1 comprising an amino acid sequence selected from the group consisting of SEQ ID NOs: 309, 315, 321, 326, 332, 335, 340, 346, 354, 360, 366, 372, 378, 387, 393, 403, 411, 420, 425, 436, 440, 444, 471, 480, 500, 510, 515, 520, 525, 537, 551, 559, 565, 582 and 589, and conservative modifications thereof; (b) a CDR2 comprising an amino acid sequence selected from the group consisting of SEQ ID NOs: 310, 316, 322, 327, 333, 336, 341, 355, 361, 367, 373, 379, 388, 404, 412, 421, 426, 431, 441, 445, 450, 466, 472, 475, 481, 496, 501, 506, 511, 516, 521, 526, 538, 552, 560, 566, 583 and 590, and conservative modifications thereof; and (c) a CDR3 comprising an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591, and conservative modifications thereof; wherein the antibody or antigen-binding fragment thereof specifically binds FcRL5.

The presently disclosed subject matter provides an isolated anti-FcRL5 antibody or antigen-binding fragment thereof, comprising a heavy chain variable region comprising CDR1, CDR2, and CDR3 sequences and a light chain variable region comprising CDR1, CDR2, and CDR3 sequences, wherein: (a) the heavy chain variable region CDR3 comprises an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591, and conservative modifications thereof; and (b) the light chain variable region CDR3 comprises an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592, and conservative modifications thereof; wherein the antibody or antigen-binding fragment thereof binds to human FcRL5.

In certain embodiments, the presently disclosed subject matter provides an isolated anti-FcRL5 antibody or antigen-binding fragment thereof, comprising a heavy chain variable region comprising CDR1, CDR2, and CDR3 sequences and a light chain variable region comprising CDR1, CDR2, and CDR3 sequences, wherein: (a) the heavy chain variable region CDR1 comprises an amino acid sequence selected from the group consisting of SEQ ID NOs: 309, 315, 321, 326, 332, 335, 340, 346, 354, 360, 366, 372, 378, 387, 393, 403, 411, 420, 425, 436, 440, 444, 471, 480, 500, 510, 515, 520, 525, 537, 551, 559, 565, 582 and 589, and conservative modifications thereof; (b) the heavy chain variable region CDR2 comprises an amino acid sequence selected from the group consisting of SEQ ID NOs: 310, 316, 322, 327, 333, 336, 341, 355, 361, 367, 373, 379, 388, 404, 412, 421, 426, 431, 441, 445, 450, 466, 472, 475, 481, 496, 501, 506, 511, 516, 521, 526, 538, 552, 560, 566, 583 and 590, and conservative modifications thereof; (c) the heavy chain variable region CDR3 comprises an amino acid sequence selected from the group consisting of SEQ ID NOs: 311, 317, 323, 328, 334, 337, 342, 347, 351, 356, 362, 368, 374, 376, 380, 384, 389, 394, 396, 400, 405, 408, 412, 415, 422, 427, 432, 437, 442, 446, 451, 453, 456, 458, 459, 463, 464, 467, 473, 476, 482, 486, 489, 492, 494, 497, 502, 507, 512, 517, 522, 527, 529, 532, 536, 539, 543, 546, 550, 553, 555, 561, 567, 570, 574, 577, 578, 579, 584, 578, 587 and 591, and conservative modifications thereof (d) the light chain variable region CDR1 comprises an amino acid sequence selected from the group consisting of SEQ ID NOs: 312, 318, 324, 329, 338, 343, 348, 352, 357, 363, 369, 381, 390, 397, 401, 406, 416, 423, 428, 433, 447, 460, 468, 474, 477, 483, 490, 498, 503, 508, 518, 533, 540, 544, 547, 556, 562, 568, 571, 580, 585 and 588, and conservative modifications thereof; (e) the light chain variable region CDR2 comprises an amino acid sequence selected from the group consisting of SEQ ID NOs:313, 319, 330, 344, 349, 358, 364, 370, 382, 385, 391, 398, 409, 417, 429, 434, 438, 448, 454, 461, 469, 478, 484, 487, 504, 513, 523, 534, 429, 448, 548, 557, 563, 572, 575 and 586, and conservative modifications thereof; and (f) the light chain variable region CDR3 comprises an amino acid sequence selected from the group consisting of SEQ ID NOs: 314, 320, 325, 331, 339, 345, 350, 353, 359, 365, 371, 377, 383, 386, 392, 395, 399, 402, 407, 410, 414, 418, 419, 424, 430, 435, 439, 443, 449, 452, 455, 457, 462, 465, 470, 479, 485, 488, 491, 493, 495, 499, 505, 509, 514, 519, 524, 528, 530, 531, 535, 541, 542, 545, 549, 554, 558, 564, 569, 573, 576, 581 and 592, and conservative modifications thereof; wherein the antibody or antigen-binding fragment thereof specifically binds FcRL5.

In certain embodiments, a presently disclosed anti-FcRL5 antibody or antigen-binding fragment thereof comprises: (a) a heavy chain variable region CDR1 comprising the amino acid sequence of SEQ ID NO:411 or conservative modifications thereof; (b) a heavy chain variable region CDR2 comprising the amino acid sequence of SEQ ID NO:412 or conservative modifications thereof; (c) a heavy chain variable region CDR3 comprising the amino acid sequence of SEQ ID NO:463 or conservative modifications thereof; (d) a light chain variable region CDR1 comprising the amino acid sequence of SEQ ID NO:318 or conservative modifications thereof; (e) a light chain variable region CDR2 comprising the amino acid sequence of SEQ ID NO:319 or conservative modifications thereof; and (f) a light chain variable region CDR3 comprising the amino acid sequence of SEQ ID NO:419 or conservative modifications thereof.

In certain embodiments, a presently disclosed anti-FcRL5 antibody or antigen-binding fragment thereof comprises: (a) a heavy chain variable region CDR1 comprising the amino acid sequence of SEQ ID NO:515 or conservative modifications thereof; (b) a heavy chain variable region CDR2 comprising the amino acid sequence of SEQ ID NO:516 or conservative modifications thereof; (c) a heavy chain variable region CDR3 comprising the amino acid sequence of SEQ ID NO:517 or conservative modifications thereof (d) a light chain variable region CDR1 comprising the amino acid sequence of SEQ ID NO:318 or conservative modifications thereof; (e) a light chain variable region CDR2 comprising the amino acid sequence of SEQ ID NO:319 or conservative modifications thereof and (f) a light chain variable region CDR3 comprising the amino acid sequence of SEQ ID NO:531 or conservative modifications thereof.

In certain embodiments, a presently disclosed anti-FcRL5 antibody or antigen-binding fragment thereof comprises: (a) a heavy chain variable region CDR1 comprising the amino acid sequence of SEQ ID NO:403 or conservative modifications thereof; (b) a heavy chain variable region CDR2 comprising the amino acid sequence of SEQ ID NO:404 or conservative modifications thereof; (c) a heavy chain variable region CDR3 comprising the amino acid sequence of SEQ ID NO:532 or conservative modifications thereof; (d) a light chain variable region CDR1 comprising the amino acid sequence of SEQ ID NO:533 or conservative modifications thereof; (e) a light chain variable region CDR2 comprising the amino acid sequence of SEQ ID NO:534 or conservative modifications thereof; and (f) a light chain variable region CDR3 comprising the amino acid sequence of SEQ ID NO:535 or conservative modifications thereof.

In certain embodiments, a presently disclosed anti-FcRL5 antibody or antigen-binding fragment thereof comprises: (a) a heavy chain variable region CDR1 comprising the amino acid sequence of SEQ ID NO:411 or conservative modifications thereof; (b) a heavy chain variable region CDR2 comprising the amino acid sequence of SEQ ID NO:412 or conservative modifications thereof; (c) a heavy chain variable region CDR3 comprising the amino acid sequence of SEQ ID NO:543 or conservative modifications thereof (d) a light chain variable region CDR1 comprising the amino acid sequence of SEQ ID NO:544 or conservative modifications thereof; (e) a light chain variable region CDR2 comprising the amino acid sequence of SEQ ID NO:448 or conservative modifications thereof and (f) a light chain variable region CDR3 comprising the amino acid sequence of SEQ ID NO:545 or conservative modifications thereof.

In certain embodiments, a presently disclosed anti-FcRL5 antibody or antigen-binding fragment thereof comprises: (a) a heavy chain variable region CDR1 comprising the amino acid sequence of SEQ ID NO:372 or conservative modifications thereof; (b) a heavy chain variable region CDR2 comprising the amino acid sequence of SEQ ID NO:475 or conservative modifications thereof; (c) a heavy chain variable region CDR3 comprising the amino acid sequence of SEQ ID NO:570 or conservative modifications thereof; (d) a light chain variable region CDR1 comprising the amino acid sequence of SEQ ID NO:571 or conservative modifications thereof; (e) a light chain variable region CDR2 comprising the amino acid sequence of SEQ ID NO:572 or conservative modifications thereof; and (f) a light chain variable region CDR3 comprising the amino acid sequence of SEQ ID NO:573 or conservative modifications thereof.

In certain embodiments, a presently disclosed anti-FcRL5 antibody or antigen-binding fragment thereof comprises: (a) a heavy chain variable region CDR1 comprising the amino acid sequence of SEQ ID NO:440 or conservative modifications thereof; (b) a heavy chain variable region CDR2 comprising the amino acid sequence of SEQ ID NO:441 or conservative modifications thereof; (c) a heavy chain variable region CDR3 comprising the amino acid sequence of SEQ ID NO:442 or conservative modifications thereof; (d) a light chain variable region CDR1 comprising the amino acid sequence of SEQ ID NO:329 or conservative modifications thereof; (e) a light chain variable region CDR2 comprising the amino acid sequence of SEQ ID NO:330 or conservative modifications thereof and (f) a light chain variable region CDR3 comprising the amino acid sequence of SEQ ID NO:443 or conservative modifications thereof.

In certain embodiments, a presently disclosed anti-FcRL5 antibody or antigen-binding fragment thereof comprises: (a) a heavy chain variable region CDR1 comprising the amino acid sequence of SEQ ID NO:309 or conservative modifications thereof; (b) a heavy chain variable region CDR2 comprising the amino acid sequence of SEQ ID NO:310 or conservative modifications thereof; (c) a heavy chain variable region CDR3 comprising the amino acid sequence of SEQ ID NO:489 or conservative modifications thereof; (d) a light chain variable region CDR1 comprising the amino acid sequence of SEQ ID NO:490 or conservative modifications thereof; (e) a light chain variable region CDR2 comprising the amino acid sequence of SEQ ID NO:313 or conservative modifications thereof and (f) a light chain variable region CDR3 comprising the amino acid sequence of SEQ ID NO:491 or conservative modifications thereof.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. Exemplary conservative amino acid substitutions are shown in Table 230. Amino acid substitutions may be introduced into an antibody of interest and the products screened for a desired activity, e.g., retained/improved antigen binding, decreased immunogenicity, or improved ADCC or CDC. In certain embodiments, a sequence disclosed herein, e.g., a CDR sequence, a $V_H$ sequence or a $V_L$ sequence, can have up to about one, up to about two, up to about three, up to about four, up to about five, up to about six, up to about seven, up to about eight, up to about nine or up to about ten amino acid residues that are modified and/or substituted.

TABLE 230

| Original Residue | Exemplary conservative amino acid Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe |
| Leu (L) | Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala |

Amino acids may be grouped according to common side-chain properties:

hydrophobic: Norleucine, Met, Ala, Val, Leu, Ile;

neutral hydrophilic: Cys, Ser, Thr, Asn, Gln;

acidic: Asp, Glu;

basic: His, Lys, Arg;

residues that influence chain orientation: Gly, Pro;

aromatic: Trp, Tyr, Phe.

In certain embodiments, non-conservative substitutions will entail exchanging a member of one of these classes for another class.

5. Anti FcRL5 Antibodies that Cross-Compete for Binding to FcRL5 with Anti FcRL5 Antibodies of the Invention The present application provides antibodies that cross-compete with any of the disclosed anti-FcRL5 antibodies for binding to FcRL5 (e.g., human FcRL5). The present application further provides antibodies that cross-compete with any of the disclosed anti-FcRL5 antibodies for binding to domain 7, domain 8 or domain 9 of FcRL5 (e.g., domain 7, domain 8 or domain 9 of human FcRL5). For example, and not by way of limitation, the cross-competing antibodies can bind to the same epitope region, e.g., same epitope, adjacent epitope or overlapping epitope as any of the anti-FcRL5 antibodies of the presently disclosed subject matter. In certain embodiments, the epitope is present within an immunoglobulin (Ig)-like domain of FcRL5, e.g., within domain 1, domain 2, domain 3, domain 4, domain 5, domain 6, domain 7, domain 8 or domain 9 of FcRL5 (see FIGS. 3A and 3C). In certain embodiments, the epitope is present within domain 9 of FcRL5. In certain embodiments, the epitope is present within domain 8 of FcRL5. In certain embodiments, the epitope is present within domain 7 of FcRL5.

In certain embodiments, the reference antibody for cross-competition studies can be any one of the anti-FcRL5 antibodies disclosed herein, e.g., ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-125, ET200-005 and ET200-124 antibodies.

Such cross-competing antibodies can be identified based on their ability to cross-compete with any one of the presently disclosed anti-FcRL5 antibodies in standard FcRL5 binding assays. For example, Biacore analysis, ELISA assays or flow cytometry can be used to demonstrate cross-competition with the antibodies of the presently disclosed subject matter. The ability of a test antibody to inhibit the binding of, for example, any one of the presently disclosed anti-FcRL5 antibodies (e.g., ET200-001, ET200-002, ET200-003, ET200-006, ET200-007, ET200-008, ET200-009, ET200-010, ET200-011, ET200-012, ET200-013, ET200-014, ET200-015, ET200-016, ET200-017, ET200-018, ET200-019, ET200-020, ET200-021, ET200-022, ET200-023, ET200-024, ET200-025, ET200-026, ET200-027, ET200-028, ET200-029, ET200-030, ET200-031, ET200-032, ET200-033, ET200-034, ET200-035, ET200-037, ET200-038, ET200-039, ET200-040, ET200-041, ET200-042, ET200-043, ET200-044, ET200-045, ET200-069, ET200-078, ET200-079, ET200-081, ET200-097, ET200-098, ET200-099, ET200-100, ET200-101, ET200-102, ET200-103, ET200-104, ET200-105, ET200-106, ET200-107, ET200-108, ET200-109, ET200-110, ET200-111, ET200-112, ET200-113, ET200-114, ET200-115, ET200-116, ET200-117, ET200-118, ET200-119, ET200-120, ET200-121, ET200-122, ET200-123, ET200-

125, ET200-005 and ET200-124 antibodies) to human FcRL5 demonstrates that the test antibody can compete with any one of the presently disclosed anti-FcRL5 antibodies for binding to human FcRL5 and thus binds to the same epitope region on human FcRL5 as any one of the presently disclosed anti-FcRL5 antibodies. In certain embodiments, the cross-competing antibody binds to the same epitope on human FcRL5 as any one of the presently disclosed anti-FcRL5 antibodies.

In a non-limiting example of a competition assay, immobilized antigen, e.g., a human FcRL5 polypeptide, can be incubated in a solution comprising a first labeled antibody that binds to the antigen and a second unlabeled antibody that is being tested for its ability to compete with the first antibody for binding to the antigen. In certain embodiments, the second antibody can be present in a hybridoma supernatant. As a control, immobilized antigen is incubated in a solution comprising the first labeled antibody but not the second unlabeled antibody. After incubation under conditions permissive for binding of the first antibody to the antigen, excess unbound antibody is removed, and the amount of label associated with immobilized antigen is measured. If the amount of label associated with immobilized antigen is substantially reduced, e.g., greater than about 50%, in the test sample relative to the control sample, then that indicates that the second antibody is competing with the first antibody for binding to the antigen. See Harlow and Lane (1988) *Antibodies: A Laboratory Manual* ch. 14 (Cold Spring Harbor Laboratory, Cold Spring Harbor, NY).

In certain embodiments, an antibody that cross-competes with any one of the presently disclosed anti-FcRL5 antibodies has a $K_d$ of $5\times10^{-7}$ M or less, $1\times10^{-7}$ M or less, $5\times10^{-8}$ M or less, $1\times10^{-8}$ M or less, $5\times10^{-9}$ M or less, $1\times10^{-9}$ M or less, $5\times10^{-10}$ M or less, or $1\times10^{-10}$ M or less.

6. Characterization of Antibody Binding to Antigen

Antibodies of the presently disclosed subject can be tested for binding to FcRL5 by, for example, standard ELISA. To determine if the selected anti-FcRL5 antibodies bind to unique epitopes, each antibody can be biotinylated using commercially available reagents (Pierce, Rockford, IL). Competition studies using unlabeled monoclonal antibodies and biotinylated monoclonal antibodies can be performed using FcRL5 coated-ELISA plates as described above. Biotinylated mAb binding can be detected with a strep-avidin-alkaline phosphatase probe.

To determine the isotype of purified antibodies, isotype ELISAs can be performed using reagents specific for antibodies of a particular isotype. Anti-FcRL5 human IgGs can be further tested for reactivity with FcRL5 antigen by Western blotting.

In certain embodiments, $K_d$ is measured by a radiolabeled antigen binding assay (RIA). In certain embodiments, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)).

In certain embodiments, $K_d$ is measured using a BIA-CORE® surface plasmon resonance assay. For example, an assay using BIACORE®-2000 or a BIACORE®-3000 (Biacore, Inc., Piscataway, NJ) is described in the Biacore Assay Handbook (2012) available at http://www.gelife-sciences.com.

In certain embodiments, an antibody or an antigen-binding fragment thereof of the present disclosure binds to a human FcRL5 polypeptide comprising the amino acid sequence set forth in SEQ ID NO: 899. In certain embodiments, an antibody or an antigen-binding fragment thereof of the present disclosure binds to an epitope in domain 9 (e.g., comprising amino acids 754-835 of SEQ ID NO:899). In certain embodiments, an antibody or an antigen-binding fragment thereof of the present disclosure binds to an epitope in domain 8 (e.g., comprising amino acids 658-731 of SEQ ID NO:899). In certain embodiments, an antibody or an antigen-binding fragment thereof of the presently disclosed subject matter binds to an epitope within domain 9 comprising amino acids 829-840 of SEQ ID NO:899. In certain embodiments, an antibody or an antigen-binding fragment thereof of the presently disclosed subject matter binds to an epitope within domain 8 comprising amino acids 657-667 of SEQ ID NO:899. For example, and not by way of limitation, an antibody or an antigen-binding fragment thereof of the present disclosure binds to an epitope comprising the amino acid sequence RSETVTLYITGL (SEQ ID NO:915). In certain embodiments, In certain embodiments, an antibody or an antigen-binding fragment thereof of the present disclosure binds to an epitope comprising the amino acid sequence SRPILTFRAPR (SEQ ID NO:916).

7. Immunoconjugates

The presently disclosed subject provides an anti-FcRL5 antibody, or a antigen-binding fragment thereof, conjugated to a therapeutic moiety (e.g., agent), such as a cytotoxin, a drug (e.g., an immunosuppressant) or a radiotoxin. Such conjugates are referred to herein as "immunoconjugates." Immunoconjugates that include one or more cytotoxins are referred to as "immunotoxins." A cytotoxin or cytotoxic agent includes any agent that is detrimental to (e.g., kills) cells. Non-limiting examples of cytotoxic agents include taxol (such as ricin, diphtheria and gelonin), cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, calecheamicin, aureastatin, antimetabolites (e.g., methotrexate, 6-mercaptopurine, 6-thioguanine, cytarabine, 5-fluorouracil decarbazine, alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an anti-FcRL5 antibody or antigen-binding fragment thereof disclosed herein include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to anti-FcRL5 antibody disclosed herein using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D). For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Anti-FcRL5 antibodies of the presently disclosed subject matter also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, $^{90}$Y, $^{131}$I, $^{225}$Ac, $^{213}$Bi, $^{223}$Ra and $^{227}$Th. Methods for preparing radioimmunconjugates are established in the art. Examples of radioimmunoconjugates are commercially available, including Zevalin™ (IDEC Pharmaceuticals) and Bexxar™ (Corixa Pharmaceuticals), and similar methods can be used to prepare radioimmunoconjugates using the antibodies of the invention.

The antibody conjugates of the presently disclosed subject matter can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor (TNF) or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moieties to antibodies are well known, see, e.g., Arnon et al., "Monoclonal Antibodies For Immunotargeting Of Drugs In Cancer Therapy," in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review," in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy," in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates," Immunol. Rev., 62:119-58 (1982).

8. Bispecific Molecules

The presently disclosed subject matter provides bispecific molecules comprising an anti-FcRL5 antibody or a fragment thereof disclosed herein. An antibody of the presently disclosed subject matter, or antigen-binding fragments thereof, can be derivatized or linked to another functional molecule, e.g., another peptide or protein (e.g., another antibody or ligand for a receptor) to generate a bispecific molecule that binds to at least two different binding sites or target molecules. The antibody of the presently disclosed subject matter can in fact be derivatized or linked to more than one other functional molecule to generate multispecific molecules that bind to more than two different binding sites and/or target molecules; such multispecific molecules are also intended to be encompassed by the term "bispecific molecule" as used herein. To create a bispecific molecule, a presently disclosed anti-FcRL5 antibody can be functionally linked (e.g., by chemical coupling, genetic fusion, noncovalent association or otherwise) to one or more other binding molecules, such as another antibody, antibody fragment, peptide or binding mimetic, such that a bispecific molecule results.

The presently disclosed subject matter provides bispecific molecules comprising at least a first binding specificity for FcRL5 and a second binding specificity for a second target epitope. The second target epitope can be a FcRL5 epitope, or a non-FcRL5 epitope, e.g., a different antigen. In certain embodiments, the bispecific molecule is multispecific, the molecule can further include a third binding specificity. Where a first portion of a bispecific antibody binds to an antigen on a tumor cell for example and a second portion of a bispecific antibody recognizes an antigen on the surface of a human immune effector cell, the antibody is capable of recruiting the activity of that effector cell by specifically binding to the effector antigen on the human immune effector cell. In certain embodiments, bispecific antibodies, therefore, are able to form a link between effector cells, for example, T cells and tumor cells, thereby enhancing effector function. In certain embodiments, a bispecific antibody of the present disclosure comprises at least a first binding to FcRL5 and at least a second binding to an immune cell. For example, and not by way of limitation, a bispecific antibody of the present disclosure comprises at least a first binding to FcRL5 and at least a second binding to a receptor present on the surface of an immune cell, e.g., CD3.

The bispecific molecules of the presently disclosed subject matter can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5, 5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see, e.g., Karpovsky et al. (1984) J. Exp. Med. 160:1686; Liu, M A et al. (1985) Proc. Natl. Acad. Sci. USA 82:8648). Other methods include those described in Paulus (1985) Behring Ins. Mitt. No. 78, 118-132; Brennan et al. (1985) Science 229:81-83), and Glennie et al. (1987) J. Immunol. 139: 2367-2375). Preferred conjugating agents are SATA and sulfo-SMCC, both available from Pierce Chemical Co. (Rockford, IL).

When the binding specificities are antibodies, they can be conjugated via sulfhydryl bonding of the C-terminus hinge regions of the two heavy chains. In one non-limiting embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule is a mAbxmAb, mAbxFab, FabxF(ab')₂ or ligand x Fab fusion protein.

Binding of the bispecific molecules to their specific targets can be confirmed by, for example, enzyme-linked immunosorbent assay (ELISA), radioimmunoassay (RIA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. Alternatively, the complexes can be detected using any of a variety of other immunoassays. For example, the antibody can be radioactively labeled and used in a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

9. Selecting a High Affinity ScFv Against a FcRL5 Polypeptide

Phage display technology allows the selection of phage that bind to the target antigen of interest with high affinity from phage in a human phage display library that either does not bind or that binds with lower affinity. This is accomplished by iterative binding of phage to the antigen, which is bound to a solid support, for example, beads or mammalian cells followed by removal of non-bound phage and by elution of specifically bound phage. In certain embodiments, antigens are first biotinylated for immobilization to, for example, streptavidin-conjugated Dynabeads M-280. The phage library is incubated with the cells, beads or other solid support and non-binding phage is removed by washing. Clones that bind are selected and tested.

Once selected, positive scFv clones are further tested for their binding to FcRL5 (e.g., human FcRL5) on live 3T3 cell surfaces by flow cytometry. Briefly, phage clones are incubated with 3T3 cells over-expressing FcRL5. The cells are washed and then incubated with a mouse anti-M13 coat protein mAb. Cells are washed again and labeled with a PE-horse anti-mouse Ig prior to flow cytometry.

In certain embodiments, binding selectively for FcRL5 can be further confirmed by testing whether the positive scFv clones do not bind to other members of the FcRL family, such as, but not limited to, FcRL1, FcRL2, FcRL3, FcRL4 or FcRL6 and SLAMF9.

In other non-limiting embodiments, the anti-FcRL5 antibodies can comprise one or more framework region amino acid substitutions designed to improve protein stability, antibody binding, expression levels or to introduce a site for conjugation of therapeutic agents. These scFv are then used to produce recombinant human monoclonal IgGs in accordance with methods known to those of skill in the art.

10. Engineering Full Length mAb Using the Selected ScFv Fragments

Phage display technology allows for the rapid selection and production of antigen-specific scFv and Fab fragments, which are useful in and of themselves, or which can be further developed to provide complete antibodies, antigen binding proteins or antigen binding fragments thereof. Complete mAbs with Fc domains have a number of advantages over the scFv and Fab antibodies. First, only full length Abs exert immunological function such as CDC and ADCC mediated via Fc domain. Second, bivalent mAbs offer stronger antigen-binding affinity than monomeric Fab Abs. Third, plasma half-life and renal clearance will be different with the Fab and bivalent mAb. The particular features and advantages of each can be matched to the planned effector strategy. Fourth, bivalent mAb may be internalized at different rates than scFv and Fab, altering immune function or carrier function. Alpha emitters, for example, do not need to be internalized to kill the targets, but many drugs and toxins will benefit from internalization of the immune complex. In one non-limiting embodiment, therefore, once scFv clones specific for FcRL5 were obtained from phage display libraries, a full length IgG mAb using the scFv fragments was produced.

To produce recombinant human monoclonal IgG in Chinese hamster ovary (CHO) cells, a full length IgG mAb can be engineered based on a method known to those of skill in the art (Tomomatsu et al., Production of human monoclonal antibodies against FceRIa by a method combining in vitro immunization with phage display. Biosci Biotechnol Biochem 73(7): 1465-1469 2009). Briefly, antibody variable regions can be subcloned into mammalian expression vectors, with matching Lambda or Kappa light chain constant sequences and IgG1 subclass Fc (for example) (Lidija P, et al. An integrated vector system for the eukaryotic expression of antibodies or their fragments after selection from phage display libraries. Gene 1997; 187(1): 9-18; Lisa J H, et al. Crystallographic structure of an intact lgG1 monoclonal antibody. Journal of Molecular Biology 1998; 275 (5): 861-872). Kinetic binding analysis (Yasmina N A, et al. Probing the binding mechanism and affinity of tanezumab, a recombinant humanized anti-NGF monoclonal antibody, using a repertoire of biosensors. Protein Science 2008; 17(8): 1326-1335) can be used to confirm specific binding of full length IgG to FcRL5, with a $K_d$ in nanomolar range.

Pharmaceutical Compositions and Methods of Treatment

Anti-FcRL5 antibodies or antigen-binding fragments thereof, e.g., scFvs, of the presently disclosed subject matter can be administered for therapeutic treatments to a patient suffering from a cancer (e.g., multiple myeloma) in an amount sufficient to prevent, inhibit or reduce the progression of the cancer. Progression includes, e.g., the growth, invasiveness, metastases and/or recurrence of the cancer, e.g., tumor. In certain embodiments, the method can include administering to a subject an effective amount of an anti-FcRL5 antibody or antigen-binding fragment thereof (or a pharmaceutical composition thereof) to produce an anti-cancer effect in the subject. Amounts effective for this use will depend upon the severity of the disease and the general state of the patient's own immune system. Dosing schedules will also vary with the disease state and status of the patient, and will typically range from a single bolus dosage or continuous infusion to multiple administrations per day (e.g., every 4-6 hours), or as indicated by the treating physician and the patient's condition.

An "anti-cancer effect" means one or more of: a reduction in aggregate cancer cell mass, a reduction in cancer cell growth rate, a reduction in cancer cell proliferation, a reduction in tumor mass, a reduction in tumor volume, a reduction in tumor cell proliferation, a reduction in tumor growth rate or a reduction in tumor metastasis. In certain embodiments, the anti-cancer effect is a reduction in the number of cancer cells. In certain embodiments, where the cancer is a solid tumor, an anti-cancer effect can be a reduction in tumor size and/or a reduction in the rate of tumor growth. In certain embodiments, the anti-cancer effect is a reduction in the aggregate cancer cell burden. In certain embodiments, the anti-cancer effect is a reduction in the rate of cell proliferation and/or an increase in the rate of cell death. In certain embodiments, the anti-cancer effect is a prolongation of survival. In certain embodiments, the anti-cancer effect is a prolongation in the interval until relapse.

The identification of medical conditions treatable by anti-FcRL5 antibodies of the presently disclosed subject matter is well within the ability and knowledge of one skilled in the art. For example, human individuals who are either suffering from multiple myeloma or who are at risk of developing multiple myeloma are suitable for administration of the presently disclosed anti-FcRL5 antibodies. A clinician skilled in the art can readily determine, for example, by the use of clinical tests, physical examination and medical/family history, if an individual is a candidate for such treatment.

In certain embodiments, the presently disclosed subject matter provides a method of treating a cancer, e.g., a tumor, by administering a presently disclosed anti-FcRL5 antibody and, optionally, in combination with one or more other agents. "In combination with" or "in conjunction with," as used interchangeably herein, means that the anti-FcRL5 antibody and the other agent are administered to a subject as part of a treatment regimen or plan. In certain embodiments, being used in combination does not require that the anti-FcRL5 antibody and the other agent are physically combined prior to administration or that they be administered over the same time frame. For example, and not by way of limitation, the anti-FcRL5 antibody and the other agent can be administered concurrently to the subject being treated, or can be administered at the same time or sequentially in any order or at different points in time. In certain embodiments, the presently disclosed subject matter provides a method of treating a cancer by administering a presently disclosed anti-FcRL5 antibody with an anti-neoplastic agent. The anti-FcRL5 antibody can be chemically or biosynthetically linked to one or more of the antineoplastic agents.

Non-limiting examples of suitable cancers that can be treated with the disclosed antibodies or antigen-binding fragments thereof include multiple myeloma, Non-Hodgkin Lymphoma (e.g., Mantle Cell), Hodgkin Lymphoma, Chronic Lymphocytic Leukemia (CLL), Acute lymphocytic leukemia (ALL), Hairy Cell Leukemia, Burketts Lymphoma and Waldenstrom's Macroglobulinemia. In certain embodiments, the cancer is multiple myeloma.

Any suitable method or route can be used to administer a presently disclosed anti-FcRL5 antibody, and optionally, to coadminister antineoplastic agents. Routes of administration include, for example, oral, intravenous, intraperitoneal, subcutaneous, or intramuscular administration. It should be emphasized, however, that the presently disclosed subject matter is not limited to any particular method or route of administration.

It is noted that presently disclosed anti-FcRL5 antibodies can be administered as a conjugate, which binds specifically to the receptor and delivers a toxic, lethal payload following ligand-toxin internalization.

The anti-FcRL5 antibodies of the presently disclosed subject matter can be administered in the form of a composition additionally comprising a pharmaceutically acceptable carrier. Suitable pharmaceutically acceptable carriers include, for example, one or more of water, saline, phosphate buffered saline, dextrose, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the binding proteins. The compositions of the injection can, as is well known in the art, be formulated so as to provide quick, sustained or delayed release of the active ingredient after administration to the mammal.

The presently disclosed subject matter also provides use of antibodies and nucleic acids that encode them for treatment of a cancer (e.g., multiple myeloma), for diagnostic and prognostic applications as well as use as research tools for the detection of FcRL5 in cells and tissues. Pharmaceutical compositions comprising the disclosed antibodies and nucleic acids are encompassed by the presently disclosed subject matter. Vectors comprising the nucleic acids of the presently disclosed subject matter for antibody-based treatment by vectored immunotherapy are also contemplated by the presently disclosed subject matter. Vectors include expression vectors which enable the expression and secretion of antibodies, as well as vectors which are directed to cell surface expression of the antigen binding proteins, such as chimeric antigen receptors.

In certain embodiments, the nucleic acid sequences encoding the presently disclosed antibodies (provided in Tables 1-228) can be inserted into a vector for expression, e.g., within a cell. Cells comprising such nucleic acids, for example cells that have been transfected with the vectors of the invention, are also encompassed by the presently disclosed subject matter.

Kits

The presently disclosed subject matter provides kits for the treatment or prevention of a cancer (e.g., multiple myeloma). In certain embodiments, the kit comprises a therapeutic composition containing an effective amount of an anti-FcRL5 antibody in unit dosage form. In certain embodiments, the kit can further comprise one or more other agents In certain embodiments, the kit comprises a sterile container which contains a therapeutic composition; such containers can be boxes, ampules, bottles, vials, tubes, bags, pouches, blister-packs, or other suitable container forms known in the art. Such containers can be made of plastic, glass, laminated paper, metal foil, or other materials suitable for holding medicaments.

In certain embodiments, the anti-FcRL5 antibody or antigen-binding fragment thereof is provided together with instructions for administration to a subject having or at risk of developing a cancer (e.g., multiple myeloma). The instructions will generally include information about the use of the composition for the treatment or prevention of a cancer (e.g., multiple myeloma). In other embodiments, the instructions include at least one of the following: description of the therapeutic agent; dosage schedule and administration for treatment or prevention of a neoplasia (e.g., multiple myeloma) or symptoms thereof precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Analysis and Production Methods

Flow cytometry analysis. For cell surface staining, cells can be incubated with appropriate mAbs for 30 minutes on ice, washed, and incubated with secondary antibody reagents when necessary. Flow cytometry data can be collected on a FACS Calibur (Becton Dickinson) and analyzed with FlowJo V8.7.1 and 9.4.8 software.

Selection and characterization of scFvs specific for FcRL5. A human scFv antibody phage display library can be used for the selection of mAb clones. In certain embodiments, phage display selection against FcRL5 can be conducted using a cell panning strategy with 31 human scFv naïve and semi-synthetic phage sub-libraries. FcRL5 overexpressing 3T3 cells can be used in positive panning, and FcRL1, 2, 3, 4 and 6 overexpressing 3T3 cells (5 cell lines in total) can be used in negative panning. Bound clones can then be eluted and used to infect E. coli XL1-Blue. The scFv phage clones expressed in the bacteria can be purified as previously described (Yasmina, et al. Probing the binding mechanism and affinity of tanezumab, a recombinant humanized anti-NGF monoclonal antibody, using a repertoire of biosensors. Protein Science 2008, 17(8):1326-1335; Roberts, et al. Vaccination with CD20 peptides induces a biologically active, specific immune response in mice. Blood 2002, 99(10):3748-3755). Panning can be performed for about 3 to about 4 cycles to enrich scFv phage clones that bind to FcRL5 specifically. Positive clones can be determined by ELISA method against His-tag FcRL5. Positive clones can be further tested for their binding to FcRL5 on live cell surfaces by flow cytometry, using FcRL5-overexpressing cell lines, e.g., 3T3 and/or Raji cells that overexpress FcRL5. The cells can be washed, and the staining can be performed using the following steps: the cells can be first stained with purified scFv phage clones, and followed by staining with a mouse anti-M13 mAb, and finally the horse anti-mouse Ig's conjugate to PE. Each step of the staining can be done between 30-60 minutes on ice and the cells were washed twice between each step of the staining. In certain embodiments, the positive clones can be further characterized for specific binding to domain 9 of FcRL5 using cells, e.g., 3T3 cells, that overexpress FcRL5 that has a domain 9 deletion (FcRL5Δdom9).

Engineering full length mAb using the selected ScFv fragments. Full-length human IgG of the selected phage clones can be produced in HEK293 and Chinese hamster ovary (CHO) cell lines, as described (Caron P C, Class K, Laird W, Co M S, Queen C, Scheinberg D A. Engineered humanized dimeric forms of IgG are more effective antibodies. J Exp Med 176:1 191-1 195. 1992). In brief, antibody variable regions can be subcloned into mammalian expression vectors, with matching human lambda or kappa light chain constant region and human IgG constant region sequences. Molecular weight of the purified full length IgG antibodies can be measured under both reducing and nonreducing conditions by electrophoresis.

Characterization of the full-length human IgG for FcRL5. Initially, specificities of the fully human IgG mAbs for the FcRL5 can be determined by staining 3T3 cells transduced to overexpress FcRL5, followed by secondary goat anti-human IgG mAb conjugate to PE or FITC. The fluorescence intensity can be measured by flow cytometry. The same method can be used to determine the binding of the mAbs to fresh tumor cells and cell lines.

Antibody-dependent cellular cytotoxicity (ADCC). Target cells used for ADCC can be 3T3 cells over-expressing FcRL5. Anti-FcRL5 antibody or its control human IgG at various concentrations can be incubated with target cells and fresh PBMCs at different effector:target (E:T) ratio for 16 hrs. The supernatant can be harvested and the cytotoxicity can be measured by LDH release assay using Cytotox 96 nonradioactive kit from Promega following their instruction. Cytotoxicity can also be measured by standard 4 hours 51 Cr-release assay.

Exemplary Anti-FcRL5 Antibodies

TABLE 1

ET200-001

DNA Sequence (light chain variable region scFv linker heavy
chain variable region His tag + HA tag)
Cagtctgtgttgacgcagccaccctcagcgtctgggaccccgggcagagg
gtcaccatctcttgttctggaagcagctccaacatcggaagtaatactgta
aactggtaccagcagctcccaggaacggcccccaaactcctcatctatagt
aataatcagcggccctcaggggtccctgaccgattctctggctccaagtct
ggcacctcagcctccctggccatcagtgggctccagtctgaggatgaggct
gattattactgtgcagcatgggatgacagcctgaatggttatgtatcggaa
ctgggaccaaggtcaccgtcctaggt [SEQ ID NO: 1]

tctagaggtggtggtggtagcggcggcggcggctctggtggtggtggatcc
ctcgagatggcc [SEQ ID NO: 305]

**caggtgcagctacagcagtggggcgcaggactgttgaagccttcggagacc
ctgtccctcacctgcgctgtgtatggtgggtccttcagtggttactactgg
agctggatccgccagcccccaggggaaggggctggagtggattgggggaaatc
aatcatagtggaagcaccaactacaacccgtccctcaagagtcgagtcacc
atatcagtagacacgtccaagaaccagttctccctgaagctgagctctgtg
accgccgcggacacggccgtgtattactgtgcgcgcgaaggtccgtacgac
ggtttcgattcttggggtcaaggtactctggtgaccgtctcctca
[SEQ ID NO: 2]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy
chain variable region His tag + HA tag)
QSVLTQPPSASGTPGQRVTISCSGSSSNIGSNTVNWYQQLPGTAPKLLIYS
NNQRPSGVPDRFSGSKSGTSASLAISGLQSEDEADYYCAAWDDSLNGYVFG
TGTKVTVLG [SEQ ID NO: 3]

SRGGGGSGGGGSGGGGSLEMA [SEQ ID NO: 307]

**QVQLQQWGAGLLKPSETLSLTCAVYGGSFSGYYWSWIRQPPGKGLEWIGEI
NHSGSTNYNPSLKSRVTISVDTSKNQFSLKLSSVTAADTAVYYCAREGPYD
GFDSWGQGTLVTVSS [SEQ ID NO: 4]**

TSGQAGQHHHHHHGAYPYDVPDYAS [SEQ ID NO: 308]

TABLE 2

ET200-002

DNA Sequence (light chain variable region scFv linker heavy
chain variable region His tag + HA tag)
Aattttatgctgactcagccccactctgtgtcggagtctccggggaagacg
gtaaccatctcctgcacccgcagcagtggcagcattgccagcaactatgtg
cagtggtaccagcagcgcccgggccagtcccctgccccaccactgtgatctatgag
gataaccaaagaccctctggggtccctgatcggttctctggctccatcgac
agctcctccaactctgcctccctcaccatctctgactgaagactgaggac
gaggctgactactactgtcagtatgatagcagcaattctgtggtattcg
gcggaggaccaagctgaccgtcctaggt [SEQ ID No. 5]

tctagaggtggtggtggtagcggcggcggcggctctggtggtggtggatcc
ctcgagatggcc [SEQ ID NO: 305]

**caggtccagctggtacagtctggcactgaggtgaagaagctggggcctca
gtgagggtcgcctgcaaggcttctggttacccctttaacaaatatgacatc
aactgggtgcgacaggcccctggacaagggcttgagtggatgggaggcatc
atccctatattcgtacaacaaactacgcacagaagttccagggcagagtca
cgattaccgcggacgaatccacgagcacagcctacatggagctgagcagcc
tgagatctgaggacacggccgtatattactgtgcgcgcgaatggttctact
gggatatctggggtcaaggtactctggtgaccgtctcctca [SEQ ID
NO: 6]**

TABLE 2-continued

ET200-002

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy
chain variable region His tag + HA tag)
NFMLTQPHSVSESPGKTVTISCTRSSGSIASNYVQWYQQRPGSAPTTVIYE
DNQRPSGVPDRFSGSIDSSSNSASLTISGLKTEDEADYYCQSYDSSNSVVF
GGGTKLTVLG [SEQ ID NO: 7]

SRGGGGSGGGGSGGGGSLEMA [SEQ ID NO: 307]

**QVQLVQSGTEVKKPGASVRVACKASGYPFNKYDINWVRQAPGQGLEWMGGI
IPIFRTTNYAQKFQGRVTITADESTSTAYMELSSLRSEDTAVYYCAREWFY
WDIWGQGTLVTVSS [SEQ ID NO: 8]**

TSGQAGQHHHHHHGAYPYDVPDYAS [SEQ ID NO: 308]

TABLE 3

ET200-003

DNA Sequence (light chain variable region scFv linker heavy
chain variable region His tag + HA tag)
cagtctgtgttgactcagccaccctcagtgtccgtgtccccaggacagaca
gccagcatctcctgctctggaaataaattggggactaagtatgtttactgg
tatcagaagaggccaggccagtcccctgtgttggtcatgtatgaagataat
cagcggccctcagggatcccggagcggttctctggctccaactctgggaac
acagccactctgaccatcagagggacccagactgtggatgaggctgactat
tactgtcaggcgtgggactccgacactttcgtggtcttcggcggagggacc
aaggtcaccgtcctaggt [SEQ ID NO: 9]

tctagaggtggtggtggtagcggcggcggcggctctggtggtggtggatcc
ctcgagatggcc [SEQ ID NO: 305]

**gaggtgcagctggtggagaccggggggaggcgtggtccagcctgggaggtcc
ctgagactctcctgtgcagcctctggattcaccttcagtagttatggcatg
cactgggtccgccaggctccaggcaagggggctggagtgggtggcagttata
tcacatgatggaagtaataaatactacgcagactccgtgaagggccgattc
accatctccagagacaattccaaggacacgctgtatctgcaaatgaacagc
ctgagaggtgaggacacggccgtatattactgtgcgcgctctaaccagtgg
tctggttacttctctttcgattactggggtcaaggtactctggtgaccgtc
tcctca [SEQ ID NO: 10]**

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy
chain variable region His tag + HA tag)
QSVLTQPPSVSVSPGQTASISCSGNKLGTKYVYWYQKRPGQSPVLVMYEDN
QRPSGIPERFSGSNSGNTATLTIRGTQTVDEADYYCQAWDSDTFVVFGGGT
KVTVLG [SEQ ID NO: 11]

SRGGGGSGGGGSGGGGSLEMA [SEQ ID NO: 307]

**EVQLVETGGGVVQPGRSLRLSCAASGFTFSSYGMHWVRQAPGKGLEWVAVI
SHDGSNKYYADSVKGRFTISRDNSKDTLYLQMNSLRGEDTAVYYCARSNQW
SGYFSFDYWGQGTLVTVSS [SEQ ID NO: 12]**

TSGQAGQHHHHHHGAYPYDVPDYAS [SEQ ID NO: 308]

TABLE 4

ET200-006

DNA Sequence (light chain variable region scFv linker heavy chain variable region His tag + HA tag)
tcctatgtgctgactcagccaccctcagtgtcagtggccccaggaaagacg
gccaggattacctgtgggggaaacaacattggaagtaaaagtgtgcactgg
taccagcagaagccaggccaggcccctgtggtggtcatccattatgatagc
gaccggccctcaggatccctgagcgattctctggctccaactctgggaac
acggccaccctgaccatcagcagggtcgaagccggggatgaggccgactat
tactgtcaggtgtgggatagtagtagtgatcatccttatgtcttcggaact
gggaccaaggtcaccgtcctaggt [SEQ ID NO: 13]

tctagaggtggtggtggtagcggcggcggcggctctggtggtggtggatcc
ctcgagatggcc [SEQ ID NO: 305]

**gaggtgcagctggtgcagtctggagctgaggtgaagaagcctgggggctca
gtgaaggtctcctgcaaggcttctggttacaccttaccacctatggtatc
agctgggtgcgacaggcccctggacaagggcttgagtggatgggatggatc
aacacttacaatggtcacacaaactatgcacagaagctccagggcagagcc
acaatgaccgcagacacatccacgaacacagcctacatggagctgaggagc
ctgagatctgacgacactgccgtgtattactgtgcgcgcgttatctacggt
tctggtgattactggggtcaaggtactctggtgaccgtctcctca**
[SEQ ID NO: 14]

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy chain variable region His tag + HA tag)
SYVLTQPPSVSVAPGKTARITCGGNNIGSKSVHWYQQKPGQAPVVVIHYDS
DRPSGIPERFSGSNSGNTATLTISRVEAGDEADYYCQVWDSSSDHPYVFGT
GTKVTVLG [SEQ ID NO: 15]

SRGGGGSGGGGSGGGGSLEMA [SEQ ID NO: 307]

**EVQLVQSGAEVKKPGASVKVSCKASGYTFTTYGISWVRQAPGQGLEWMGWI
NTYNGHTNYAQKLQGRATMTADTSTNTAYMELRSLRSDDTAVYYCARVIYG
SGDYWGQGTLVTVSS [SEQ ID NO: 16]**

TSGQAGQHHHHHGAYPYDVPDYAS [SEQ ID NO: 308]

TABLE 5

ET200-007

DNA Sequence (light chain variable region scFv linker heavy chain variable region His tag + HA tag)
tcctatgtgctgactcagccactctcagtgtcagtggccccaggaaagacg
gccaggattacctgtgggggaaacaacattggaagtaaaactgtgcactgg
taccagcagaagccaggccaggcccctgtgctggtcatctattatgatagc
gaccggccctcaggatccctgagcgattctctggctccaactctgggaac
acggccaccctgaccatcagcagggtcgaagccggggatgaggccgactat
tactgtcaggtgtgggatagtagtagtgatcatcgggtgttcggcggaggg
accaagctgaccgtcctaggt [SEQ ID NO: 17]

tctagaggtggtggtggtagcggcggcggcggctctggtggtggtggatcc
ctcgagatggcc [SEQ ID NO: 305]

caggtgcagctgcaggagtcgggcccaggactggtgaagccttcggagacc
ctgtccctcacctgcaatgtctctggttactccatcagcagtggttacttt
tggggctggatccggcagcccccagggaaggggctggagtggattgggagt
atctatcatagtaggagcacctactacaacccgtccctcaagagtcgagtc
accatatcagtagacacgtccaagaaccagttctccctgaagctgaactct
gtgaccgccgcagacacgggcgtgtattactgtgcgcgcggttacggttac
ttcgattactggggtcaaggtactctggtgaccgtctcctca
[SEQ ID NO: 18]

---

TABLE 5-continued

ET200-007

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy chain variable region His tag + HA tag)
SYVLTQPLSVSVAPGKTARITCGGNNIGSKTVHWYQQKPGQAPVLVIYYDS
DRPSGIPERFSGSNSGNTATLTISRVEAGDEADYYCQVWDSSSDHRVFGGG
TKLTVLG [SEQ ID NO: 19]

SRGGGGSGGGGSGGGGSLEMA [SEQ ID NO: 307]

**QVQLQESGPGLVKPSETLSLTCNVSGYSISSGYFWGWIRQPPGKGLEWIGS
IYHSRSTYYNPSLKSRVTISVDTSKNQFSLKLNSVTAADTAVYYCARGYGY
FDYWGQGTLVTVSS [SEQ ID NO: 20]**

TSGQAGQHHHHHGAYPYDVPDYAS [SEQ ID NO: 308]

TABLE 6

ET200-008

DNA Sequence (light chain variable region scFv linker heavy chain variable region His tag + HA tag)
caatctgccctgactcagcctgcctccgtgtctgggtctcctggacagtcg
atcaccatctcctgcactggaaccagcagtgacgttggtggttataactat
gtctcctggtaccaacaacacccaggcaaagcccccaaactcatgatttat
gatgtcagtaatcggccctcaggggtttctaatcgcttctctggctccaag
tctggcaacacggcctccctgaccatctctgggctccaggctgaggacgag
gctgattattactgcagctcatatacaagcagcagcacttcgaaggtgttc
ggcggagggaccaagctgaccgtcctaggt [SEQ ID NO: 21]

tctagaggtggtggtggtagcggcggcggcggctctggtggtggtggatcc
ctcgagatggcc [SEQ ID NO: 305]

**gaggtgcagctggtggagtctggggggaggtgtggtacggctggggggtcc
ctgagactctcctgtgcagcctctggattcacctttggtgattatggcatg
agctgggtccgccaagctccagggaaggggctggagtgggtctctggtatt
aattggaatggtggtagcacaggttatgcagactctgtgaagggccgattc
accatctccagagacaacgccaagaactccctgtatctgcaaatgaacagt
ctgagagccgaggacacggccgtatattactgtgcgcgctctaaatacaac
ttccatgtttactacgattactggggtcaaggtactctggtgaccgtctcc
tca [SEQ ID NO: 22]**

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy chain variable region His tag + HA tag)
QSALTQPASVSGSPGQSITISCTGTSSDVGGYNYVSWYQQHPGKAPKLMIY
DVSNRPSGVSNRFSGSKSGNTASLTISGLQAEDEADYYCSSYTSSSTSKVF
GGGTKLTVLG [SEQ ID NO: 23]

SRGGGGSGGGGSGGGGSLEMA [SEQ ID NO: 307]

**EVQLVESGGGVVRPGGSLRLSCAASGFTFGDYGMSWVRQAPGKGLEWVSGI
NWNGGSTGYADSVKGRFTISRDNAKNSLYLQMNSLRAEDTAVYYCARSKYN
FHVYYDYWGQGTLVTVSS [SEQ ID NO: 24]**

TSGQAGQHHHHHGAYPYDVPDYAS [SEQ ID NO: 308]

TABLE 7

ET200-009

DNA Sequence (light chain variable region <u>scFv linker</u> **heavy
chain variable region** His tag + HA tag)
cagtctgtgttgacgcagccaccctcagcgtctgggaccccgggcagaca
gtcaccatctcttgttctggaagcaactccaacatcggaagtaattatgta
tactggtaccagcagctcccaggaacggcccccaaactcctcatctatagg
aataatcagcggccctcaggggtccctgaccgattctcaggctccaagtct
ggcacctcagcctccctggccatcagtgggctccgctccgaggatgaggct
gattattactgtgcagcatgggatgacagcctgagtgatatgtatcggaac
tgggaccaaggtcaccgtcctaggt [SEQ ID NO: 25]

<u>tctagaggtggtggtggtagcggcggcggcggctctggtggtggtggatcc
ctcgagatggcc</u> [SEQ ID NO: 305]

**caggtgcagctggtgcagtctggagctgaggtgaagaagcctggggcctca
gtgaaggtctcctgcaaggcttctggttacacctttaccagctatggtatc
agctgggtgcgacaggcccctggacaagggcttgagtggatgggatggatc
agcgcttacaatggtaacacaaactatgcacagaagctccagggcagagtc
accatgaccacagacacatccacgagcacagcctacatggagctgaggagc
ctgagatctgacgacgccgtgtattactgtgcgcgctcttctggtaac
atggtttcttggaaagatatgtggggtcaaggtactctggtgaccgtctcc
tca** [SEQ ID NO: 26]

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region <u>scFv linker</u> **heavy
chain variable region** His tag + HA tag)
QSVLTQPPSASGTPGQTVTISCSGSNSNIGSNYVYWYQQLPGTAPKLLIYR
NNQRPSGVPDRFSGSKSGTSASLAISGLRSEDEADYYCAAWDDSLSAYVFG
TGTKVTVLG [SEQ ID NO: 27]

<u>SRGGGGSGGGGSGGGGSLEMA</u> [SEQ ID NO: 307]

**QVQLVQSGAEVKKPGASVKVSCKASGYTFTSYGISWVRQAPGQGLEWMGWI
SAYNGNTNYAQKLQGRVTMTTDTSTSTAYMELRSLRSDDTAVYYCARSSGN
MVSWKDMWGQGTLVTVSS** [SEQ ID NO: 28]

TSGQAGQHHHHHHGAYPYDVPDYAS [SEQ ID NO: 308]

TABLE 8

ET200-010

DNA Sequence (light chain variable region <u>scFv linker</u> **heavy
chain variable region** His tag + HA tag)
caatctgccctgactcagcctgcctccgtgtctgggtctcctggacagtcg
atcaccatctcttgcactggaaccagcagtgacgttggtggttataactct
gtctcctggtaccaacaacacccaggcaaagcccccagactcatgatttat
gatgtcagtaatcggccctcaggggtttctaatcgcttctctggctccaag
tctggcaacacggcctccctgaccatctctgggctccaggctgaggacgag
gctgattattactgcagctcatatacaagcagcagcacccctttagtcttc
ggaactgggaccaaggtcaccgtcctaggt [SEQ ID NO: 29]

<u>tctagaggtggtggtggtagcggcggcggcggctctggtggtggtggatcc
ctcgagatggcc</u> [SEQ ID NO: 305]

**caggtgcagctggtgcagtctggggctgaggtgaagaagcctggggcctca
gtgaaggtctcctgcaaggcttctggttacacctttaccagctatggtatc
agctgggtgcgacaggcccctggacaagggcttgagtggatgggatggatc
agcgcttacaatggtaacacaaactatgcacagaagctccagggcagagtc
accatgaccacagacacatccacgagcacagcctacatggagctgaggagc
ctgagatctgacgacaggccgtgtattactgtgcgcgcggtgctgttgct
taccatgattggggtcaaggtactctggtgaccgtctcctca**
[SEQ ID NO: 30]

TABLE 8-continued

ET200-010

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region <u>scFv linker</u> **heavy
chain variable region** His tag + HA tag)
QSALTQPASVSGSPGQSITISCTGTSSDVGGYNSVSWYQQHPGKAPRLMIY
DVSNRPSGVSNRFSGSKSGNTASLTISGLQAEDEADYYCSSYTSSSTPLVF
GTGTKVTVLG [SEQ ID NO: 31]

<u>SRGGGGSGGGGSGGGGSLEMA</u> [SEQ ID NO: 307]

**QVQLVQSGAEVKKPGASVKVSCKASGYTFTSYGISWVRQAPGQGLEWMGWI
SAYNGNTNYAQKLQGRVTMTTDTSTSTAYMELRSLRSDDTAVYYCARGAVA
YHDWGQGTLVTVSS** [SEQ ID NO: 32]

TSGQAGQHHHHHHGAYPYDVPDYAS [SEQ ID NO: 308]

TABLE 9

ET200-011

DNA Sequence (light chain variable region <u>scFv linker</u> **heavy
chain variable region** His tag + HA tag)
cagtctgtcgtgacgcagccgccctcagtgtctgcggccccaggacagagg
gtcaccatctcctgctctggaagcagctccaacatttcgatttatgatgta
tcctggtatcagcagctcccaggaacagcccccaaactcctcatttatggc
aataataagcgaccctcggggattgctgaccgattctctggctccacgtct
ggcacgtcagccaccctgggcatcaccggactccagactggggacgaggcc
gattattactgcggaacatgggatgacagtctgagtgggggggtgttcggc
ggagggaccaagctgaccgtcctaggt [SEQ ID NO: 33]

<u>tctagaggtggtggtggtagcggcggcggcggcggctctggtggtggtgga
tccctcgagatggcc</u> [SEQ ID NO: 305]

**cagatgcagctggtgcaatctggggctgaggtgaagaagcctgggtcctcg
gtgaaggtctcctgcgaggcttctggaggcaccctcagcagctatgctatc
aactgggtgcgacaggcccctggacaagggcttgagtggatgggagggatc
atccctatgtttggtacagcacactacgcacagaagttccagggcagagtc
acgattaccgggacgaatccacgaaaacagcctacatggagctgagcagc
ctgagatctgaggacactgccgtgtattactgtgcgcgcggtgttcattac
gcttctttcgatcattggggtcaaggtactctggtgaccgtctcctca**
[SEQ ID NO: 34]

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region <u>scFv linker</u> **heavy
chain variable region** His tag + HA tag)
QSVVTQPPSVSAAPGQRVTISCSGSSSNISIYDVSWYQQLPGTAPKLLIYG
NNKRPSGIADRFSGSTSGTSATLGITGLQTGDEADYYCGTWDDSLSGGVFG
GGTKLTVLG [SEQ ID NO: 35]

<u>SRGGGGSGGGGSGGGGSLEMA</u> [SEQ ID NO: 307]

**QMQLVQSGAEVKKPGSSVKVSCEASGGTLSSYAINWVRQAPGQGLEWMGGI
IPMFGTAHYAQKFQGRVTITADESTKTAYMELSSLRSEDTAVYYCARGVHY
ASFDHWGQGTLVTVSS** [SEQ ID NO: 36]

TSGQAGQHHHHHHGAYPYDVPDYAS [SEQ ID NO: 308]

TABLE 10

ET200-012

DNA Sequence (light chain variable region scFv linker heavy chain variable region His tag + HA tag)
cagtctgtgttgacgcagccgccctcagtgtctgcggccgcaggacagaag
gtcaccatctcctgctctggaagcgactccaacattgggaataattatgtg
tcctggtatcaacacctcccagggacagcccccaaactcctcatttatgac
gttaaaaatcgaccctcagggattcctgaccggttctccggctccaagtct
ggctcgtcagccaccctaggcatcgccggactccagcctggggacgaggcc
gattattactgcggaacatgggacagtcggctggatgcctatgtcttcgga
actgggaccaaggtcaccgtcctaggt [SEQ ID NO: 37]

tctagaggtggtggtggtagcggcggcggcggctctggtggtggtggatcc
ctcgagatggcc [SEQ ID NO: 305]

**cagatgcagctggtgcaatctggagctgaggtgaagaagcctggggcctca
gtgaaggtctcctgcaagacttctggtttcccctttaatatctttggaatc
acctgggtgcgacaggcccctggacaaagggcttgagtggatgggatggatc
agcggttacaacggtaacacagactacccacagaagttccagggcagagtc
accatgtccacagacacatccacagtacgatcatccacagtacatggactacgaggaac
ctgaaatctgacgacacggccgtgtattactgtgcgcgcggtgcttacggt
ggtatggatacttggggtcaaggtactctggtgaccgtctcctca
[SEQ ID NO: 38]**

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy chain variable region His tag + HA tag)
QSVLTQPPSVSAAAGQKVTISCSGSDSNIGNNYVSWYQHLPGTAPKWYDVK
NRPSGIPDRFSGSKSGSSATLGIAGLQPGDEADYYCGTWDSRLDAYVFGTG
TKVTVLG [SEQ ID NO: 39]

SRGGGGSGGGGSGGGGSLEMA [SEQ ID NO: 307]

**QMQLVQSGAEVKKPGASVKVSCKTSGFPFNIFGITWVRQAPGQGLEWMGWI
SGYNGNTDYPQKFQGRVTMSTDTSTSTAYMELRNLKSDDTAVYYCARGAYG
GMDTWGQGTLVTVSS [SEQ ID NO: 40]**

TSGQAGQHHHHHHGAYPYDVPDYAS [SEQ ID NO: 308]

TABLE 11

ET200-013

DNA Sequence (light chain variable region scFv linker heavy chain variable region His tag + HA tag)
cagtctgtcgtgacgcagccgccctcagtgtctggggcccccagggcagagg
gtcaccatctcctgcactgggagcacctccaacatcggggcaggttatgat
gtacactgtgtatcagcagcttccaggaacagcccccaaactcctcatctat
actaacaactttcggccctcaggggtccctgaccgattctctgcctccaag
tctggcacttcagcttcctggccatcactggtctccaggctgaggatgag
gctgattattactgcggaacatgggatagcagcctgagtgccgttgtgttc
ggcggagggaccaagctgaccgtcctaggt [SEQ ID NO: 41]

tctagaggtggtggtggtagcggcggcggcggctctggtggtggtggatcc
ctcgagatggcc [SEQ ID NO: 305]

**gaggtgcagctggtggagtctggaactgaggtgaagaagcctggggcctca
gtgaaagtctcctgcaaggcttctggttacatgtttaccagttatggtctc
aactgggtgcgacaggcccctggacaaagggcttgagtggatgggatggatc
agcgctaacaatggtaagacaaattatgctaagaaattccaggacagagtc
accatgaccagagacacttccacgagcacaggctacatggaactgaggagc
ctgagatctgacgacacggccgtatattactgtgcgcgccatatcggtggt
tcttacttcgatcgttggggtcaaggtactctggtgaccgtctcctca
[SEQ ID NO: 42]**

TABLE 11-continued

ET200-013

ACTAGTGGCCAGGCCGGCCAGCACCATCACCATCACCATGGCGCATACCCG
TACGACGTTCCGGACTACGCTTCT [SEQ ID NO: 306]

Amino Acid Sequence (light chain variable region scFv linker heavy chain variable region His tag + HA tag)
QSVVTQPPSVSGAPGQRVTISCTGSTSNIGAGYDVHWYQQLPGTAPKWYTN
NFRPSGVPDRFSASKSGTSASLAITGLQAEDEADYYCGTWDSSLSAVVFGG
GTKLTVLG [SEQ ID NO: 43]

SRGGGGSGGGGSGGGGSLEMA [SEQ ID NO: 307]

**EVQLVESGTEVKKPGASVKVSCKASGYMFTSYGLNWVRQAPGQGLEWMGWI
SANNGKTNYAKKFQDRVTMTRDTSTSTGYMELRSLRSDDTAVYYCARHIGG
SYFDRWGQGTLVTVSS [SEQ ID NO: 44]**

TSGQAGQHHHHHHGAYPYDVPDYAS [SEQ ID NO: 308]

TABLE 12

ET200-014

DNA Sequence (light chain variable region scFv linker heavy chain variable region His tag + HA tag)
tcctatgtgctgactcagccaccctcagtgtcagtggccccaggaaaga
cggccaggattacctgtgggggaaacaacattggaagtaaaagtgtgca
ctggtaccagcagaagccaggccaggcccctgtgctggtcatctattat
gatagcgaccggccctcagggatccctgagcgattctctggctccaact
ctgggaacacggccacccctgaccatcagcagggtcgaagccggggatga
ggccgactattactgtcaggtgtgggatagtagtagtgatcattatgtc
ttcggaactgggaccaaggtcaccgtcctaggt [SEQ ID NO: 45]

tctagaggtggtggtggtagcggcggcggcggctctggtggtggtggat
ccctcgagatggcc [SEQ ID NO: 305]

**gaggtgcagctggtggagactggggggaggcttggtacagcctggggggt
ccctgagactctcctgtgcagcctctggattcacctttagcagctatgc
catgagctgggtccgccaggctccagggaaggggctggagtgggtctca
gctattagtggtagtgatggtagcacatactacgcagactccgtgaagg
gccggttcaccatctccagagacaattccaagaacacgctgtatctgca
aatgaacagcctgagagacgaggacacggccgtatattactgtgcgcgc
tctcatgaagctaacctggttggtgattggtggggtcaaggtactctgg
tgaccgtctcctca [SEQ ID NO: 46]**

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
SYVLTQPPSVSVAPGKTARITCGGNNIGSKSVHWYQQKPGQAPVLVIYY
DSDRPSGIPERFSGSNSGNTATLTISRVEAGDEADYYCQVWDSSSDHYV
FGTGTKVTVLG [SEQ ID NO: 47]

SRGGGGSGGGGSGGGGSLEMA [SEQ ID NO: 307]

**EVQLVETGGGLVQPGGSLRLSCAASGFTFSSYAMSWVRQAPGKGLEWVS
AISGSDGSTYYADSVKGRFTISRDNSKNTLYLQMNSLRDEDTAVYYCAR
SHEANLVGDWWGQGTLVTVSS [SEQ ID NO: 48]**

TSGQAGQHHHHHHGAYPYDVPDYAS [SEQ ID NO: 308]

TABLE 13

ET200-015

DNA Sequence (light chain variable region scFv linker heavy chain variable region His tag + HA tag)
cagtctgtggtgactcagccacccctcagtgtcagtggccccaggaaaga
cggccaggattacctgtgggggaaacaacattggaagtaaaagtgtgca
ctggtaccagcagaagccaggccaggcccctgtgctggtcatctattat
gatagcgaccgcccctcagggatccctgagcgattctctggctccaact
ctgggaacacggccaccctgaccatcagcagggtcgaagccggggatga
ggccgactattactgtcaggtgtgggatagtagtagtgatgtggtattc
ggcggagggaccaagctgaccgtcctaggt [SEQ ID NO: 49]

tctagaggtggtggtggtagcggcggcggcggctctggtggtggtggat
ccctcgagatggcc [SEQ ID NO: 305]

**gaggtccagctggtacagtctggagctgaggtgaagaagcctggggcct
cagtgaaggtctcctgcaaggcttctggttacacctttaccagctacgg
tatcagctgggtgcgacaggcccctggacaagggcttgagtggatggga
tggatcagcgcttacaatggtaacacaaactatgcacagaagctccagg
gcagagtcaccatgaccacagacacatccacgagcacagcctacatgga
gctgaggagcctgagatctgacgacacggccgtgtattactgcgcgc
tggggtggtttcggtgctgttgatcattggggtcaaggtactctggtga
ccgtctcctca** [SEQ ID NO: 50]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
QSVVTQPPSVSVAPGKTARITCGGNNIGSKSVHWYQQKPGQAPVLVIYY
DSDRPSGIPERFSGSNSGNTATLTISRVEAGDEADYYCQVWDSSSDVVF
GGGTKLTVLG [SEQ ID NO: 51]

SRGGGGSGGGGSGGGGSLEMA [SEQ ID NO: 307]

**EVQLVQSGAEVKKPGASVKVSCKASGYTFTSYGISWVRQAPGQGLEWMG
WISAYNGNTNYAQKLQGRVTMTTDTSTSTAYMELRSLRSDDTAVYYCAR
WGGFGAVDHWGQGTLVTVSS** [SEQ ID NO: 52]

TSGQAGQHHHHHHGAYPYDVPDYAS [SEQ ID NO: 308]

TABLE 14

ET200-016

DNA Sequence (light chain variable region scFv linker heavy chain variable region His tag + HA tag)
tcttctgagctgactcaggaccctgctgtgtctgtggccttgggacaga
cagtcaagatcacgtgccaaggagacagcctcacagactaccatgcaac
ctggtaccagcagaagccaggacaggcccctgtcgctgtcatctatgct
acaaacaaccggcccactgggatcccagaccgattctctggttccagtt
ccggaaacacagatattgaccatcactggggctcaggcggaagatgagg
ctgactattactgtaattcccgggacagcggcacggacgaagtgttatt
cggcggagggaccaagctgaccgtcctaggt [SEQ ID NO: 53]

tctagaggtggtggtggtagcggcggcggcggctctggtggtggtggat
ccctcgagatggcc [SEQ ID NO: 305]

**gaggtgcagctggtggagactggggggaggcctggtcaagcctggggggt
ccctgagactctcctgtgcagcctctggattcacttcagtagctatag
catgaactgggtccgcaggctccagggaaggggctggagtgggtctca
tccattagtagtagtagtagtataactacgcagactcagtgaagg
gccgattcaccatctccagagacaacgccaagaactcactgtatctgca
aatgaacagcctgagagccgaggacacggccgtgtattactgtgcgcgc
ggtcaggggtacgattactggggtcaaggtactctggtgaccgtctcct
ca** [SEQ ID NO: 54]

TABLE 14-continued

ET200-016

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
SSELTQDPAVSVALGQTVKITCQGDSLTDYHATWYQQKPGQAPVAVIYA
TNNRPTGIPDRFSGSSSGNTASLTITGAQAEDEADYYCNSRDSGTDEVL
FGGGTKLTVLG [SEQ ID NO: 55]

SRGGGGSGGGGSGGGGSLEMA [SEQ ID NO: 307]

**EVQLVETGGGLVKPGGSLRLSCAASGFTFSSYSMNWVRQAPGKGLEWVS
SISSSSSYIYYADSVKGRFTISRDNAKNSLYLQMNSLRAEDTAVYYCAR
GQGYDYWGQGTLVTVSS** [SEQ ID NO: 56]

TSGQAGQHHHHHHGAYPYDVPDYAS [SEQ ID NO: 308]

TABLE 15

ET200-017

DNA Sequence (light chain variable region scFv linker heavy chain variable region His tag + HA tag)
tcctatgtgctgactcagccacccctcggtgtcagtggccccaggaaaga
cggccaggattacctgtgggggaaacaacattggaagtaaaagtgtgca
ctggtaccagcagaagccaggccaggcccctgtgctggtcgtctatgat
gatagcgaccggcccctcagggatccctgagcgattctctggctccaact
ctgggaacacggccaccctgagcatcagcagggtcgaagccggggatga
ggccgactattactgtcaggtgtgggatagtagtagtgatcatactgtc
ttcggaactgggaccaaggtcaccgtcctaggt [SEQ ID NO: 57]

tctagaggtggtggtggtagcggcggcggcggctctggtggtggtggat
ccctcgagatggcc [SEQ ID NO: 305]

**caggtgcagctacagcagtggggcgcaggactgttgaagccttcggaga
ccctgtccctcacctgcgctgtctatggtgggtccttcagtggttacta
ctggagctggatccgccagcccccagggaaggggctggagtggattggg
gaaatcaatcatagtggaagcaccaactacaaccgtccctcaagagtc
gagtcaccatatcagtagacacgtccaagaaccagttctccctgaagct
gagctctgtgaccgccgcggacacggccgtgtattactgtgcgcgctac
tacccgggtatggatatgtggggtcaaggtactctggtgaccgtctcct
ca** [SEQ ID NO: 58]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
SYVLTQPPSVSVAPGKTARITCGGNNIGSKSVHWYQQKPGQAPVLVVYD
DSDRPSGIPERFSGSNSGNTATLSISRVEAGDEADYYCQVWDSSSDHTV
FGTGTKVTVLG [SEQ ID NO: 59]

SRGGGGSGGGGSGGGGSLEMA [SEQ ID NO: 307]

**QVQLQQWGAGLLKPSETLSLTCAVYGGSFSGYYWSWIRQPPGKGLEWIG
EINHSGSTNYNPSLKSRVTISVDTSKNQFSLKLSSVTAADTAVYYCARY
YPGMDMWGQGTLVTVSS** [SEQ ID NO: 60]

TSGQAGQHHHHHHGAYPYDVPDYAS [SEQ ID NO: 308]

TABLE 16

ET200-018

DNA Sequence (light chain variable region <u>scFv linker</u> heavy chain variable region His tag + HA tag)
caggctgtgctgactcagccgccctcaacgtctgggaccccgggcaga
gggtcaccatctcttgttctggaagcagctccaacatcgggagaaatgg
tgtaaactggtaccagcagctcccaggagcggcccccaaagtcctcatc
tataatgataatcagcgaccctcaggggtccctgaccgagtctctggct
cccagtctggctcctcaggcaccctgccatcgatgggcttcggtctga
ggatgaggctgattattactgtgcggcatgggatgacagcctgcatggt
gtggtattcggcggagggaccaagctgaccgtcctaggt
[SEQ ID NO: 61]

<u>tctagaggtggtggtggtagcggcggcggcggctctggtggtggtggat
ccctcgagatggcc</u> [SEQ ID NO: 305]

**caggtccagctggtacagtctgggggctgaggtgaagaagcctggggcct
cagtgaaggtctcctgcaaggtttccggatacaccctcaatgaattatc
catgcactgggtgcgacaggctcctggaaaagggcttgagtggatggga
ggttttgatcctgaagatggtgaaacaatctacgcacagaagttccagg
gcagagtcaccatgaccgaggacacatctacagacacagcctacatgga
gctgagcagcctgagatctgaggacactgccgtgtattactgtgcgcgc
ggtggttacggtgattcttggggtcaaggtactctggtaccgtctcct
ca** [SEQ ID NO: 62]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region <u>scFv linker</u> heavy chain variable region His tag + HA tag)
QAVLTQPPSTSGTPGQRVTISCSGSSSNIGRNGVNWYQQLPGAAPKVLI
YNDNQRPSGVPDRVSGSQSGSSGTLAIDGLRSEDEADYYCAAWDDSLHG
VVFGGGTKLTVLG [SEQ ID NO: 63]

<u>SRGGGGSGGGGSGGGGSLEMA</u> [SEQ ID NO: 307]

**QVQLVQSGAEVKKPGASVKVSCKVSGYTLNELSMHWVRQAPGKGLEWMG
GFDPEDGETIYAQKFQGRVTMTEDTSTDTAYMELSSLRSEDTAVYYCAR
GGYGDSWGQGTLVTVSS** [SEQ ID NO: 64]

TSGQAGQHHHHHHGAYPYDVPDYAS [SEQ ID NO: 308]

TABLE 17

ET200-019

DNA Sequence (light chain variable region <u>scFv linker</u> heavy chain variable region His tag + HA tag)
aattttatgctgactcagccccactctgtgtcggagtctccggggaaga
cggtaaccatctcctgcacccgcagcagtggcagcattgccagcaacta
tgtgcagtggtaccagcagcgcccgggcagtgcccccaccactgtgatc
tatgaggataaccaaagaccctctggggtccctgatcggttctctggct
ccatcgacagctcctccaactctgcctccctcaccatctctggactgaa
gactgaggacgaggctgactactactgtcagtcttatgatagcagcaat
tatgggtgttcggcggagggaccaagctgaccgtcctaggt
[SEQ ID NO: 65]

<u>tctagaggtggtggtggtagcggcggcggcggctctggtggtggtggat
ccctcgagatggcc</u> [SEQ ID NO: 305]

**caggtgcagctggtgcaatctggggctgaggtgaagaggcctggtcct
cggtgaaggtctcctgcacggcttctggaggcaccttcagcagcgatgc
tatcagctgggtgcgacaggcccctggacaagggcttgagtggatggga
ggaatcatccctatgtttggtacagcaaactacgcacagaagttccagg
gcagagtcaccattaccgcggacgaatccacgagcacagcctacatgga
gctgagcagcctgagatctgaggacacgccgtgtattactgtgcgcgc
gaaggttactactaccgtctgcttacctgggttctgttctgaacgaca
tctcttctgtttacgatgaatggggtcaaggtactctggtgaccgtctc
ctca** [SEQ ID NO: 66]

TABLE 17-continued

ET200-019

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region <u>scFv linker</u> heavy chain variable region His tag + HA tag)
NFMLTQPHSVSESPGKTVTISCTRSSGSIASNYVQWYQQRPGSAPTTVI
YEDNQRPSGVPDRFSGSIDSSSNSASLTISGLKTEDEADYYCQSYDSSN
SWVFGGGTKLTVLG [SEQ ID NO: 67]

<u>SRGGGGSGGGGSGGGGSLEMA</u> [SEQ ID NO: 307]

**QVQLVQSGAEVKRPGSSVKVSCTASGGTFSSDAISWVRQAPGQGLEWMG
GIIPMFGTANYAQKFQGRVTITADESTSTAYMELSSLRSEDTAVYYCAR
EGYYYPSAYLGSVLNDISSVYDEWGQGTLVTVSS** [SEQ ID NO: 68]

TSGQAGQHHHHHHGAYPYDVPDYAS [SEQ ID NO: 308]

TABLE 18

ET200-020

DNA Sequence (light chain variable region <u>scFv linker</u> heavy chain variable region His tag + HA tag)
cagtctgtcgtgacgcagccgccctcagtgtctgcggccccaggacaga
aggtcaccatctcctgctctggaagcacctccaacattggaaataatga
tgtatcctggtaccagcagctcccaggaacagcccccaaactcctcatt
tatgacaataataagcgaccctcaggggattcctgaccgattctctggct
ccaagtctggcacgtcagccaccctgggcatcaccggactccagactgg
ggacgaggccgattattactgcggaacatgggatagcagctgagtgct
tcttgggtcttcggcagagggaccaagctgaccgtcctaggt
[SEQ ID NO: 69]

<u>tctagaggtggtggtggtagcggcggcggcggctctggtggtggtggat
ccctcgagatggcc</u> [SEQ ID NO: 305]

**caggtgcagctggtgcagtctggagctgaggtgaagaagcctggggcct
cagtgaaggtctcctgcaaggcttctggttacacctttaccagctatgg
tatcagctgggtgcgacaggcccctggacaagggcttgagtggatggga
tggatcagcgcttacaatggtaacacaaactatccacagaagctccagg
gcagagtcaccatgaccacagacacgagcacagcctacatgga
gctgaggagcctgagatctgacgacacgccgtgtattactgtgcgcgc
tctatgacttctttcgattactggggtcaaggtactctggtgaccgtct
cctca** [SEQ ID NO: 70]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region <u>scFv linker</u> heavy chain variable region His tag + HA tag)
QSVVTQPPSVSAAPGQKVTISCSGSTSNIGNNDVSWYQQLPGTAPKWYD
NNKRPSGIPDRFSGSKSGTSATLGITGLQTGDEADYYCGTWDSSVSASW
VFGRGTKLTVLG [SEQ ID NO: 71]

<u>SRGGGGSGGGGSGGGGSLEMA</u> [SEQ ID NO: 307]

**QVQLVQSGAEVKKPGASVKVSCKASGYTFTSYGISWVRQAPGQGLEWMG
WISAYNGNTNYPQKLQGRVTMTTDPSTSTAYMELRSLRSDDTAVYYCAR
SMTSFDYWGQGTLVTVSS** [SEQ ID NO: 72]

TSGQAGQHHHHHHGAYPYDVPDYAS [SEQ ID NO: 308]

TABLE 19

ET200-021

DNA Sequence (light chain variable region scFv linker heavy chain variable region His tag + HA tag)
cagtctgtgttgacgcagccgccctcagtgtctgcggccccaggacaga
aggtcaccatctcctgctctggaagcaactccaacattgggaataatta
tgtatcctggtatcagcaactcccagggacagcccccaaactcctcatt
tatgacaataataagcgaccctcagggattcctgaccgattctctggct
ccaggtctggcacgtcagccaccctgggcatcaccggactccagactgg
ggacgaggccgattattactgcggaacatggaataccactgtgactcct
ggctatgtatcggaactgggaccaaggtcaccgtcctaggt
[SEQ ID NO: 73]

tctagaggtggtggtggtagcggcggcggcggctctggtggtggtggat
ccctcgagatggcc [SEQ ID NO: 305]

**gaagtgcagctggtgcagtctggagctgaggtgaagaagcctggggcct
cagtgaaggtctcctgcaaggcttctggttacacctttaccagctatgg
tatcagctgggtgcgacaggcccctggacaagggcttgagtggatggga
tggatcagcgcttacaatggtaacacaaactatgcacagaagctccagg
gcagagtcaccatgaccacagacacatccacgagcacagcctacatgga
gctgaggagcctgagatctgacgacaccgccatgtattactgtgcgcgc
tctgtttacgacctggatacttggggtcaaggtactctggtgaccgtct
cctca [SEQ ID NO: 74]**

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
QSVLTQPPSVSAAPGQKVTISCSGSNSNIGNNYVSWYQQLPGTAPKWYD
NNKRPSGIPDRFSGSRSGTSATLGITGLQTGDEADYYCGTWNTTVTPGY
VFGTGTKVTVLG [SEQ ID NO: 75]

SRGGGGSGGGGSGGGGSLEMA [SEQ ID NO: 307]

**EVQLVQSGAEVKKPGASVKVSCKASGYTFTSYGISWVRQAPGQGLEWMG
WISAYNGNTNYAQKLQGRVTMTTDTSTSTAYMELRSLRSDDTAMYYCAR
SVYDLDTWGQGTLVTVSS [SEQ ID NO: 76]**

TSGQAGQHHHHHHGAYPYDVPDYAS [SEQ ID NO: 308]

TABLE 20

ET200-022

DNA Sequence (light chain variable region scFv linker heavy chain variable region His tag + HA tag)
cagtctgtcgtgacgcagccgccctcagtgtctgcggcccaggacaga
aggtcaccatctcctgctctggaagcagctccaacattgggaataatta
tgtatcctggtaccagcagctcccaggaacagcccccaaactcctcatt
tatgacaataataagcgaccctcagggattcctgaccgattctctggct
ccaagtctggcacgtcagccaccctgggcatcaccggactccagactgg
ggacgaggccgattattactgcggaacatgggatagcagctggggggcc
catatgtatcggaactgggaccaaggtcaccgtcctaggt
[SEQ ID NO: 77]

tctagaggtggtggtggtagcggcggcggcggctctggtggtggtggat
ccctcgagatggcc [SEQ ID NO: 305]

**gaggtgcagctggtgcagtcttggggaggctcggaacagcctggcaggt
ccctgagactctcctgtgcagcctctggattcacctttgatgattatgc
catgcactgggtccggcaagctccagggaagggcctggagtgggtctca
ggtattagttggaatagcggtagcataggctatgcagactctgtgaagg
gccgattcaccatctccagagacaacgccaagaattcctgtatctgca
aatgaacagtctgagagctgaggacaccgccatgtattactgtgcgcgc
taccgtcaggttggttctgcttacgattcttggggtcaaggtactctgg
tgaccgtctcctca [SEQ ID NO: 78]**

TABLE 20-continued

ET200-022

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
QSVVTQPPSVSAAPGQKVTISCSGSSSNIGNNYVSWYQQLPGTAPKLLI
YDNNKRPSGIPDRFSGSKSGTSATLGITGLQTGDEADYYCGTWDSSLGA
PYVFGTGTKVTVLG [SEQ ID NO: 79]

SRGGGGSGGGGSGGGGSLEMA [SEQ ID NO: 307]

**EVQLVQSWGGSEQPGRSLRLSCAASGFTFDDYAMHWVRQAPGKGLEWVS
GISWNSGSIGYADSVKGRFTISRDNAKNSLYLQMNSLRAEDTAMYYCAR
YRQVGSAYDSWGQGTLVTVSS [SEQ ID NO: 80]**

TSGQAGQHHHHHHGAYPYDVPDYAS [SEQ ID NO: 308]

TABLE 21

ET200-023

DNA Sequence (light chain variable region scFv linker heavy chain variable region His tag + HA tag)
ctgcctgtgctgactcagccaccctcggtgtcagtggccccaggaaaga
cggccaggattacctgtggggggaaacaacattggaagtaaaagtgtgca
ctggtatcagcagaagccaggccaggcccctgtgctggtcgtctatgct
gatagcgaccctcagggatccctgagcgattctctggctccaact
ctgggaacacggccaccctgaccatcagcagggtcgaagccgggggatga
ggccgactattactgtcaggtgtgggatagtagtagttatcataattat
gtatcggaactgggaccaaggtcaccgtcctaggt
[SEQ ID NO: 81]

tctagaggtggtggtggtagcggcggcggcggctctggtggtggtggat
ccctcgagatggcc [SEQ ID NO: 305]

**gaggtgcagctggtgcagtctggagctgaggtgaagaagcctggggcct
cagtgaaggtctcctgcaaggcttctggttacacctttaccagctatgg
tatcagctgggtgcgacaggcccctggacaagggcttgagtggatggga
tggatcagcgcttacaatggtaacacaaactatgcacagaagctccagg
gcagagtcaccatgaccacagacacatccacgagcacagcctacatgga
gctgagcagcctgagatctgaggacaccgccatgtattactgtgcgcgc
tactggggtttcggtgtttctgatcgttggggtcaaggtactctggtga
ccgtctcctca [SEQ ID NO: 82]**

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy chain variable region His tag + HA tag)
LPVLTQPPSVSVAPGKTARITCGGNNIGSKSVHWYQQKPGQAPVLVVYA
DSDRPSGIPERFSGSNSGNTATLTISRVEAGDEADYYCQVWDSSSYHNY
VFGTGTKVTVLG [SEQ ID NO: 83]

SRGGGGSGGGGSGGGGSLEMA [SEQ ID NO: 307]

**EVQLVQSGAEVKKPGASVKVSCKASGYTFTSYGISWVRQAPGQGLEWMG
WISAYNGNTNYAQKLQGRVTMTTDTSTSTAYMELSSLRSEDTAMYYCAR
YWGFGVSDRWGQGTLVTVSS [SEQ ID NO: 84]**

TSGQAGQHHHHHHGAYPYDVPDYAS [SEQ ID NO: 308]

TABLE 22

ET200-024

DNA Sequence (light chain variable region scFv linker heavy
chain variable region His tag + HA tag)
aattttatgctgactcagccccactctgtgtcggagtctccggggaaga
cggtaaccatctcctgcaccggcagcagtggcagcattgccagcaacta
tgtgcagtggtaccagcagcgcccgggcagtgcccccaccactgtgatc
tatgaggataaccaaagaccctctggggtccccgatcggttctctggct
ccatcgacagctcctccaactctgcctccctcaccatctctggacttgaa
gactgaggacgaggctgactactactgtcagtcttatgacagcagcaat
ctttgggtgttcggcggagggaccaagctgaccgtcctaggt
[SEQ ID NO: 85]

tctagaggtggtggtggtagcggcggcggcggctctggtggtggtggat
ccctcgagatggcc [SEQ ID NO: 305]

cagatgcagctggtgcagtctgggggctgaggtgaagaagcctgggtcct
cggtgaaggtctcctgcaaggcttctggaggcaccttcagcagctatgc
tatcagctgggtgcgacaggcccctggacaagggcttgagtggatggga
gggatcatccctatctttggtacagcaaactacgcacagaagttccagg
gcagagtcacgattaccgcggacgaatccacgagcacagcctacatgga
gctgagcagcctgagatctgaggacactgccgtgtattactgtgcgccg
tacaactactactactacgattcttggggtcaaggtactctggtgaccg
tctcctca [SEQ ID NO: 86]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy
chain variable region His tag + HA tag)
NFMLTQPHSVSESPGKTVTISCTGSSGSIASNYVQWYQQRPGSAPTTVI
YEDNQRPSGVPDRFSGSIDSSSNSASLTISGLKTEDEADYYCQSYDSSN
LWVFGGGTKLTVLG [SEQ ID NO: 87]

SRGGGGSGGGGSGGGGSLEMA [SEQ ID NO: 307]

QMQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
YNYYYYDSWGQGTLVTVSS [SEQ ID NO: 88]

TSGQAGQHHHHHGAYPYDVPDYAS [SEQ ID NO: 308]

TABLE 23

ET200-025

DNA Sequence (light chain variable region scFv linker heavy
chain variable region His tag + HA tag)
gacatccagatgacccagtctccatcctccctgtctgcatctgtaggag
acagagtcaccatcacttgccgggcaagtcagagcattagcagctattt
aaattggtatcagcagaaaccagggaaagcccctaagctcctgatctat
gctgcatccagtttgcaaagtggggtcccatcaaggttcagtggcagtg
gatctgggacagatttcactctcaccatcagcagtctgcaacctgaaga
ttttgcaacttactactgtcaacagagttacagtacccccattcacttc
ggccctgggaccaaagtggatatcaaacgt [SEQ ID NO: 89]

tctagaggtggtggtggtagcggcggcggcggctctggtggtggtggat
ccctcgagatggcc [SEQ ID NO: 305]

gaggtgcagctggtgcagtctgggggctgaggtgaagaagcctgggtcct
cggtgaaggtctcctgcaaggcttctggaggcaccttcagcagctatgc
tatcagctgggtgcgacaggcccctggacaagggcttgagtggatggga
gggatcatccctatctttggtacagcaaactacgcacagaagttccagg
gcagagtcacgattaccgcggacgaatccacgagcacagcctacatgga
gctgagcagcctgagatctgaggacaccgccgtgtattactgtgcgcgc
tactggggttacgactcttacgatgaatggggtcaaggtactctggtga
ccgtctcctca [SEQ ID NO: 90]

TABLE 23-continued

ET200-025

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy
chain variable region His tag + HA tag)
DIQMTQSPSSLSASVGDRVTITCRASQSISSYLNWYQQKPGKAPKLLIY
AASSLQSGVPSRFSGSGSGTDFTLTISSLQPEDFATYYCQQSYSTPFTF
GPGTKVDIKR [SEQ ID NO: 91]

SRGGGGSGGGGSGGGGSLEMA [SEQ ID NO: 307]

EVQLVQSGAEVKKPGSSVKVSCKASGGTFSSYAISWVRQAPGQGLEWMG
GIIPIFGTANYAQKFQGRVTITADESTSTAYMELSSLRSEDTAMYYCAR
YWGYDSYDEWGQGTLVTVSS [SEQ ID NO: 92]

TSGQAGHHHHHGAYPYDVPDYAS [SEQ ID NO: 308]

TABLE 24

ET200-026

DNA Sequence (light chain variable region scFv linker heavy
chain variable region His tag + HA tag)
aattttatgctgactcagccccactctgtgtcggagtctccggggaaga
cggtaaccatctcctgcaccggcagcagtggcagcattgccagcaacta
tgtgcagtggtaccagcagcgcccgggcagtgcccccaccactgtgatc
tatgaggataaccaaagaccctctggggtccctgatcggttctctggct
ccatcgacagctcctccaactctgcctccctcaccatctctggactgaa
gactgaggacgaggctgactactactgtcagtcttatgatagcagcaat
tgggtgttcggcggagggaccaagctgaccgtcctaggt
[SEQ ID NO: 93]

tctagaggtggtggtggtagcggcggcggcggctctggtggtggtggat
ccctcgagatggcc [SEQ ID NO: 305]

gaggtccagctggtgcagtctgggggctgaggtgaagaagcctgggtcct
cggtgaaggtctcctgcaaggcttctggaggcaccttcagcagctatgc
tatcagctgggtgcgacaggcccctggacaagggcttgagtggatggga
gggatcatccctatctttggtacagcaaactacgcacagaagttccagg
gcagagtcacgattaccgcggacgaatccacgagcacagcctacatgga
gctgagcagcctgagatctgaggacacggccgtgtattactgtgcgcgc
aacaaccattactacaacgattactggggtcaaggtactctggtgaccg
tctcctca [SEQ ID NO: 94]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy
chain variable region His tag + HA tag)
NFMLTQPHSVSESPGKTVTISCTGSSGSIASNYVQWYQQRPGSAPTTVI
YEDNQRPSGVPDRFSGSIDSSSNSASLTISGLKTEDEADYYCQSYDSSN
WVFGGGTKLTVLG [SEQ ID NO: 95]

SRGGGGSGGGGSGGGGSLEMA [SEQ ID NO: 307]

EVQLVQSGAEVKKPGSSVKVSCKASGGTFSSYAISWVRQAPGQGLEWMG
GIIPIFGTANYAQKFQGRVTITADESTSTAYMELSSLRSEDTAVYYCAR
NNHYYNDYWGQGTLVTVSS [SEQ ID NO: 96]

TSGQAGQHHHHHGAYPYDVPDYAS [SEQ ID NO: 308]

TABLE 25

ET200-027

DNA Sequence (light chain variable region scFv linker heavy
chain variable region His tag + HA tag)
cagtctgtgttgacgcagccgccctcagtgtctggggcccccagggcagg
gggtcaccatcccctgcactgggagcagctccaacatcggggcaggtta
tgatgtacactggtaccagcagcttccagggacagcccccaaactcctc
atctatggtaacaacaatcggccctcaggggtccctgacccgcttctctg
gctccaggtctctggctcctccctcccctggccatcactgggctccaggc
tgaggatgaggctgattattactgccagtcctatgacagcagcctgagt
gatgtggtattcggcggagggaccaaggtcaccgtcctaggt
[SEQ ID NO: 97]

tctagaggtggtggtggtagcggcggcggcggctctggtggtggtggat
ccctcgagatggcc [SEQ ID NO: 305]

gaggtccagctggtgcagtctgggggctgaggtgaagaagcctggggcta
cagtgaaaatctcctgcaaggtttctggatacaccttcaccgactacta
catgcactgggtgcaacaggcccctggaaaagggcttgagtggatggga
cttgttgatcctgaagatggtgaaacaatatacgcagagaagttccagg
gcagagtcaccataaccgcggacacgtctacagacacagcctacatgga
gctgagcagcctgagatctgaggacacggccgtgtattactgtgcgcgc
tactggtcttactcttttcgactacctgtacatgccggaaggtaacgatt
ggtggggtcaaggtactctggtgaccgtctcctca
[SEQ ID NO: 98]

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy
chain variable region His tag + HA tag)
QSVLTQPPSVSGAPGQGVTIPCTGSSSNIGAGYDVHWYQQLPGTAPKWY
GNNNRPSGVPDRFSGSRSGSSASLAITGLQAEDEADYYCQSYDSSLSDV
VFGGGTKVTVLG [SEQ ID NO: 99]

SRGGGGSGGGGSGGGGSLEMA [SEQ ID NO: 307]

EVQLVQSGAEVKKPGATVKISCKVSGYTFTDYYMHVQQAPGKGLEWMG
LVDPEDGETIYAEKFQGRVTITADTSTDTAYMELSSLRSEDTAVYYCAR
YWSYSFDYLYMPEGNDWWGQGTLVTVSS [SEQ ID NO: 100]

TSGQAGQHFIFIRHHGAYPYDVPDYAS [SEQ ID NO: 308]

TABLE 26

ET200-028

DNA Sequence (light chain variable region scFv linker heavy
chain variable region His tag + HA tag)
cagtctgtgttgactcagccacccgcagcgtctgggacccccggacaga
gagtcaccatctcttgttctggggggcgtctccaacatcgggagtggtgc
tctaaattgtaccagcaactcccaggaacggccccccaaactcctcatc
tatagttacaatcagcggccctcaggggtctctgaccgattctctggct
ccaggtctgccacctcagcctccctggccatcagtgggctccagtctga
ggatgaggctgattattactgtgcaacctgggatgatagtgtgaatggt
tgggtgttcggcggagggaccaagctgaccgtcctaggt
[SEQ ID NO: 101]

tctagaggtggtggtggtagcggcggcggcggctctggtggtggtggat
ccctcgagatggcc [SEQ ID NO: 305]

caggtccagctggtacagtctggagctgaggtgaagaagcctggggatt
cagtgaaggtctcctgcaagccttctggttacaatttttctcaactatgg
tatcaactgggtgcgacaggcccctggacaagggcttgagtggatggga
tggattagcacttacaccggtaacaaactatgcacagaagctgcagg
gcagagtcaccttcaccacagacacatccacgagcacagcctacatgga
gatgaggagcctgagatctgacgacacggccgtgtattactgtgcgcgc
gacctgtactactacgaaggtgttgattactggggtcaaggtactctgg
tgaccgtctcctca [SEQ ID NO: 102]

TABLE 26-continued

ET200-028

ACTAGTGGCCAGGCCGGCCAGCACCATCACCATCACCATGGCGCATACC
CGTACGACGTTCCGGACTACGCTTCT [SEQ ID NO: 306]

Amino Acid Sequence (light chain variable region scFv linker heavy
chain variable region His tag + HA tag)
QSVLTQPPAASGTPGQRVTISCSGGVSNIGSGALNWYQQLPGTAPKLLI
YSYNQRPSGVSDRFSGSRSATSASLAISGLQSEDEADYYCATWDDSVNG
WVFGGGTKLTVLG [SEQ ID NO: 103]

SRGGGGSGGGGSGGGGSLEMA [SEQ ID NO: 307]

QVQLVQSGAEVKKPGDSVKVSCKPSGYNFLNYGINWVRQAPGQGLEWMG
WISTYTGNTNYAQKLQGRVTFTTDTSTSTAYMEMRSLRSDDTAVYYCAR
DLYYYEGVDYWGQGTLVTVSS [SEQ ID NO: 104]

TSGQAGQHHHHHHGAYPYDVPDYAS [SEQ ID NO: 308

TABLE 27

ET200-029

DNA Sequence (light chain variable region scFv linker
heavy chain variable region His tag + HA tag)
caggctgtgctgactcagccaccctcagtgtcagtggccccaggaaagac
ggccagggttacctgtgggggaaacaacattggaagtgaaagtgtgcact
ggtaccagcagaagccaggccaggccctgtgttggtcatctattattgat
accgaccggccctcagggatccctgagcgattctctggctcccactctgg
gaccacggccaccctgaccatcagcagggtcgaagccgggggatgaggccg
actattactgtcaggtgtgggatagtagtagggatcatgtggtattcggc
ggagggaccaagctgaccgtcctaggt [SEQ ID NO: 105]

tctagaggtggtggtggtagcggcggcggcggctctggtggtggtggatc
cctcgagatggcc [SEQ ID NO: 305]

caggtgcagctggtgcagtctggggggaggcgtggtccagcctggggaggtc
cctgagactctcctgtgcggcctctggattcaccttcagtagctatgcta
tgcactgggtccgccaggctccaggcaagggactggagtgggtggcagtt
atatcatatgatggaagcaataaatactacgcagactccgtgaagggcct
attcaccatctccagagacaattccaagaacacgctgtatctgcaaatga
acagcctgagagctgaggacacggccgtgtattactgtgcgcgctcttac
ttcacttctggtttctacgattactggggtcaaggtactctggtgaccgt
ctcctca [SEQ ID NO: 106]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
QAVLTQPPSVSVAPGKTARVTCGGNNIGSESVHWYQQKPGQAPVLVIYYD
TDRPSGIPERFSGSHSGTTATLTISRVEAGDEADYYCQVWDSSRDHVVFG
GGTKLTVLG [SEQ ID NO: 107]

SRGGGGSGGGGSGGGGSLEMA [SEQ ID NO: 307]

QVQLVQSGGGVVQPGRSLRLSCAASGFTFSSYAMHWVRQAPGKGLEWVAV
ISYDGSNKYYADSVKGLFTISRDNSKNTLYLQMNSLRAEDTAVYYCARSY
FTSGFYDYWGQGTLVTVSS [SEQ ID NO: 108]

TSGQAGQHHHHHHGAYPYDVPDYAS [SEQ ID NO: 308]

TABLE 28

ET200-030

DNA Sequence (light chain variable region scFv linker
heavy chain variable region His tag + HA tag)
cagtctgtcgtgacgcagccgccctcagtgtctggggcccccagggcagag
ggtcaccatctcctgcactgggagcagttccaacatcggggcaggttatg
atgtaaattggtatcagcagtttccaggaacagcccccaaactcctcatc
ctatggtaacagcaatcggccctcaggggtccctgacgattctctggctc
caagtctggcacctcagcctccctggccatcactgggctccaggctgagg
atgaggctgattattactgccagtcctatgacagcagcctgagtggctat
atgtatcggaactgggaccaaggtcaccgtcctaggt [SEQ ID NO:
109]

tctagaggtggtggtggtagcggcggcggcggctctggtggtggtggatc
cctcgagatggcc [SEQ ID NO: 305]

**cagatgcagctggtgcagtctgggggctgaggtgaagaagcctggggcctc
agtgaaggtctcctgcaaggcttccggatacaccctcactgaattatcca
tgcactgggtgcgacaggtcctggaaaagggcttgagtggatgggaggt
tttgatcctgaagatggtgaaacaatctacgcacagaagttccagggcag
agtcaccatgaccgaggacacatctacagacacagcctacatggagctga
gcagcctgagatctgaggacactgccgtgtattactgtgcgcgcatgtct
tctatgtactacgattgggggtcaaggtactctggtgaccgtctcctca
[SEQ ID NO: 110]**

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
QSVVTQPPSVSGAPGQRVTISCTGSSSNIGAGYDVNWYQQFPGTAPKLLI
YGNSNRPSGVPDRFSGSKSGTSASLAITGLQAEDEADYYCQSYDSSLSGS
YVFGTGTKVTVLG [SEQ ID NO: 111]

SRGGGGSGGGGSGGGGSLEMA [SEQ ID NO: 307]

**QMQLVQSGAEVKKPGASVKVSCKASGYTLTELSMHWVRQAPGKGLEWMGG
FDPEDGETIYAQKFQGRVTMTEDTSTDTAYMELSSLRSEDTAVYYCARMS
SMYYDWGQGTLVTVSS [SEQ ID NO: 112]**

TSGQAGQHHHHHHGAYPYDVPDYAS [SEQ ID NO: 308]

TABLE 29

ET200-031

DNA Sequence (light chain variable region scFv linker
heavy chain variable region His tag + HA tag)
tcctatgtgctgactcagccaccctcagtgtcagtggcccccaggaaagac
ggcaggattacctgtggggggaaacaacattggaagtaaaagtgtgcaat
ggtaccagcagaagcaggccaggcccctgtgctggtcatctattatgat
agcgaccggccctcagggatccctgagcgattctctggctccaactctgg
gaacacggccaccctgaccatcagcagggtcgaagccggggatgaggccg
actattactgtcaggtgtgggatagtagtagtgattatgtcttcggaact
gggaccaaggtcaccgtcctaggt [SEQ ID NO: 113]

tctagaggtggtggtggtagcggcggcggcggctctggtggtggtggatc
cctcgagatggcc [SEQ ID NO: 305]

**gaggtgcagctggtggagactgggggaggcttggtcaagcctggagggtc
cctgagactctcctgtgcagcctctggattcaccgtcagtgactactaca
tgagctggatccgccaggctccaggggaagggcctggagtggatttcatac
attagtggtagtggtaatagcatatactacgcagactctgtgaagggccg
attcaccatctccagggacaacgccaagaactcactggatctgcaaatga
ccagcctgagagccgaggacacggccgtatattactgtgcgcgctctact
aaaattcgattactggggtcaaggtactctggtgaccgtctcctca [SEQ
ID NO: 114]**

TABLE 29-continued

ET200-031

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
SYVLTQPPSVSVAPGKTARITCGGNNIGSKSVHWYQQKPGQAPVLIYYD
SDRPSGIPERFSGSNSGNTATLTISRVEAGDEADYYCQVWDSSSDYVFGT
GTKVTVLG [SEQ ID NO: 115]

SRGGGGSGGGGSGGGGSLEMA [SEQ ID NO: 307]

**EVQLVETGGGLVKPGGSLRLSCAASGFTVSDYYMSWIRQAPGKGLEWISY
ISGSGNSIYVADSVKGRFTISRDNAKNSLDLQMTSLRAEDTAVYYCARST
KFDYWGQGTLVTVSS [SEQ ID NO: 116]**

TSGQAGQHHHHHHGAYPYDVPDYAS [SEQ ID NO: 308]

TABLE 30

ET200-032

DNA Sequence (light chain variable region scFv linker
heavy chain variable region His tag + HA tag)
ctgcctgtgctgactcagccaccctcagcgtctgggacccccgggcagag
ggtcaccatctcttgttctggaagcagctccaacgtcggaagttacactg
taaactggtaccggcaactcccaggaacggcccccacactcctcatctat
aataataatcagcggccctcaggggtccctgaccgattctctgactccaa
gtctggcacctcggcctccctgaccattagtgggctccagcctgaggatg
aggctgattattattgtgcagcatgggatgacaggctgggtggttatgtc
ttcggaactgggaccaaggtcaccgtcctaggt [SEQ ID NO: 117]

tctagaggtggtggtggtagcggcggcggcggctctggtggtggtggatc
cctcgagatggcc [SEQ ID NO: 305]

**gaggtgcagctggtgcagtctggagcagaggtgaaaaagccggggggagtc
tctgaagatctcctgtaagggttctggatacagctttaccaactactgga
tcggctgggtgcgccagatgcccgggaaaggcctggagtggatggggatc
atctatcctggtgactctgataccagatacagccgtccttccaaggcca
ggtcaccatctcagccgacaagtccatcagcaccgcctacctacagtgga
gcagcctgaaggcctcggacaccgccatgtattactgtgcgcgctctact
ggttcttctcatatgtctgatgaatggggtcaaggtactctggtgaccgt
ctcctca [SEQ ID NO: 118]**

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
LPVLTQPPSASGTPGQRVTISCSGSSSNVGSYTVNWYRQLPGTAPTLLIY
NNNQRPSGVPDRFSDSKSGTSASLTISGLQPEDEADYYCAAWDDRLGGYV
FGTGTKVTVLG [SEQ ID NO: 119]

SRGGGGSGGGGSGGGGSLEMA [SEQ ID NO: 307]

**EVQLVQSGAEVKKPGESLKISCKGSGYSFTNYWIGWVRQMPGKGLEWMGH
YPGDSDTRYSPSFQGQVTISADKSISTAYLQWSSLKASDTAMYYCARSTG
SSHMSDEWGQGTLVTVSS [SEQ ID NO: 120]**

TSGQAGQHHHHHHGAYPYDVPDYAS [SEQ ID NO: 308]

TABLE 31

ET200-033

DNA Sequence (light chain variable region scFv linker
heavy chain variable region His tag + HA tag)
aattttatgctgactcagccccactctgtgtcggagtctccggggaagac
ggtaaccatctcctgcaccggcagcagtggcagcattgccagcaactatg
tgcagtggtaccagcagcgcccgggcagtgccccaccactgtgatctat
gaggataaccaaagaccctctggggtccctgatcggttctctggctccat
cgacagctcctccaactctgcctccctcaccatctctggactgaagactg
aggacgaggctgactactactgtcagtcttatgatagcagcaatcattgg
gtgttcggcggagggaccaagctgaccgtcctaggt [SEQ ID NO:
121]

<u>tctagaggtggtggtggtagcggcggcggcggctctggtggtggtggatc</u>
<u>cctcgagatggcc</u> [SEQ ID NO: 305]

caagtgcagctacagcagtggggcgcaggactgttgaagccttcggagac
cctgtccctcacctgcgctgtctatggtgggtccttcagtggttactact
ggagctggatccgcagccccagggaaggggctggagtggattgggagag
atcactcatagtggaaggtccaactacaacccgtccctcaagagtcgagt
caccatatcagtagacacgtccaagaaccagttctccctgaagctgagct
ctgtgaccgccgcggacacggccgtgtattactgtgcgcggctcttctatc
atgtctgattactggggtcaaggtactctggtgaccgtctcctca [SEQ
ID NO: 122]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region <u>scFv linker</u>
heavy chain variable region His tag + HA tag)
NFMLTQPHSVSESPGKTVTISCTGSSGSIASNYVQWYQQRPGSAPTTVIY
EDNQRPSGVPDRFSGSIDSSSNSASLTISGLKTEDEADYYCQSYDSSNHW
VFGGGTKLTVLG [SEQ ID NO: 123]

<u>SRGGGGSGGGGSGGGGSLEMA</u> [SEQ ID NO: 307]

QVQLQQWGAGLLKPSETLSLTCAVYGGSFSGYYWSWIRQPPGKGLEWIGE
ITHSGRSNYNPSLKSRVTISVDTSKNQFSLKLSSVTAADTAVYYCARSSI
MSDYWGQGTLVTVSS [SEQ ID NO: 124]

TSGQAGQHHHHHHGAYPYDVPDYAS [SEQ ID NO: 308]

TABLE 32

ET200-034

DNA Sequence (light chain variable region <u>scFv linker</u>
heavy chain variable region His tag + HA tag)
cagtctgtgttgacgcagccgccctcagtgtctggggccccagggcagag
ggtcaccatctcctgcactgggagcacctccaacatcggggcaggttatg
atgtacactggtaccagcagatccaggaacagcccccaaactcctcatca
acaataacaggaatcggccctcagggttccctgaccgattctctggctcc
aagtctggcacgtcagccaccctgggcatcaccggactccagactgggga
cgaggccgattattactgcggaacatgggatggcagcctgactggtgcag
tgttcggcggagggaccaagctgaccgtcctaggt [SEQ ID NO:
125]

<u>tctagaggtggtggtggtagcggcggcggcggctctggtggtggtggatc</u>
<u>cctcgagatggcc</u> [SEQ ID NO: 305]

gaggtccagctggtgcagtctggggctgaggtgaagaagcctgggtcctc
ggtgaaggtctcatgcaaggcttctggaggcaccttcagcagctatgcta
tcagctgggtgcgacaggcccctggacaagggcttgagtggatgggaggg
atcatccctatctttggtacagcaaactacgcacagaagttccagggcag
agtcacgattaccgcggacgaatccacgagcacagcctacatggagctga
gcagcctgagatctgaggacacggccgtgtattactgtgcgcgcggttct
gctctggaccattacgatcgttggggtcaaggtactctggtgaccgtctc
ctca [SEQ ID NO: 126]

TABLE 32-continued

ET200-034

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region <u>scFv linker</u>
heavy chain variable region His tag + HA tag)
QSVLTQPPSVSGAPGQRVTISCTGSTSNIGAGYDVHWYQQLPGTAPKLLI
NNNRNRPSGVPDRFSGSKSGTSATLGITGLQTGDEADYYCGTWDGSLTGA
VFGGGTKLTVLG [SEQ ID NO: 127]

<u>SRGGGGSGGGGSGGGGSLEMA</u> [SEQ ID NO: 307]

EVQLVQSGAEVKKPGSSVKVSCKASGGTFSSYAISWVRQAPGQGLEWMGG
IIPIFGTANYAQKFQGRVTITADESTSTAYMELSSLRSEDTAVYYCARGS
ALDHYDRWGQGTLVTVSS [SEQ ID NO: 128]

TSGQAGQHHHHHHGAYPYDVPDYAS [SEQ ID NO: 308]

TABLE 33

ET200-035

DNA Sequence (light chain variable region <u>scFv linker</u>
heavy chain variable region His tag + HA tag)
aattttatgctgactcagccccactctgtgtcggagtctccggggaagac
ggtaaccatctcctgcacccgcagcagtggcagcattgccagcaactatg
tgcagtggtaccagcagcgcccgggcagtgccccaccactgtgatctat
ggaggataaccaaagaccctctggggtccctgatcgttctctggctccat
cgacagctcctccaactctgcctccctcaccatctctggactgaagactg
aggacgaggctgactactactgtcagtcttatgatagcaccaattgggtg
ttcggcggagggaccaagctgaccgtcctaggt [SEQ ID NO: 129]

<u>tctagaggtggtggtggtagcggcggcggcggctctggtggtggtggatc</u>
<u>cctcgagatggcc</u> [SEQ ID NO: 305]

caggtgcagctggtgcagtctggggctgaggtgaagaagcctgggtcctc
ggtgaaggtctcctgcaaggcttctggaggcaccttcagcagctatgcta
tcagctgggtgcgacaggcccctggacaagggcttgagtggatgggaggg
atcatccctatctttggtacagcaaactacgcacagaagttccagggcag
agtcacgattaccgcggacgaatccacgagcacagcctacatggagctga
gcagcctgagatctgaggacactgccgtgtattactgtgcgcgctacaac
tactacttcaacgattactggggtcaaggtactctggtgaccgtctcctc
a [SEQ ID NO: 130]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region <u>scFv linker</u>
heavy chain variable region His tag + HA tag)
NFMLTQPHSVSESPGKTVTISCTRSSGSIASNYVQWYQQRPGSAPTTVIY
EDNQRPSGVPDRFSGSIDSSSNSASLTISGLKTEDEADYYCQSYDSTNWV
FGGGTKLTVLG [SEQ ID NO: 131]

<u>SRGGGGSGGGGSGGGGSLEMA</u> [SEQ ID NO: 307]

QVQLVQSGAEVKKPGSSVKVSCKASGGTFSSYAISWVRQAPGQGLEWMGG
IIPIFGTANYAQKFQGRVTITADESTSTAYMELSSLRSEDTAVYYCARYN
YYFNDYWGQGTLVTVSS [SEQ ID NO: 132]

TSGQAGQHHHHHHGAYPYDVPDYAS [SEQ ID NO: 308]

TABLE 34

ET200-037

DNA Sequence (light chain variable region scFv linker
heavy chain variable region His tag + HA tag)
tcctatgtgctgactcagccaccctcagtgtcagtggccccaggaaagac
ggccaggattacctgtgggggaaacaacattggaagtaaaagtgtgcact
ggtaccagcagaagccaggccaggcccctgtgctggtcatctattatgat
agcgaccggccctcagggatccctgagcgattctctggctccaactctgg
gaacacggccaccctgaccatcagcagggtcgaagccggggatgaggccg
actattactgtcaggtgtgggatagtagtagtgatcatccttatgtatcg
gaactgggaccaaggtcaccgtcctaggt [SEQ ID NO: 133]

tctagaggtggtggtggtagcggcggcggcggctctggtggtggtggatc
cctcgagatggcc [SEQ ID NO: 305]

cagatgcagctggtgcagtctggagctgaggtgaagaagcctgggcctc
agtgaaggtctcctgcaaggcttctggttacacctttaccagctatggta
tcagctgggtgcgacaggcccctggacaagggcttgagtggatgggatgg
atcagcgcttacaatggtaacacaaactatgcacagaagctccagggcag
agtcaccatgaccacagacacatccacgagcacagcctacatggagctga
ggagcctgagatctgacgacactgccgtgtattactgtgcgcgctctatg
ttcggtgctcatgattcttggggtcaaggtactctggtgaccgtctcctc
a [SEQ ID NO: 134]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
SYVLTQPPSVSVAPGKTARITCGGNNIGSKSVHWYQQKPGQAPVLVIYYD
SDRPSGIPERFSGSNSGNTATLTISRVEAGDEADYYCQVWDSSSDHPYVF
GTGTKVTVLG [SEQ ID NO: 135]

SRGGGGSGGGGSGGGGSLEMA [SEQ ID NO: 307]

**QMQLVQSGAEVKKPGASVKVSCKASGYTFTSYGISWVRQAPGQGLEWMGW
ISAYNGNTNYAQKLQGRVTMTTDTSTSTAYMELRSLRSDDTAVYYCARSM
FGAHDSWGQGTLVTVSS** [SEQ ID NO: 136]

TSGQAGQHHHHHHGAYPYDVPDYAS [SEQ ID NO: 308]

TABLE 35

ET200-038

DNA Sequence (light chain variable region scFv linker
heavy chain variable region His tag + HA tag)
cagtctgtgttgacgcagccgccctcagtgtctgggggccccagggcagag
ggtcaccatctcctgcactgggagcagctccaacatcggggcaggttttg
atgtacactggtaccagctacttccaggaacagcccccaaactcctcatc
tatgctaacagcaatcggccctcaggggtccctgaccgattctctggctc
caagtctggcacctcagcctccctggccatcactgggctcctggctgagg
atgaggctgattattactgccagtctatgacagcagcctgagtggtgtg
gtattcggcggagggaccaagctgaccgtcctaggt [SEQ ID NO:
137]

tctagaggtggtggtggtagcggcggcggcggctctggtggtggtggatc
cctcgagatggcc [SEQ ID NO: 305]

caggtgcagctggtgcaatctggggctgaggtgaagaagcctgggtcctc
ggtgaaggtctcctgcaaggcttctggaggcaccttcagcagctatgcta
tcagctgggtgcgacaggcccctggacaagggcttgagtggatgggaggg
atcatccctatcffiggtacagcaaactacgcacagaagttccagggcag
agtcacgattaccgcggacgaatccacgagcacagcctacatggagctga
gcagcctgagatctgaggacacggccgtgtattactgtgcgcgcggtgct
tctttcgaccgtcatgataactgggggtcaaggtactctggtgaccgtctc
ctca [SEQ ID NO: 138]

TABLE 35-continued

ET200-038

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
QSVLTQPPSVSGAPGQRVTISCTGSSSNIGAGFDVHWYQLLPGTAPKLLI
YANSNRPSGVPDRFSGSKSGTSASLAITGLLAEDEADYYCQSYDSSLSGV
VFGGGTKLTVLG [SEQ ID NO: 139]

SRGGGGSGGGGSGGGGSLEMA [SEQ ID NO: 307]

**QVQLVQSGAEVKKPGSSVKVSCKASGGTFSSYAISWVRQAPGQGLEWMGG
IIPIFGTANYAQKFQGRVTITADESTSTAYMELSSLRSEDTAVYYCARGA
SFDRHDNWGQGTLVTVSS** [SEQ ID NO: 140]

TSGQAGQHHHHHHGAYPYDVPDYAS [SEQ ID NO: 308]

TABLE 36

ET200-039

DNA Sequence (light chain variable region scFv linker
heavy chain variable region His tag + HA tag)
aattttatgctgactcagccccactctgtgtcggagtctccggggaagac
ggtaaccatctcctgcacccgcagcagtggcagcattgccagcaactatg
tgcagtggtaccagcagcgcccgggcagttcccccaccactgtgatctat
gaggataaccaaagaccctctggggtccctgatcggttctctggctccat
cgacagctcctccaactctgcctccctcaccatctctgggactgaagactg
aggacgaggctgactactactgtcagtcttatgatagcagcaattgggtg
ttcggcggagggaccaagctgaccgtcctaggt [SEQ ID NO: 141]

tctagaggtggtggtggtagcggcggcggcggctctggtggtggtggatc
cctcgagatggcc [SEQ ID NO: 305]

gaggtccagctggtgcagtctggggctgaggtgaagaagcctgggtcctc
ggtgaaggtctcctgcaaggcttctggaggcaccttcagcagctatgcta
tcagctgggtgcgacaggcccctggacaagggcttgagtggatgggaggg
atcatccctatcffiggtacagcaaactacgcacagaagttccagggcag
agtcacgattaccgcggacgaatccacgagcacagcctacatggagctga
gcagcctgagatctgaggacacggccgtgtattactgtgcgcgctctaac
tactactacaacgattactggggtcaaggtactctggtgaccgtctcctc
a [SEQ ID NO: 142]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
NFMLTQPHSVSESPGKTVTISCTRSSGSIASNYVQWYQQRPGSSPTTVIY
EDNQRPSGVPDRFSGSIDSSSNSASLTISGLKTEDEADYYCQSYDSSNWV
FGGGTKLTVLG [SEQ ID NO: 143]

SRGGGGSGGGGSGGGGSLEMA [SEQ ID NO: 307]

**EVQLVQSGAEVKKPGSSVKVSCKASGGTFSSYAISWVRQAPGQGLEWMGG
IIPIFGTANYAQKFQGRVTITADESTSTAYMELSSLRSEDTAVYYCARSN
YYYNDYWGQGTLVTVSS** [SEQ ID NO: 144]

TSGQAGQHHHHHHGAYPYDVPDYAS [SEQ ID NO: 308]

TABLE 37

ET200-040

DNA Sequence (light chain variable region scFv linker
heavy chain variable region His tag + HA tag)
cagtctgtgttgacgcagccgccctcagtgtctggggcccccagggcagag
ggtcaccatctcctgcactgggagcagctccaacatcggggcaggttatg
atgtacactggtaccagcagcttccaggaacagcccccaaactcctcatc
tatggtaacagcaatcggccctcaggggtccctgaccgattctctggctc
caagtctggcacctcagcctccctggccatcactgggctccaggctgagg
atgaggctgattattactgccagtctatgacagcagcctgagtggttat
gtcttcggaactgggaccaaggtcaccgtcctaggt [SEQ ID NO: 145]

tctagaggtggtggtggtagcggcggcggcggctctggtggtggtggatc
cctcgagatggcc [SEQ ID NO: 305]

**caggtgcagctggtgcagtctgggggctgaggtgaagaagcctggggcctc
agtgaaggtctcctgcaaggtttccggatacaccctcactgaattatcca
tgcactgggtgcgacaggctcctggaaaagggcttgagtggatgggaggt
tttgatcctgaagatggtgaaacaatctacgcacagaagttccagggcag
agtcaccatgaccgaggacacatctacagacacagcctacatggagctga
gcagcctgagatctgaggacactgccgtgtattactgtgcgcgctactct
ggtgtttactacgattggggtcaaggtactctggtgaccgtctcctca**
[SEQ ID NO: 146]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
QSVLTQPPSVSGAPGQRVTISCTGSSSNIGAGYDVHWYQQLPGTAPKWYG
NSNRPSGVPDRFSGSKSGTSASLAITGLQAEDEADYYCQSYDSSLSGYVF
GTGTKVTVLG [SEQ ID NO: 147]

SRGGGGSGGGGSGGGGSLEMA [SEQ ID NO: 307]

**QVQLVQSGAEVKKPGASVKVSCKVSGYTLTELSMHWVRQAPGKGLEWMGG
FDPEDGETIYAQKFQGRVTMTEDTSTDTAYMELSSLRSEDTAVYYCARYS
GVYYDWGQGTLVTVSS** [SEQ ID NO: 148]

TSGQAGQHHHHHHGAYPYDVPDYAS [SEQ ID NO: 308]

TABLE 38

ET200-041

DNA Sequence (light chain variable region scFv linker
heavy chain variable region His tag + HA tag)
aattttatgctgactcagccccactctgtgtcggggtctccggggaagac
ggtaaccatctcctgcaccggcagcagtggcagcattgccgacaactttg
tgcactggtaccagcagcccgggcggtgtcccaccactgtgatcttt
aatgatgacgaaagaccctctggcgtccctgatcggttctctggctccat
cgacacctcctccaattctgcctccctcaccatctctggactgaagactg
aggacgaggctgactactactgtcagtcttatgataataataatcgaggg
gtgttcggcggagggaccaagctgaccgtcctaggt [SEQ ID NO: 149]

tctagaggtggtggtggtagcggcggcggcggctctggtggtggtggatc
cctcgagatggcc [SEQ ID NO: 305]

**caggtccagctggtgcagtctggggctgaggtgaagaagcctggggtcctc
ggtgaaggtctcctgcaaggcttctggaggcaccttcagcagctatgcta
tcagctgggtgcgacaggcccctggacaagggcttgagtggatgggatgg
atgaaccctaacagtggtaacacaggctatgcacagaagttccagggcag
agtcaccatgaccaggaacacctccataagcacagcctacatggagctga
gcaacctgagatctgaggacacggccgtgtattactgtgcgcgctactac
tcttacggttacgattggggtcaaggtactctggtgaccgtctcctca**
[SEQ ID NO: 150]

TABLE 38-continued

ET200-041

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
NFMLTQPHSVSGSPGKTVTISCTGSSSGSIADNFVQWYQQRPGGVPTTVIF
NDDERPSGVPDRFSGSIDTSSNSASLTISGLKTEDEADYYCQSYDNNNRG
VFGGGTKLTVLG [SEQ ID NO: 151]

SRGGGGSGGGGSGGGGSLEMA [SEQ ID NO: 307]

**QVQLVQSGAEVKKPGSSVKVSCKASGGTFSSYAISWVRQAPGQGLEWMGW
MNPNSGNTGYAQKFQGRVTMTRNTSISTAYMELSNLRSEDTAVYYCARYY
SYGYDWGQGTLVTVSS** [SEQ ID NO: 152]

TSGQAGQHHHHHHGAYPYDVPDYAS [SEQ ID NO: 308]

TABLE 39

ET200-042

DNA Sequence (light chain variable region scFv linker
heavy chain variable region His tag + HA tag)
cagtctgtcgtgacgcagccgccctcagtgtctggggcccccagggcagac
ggtcaccatctcctgcactgggggcagctccaacatcgggacaggttatt
ttgtaaattggtaccagcaggttccaggaaaagcccccaaactcctcatc
ctgggtaacaataatcggccctcgggggtccctgaccgactctccggctc
cacgtccggcacctcagcctccctggccatcactgggctccaggctgagg
atgagggtacttattactgccagtctatgacagcagcctgagtggttat
gtatcggaactgggaccaaggtcaccgtcctaggt [SEQ ID NO: 153]

tctagaggtggtggtggtagcggcggcggcggctctggtggtggtggatc
cctcgagatggcc [SEQ ID NO: 305]

**caggtacagctgcagcagtcaggtccaggactggtgaagccctcgcagac
cctctcactcacctgtggcatctccggggacagtgtctctaccaacagtg
ttgcttggcactggatcaggcagtccccatcgagaggccttgagtggctg
ggaaggacatactacaggtccaagtggtctaatgactatggagtatctgt
gaaaagtcgaatcaccatcatcccagacacaatccaagaaccagttctccc
tgcagctgaactctgtgactcccgaggacacggctgtgtattactgtgcg
cgctcttcttcttggtaccagatcttcgattactggggtcaaggtactct
ggtgaccgtctcctca** [SEQ ID NO: 154]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
QSVVTQPPSVSGAPGQTVTISCTGSSSNIGTGYFVNAVYQQVPGKAPKLL
ILGNNNRPSGVPDRLSGSTSGTSASLAITGLQAEDEGTYYCQSYDSSLSG
YVFGTGTKVTVLG [SEQ ID NO: 155]

SRGGGGSGGGGSGGGGSLEMA [SEQ ID NO: 307]

**QVQLQQSGPGLVKPSQTLSLTCGISGDSVSTNSVAWHWIRQSPSRGLEWL
GRTYYRSKWSNDYGVSVKSRITIIPDTSKNQFSLQLNSVTPEDTAVYYCA
RSSSWYQIFDYWGQGTLVTVSS** [SEQ ID NO: 156]

TSGQAGQHHHHHHGAYPYDVPDYAS [SEQ ID NO: 308]

TABLE 40

ET200-043

DNA Sequence (light chain variable region scFv linker
heavy chain variable region His tag + HA tag)
aattttatgctgactcagccccactctgtgtcggagtctccggggaagac
ggtaaccatctcctgcaccggcagcagcgacagcatagccaacaactatg
ttcagtggtaccagcagcgcccgggcagtgcccccaccaatgtgatctac
gaagatgtccaaagaccctctgggtccctgatcggttctctgggtccat
cgacagctcctccaactctgcctccctcaccatctctggactgaagactg
aggacgaggctgtctactattgtcagtcttatcatagcgacaatcgttgg
gtgttcggcggcgggaccaagctgaccgtcctaggt [SEQ ID NO:
157]

<u>tctagaggtggtggtggtagcggcggcggcggctctggtggtggtggatc</u>
<u>cctcgagatggcc</u> [SEQ ID NO: 305]

**caggtgcagctggtggagtctgggggaggcttggtacagcctggggggtc
cctgagactctcctgtgcagcctctggattcaccttagcagctatgcca
tgagctgggtccgccaggctccagggaaggggctggagtgggtctcagct
attagtggtagtggtggtagcacatactacgcagactccgtgaagggccg
gttcaccatctccagagacaattccaagaacacgctgtatctgcaaatga
acagcctgagagccgaggacacggccgtatattactgtgcgcgctctggt
gcttactgggactactctgtttacgatgaatggggtcaaggtactctggt
gaccgtctcctca** [SEQ ID NO: 158]

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
NFMLTQPHSVSESPGKTVTISCTGSSDSIANNYVQWYQQRPGSAPTNVIY
EDVQRPSGVPDRFSGSIDSSSNSASLTISGLKTEDEAVYYCQSYHSDNRW
VFGGGTKLTVLG [SEQ ID NO: 159]

<u>SRGGGGSGGGGSGGGGSLEMA</u> [SEQ ID NO: 307]

**QVQLVESGGGLVQPGGSLRLSCAASGFTFSSYAMSWVRQAPGKGLEWVSA
ISGSGGSTYYADSVKGRFTISRDNSKNTLYLQMNSLRAEDTAVYYCARSG
AYWDYSVYDEWGQGTLVTVSS** [SEQ ID NO: 160]

TSGQAGQHHHHHHGAYPYDVPDYAS [SEQ ID NO: 308]

TABLE 41

ET200-044

DNA Sequence (light chain variable region scFv linker
heavy chain variable region His tag + HA tag)
cagtctgtgttgactcagccaccctcagtgtccgtgtccccaggacagac
agccaccatcgcctgttctggacataaattggggggataaatatgcttcct
ggtatcagcagaagtcgggccagtcccctgtgttgatcatctatcaggat
aataagcggccctcagggattcctgagcgattctctggctccaactctgg
gaacacagccactctgaccatcagcgggacccaggctctggatgaggctg
actattattgtcaggcgtgggacagtagtacttatggcattcggcgga
gggaccaagctgaccgtcctaggt [SEQ ID NO: 161]

<u>tctagaggtggtggtggtagcggcggcggcggctctggtggtggtggatc</u>
<u>cctcgagatggcc</u> [SEQ ID NO: 305]

**caggtgcagctgcaggagtccggcccaggactggtgaagccttcggagac
cctgtccctcacctgcgttgtctctggtggctccatcagcagtagtaact
ggtggagctgggtccgccagcccccagggaaggggctggagtggattggg
gaaatctatcatagtgggagccccaactacaacccatccctcaagagtcg
agtcaccatatcagtagacaagtccaagaaccagttctccctgaagctga
gctctgtgaccgccgcggacacggccgtgtattactgtgcgcgcatgact
actcatactttcggttacgatgcttggggtcaaggtactctggtgaccgt
ctcctca** [SEQ ID NO: 162]

TABLE 41-continued

ET200-044

ACTAGTGGCCAGGCCGGCCAGCACCATCACCATCACCATGGCGCATACCC
GTACGACGTTCCGGACTACGCTTCT [SEQ ID NO: 306]

Amino Acid Sequence (light chain variable region scFv linker
heavy chain variable region His tag + HA tag)
QSVLTQPPSVSVSPGQTATIACSGHKLGDKYASWYQQKSGQSPVLIIYQD
NKRPSGIPERFSGSNSGNTATLTISGTQALDEADYYCQAWDSSTYVAFGG
GTKLTVLG [SEQ ID NO: 163]

<u>SRGGGGSGGGGSGGGGSLEMA</u> [SEQ ID NO: 307]

**QVQLQESGPGLVKPSETLSLTCVVSGGSISSSNWWSWVRQPPGKGLEWIG
EIYHSGSPNYNPSLKSRVTISVDKSKNQFSLKLSSVTAADTAVYYCARMT
THTFGYDAWGQGTLVTVSS** [SEQ ID NO: 164]

TSGQAGQHHHHHHGAYPYDVPDYAS [SEQ ID NO: 308]

TABLE 42

ET200-045

DNA Sequence (light chain variable region scFv linker **heavy
chain variable region** His tag + HA tag)
cagcctgtgctgactcagccaccctcagtgtcagtggccccaggaaag
acggccacgattacttgtgggggaaacaacattggaagtgaaagtgtg
cactggtaccaccagaagccaggccaggccctgtgttggtcatctat
gatgatgccggccggccctcagggatccctgagcgattcactggctcc
aactctgggaacacggccaccctgaccatcagcagggtcgaagccgag
gatgaggccgactattactgtcaggtgtgggacagaaatagtgctcag
tttgtatcggacctgggaccaaggtcaccgtcctaggt
[SEQ ID NO: 165]

<u>tctagaggtggtggtggtagcggcggcggcggctctggtggtggtgga</u>
<u>tccctcgagatggcc</u> [SEQ ID NO: 305]

**gaggtccagctggtgcagtctggagctgaggtgaagaagcctggggcc
tcagtgaaggtctcctgcaaggcttctggttacacctttaccagctat
ggtatcagctgggtgcgacaggcccctggacaagggcttgagtggatg
ggatggatcagcgcttacaatggtaacacaaactatgcacagaagctc
cagggcagagtcaccatgaccacagacacatccacgagcacagcctac
atggagctgaggagcctgagatctgacgacacggccgtgtattactgt
gcgcgcggtgttcatctggattggtggggtcaaggtactctggtgacc
gtctcctca** [SEQ ID NO: 166]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker **heavy
chain variable region** His tag + HA tag)
QPVLTQPPSVSVAPGKTATITCGGNNIGSESVHWYHQKPGQAPVLVIY
DDAGRPSGIPERFTGSNSGNTATLTISRVEAGDEADYYCQVWDRNSAQ
FVFGPGTKVTVLG [SEQ ID NO: 167]

<u>SRGGGGSGGGGSGGGGSLEMA</u> [SEQ ID NO: 307]

**EVQLVQSGAEVKKPGASVKVSCKASGYTFTSYGISWVRQAPGQGLEWM
GWISAYNGNTNYAQKLQGRVTMTTDTSTSTAYMELRSLRSDDTAVYYC
ARGVHLDWWGQGTLVTVSS** [SEQ ID NO: 168]

TSGQAGQHHHHHHGAYPYDVPDYAS [SEQ ID NO: 308]

TABLE 43

ET200-069

DNA Sequence (light chain variable region scFv linker heavy chain variable region His tag + HA tag)
cagtctgtcgtgacgcagccaccctcagcgtctgggaccccgggcag
agggtcaccatctcttgttctggaagcagctccaacatcggaagtaat
tatgtatactggtaccagcagctcccaggaacggccccaaactcctc
atctatagtaataatcagcggccctcaggggtccctgaccgattctct
ggctccaagtctggcacctcagcctccctggccatcagtgggctccgg
tccgaggatgaggctgattattactgtgcagcatgggatgacagcctg
agtggttatgtatcggaactgggaccaagctgaccgtcctaggt
[SEQ ID NO: 169]

tctagaggtggtggtggtagcggcggcggcggctctggtggtggtgga
tccctcgagatggcc [SEQ ID NO: 305]

**caggtgcagctacagcagtggggcgcaggactgttgaagccttcggag
accctgtccctcacctgcgctgtctatggtgggtccttcagtggttac
tactggagctggatccgccagcccccagggaaggggctggagtggatt
gggggaaatcaatcatagtggaagcaccaactacaacccgtccctcaag
agtcgagtcaccatatcagtagacacgtccaagaaccagttctccctg
aagctgagctctgtgaccgccgcggacacggccgtgtattactgtgcg
cgcctgtacgaaggtggttaccatggttgggggttcttggctgtcttct
gattctggggtcaaggtactctggtgaccgtctcctca
[SEQ ID NO: 170]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVVTQPPSASGTPGQRVTISCSGSSSNIGSNYVYWYQQLPGTAPKLL
IYSNNQRPSGVPDRFSGSKSGTSASLAISGLRSEDEADYYCAAWDDSL
SGYVFGTGTKLTVLG [SEQ ID NO: 171]

SRGGGGSGGGGSGGGGSLEMA [SEQ ID NO: 307]

**QVQLQQWGAGLLKPSETLSLTCAVYGGSFSGYYWSWIRQPPGKGLEWI
GEINHSGSTNYNPSLKSRVTISVDTSKNQFSLKLSSVTAADTAVYYCA
RLYEGGYHGWGSWLSSDSWGQGTLVTVSS [SEQ ID NO: 172]**

TSGQAGQHHHHHHGAYPYDVPDYAS [SEQ ID NO: 308]

TABLE 44

ET200-078

DNA Sequence (light chain variable region scFv linker heavy chain variable region His tag + HA tag)
cagtctgtgttgactcagccaccctcagcgtctgggaccccgggcag
agggtcaccatctcttgttctggaagcagctccaacatcggaagtaat
actgtaaactggtaccagcagctcccaggaacggccccaaactcctc
atctatagtaataatcagcggccctcaggggtccctgaccgattctct
ggctccaagtctggcacctcagcctccctggccatcagtgggctccag
tctgaggatgaggctgattattactgtgcagcatgggatgacagcctg
aatggttattgggtgttcggcggagggaccaagctgaccgtcctaggt
[SEQ ID NO: 173]

tctagaggtggtggtggtagcggcggcggcggctctggtggtggtgga
tccctcgagatggcc [SEQ ID NO: 305]

**caggtgcagctacagcagtggggcgcaggactgttgaagccttcggag
accctgtccctcacctgcgctgtctatggtgggtccttcagtggttac
tactggagctggatccgccagcccccagggaaggggctggagtggatt
gggggaaatcaatcatagtggaagcaccaactacaacccgtccctcaag
agtcgagtcaccatatcagtagacacgtccaagaaccagttctccctg
aagctgagctctgtgaccgccgcggacacggctgtgtattactgtgcg
cgcgaagggcatttgatgcttttgatatctggggccaagggacaatg
gtcaccgtctcttca [SEQ ID NO: 174]**

TABLE 44-continued

ET200-078

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVLTQPPSASGTPGQRVTISCSGSSSNIGSNTVNWYQQLPGTAPKLL
IYSNNQRPSGVPDRFSGSKSGTSASLAISGLQSEDEADYYCAAWDDSL
NGYWVFGGGTKLTVLG [SEQ ID NO: 175]

SRGGGGSGGGGSGGGGSLEMA [SEQ ID NO: 307]

**QVQLQQWGAGLLKPSETLSLTCAVYGGSFSGYYWSWIRQPPGKGLEWI
GEINHSGSTNYNPSLKSRVTISVDTSKNQFSLKLSSVTAADTAVYYCA
REGAFDAFDIWGQGTMVTVS[SEQ ID NO: 176]**

TSGQAGQHHHHHHGAYPYDVPDYAS [SEQ ID NO: 308]

TABLE 45

ET200-079

DNA Sequence (light chain variable region scFv linker heavy chain variable region His tag + HA tag)
tcctatgagctgactcagccaccctcagcgtctgggaccccgggcag
agggtcaccatctcttgttctggaagcagctccaacatcggaagtaat
tatgtatactggtaccagcagctcccaggaacggccccaaactcttc
atctatagtaataatcagcggccctcaggggtccctgaccgattctct
ggctccaagtctggcacctcagcctccctggccatcagtgggctccgg
tccgaggatgaggctgattattactgtgcagcatgggatgacagcctg
agtggttatctatcggaactgggaccaaggtcaccgtcctaggt
[SEQ ID NO: 177]

tctagaggtggtggtggtagcggcggcggcggctctggtggtggtgga
tccctcgagatggcc [SEQ ID NO: 305]

**gaggtgcagctggtggagtctggggggaggcttggtacagcctggcagg
tccctgagactctcctgtgcagcctctctgattcacctttgatgattat
gccatgcactgggtccggcaagctccagggaagggcctggagtgggtc
tcaggtattagttggaatagtggtagcataggctatgcggactctgtg
aagggccgattcaccatctccagagacaacgccaagaactccctgtat
ctgcaaatgaacagtctgagagctgaggacacggccttgtattactgt
gcaaatggcgactccaactactactacggtatggacgtctggggccaa
gggaccacggtcaccgtctcctca [SEQ ID NO: 178]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
SYELTQPPSASGTPGQRVTISCSGSSSNIGSNYVYWYQQLPGTAPKLF
IYRNNQRPSGVPDRFSGSKSGTSASLAISGLRSEDEADYYCAAWDDSL
SGYLFGTGTKVTVLG [SEQ ID NO: 179]

SRGGGGSGGGGSGGGGSLEMA [SEQ ID NO: 307]

**EVQLVESGGGLVQPGRSLRLSCAASGFTFDDYAMHWVRQAPGKGLEWV
SGISWNSGSIGYADSVKGRFTISRDNAKNSLYLQMNSLRAEDTALYYC
ANGDSNYYYGMDVWGQGTTVTVSS [SEQ ID NO: 180]**

TSGQAGQHHHHHHGAYPYDVPDYAS [SEQ ID NO: 308]

TABLE 46

ET200-081

DNA Sequence (light chain variable region <u>scFv linker</u> heavy chain variable region His tag + HA tag)
cagtctgccctgactcagcctgcctccgtgtccgggtctcctggacag
tcgatcaccatctcctgcactggaaccagcagtgacattggtggttat
aactatgtctcctggtaccaacaacacccaggcaaagcccccaaactc
atgatttatgatgtcagtaatcggccctcaggggtttctaatcggttc
tctggctccaagtctggcaacacggcctccctgaccatctctgggctc
caggctgaggacgaggctgattattactgcatctcatatacacgcacc
tggaaccccatgtatcgggagtgggaccaaggtcaccgtcctaggt
[SEQ ID NO: 181]

<u>tctagaggtggtggtggtagcggcggcggcggctctggtggtggtgga
tccctcgagatggcc</u> [SEQ ID NO: 305]

**gaggtgcagctggtgcagtctgggggaggcgtggtacagcctggggggg
tccctgagactctcctgtgcagcctctggattcacctttgatgattat
gccatgcactgggtccgtcaagctccagggaagggtctggagtgggtc
tctcttattagtggggatggtggtagcacatactatgcagactctgtg
aagggccgattcaccatctccagagacaacagcaaaaactccctgtat
ctgcaaatgaacagtctgagaactgaggacaccgccttgtattactgt
gcaaaagatcgggcagcagctggctactactactacggtatggacgtc
tggggccaagggaccacggtcaccgtctcctca**
[SEQ ID NO: 182]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region <u>scFv linker</u> heavy chain variable region His tag + HA tag)
QSALTQPASVSGSPGQSITISCTGTSSDIGGYNYVSWYQQHPGKAPKL
MIYDVSNRPSGVSNRFSGSKSGNTASLTISGLQAEDEADYYCISYTRT
WNPYVFGSGTKVTVLG [SEQ ID NO: 183]

<u>SRGGGGSGGGGSGGGGSLEMA</u> [SEQ ID NO: 307]

**EVQLVQSGGGVVQPGGSLRLSCAASGFTFDDYAMHWVRQAPGKGLEWV
SLISGDGGSTYYADSVKGRFTISRDNSKNSLYLQMNSLRTEDTALYYC
AKDRAAAGYYYYGMDVWGQGTTVTVSS** [SEQ ID NO: 184]

TSGQAGQHHHHHHGAYPYDVPDYAS [SEQ ID NO: 308]

TABLE 47

ET200-097

DNA Sequence (light chain variable region <u>scFv linker</u> heavy chain variable region His tag + HA tag)
ctgcctgtgctgactcagccaccctcagtgtccgtgtccccaggacag
acagccatcatcacctgctctggagataaattgggggaaaaatatgtt
tcctggtatcagcagaagccaggccagtcccctgtactggtcatcgat
caagataccaggaggccctcagggatccctgagcgattctctggctcc
aactctgggaccacagccactctgaccatcagcgggacccaggctatg
gatgaggctgactattactgtcaggcgtgggacaggggtgtggtattc
ggcggagggaccaagctgaccgtcctaggt [SEQ ID NO: 185]

<u>tctagaggtggtggtggtagcggcggcggcggctctggtggtggtgga
tccctcgagatggcc</u> [SEQ ID NO: 305]

**gaggtgcagctggtggagtctggggagacttggtacagcctggcagg
tccctgagactctcctgtgcagcctctggattcacctttaatgattat
gccatgcactgggtccggcaagctccagggaagggctggagtgggtc
tcaggtattagttgggagtggtaataacataggctatgcggactctgtg
aagggccgattcaccatctccagagacaacagcaagaactccctgtat
ctgcaaatgaacagtctgagactgaggacacgccttgtattactgt
gcaaaagatagtatacggtatggcatcacctgggaggttttgactac
tggggccagggaaccctggtcaccgtctcctca**
[SEQ ID NO: 186]

TABLE 47-continued

ET200-097

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region <u>scFv linker</u> heavy chain variable region His tag + HA tag)
LPVLTQPPSVSVSPGQTAIITCSGDKLGEKYVSWYQQKPGQSPVLVID
QDTRRPSGIPERFSGSNSGTTATLTISGTQAMDEADYYCQAWDRGVVF
GGGTKLTVLG [SEQ ID NO: 187]

<u>SRGGGGSGGGGSGGGGSLEMA</u> [SEQ ID NO: 307]

**EVQLVESGGDLVQPGRSLRLSCAASGFTFNDYAMHWVRQAPGKGLEWV
SGISWSGNNIGYADSVKGRFTISRDNAKNSLYLQMNSLRAEDTALYYC
AKDSIRYGITWGGFDYWGQGTLVTVSS** [SEQ ID NO: 188]

TSGQAGQHHHHHHGAYPYDVPDYAS [SEQ ID NO: 308]

TABLE 48

ET200-098

DNA Sequence (light chain variable region <u>scFv linker</u> heavy chain variable region His tag + HA tag)
cagcctgtgctgactcagccaccctcggtgtccaagggcttgagacag
accgccacactcacctgcactgggaacagcaacaatgttggcaaccta
ggagtagcttggctgcagcagcaccagggccaccctcccaaactccta
tcctacaggaataacaaccggccctcagggatctcagagagattatct
gcatccaggtcaggaaacacagcctccctgaccattactggactccag
cctgaggacgaggctgactattactgctcagcatggacagtagcctc
agtgcttgggtgttcggcggagggaccaagctgaccgtcctaggt
[SEQ ID NO: 189]

<u>tctagaggtggtggtggtagcggcggcggcggctctggtggtggtgga
tccctcgagatggcc</u> [SEQ ID NO: 305]

**gaggtgcagctggtggagtctggggggagtcgtggtacagcctggggggg
tccctgagactctcctgtgcagcctctggattcacctttgatgattat
gccatgcactgggtccgtcaagctccgggggaagggtctggagtgggtc
tctcttattaattgggatggtggtagcacctactatgcagactctgtg
aagggccgattcaccatctccagagacaacagcaaaaactccctgtat
ctgcaaatgaacagtctgagagctgaggacaccgccttgtattactgt
gcaaaagggatgggctgagggcgtttgactactggggccagggaacc
ctggtcaccgtctcctca** [SEQ ID NO: 190]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region <u>scFv linker</u> heavy chain variable region His tag + HA tag)
QPVLTQPPSVSKGLRQTATLTCTGNSNNVGNLGVAWLQQHQGHPPKLL
SYRNNNRPSGISERLSASRSGNTASLTITGLQPEDEADYYCSAWDSSL
SAWVFGGGTKLTVLG [SEQ ID NO: 191]

<u>SRGGGGSGGGGSGGGGSLEMA</u> [SEQ ID NO: 307]

**EVQLVESGGVVVQPGGSLRLSCAASGFTFDDYAMHWVRQAPGKGLEWV
SLINWDGGSTYYADSVKGRFTISRDNSKNSLYLQMNSLRAEDTALYYC
AKGMGLRAFDYWGQGTLVTVSS** [SEQ ID NO: 192]

TSGQAGQHHHHHHGAYPYDVPDYAS [SEQ ID NO: 308]

TABLE 49

ET200-099

DNA Sequence (light chain variable region scFv linker heavy chain variable region His tag + HA tag)
cagtctgtgttgactcagccaccctcagcgtctgggacccccgggcag
agggtcaccatctcctgttctggaagcagctccaacatcggaagtaat
actgtaaactggtaccagcagctcccaggaacggcccccaaactcctc
atctatagtaatgatcagcggccctcagggggtccctgaccgattctct
ggctccaagtccggcacctcagcctccctggccatcagtgggctccag
tctgaggatgaggctgattattactgtgcttcatgggatgacagcctg
aatggccgttatgtatcggaactgggaccaaggtcaccgtcctaggt
[SEQ ID NO: 193]

tctagaggtggtggtggtagcggcggcggcggctctggtggtggtgga
tccctcgagatggcc [SEQ ID NO: 305]

**caggtccagctggtacagtctggggctgaggtgaggaagcctggggcc
tcagtgaaggtttcctgcaagacttctggatacaccttcagttggtat
gctatacattgggtgcgccaggcccccggacaaaggcttgagtggatg
ggatggatcaacgctggcaatggaaacacaaaatattcacagaaattt
cagggcagagtcagtcttaccagggacacatccgcgagcacagcctac
atggagctgagcagcctgagatctgatgacacggctgtgtattactgt
gcgagacccgataattatggttcgggtgggatgttttttgatatctgg
ggccaagggacaatggtcaccgtctcttca [SEQ ID NO: 194]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVLTQPPSASGTPGQRVTISCSGSSSNIGSNTVNWYQQLPGTAPKLL
IYSNDQRPSGVPDRFSGSKSGTSASLAISGLQSEDEADYYCASWDDSL
NGRYVFGTGTKVTVLG [SEQ ID NO: 195]

SRGGGGSGGGGSGGGGSLEMA [SEQ ID NO: 307]

**QVQLVQSGAEVRKPGASVKVSCKTSGYTFSWYAIHWVRQAPGQRLEWM
GWINAGNGNTKYSQKFQGRVSLTRDTSASTAYMELSSLRSDDTAVYYC
ARPDNYGSGGDVFDIWGQGTMVTVSS [SEQ ID NO: 196]**

TSGQAGQHHHHHHGAYPYDVPDYAS [SEQ ID NO: 308]

TABLE 50

ET200-100

DNA Sequence (light chain variable region scFv linker heavy chain variable region His tag + HA tag)
aattttatgctgactcagccccactctgtgtcggagtctccggggaag
acggtaaccatctcctgcacccgcagcagtggcagcattgccagcaac
tttgtgcagtggtaccagcagcgccgggcagtgcccccacccctatg
atctatgaggataacaacagaccccctggggtccctgatcggttctct
gcctccgtcgacagctcctccaactctgcctccctcaccatctctgga
ctgaagactgaggacgaggctgactactactgtcagtcttatgatacc
agcaatgtggtattcggcggggggaccaagctgaccgtcctaggt
[SEQ ID NO: 197]

tctagaggtggtggtggtagcggcggcggcggctctggtggtggtgga
tccctcgagatggcc [SEQ ID NO: 305]

**gaggtgcagctggtggagtctgggggaggcttggtacagcctggaggg
tccctgagactctcctgtgcagcctctggattcaccttcagtagttat
gaaatgaactgggtccgccaggctccagggaaggggctggagtgggtt
tcatacattagtagtagtggtagtacatatactacgcagactctgtg
aagggccgattcaccatctccagagacaacgccaagaactcactgtat
ctgcaaatgaacagcctgagagccgaggacacggctgtttattactgt
gcacgctgggactacggtatggacgtctgggccaagggaccacggtc
accgtctcctca [SEQ ID NO: 198]**

TABLE 50-continued

ET200-100

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
NFMLTQPHSVSESPGKTVTISCTRSSGSIASNFVQWYQQRPGSAPTPM
IYEDNNRPPGVPDRFSASVDSSSNSASLTISGLKTEDEADYYCQSYDT
SNVVFGGGTKLTVLG [SEQ ID NO: 199]

SRGGGGSGGGGSGGGGSLEMA [SEQ ID NO: 307]

**EVQLVESGGGLVQPGGSLRLSCAASGFTFSSYEMNWVRQAPGKGLEWV
SYISSSGSTIVYADSVKGRFTISRDNAKNSLYLQMNSLRAEDTAVYYC
ARWDYGMDVWGQGTTVTVSS [SEQ ID NO: 200]**

TSGQAGQHHHHHHGAYPYDVPDYAS [SEQ ID NO: 308]

TABLE 51

ET200-101

DNA Sequence (light chain variable region scFv linker heavy chain variable region His tag + HA tag)
caggctgtgctgactcagccaccctcagcgtctggggccccgggcag
agggtcaccgtctcttgttctggaagcaactccaacatcggaagtaac
tacgttaactggtaccagcagttcccaggaacggccccaaactcctc
atgtatagtagtcagcggccctcagggggtccctgaccgattctct
ggctccaagtctggcacctcagcctccctggccatcagtgggctccac
tctgaggatgaggctgattattactgtgctacatgggatgacagcctg
aatgcttgggtgttcggcggagggaccaagctgaccgtcctaggt
[SEQ ID NO: 201]

tctagaggtggtggtggtagcggcggcggcggctctggtggtggtgga
tccctcgagatggcc [SEQ ID NO: 305]

**gaggtccagctggtgcagtctgggggctgaggtgaggaagcctggggcc
tcagtgaaggtttcctgcaagacttctggatacaccttcacttggtat
gctatacattgggtgcgccaggcccccggacaaaggcttgagtggatg
ggatggatcaacgctggcagtggaaacacaaaatattcacagaaattt
cagggcagagtcaccccttaccagggacacatccgcgagcacagcgtac
atggagctgagcagcctgagatctgatgacacggctgtgtattactgt
gcgagacccaataactatggttcgggtgggatgttttttgatatctgg
ggccaagggacaatggtcaccgtctcttca [SEQ ID NO: 202]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QAVLTQPPSASGAPGQRVTVSCSGSNSNIGSNYVNWYQQFPGTAPKLL
MYSSSQRPSGVPDRFSGSKSGTSASLAISGLHSEDEADYYCATWDDSL
NAWVFGGGTKLTVLG [SEQ ID NO: 203]

SRGGGGSGGGGSGGGGSLEMA [SEQ ID NO: 307]

**EVQLVQSGAEVRKPGASVKVSCKTSGYTFTWYAIHWVRQAPGQRLEWM
GWINAGSGNTKYSQKFQGRVTLTRDTSASTAYMELSSLRSDDTAVYYC
ARPNNYGSGGDVFDIWGQGTMVTVSS [SEQ ID NO: 204]**

TSGQAGQHHHHHHGAYPYDVPDYAS [SEQ ID NO: 308]

TABLE 52

ET200-102

DNA Sequence (light chain variable region scFv linker heavy chain variable region His tag + HA tag)
cagtctgtcgtgacgcagccgccctcagtgtctgcggccccaggacag
aaggtcaccatctcctgctctggaagcagctccaacattgggaataat
tatgtatcctggtaccagcagctcccaggaacagcccccaaactcctc
atttatgacaataataagcgaccctcagggattcctgaccgattctct
ggctccaagtctggcacgtcagccaccctgggcatcaccgggactccag
actgggacgaggccgattattactgcggaacatgggatagcagcctg
agtgatatgtatcggaactgggaccaaggtcaccgtcctaggt
[SEQ ID NO: 205]

tctagaggtggtggtggtagcggcggcggcggctctggtggtggtgga
tccctcgagatggcc [SEQ ID NO: 305]

**caggtccagctggtgcagtctgggggctgaggtgaagaagcctggggcc
tcagtgaaagtttcctgcaaggcttctggatacaccttcacgaactat
gctctgcattgggtgcgccaggcccccggacaagggcttgagtggatg
gcatggatcaacggtggcaatggtaacacaaaatattcacagaacttc
cagggcagagtcaccattaccagggacacatccgcgagcacagcctat
atggagctgagcagcctgagatctgaagacacggctgtgtattactgt
gcgaaaccggaggaaacagctggaacaatccactttgactactgggc
cagggaaccccggtcaccgtctcctca [SEQ ID NO: 206]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVVTQPPSVSAAPGQKVTISCSGSSSNIGNNYVSWYQQLPGTAPKLL
IYDNNKRPSGIPDRFSGSKSGTSATLGITGLQTGDEADYYCGTWDSSL
SAYVFGTGTKVTVLG [SEQ ID NO: 207]

SRGGGGSGGGGSGGGGSLEMA [SEQ ID NO: 307]

**QVQLVQSGAEVKKPGASVKVSCKASGYTFTNYALHWVRQAPGQGLEWM
AWINGGNGNTKYSQNFQGRVTITRDTSASTAYMELSSLRSEDTAVYYC
AKPEETAGTIHFDYWGQGTPVTVSS [SEQ ID NO: 208]**

TSGQAGQHHHHHHGAYPYDVPDYAS [SEQ ID NO: 308]

TABLE 53

ET200-103

DNA Sequence (light chain variable region scFv linker heavy chain variable region His tag + HA tag)
caggctgtgctgactcagccccactctgtgtcggagtctccggggaag
acggtaaccatctcctgcacccgcagcagtggcagcattgccagcaac
tatgtgcagtggtaccagcagcgcccgggcagtgcccccaccactgtg
atctatgaggataaccaaagaccctctggggtccctgatcggttctct
ggctccatcgacagctcctccaactctgcctccctcaccatctctgga
ctgaagactgaggacgaggctgactactactgtcagtatgatagca
ccatcacggtgttcggcggagggaccaagctgaccgtcctaggt
[SEQ ID NO: 209]

tctagaggtggtggtggtagcggcggcggcggctctggtggtggtgga
tccctcgagatggcc [SEQ ID NO: 305]

**caggtccagctggtacagtctgggggctgaggtgaagaagcctgggtcc
tcggtgaaggtctcctgcaaggcttctggaggcaccttcagcagctat
gctatcagctgggtgcgacaggcccctggacaagggcttgagtggatg
ggagggatcatccctatctttggtacagcaaactacgcacagaagttc
cagggcagagtcacgattaccagggacgaatccacgagcacagcctac
atggagctgagcagcctgagatctgaggacacggccgtgtattactgt
gcgggggagggttactatgatagtagtggttattccaacggtgatgct
tttgatatctggggccaagggacaatggtcaccgtctcttca**
[SEQ ID NO: 210]

TABLE 53-continued

ET200-103

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QAVLTQPHSVSESPGKTVTISCTRSSGSIASNYVQWYQQRPGSAPTTV
IYEDNQRPSGVPDRFSGSIDSSSNSASLTISGLKTEDEADYYCQSYDS
TITVFGGGTKLTVLG [SEQ ID NO: 211]

SRGGGGSGGGGSGGGGSLEMA [SEQ ID NO: 307]

**QVQLVQSGAEVKKPGSSVKVSCKASGGTFSSYAISWVRQAPGQGLEWM
GGIIPIFGTANYAQKFQGRVTITADESTSTAYMELSSLRSEDTAVYYC
AGEGYYDSSGYSNGDAFDIWGQGTMVTVSS [SEQ ID NO: 212]**

TSGQAGQHHHHHHGAYPYDVPDYAS [SEQ ID NO: 308]

TABLE 54

ET200-104

DNA Sequence (light chain variable region scFv linker heavy chain variable region His tag + HA tag)
aattttatgctgactcagccccactctgtgtcggagtctccggggaag
acggtaaccatctcctgcacccgcagcagtggcagcattgccagcaac
tatgtgcagtggtaccagcagcgcccgggcagtgcccccaccactgtg
atctatgaggataaccaaagaccctctggggtccctgatcggttctct
ggctccatcgacagctcctccaactctgcctccctcaccatctctgga
ctgaagactgaggacgaggctgactactactgtcagtcttatgatagc
agcaatgtggtattcggcggagggaccaaggtcaccgtcctaggt
[SEQ ID NO: 213]

tctagaggtggtggtggtagcggcggcggcggctctggtggtggtgga
tccctcgagatggcc [SEQ ID NO: 305]

**gaggtgcagctggtggagtctggggggaggcttggtacagcctggaggg
tccctgagactctcctgtgcagcctctggattcaccttcagtagttat
gaaatgaactgggtccgccaggctccagggaaggggctggagtgggtt
tcatacattagtagtagtggtagtaccatatactacgcagactctgtg
aagggccgattcaccatctccagagacaacgccaagaactcactgtat
ctgcaaatgaacagcctgagagccgaggacacggctgtttattactgt
gcacgctgggactacggtatggacgtctggggccaagggaccacggtc
accgtctcctca [SEQ ID NO: 214]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
NFMLTQPHSVSESPGKTVTISCTRSSGSIASNYVQWYQQRPGSAPTTV
IYEDNQRPSGVPDRFSGSIDSSSNSASLTISGLKTEDEADYYCQSYDS
SNVVFGGGTKVTVLG [SEQ ID NO: 215]

SRGGGGSGGGGSGGGGSLEMA [SEQ ID NO: 307]

**EVQLVESGGGLVQPGGSLRLSCAASGFTFSSYEMNWVRQAPGKGLEWV
SYISSSGSTIVYADSVKGRFTISRDNAKNSLYLQMNSLRAEDTAVYYC
ARWDYGMDVWGQGTTVTVSS [SEQ ID NO: 216]**

TSGQAGQHHHHHHGAYPYDVPDYAS [SEQ ID NO: 308]

TABLE 55

ET200-105

DNA Sequence (light chain variable region scFv linker heavy
chain variable region His tag + HA tag)
tcctatgtgctgactcagccaccctcagtgtccgtgtccccaggacag
acagccagcatcacctgctctggagatagattgacgaataaatatgtt
tcctggtatcaacagaagccaggccagtccctgtgttggtcatctat
gaggatgccaagcggccctcagggatccctgcgcgattctctggctcc
aactctgggaacacagccactctgaccatcagcggaccaggcctatg
gatgagtctgaatattactgtcaggcgtgggacagcagtgtggtggt
tttggcggagggaccaagctgaccgtcctaggt
[SEQ ID NO: 217]

tctagaggtggtggtggtagcggcggcggcggctctggtggtggtgga
tccctcgagatggcc [SEQ ID NO: 305]

gaggtgcagctggtggagtctgggggaggcttggtacagcctggcagg
tccctgagactctcctgtgcagcctctggatttacctttgatgattat
gccatgcactgggtccggcaagctccagggaagggcctggagtgggtc
tcaggtattagttggaatagtggtagtataggctatgcggactctgtg
aagggccgattcaccatctccagagacaacgccaagaactccctgtat
ctgcaaatgaacagtctgagagatgaggacacggccttgtattactgt
gcaaaagaccgaggggggggagttatcgttaaggatgcttttgatatc
tggggccaagggacaatggtcaccgtctcttca
[SEQ ID NO: 218]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy
chain variable region His tag + HA tag)
SYVLTQPPSVSVSPGQTASITCSGDRLTNKYVSWYQQKPGQSPVLVIY
EDAKRPSGIPARFSGSNSGNTATLTISGTQAMDESEYYCQAWDSSVVV
FGGGTKLTVLG [SEQ ID NO: 219]

SRGGGGSGGGGSGGGGSLEMA [SEQ ID NO: 307]

**EVQLVESGGGLVQPGRSLRLSCAASGFTFDDYAMHWVRQAPGKGLEWV
SGISWNSGSIGYADSVKGRFTISRDNAKNSLYLQMNSLRDEDTALYYC
AKDRGGGVIVKDAFDIWGQGTMVTVSS** [SEQ ID NO: 220]

TSGQAGQHHHHHHGAYPYDVPDYAS [SEQ ID NO: 308]

TABLE 56

ET200-106

DNA Sequence (light chain variable region scFv linker heavy
chain variable region His tag + HA tag)
tcctatgagctgactcagccaccgcagcgtctgggaccccggacag
agagtcaccatctcttgttctgggggcgtctccaacatcgggagtggt
gctctaaattggtaccagcaactcccaggaacggcccccaaactcctc
atctatagttacaatcagcggccctcaggggtctctgaccgattctct
ggctccaggtctgccacctcagcctcctggccatcagtgggctccag
tctgaggatgaggctgattattactgtgcaacctgggatgatagtgtg
aatggttgggtgttcggcggagggaccaagctgaccgtcctaggt
[SEQ ID NO: 221]

tctagaggtggtggtggtagcggcggcggcggctctggtggtggtgga
tccctcgagatggcc [SEQ ID NO: 305]

gaggtgcagctggtggagtctggagctgaggtgaagaagcctggggat
tcagtgaaggtctcctgcaaggcttctggttacaattttctcaactat
ggtatcaactgggtgcgacaggcccctggacaagggcttgagtggatg
ggatggattagcacttacaatggtctcacaaactatgcacagaagctg
cagggcagagtcaccttcaccacagacacatccacgagcacagcctac
atggagatgaggagcctgagatctgacgacacggccgtgtattactgt
gcgcgccagcagggtggtggttggtacgatgtttggggtcaagggact
ctggtcaccgtctcctca [SEQ ID NO: 222]

TABLE 56-continued

ET200-106

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy )
chain variable region His tag + HA tag
SYELTQPPAASGTPGQRVTISCSGGVSNIGSGALNWYQQLPGTAPKLL
IYSYNQRPSGVSDRFSGSRSATSASLAISGLQSEDEADYYCATWDDSV
NGWVFGGGTKLTVLG [SEQ ID NO: 223]

SRGGGGSGGGGSGGGGSLEMA [SEQ ID NO: 307]

**EVQLVESGAEVKKPGDSVKVSCKPSGYNFLNYGINWVRQAPGQGLEWM
GWISTYTGNTNYAQKLQGRVTFTTDTSTSTAYMEMRSLRSDDTAVYYC
ARQQGGGWYDVWGQGTLVTVSS** [SEQ ID NO: 224]

TSGQAGQHHHHHHGAYPYDVPDYAS [SEQ ID NO: 308]

TABLE 57

ET200-107

DNA Sequence (light chain variable region scFv linker heavy
chain variable region His tag + HA tag)
cagtctgtctgtgacgcagccgccctcagtgtctgcggccccaggagag
aaggtcaccatctcctgctctggaagcaacttcaatgttggaaataat
gatgtatcctggtatcagcaactcccaggtgcagcccccaaactcctc
atttatgacaataataagcgaccctcagggattcctgaccgattctct
ggctccaagtctggcacgtcagccaccctggacatcaccgggctccac
agtgacgacgaggccgattattactgcggaacatgggatagcagcctg
aatgctggggggggtatcgaactgggaccaaggtcaccgtcctaggt
[SEQ ID NO: 225]

tctagaggtggtggtggtagcggcggcggcggctctggtggtggtgga
tccctcgagatggcc [SEQ ID NO: 305]

gaggtccagctggtgcagtctggagctgaggtgaagaagcctggggcc
tcagtgaaggtctcctgcaaggcttctggttacacctttaccagctat
actatcagctgggtacgacaggcccctggacaagggcttgagtggatg
ggatggatcagcacttacaatggtctcacaaactatgcacagaacctc
cagggcagagtcaccatgactacagacacattcacgaccacagcctac
atggagctgaggagcctcagatctgacgacacggccgtgtattactgt
gtgagagagggtcccccgactacggtgacttcgcgtcctttgactac
tggggccagggaaccctggtcaccgtctcctca
[SEQ ID NO: 226]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy
chain variable region His tag + HA tag)
QSVVTQPPSVSAAPGEKVTISCSGSNFNVGNNDVSWYQQLPGAAPKLL
IYDNNKRPSGIPDRFSGSKSGTSATLDITGLHSDDEADYYCGTWDDSL
NTGGVFGTGTKVTVLG [SEQ ID NO: 227]

SRGGGGSGGGGSGGGGSLEMA [SEQ ID NO: 307]

**EVQLVQSGAEVKKPGASVKVSCKASGYTFTSYTISWVRQAPGQGLEWM
GWISTYNGLTNYAQNLQGRVTMTTDTFTTTAYMELRSLRSDDTAVYYC
VREGSPDYGDFASFDYWGQGTLVTVSS** [SEQ ID NO: 228]

TSGQAGQHHHHHHGAYPYDVPDYAS [SEQ ID NO: 308]

TABLE 58

ET200-108

DNA Sequence (light chain variable region scFv linker heavy chain variable region His tag + HA tag)
cagtctgtgttgacgcagccgccctcagtgtctgcgccccgggacag
aaggtcaccatctcctgctctggaagcagctccaacattgggaataat
tatgtatcctggtaccagcagttcccaggaacagccccccaaactcctc
atttatgacaataataagcgaccctcaggatttctgaccgattctct
ggctccaagtctggcacgtcagccaccctgggcatcgccggactccag
actgggacgaggccgattattactgcggaacatgggataccagcctg
agtggttttatgtcttcggaagtgggaccaaggtcaccgtcctaggt
[SEQ ID NO: 229]

tctagaggtggtggtggtagcggcggcggcggctctggtggtggtgga
tccctcgagatggcc [SEQ ID NO: 305]

**gaggtccagctggtacagtctggagctgaggtgaagaagcctggggcc
tcagtgaaggtctcctgcaaggcttctggttacacctttaccagctat
actatcagctgggtacgacaggcccctggacaagggcttgagtggatg
ggatggatcagcacttacaatggtctcacaaactatgcacagaacctc
cagggcagagtcaccatgactacagacacattcacgaccacagcctac
atggagctgaggagcctcagatctgacgacacggccgtgtattactgt
gtgagagaggggtccccgactacggtgacttcgcgtcctttgactac
tggggccaggggaaccctggtcaccgtctcctca**
[SEQ ID NO: 230]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVLTQPPSVSAPPGQKVTISCSGSSSNIGNNYVSWYQQFPGTAPKLL
IYDNNKRPSGISDRFSGSKSGTSATLGIAGLQTGDEADYYCGTWDTSL
SGFYVFGSGTKVTVLG [SEQ ID NO: 231]

SRGGGGSGGGGSGGGGSLEMA [SEQ ID NO: 307]

**EVQLVQSGAEVKKPGASVKVSCKASGYTFTSYTISWVRQAPGQGLEWM
GWISTYNGLTNYAQNLQGRVTMTTDTFTTTAYMELRSLRSDDTAVYYC
VREGSPDYGDFASFDYWGQGTLVTVSS** [SEQ ID NO: 232]

TSGQAGQHHHHHHGAYPYDVPDYAS [SEQ ID NO: 308]

TABLE 59

ET200-109

DNA Sequence (light chain variable region scFv linker heavy chain variable region His tag + HA tag)
ctgcctgtgctgactcagccaccctcagcgtctgcgacccccgggcag
aaggtcaccatctcttgttctggaaccacctccaacatcggaagtaat
actgtacactggtaccagcagctcccagggacggccccccaaactcctc
atctataataataatcagcggccctcaggggtccctgaccggattctct
ggctccaagtctggcacctcagcctccctggccatcagtgggctccgg
tccgaggatgaggcacatattcctgtgtcaacatgggatgacagcctg
agtggtgtggtatcggcggagggaccaagctgaccgtcctaggt
[SEQ ID NO: 233]

tctagaggtggtggtggtagcggcggcggcggctctggtggtggtgga
tccctcgagatggcc [SEQ ID NO: 305]

**gaggtccagctggtgcagtctggggctgaggtgaagaagcctgggtcc
tcggtgaaggtctcctgcaaggcttctggaggcaccttcagcagctat
gctatcagctgggtgcgacaggcccctggacaagggcttgagtggatg
ggagggatcatccctatctttggtacagcaaactacgcacagaagttc
cagggcagagtcacgattaccgcggacgaatccacgagcacagcctac
atggagctgagcagcctgagatctgaggacacggccgtgtattactgt
gcgagagatcccgcctacggtgactacgagtatgatgctttt gatatc
tggggccaagggacaatggtcaccgtctcttca**
[SEQ ID NO: 234]

TABLE 59-continued

ET200-109

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
LPVLTQPPSASATPGQRVTISCSGTTSNIGSNTVHWYQQLPGTAPKLL
IYNNNQRPSGVPDRFSGSKSGTSASLAISGLRSEDEATYSCATWDDSL
SGVVFGGGTKLTVLG [SEQ ID NO: 235]

SRGGGGSGGGGSGGGGSLEMA [SEQ ID NO: 307]

**EVQLVQSGAEVKKPGSSVKVSCKASGGTFSSYAISWVRQAPGQGLEWM
GGIIPIFGTANYAQKFQGRVTITADESTSTAYMELSSLRSEDTAVYYC
ARDPAYGDYEYDAFDIWGQGTMVTVSS** [SEQ ID NO: 236]

TSGQAGQHHHHHHGAYPYDVPDYAS [SEQ ID NO: 308]

TABLE 60

ET200-110

DNA Sequence (light chain variable region scFv linker heavy chain variable region His tag + HA tag)
cagtctgtgttgacgcagccgccctcagcgtctgggaccccgggcag
aaggtcaccatctcttgttctggaagcagctccaacatcggaactaat
ggtgtaaactggttccagcagttcccaggaacggcccccaaactcctc
atctataataatgatcagcggccctcaggggtccctgaccgattctct
ggctccaagtctggcacctcagcctccctggccatcagtgggctccag
tctgcggatgaggctgattattactgtgcagtgtggatgacacagcctg
aatggtccggtgttcggcggagggaccaagctgaccgtcctaggt
[SEQ ID NO: 237]

tctagaggtggtggtggtagcggcggcggcggctctggtggtggtgga
tccctcgagatggcc [SEQ ID NO: 305]

**caggtgcagctggtgcagtctggggctgaggtgaagaagcctgggtcc
tcggtgaaggtctcctgcaaggcttctggaggcaccttcagcagctat
gctatcagctgggtgcgacaggcccctggacaagggcttgagtggatg
ggagggatcatccctatctttggtacagcaaactacgcacagaagttc
cagggcagagtcacgattaccgcggacgaatccacgagcacagcctac
atggagctgagcagcctgagatctgaggacacggccgtgtattactgt
gcgagagggcggtttttgatgcttttgatatctggggccaagggaca
atggtcaccgtctcttca** [SEQ ID NO: 238]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVLTQPPSASGTPGQRVTISCSGSSSNIGTNGVNWFQQFPGTAPKLL
IYTNDQRPSGVPDRFSGSKSGTSASLAISGLQSADEADYYCAVWDHSL
NGPVFGGGTKLTVLG [SEQ ID NO: 239]

SRGGGGSGGGGSGGGGSLEMA [SEQ ID NO: 307]

**QVQLVQSGAEVKKPGSSVKVSCKASGGTFSSYAISWVRQAPGQGLEWM
GGIIPIFGTANYAQKFQGRVTITADESTSTAYMELSSLRSEDTAVYYC
ARGAGFDAFDIWGQGTMVTVSS** [SEQ ID NO: 240]

TSGQAGQHHHHHHGAYPYDVPDYAS [SEQ ID NO: 308]

TABLE 61

ET200-111

DNA Sequence (light chain variable region scFv linker heavy chain variable region His tag + HA tag)
caggctgtgctgactcagccaccctcagcgtctgggaccccgggcag
agggtcaccatctcttgttctggaagcagctccaacatcggaagtaat
actgtaaactggtaccagcagctcccaggaacggcccccaaactcctc
atctatagtaataatcagcggccctcagggggtccctgaccgattctct
ggctccaagtctggcacctcagcctccctggccatcagtgggctccag
tctgaggatgagactgattattactgtgcagcatgggatgacagcctg
aatggttatgtatcggaactgggaccaaggtcaccgtcctaggt
[SEQ ID NO: 241]

tctagaggtggtggtggtagcggcggcggcggctctggtggtggtgga
tccctcgagatggcc [SEQ ID NO: 305]

**caggtgcagctacagcagtggggcgcaggactgttgaagccttcggag
accctgtccctcacctgcgctgtctatggtgggtccttcagtggttac
tactggagctggatccgccagcccccagggaaggggctggagtggatt
gggggaaatcaatcatagtggaagcaccaactacaaccgtccctcaag
agtcgagtcaccatatcagtagacacgtccaagaaccagttctccctg
aagctgagctctgtgaccgccgcggacacggctgtgtattactgtgcg
agagaggggctagatgcttttgatatctggggccaagggacaatggtc
accgtctcttca** [SEQ ID NO: 242]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QAVLTQPPSASGTPGQRVTISCSGSSSNIGSNTVNWYQQLPGTAPKLL
IYSNNQRPSGVPDRFSGSKSGTSASLAISGLQSEDETDYYCAAWDDSL
NGYVFGTGTKVTVLG [SEQ ID NO: 243]

SRGGGGSGGGGSGGGGSLEMA [SEQ ID NO: 307]

**QVQLQQWGAGLLKPSETLSLTCAVYGGSFSGYYWSWIRQPPGKGLEWI
GEINHSGSTNYNPSLKSRVTISVDTSKNQFSLKLSSVTAADTAVYYCA
REGLDAFDIWGQGTMVTVSS** [SEQ ID NO: 244]

TSGQAGQHHHHHHGAYPYDVPDYAS [SEQ ID NO: 308]

TABLE 62

ET200-112

DNA Sequence (light chain variable region scFv linker heavy chain variable region His tag + HA tag)
caggctgtgctgactcagccaccctcagcgtctgggaccccgggcag
agggtcaccatctcttgttctggaagcagctccaacatcggaagtaat
actgtaaactggtaccagcagctcccaggaacggcccccaaactcctc
atgtatagtaatgatcagcggccctcagggggtccctgaccgattctct
ggctccaagtctggcacctcagcctccctggccatcagtgggctccag
tctgaggatgaggctgattattattgtgcagcatgggatgacagcctg
aatggttatgtcttcgcagctgggacccagctcaccgtttttaagt
[SEQ ID NO: 245]

tctagaggtggtggtggtagcggcggcggcggctctggtggtggtgga
tccctcgagatggcc [SEQ ID NO: 305]

**caggtgcagctacagcagtggggcgcaggactgttgaagccttcggag
accctgtccctcacctgcgctgtctatggtgggtccttcagtggttac
tactggagctggatccgccagcccccagggaaggggctggagtggatt
gggggaaatcaatcatagtggaagcaccaactacaaccgtccctcaag
agtcgagtcaccatatcagtagacacgtccaagaaccagttctccctg
aagctgagctctgtgaccgccgcggacacggctgtgtattactgtgcg
agagaggggctagatgcttttgatatctggggccaagggacaatggtc
accgtctcttca** [SEQ ID NO: 246]

TABLE 62-continued

ET200-112

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QAVLTQPPSASGTPGQRVTISCSGSSSNIGSNTVNWYQQLPGTAPKLL
MYSNDQRPSGVPDRFSGSKSGTSASLAISGLQSEDEADYYCAAWDDSL
NGYVFAAGTQLTVLS [SEQ ID NO: 247]

SRGGGGSGGGGSGGGGSLEMA [SEQ ID NO: 307]

**QVQLQQWGAGLLKPSETLSLTCAVYGGSFSGYYWSWIRQPPGKGLEWI
GEINHSGSTNYNPSLKSRVTISVDTSKNQFSLKLSSVTAADTAVYYCA
REGLDAFDIWGQGTMVTVSS** [SEQ ID NO: 248]

TSGQAGQHHHHHHGAYPYDVPDYAS [SEQ ID NO: 308]

TABLE 63

ET200-113

DNA Sequence (light chain variable region scFv linker heavy chain variable region His tag + HA tag)
cagtctgtctgacgcagccgccctcagtgtctgcggccccaggacag
aaggtcaccatctcctgctctggaagcagctccaacattgggaataat
tatgtatcctggtaccagcagctcccaggaacagcccccaaactcctc
atttatgacaataataagcgaccctcagggattcctgaccgattctct
ggctccaagtctggcacgtcagccaccctgggcatcactggactccag
actgggacgaggccgattattactgggaacatgggatagcagcctg
agtgctgatatgtatcggaactgggaccaaggtcaccgtcctaggt
[SEQ ID NO: 249]

tctagaggtggtggtggtagcggcggcggcggctctggtggtggtgga
tccctcgagatggcc [SEQ ID NO: 305]

**caggtccagctggtacagtctggagctgaggtgaagaagcctggggcc
tcagtgaaggtctcctgcaaggcttctggttacagctttaccagctat
actatcagctgggttcgacaggcccctggacaaggccttgagtggatg
ggatgggtcagcacttacaatggtctcagaaactatgcacagaacctc
cagggcagagtcaccatgactacagacacactcacgaccacagcctac
atggagctgaggagcctcagatctgacgacacggccgtgtattattgt
gtgagagaggggtcccccgactacggtgacttcgcggcctttgactac
tggggccagggcaccctggtcaccgtctcctca**
[SEQ ID NO: 250]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVVTQPPSVSAAPGQKVTISCSGSSSNIGNNYVSWYQQLPGTAPKLL
IYDNNKRPSGIPDRFSGSKSGTSATLGITGLQTGDEADYYCGTWDSSL
SAAYVFGTGTKVTVLG [SEQ ID NO: 251]

SRGGGGSGGGGSGGGGSLEMA [SEQ ID NO: 307]

**QVQLVQSGAEVKKPGASVKVSCKASGYSFTSYTISWVRQAPGQGLEWM
GWVSTYNGLRNYAQNLQGRVTMTTDTLTTTAYMELRSLRSDDTAVYYC
VREGSPDYGDFAAFDYWGQGTLVTVSS** [SEQ ID NO: 252]

TSGQAGQHHHHHHGAYPYDVPDYAS [SEQ ID NO: 308]

TABLE 64

ET200-114

DNA Sequence (light chain variable region scFv linker heavy chain variable region His tag + HA tag)
caggctgtgctgactcagccaccctcagcgtctgagacccccgggcag
agggtcaccatctcttgttctggaagcaggtccaacatcggaactaat
attgtacactggtaccagcagcgcccaggaatggcccccaaactcctc
acttatggtagtcggcggccctcaggggtcccggaccgattctctggc
tccaagtttggcacctcagcctccctggccatcagtgggctccagtct
gaggatgaggctgattattattgtgcagcatgggatgacagtctgaat
ggtccggctttcggcgcgagggaccaagctgaccgtcctaggt
[SEQ ID NO: 253]

tctagaggtggtggtggtagcggcggcggcggctctggtggtggtgga
tccctcgagatggcc [SEQ ID NO: 305]

**caggtgcagctacagcagtggggcgcaggactgttgaagccttcggag
accctgtccctcacctgcgctgtctatggtgggtccttcagtggttac
tactggagctggatccgccagcccccagggaaggggctggagtggatt
gggggaaatcaatcatagtggaagcaccaactacaaccgtccctcaag
agtcgagtcaccatatcagtagacacgtccaagaaccagttctccctg
aagctgagctctgtgaccgccgcggacacggctgtgtattactgtgcg
agagacggtgggggctactttgactactggggccagggaaccctggtc
accgtctcctca [SEQ ID NO: 254]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QAVLTQPPSASETPGQRVTISCSGSRSNIGTNIVHWYQQRPGMAPKLL
TYGSRRPSGVPDRFSGSKFGTSASLAISGLQSEDEADYYCAAWDDSLN
GPAFGGGTKLTVLG [SEQ ID NO: 255]

SRGGGGSGGGGSGGGGSLEMA [SEQ ID NO: 307]

**QVQLQQWGAGLLKPSETLSLTCAVYGGSFSGYYWSWIRQPPGKGLEWI
GEINHSGSTNYNPSLKSRVTISVDTSKNQFSLKLSSVTAADTAVYYCA
RDGGGYFDYWGQGTLVTVSS [SEQ ID NO: 256]**

TSGQAGQHHHHHHGAYPYDVPDYAS [SEQ ID NO: 308]

TABLE 65

ET200-115

DNA Sequence (light chain variable region scFv linker heavy chain variable region His tag + HA tag)
cagtctgtgttgacgcagccgccctcagtgtctggggcccccgggcag
agggtcaccatctcctgcactgggagcagctccaatatcggggcacgt
tatgatgtacactggtaccagcagcttcccaggaacagcccccccgactc
ctcatctctgctaactacaggcccctcaggggtccctgaccgattc
tctggctccaagtctggcacctcagcctccctggccatcactgggctc
caggctgaggatgaggctgattattactgccagtcctatgacagcagt
gtgagtgatgggtgttcggcggagggaccaaggtcaccgtcctaggt
[SEQ ID NO: 257]

tctagaggtggtggtggtagcggcggcggcggctctggtggtggtgga
tccctcgagatggcc [SEQ ID NO: 305]

**gaagtgcagctggtgcagtctgggggctgaagtgaaggagcctggggcc
tcagtgaggatctcctgccaggcatctggatacaacttcatcagttat
tatatgcactgggtgcggcaggcccctgggcaaggtcttgagtggatg
ggcaccatcaacccaggcagtggtgagacagactactacaaggttg
cagggcagagtcaccatgaccagggacccgtccacgggtacattcgac
atggggctgagcagcctgacatctggggacacggccgtctattattgt
gcgacaggtctcatcagaggagctagcgatgcttttaatatctgggc
cggggacaatggtcaccgtctcttca [SEQ ID NO: 258]**

TABLE 65-continued

ET200-115

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVLTQPPSVSGAPGQRVTISCTGSSSNIGARYDVHWYQQLPGTAPRL
LISANYDRPSGVPDRFSGSKSGTSASLAITGLQAEDEADYYCQSYDSS
VSAWVFGGGTKVTVLG [SEQ ID NO: 259]

SRGGGGSGGGGSGGGGSLEMA [SEQ ID NO: 307]

**EVQLVQSGAEVKEPGASVRISCQASGYNFISYYMHWVRQAPGQGLEWM
GTINPGSGETDYSQKLQGRVTMTRDPSTGTFDMGLSSLTSGDTAVYYC
ATGLIRGASDAFNIWGRGTMVTVSS [SEQ ID NO: 260]**

TSGQAGQHHHHHHGAYPYDVPDYAS [SEQ ID NO: 308]

TABLE 66

ET200-116

DNA Sequence (light chain variable region scFv linker heavy chain variable region His tag + HA tag)
cagcctgtgctgactcagccaccctcagtgtccgtgtccccaggacag
acggccgccatccctgttctggagataagttggggggataaatttgat
cctggtatcagcagaagccaggccagtccctgtgctggtcatctatc
aagatactaagcggccctcaggatccctgagcgattctctggctcca
actctgggaacacagccactctgaccatcagcgggacccaggctatgg
atgaggctgactattactgtcagacgtgggccagcggcattgtggtgt
tcggcggagggaccaagctgaccgtcctaggt
[SEQ ID NO: 261]

tctagaggtggtggtggtagcggcggcggcggctctggtggtggtgga
tccctcgagatggcc [SEQ ID NO: 305]

**caggtacagctgcagcagtcaggtccaggactggtgaagccctcgcag
accctctcactcacctgtgccatctccggggacagtgtctctagcaac
agtgctgcttggaactggatcaggcagtccccatcgagaggccttgag
tggctgggaaggacatactacaggtccaagtggtataatgattatgca
gtatctgtgaaaagtcgaataaccatcaacccagacacatccaagaac
cagttctccctgcagctgaactctgtgactcccgaggacacggctgtg
tattactgtgcaagagagcgcagtggctggaagggatttgactactgg
ggccagggaaccctggtcaccgtctcctca [SEQ ID NO: 262]**

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QPVLTQPPSVSVSPGQTAAIPCSGDKLGDKFASWYQQKPGQSPVLVIY
QDTKRPSGIPERFSGSNSGNTATLTISGTQAMDEADYYCQTWASGIVV
FGGGTKLTVLG [SEQ ID NO: 263]

SRGGGGSGGGGSGGGGSLEMA [SEQ ID NO: 307]

**QVQLQQSGPGLVKPSQTLSLTCAISGDSVSSNSAAWNWIRQSPSRGLE
WLGRTYYRSKWYNDYAVSVKSRITINPDTSKNQFSLQLNSVTPEDTAV
YYCARERSGWKGFDYWGQGTLVTVSS [SEQ ID NO: 264]**

TSGQAGQHHHHHHGAYPYDVPDYAS [SEQ ID NO: 308]

TABLE 67

ET200-117

DNA Sequence (light chain variable region <u>scFv linker</u> heavy chain variable region His tag + HA tag)
gatgttgtgatgactcagtctccaccctccctgtccgtcacccctgga
gagccggcctccatcacctgcaggtctagtcagagcctcctggaaaga
aatgcatacaactacttggattggtacctgcagaggccaggacagtct
ccacagctcctgatctacttgggttctaatcgggccgccgggtccct
gacaggttcagtggcagtggatcaggcagagattttacactgaaaatc
agcagagtggagcctgaggatgttggggtttattactgcatgcaagct
ctacaagctccgttcacttctcggcggagggaccaaggtggagatcaaa
cgt [SEQ ID NO: 265]

<u>tctagaggtggtggtggtagcggcggcggcggctctggtggtggtgga</u>
<u>tccctcgagatggcc</u> [SEQ ID NO: 305]

gaagtgcagctggtgcagtctggggggaggcttggtacagcctggggg
tccctgagactctcctgtgcagcctctggattcacctttagcagctat
gccatgagctgggtccgccaggctccagggaaggggctggagtgggtc
tcagctattagtggtagtggtggtagcacatactacgcagactccgtg
aagggccggttcaccatctccagagacaattccaagaacacgctgtat
ctgcaaatgaacagcctgagagccgaggacacggccgtatattactgt
gcgaaatgggggcccgtttcaggatgcttttgatatctgggggccaaggg
acaatggtcaccgtctcttca [SEQ ID NO: 266]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region <u>scFv linker</u> heavy chain variable region His tag + HA tag)
DVVMTQSPPSLSVTPGEPASITCRSSQSLLERNAYNYLDWYLQRPGQS
PQLLIYLGSNRAAGVPDRFSGSGSGRDFTLKISRVPEDVGVYYCMQA
LQAPFTFGGGTKVEIKR [SEQ ID NO: 267]

<u>SRGGGGSGGGGSGGGGSLEMA</u> [SEQ ID NO: 307]

EVQLVQSGGGLVQPGGSLRLSCAASGFTFSSYAMSWVRQAPGKGLEWV
SAISGSGGSTYYADSVKGRFTISRDNSKNTLYLQMNSLRAEDTAVYYC
AKWGPFQDAFDIWGQGTMVTVSS [SEQ ID NO: 268]

TSGQAGQHHHHHHGAYPYDVPDYAS [SEQ ID NO: 308]

TABLE 68

ET200-118

DNA Sequence (light chain variable region <u>scFv linker</u> heavy chain variable region His tag + HA tag)
caggctgtgctgactcagcctgctccgtgtctgggtctcctggacag
tcgatcaccatctcctgcactggaaccagcagtgacgttggtggttat
aactatgtctcctggtaccaacagcacccgggcaaagcccccaaactc
atgatttatgaggtcagtaatcggccctcaggggtttctaatcgcttc
tctggctccaagtctggcaacagcggcctccctgaccatctctgggctc
caggctgaggacgaggctgattattactgcagctcatatacaagcagc
agcacccatatgtcggagcagggaccaaggtcaccgtcctaggt
[SEQ ID NO: 269]

<u>tctagaggtggtggtggtagcggcggcggcggctctggtggtggtgga</u>
<u>tccctcgagatggcc</u> [SEQ ID NO: 305]

gaggtgcagctggtggagtctgggggaggcttggtacagcctggcagg
tccctgagactctcctgtgcagcctctggattcacctttgatgattat
gccatgcactgggtccggcaagctccagggaagggcctggagtgggtc
tcaggtattagtggaatagtggtagcataggctatgcggactctgtg
aagggccgattcaccatctccagagacaacgccaagaactccctgtat
ctgcaaatgaacagtctgagagctgaggacacggccttgtattactgt
gcaaaagccaggtggacagcagtggcatcagaccaccactttgactac
tggggccagggaacgctggtcaccgtctcctca
[SEQ ID NO: 270]

TABLE 68-continued

ET200-118

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region <u>scFv linker</u> heavy chain variable region His tag + HA tag)
QAVLTQPASVSGSPGQSITISCTGTSSDVGGYNYVSWYQQHPGKAPKL
MIYEVSNRPSGVSNRFSGSKSGNTASLTISGLQAEDEADYYCSSYTSS
STPYVFGAGTKVTVLG [SEQ ID NO: 271]

<u>SRGGGGSGGGGSGGGGSLEMA</u> [SEQ ID NO: 307]

EVQLVESGGGLVQPGRSLRLSCAASGFTFDDYAMHWVRQAPGKGLEWV
SGISWNSGSIGYADSVKGRFTISRDNAKNSLYLQMNSLRAEDTALYYC
AKARWTAVASDHHFDYWGQGTLVTVSS [SEQ ID NO: 272]

TSGQAGQHHHHHHGAYPYDVPDYAS [SEQ ID NO: 308]

TABLE 69

ET200-119

DNA Sequence (light chain variable region <u>scFv linker</u> heavy chain variable region His tag + HA tag)
caggctgtgcttactcagccaccctcagcgtctgggaccccgggcag
agggtcaccatctcttgttctggaagcagctccaacatcggaagtaat
actgtaaactggtaccagcagctcccaggaacggcccccaaactcctc
atctatagtaataatcagcggccctcaggggtccctgaccgattctct
ggctccaagtctggcacctcagcctccctggccatcagtgggctccag
tctgaggatgaggctgattattactgtgcagcatgggatgacagcctg
aatggttatgtatcggaactgggaccaagctgaccgtcctaggt
[SEQ ID NO: 273]

<u>tctagaggtggtggtggtagcggcggcggcggctctggtggtggtgga</u>
<u>tccctcgagatggcc</u> [SEQ ID NO: 305]

gaggtgcagctggtgcagtctggggctgaggtgaagaagcctgggtcc
tcggtgaaggtctcctgcaaggcttctggaggcaccttcagcagctat
gctatcagctgggtgcgacaggcccctggacaagggcttgagtggatg
ggagggatcatccctatcifiggtacagcaaactacgcacagaagttc
cagggcaggtcacgattaccgcggaacatccacgagcacagcctac
atggagctgagcagcctgagatctgaggacacggccgtgtattactgt
gcgagagattgggactacatggacgtctggggcaaagggaccacggtc
accgtctcctca [SEQ ID NO: 274]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region <u>scFv linker</u> heavy chain variable region His tag + HA tag)
QAVLTQPPSASGTPGQRVTISCSGSSSNIGSNTVNWYQQLPGTAPKLL
IYSNNQRPSGVPDRFSGSKSGTSASLAISGLQSEDEADYYCAAWDDSL
NGYVFGTGTKLTVLG [SEQ ID NO: 275]

<u>SRGGGGSGGGGSGGGGSLEMA</u> [SEQ ID NO: 307]

EVQLVQSGAEVKKPGSSVKVSCKASGGTFSSYAISWVRQAPGQGLEWM
GGIIPIFGTANYAQKFQGRVTITADESTSTAYMELSSLRSEDTAVYYC
ARDWDYMDVWGKGTTVTVSS [SEQ ID NO: 276]

TSGQAGQHHHHHHGAYPYDVPDYAS [SEQ ID NO: 308]

TABLE 70

ET200-120

DNA Sequence (light chain variable region scFv linker heavy chain variable region His tag + HA tag)
tcctatgagctgactcagccaccctcagcgtctgggacccccggcag
agggtcaccatctcttgttctggaagcagctccaacatcggaagtaat
actgtaaactggtaccagcagctcccaggaacggcccccaaactcctc
atctatagtaataatcagcggccctcaggggtccctgaccgattctct
ggctccaagtctggcacctcagcctccctggccatcagtgggctccag
tctgaggatgaggctgattattactgtgcagcatgggatgacagcctg
aatggttatgtatcggaactgggaccaaggtcaccgtcctaggt
[SEQ ID NO: 277]

tctagaggtggtggtggtagcggcggcggcggctctggtggtggtgga
tccctcgagatggcc [SEQ ID NO: 305]

**gaggtgcagctggtggagtctggagctgaggt-
gaagaagcctggggcctcagtgaaggtctcctgcaaggcttctggtta-
cacctttα
ccagctatggtatcagctgggtgcgacaggcccctggacaagggctt-
gagtggatgggatggatcagcgcttacaatggtaacacaα
actatgcacagaagctccagggcagagtcaccatgaccacagacacatc-
cacgagcacagcctacatggagctgaggagcctgag
atctgacgacacggccgtgtattactgtgcgagagacctatctcggg-
gagctaacccgcattactactactactacggtatggacgtct
ggggccaagggaccacggtcaccgtctcctca** [SEQ ID NO: 278]

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
SYELTQPPSASGTPGQRVTISCSGSSSNIGSNTVNWYQQLPGTAPKLL
IYSNNQRPSGVPDRFSGSKSGTSASLAISGLQSEDEADYYCAAWDDSL
NGYVFGTGTKVTVLG [SEQ ID NO: 279]

SRGGGGSGGGGSGGGGSLEMA [SEQ ID NO: 307]

**EVQLVESGAEVKKPGASVKVSCKASGYTFTSYGISWVRQAPGQGLEWM
GWISAYNGNTNYAQKLQGRVTMTTDTSTSTAYMELRSLRSDDTAVYYC
ARDLSRGANPHYYYYYGMDVWGQGTTVTVSS** [SEQ ID NO: 280]

TSGQAGQHFIEIHHHGAYPYDVPDYAS [SEQ ID NO: 308]

TABLE 71

ET200-121

DNA Sequence (light chain variable region scFv linker heavy chain variable region His tag + HA tag)
cagtctgtgttgacgcagccgcctcagtgtctggggcccagggcag
agggtcaccgtctcctgcactgggagcagatccaacatcggggcagga
tatgatgtacactggtaccagcaacttccaggaacagcccccaaactc
ctcatctatggaaatagtaatcggcctccaggggtccctgaccgattc
tctgggtctaagtctggcacctccctggtcatcactgggctc
caggctgaggatgccgctgattattactgccagtcctatgacaacact
gtgcgtgaatcaccttatgtcttcggaactgggaccaaggtcaccgtc
ctaggt [SEQ ID NO: 281]

tctagaggtggtggtggtagcggcggcggcggctctggtggtggtgga
tccctcgagatggcc [SEQ ID NO: 305]

**gaggtccagctggtacagtctggggctgaggtgaagaagcctggggcc
tcagtgaaggtctcctgcaaggtttccggatacacccctcactgaatta
tccatgcactgggtgcgacaggctcctggaaaagggcttgagtggatg
ggaggttttgatcctgaagatggtgaaacaatctacgcacagaagttc
cagggcagagtcaccatgaccgaggacacatctacagacacagcctac
atggagctgagcagcctgagatctgaggacacggccgtgtattactgt
gcaacagagagtaatttagtgtcccggcactactactactacggtatg
gacgtctggggccaagggaccacggtcaccgtctcctca**
[SEQ ID NO: 282]

TABLE 71-continued

ET200-121

ACTAGTGGCCAGGCCGGCCAGCACCATCACCATCACCATGGCGCATAC
CCGTACGACGTTCCGGACTACGCTTCT [SEQ ID NO: 306]

Amino Acid Sequence (light chain variable region scFv linker heavy chain variable region His tag + HA tag)
QSVLTQPPSVSGAPGQRVTVSCTGSRSNIGAGYDVHWYQQLPGTAPKW
YGNSNRPPGVPDRFSGSKSGTSASLVITGLQAEDAADYYCQSYDNTVR
ESPYVFGTGTKVTVLG [SEQ ID NO: 283]

SRGGGGSGGGGSGGGGSLEMA [SEQ ID NO: 307]

**EVQLVQSGAEVKKPGASVKVSCKVSGYTLTELSMHWVRQAPGKGLEWM
GGFDPEDGETIYAQKFQGRVTMTEDTSTDTAYMELSSLRSEDTAVYYC
ATESNLVSRHYYYYGMDVWGQGTTVTVSS** [SEQ ID NO: 284]

TSGQAGQHHHHHHGAYPYDVPDYAS [SEQ ID NO: 308]

TABLE 72

ET200-122

DNA Sequence (light chain variable region scFv linker heavy chain variable region His tag + HA tag)
ctgcctgtgctgactcagccaccctcagcgtctgggacccccggg
cagagggtcaccatctcttgttctggaaccagctccaacatcgga
agtaattctgtagactggtaccagcagctcccaggaacggcccccc
aaactcctcatctatagtaataatcagcggccctcaggggtccct
gaccgaatctctggctccaagtctggcacctcagcctccctggcc
atcagtgggctccagtctgaggatgaggctgattattactgtgca
gcatgggatgacagcctgaatggttatgtatcggaactgggacca
aggtcaccgtcctaggt
[SEQ ID NO: 285]

tctagaggtggtggtggtagcggcggcggcggctctggtggtggt
ggatccctcgagatggcc
[SEQ ID NO: 305]

**gaagtgcagctggtgcagtctggggctgaggtgaagaagcctggg
gcctcagtgaaggtctcctgcaaggcttctggatacaccttcacc
ggctactatatgcactgggtgcgacaggcccctggacaagggctt
gagtggatgggatggatcaaccctaacagtggtggcacaaactat
gcacagaagtttcagggcagggtcaccatgaccagggacacgtcc
atcagcacagcctacatggagctgagcaggctgagatctgacgac
acggccgtgtattactgtgcgagagattacgatactatggttcg
gggagttattcgagcggcccccctttactactactacggtatggac
gtctggggccaagggaccacggtcaccgtctcctca**
[SEQ ID NO: 286]

ACTAGTGGCCAGGCCGGCCAGCACCATCACCATCACCATGGCGCA
TACCCGTACGACGTTCCGGACTACGCTTCT
[SEQ ID NO: 306]

Amino Acid Sequence (light chain variable region scFv linker heavy chain variable region His tag + HA tag)
LPVLTQPPSASGTPGQRVTISCSGTSSNIGSNSVDWYQQLPGTAP
KLLIYSNNQRPSGVPDRISGSKSGTSASLAISGLQSEDEADYYCA
AWDDSLNGYVFGTGTKVTVLG
[SEQ ID NO: 287]

SRGGGGSGGGGSGGGGSLEMA
[SEQ ID NO: 307]

TABLE 72-continued

ET200-122

EVQLVQSGAEVKKPGASVKVSCKASGYTFTGYYMHWVRQAPGQGLE
WMGWINPNSGGTNYAQKFQGRVTMTRDTSISTAYMELSRLRSDDTA
VYYCARDYGYYGSGSYSSGPLYYYYGMDVWGQGTTVTVSS
[SEQ ID NO: 288]

TSGQAGQHFIEIHHHGAYPYDVPDYAS
[SEQ ID NO: 308]

TABLE 73

ET200-123

DNA Sequence (light chain variable region sfFv linker heavy
chain variable region His tag + HA tag)
caggctgtgctgactcagccaccctcagcgtctgggaccccggg
cagagggtcaccatctcttgttctggaagcagctccaacatcgga
agtaatactgtaaactggtaccagcagctcccaggaacggcccc
aaactcctcatgtataataatgatcagcggccctcagggg tccct
gaccgattctctggctccaagtctggcacctcagcctccctggc
atcagtgggctccagtctgaggatgaggctgattattactgtgca
gcatgggatgacagcctcaatggttatgtatcggacctgggacca
aggtcaccgtcctaggt [SEQ ID NO: 289]

tctagaggtggtggtggtagcggcggcggcggctctggtggtggt
ggatccctcgagatggcc [SEQ ID NO: 305]

caggtgcagctggtggagtctggagctgaggtgaagaagcctggg
gcctcagtgaaggtctcctgcaaggcttctggttacacctttacc
agctatggtatcagctgggtgcgacaggcccctggacaagggctt
gagtggatgggatggatcagcgcttacaatggtaacacaaactat
gcacagaagctccagggcagagtcaccatgaccacagacacatcc
acgagcacagcctacatggagctgaggagcctgagatctgacgac
acggccgtgtattactgtgcgagagacctatctcggggagctaac
ccgcattactactactacggtatggacgtctggggccaaggg
accacggtcaccgtctcctca [SEQ ID NO: 290]

ACTAGTGGCCAGGCCGGCCAGCACCATCACCATCACCATGGCGCA
TACCCGTACGACGTTCCGGACTACGCTTCT
[SEQ ID NO: 306]

Amino Acid Sequence (light chain variable region scFv linker heavy
chain variable region His tag + HA tag)
QAVLTQPPSASGTPGQRVTISCSGSSSNIGSNTVNWYQQLPGTAPK
LLMYNNDQRPSGVPDRFSGSKSGTSASLAISGLQSEDEADYYCAAW
DDSLNGYVFGPGTKVTVLG [SEQ ID NO: 291]

SRGGGGSGGGGSGGGGSLEMA
[SEQ ID NO: 307]

QVQLVESGAEVKKPGASVKVSCKASGYTFTSYGISWVRQAPGQGLE
WMGWISAYNGNTNYAQKLQGRVTMTTDTSTSTAYMELRSLRSDDTA
VYYCARDLSRGANPHYVYYYGMDVWGQGTTVTVSS
[SEQ ID NO: 292]

TSGQAGQHFIEIHHHGAYPYDVPDYAS
[SEQ ID NO: 308]

TABLE 74

ET200-125

DNA Sequence (light chain variable region scFv linker
heavy chain variable region His tag + HA tag)
aattttatgctgactcagccccacgctgtgtcggagtctccgggga
agacggtaaccatctcctgcacccgcagcagtggcagtattgccag
caactatgtgcagtggtaccagcagcgcccgggcagttcccccgc
actgtgatttatgaggataatcaaagaccctctggggtcctggtc TABLE 74-continued

ET200-125 ggttctctggctccatcgacagctcctccaactctgcctccctcac
catctctggactgaagactgaggacgaggctgactactactgtcag
tcttatgattccaccagtgtgatttcggcggagggaccaagctgac
cgtcctaggt [SEQ ID NO: 293]

tctagaggtggtggtggtagcggcggcggcggctctggtggtggtg
gatccctcgagatggcc [SEQ ID NO: 305]

gaggtccagctggtgcagtctgggggctgaggtgaagaagccagggt
cctcggtgaaggtctcctgcaaggcctcgggaggcaccttcagcag
caattctctcagctgggtgcgacaggcccctggacaagggcttgag
tggatgggaaggatcttccctatcctgggtataacaaactatgcac
agaagttccagggcagagtcacgattaccgcggacaaatccacgag
cacagcctacatggagctgagcagcctgagatctgaggacacggcc
gtctattactgtgcgagaggaaactaccaatggtatgatgcttttg
atatctggggccaagggacaatggtcaccgtctcttca
[SEQ ID NO: 294]

ACTAGTGGCCAGGCCGGCCAGCACCATCACCATCACCATGGCGCAT
ACCCGTACGACGTTCCGGACTACGCTTCT
[SEQ ID NO: 306]

Amino Acid Sequence (light chain variable region scFv linker heavy
chain variable region His tag + HA tag)
NFMLTQPHAVSESPGKTVTISCTRSSGSIASNYVQWYQQRPGSSPR
TVIYEDNQRPSGVPGRFSGSIDSSSNSASLTISGLKTEDEADYYCQ
SYDSTSVLFGGGTKLTVLG
[SEQ ID NO: 295]

SRGGGGSGGGGSGGGGSLEMA
[SEQ ID NO: 307]

EVQLVQSGAEVKKPGSSVKVSCKASGGTFSSNSLSWVRQAPGQGL
EWMGRIFPILGITNYAQKFQGRVTITADKSTSTAYMELSSLRSED
TAVYYCARGNYQWYDAFDIWGQGTMVTVSS
[SEQ ID NO: 296]

TSGQAGQHFIFIRHHGAYPYDVPDYAS
[SEQ ID NO: 308]

TABLE 75

ET200-005

DNA Sequence (light chain variable region scFv linker heavy
chain variable region His tag + HA tag)
cagcctgtgctgactcagccaccctcagtgtcagtggtcccaggaa
agacggccaggattacctgtgggggaaaaaacattggaagtaaaag
tgtgcactggtaccagcagaagccaggccaggcccctgtggtggtc
atccattatgatagtgaccggccctcagggatccctgagcgattct
ctggctccaactctgggaacacggccaccctgaccatcagcagggt
cgaagccggggatgaggccgactattactgtcaggtgtgggatagt
agtagtgatcatccttatgtatcggaactgggaccaaggtcaccgt
cctaggt [SEQ ID NO: 297]

tctagaggtggtggtggtagcggcggcggcggctctggtggtggtg
gatccctcgagatggcc [SEQ ID NO: 305]

caggtgcagctggtgcagtctggagctgaggtgaagaagcctggg
cctcagtgaaggtctcctgcaaggcttctggttacacctttaccaa
ctatggtatcagctgggtgcgacaggcccctggacaagggcttgag
tggatgggatggatcagcgcttacaatggtaacacaaactatgcac
ataagctccagggcagagtcaccatgaccacagacacatccacgag
cacagccaacatggagctgaggagcctgagacctgacgacactgcc
gtgtattactgtgcgcgctcttacttcggttctcatgattactggg
gtcaaggtactctggtgaccgtctcctca
[SEQ ID NO: 298]

TABLE 75 -continued

ET200-005

ACTAGTGGCCAGGCCGGCCAGCACCATCACCATCACCATGGCGCAT
ACCCGTACGACGTTCCGGACTACGCTTCT
[SEQ ID NO: 306]

Amino Acid Sequence (light chain variable region scFv linker heavy
chain variable region His tag + HA tag)
QPVLTQPPSVSVVPGKTARITCGGKNIGSKSVHWYQQKPGQAPVVV
IHYDSDRPSGIPERFSGSNSGNTATLTISRVEAGDEADYYCQVWDS
SSDHPYVFGTGTKVTVLG [SEQ ID NO: 299]

SRGGGGSGGGGSGGGGSLEMA
[SEQ ID NO: 307]

QVQLVQSGAEVKKPGASVKVSCKASGYTFTNYGISWVRQAPGQGLE
WMGWISAYNGNTNYAHKLQGRVTMTTDTSTSTANMELRSLRPDDTA
VYYCARSYFGSHDYWGQGTLVTVSS
[SEQ ID NO: 300]

TSGQAGQHFIREIHHGAYPYDVPDYAS
[SEQ ID NO: 308]

TABLE 76

ET200-124

DNA Sequence (light chain variable region scFv linker heavy
chain variable region His tag + HA tag)
tcctatgtgctgactcagccaccctcggtgtcagtggccccaggaaa
gacggcaggatttcctgtgggggaaacgacattggaagtaaaagtg
ttttctggtatcagcagaggccaggccaggcccctgtgttggtcgtc
tatgatgatagcgaccggccctcagggtccctgagcgattctctgg
atcaactctgggaacacggccaccctgaccatcagcagggtcgaagc
cggggatgaggccgactattactgtcaagtgtgggatagtagtagtg
atcattatgtcttcggaactgggaccaaggtcaccgtcctaggt
[SEQ ID NO: 301]

tctagaggtggtggtggtagcggcggcggcggctctggtggtggtgg
atccctcgagatggcc [SEQ ID NO: 305]

caggtgcagctggtggagtctgggggaggcttggtacagcctggcag
gtccctgagactctcctgtgcagcctctggattcaccttgatgatt
atgccatgcactgggtccggcaagctccagggaagggcctggagtgg
gtctcaggtattagttggaatagtggtagtaggctatgcggactc
tgtgaagggccgattcaccatctccagagacaacgccaagaactccc
tgtatctgcaaatgaacagtctgagagctgaggacacggccttgtat
tactgtgcaaaagatataacctatggttcgggggagttatggtgcttt
tgatatctgggccaagggacaatggtcaccgtctcttca
[SEQ ID NO: 302]

ACTAGTGGCCAGGCCGGCCAGCACCATCACCATCACCATGGCGCAT
ACCCGTACGACGTTCCGGACTACGCTTCT
[SEQ ID NO: 306]

Amino Acid Sequence (light chain variable region scFv linker heavy
chain variable region His tag + HA tag)
SYVLTQPPSVSVAPGKTARISCGGNDIGSKSVFWYQQRPGQAPVLV
VYDDSDRPSGLPERFSGFNSGNTATLTISRVEAGDEADYYCQVWDS
SSDHYVFGTGTKVTVLG [SEQ ID NO: 303]

SRGGGGSGGGGSGGGGSLEMA
[SEQ ID NO: 307]

TABLE 76-continued

ET200-124

QVQLVESGGGLVQPGRSLRLSCAASGFTFDDYAMHWVRQAPGKGLE
WVSGISWNSGSIGYADSVKGRFTISRDNAKNSLYLQMNSLRAEDTA
LYYCAKDITYGSGSYGAFDIWGQGTMVTVSS
[SEQ ID NO: 304]

TSGQAGQHFIEIHHHGAYPYDVPDYAS
[SEQ ID NO: 308]

Exemplary Anti-FcRL5 Antibodies Comprising a Heavy
Chain Variable Region, a Light Chain Variable Region and
a Linker Peptide

TABLE 77

ET200-001

DNA Sequence cagtctgtgttgacgcagccaccctcagcgtctgggacccccgggc
agagggtcaccatctcttgttctggaagcagctccaacatcggaag
taatactgtaaactggtaccagcagctcccaggaacggcccccaaa
ctcctcatctatagtaataatcagcggccctcaggggtccctgacc
gattctctggctccaagtctggcacctcagcctccctggccatcag
tgggctccagtctgaggatgaggctgattattactgtgcagcatgg
gatgacagcctgaatggttatgtatcggaactgggaccaaggtcac
cgtcctaggttctagaggtggtggtggtagcggcggcggcggctct
ggtggtggtggatccctcgagatggcccaggtgcagctacagcagt
ggggcgcaggactgttgaagccttcggagaccctgtccctcacctg
cgctgtatggtgggtccttcagtggttactactggagctggatc
cgccagccccagggaaggggctggagtggattgggaaatcaatc
atagtggaagcaccaactacaacccgtccctcaagagtcgagtcac
catatcagtagacacgtccaagaaccagttctccctgaagctgagc
tctgtgaccgccggacacggccgtgtattactgtgcgcgcgaag
gtccgtacgacggMcgattatggggtcaaggtactctggtgaccgt
ctcctcaactagtggccaggccggccagcaccatcaccatcaccat
ggcgcatacccgtacgacgttccggactacgcttct
[SEQ ID NO: 593]

Amino Acid Sequence

QSVLTQPPSASGTPGQRVTISCSGSSSNIGSNTVNWYQQLPGTAPK
LLIYSNNQRPSGVPDRFSGSKSGTSASLAISGLQSEDEADYYCAAW
DDSLNGYVFGTGTKVTVLGSRGGGGSGGGGSGGGGSLEMAQVQLQQ
WGAGLLKPSETLSLTCAVYGGSFSGYYWSWIRQPPGKGLEWIGEIN
HSGSTNYNPSLKSRVTISVDTSKNQFSLKLSSVTAADTAVYYCARE
GPYDGFDSWGQGTLVTVSSTSGQAGQHFIRHHHGAYPYDVPDYAS
[SEQ ID NO: 594]

TABLE 78

ET200-002

DNA Sequence aattttatgctgactcagccccactctgtgtcggagtctccgggga
agacggtaaccatctcctgcacccgcagcagtggcagcattgccag
caactatgtgcagtggtaccagcagcgcccgggcagtgccccacc
actgtgatctatgaggataaccaaagaccctctggggtccctgatc
ggttctctggctccatcgacagctcctccaactctgcctccctcac
catctctggactgaagactgaggacgaggctgactactactgtcag
tcttatgatagcagcaattctgtggtattcggcggagggaccaagc
tgaccgtcctaggttctagaggtggtggtggtagcggcggcggcggc
ctctggtggtggtggatccctcgagatgcccaggtccagctggta
cagtctggcactgaggtgaagaagcctggggcctcagtgagggtcg
cctgcaaggatctggttacccattaacaaatatgacatcaactggg
tgcgacaggcccctggacaaggcttgagtggatggtgatggagcatcat
ccctatctttcgtacaacaaactacgcacagaagttccagggcaga
gtcacgattaccgcgacgaatccacgagcacagcctacatggagc
tgagcagcctgagatctgaggacacggccgtatattactgtgcgcg
cgaatggttctactggatatctggggtcaaggtactctggtgaccgt
gtctcctcaactagtggccaggccggccagcaccatcaccatcacc
atggcgcatacccgtacgacgttccggactacgcttct
[SEQ ID NO: 595]

TABLE 78-continued

ET200-002

Amino Acid Sequence

NFMLTQPHSVSESPGKTVTISCTRSSGSIASNYVQWYQQRPGSAPT
TVIYEDNQRPSGVPDRFSGSIDSSSNSASLTISGLKTEDEADYYCQ
SYDSSNSVVFGGGTKLTVLGSRGGGGSGGGGSGGGGSLEMAQVQLV
QSGTEVKKPGASVRVACKASGYPFNKYDINWVRQAPGQGLEWMGGI
IPIFRTTNYAQKFQGRVTITADESTSTAYMELSSLRSEDTAVYYCA
REWFYWDIWGQGTLVTVSSTSGQAGQHHHHHHGAYPYDVPDYAS
[SEQ ID NO: 596]

TABLE 79

ET200-003

DNA Sequence cagtctgtgttgactcagccaccctcagtgtccgtgtccccagga
cagacagccagcatctcctgctctggaaataaattggggactaag
tatgtttactggtatcagaagaggccaggccagtccctgtgttg
gtcatgtatgaagataatcagcggccctcagggatcccggagcgg
ttctctggctccaactctgggaacacagccactctgaccatcaga
gggacccagactgtggatgaggctgactattactgtcaggcgtgg
gactccgacactttcgtggtcttcggcggagggaccaaggtcacc
gtcctaggttctagaggtggtggtggtagcggcggcggcggctct
ggtggtggtggatccctcgagatggccgaggtgcagctggtggag
accgggggaggcgtggtccagcctggggaggtccctgagactctcc
tgtgcagcctctggattcaccttcagtagttatggcatgcactgg
gtccgccaggctccaggcaaggggctggagtgggtggcagttata
tcacatgatggaagtaataaaatactacgcagactccgtgaagggc
cgattcaccatctccagagacaattccaaggacacgctgtatctg
caaatgaacagcctgagaggtgaggacacggccgtatattactgt
gcgcgctcaaccagtggtcggttacttctctttcgattactgg
ggtcaaggtactctggtaccgtctcctcaactagtggccaggcc
ggccagcaccatcaccatcaccatggcgcatacccgtacgacgtt
ccggactacgcttct [SEQ ID NO: 597]

Amino Acid Sequence

QSVLTQPPSVSVSPGQTASISCSGNKLGTKYVYWYQKRPGQSPVL
VMYEDNQRPSGIPERFSGSNSGNTATLTIRGTQTVDEADYYCQAW
DSDTFVVFGGGTKVTVLGSRGGGGSGGGGSGGGGSLEMAEVQLVE
TGGGVVQPGRSLRLSCAASGFTFSSYGMHWVRQAPGKGLEWVAVI
SHDGSNKYYADSVKGRFTISRDNSKDTLYLQMNSLRGEDTAVYYC
ARSNQWSGYFSFDYWGQGTLVTVSSTSGQAGQHHHHHHGAYPYDV
PDYAS
[SEQ ID NO: 598]

TABLE 80

ET200-006

DNA Sequence tcctatgtgctgactcagccaccctcagtgtcagtggccc
caggaaagacggccaggattacctgtgggggaaacaacat
tggaagtaaaagtgtgcactggtaccagcagaagccaggc
caggcccctgtggtggtcatccattatgatagcgaccggc
cctcagggatccctgagcgattctctggctccaactctgg
gaacacggccaccctgaccatcagcagggtcgaagccggg
gatgaggccgactattactgtcaggtgtgggatagtagta
gtgatcatccttatgtcttcggaactgggaccaaggtcac
cgtcctaggttctagaggtggtggtggtagcggcggcggc
ggctctggtggtggtggatccctcgagatggccgaggtgc
agctggtgcagtctggagctgaggtgaagaagcctggggc
ctcagtgaaggtctcctgcaaggcttctggttacaccttt
accacctatggtatcagctgggtgcgacaggcccctggac
aagggcttgagtggatgggatggatcaacacttacaatgg
tcacaaaactatgcacagaagctccagggcagagccaca
atgaccgacagacaatccacgaacacagcctacatggagc
tgaggagcctgagatctgacgacactgccgtgtattactg
tgcgcgcgttatctacggttctggtgattactggggtcaa
ggtactctggtaccgtctcctcaactagtggccaggcg
gccagcaccatcaccatcaccatggcgcatacccgtacga

TABLE 80-continued

ET200-006 cgttccggactacgcttct
[SEQ ID NO: 599]

Amino Acid Sequence

SYVLTQPPSVSVAPGKTARITCGGNNIGSKSVHWYQQKPG
QAPVVVIHYDSDRPSGIPERFSGSNSGNTATLTISRVEAG
DEADYYCQVWDSSSDHPYVFGTGTKVTVLGSRGGGGSGGGG
GSGGGGSLEMAEVQLVQSGAEVKKPGASVKVSCKASGYTF
TTYGISWVRQAPGQGLEWMGWINTYNGHTNYAQKLQGRAT
MTADTSTNTAYMELRSLRSDDTAVYYCARVIYGSGDYWGQ
GTLVTVSSTSGQAGQHHHHHHGAYPYDVPDYAS
[SEQ ID NO: 600]

TABLE 81

ET200-007

DNA Sequence tcctatgtgctgactcagccactctcagtgtcagtggccc
caggaaagacggccaggattacctgtgggggaaacaacat
tggaagtaaaactgtgcactggtaccagcagaagccaggc
caggcccctgtggtcatctattatgatagcgaccggc
cctcagggatccctgagcgattctctggctccaactctgg
gaacacggccaccctgaccatcagcagggtcgaagccggg
gatgaggccgactattactgtcaggtgtgggatagtagta
gtgatcatcctgatgttcggcggagggaccaagctgaccgt
cctaggttctagaggtggtggtggtagcggcggcggcggc
tctggtggtggtggatccctcgagatggcccaggtgcagc
tgcaggagtcgggcccaggactggtgaagccttcggagac
cctgtccctcacctgcaatgtctctggttactccatcagc
agtggttactttggcggtggatccggcagcccccaggga
aggggctggagtggattgggagtatctatcatagtaggag
cacctactacaacccgtccctcaagagtcgagtcaccata
tcagtagacacgtccaagaaccagttctccctgaagctga
actctgtgaccgccgcagacacggccgtgtattactgtgc
gcgcggttacggttacttcgattactggggtcaaggtact
ctggtgaccgtctcctcaactagtggccaggccggccagc
accatcaccatcaccatggcgcatacccgtacgacgttcc
ggactacgcttct
[SEQ ID NO: 601]

Amino Acid Sequence

SYVLTQPLSVSVAPGKTARITCGGNNIGSKTVHYVYQQKP
GQAPVLVIYYDSDRPSGIPERFSGSNSGNTATLTISRVEA
GDEADYYCQVWDSSSDHRVFGGGTKLTVLGSRGGGGSGGG
GSGGGGSLEMAQVQLQESGPGLVKPSETLSLTCNVSGYSI
SSGYFWGW1RQPPGKGLEWIGSIYHSRSTYYNPSLKSRVT
ISVDTSKNQFSLKLNSVTAADTAVYYCARGYGYFDYWGQG
TLVTVSSTSGQAGQHHHHHHGAYPYDVPDYAS
[SEQ ID NO: 602]

TABLE 82

ET200-008

DNA Sequence caatctgccctgactcagcctgcctccgtgtctgggtctc
ctggacagtcgatcaccatctcctgcactggaaccagcag
tgacgttggtggttataactatgtctcctggtaccaacaa
cacccaggcaaagcccccaaactcatgatttatgatgtca
gtaatcggccctcagggtttctaatcgcttctctggctc
caagtctgccaacacggcctccctgaccatctctgggctc
caggctgaggacgaggctgattattactgcagctcatata
caagcagcagcacttcgaaggtgttcggcggagggaccaa
gctgaccgtcctaggttctagaggtggtggtggtagcggc
ggcggcggctctggtggtggtggatccctcgagatggccg
aggtgcagctggtggagtctggggganggtgtggtacggcc
tgggggtccctgagactctcctgtgcagcctctggattc
acctttggtgattatggcatgagctgggtccgccaagctc TABLE 82 -continued

ET200-008

```
cagggaaggggctggagtgggtctctggtattaattggaa
tggtggtagcacaggttatgcagactctgtgaagggccga
ttcaccatctccagagacaacgccaagaactccctgtatc
tgcaaatgaacagtctgagagccgaggacacggccgtata
ttactgtgcgcgctctaaatacaacttccatgtttactac
gattactggggtcaaggtactctggtgaccgtctcctcaa
ctagtggccaggccggccagcaccatcaccatcaccatgg
cgcatacccgtacgacgttccggactacgcttct
[SEQ ID NO: 603]
```

Amino Acid Sequence

```
QSALTQPASVSGSPGQSITISCTGTSSDVGGYNYVSWYQQ
HPGKAPKLMIYDVSNRPSGVSNRFSGSKSGNTASLTISGL
QAEDEADYYCSSYTSSSTSKVFGGGTKLTVLGSRGGGGSG
GGGSGGGGSLEMAEVQLVESGGGVVRPGGSLRLSCAASGF
TFGDYGMSWVRQAPGKGLEWVSGINWNGGSTGYADSVKGR
FTISRDNAKNSLYLQMNSLRAEDTAVYYCARSKYNPHVYY
DYWGQGTLVTVSSTSGQAGQHHHHHGAYPYDVPDYAS
[SEQ ID NO: 604]
```

TABLE 83

ET200-009

DNA Sequence

```
cagtctgtgttgacgcagccaccctcagcgtctgggaccc
ccgggcagacagtcaccatctcttgttctggaagcaactc
caacatcggaagtaattatgtatactggtaccagcagctc
ccaggaacggcccccaaactcctcatctataggaataatc
agcggccctcaggggtccctgaccgattctcaggctccaa
gtctggcacctcagcctccctggccatcagtgggctccgc
tccgaggatgaggctgattattactgtgcagcatgggatg
acagcctgagtgcttatgtcttcggaactgggaccaaggt
caccgtcctaggttctagaggtggtggtggtagcggcggc
ggcggctctggtggtggtggatccctcgagatggcccagg
tgcagctggtgcagtctggagctgaggtgaagaagcctgg
ggcctcagtgaaggtctcctgcaaggcttctggttacacc
tttaccagctatggtatcagctgggtgcgacaggccctg
gacaagggcttgagtggatgggatggatcagcgcttacaa
tggtaacacaaactatgcacagaagctccagggcagagtc
accatgaccacagacacatccacgagcacagcctacatgg
agctgaggagcctgagatctgacgacacgccgtgtatta
ctgtgcgcgctcttctggtaacatggtttcttggaaagat
atgtggggtcaaggtactctggtgaccgtctcctcaacta
gtggccaggccggccagcaccatcaccatcaccatggcgc
atacccgtacgacgttccggactacgcttct
[SEQ ID NO: 605]
```

Amino Acid Sequence

```
QSVLTQPPSASGTPGQTVTISCSGSNSNIGSNYVYWYQQL
PGTAPKLLIYRNNQRPSGVPDRFSGSKSGTSASLAISGLR
SEDEADYYCAAWDDSLSAYVFGTGTKVTVLGSRGGGGSGG
GGSGGGGSLEMAQVQLVQSGAEVKKPGASVKVSCKASGYT
FTSYGISWVRQAPGQGLEWMGWISAYNGNTNYAQKLQGRV
TMTTDTSTSTAYMELRSLRSDDTAVYYCARSSGNMVSWKD
MWGQGTLVTVSSTSGQAGQHHHHHGAYPYDVPDYAS
[SEQ ID NO: 606]
```

TABLE 84

ET200-010

DNA Sequence

```
caatctgccctgactcagcctgcctccgtgtctgggtctc
ctggacagtcgatcaccatctcctgcactggaaccagcag
tgacgttggtggttataactctgtctcctggtaccaacaa
cacccaggcaaagcccccagactcatgatttatgatgtca
gtaatcggccctcagggggtttctaatcgcttctctggctc
caagtctggcaacacggcctccctgaccatctctgggctc
```

TABLE 86

ET200-012

DNA Sequence

```
cagtctgtgttgacgcagccgccctcagtgtctgcggccg
caggacagaaggtcaccatctcctgctctggaagcgactc
caacattgggaataattatgtgtcctggtatcaacacctc
ccaggacagcccccaaactcctcatttatgacgttaaaa
atcgaccctcagggattcctgaccggttctccggctccaa
gtctggctcgtcagccaccctaggcatcgccggactccag
cctggggacgaggccgattattactgcggaacatgggaca
gtcggctggatgcctatgtcttcggaactgggaccaaggt
caccgtcctaggttctagaggtggtggtggtagcggcggc
ggcggctctggtggtggtggatccctcgagatggcccaga
tgcagctggtgcaatctggagctgaggtgaagaagcctgg
ggcctcagtgaaggtctcctgcaagacttctggtttcccc
tttaatatctttggaatcacctgggtgcgacaggcccctg
gacaagggcttgagtggatgggatggatcagcggttacaa
cggtaacacagactacccacagaagttccagggcagagtc
accatgtccacagacacatccacgagtacagcctacatgg
agctgaggaacctgaaatctgacgacacggccgtgtatta
ctgtgcgcgcggtgcttacggtggtatggatacttggggt
caaggtactctggtgaccgtctcctcaactagtggccagg
ccggccagcaccatcaccatcaccatggcgcatacccgta
cgacgttccggactacgcttct
[SEQ ID NO: 611]
```

Amino Acid Sequence

```
QSVLTQPPSVSAAAGQKVTISCSGSDSNIGNNYVSWYQHL
PGTAPKLLIYDVKNRPSGIPDRFSGSKSGSSATLGIAGLQ
PGDEADYYCGTWDSRLDAYVFGTGTKVTVLGSRGGGGSGG
GGSGGGGSLEMAQMQLVQSGAEVKKPGASVKVSCKTSGFP
FNIFGITWVRQAPGQGLEWMGWISGYNGNTDYPQKFQGRV
TMSTDTSTSTAYMELRNLKSDDTAVYYCARGAYGGMDTWG
QGTLVTVSSTSGQAGQHHHHHHGAYPYDVPDYAS
[SEQ ID NO: 612]
```

TABLE 87

ET200-013

DNA Sequence

```
cagtctgtcgtgacgcagccgccctcagtgtctgggccc
cagggcagagggtcaccatctcctgcactgggagcacctc
caacatcggggcaggttatgatgtacactggtatcagcag
cttccaggaacagcccccaaactcctcatctatactaaca
actttcggccctcaggggtccctgaccggattctctgcctc
caagtctggcacttcagcttccctggccatcactggtctc
caggctgaggatgaggctgattattactgcggaacatggg
atagcagctgagtgccgttgtgttcggcggagggaccaa
gctgaccgtcctaggttctagaggtggtggtggtagcggc
ggcggcggctctggtggtggtggatccctcgagatggccg
aggtgcagctggtggagtctggggaggcttggtacagcctggg
tggggcctcagtgaaagtctcctgcaaggcttctggttac
atgtttaccagttatggtctcaactgggtgcgacaggccc
ctggacaagggcttgagtggatgggatggatcagcgctaa
caatggtaagacaaattatgctaagaaattccaggacaga
gtcaccatgaccagagacacttccacgagcacagctaca
tggaactgaggagcctgagatctgacgacacggccgtata
ttactgtgcgcgccatatcggtggttcttacttcgatcgt
tggggtcaaggtactctggtgaccgtctcctcaactagtg
gccaggccggccagcaccatcaccatcaccatggcgcata
cccgtacgacgttccggactacgcttct
[SEQ ID NO: 613]
```

Amino Acid Sequence

```
QSVVTQPPSVSGAPGQRVTISCTGSTSNIGAGYDVHWYQQ
LPGTAPKLLIYTNNFRPSGVPDRFSASKSGTSASLAITGL
QAEDEADYYCGTWDSSLSAVVFGGGTKLTVLGSRGGGGSG
```

TABLE 87-continued

ET200-013

```
GGGSGGGGSLEMAEVQLVESGTEVKKPGASVKVSCKASGY
MFTSYGLNWVRQAPGQGLEWMGWISANNGKTNYAKKFQDR
VTMTRDTSTSTGYMELRSLRSDDTAVYYCARHIGGSYFDR
WGQGTLVTVSSTSGQAGQHHHHHHGAYPYDVPDYAS
[SEQ ID NO: 614]
```

TABLE 88

ET200-014

DNA Sequence

```
tcctatgtgctgactcagccaccctcagtgtcagtggccc
caggaaagacggccaggattacctgtgggggaaacaacat
tggaagtaaaagtgtgcactggtaccagcagaagccaggc
caggcccctgtgctggtcatctattatgatagcgaccggc
cctcagggatccctgagcgattctctggctccaactctgg
gaacacggccaccctgaccatcagcagggtcgaagccggg
gatgaggccgactattactgtcaggtgtgggatagtagta
gtgatcattatgtcttcggaactgggaccaaggtcaccgt
cctaggttctagaggtggtggtgtagcggcggcggcggc
tctggtggtggtggatccctcgagatggccgaggtgcagc
tggtggagactggggggaggcttggtacagcctggggggtc
cctgagactctcctgtgcagcctctggattcacctttagc
agctatgccatgagctgggtccgccaggctccagggaagg
ggctggagtgggtctcagctattagtggtagtgatggtag
cacatactacgcagactccgtgaagggccggttcaccatc
tccagagacaattccaagaacacgctgtatctgcaaatga
acagcctgagagacgaggacacggccgtatattactgtgc
gcgctctcatgaagctaacctggttggtgattggtggggt
caaggtactctggtgaccgtctcctcaactagtggccagg
ccggccagcaccatcaccatcaccatggcgcatacccgta
cgacgttccggactacgcttct
[SEQ ID NO: 615]
```

Amino Acid Sequence

```
SYVLTQPPSVSVAPGKTARITCGGNNIGSKSVHWYQQKPG
QAPVLVIYYDSDRPSGIPERFSGSNSGNTATLTISRVEAG
DEADYYCQVWDSSSDHYWGTGTKVTVLGSRGGGGSGGGGS
GGGGSLEMAEVQLVETGGGLVQPGGSLRLSCAASGFTFSS
YAMSWVRQAPGKGLEWVSAISGSDGSTYYADSVKGRFTIS
RDNSKNTLYLQMNSLRDEDTAVYYCARSHEANLVGDWWGQ
GTLVTVSSTSGQAGQHHHHHHGAYPYDVPDYAS
[SEQ ID NO: 616]
```

TABLE 89

ET200-015

DNA Sequence

```
cagtctgtggtgactcagccaccctcagtgtcagtggccc
caggaaagacggccaggattacctgtgggggaaacaacat
tggaagtaaaagtgtgcactggtaccagcagaagccaggc
caggcccctgtgctggtcatctattatgatagcgaccggc
cctcagggatccctgagcgattctctggctccaactctgg
gaacacggccaccctgaccatcagcagggtcgaagccggg
gatgaggccgactattactgtcaggtgtgggatagtagta
gtgatgtggtattcggcggagggaccaagctgaccgtcct
aggttctagaggtggtggtagcggcggcggcggctct
ggtggtggtggatccctcgagatggccgaggtgcagctgg
tacagtctggagctgaggtgaagaagcctggggcctcagt
gaaggtctcctgcaaggcttctggttacacctttaccagc
tacggctatcagctgggtgcgacaggcccctggacaaggc
ttgagtggatgggatggatcagcgcttacaatggtaacac
aaactatgcacagaagctccagggcagagtcaccatgacc
acagacacatccacgagcacagcctacatggagctgagga
gcctgagatctgacgacacggccgtgtattactgtgcgcg
```

TABLE 89-continued

ET200-015

```
ctggggtggtttcggtgctgttgatcattggggtcaaggt
actctggtgaccgtctcctcaactagtggccaggccggcc
agcaccatcaccatcaccatggcgcatacccgtacgacgt
tccggactacgcttct
[SEQ ID NO: 617]
```

Amino Acid Sequence

```
QSVVTQPPSVSVAPGKTARITCGGNNIGSKSVHWYQQKPG
QAPVLVIYYDSDRPSGIPERFSGSNSGNTATLTISRVEAG
DEADYYCQVWDSSSDVVFGGGTKLTVLGSRGGGGSGGGGS
GGGGSLEMAEVQLVQSGAEVKKPGASVKVSCKASGYTFTS
YGISWVRQAPGQGLEWMGWISAYNGNTNYAQKLQGRVTMT
TDTSTSTAYMELRSLRSDDTAVYYCARWGGFGAVDHWGQG
TLVTVSSTSGQAGQHHHHHHGAYPYDVPDYAS
[SEQ ID NO: 618]
```

TABLE 90

ET200-016

DNA Sequence

```
tcttctgagctgactcaggaccctgctgtgtctgtggcct
tgggacagacagtcaagatcacgtgccaaggagacagcct
cacagactaccatgcaacctggtaccagcagaagccagga
caggcccctgtcgctgtcatctatgctacaaacaaccggc
ccactgggatcccagaccgattctctggttccagttccgg
aaacacagcttctttgaccatcactggggctcaggcggaa
gatgaggctgactattactgtaattcccgggacagcggca
cggacgaagtgttattcggcggagggaccaagctgaccgt
cctaggttctagaggtggtggtggtagcggcggcggcggc
tctggtggtggtggatccctcgagatggccgaggtgcac
tggtggagactgggggaggcctggtcaagcctggggggtc
cctgagactctcctgtgcagcctctggattcaccttcagt
agctatagcatgaactgggtccgccaggctccagggaagg
ggctggagtgggtctcatccattagtagtagtagtagtta
catatactacgcagactcagtgaagggccgattcaccatc
tccagagacaacgccaagaactcactgtatctgcaaatga
acagcctgagagccgaggacacggccgtgtattactgtgc
gcgcggtcagggttacgattactggggtcaaggtactctg
gtgaccgtctcctcaactagtggccaggccggccagcacc
atcaccatcaccatggcgcatacccgtacgacgttccgga
ctacgcttct
[SEQ ID NO: 619]
```

Amino Acid Sequence

```
SSELTQDPAVSVALGQTVKITCQGDSLTDYHATWYQQKPG
QAPVAVIYATNNRPTGIPDRFSGSSSGNTASLTITGAQAE
DEADYYCNSRDSGTDEVLFGGGTKLTVLGSRGGGGSGGGG
SGGGGSLEMAEVQLVETGGGLVKPGGSLRLSCAASGFTFS
SYSMNWVRQAPGKGLEWVSSISSSSSYIYYADSVKGRFTI
SRDNAKNSLYLQMNSLRAEDTAVYYCARGQGYDYWGQGTL
VTVSSTSGQAGQHHHHHHGAYPYDVPDYAS
[SEQ ID NO: 620]
```

TABLE 91

ET200-017

DNA Sequence

```
tcctatgtgctgactcagccaccctcggtgtcagtggccc
caggaaagacggccaggattacctgtgggggaaacaacat
tggaagtaaaagtgtgcactggtaccagcagaagccaggc
caggcccctgtgctggtcgtctatgatgatagcgaccggc
cctcagggatccctgagcgattctctggctccaactctgg
gaacacgcaccctgagcatcagcagggtcgaggtcgggg
gatgaggccgactattactgtcaggtgtgggatagtagta
gtgatcatactgtcttcggaactgggaccaaggtcaccgt
cctaggttctagaggtggtggtggtagcggcggcggcggc
tctggtggtggtggatccctcgagatggcccaggtgcagc
```

TABLE 91-continued

ET200-017

```
tacagcagtggggcgcaggactgttgaagccttcggagac
cctgtccctcacctgcgctgtctatggtgggtccttcagt
ggttactactggagctggatccgccagcccccagggaagg
ggctggagtggattggggaaatcaatcatagtggaagcac
caactacaacccgtccctcaagagtcgagtcaccatatca
gtagacacgtccaagaaccagttctccctgaagctgagct
ctgtgaccgccgcggacacggccgtgtattactgtgcgcg
ctactacccgggtatggatatgtggggtcaaggtactctg
gtgaccgtctcctcaactagtggccaggccggccagcacc
atcaccatcaccatggcgcatacccgtacgacgttccgga
ctacgcttct
[SEQ ID NO: 621]
```

Amino Acid Sequence

```
SYVLTQPPSVSVAPGKTARITCGGNNIGSKSVHWYQQKPG
QAPVLVVYDDSDRPSGIPERFSGSNSGNTATLSISRVEAG
DEADYYCQVWDSSSDHTVFGTGTKVTVLGSRGGGGSGGGG
SGGGGSLEMAQVQLQQWGAGLLKPSETLSLTCAVYGGSFS
GYYWSWIRQPPGKGLEWIGEINHSGSTNYNPSLKSRVTIS
VDTSKNQFSLKLSSVTAADTAVYYCARYYPGMDMWGQGTL
VTVSSTSGQAGQHHHHHHGAYPYDVPDYAS
[SEQ ID NO: 622]
```

TABLE 92

ET200-018

DNA Sequence

```
caggctgtgctgactcagccgccctcaacgtctgggaccc
ccgggcagagggtcaccatctcttgttctggaagcagctc
caacatcgggagaaatggtgtaaactggtaccagcagctc
ccaggagcggccccaaagtcctcatctataatgataatc
agcgaccctcaggggtccctgaccgagtctctggctccca
gtctggctcctcaggcaccctggccatcgatgggcttcgg
tctgaggatgaggctgattattactgtgcgcatggcatg
acagcctgcatggtgtgtattcggcggagggaccaagct
gaccgtcctaggttctagaggtggtggtggtagcggcggc
ggcggctctggtggtggtggatccctcgagatggcccagg
tccagctgatgacgtctgggctgaggtgaagaagcctgg
ggcctcagtgaaggtctcctgcaaggtttccggatacacc
ctcaatgaattatccatgcactgggtgcgacaggctcctg
gaaaagggcttgagtggatgggaggttttgatcctgaaga
tggtgaaacaatctacgcacagaagttccagggcagagtc
accatgaccgaggacacatctacagacacagcctacatgg
agctgagcagcctgagatctgaggacactgccgtgtatta
ctgtgcgcgcggtggttacggtgattcttggggtcaaggt
actctggtgaccgtctcctcaactagtggccaggccggcc
agcaccatcaccatcaccatggcgcatacccgtacgacgt
tccggactacgcttct
[SEQ ID NO: 623]
```

Amino Acid Sequence

```
QAVLTQPPSTSGTPGQRVTISCSGSSSNIGRNGVNWYQQL
PGAAPKVLIYNDNQRPSGVPDRVSGSQSGSSGTLAIDGLR
SEDEADYYCAAWDDSLHGVVFGGGTKLTVLGSRGGGGSGG
GGSGGGGSLEMAQVQLVQSGAEVKKPGASVKVSCKVSGYT
LNELSMHWVRQAPGKGLEWMGGFDPEDGETIYAQKFQGRV
TMTEDTSTDTAYMELSSLRSEDTAVYYCARGGYGDSWGQG
TLVTVSSTSGQAGQHHHHHHGAYPYDVPDYAS
[SEQ ID NO: 624]
```

TABLE 93

ET200-019

DNA Sequence

```
aattttatgctgactcagccccactctgtgtcggagtctc
cgggggaagacggtaaccatctcctgcacccgcagcagtgg
cagcattgccagcaactatgtgcagtggtaccagcagcgc
```

TABLE 93-continued

ET200-019

```
ccgggcagtgcccccaccactgtgatctatgaggataacc
aaagaccctctggggtccctgatcggttctctggctccat
cgacagctcctccaactctgcctccctcaccatctctgga
ctgaagactgaggacgaggctgactactactgtcagtctt
atgatagcagcaattcttgggtgttcggcggagggaccaa
gctgaccgtcctaggttctagaggtggtggtggtagcggc
ggcggcggctctggtggtggtggatccctcgagatggccc
aggtgcagctggtgcaatctggggctgaggtgaagaggcc
tgggtcctcggtgaaggtctcctgcacggcttctggaggc
accttcagcagcgatgctatcagctgggtgcgacaggccc
ctggacaagggcttgagtggatgggaggaatcatccctat
gtttggtacagcaaactacgcacagaagttccagggcaga
gtcacgattaccgcggacgaatccacgagcacagcctaca
tggagctgagcagcctgagatctgaggacacggccgtgta
ttactgtgcgcgcgaaggttactactacccgtctgcttac
ctgggttctgttctgaacgacatctcttctgtttacgatg
aatggggtcaaggtactctggtgaccgtctcctcaactag
tggccaggccggccagcaccatcaccatcaccatggcgca
tacccgtacgacgttccggactacgcttct
[SEQ ID NO: 625]
```

Amino Acid Sequence

```
NFMLTQPHSVSESPGKTVTISCTRSSGSIASNYVQWYQQR
PGSAPTTVIYEDNQRPSGVPDRFSGSIDSSSNSASLTISG
LKTEDEADYYCQSYDSSNSWVFGGGTKLTVLGSRGGGGSG
GGGSGGGGSLEMAQVQLVQSGAEVKRPGSSVKVSCTASGG
TFSSDAISWVRQAPGQGLEWMGGIIPMFGTANYAQKFQGR
VTITADESTSTAYMELSSLRSEDTAVYYCAREGYYYPSAY
LGSVLNDISSVYDEWGQGTLVTVSSTSGQAGQHHFIFIFI
HGAYPYDVPDYAS
[SEQ ID NO: 626]
```

TABLE 94

ET200-020

DNA Sequence

```
cagtctgtcgtgacgcagccgccctcagtgtctgcggccc
caggacagaaggtcaccatctcctgctctggaagcacctc
caacattggaaataatgatgtatcctggtaccagcagctc
ccaggaacagcccccaaactcctcatttatgacaataata
agcgaccctcagggattcctgaccgattctctggctccaa
gtctggcacgtcagccaccctgggcatcaccggactccag
actgggacgaggccgattattactgcggaacatgggata
gcagcgtgagtgcttctgggtcttcggcagagggaccaa
gctgaccgtcctaggttctagaggtggtggtggtagcggc
ggcggcggctctggtggtggtggatccctcgagatggccc
aggtgcagctggtgcagtctggagctgaggtgaagaagcc
tgggggcctcagtgaaggtctcctgcaaggcttctggttac
acctttaccagctatggtatcagctgggtgcgacaggccc
ctggacaagggcttgagtggatgggatggatcagcgctta
caatggtaacacaaactatccacagaagtccagggcaga
gtcaccatgaccacagacccatccacgagcacagcctaca
tggagctgaggagcctgagatctgacgacacggccgtgta
ttactgtgcgcgctctatgacttcttttcgattactggggt
caaggtactctggtgaccgtctcctcaactagtggccagg
ccggccagcaccatcaccatcaccatggcgcatacccgta
cgacgttccggactacgcttct
[SEQ ID NO: 627]
```

Amino Acid Sequence

```
QSVVTQPPSVSAAPGQKVTISCSGSTSNIGNNDVSWYQQL
PGTAPKLLIYDNNKRPSGIPDRFSGSKSGTSATLGITGLQ
TGDEADYYCGTWDSSVSASWVFGRGTKLTVLGSRGGGGSG
GGGSGGGGSLEMAQVQLVQSGAEVKKPGASVKVSCKASGY
TFTSYGISWVRQAPGQGLEWMGWISAYNGNTNYPQKLQGR
VTMTTDPSTSTAYMELRSLRSDDTAVYYCARSMTSFDYWG
QGTLVTVSSTSGQAGQHHHHHGAYPYDVPDYAS
[SEQ ID NO: 628]
```

TABLE 95

ET200-021

DNA Sequence

```
cagtctgtgttgacgcagccgccctcagtgtctgcggccccaggacag
aaggtcaccatctcctgctctggaagcaactccaacattgggaataat
tatgtatcctggtatcagcaactcccagggacagccccaaactcctc
atttatgacaataataagcgaccctcagggattcctgaccgattctct
ggctccaggtctggcacgtcagccaccctgggcatcaccggactccag
actgggacgaggccgattattactgcggaacatggaataccactgtg
actcctggctatgtcttcggaactgggaccaaggtcaccgtcctaggt
tctagaggtggtggtggtagcggcggcggcggctctggtggtggtgga
tccctcgagatggccgaagtgcagctggtgcagtctggagctgaggtg
aagaagcctggggcctcagtgaaggtctcctgcaaggcttctggttac
acctttaccagctatggtatcagctgggtgcgacaggcccctggacaa
gggcttgagtggatgggatggatcagcgcttacaatggtaacacaaac
tatgcacagaagctccagggcagagtcaccatgaccacagacacatcc
acgagcacagcctacatggagctgaggagcctgagatctgacgacacc
gccatgtattactgtgcgcgctctgtttacgacctggatacttggggt
caaggtactctggtgaccgtctcctcaactagtggccaggccggccag
caccatcaccatcaccatggcgcatacccgtacgacgttccggactac
gcttct [SEQ ID NO: 629]
```

Amino Acid Sequence

```
QSVLTQPPSVSAAPGQKVTISCSGSNSNIGNNYVSWYQQLPGTAPKLL
IYDNNKRPSGIPDRFSGSRSGTSATLGITGLQTGDEADYYCGTWNTTV
TPGYVFGTGTKVTVLGSRGGGGSGGGGSGGGGSLEMAEVQLVQSGAEV
KKPGASVKVSCKASGYTFTSYGISWVRQAPGQGLEWMGWISAYNGNTN
YAQKLQGRVTMTTDTSTSTAYMELRSLRSDDTAMYYCARSVYDLDTWG
QGTLVTVSSTSGQAGQHHHHHGAYPYDVPDYAS
[SEQ ID NO: 630]
```

TABLE 96

ET200-022

DNA Sequence

```
cagtctgtcgtgacgcagccgccctcagtgtctgcggccccaggacag
aaggtcaccatctcctgctctggaagcagctccaacattgggaataat
tatgtatcctggtaccagcagctcccaggaacagccccaaactcctc
atttatgacaataataagcgaccctcagggattcctgaccgattctct
ggctccaagtctggcacgtcagccaccctgggcatcaccggactccag
actgggacgaggccgattattactgcggaacatgggatagcagcctg
ggggcccttatgtcttcggaactgggaccaaggtcaccgtcctaggt
tctagaggtggtggtggtagcggcggcggcggctctggtggtggtgga
tccctcgagatggccgaggtgcagctggtgcagtctggggaggctcg
gaacagcctggaggtccctgagactctcctgtgcagcctctggattc
acctttgatgattatgccatgcactgggtccggcaagctccagggaag
ggcctggagtgggtctcaggtattagttggaatagcggtagcataggc
tatgcggactctgtgaagggccgattcaccatctccagagacaacgcc
aagaattccctgtatctgcaaatgaacagtctgagagctgaggacacc
gccatgtattactgtgcgcgctaccgtcaggttggttctgatacgatt
atggggtcaaggtactctggtgaccgtctcctcaactagtggccaggc
cggccagcaccatcaccatcaccatggcgcatacccgtacgacgttcc
ggactacgcttct [SEQ ID NO:631]
```

Amino Acid Sequence

```
QSVVTQPPSVSAAPGQKVTISCSGSSSNIGNNYVSWYQQLPGTAPKWY
DNNKRPSGIPDRFSGSKSGTSATLGITGLQTGDEADYYCGTWDSSLGA
PYVFGTGTKVTVLGSRGGGGSGGGGSGGGGSLEMAEVQLVQSWGGSEQ
PGRSLRLSCAASGFTFDDYAMHWVRQAPGKGLEWVSGISWNSGSIGYA
DSVKGRFTISRDNAKNSLYLQMNSLRAEDTAMYYCARYRQVGSAYDSW
GQGTLVTVSSTSGQAGQHHHHHGAYPYDVPDYAS
[SEQ ID NO: 632]
```

TABLE 97

ET200-023

DNA Sequence ctgcctgtgctgactcagccaccctcggtgtcagtggccccaggaaag
acggccaggattacctgtggggggaaacaacattggaagtaaaagtgtg
cactggtatcagcagaagccaggccaggcccctgtgctggtcgtctat
gctgatagcgaccggccctcagggatccctgagcgattctctggctcc
aactctgggaacacggccaccctgaccatcagcagggtcgaagccggg
gatgaggccgactattactgtcaggtgtgggatagtagtagttatcat
aattatgtatcggaactgggaccaaggtcaccgtcctaggttctagag
gtggtggtggtagcggcggcggcggctctggtggtggtggatccctcg
agatggccgaggtgcagctggtgcagtctggagctgaggtgaagaagc
ctgggGcctcagtgaaggtctcctgcaaggcttctggttacacctta
ccagctatggtatcagctgggtgcgacaggcccctggacaagggcttg
agtggatgggatggatcagcgcttacaatggtaacacaaactatgcac
agaagctccagggcagagtcaccatgaccacagacacatccacgagca
cagcctacatggagctgagcagcctgagatctgaggacaccgccatgt
attactgtgcgcgctactgggggtttcggtgtttctgatcgttggggtc
aaggtactctggtgaccgtctcctcaactagtggccaggccgccagc
accatcaccatcaccatggcgcataccgtacgacgttccggactacg
cttct [SEQ ID NO: 633]

Amino Acid Sequence

LPVLTQPPSVSVAPGKTARITCGGNNIGSKSVHWYQQKPGQAPVLVVY
ADSDRPSGIPERFSGSNSGNTATLTISRVEAGDEADYYCQVWDSSSYH
NYVFGTGTKVTVLGSRGGGGSGGGGSGGGGSLEMAEVQLVQSGAEVKK
PGASVKVSCKASGYTFTSYGISWVRQAPGQGLEWMGWISAYNGNTNYA
QKLQGRVTMTTDTSTSTAYMELSSLRSEDTAMYYCARYWGFGVSDRWG
QGTLVTVSSTSGQAGQHHHHHHGAYPYDVPDYAS
[SEQ ID NO: 634]

TABLE 98

ET200-024

DNA Sequence aattttatgctgactcagccccactctgtgtcggagtctccggggaag
acggtaaccatctcctgcaccggcagcagtggcagcattgccagcaac
tatgtgcagtggtaccagcagcgcccgggcagtgcccccaccactgtg
atctatgaggataaccaaagaccctctggggtccccgatcggttctct
ggctccatcgacagctcctccaactctgcctccctcaccatctctgga
ctgaagactgaggacgaggctgactactactgtcagtcttatgacac
agcaatctttgggtgttcggcggagggaccaagctgaccgtcctaggt
tctagaggtggtggtggtagcggcggcggcggctctggtggtggtgga
tccctcgagatggcccagatgcagctggtgcagtctggggctgaggtg
aagaagcctgggtcctcggtgaaggtctcctgcaaggcttctggaggc
accttcagcagctatgctatcagctgggtgcgacaggcccctggacaa
gggcttgagtggatgggagggatcatccctatctttggtacagcaaac
tacgcacagaagttccagggcagagtcacgattaccgcggacgaatcc
acgagcacagcctacatggagctgagcagcctgagatctgaggacact
gccgtgtattactgtgcgcgctacaactactactactacgattcttgg
ggtcaaggtactctggtgaccgtctcctcaactagtggccaggccggc
cagcaccatcaccatcaccatggcgcataccgtacgacgttccggac
tacgcttct [SEQ ID NO: 635]

Amino Acid Sequence

NFMLTQPHSVSESPGKTVTISCTGSSGSIASNYVQWYQQRPGSAPTTV
IYEDNQRPSGVPDRFSGSIDSSSNSASLTISGLKTEDEADYYCQSYDS
SNLWVFGGGTKLTVLGSRGGGGSGGGGSGGGGSLEMAQMQLVQSGAEV
KKPGSSVKVSCKASGGTFSSYAISWVRQAPGQGLEWMGGIIPIFGTAN
YAQKFQGRVTITADESTSTAYMELSSLRSEDTAVYYCARYNYYYDSW
GQGTLVTVSSTSGQAGQHHHHHHGAYPYDVPDYAS
[SEQ ID NO: 636]

TABLE 99

ET200-025

DNA Sequence gacatccagatgacccagtctccatcctccctgtctgcatctgtagga
gacagagtcaccatcacttgccgggcaagtcagagcattagcagctat
ttaaattggtatcagcagaaaccagggaaagcccctaagctcctgatc
tatgctgcatccagtttgcaaagtggggtcccatcaaggttcagtggc
agtggatctgggacagatttcactctcaccatcagcagtctgcaacct
gaagattttgcaacttactactgtcaacagagttacagtaccccattc
actttcggccctgggaccaaagtggatatcaaacgttctagaggtggt
ggtggtagcggcggcggcggctctggtggtggtggatccctcgagatg
gccgaggtgcagctggtgcagtctggggctgaggtgaagaagcctggg
tcctcggtgaaggtctcctgcaaggcttctggaggcaccttcagcagc
tatgctatcagctgggtgcgacaggcccctggacaagggcttgagtgg
atgggagggatcatccctatctttggtacagcaaactacgcacagaag
ttccagggcagagtcacgattaccgcggacgaatccacgagcacagcc
tacatggagctgagcagcctgagatctgaggacaccgccatgtattac
tgtgcgcgctactgggggttacgactcttacgatgaatggggtcaaggt
actctggtgaccgtctcctcaactagtggccaggccgccagcaccat
caccatcaccatggcgcataccgtacgacgttccggactacgcttct
[SEQ ID NO: 637]

Amino Acid Sequence

DIQMTQSPSSLSASVGDRVTITCRASQSISSYLNWYQQKPGKAPKLLI
YAASSLQSGVPSRFSGSGSGTDFTLTISSLQPEDFATYYCQQSYSTPF
TFGPGTKVDIKRSRGGGGSGGGGSGGGGSLEMAEVQLVQSGAEVKKPG
SSVKVSCKASGGTFSSYAISWVRQAPGQGLEWMGGIIPIFGTANYAQK
FQGRVTITADESTSTAYMELSSLRSEDTAMYYCARYWGYDSYDEWGQG
TLVTVSSTSGQAGQHHHHHHGAYPYDVPDYAS
[SEQ ID NO: 638]

TABLE 100

ET200-026

DNA Sequence aattttatgctgactcagccccactctgtgtcggagtctccggggaag
acggtaaccatctcctgcaccggcagcagtggcagcattgccagcaac
tatgtgcagtggtaccagcagcgcccgggcagtgcccccaccactgtg
atctatgaggataaccaaagaccctctggggtccctgatcggttctct
ggctccatcgacagctcctccaactctgcctccctcaccatctctgga
ctgaagactgaggacgaggctgactactactgtcagtcttatgatagc
agcaattgggtgttcggcggagggaccaagctgaccgtcctaggttct
agaggtggtggtggtagcggcggcggcggctctggtggtggtggatcc
ctcgagatggccgaggtccagctggtgcagtctggggctgaggtgaag
aagcctgggtcctcggtgaaggtctcctgcaaggcttctggaggcacc
ttcagcagctatgctatcagctgggtgcgacaggcccctggacaaggg
cttgagtggatgggagggatcatccctatctttggtacagcaaactac
gcacagaagttccagggcagagtcacgattaccgcggacgaatccacg
agcacagcctacatggagctgagcagcctgagatctgaggacaccgcc
gtgtattactgtgcgcgcaacaaccattactacaacgattactgGGGt
caaggtactctggtgaccgtctcctcaactagtggccaggccggccag
caccatcaccatcaccatggcgcataccgtacgacgttccggactac
gcttct [SEQ ID NO: 639]

Amino Acid Sequence

NFMLTQPHSVSESPGKTVTISCTGSSGSIASNYVQWYQQRPGSAPTTV
IYEDNQRPSGVPDRFSGSIDSSSNSASLTISGLKTEDEADYYCQSYDS
SNWVFGGGTKLTVLGSRGGGGSGGGGSGGGGSLEMAEVQLVQSGAEVK
KPGSSVKVSCKASGGTFSSYAISWVRQAPGQGLEWMGGIIPIFGTANY
AQKFQGRVTITADESTSTAYMELSSLRSEDTAVYYCARNNHYYNDYWG
QGTLVTVSSTSGQAGQHHHHHHGAYPYDVPDYAS
[SEQ ID NO: 640]

TABLE 101

ET200-027

DNA Sequence

```
cagtctgtgttgacgcagccgccctcagtgtctggggcccccagggcag
ggggtcaccatccctgcactgggagcagctccaacatcggggcaggt
tatgatgtacactggtaccagcagatccagggacagccccaaactcc
tcatctatggtaacaacaatcggccctcaggggtccctgaccgcttct
ctggctccaggtctggctcctcagcctccctggccatcactgggctcc
aggctgaggatgaggctgattattactgccagtcctatgacagcagcc
tgagtgatgtggtattcggcggagggaccaaggtcaccgtcctaggtt
ctagaggtggtggtggtagcggcggcggcggctctggtggtggtggat
ccctcgagatggccgaggtccagctggtgcagtctggggctgaggtga
agaagcctggggctacagtgaaaatctcctgcaaggttttctggataca
ccttcaccgactactacatgcactgggtgcaacaggcccctggaaaag
ggcttgagtggatgggacttgttgatcctgaagatggtgaaacaatat
acgcagagaagttccagggcagagtcaccataaccgcggacacgtcta
cagacacagcctcatggagctgagcagcctgagatctgaggacacgg
ccgtgtattactgtgcgcgctactggtcttactctttcgactacctgt
acatgccggaaggtaacgattggtggggtcaaggtactctggtgaccg
tctcctcaactagtggccaggccgccagcaccatcaccatcaccatg
gcgcatacccgtacgacgttccggactacgcttct
[SEQ ID NO: 641]
```

Amino Acid Sequence

```
QSVLTQPPSVSGAPGQGVTIPCTGSSSNIGAGYDVHWYQQLPGTAPKL
LIYGNNNRPSGVPDRFSGSRSGSSASLAITGLQAEDEADYYCQSYDSS
LSDVVFGGGTKVTVLGSRGGGSGGGGSGGGGSLEMAEVQLVQSGAEV
KKPGATVKISCKVSGYTFTDYYMHWVQQAPGKGLEWMGLVDPEDGETI
YAEKFQGRVTITADTSTDTAYMELSSLRSEDTAVYYCARYWSYSFDYL
YMPEGNDWWGQGTLVTVSSTSGQAGQHHHHHGAYPYDVPDYAS
[SEQ ID NO: 642]
```

TABLE 102

ET200-028

DNA Sequence

```
cagtctgtgttgactcagcccaccccgcagcgtctgggaccccccggacag
agagtcaccatctcttgttctgggggcgtctccaacatcgggagtggt
gctctaaattggtaccagcaactcccaggaacggcccccaaactcctc
atctatagttacaatcagcggcctcaggggtctctgaccgattctct
ggctccaggtctgccacctcagcctccctggccatcagtgggctccag
tctgaggatgaggctgattattactgtgcaacctgggatgatagtgtg
aatggttgggtgttcggcggagggaccaagctgaccgtcctaggttct
agaggtggtggtggtagcggcggcggcggctctggtggtggtggatcc
ctcgagatggcccaggtccagctggtacagtctggagctgaggtgaag
aagcctggggattcagtgaaggtctcctgcaagcttctggttacaat
tttctcaactatggtatcaactgggtgcgacaggcccctggacaaggg
cttgagtggatgggatgattagcacttacaccggtaacacaaactat
gcacagaagctgcagggcagagtcaccttcaccacagacacatccacg
agcacagcctacatggagatgaggagcctgagatctgacgacacggcc
gtgtattactgtgcgcgcgacctgtactactacgaaggtgttgattac
tggggtcaaggtactctggtgaccgtctcctcaactagtggccaggcc
ggccagcaccatcaccatcaccatggcgcatacccgtacgacgttccg
gactacgcttct [SEQ ID NO: 643]
```

Amino Acid Sequence

```
QSVLTQPPAASGTPGQRVTISCSGGVSNIGSGALNWYQQLPGTAPKLL
IYSYNQRPSGVSDRFSGSRSATSASLAISGLQSEDEADYYCATWDDSV
NGWVFGGGTKLTVLGSRGGGSGGGGSGGGGSLEMAQVQLVQSGAEVK
KPGDSVKVSCKPSGYNFLNYGINWVRQAPQGLEWMGWISTYTGNTNY
AQKLQGRVTFTTDTSTSTAYMEMRSLRSDDTAVYYCARDLYYYEGVDY
WGQGTLVTVSSTSGQAGQHHHHHGAYPYDVPDYAS
[SEQ ID NO: 644]
```

TABLE 103

ET200-029

DNA Sequence

```
caggctgtgctgactcagccaccctcagtgtcagtggccccaggaaag
acggccagggttacctgtgggggaaacaacattggaagtgaaagtgtg
cactggtaccagcagaagccaggccaggcccctgtgttggtcatctat
tatgataccgaccggccctcagggatccctgagcgattctctggctcc
cactctgggaccacggccaccctgaccatcagcagggtcgaagccggg
gatgaggccgactattactgtcaggtgtgggatagtagtagggatcat
gtggtattcggcggagggaccaagctgaccgtcctaggttctagaggt
ggtggtggtagcggcggcggcggctctggtggtggtggatccctcgag
atggcccaggtgcagctggtgcagtctggggggaggcgtggtccagcct
gggaggtccctgagactctcctgtgcggcctctggattcaccttcagt
agctatgctatgcactgggtccgccaggctccaggcaagggactggag
tgggtggcagttatatcatatgatggaagcaataaatactacgcagac
tccgtgaagggcctattcaccatctccagagacaattccaagaacacg
ctgtatctgcaaatgaacagcctgagagctgaggacacggccgtgtat
tactgtgcgcgctatacttcacttctggtttctacgattactgggtc
aaggtactctggtgaccgtctcctcaactagtggccaggccggccagc
accatcaccatcaccatggcgcatacccgtacgacgttccggactacg
cttct [SEQ ID NO: 645]
```

Amino Acid Sequence

```
QAVLTQPPSVSVAPGKTARVTCGGNNIGSESVHWYQQKPGQAPVLVIY
YDTDRPSGIPERFSGSHSGTTATLTISRVEAGDEADYYCQVWDSSRDH
VVFGGGTKLTVLGSRGGGSGGGGSGGGGSLEMAQVQLVQSGGGVVQP
GRSLRLSCAASGFTFSSYAMHWVRQAPGKGLEWVAVISYDGSNKYYAD
SVKGLFTISRDNSKNTLYLQMNSLRAEDTAVYYCARSYFTSGFYDYWG
QGTLVTVSSTSGQAGQHHHHHGAYPYDVPDYAS
[SEQ ID NO: 646]
```

TABLE 104

ET200-030

DNA Sequence

```
cagtctgtcgtgacgcagccgccctcagtgtctggggcccccagggcag
agggtcaccatctcctgcactgggagcagttccaacatcgggggcaggt
tatgatgtaaattggtatcagcagtttccaggaacagccccccaaactc
ctcatctatggtaacagcaatcggccctcaggggtccctgaccgattc
tctggctccaagtctggcacctcagcctccctggccatcactgggctc
caggctgaggatgaggctgattattactgccagtcctatgacagcagc
ctgagtggctcttatgtcttcggaactgggaccaaggtcaccgtcctc
ggttctagaggtggtggtggtagcggcggcggcggctctggtggtggt
ggatccctcgagatggcccagatgcagctggtgcagtctggggctgag
gtgaagaagcctggggtctcctgcaaggatctcagt
acacctcactgaattatccatgcactgggtgcgacaggctcctggaa
aagggcttgagtggatgggaggttttgatcctgaagatggtgaaacaa
tctacgcacagaagttccagggcagagtcaccatgaccgaggacacat
ctacagacacagcctacatggagctgagcagcctgagatctgaggaca
ctgccgtgtattactgtgcgcgcatgtatctatgtactacgattgggg
tcaaggtactctggtgaccgtctcctcaactagtggccaggccggcca
gcaccatcaccatcaccatggcgcatacccgtacgacgttccggacta
cgcttct [SEQ ID NO: 647]
```

Amino Acid Sequence

```
QSVVTQPPSVSGAPGQRVTISCTGSSSNIGAGYDVNWYQQFPGTAPKL
LIYGNSNRPSGVPDRFSGSKSGTSASLAITGLQAEDEADYYCQSYDSS
LSGSYVFGTGTKVTVLGSRGGGSGGGGSGGGGSLEMAQMQLVQSGAE
VKKPGASVKVSCKASGYTLTELSMHWVRQAPGKGLEWMGGFDPEDGET
IYAQKFQGRVTMTEDTSTDTAYMELSSLRSEDTAVYYCARMSSMYYDW
GQGTLVTVSSTSGQAGQHHHHHGAYPYDVPDYAS
[SEQ ID NO: 648]
```

TABLE 105

ET200-031

DNA Sequence

```
tcctatgtgctgactcagccaccctcagtgtcagtggccccaggaaag
acggccaggattacctgtgggggaaacaacattggaagtaaaagtgtg
cactggtaccagcagaagcaggccaggcccctgtgctggtcatctat
tatgatagcgaccggccctcagggatccctgagcgattctctggctcc
aactctgggaacacggccaccctgaccatcagcagggtcgaagccggg
gatgaggccgactattactgtcaggtgtgggatagtagtagtgattat
gtcttcggaactgggaccaaggtcaccgtcctaggttctagaggtggt
ggtggtagcggcggcggcggctctggtggtggtggatccctcgagatg
gccgaggtgcagctggtggagactgggggaggcttggtcaagcctgga
gggtccctgagactctcctgtgcagcctctggattcaccgtcagtgac
tactacatgagctggatccgccaggctccagggaagggcctggagtgg
atttcatacattagtggtagtggtaatagcatatactacgcagactct
gtgaagggccgattcaccatctccagggacaacgccaagaactcactg
gatctgcaaatgaccagcctgagagccgaggacacggccgtatattac
tgtgcgcgctctactaaaattcgattactggggtcaaggtactctggtg
accgtctcctcaactagtggccaggccggccagcaccatcaccatcac
catggcgcatacccgtacgacgttccggactacgcttct
[SEQ ID NO: 649]
```

Amino Acid Sequence

```
SYVLTQPPSVSVAPGKTARITCGGNNIGSKSVHWYQQKPGQAPVLVIY
YDSDRPSGIPERFSGSNSGNTATLTISRVEAGDEADYYCQVWDSSSDY
VFGTGTKVTVLGSRGGGGSGGGGSGGGGSLEMAEVQLVETGGGLVKPG
GSLRLSCAASGFTVSDYYMSWIRQAPGKGLEWISYISGSGNSIYYADS
VKGRFTISRDNAKNSLDLQMTSLRAEDTAVYYCARSTKFDYWGQGTLV
TVSSTSGQAGQHHHHHGAYPYDVPDYAS [SEQ ID NO: 650]
```

TABLE 106

ET200-032

DNA Sequence

```
ctgcctgtgctgactcagccaccctcagcgtctgggaccccggggcag
agggtcaccatctcttgttctggaagcagctccaacgtcggaagttac
actgtaaactggtaccggcaactcccaggaacggcccccacactcctc
atctataataataatcagcggccctcaggggtccctgaccgattctct
gactccaagtctggcacctcggcctccctgaccattagtggcctccag
cctgaggatgaggctgattattattgtgcagcatgggatgacaggctg
ggtggttatgtatcggaactgggaccaaggtcaccgtcctaggttcta
gaggtggtggtggtagcggcggcggcggctctggtggtggtggatccc
tcgagatggccgaggtgcagctggtgcagtctgggggcagaggatgaaa
agccggggggagtctctgaagatctcctgtaagggttctggatacagct
ttaccaactactggatcggctgggtgcgccagatgcccgggaaaggcc
tggagtggatggggatcatctatcctggtgactctgataccagataca
gcccgtccttccaaggccaggtcaccatctcagccgacaagtccatca
gcaccgcctacctacagtggagcagcctgaaggcctcggacaccgcca
tgtattactgtgcgcgctctactggttcttctcatatgtctgatgaat
ggggtcaaggtactctggtgaccgtctcctcaactagtggccaggccg
gccagcaccatcaccatcaccatggcgcatacccgtacgacgttccgg
actacgcttct [SEQ ID NO: 651]
```

Amino Acid Sequence

```
LPVLTQPPSASGTPGQRVTISCSGSSSNVGSYTVNWYRQLPGTAPTLL
IYNNNQRPSGVPDRFSDSKSGTSASLTISGLQPEDEADYYCAAWDDRL
GGYVFGTGTKVTVLGSRGGGGSGGGGSGGGGSLEMAEVQLVQSGAEVK
KPGESLKISCKGSGYSFTNYWIGWVRQMPGKGLEWMGIIYPGDSDTRY
SPSFQGQVTISADKSISTAYLQWSSLKASDTAMYYCARSTGSSHMSDE
WGQGTLVTVSSTSGQAGQHHHHHGAYPYDVPDYAS
[SEQ ID NO: 652]
```

TABLE 107

ET200-033

DNA Sequence

```
aattttatgctgactcagccccactctgtgtcggagtctccggggaag
acggtaaccatctcctgcaccggcagcagtggcagcattgccagcaac
```

TABLE 107-continued

ET200-033

```
tatgtgcagtggtaccagcagcgcccgggcagtgcccccaccactgtg
atctatgaggataaccaaagaccctctggggtccctgatcggttctct
ggctccatcgacagctcctccaactctgcctccctcaccatctctgga
ctgaagactgaggacgaggctgactactactgtcagtcttatgatagc
agcaatcattgggtgttcggcggagggaccaagctgaccgtcctaggt
tctagaggtggtggtggtagcggcggcggcggctctggtggtggtgga
tccctcgagatggccgaggtgcagctacagcagtggggcggcaggactg
ttgaagccttcggagaccgtgtccctcacctgcgctgtctatggtggg
tccttcagtggttactactggagctggatccgccagcccccagggaag
gggctggagtggattggggagatcactcatagtggaaggtccaactac
aacccgtccctcaagagtcgagtcaccatatcagtagacacgtccaag
aaccagttctctccctgaagctgagctcctgtgaccgccgcggacacggcc
gtgtattactgtgcgcgctcttctatcatgtctgattactggggtcaa
ggtactctggtgaccgtctcctcaactagtggccaggccggccagcac
catcaccatcaccatggcgcatacccgtacgacgttccggactacgct
tct [SEQ ID NO: 653]
```

Amino Acid Sequence

```
NFMLTQPHSVSESPGKTVTISCTGSSGSIASNYVQWYQQRPGSAPTTV
IYEDNQRPSGVPDRFSGSIDSSSNSASLTISGLKTEDEADYYCQSYDS
SNHWVFGGGTKLTVLGSRGGGGSGGGGSGGGGSLEMAQVQLQQWGAGL
LKPSETLSLTCAVYGGSFSGYYWSWIRQPPGKGLEWIGEITHSGRSNY
NPSLKSRVTISVDTSKNQFSLKLSSVTAADTAVYYCARSSIMSDYWGQ
GTLVTVSSTSGQAGQHHHHHGAYPYDVPDYAS
[SEQ ID NO: 654]
```

TABLE 108

ET200-034

DNA Sequence

```
cagtctgtgttgacgcagccgccctcagtgtctggggcccccagggcag
agggtcaccatctcctgcactgggagcacctccaacatcggggcaggt
tatgatgtacactggtaccagcagatccaggaacagccccccaaactcc
tcatcaacaataacaggaatcggccctcaggggtccctgaccgattct
ctggctccaagtctggcacgtcagccaccctgggcatcaccggactcc
agactgggggacgaggccgattattactgcggaacatgggatggcagcc
tgactggtgcagtgttcggcggagggaccaagctgaccgtcctaggtt
ctagaggtggtggtggtagcggcggcggcggctctggtggtggtggat
ccctcgagatggccgaggtccagctggtggcagtctggggggtgaggtga
agaagcctgggtcctcggtgaaggtctcatgcaaggcttctggaggca
ccttcagcagctatgctatcagctgggtgcgacaggcccctggacaag
ggcttgagtggatggggatcatccctatctttggtacagcaaact
acgcacagaagttccagggcagagtcacgattaccgcggacgaatcca
cgagcacagcctacatggagctgagcagcctgagatctgaggacacgg
ccgtgtattactgtgcgcgcggttctgctctggaccattacgatcgtt
ggggtcaaggtactctggtgaccgtctcctcaactagtggccaggccg
gccagcaccatcaccatcaccatggcgcatacccgtacgacgttccgg
actacgcttct [SEQ ID NO: 655]
```

Amino Acid Sequence

```
QSVLTQPPSVSGAPGQRVTISCTGSTSNIGAGYDVHWYQQLPGTAPKL
LINNNRNRPSGVPDRFSGSKSGTSATLGITGLQTGDEADYYCGTWDGS
LTGAVFGGGTKLTVLGSRGGGGSGGGGSGGGGSLEMAEVQLVQSGAEV
KKPGSSVKVSCKASGGTFSSYAISWVRQAPGQGLEWMGGIIPIFGTAN
YAQKFQGRVTITADESTSTAYMELSSLRSEDTAVYYCARGSALDHYDR
WGQGTLVTVSSTSGQAGQHHHHHGAYPYDVPDYAS
[SEQ ID NO: 656]
```

TABLE 109

ET200-035

DNA Sequence

```
aattttatgctgactcagccccactctgtgtcggagtctccggggaag
acggtaaccatctcctgcacccgcagcagtggcagcattgccagcaac
tatgtgcagtggtaccagcagcgcccgggcagtgcccccaccactgtg
atctatgaggataaccaaagaccctctggggtccctgatcggttctct
ggctccatcgacagctcctccaactctgcctccctcaccatctctgga
```

TABLE 109-continued

ET200-035

```
ctgaagactgaggacgaggctgactactactgtcagtcttatgatagc
accaattgggtgttcggcggagggaccaagctgaccgtcctaggttct
agaggtggtggtggtggtagcggcggcggcggctctggtggtggtggatcc
ctcgagatggcccaggtgcagctggtgcagtctggggctgaggtgaag
aagcctgggcctcggtgaaggtctcctgcaaggcttctggaggcacc
ttcagcagctatgctatcagctgggtgcgacaggcccctggacaaggg
cttgagtggatgggagggatcatccctatctttggtacagcaaactac
gcacagaagttccagggcagagtcacgattaccgcggacgaatccacg
agcacagcctacatggagctgagcagcctgagatctgaggacactgcc
gtgtattactgtgcgcgctacaactactacttcaacgattactggggt
caaggtactctggtgaccgtctcctcaactagtggccaggccggccag
caccatcaccatcaccatggcgcatacccgtacgacgttccggactac
gcttct [SEQ ID NO: 657]
```

Amino Acid Sequence

```
NFMLTQPHSVSESPGKTVTISCTRSSGSIASNYVQWYQQRPGSAPTTV
IYEDNQRPSGVPDRFSGSIDSSSNSASLTISGLKTEDEADYYCQSYDS
TNWVFGGGTKLTVLGSRGGGGSGGGGSGGGGSLEMAQVQLVQSGAEVK
KPGSSVKVSCKASGGTFSSYAISWVRQAPGQGLEWMGGIIPIFGTANY
AQKFQGRVTITADESTSTAYMELSSLRSEDTAVYYCARYNYYFNDYWG
QGTLVTVSSTSGQAGQHHHHHHGAYPYDVPDYAS
[SEQ ID NO: 658]
```

TABLE 110

ET200-037

DNA Sequence

```
tcctatgtgctgactcagccaccctcagtgtcagtggccccaggaaa
gacggccaggattacctgtgggggaaacaacattggaagtaaaagtg
tgcactggtaccagcagaagccaggccccagtgctgctggtcatc
tattatgatagcgaccggccctcagggatccctgagcgattctctgg
ctccaactctgggaacacggccaccctgaccatcagcagggtcgaag
ccggggatgaggccgactattactgtcaggtgtgggatagtagtagt
gatcatccttatgtcttcggaactgggaccaaggtcaccgtcctagg
ttctagaggtggtggtggtagcggcggcggcggctctggtggtggt
gatccctcgagatggcccagatgcagctggtgcagtctggagctgag
gtgaagaagcctggggcctcagtgaaggtctcctgcaaggcttctgg
ttacacctttaccagctatggtatcagctgggtgcgacaggcccctg
gacaagggcttgagtggatgggatggatcagcgcttacaatggtaac
acaaactatgcacagaagttccagggcagagtcaccatgaccacaga
cacatccacgagcacagcctacatggagctgaggagcctgagatctg
acgacactgccgtgtattactgtgcgcgctctaactactttcggttcat
gattcttggggtcaaggtactctggtgaccgtctcctcaactagtgg
ccaggccggcagcaccatcaccatcaccatggcgcatacccgtacg
acgttccggactacgcttct [SEQ ID NO: 659]
```

Amino Acid Sequence

```
SYVLTQPPSVSVAPGKTARITCGGNNIGSKSVHWYQQKPGQAPVLVI
YYDSDRPSGIPERFSGSNSGNTATLTISRVEAGDEADYYCQVWDSSS
DHPYVFGTGTKVTVLGSRGGGGSGGGGSGGGGSLEMAQMQLVQSGAE
VKKPGASVKVSCKASGYTFTSYGISWVRQAPGQGLEWMGWISAYNGN
TNYAQKLQGRVTMTTDTSTSTAYMELRSLRSDDTAVYYCARSMFGAH
DSWGQGTLVTVSSTSGQAGQHHHHHHGAYPYDVPDYAS
[SEQ ID NO: 660]
```

TABLE 111

ET200-038

DNA Sequence

```
cagtctgtgttgacgcagccgccctcagtgtctggggcccccagggca
gagggtcaccatctcctgcactgggagcagctccaacatcggggcagg
gttttgatgtacactggtaccagctacttccaggaacagccccaaa
ctcctcatctatgctaacagcaatcggccctcaggggtccctgaccg
attctctggctccaagtctggcacctcagcctccctggccatcactg
ggctcctggctgaggatgaggctgattattactgccagtcctatgac
agcagcctgagtggtgtggtattcggcggagggaccaagctgaccgt
cctaggttctagaggtggtggtggtagcggcggcggcggctctggtg
```

TABLE 111-continued

ET200-038

```
gtggtggatccctcgagatggcccaggtgcagctggtgcaatctggg
gctgaggtgaagaagcctgggtcctcggtgaaggtctcctgcaaggc
ttctgaggcaccttcagcagctatgctatcagctgggtgcgacagg
cccctggacaagggcttgagtggatgggagggatcatccctatcttt
ggtacagcaaactacgcacagaagttccagggcagagtcacgattac
cgcggacgaatccacgagcacagcctacatggagctgagcagcctga
gatctgaggacactgccgtgtattactgtgcgcgcggtgcttctttc
gaccgtcatgataactggggtcaaggtactctggtgaccgtctcctc
aactagtggccaggccggccagcaccatcaccatcaccatggcgcat
acccgtacgacgttccggactacgcttct [SEQ ID NO: 661]
```

Amino Acid Sequence

```
QSVLTQPPSVSGAPGQRVTISCTGSSSNIGAGFDVHWYQLLPGTAPK
LLIYANSNRPSGVPDRFSGSKSGTSASLAITGLLAEDEADYYCQSYD
SSLSGVVFGGGTKLTVLGSRGGGGSGGGGSGGGGSLEMAQVQLVQSG
AEVKKPGSSVKVSCKASGGTFSSYAISWVRQAPGQGLEWMGGIIPIF
GTANYAQKFQGRVTITADESTSTAYMELSSLRSEDTAVYYCARGASF
DRHDNWGQGTLVTVSSTSGQAGQHHHHHHGAYPYDVPDYAS
[SEQ ID NO: 662]
```

TABLE 112

ET200-039

DNA Sequence

```
aattttatgctgactcagccccactctgtgtcggagtctccggggaag
acggtaaccatctcctgcacccgcagcagtggcagcattgccagcaac
tatgtgcagtggtaccagcagcgcccgggcagttcccccaccactgtg
atctatgaggataaccaaagaccctctggggtccctgatcggttctct
ggctccatcgacagctcctccaactctgcctccctccaccatctctgga
ctgaagactgaggacgaggctgactactactgtcagtcttatgatagc
agcaattgggtgttcggcggagggaccaagctgaccgtcctaggttct
agaggtggtggtggtagcggcggcggcggctctggtggtggtggatcc
ctcgagatggcccgaggtccagctggtgcagtctggggctgaggtgaag
aagcctgggcctcggtgaaggtctcctgcaaggcttctggaggcacc
ttcagcagctatgctatcagctgggtgcgacaggcccctggacaaggg
cttgagtggatgggagggatcatccctatctttggtacagcaaactac
gcacagaagttccagggcagagtcacgattaccgcggacgaatccacg
agcacagcctacatggagctgagcagcctgagatctgaggacacggcc
gtgtattactgtgcgcgctctaactactactacaacgattactggggt
caaggtactctggtgaccgtctcctcaactagtggccaggccggccag
caccatcaccatcaccatggcgcatacccgtacgacgttccggactac
gcttct [SEQ ID NO: 663]
```

Amino Acid Sequence

```
NFMLTQPHSVSESPGKTVTISCTRSSGSIASNYVQWYQQRPGSSPTTV
IYEDNQRPSGVPDRFSGSIDSSSNSASLTISGLKTEDEADYYCQSYDS
SNWVFGGGTKLTVLGSRGGGGSGGGGSGGGGSLEMAEVQLVQSGAEVK
KPGSSVKVSCKASGGTFSSYAISWVRQAPGQGLEWMGGIIPIFGTANY
AQKFQGRVTITADESTSTAYMELSSLRSEDTAVYYCARSNYYYNDYWG
QGTLVTVSSTSGQAGQHHHHHHGAYPYDVPDYAS
[SEQ ID NO: 664]
```

TABLE 113

ET200-040

DNA Sequence

```
cagtctgtgttgacgcagccgccctcagtgtctggggcccccagggcag
agggtcaccatctcctgcactgggagcagctccaacatcggggcaggt
tatgatgtacactggtaccagcagatccaggaacagcccccaaactcc
tcatctatgataacagcaatcggccctcaggggtccctgaccgattct
ctggctccaagtctggcacctcagcctccctggccatcactgggctcc
aggctgaggatgaggctgattattactgccagtcctatgacagcagcc
tgatggttatgtcttcggaactgggaccaaggtcaccgtcctaggtt
ctagaggtggtggtggtagcggcggcggcggctctggtggtggtgat
ccctcgagatggcccaggtgcagctggtgcagtctggggctgaggtga
agaagcctgggggcctcagtgaaggtctcctgcaaggtttccggataca
ccctcactgaattatccatgcactgggtgcgacaggctcctggaaaag
```

TABLE 113-continued

ET200-040

```
ggcttgagtggatgggaggttttgatcctgaagatggtgaaacaatct
acgcacagaagttccagggcagagtcaccatgaccgaggacacatcta
cagacacagcctacatggagctgagcagcctgagatctgaggacactg
ccgtgtattactgtgcgcgctactctggtgtttactacgattggggtc
aaggtactctggtgaccgtctcctcaactagtggccaggccggccagc
accatcaccatcaccatggcgcataccgtacgacgttccggactacg
cttct [SEQ ID NO: 665]
```

Amino Acid Sequence

```
QSVLTQPPSVSGAPGQRVTISCTGSSSNIGAGYDVHWYQQLPGTAPKL
LIYGNSNRPSGVPDRFSGSKSGTSASLAITGLQAEDEADYYCQSYDSS
LSGYVFGTGTKVTVLGSRGGGGSGGGGSGGGGSLEMAQVQLVQSGAEV
KKPGASVKVSCKVSGYTLTELSMHWVRQAPGKGLEWMGGFDPEDGETI
YAQKFQGRVTMTEDTSTDTAYMELSSLRSEDTAVYYCARYSGVYYDWG
QGTLVTVSSTSGQAGQHHHHHGAYPYDVPDYAS
[SEQ ID NO: 666]
```

TABLE 114

ET200-041

DNA Sequence

```
aattttatgctgactcagccccactctgtgtcggggtctccggggaag
acggtaaccatctcctgcaccggcagcagtggcagcattgccgacaac
tttgtgcagtggtaccagcagcgcccgggcggtgtccccaccactgtg
atctttaatgatgacgaaagaccctctggcgtccctgatcggttctct
ggctccatcgacacctcctccaattctgcctccctcaccatctctgga
ctgaagactgaggacgaggctgactactactgtcagtcttatgataat
aataatcgaggggtgttcggcggagggaccaagctgaccgtcctaggt
tctagaggtggtggtggtagcggcggcggcggctctggtggtggtgga
tccctcgagatggcccaggtcagctggtgcagtctgggtctgaggtg
aagaagcctgggtcctcggtgaaggtctcctgcaaggcttctggaggc
accttcagcagctatgctatcagctgggtgcgacaggcccctggacaa
gggcttgagtggatgggatggatgaaccctaacagtggtaacacaggc
tatgcacagaagttccagggcagagtcaccatgaccaggaacacctcc
ataagcacagcctacatgggagctgagcaacctgagatctgaggacacg
gccgtgtattactgtgcgcgctactactcttacggttacgattggggt
caaggtactctggtgaccgtctcctcaactagtggccaggccggccag
caccatcaccatcaccatggcgcataccgtacgacgttccggactac
gcttct [SEQ ID NO: 667]
```

Amino Acid Sequence

```
NFMLTQPHSVSGSPGKTVTISCTGSSGSIADNFVQWYQQRPGGVPTTV
IFNDDERPSGVPDRFSGSIDTSSNSASLTISGLKTEDEADYYCQSYDN
NNRGVFGGGTKLTVLGSRGGGGSGGGGSGGGGSLEMAQVQLVQSGAEV
KKPGSSVKVSCKASGGTFSSYAISWVRQAPGQGLEWMGWMNPNSGNTG
YAQKFQGRVTMTRNTSISTAYMELSNLRSEDTAVYYCARYYSGYDWG
QGTLVTVSSTSGQAGQHRHHHHGAYPYDVPDYAS
[SEQ ID NO: 668]
```

TABLE 115

ET200-042

DNA Sequence

```
cagtctgtcgtgacgcagccgccctcagtgtctgggggccccagggcag
acggtcaccatctcctgcactggggggcagctccaacatcgggacaggt
tattttgtaaattggtaccagcaggttccaggaaaagcccccaaactc
ctcatcctgggtaacaataatcggccctcggggtccctgaccgactc
tccggctccacgtccggcacctcagcctccctggccatcactgggctc
caggctgaggtgagggtacttattactgccagtctatgacagcagc
ctgagtggttatgtcttcggaactgggaccaaggtcaccgtcctaggt
tctagaggtggtggtggtagcggcggcggcggctctggtggtggtgga
tccctcgagatggcccaggtacagctgcagcagtcaggtccaggactg
gtgaagcctcgcagaccctctcactcgtgtgcagtctgtatccaca
agtgtctctaccaacagtgttgcttggcactggatcaggcagtcccca
tcgagaggccttgagtggctgggaaggacatactacaggtccaagtg
tctaatgactatggagtatctgtgaaaagtcgaatcaccatcatccca
gacacatccaagaaccagttctccctgcagctgaactctgtgactccc
```

TABLE 115-continued

ET200-042

```
gaggacacggctgtgtattactgtgcgcgctatcttcttggtaccaga
tcttcgattactggggtcaaggtactctggtgaccgtctcctcaacta
gtggccaggccggccagcaccatcaccatcaccatggcgcataccgt
acgacgttccggactacgcttct [SEQ ID NO: 669]
```

Amino Acid Sequence

```
QSVVTQPPSVSGAPGQTVTISCTGGSSNIGTGYFVNWYQVPGKAPKL
LILGNNNRPSGVPDRLSGSTSGTSASLAITGLQAEDEGTYYCQSYDSS
LSGYVEGTGTKVTVLGSRGGGGSGGGGSGGGGSLEMAQVQLQQSGPGL
VKPSQTLSLTCGISGDSVSTNSVAWHWIRQSPSRGLEWLGRTYYRSKW
SNDYGVSVKSRITIIPDTSKNQFSLQLNSVTPEDTAVYYCARSSSWYQ
IFDYWGQGTLVTVSSTSGQAGQHHHHHGAYPYDVPDYAS
[SEQ ID NO: 670]
```

TABLE 116

ET200-043

DNA Sequence

```
aattttatgctgactcagccccactctgtgtcggagtctccggggaag
acggtaaccatctcctgcaccggcagcagcgacagcatagccaacaac
tatgttcagtggtaccagcagcgcccgggcagtgcccccaccaatgtg
atctacgaagatgtccaaagaccctctggggtccctgatcggttctct
gggtccatcgacagctcctccaactctgcctccctcaccatctctgga
ctgaagactgaggacgaggctgtctactattgtcagtcttatcatagc
gacaatcgttgggtgttcggcggcgggaccaagctgaccgtcctaggt
tctagaggtggtggtggtagcggcggcggcggctctggtggtggtgga
tccctcgagatggcccaggtgcagctggtggagtctgggggaggcttg
gtacagcctgggggggtccctgagactctcctgtgcagcctctggattc
acctttagcagctatgccatgagctgggtccgccaggctccagggaag
gggctggagtgggtctcagctattagtggtagtggtggtagcacatac
tacgcagactccgtgaagggccggttcaccatctccagagacaattcc
aagaacacgctgtatctgcaaatgaacagcctgagagccgaggacacg
gccgtatattactgtgcgcgctctggtgatactgggactactctgttt
acgatgaatggggtcaaggtactctggtgaccgtctcctcaactagtg
gccaggccggccagcaccatcaccatcaccatggcgcataccgtacg
acgttccggactacgcttct [SEQ ID NO: 671]
```

Amino Acid Sequence

```
NFMLTQPHSVSESPGKTVTISCTGSSDSIANNYVQWYQQRPGSAPTNV
IYEDVQRPSGVPDRFSGSIDSSSNSASLTISGLKTEDEAVYYCQSYHS
DNRWVFGGGTKLTVLGSRGGGGSGGGGSGGGGSLEMAQVQLVESGGGL
VQPGGSLRLSCAASGFTFSSYAMSWVRQAPGKGLEWVSAISGSGGSTY
YADSVKGRFTISRDNSKNTLYLQMNSLRAEDTAVYYCARSGAYWDYSV
YDEWGQGTLVTVSSTSGQAGQHHHHHGAYPYDVPDYAS
[SEQ ID NO: 672]
```

TABLE 117

ET200-044

DNA Sequence

```
cagtctgtgttgactcagccacccctcagtgtccgtgtccccaggacag
acagccaccatcgcctgttctggacataaattgggggataaatatgct
tcctggtatcagcagaagtcgggccagtcccctgtgttgatcatctat
caggataataagcggccctcagggattcctgagcgattctctggctcc
aactctgggaacacagccactctgaccatcagcggcgggacccaggctctg
gatgaggctgactattattgtcaggcgtgggacagtagtacttatgtg
gcattcggcggagggaccaagctgaccgtcctaggttctagaggtggt
ggtggtagcggcggcggcggctctggtggtggtggatccctcgagatg
gcccaggtgcagctggtgcaggtccaggactggtgaagccttcg
gagaccctgtccctcacctgcgttgtctctggtggctccatcagcagt
agtaactggtggagctgggtccgccagcccccaggaaggggctggag
tggattggggaaatctatcatagtgggagccccaactacaacccatcc
ctcaagagtcgagtcaccatatcagtagacaagtccaagaaccagttc
```

TABLE 117-continued

ET200-044

```
tccctgaagctgagctctgtgaccgccgcggacacggccgtgtattac
tgtgcgcgcatgactactcatactttcggttacgatgatgggggtcaag
gtactctggtgaccgtctcctcaactagtggccaggccggccagcacc
atcaccatcaccatggcgcatacccgtacgacgttccggactacgctt
ct [SEQ ID NO: 673]
```

Amino Acid Sequence

```
QSVLTQPPSVSVSPGQTATIACSGHKLGDKYASWYQQKSGQSPVLIIY
QDNKRPSGIPERFSGSNSGNTATLTISGTQALDEADYYCQAWDSSTYV
AFGGGTKLTVLGSRGGGGSGGGGSGGGGSLEMAQVQLQESGPGLVKPS
ETLSLTCVVSGGSISSSNWWSWVRQPPGKGLEWIGEIYHSGSPNYNPS
LKSRVTISVDKSKNQFSLKLSSVTAADTAVYYCARMTTHTFGYDAWGQ
GTLVTVSSTSGQAGQHHHHHHGAYPYDVPDYAS
[SEQ ID NO: 674]
```

TABLE 118

ET200-045

DNA Sequence

```
cagcctgtgctgactcagccaccctcagtgtcagtggccccaggaaag
acggccacgattacttgtggggggaaacaacattggaagtgaaagtgtg
cactggtaccaccagaagccaggccaggccctgtgttggtcatctat
gatgatgccggccggccctcagggatccctgagcgattcactggctcc
aactctgggaacacggccaccctgaccatcagcagggtcgaagccggg
gatgaggccgactattactgtcaggtgtgggacagaaatagtgctcag
tttgtatcggacctgggaccaaggtcaccgtcctaggttctagaggtg
gtggtggtagcggcggcggcggctctggtggtggtggatccctcgaga
tggccgaggtccagctggtgcagtctggagctgaggtgaagaagcctg
gggcctcagtgaaggtctcctgcaaggcttctggttacacctttacca
gctatggtatcagctgggtgcgacaggcccctggacaaggcgttgagt
ggatgggatggatcagcgcttacaatggtaacacaaactatgcacaga
agctccagggcagagtcaccatgaccacagacacatccacgagcacag
cctacatggagctgaggagcctgagatctgacgacacggccgtgtatt
actgtgcgcgcggtgttcatctggattggtggggtcaaggtactctgg
tgaccgtctcctcaactagtggccaggccggccagcaccatcaccatc
accatggcgcatacccgtacgacgttccggactacgcttct
[SEQ ID NO: 675]
```

Amino Acid Sequence

```
QPVLTQPPSVSVAPGKTATITCGGNNIGSESVHWYHQKPGQAPVLVIY
DDAGRPSGIPERFSGSNSGNTATLTISRVEAGDEADYYCQVWDRNSAQ
FVFGPGTKVTVLGSRGGGGSGGGGSGGGGSLEMAEVQLVQSGAEVKKP
GASVKVSCKASGYTFTSYGISWVRQAPGQGLEWMGWISAYNGNTNYAQ
KLQGRVTMTTDTSTSTAYMELRSLRSDDTAVYYCARGVHLDWWGQGTL
VTVSSTSGQAGQHHHHHHGAYPYDVPDYAS
[SEQ ID NO: 676]
```

TABLE 119

ET200-069

DNA Sequence

```
cagtctgtcgtgacgcagccaccctcagcgtctgggacccccgggcag
agggtcaccatctcttgttctggaagcagctccaacatcggaagtaat
tatgtatactggtaccagcagctcccaggaacggcccccaaactcttc
atctatagtaataatcagcggccctcaggggtccctgaccgattctct
ggctccaagtctggcacctcagcctccctggccatcagtgggctccgg
tccgaggatgaggctgattattactgtgcagcatgggatgacagcctg
agtggttatgtatcggaactgggaccaagctgaccgtcctaggttcta
gaggtggtggtggtagcggcggcggcggctctggtggtggtggatccc
tcgagatggcccaggtcagctacagcagtggggcgcaggactgttga
gccttcggagaccctgtccctcacctgcgctgtctatggtgggtcct
tcagtggttactactggagctggatccgccagcccccagggaaggggc
tggagtggattggggaaatcaatcatagtggaagcaccaactacaacc
cgtccctcaagagtcgagtcaccatatcagtagacacgtccaagaacc
agttctccctgaagctgagctctgtgaccgccgcggacacggccgtgt
attactgtgcgcgcctgtacgaaggtggttaccatggttggggttctt
ggctgtatctgattcttggggtcaaggtactctggtgaccgtctcctc
```

TABLE 119-continued

ET200-069

```
aactagtggccaggccggccagcaccatcaccatcaccatggcgcata
cccgtacgacgttccggactacgcttct [SEQ ID NO: 677]
```

Amino Acid Sequence

```
QSVVTQPPSASGTPGQRVTISCSGSSSNIGSNYVYWYQQLPGTAPKLL
IYSNNQRPSGVPDRFSGSKSGTSASLAISGLRSEDEADYYCAAWDDSL
SGYVFGTGTKLTVLGSRGGGGSGGGGSGGGGSLEMAQVQLQQWGAGLL
KPSETLSLTCAVYGGSFSGYYWSWIRQPPGKGLEWIGEINHSGSTNYN
PSLKSRVTISVDTSKNQFSLKLSSVTAADTAVYYCARLYEGGYHGWGS
WLSSDSWGQGTLVTVSSTSGQAGQHHHHHHGAYPYDVPDYAS
[SEQ ID NO: 678]
```

TABLE 120

ET200-078

DNA Sequence

```
cagtctgtgttgactcagccaccctcagcgtctgggaccccegggcag
agggtcaccatctcttgttctggaagcagctccaacatcggaagtaat
actgtaaactggtaccagcagctcccaggaacggcccccaaactcctc
atctatagtaataatcagcggccctcaggggtccctgaccgattctct
ggctccaagtctggcacctcagcctccctggccatcagtgggctccag
tctgaggatgaggctgattattactgtgcagcatgggatgacagcctg
aatggttattgggtgttcggcggagggaccaagctgaccgtcctaggt
tctagaggtggtggtggtagcggcggcggcggctctggtggtggtgga
tccctcgagatggcccaggtgcagctacagcagtggggcgcaggactg
ttgaagccttcggagaccctgtccctcacctgcgctgtctatggtggg
tccttcagtggttactactggagctggatccgccagcccccagggaag
gggctggagtggattggggaaatcaatcatagtggaagcaccaactac
aacccgtccctcaagagtcgagtcaccatatcagtagacacgtccaag
aaccagttctccctgaagctgagctctgtgaccgccgcggacacggct
gtgtattactgtgcgcgcgaaggggcatttgatgctttgatatctgg
ggccaagggacaatggtcaccgtctcttcaactagtggccaggccggc
cagcaccatcaccatcaccatggcgcatacccgtacgacgttccggac
tacgcttct [SEQ ID NO: 679]
```

Amino Acid Sequence

```
QSVLTQPPSASGTPGQRVTISCSGSSSNIGSNTVNWYQQLPGTAPKLL
IYSNNQRPSGVPDRFSGSKSGTSASLATSGLQSEDEADYYCAAWDDSL
NGYWVFGGGTKLTVLGSRGGGGSGGGGSGGGGSLEMAQVQLQQWGAGL
LKPSETLSLTCAVYGGSFSGYYWSWIRQPPGKGLEWIGEINHSGSTNY
NPSLKSRVTISVDTSKNQFSLKLSSVTAADTAVYYCAREGAFDAFDIW
GQGTMVTVSSTSGQAGQHHHHHHGAYPYDVPDYAS
[SEQ ID NO: 680]
```

TABLE 121

ET200-079

DNA Sequence

```
tcctatgagctgactcagccaccctcagcgtctgggaccccegggcag
agggtcaccatctcttgttctggaagcagctccaacatcggaagtaat
tatgtatactggtaccagcagctcccaggaacggcccccaaactcttc
atctataggaataatcagcggccctcaggggtccctgaccgattctct
ggctccaagtctggcacctcagcctccctggccatcagtgggctccgg
tccgaggatgaggctgattattactgtgcagcatgggatgacagcctg
agtggttatctatcggaactgggaccaagctgaccgtcctaggttcta
gaggtggtggtggtagcggcggcggcggctctggtggtggtggatccc
tcgagatggcccaggtcagctggtggagtctggggaggcttggtac
agcctggcaggtccctgagactctcctgtgcagcctctggattcacct
ttgatgattatgccatgcactgggtccggcaagctccagggaagggcc
tggagtgggtctcaggtattagttggaatagtggtagcataggctatg
cggactctgtgaagggccgattcaccatctccagagacaacgccaaga
actccctgtatctgcaaatgaacagtctgagagctgaggacacggcct
tgtattactgtgcaaatggcgactccaactactactacggtatggacg
tctggggccaagggaccacggtcaccgtctcctcaactagtggccagg
ccggccagcaccatcaccatcaccatggcgcatacccgtacgacgttc
cggactacgcttct [SEQ ID NO: 681]
```

TABLE 121-continued

ET200-079

Amino Acid Sequence

SYELTQPPSASGTPGQRVTISCSGSSSNIGSNYVYWYQQLPGTAPKLF
IYRNNQRPSGVPDRFSGSKSGTSASLAISGLRSEDEADYYCAAWDDSL
SGYLFGTGTKVTVLGSRGGGGSGGGGSGGGGSLEMAEVQLVESGGGLV
QPGRSLRLSCAASGFTFDDYAMHWVRQAPGKGLEWVSGISWNSGSIGY
ADSVKGRFTISRDNAKNSLYLQMNSLRAEDTALYYCANGDSNYYYGMD
VWGQGTTVTVSSTSGQAGQHHHHHHGAYPYDVPDYAS
[SEQ ID NO: 682]

TABLE 122

ET200-081

DNA Sequence cagtctgccctgactcagcctgcctccgtgtccgggtctcctggacag
tcgatcaccatctcctgcactggaaccagcagtgacattggtggttat
aactatgtctcctggtaccaacaacacccaggcaaagcccccaaactc
atgatttatgatgtcagtaatcggccctcaggggtttctaatcgcttc
tctggctccaagtctggcaacacggcctccctgaccatctctgggctc
caggctgaggacgaggctgattattactgcatctcatatacacgcacc
tggaacccctatgtcttcgggagtgggaccaaggtcaccgtcctaggt
tctagaggtggtggtggtagcggcggcggcggctctggtggtggtgga
tccctcgagatggccgaggtgcagctggtgcagtctgggggaggcgtg
gtacagcctgggggggtccctgagactctcctgtgcagcctctggattc
acctttgatgattatgccatgcactgggtccgtcaagctccagggaag
ggtctggagtgggtctctcttattagtgggagtggtggtagcacatac
tatgcagactctgtgaagggccgattcaccatctccagagacaacagc
aaaaaactccctgtatctgcaaatgaacagtctgagaactgaggacacc
gccttgtattactgtgcaaaagatcgggcagcagctggctactactac
tacggtatggacgtctggggccaagggaccacggtcaccgtctcctca
actagtggcaggccggccagcaccatcaccatcaccatggcgcatac
ccgtacgacgttccggactacgcttct [SEQ ID NO: 683]

Amino Acid Sequence

QSALTQPASVSGSPGQSITISCTGTSSDIGGYNYVSWYQQHPGKAPKL
MIYDVSNRPSGVSNRFSGSKSGNTASLTISGLQAEDEADYYCISYTRT
WNPYVFGSGTKVTVLGSRGGGGSGGGGSGGGGSLEMAEVQLVQSGGGV
VQPGGSLRLSCAASGFTFDDYAMHWVRQAPGKGLEWVSLISGDGGSTY
YADSVKGRFTISRDNSKNSLYLQMNSLRTEDTALYYCAKDRAAAGYYY
YGMDVWGQGTTVTVSSTSGQAGQHHHHHHGAYPYDVPDYAS
[SEQ ID NO: 684]

TABLE 123

ET200-097

DNA Sequence ctgcctgtgctgactcagcctcaccctcagtgtccgtgtccccaggacag
acagccatcatcacctgctctggagataaattgggggaaaaatatgtt
tcctggtatcagcagaagccaggccagtccctgtactggtcatcgat
caagataccaggaggccctcagggatccctgagcgattctctggctcc
aactctgggaccacagccactctgaccatcagcgggacccaggctatg
gatgaggctgactattactgtcaggcgtggacaggtgtggtattc
ggcggagggaccaagctgaccgtcctaggttctagaggtggtggtggt
agcggcggcggcggctctggtggtggtggatccctcgagatggccgag
gtgcagctggtggagtctggggggagacttggtacagcctggcaggtcc
ctgagactctcctgtgcagcctctggattcacctttgatgattatgcc
atgcactgggtccgtcaagctccagggaagggcctggagtgggtctca
ggtattagttggagtggtaataacataggctatgcggactctgtgaag
ggccgattcaccatctccagagacaacgccaagaactccctgtatctg
caaatgaacagtctgagaactgaggacacggccttgtattactgtgca
aaagatagtatacggtatggcatcacctgggaggtttgactactgga
ggccagggaaccctggtcaccgtctcctcaactagtggcaggccggc
cagcaccatcaccatcaccatggcgcatacccgtacgacgttccggac
tacgcttct [SEQ ID NO: 685]

TABLE 123-continued

ET200-097

Amino Acid Sequence

LPVLTQPPSVSVSPGQTAIITCSGDKLGEKYVSWYQQKPGQSPVLVID
QDTRRPSGIPERFSGSNSGTTATLTISGTQAMDEADYYCQAWDRGVVF
GGGTKLTVLGSRGGGGSGGGGSGGGGSLEMAEVQLVESGGDLVQPGRS
LRLSCAASGFTFNDYAMEIWVRQAPGKGLEWVSGISWSGNNIGYADSV
KGRFTISRDNAKNSLYLQMNSLRAEDTALYYCAKDSIRYGITWGGFDY
WGQGTLVTVSSTSGQAGQHHHHHHGAYPYDVPDYAS
[SEQ ID NO: 686]

TABLE 124

ET200-098

DNA Sequence cagcctgtgctgactcagccaccctcggtgtccaagggcttgagacag
accgccacactcacctgcactgggaacagcaacaatgttggcaaccta
ggagtagcttggctgcagcagcaccagggccaccctcccaaactccta
tcctacaggaataacaaccggccctcagggatctcagagagattatct
gcatccaggtcaggaaacacagcctccctgaccattactggactccag
cctgaggacgaggctgactattactgctcagcatgggacagtagcctc
agtgcttgggtgttcggcggagggaccaagctgaccgtcctaggttct
agaggtggtggtagcggcggcggcggctctggtggtggtggatcc
ctcgagatggccgaggtgcagctggtggagtctggggggagtcgtggta
cagcctgggggggtccctgagactctcctgtgcagcctctggattcacc
tttgatgattatgccatgcactgggtccgtcaagctccagggaagggt
ctggagtgggtctctcttattaattgggatggtggtagcacctactat
gcagactctgtgaagggtcgattcaccatctccagagacaacagcaaa
aactccctgtatctgcaaatgaacagtctgagagctgaggacaccgcc
ttgtattactgtgcaaaagggatgggcctgagggcgtttgactactgg
ggccagggaaccctggtcaccgtctcctcaactagtggcaggccggc
cagcaccatcaccatcaccatggcgcatacccgtacgacgttccggac
tacgcttct [SEQ ID NO: 687]

Amino Acid Sequence

QPVLTQPPSVSKGLRQTATLTCTGNSNNVGNLGVAWLQQHQGHPPKLL
SYRNNNRPSGISERLSASRSGNTASLTITGLQPEDEADYYCSAWDSSL
SAWVFGGGTKLTVLGSRGGGGSGGGGSGGGGSLEMAEVQLVESGGVVV
QPGGSLRLSCAASGFTFDDYAMHWVRQAPGKGLEWVSLINWDGGSTYY
ADSVKGRFTISRDNSKNSLYLQMNSLRAEDTALYYCAKGMGLRAFDYW
GQGTLVTVSSTSGQAGQHHHHHHGAYPYDVPDYAS
[SEQ ID NO: 688]

TABLE 125

ET200-099

DNA Sequence cagtctgtgttgactcagccaccctcagcgtctgggaccccgcgggcag
agggtcaccatctcctgttctggaagcagctccaacatcggaagtaat
actgtaaactggtaccagcagctcccaggaacggcccccaaactcctc
atctatagtaatgatcagcggccctcaggggtccctgaccgattctct
ggctccaagtccggcacctcagcctccctggccatcagtgggctccag
tctgaggatgaggctgattattactgtgcttcatgggatgacagcctg
aatggccgttatgtcttcggaactgggaccaaggtcaccgtcctaggt
tctagaggtggtggtggtagcggcggcggcggctctggtggtggtgga
tccctcgagatggcccaggtgcagctggtacagtctggggctgaggtg
aggaagcctgggccctcagtgaaggtttcctgcaaggcttctggatac
accttcagtggttatgctatacattgggtgcgccaggcccccggacaa
aggcttgagtggatgggatggatcaacgctggcaatggaaacacaaaa
tattcacagaaatttcagggcagagtcagtcttaccagggacacatcc
gcgagcacagcctacatggagctgagcagcctgagatctgatgacacg
gctgtgtattactgtgcgagacccgataattatggttcgggtggggat
gtttttgatatctggggccaagggacaatggtcaccgtctcttcaact
agtggcaggccggccagcaccatcaccatcaccatggcgcatacccg
tacgacgttccggactacgcttct [SEQ ID NO: 689]

TABLE 125 -continued

ET200-099

Amino Acid Sequence

QSVLTQPPSASGTPGQRVTISCSGSSSNIGSNTVNWYQQLPGTAPKLL
IYSNDQRPSGVPDRFSGSKSGTSASLAISGLQSEDEADYYCASWDDSL
NGRYVFGTGTKVTVLGSRGGGGSGGGGSGGGGSLEMAQVQLVQSGAEV
RKPGASVKVSCKTSGYTFSWYAITIWVRQAPGQRLEWMGWINAGNGNT
KYSQKFQGRVSLTRDTSASTAYMELSSLRSDDTAVYYCARPDNYGSGG
DVFDIWGQGTMVTVSSTSGQAGQHHHHHHGAYPYDVPDYAS
[SEQ ID NO: 690]

TABLE 126

ET200-100

DNA Sequence aattttatgctgactcagcccactctgtgtcggagtctccggggaagac
ggtaaccatctcctgcacccgcagcagtggcagcattgccagcaactttg
tgcagtggtaccagcagcgcccgggcagtgcccccaccctatgatctat
gaggataacaacagaccccctggggtccctgatcggttctctgctccgt
cgacagctcctccaactctgcctccctcaccatctctggactgaagactg
aggacgaggctgactactactgtcagtcttatgataccagcaatgtggta
ttcggcgggggggaccaagctgaccgtcctaggttctagaggtggtggtgg
tagcggcggcggcggctctggtggtggtggatccctcgagatggccgagg
tgcagctggtggagtctggggggaggcttggtacagcctggagggtccctg
agactctcctgtgcagcctctggattcaccttcagtagttatgaaatgaa
ctggtccgccaggctccaggggaagggggctggagtggtgtttcatacatta
gtagtagtggtagtaccatatactacgcagactctgtgaagggccgattc
accatctccagagacaacgccaagaactcactgtatctgcaaatgaacag
cctgagagccgaggacacggctgtttattactgtgcacgctgggactacg
gtatggacgtctggggccaagggacacggtcaccgtctcctcaactagt
ggccaggccggccagcaccatcaccatcaccatggcgcatacccgtacga
cgttccggactacgcttct [SEQ ID NO: 691]

Amino Acid Sequence

NFMLTQPHSVSESPGKTVTISCTRSSGSIASNFVQWYQQRPGSAPTPMIY
EDNNRRPPGVPDRFSASVDSSSNSASLTISGLKTEDEADYYCQSYDTSNVV
FGGGTKLTVLGSRGGGGSGGGGSGGGGSLEMAEVQLVESGGGLVQPGGSL
RLSCAASGFTFSSYEMNWVRQAPGKGLEWVSYISSSGSTIYYADSVKGRF
TISRDNAKNSLYLQMNSLRAEDTAVYYCARWDYGMDVWGQGTTVTVSSTS
GQAGQHFIREIHHGAYPYDVPDYAS [SEQ ID NO: 692]

TABLE 127

ET200-101

DNA Sequence caggctgtgctgactcagccaccctcagcgtctggggcccccgggcagag
ggtcaccgtctcttgttctggaagcaactccaacatcggaagtaactacg
ttaactggtaccagcagttcccaggaacggcccccaaactcctcatgtat
agtagtagtcagcggccctcaggggtccctgacccgattctctggctccat
cgacagctcctccaactctgcctccctcaccatctctggactgaagactg
aggctgattattactgtgctacatgggatgacagcctgaatgcttgggtg
ttcggcggagggaccaagctgaccgtcctaggttctagaggtggtggtgg
tagcggcggcggcggctctggtggtggtggatccctcgagatggccgagg
tccagctggtgcagtctggggctgaggtgaggaagcctggggcctcagtg
aaggtttcctgcaagacttctggatacaccttcacttggtatgctataca
ttgggtgcgccaggcccccggacaaaggcttgagtggatgggatggatca
acggctggcagtggaaacacaaaatattcacagaaatttcagggcagagtc
acccttaccagggacacatccgcgagcacagcgtacatggagctgagcag
cctgagatctgatgacacggctgtgtattactgtgcgagacccaataact
atggttcgggtgggatgtttttgatatctggggccaagggacaatggtc
accgtctcttcaactagtggccaggccggccagcaccatcaccatcacca
tggcgcatacccgtacgacgttccggactacgcttct [SEQ ID
NO: 693]

Amino Acid Sequence

QAVLTQPPSASGAPGQRVTVSCSGSNSNIGSNYVNWYQQFPGTAPKLLMY
SSSQRPSGVPDRFSGSKSGTSASLAISGLHSEDEADYYCATWDDSLNAWV

TABLE 127 -continued

ET200-101

FGGGTKLTVLGSRGGGGSGGGGSGGGGSLEMAEVQLVQSGAEVRKPGASV
KVSCKTSGYTFTWYAIHWVRQAPGQRLEWMGWINAGSGNTKYSQKFQGRV
TLTRDTSASTAYMELSSLRSDDTAVYYCARPNNYGSGGDVFDIWGQGTMV
TVSSTSGQAGQHHHHHHGAYPYDVPDYAS [SEQ ID NO: 694]

TABLE 128

ET200-102

DNA Sequence cagtctgtcgtgacgcagccgccctcagtgtctgcggccccaggacagaa
ggtcaccatctcctgctctggaagcagctccaacattgggaataattatg
tatcctggtaccagcagctcccaggaacagcccccaaactcctcatttat
gacaataataagcgaccctcagggattcctgaccgattctctggctccaa
gtctggcacgtcagccaccctgggcatcaccggactccagactggggacg
aggccgattattactgcgcacatgggatagcagcctgagtgcttatgtc
ttcggaactgggaccaaggtcaccgtcctaggttctagaggtggtggtgg
tagcggcggcggcggctctggtggtggtggatccctcgagatggcccagg
tccagctggtgcagtctggggctgaggtgaagaagcctggggcctcagtg
aaagttttcctgcaaggcttctggatacacccttcacgaactatgctctgca
ttgggtgcgccaggcccccggacaagggcttgagtggatggcatggatca
acggtggcaatggtaacacaaaatattcacagaacttccagggcagagtc
accattaccagggacacatccgcgagcacagcctatatggagctgagcag
cctgagatctgaagacacggctgtgtattactgtgcgaaaccggaggaaa
cagctggaacaatccactttgactactggggcaggggaaccccggtcacc
gtctcctcaactagtggccaggccggccagcaccatcaccatcaccatgg
cgcataccgtacgacgttccggactacgcttct [SEQ ID NO:
695]

Amino Acid Sequence

QSVVTQPPSVSAAPGQKVTISCSGSSSNIGNNYVSWYQQLPGTAPKLLIY
DNNKRPSGIPDRFSGSKSGTSATLGITGLQTGDEADYYCGTWDSSLSAYV
FGTGTKVTVLGSRGGGGSGGGGSGGGGSLEMAQVQLVQSGAEVKKPGASV
KVSCKASGYTFTNYALHWVRQAPGQGLEWMAWINGGNGNTKYSQNFQGRV
TITRDTSASTAYMELSSLRSEDTAVYYCAKPEETAGTIHFDYWGQGTPVT
VSSTSGQAGQHHHHHHGAYPYDVPDYAS [SEQ ID NO: 696]

TABLE 129

ET200-103

DNA Sequence caggctgtgctgactcagcccactctgtgtcggagtctccggggaagac
ggtaaccatctcctgcacccgcagcagtggcagcattgccagcaactatg
tgcagtggtaccagcagcgcccgggcagtgcccccaccactgtgatctat
gaggataacaaagaccctctggggtccctgatcggttctctggctccat
cgacagctcctccaactctgcctccctcaccatctctggactgaagactg
aggacgaggctgactactactgtcagtcttatgatagcaccatcacggtg
ttcggcggagggaccaagctgaccgtcctaggttctagaggtggtggtgg
tagcggcggcggcggctctggtggtggtggatccctcgagatggccagg
tccagctggtacagtctggggctgaggtgaagaagcctgggtcctcggtg
aaggtctcctgcaaggcttctggaggcaccttcagcagctatgctatcag
ctgggtgcgacaggcccccggacaaagggcttgagtggatggggagggatca
tccctatctttggtacagcaaactacgcacagaagttccagggcagagtc
acgattaccgcggacgaatccacgagcacagcctacatggagctgagcag
cctgagatctgaggacacggccgtgtattactgtgcggggggagggttact
atgatagtagtggttattccaacggtgatgcttttgatatctggggccaa
gggacaatggtcaccgtctcttcaactagtggccaggccggccagcacca
tcaccatcaccatggcgcatacccgtacgacgttccggactacgcttct
[SEQ ID NO: 697]

Amino Acid Sequence

QAVLTQPHSVSESPGKTVTISCTRSSGSIASNYVQWYQQRPGSAPTTVIY
EDNQRPSGVPDRFSGSIDSSSNSASLTISGLKTEDEADYYCQSYDTSTITV
FGGGTKLTVLGSRGGGGSGGGGSGGGGSLEMAQVQLVQSGAEVKKPGSSV
KVSCKASGGTFSSYAISWVRQAPGQGLEWMGGIIPIFGTANYAQKFQGRV
TITADESTSTAYMELSSLRSEDTAVYYCAGEGYYDSSGYSNGDAFDIWGQ
GTMVTVSSTSGQAGQHHHHHHGAYPYDVPDYAS [SEQ ID NO: 698]

TABLE 130

ET200-104

DNA Sequence

```
aattttatgctgactcagccccactctgtgtcggagtctccggggaagac
ggtaaccatctcctgcacccgcagcagtggcagcattgccagcaactatg
tgcagtggtaccagcagcgcccgggcagtgcccccaccactgtgatctat
gaggataaccaaagaccctctggggtccctgatcggttctctggctccat
cgacagctcctccaactctgcctccctcaccatctctggactgaagactg
aggacgaggctgactactactgtcagtcttatgatagcagcaatgtggta
ttcggcggagggaccaaggtcaccgtcctaggttctagaggtggtggtgg
tagcggcggcggcggctctggtggtggtggatccctcgagatggccgagg
tgcagctggtggagtctgggggaggcttggtacagcctggagggtccctg
agactctcctgtgcagcctctggattcacettcagtagttatgaaatgaa
ctgggtccgccaggctccagggaaggggctggagtggggtttcatacatta
gtagtagtggtagtaccatatactacgcagactctgtgaagggccgattc
accatctccagagacaacgccaagaactcactgtatctgcaaatgaacag
cctgagagccgaggacacggctgtttattactgtgcacgctgggactacg
gtatggacgtctggggccaagggaccacggtcaccgtctcctcaactagt
ggccaggccggccagcaccatcaccatcaccatggcgcatacccgtacga
cgttccggactacgcttct [SEQ ID NO: 699]
```

Amino Acid Sequence

```
NFMLTQPHSVSESPGKTVTISCTRSSGSIASNYVQWYQQRPGSAPTTVIY
EDNQRPSGVPDRFSGSIDSSSNSASLTISGLKTEDEADYYCQSYDSSNVV
FGGGTKVTVLGSRGGGGSGGGGSGGGGSLEMAEVQLVESGGGLVQPGGSL
RLSCAASGFTFSSYEMNWVRQAPGKGLEWVSYISSSGSTIYYADSVKGRF
TISRDNAKNSLYLQMNSLRAEDTAVYYCARWDYGMDVWGQGTTVTVSSTS
GQAGQHFIREIHHGAYPYDVPDYAS [SEQ ID NO: 700]
```

TABLE 131

ET200-105

DNA Sequence

```
tcctatgtgctgactcagccaccctcagtgtccgtgtccccaggacagac
agccagcatcacctgctctggagatagattgacgaataaatatgtttcct
ggtatcaacagaagccaggccagtccctgtgttggtcatctatgaggat
gccaagcggccctcagggatccctgcgcgattctctggctccaactctgg
gaacagcactctgaccatcagcgggacccaggctatggatgagtctg
aatattactgtcaggcgtggacagcagtgtggtggtttttggcggaggg
accaagctgaccgtcctaggttctagaggtggtggtggtagcggcggcgg
cggctctggtggtggtggatccctcgagatggccgaggtgcagctggtg
agtctgggggaggcttggtacagcctggcaggtccctgagactctcctgt
gcagcctctggatttacctttgatgattatgccatgcactgggtccggca
agctccagggaaggggctggagtgggtctcaggtattagttggaatagtg
gtagtataggctatgcggactctgtgaagggccgattcaccatctccaga
gacaacgccaagaactccctgtatctgcaaatgaacagtctgagagatga
ggacacggccttgtattactgtgcaaaagaccgaggggggggagttatcg
ttaaggatgatttgatatctggggcaagggacaatggtcaccgtctctt
caactagtggccaggccggccagcaccatcaccatcaccatggcgcatac
ccgtacgacgttccggactacgcttct [SEQ ID NO: 701]
```

Amino Acid Sequence

```
SYVLTQPPSVSVSPGQTASITCSGDRLTNKYVSWYQQKPGQSPVLVIYED
AKRPSGIPARFSGSNSGNTATLTISGTQAMDESEYYCQAWDSSVVVFGGG
TKLTVLGSRGGGGSGGGGSGGGGSLEMAEVQLVESGGGLVQPGRSLRLSC
AASGFTFDDYAMEIWVRQAPGKGLEWVSGISWNSGSIGYADSVKGRFTIS
RDNAKNSLYLQMNSLRDEDTALYYCAKDRGGGVIVKDAFDIWGQGTMVTV
SSTSGQAGQHHHHHHGAYPYDVPDYAS [SEQ ID NO: 702]
```

TABLE 132

ET200-106

DNA Sequence

```
tcctatgagctgactcagccacccgcagcgtctgggaccccggacagag
agtcaccatctcttgttctgggggcgtctccaacatcgggagtggtgctc
taaattggtaccagcaactcccaggaacggcccccaaactcctcatctat
agttacaatcagcggccctcaggggtctctgaccgattctctggctccag
gtctgccacctcagcctccctggccatcagtgggctccagtctgaggatg
```

TABLE 132 -continued

ET200-106

```
aggctgattattactgtgcaacctgggatgatagtgtgaatggttgggtg
ttcggcggagggaccaagctgaccgtcctaggttctagaggtggtggtgg
tagcggcggcggcggctctggtggtggtggatccctcgagatggccgagg
tgcagctggtggagtctgagagctgaggtgaagaagcctggggattcagtg
aaggtctcctgcaagccttctggttacaattttctcaactatggtatcaa
ctgggtgcgacaggcccctggacaagggcttgagtggatgggatggatta
gcacttacaccggtaacacaaactatgcacagaagctgcaggggcagagtc
accttcaccacagacacatccacgagcacagcctacatggagatgaggag
cctgagatctgacgacacggccgtgtattactgtgcgcgccagcagggtg
gtggttggtacgatgtttggggtcaaggtactctggtcaccgtctcctca
actagtggccaggccggccagcaccatcaccatcaccatggcgcataccc
gtacgacgttccggactacgcttct [SEQ ID NO: 703]
```

Amino Acid Sequence

```
SYELTQPPAASGTPGQRVTISCSGGVSNIGSGALNWYQQLPGTAPKWYSY
NQRPSGVSDRFSGSRSATSASLAISGLQSEDEADYYCATWDDSVNGWVFG
GGTKLTVLGSRGGGGSGGGGSGGGGSLEMAEVQLVESGAEVKKPGDSVKV
SCKPSGYNFLNYGINWVRQAPGQGLEWMGWISTYTGNTNYAQKLQGRVTF
TTDTSTSTAYMEMRSLRSDDTAVYYCARQQGGGWYDVWGQGTLVTVSSTS
GQAGQHHIREIHHGAYPYDVPDYAS [SEQ ID NO: 704]
```

TABLE 133

ET200-107

DNA Sequence

```
cagtctgtcgtgacgcagccgccctcagtgtctgcggccccaggagagaag
gtcaccatctcctgctctggaagcaacttcaatgttggaaataatgatgta
tcctggtatcagcaactcccaggtgcagcccccaaactcctcatttatgac
aataataagcgaccctcagggattcctgaccgattctctggctccaagtct
ggcacgtcagccaccctggacatcaccgggctccacagtgacgacgaggcc
gattattactgcggaacatgggatagcagcctgaatactggggggggtcttc
ggaactgggaccaaggtcaccgtcctaggttctagaggtggtggtggtagc
ggcggcggcggctctggtggtggtggatccctcgagatggccgaggtccag
ctggtgcagtctggagctgaggtgaagaagcctgggcctcagtgaaggtc
tcctgcaaggcttctggttacacctttaccagctatactatcagctggta
cgacaggcccctggacaagggcttgagtggatgggatggatcagcacttac
aatggtctcacaaactatgcacagaacctccagggcagagtcaccatgact
acagacaattcacgaccacagcctacatggagctgaggagctcagatct
gacgacacggccgtgtattactgtgtgagagaggggtcccccgactacggt
gacttcgcgtcctttgactactggggccagggaaccctggtcaccgtctcc
tcaactagtggccaggccggccagcaccatcaccatcaccatggcgcatac
ccgtacgacgttccggactacgcttct [SEQ ID NO: 705]
```

Amino Acid Sequence

```
QSVVTQPPSVSAAPGEKVTISCSGSNFNVGNNDVSWYQQLPGAAPKLLIYD
NNKRPSGIPDRFSGSKSGTSATLDITGLHSDDEADYYCGTWDSSLNTGGVF
GTGTKVTVLGSRGGGGSGGGGSGGGGSLEMAEVQLVQSGAEVKKPGASVKV
SCKASGYTFTSYTISWVRQAPGQGLEWMGWISTYNGLTNYAQNLQGRVTMT
TDTFTTTAYMELRSLRSDDTAVYYCVREGSPDYGDFASFDYWGQGTLVTVS
STSGQAGQHHHHHHGAYPYDVPDYAS [SEQ ID NO: 706]
```

TABLE 134

ET200-108

DNA Sequence

```
cagtctgtgttgacgcagccgccctcagtgtctgcgcccccgggacagaag
gtcaccatctcctgctctggaagcagctccaacattgggaataattatgta
tcctggtaccagcagttcccaggaacagcccccaaactcctcatttatgac
aataataagcgaccctcagggatttctgaccgattctctggctccaagtct
ggcacgtcagccaccctgggcatcgccggactccagactggggacgaggcc
gattattactgcggaacatgggataccagctgagtggtttttatgtatcg
gaagtgggaccaaggtcaccgtcctaggttctagaggtggtggtggtagcg
gcggcggcggctctggtggtggtggatccctcgagatggccgaggtccagc
tggtacagtctggagctgaggtgaagaagcctgggcctcagtgaaggtct
cctgcaaggcttctggttacacctttaccagctatactatcagctgggtac
gacaggcccctggacaagggcttgagtggatgggatggatcagcacttaca
atggtctcacaaactatgcacagaacctccagggcagagtcaccatgacta
```

TABLE 134 -continued

ET200-108

```
cagacacattcacgaccacagcctacatggagctgaggagcctcagatctg
acgacacggccgtgtattactgtgtgagagaggggtcccccgactacggtg
acttcgcgtcctttgactactggggccagggaaccctggtcaccgtctcct
caactagtggccaggccggccagcaccatcaccatcaccatggcgcatacc
cgtacgacgttccggactacgcttct [SEQ ID NO: 707]
```

Amino Acid Sequence

```
QSVLTQPPSVSAPPGQKVTISCSGSSSNIGNNYVSWYQQFPGTAPKWYDNN
KRPSGISDRFSGSKSGTSATLGIAGLQTGDEADYYCGTWDTSLSGFYVFGS
GTKVTVLGSRGGGGSGGGGSGGGGSLEMAEVQLVQSGAEVKKPGASVKVSC
KASGYTFTSYTISWVRQAPGQGLEWMGWISTYNGLTNYAQNLQGRVTMTTD
TFTTTAYMELRSLRSDDTAVYYCVREGSPDYGDFASFDYWGQGTLVTVSST
SGQAGQHFIREIHHGAYPYDVPDYAS [SEQ ID NO: 708]
```

TABLE 135

ET200-109

DNA Sequence

```
ctgcctgtgctgactcagccaccctcagcgtctgcgacccccgggcagagg
gtcaccatctcttgttctggaaccacctccaacatcggaagtaatactgta
cactggtaccagcagctcccagggacggcccccaaactcctcatctataat
aataatcagcggccctcaggggtccctgaccgattctctggctccaagtct
ggcacctcagcctccctggccatcagtgggctccggtccgaggatgaggct
acatattcctgtgcaacatgggatgacagcctgagtggtgtggtcttcggc
ggagggaccaagctgaccgtcctaggttctagaggtggtggtggtagcggc
ggcggcggctctggtggtggtggatccctcgagatggccgaggtccagctg
gtgcagtctggggctgaggtgaagaagcctgggtcctcggtgaaggtctcc
tgcaaggcttctggaggcaccttcagcagctatgctatcagctgggtgcga
caggcccctggacaagggcttgagtggatgggagggatcatccctatcttt
ggtacagcaaactacgcacagaagttccagggcagagtcacgattaccgcg
gacgaatccacgagcacagcctacatggagctgagcagcctgagatctgag
gacacggccgtgtattactgtgcgagagatcccgcctacggtgactacgag
tatgatgcttttgatatctggggccaagggacaatggtcaccgtctcttca
actagtggccaggccggccagcaccatcaccatcaccatggcgcatacccg
tacgacgttccggactacgcttct [SEQ ID NO: 709]
```

Amino Acid Sequence

```
LPVLTQPPSASATPGQRVTISCSGTTSNIGSNTVHWYQQLPGTAPKLLIYN
NNQRPSGVPDRFSGSKSGTSASLAISGLRSEDEATYSCATWDDSLSGVVFG
GGTKLTVLGSRGGGGSGGGGSGGGGSLEMAEVQLVQSGAEVKKPGSSVKVS
CKASGGTFSSYAISWVRQAPGQGLEWMGGIIPIFGTANYAQKFQGRVTITA
DESTSTAYMELSSLRSEDTAVYYCARDPAYGDYEYDAFDIWGQGTMVTVSS
TSGQAGQHHHHHHGAYPYDVPDYAS [SEQ ID NO: 710]
```

TABLE 136

ET200-110

DNA Sequence

```
cagtctgtgttgacgcagccgcctcagcgtctgggacccccgggcagagg
gtcaccatctcttgttctggaagcagctccaacatcggaactaatggtgta
aactggttccagcagttcccaggaacggcccccaaactcctcatctatact
aatgatcagcggccctcaggggtccctgaccgattctctggctccaagtct
ggcacctcagcctccctggccatcagtgggctccagtctgcggatgaggct
gattattactgtgcagtgtgggaccacagcctgaatggtccggtgttcggc
ggagggaccaagctgaccgtcctaggttctagaggtggtggtggtagcggc
ggcggcggctctggtggtggtggatccctcgagatggcccaggtgcagctg
gtgcagtctggggctgaggtgaagaagcctgggtcctcggtgaaggtctcc
tgcaaggcttctggaggcaccttcagcagctatgctatcagctgggtgcga
caggcccctggacaagggcttgagtggatgggagggatcatccctatcttt
ggtacagcaaactacgcacagaagttccagggcagagtcacgattaccgcg
gacgaatccacgagcacagcctacatggagctgagcagcctgagatctgag
gacacggccgtgtattactgtgcgagagggccggttttgatgcttttgat
atctggggccaagggacaatggtcaccgtctcttcaactagtggccaggcc
ggccagcaccatcaccatcaccatggcgcatacccgtacgacgttccggac
tacgcttct [SEQ ID NO: 711]
```

TABLE 136 -continued

ET200-110

Amino Acid Sequence

```
QSVLTQPPSASGTPGQRVTISCSGSSSNIGTNGVNWFQQFPGTAPKLLIYT
NDQRPSGVPDRFSGSKSGTSASLAISGLQSADEADYYCAVWDHSLNGPVFG
GGTKLTVLGSRGGGGSGGGGSGGGGSLEMAQVQLVQSGAEVKKPGSSVKVS
CKASGGTFSSYAISWVRQAPGQGLEWMGGIIPIFGTANYAQKFQGRVTITA
DESTSTAYMELSSLRSEDTAVYYCARGAGFDAFDIWGQGTMVTVSSTSGQA
GQHHHHHHGAYPYDVPDYAS [SEQ ID NO: 712]
```

TABLE 137

ET200-111

DNA Sequence

```
caggctgtgctgactcagccaccctcagcgtctgggacccccgggcagagg
gtcaccatctcttgttctggaagcagctccaacatcggaagtaatactgta
aactggtaccagcagctcccaggaacggcccccaaactcctcatctatagt
aataatcagcggccctcaggggtccctgaccgattctctggctccaagtct
ggcacctcagcctccctggccatcagtgggctccagtctgaggatgagact
gattattactgtgcagcatgggatgacagcctgaatggttatgtcttcgga
actgggaccaaggtcaccgtcctaggttctagaggtggtggtggtagcggc
ggcggcggctctggtggtggtggatccctcgagatggcccaggtgcagcta
cagcagtggggcgcaggactgttgaagccttcggagaccctgtccctcacc
tgcgctgtctatggtgggtccttcagtggttactactggagctggatccgc
cagcccccaggaaggggctggagtggattgggaaatcaatcatagtgga
agcaccaactacaaccgtccctcaagagtcgagtcaccatatcagtagac
acgtccaagaaccagttctccctgaagctgagctctgtgaccgccgcggac
acggctgtgtattactgtgcgagagaggggctagatgcttttgatatctgg
ggccaagggacaatggtcaccgtctcttcaactagtggccaggccggccag
caccatcaccatcaccatggcgcatacccgtacgacgttccggactacgct
tct [SEQ ID NO: 713]
```

Amino Acid Sequence

```
QAVLTQPPSASGTPGQRVTISCSGSSSNIGSNTVNWYQQLPGTAPKLLIYS
NNQRPSGVPDRFSGSKSGTSASLAISGLQSEDETDYYCAAWDDSLNGVVFG
TGTKVTVLGSRGGGGSGGGGSGGGGSLEMAQVQLQQWGAGLLKPSETLSLT
CAVYGGSFSGYYWSWIRQPPGKGLEWIGEINHSGSTNYNPSLKSRVTISVD
TSKNQFSLKLSSVTAADTAVYYCAREGLDAFDIWGQGTMVTVSSTSGQAGQ
HHHEIHHGAYPYDVPDYAS [SEQ ID NO: 714]
```

TABLE 138

ET200-112

DNA Sequence

```
caggctgtgctgactcagccaccctcagcgtctgggacccccgggcagagg
gtcaccatctcttgttctggaagcagctccaacatcggaagtaatactgta
aactggtaccagcagctcccaggaacggcccccaaactcctcatgtatagt
aatgatcagcggccctcaggggtccctgaccgattctctggctccaagtct
ggcacctcagcctccctggccatcagtgggctccagtctgaggatgaggct
gattattattgtgcagcatgggatgacagcctgaatggttatgtcttcgca
gctgggacccagctcaccgttttaagttctagaggtggtggtggtagcggc
ggcggcggctctggtggtggtggatccctcgagatggcccaggtgcagcta
cagcagtggggcgcaggactgttgaagccttcggagaccctgtccctcacc
tgcgctgtctatggtgggtccttcagtggttactactggagctggatccgc
cagcccccaggaagggggtggagtggattgggaaatcaatcatagtgga
agcaccaactacaaccgtccctcaagagtcgagtcaccatatcagtagac
acgtccaagaaccagttctccctgaagctgagctctgtgaccgccgcggac
acggctgtgtattactgtgcgagagaggggctagatgcttttgatatctgg
ggccaagggacaatggtcaccgtctcttcaactagtggccaggccggccag
caccatcaccatcaccatggcgcatacccgtacgacgttccggactacgct
tct [SEQ ID NO: 715]
```

Amino Acid Sequence

```
QAVLTQPPSASGTPGQRVTISCSGSSSNIGSNTVNWYQQLPGTAPKLLMYS
NDQRPSGVPDRFSGSKSGTSASLAISGLQSEDEADYYCAAWDDSLNGYVFA
```

TABLE 138 -continued

ET200-112

AGTQLTVLSSRGGGGSGGGGSGGGGSLEMAQVQLQQWGAGLLKPSETLSLT
CAVYGGSFSGYYWSWIRQPPGKGLEWIGEINHSGSTNYNPSLKSRVTISVD
TSKNQFSLKLSSVTAADTAVYYCAREGLDAFDIWGQGTMVTVSSTSGQAGQ
HHHHHHGAYPYDVPDYAS [SEQ ID NO: 716]

TABLE 139

ET200-113

DNA Sequence cagtctgtcgtgacgcagccgccctcagtgtctgcggccccaggacagaag
gtcaccatctcctgctctggaagcagctccaacattgggaataattatgta
tcctggtaccagcagctcccaggaacagcccccaaactcctcatttatgac
aataataagcgaccctcagggattcctgaccgattctctggctccaagtct
ggcacgtcagccaccctgggcatcactggactccagactggggacgaggcc
gattattactgcggaacatgggatagcagcctgagtgctgatatgtatcgg
aactgggaccaaggtcaccgtcctaggttctagaggtggtggtggtagcgg
cggcggcggctctggtggtggtggatccctcgagatggcccaggtccagct
ggtacagtctgagctgaggtgaagaagcctgggggcctcagtgaaggtctc
ctgcaaggatctggttacagattaccagctatactatcagctgggttcgac
aggcccctggacaaggccttgagtggatgggatgggtcagcacttacaatg
gtctcagaaactatgcacagaacctccagggcagagtcaccatgactacag
acacactcacgaccacagcctacatggagctgaggagcctcagatctgacg
acacggccgtgtattattgtgtgagagaggggtcccccgactacggtgact
tcgccggcctttgactactggggccagggaaccctggtcaccgtctcctcaa
ctagtggccaggccggccacaccatcaccatcaccatggcgcatacccgt
acgacgttccggactacgcttct [SEQ ID NO: 717]

Amino Acid Sequence

QSVVTQPPSVSAAPGQKVTISCSGSSSNIGNNYVSWYQQLPGTAPKWYDNN
KRPSGIPDRFSGSKSGTSATLGITGLQTGDEADYYCGTWDSSLSAAYVFGT
GTKVTVLGSRGGGGSGGGGSGGGGSLEMAQVQLQQWGAGLLKPSETLS
LTCAVYGGSFSGYYWSWIRQPPGKGLEWIGEINHSGSTNYNPSLKSRVTI
SVDTSKNQFSLKLSSVTAADTAVYYCREGSPDYGDFAAFDYWGQGTLVTVSST
SGQAGQHHHHHHGAYPYDVPDYAS [SEQ ID NO: 718]

TABLE 140

ET200-114

DNA Sequence caggctgtgctgactcagccaccctcagcgtctgagaccccgggcagag
ggtcaccatctcttgttctggaagcaggtccaacatcggaactaatattg
tacactggtaccagcagcgcccaggaatggcccccaaactcctcacttat
ggtagtcggcggccctcaggggtcccggaccgattctctggctccaagtt
tggcacctcagcctccctggccatcagtgggctccagtctgaggatgagg
ctgattattattgtgcagcatgggatgacagtcgaatggtccggctttc
ggcgagggaccaagctgaccgtcctaggttctagaggtggtggtggtag
cggcggcggcggctctggtggtggtggatccctcgagatggcccaggtgc
agctacagcagtggggcgcaggactgttgaagccttcggagaccctgtcc
ctcacctgcgctgtctatggtgggtccttcagtggttactactggagctg
gatccgccagcccccaggaagggctggagtggattgggaaatcaatc
atagtggaagcaccaactacaacccgtccctcaagagtcgagtcaccata
tcagtagacacgtccaagaaccagttctccctgaagctgagctctgtgac
cgccgcggacacggctgtgtattactgtgcgagagacggtgggggctact
ttgactactggggccagggaaccctggtcaccgtctcctcaactagtggc
caggccggccagcaccatcaccatcaccatggcgcatacccgtacgacgt
tccggactacgcttct [SEQ ID NO: 719]

Amino Acid Sequence

QAVLTQPPSASETPGQRVTISCSGSRSNIGTNIVHWYQQRPGMAPKLLTY
GSRRPSGVPDRFSGSKFGTSASLAISGLQSEDEADYYCAAWDDSLNGPAF
GGGTKLTVLGSRGGGGSGGGGSGGGGSLEMAQVQLQQWGAGLLKPSETLS
LTCAVYGGSFSGYYWSWIRQPPGKGLEWIGEINHSGSTNYNPSLKSRVTI
SVDTSKNQFSLKLSSVTAADTAVYYCARDGGGYFDYWGQGTLVTVSSTSG
QAGQHHEIREIFIGAYPYDVPDYAS [SEQ ID NO: 720]

TABLE 141

ET200-115

DNA Sequence cagtctgtgttgacgcagccgccctcagtgtctggggcccccagggcagag
ggtcaccatctcctgcactgggagcagctccaatatcggggcacgttatg
atgtacactggtaccagcaactcccaggaacagccccccgactcctcatc
tctgctaactacgatcggccctcaggggtccctgaccgattctctggctc
caagtctggcacctcagcctccctggccatcactgggctccaggctgagg
atgaggctgattattactgccagtcctatgacagcagtgtgagtgcttgg
gtgttcggcggagggaccaaggtcaccgtcctaggttctagaggtggtgg
tggtagcggcggcggcggctctggtggtggtggatccctcgagatggccg
aagtgcagctggtgcagtctgggggtgaagtgaaggagcctggggggcctca
gtgaggatctcctgccaggcatctggatacaacttcatcagttattatat
gcactgggtgcggcaggcccctgggcaaggtcttgagtggatgggcacca
tcaacccaggcagtggtgagacagactactcacagaagttgcagggcaga
gtcaccatgaccagggacccgtccagggtacattcgacatgggctgag
cagcctgacatctggggacacggccgtctattattgtgcgacaggtctca
tcagaggagctagcgatgcttttaatatctggggccggggacaatggtc
accgtctcttcaactagtggccaggccggccagcaccatcaccatcacca
tggcgcatacccgtacgacgttccggactacgcttct [SEQ ID NO:
721]

Amino Acid Sequence

QSVLTQPPSVSGAPGQRVTISCTGSSSNIGARYDVHWYQQLPGTAPRLLI
SANYDRPSGVPDRFSGSKSGTSASLAITGLQAEDEADYYCQSYDSSVSAW
VFGGGTKVTVLGSRGGGGSGGGGSGGGGSLEMAEVQLVQSGAEVKEPGAS
VRISCQASGYNFISYYMEIWVRQAPGQGLEWMGTINPGSGETDYSQKLQG
RVTMTRDPSTGTFDMGLSSLTSGDTAVYYCATGLIRGASDAFNIWGRGTM
VTVSSTSGQAGQHHIREIHHGAYPYDVPDYAS [SEQ ID NO: 722]

TABLE 142

ET200-116

DNA Sequence cagcctgtgctgactcagccaccctcagtgtccgtgtccccaggacagac
ggccgccatcccctgttctggagataagttgggggataaatttgcttcct
ggtatcagcagaagccaggccagtcccctgtgctggtcatctatcaagat
actaagcggccctcagggatccctgagcgattctctggctccaactctgg
gaacaacgcactctgaccatcagcgggacccaggctatggatgaggctg
actattactgtcagacgtgggccagcggcattgtggtgttcggcggaggg
accaagctgaccgtcctaggttctagaggtggtggtggtagcggcggcgg
cggctctggtggtggtggatccctcgagatggcccaggtacagctgcagc
agtcaggtccaggactggtgaagccctcgcagaccctctcactcacctgt
gccatctccgggacagtgtctctagcaacagtgctgcttggaactggat
caggcagtcccatcgagaggccttgagtggctgggaaggacatactaca
ggtccaagtggtataatgattatgcagtatctgtgaaaagtcgaataacc
atcaaccagacacatccaagaaccagttctccctgcagctgaactctgt
gactcccgaggacacggctgtgtattactgtgcaagagagcgcagtggct
ggaagggatttgactactggggccagggaaccctggtcaccgtctcctca
actagtggccaggccggccagcaccatcaccatcaccatggcgcataccc
gtacgacgttccggactacgcttct [SEQ ID NO: 723]

Amino Acid Sequence

QPVLTQPPSVSVSPGQTAAIPCSGDKLGDKFASWYQQKPGQSPVLVIYQD
TKRPSGIPERFSGSNSGNTATLTISGTQAMDEADYYCQTWASGIVVFGGG
TKLTVLGSRGGGGSGGGGSGGGGSLEMAQVQLQQSGPGLVKPSQTLSLTC
AISGDSVSSNSAAWNWIRQSPSRGLEWLGRTYYRSKWYNDYAVSVKSRIT
INPDTSKNQFSLQLNSVTPEDTAVYYCARERSGWKGFDYWGQGTLVTVSS
TSGQAGQHHIREIHHGAYPYDVPDYAS [SEQ ID NO: 724]

TABLE 143

ET200-117

DNA Sequence gatgttgtgatgactcagtctccaccctccctgtccgtcacccctggaga
gccggcctccatcacctgcaggtctagtcagagcctcctggaaagaaatg
catacaactacttggattggtacctgcagaggccaggacagtctccacag
ctcctgatctacttgggttctaatcgggccgccggggtccctgacaggtt TABLE 143-continued

ET200-117

```
cagtggcagtggatcaggcagagattttacactgaaaatcagcagagtgg
agcctgaggatgttggggtttattactgcatgcaagctctacaagctccg
ttcactttcggcggagggaccaaggtggagatcaaacgttctagaggtga
tggtggtagcggcggcggcggctctggtggtggtggatccctcgagatgg
ccgaagtgcagctggtgcagtctgggggaggcttggtacagcctggggggg
tccctgagactctcctgtgcagcctctggattcacctttagcagctatgc
catgagctgggtccgccaggctccagggaaggggctggagtgggtctcag
ctattagtggtagtggtggtagcacatactacgcagactccgtgaagggc
cggttcaccatctccagagacaattccaagaacacgctgtatctgcaaat
gaacagcctgagagccgaggacacggccgtatattactgtgcgaaatggg
gcccgtttcaggatgcttttgatatctggggccaagggacaatggtcacc
gtctcttcaactagtggcaggccggccagcaccatcaccatcaccatgg
cgcatacccgtacgacgttccggactacgcttct [SEQ ID NO:
725]
```

Amino Acid Sequence

```
DVVMTQSPPSLSVTPGEPASITCRSSQSLLERNAYNYLDWYLQRPGQSPQ
LLIYLGSNRAAGVPDRFSGSGSGRDFTLKISRVEPEDVGVYYCMQALQAP
FTFGGGTKVEIKRSRGGGGSGGGGSGGGGSLEMAEVQLVQSGGGLVQPGG
SLRLSCAASGFTFSSYAMSWVRQAPGKGLEWVSAISGSGGSTYYADSVKG
RFTISRDNSKNTLYLQMNSLRAEDTAVYYCAKWGPFQDAFDIWGQGTMVT
VSSTSGQAGQHHEIREIFIGAYPYDVPDYAS [SEQ ID NO: 726]
```

TABLE 144

ET200-118

DNA Sequence

```
caggctgtgctgactcagcctgcctccgtgtctgggtctcctggacagtc
gatcaccatctcctgcactggaaccagcagtgacggttggtggttataact
atgtctctggtaccaacagcacccgggcaaagccccaaactcatgatt
tatgaggtcagtaatcggccctcaggggtttctaatcgcttctctggctc
caagtctggcaacacggcctccctgaccatctctgggctccaggctgagg
acgaggctgattattactgcagctcatatacaagcagcagcaccccttat
gtcttcggacagggaccaaggtcaccgtcctaggttctagaggtggttgg
tggtagcggcggcggcggctctggtggtggtggatccctcgagatggccg
aggtgcagctggtggagtctggggggaggcttggtacagcctggcaggtcc
ctgagactctcctgtgcagcctctggattcacctttgatgattatgccat
gcactgggtccgccaagctccagggaaggggcctggagtgggtctcaggta
ttagttggaatagtggtagcataggctatgcggactctgtgaagggccga
ttcaccatctccagagacaacgccaagaactccctgtatctgcaaatgaa
cagtctgagagctgaggacacggccttgtattactgtgcaaaagccaggt
ggacagcagtggcatcagaccaccactttgactactggggccagggaacg
ctggtcaccgtctcctcaactagtggcaggccggccagcaccatcacca
tcaccatggcgcatacccgtacgacgttccggactacgcttct [SEQ
ID NO: 727]
```

Amino Acid Sequence

```
QAVLTQPASVSGSPGQSITISCTGTSSDVGGYNYVSWYQQHPGKAPKLMI
YEVSNRPSGVSNRFSGSKSGNTASLTISGLQAEDEADYYCSSYTSSSTPY
VFGAGTKVTVLGSRGGGGSGGGGSGGGGSLEMAEVQLVESGGGLVQPGRS
LRLSCAASGFTFDDYAMHWVRQAPGKGLEWVSGISWNSGSIGYADSVKGR
FTISRDNAKNSLYLQMNSLRAEDTALYYCAKARWTAVASDHHFDYWGQGT
LVTVSSTSGQAGQHFIREIHHGAYPYDVPDYAS [SEQ ID NO: 728]
```

TABLE 145

ET200-119

DNA Sequence

```
caggctgtgatactcagccaccctcagcgtctgggacccccgggcagagg
gtcaccatctcttgttctggaagcagctccaacatcggaagtaatactgt
aaaactggtaccagcagctcccaggaacggcccccaaactcctcatctata
gtaataatcagcggccctcaggggtccctgaccgattctctggctccaag
tctggcacctcagcctccctggtcatcactgggctccaggctgaggatga
ggctgattattactgtgcagcatgggatgacagcctgaatggttatgtct
tcggaactgggaccaagctgaccgtcctaggttctagaggtggttggtggt
agcggcggcggcggctctggtggtggtggatccctcgagatggccgaggt
gcagctggtgcagtctggggctgaggtgaagaagcctgggtcctcggtga
```

TABLE 145-continued

ET200-119

```
aggtctcctgcaaggcttctggaggcaccttcagcagctatgctatcagc
tgggtgcgacaggcccctggacaagggcttgagtggatgggagggatcat
ccctatctttggtacagcaaactacgcacagaagttccagggcagagtca
cgattaccggcgacgaatccacgacacagcctacatggagctgagcagc
ctgagatctgaggacacggccgtgtattactgtgcgagagattgggacta
catggacgtctgggcaaagggaccacggtcaccgtctcctcaactagtg
gccaggccggccagcaccatcaccatggcgcatacccgtacgac
gttccggactacgcttct [SEQ ID NO: 729]
```

Amino Acid Sequence

```
QAVLTQPPSASGTPGQRVTISCSGSSSNIGSNTVNWYQQLPGTAPKLLIY
SNNQRPSGVPDRFSGSKSGTSASLAISGLQSEDEADYYCAAWDDSLNGYV
FGTGTKLTVLGSRGGGGSGGGGSGGGGSLEMAEVQLVQSGAEVKKPGSSV
KVSCKASGGTFSSYAISWVRQAPGQGLEWMGGIIPIFGTANYAQKFQGRV
TITADESTSTAYMELSSLRSEDTAVYYCARDWDYMDVWGKGTTVTVSSTS
GQAGQHFIREIHHGAYPYDVPDYAS [SEQ ID NO: 730]
```

TABLE 146

ET200-120

DNA Sequence

```
tcctatgagctgactcagccaccctcagcgtctgggaccccgggcagag
ggtcaccatctcttgttctggaagcagctccaacatcggaagtaatactg
taaactggtaccagcagctcccaggaacggcccccaaactcctcatctat
agtaataatcagcggccctcaggggtccctgaccgattctctggctccaa
gtctggcacctcagcctccctggccatcagtgggctccagtctgaggatg
aggctgattattactgtgcagcatgggatgacagcctgaatggttatgtc
ttcggaactgggaccaaggtcaccgtcctaggttctagaggtggttggtgg
tagcggcggcggcggctctggtggtggtggatccctcgagatggccgagg
tgcagctggtggagtctggaggtgaagaagcctgggtcctcggtcagtg
aaggtctcctgcaaggcttctggttacacctttaccagctatgctatcag
ctgggtgcgacaggcccctggacaagggcttgagtggatgggatggatca
gcgcttacaatggtaacacaaactatgcacagaagtccagggcagagtc
accatgaccacagacacatccacgacacagcctacatggagctgaggag
cctgagatctgacgacacgccgtgtattactgtgcgagagacctatctc
ggggagctaacccgcattactactactactacggtatggacgtctgggc
caagggaccacggtcaccgtctcctcaactagtggccaggccggccagca
ccatcaccatcaccatggcgcatacccgtacgacgttccggactacgctt
ct [SEQ ID NO: 731]
```

Amino Acid Sequence

```
SYELTQPPSASGTPGQRVTISCSGSSSNIGSNTVNWYQQLPGTAPKLLIY
SNNQRPSGVPDRFSGSKSGTSASLAISGLQSEDEADYYCAAWDDSLNGYV
FGTGTKVTVLGSRGGGGSGGGGSGGGGSLEMAEVQLVESGAEVKKPGASV
KVSCKASGYTFTSYGISWVRQAPGQGLEWMGWISAYNGNTNYAQKLQGRV
TMTTDTSTSTAYMELRSLRSDDTAVYYCARDLSRGANPHYYYYYGMDVWG
QGTTVTVSSTSGQAGQHHHHHHGAYPYDVPDYAS [SEQ ID NO:
732]
```

TABLE 147

ET200-121

DNA Sequence

```
cagtctgtgttgacgcagccgccctcagtgtctggggcccccagggcagag
ggtcaccgtctcctgcactgggagcagatccaacatcggggcaggatatg
atgtacactggtaccagcaacttccaggaacagcccccaaactcctcatc
tatggaaatagtaatcggcctccaggggtccctgaccgattctctgggtc
taagtctggcacctcagcctccctggtcatcactgggctccaggctgagg
atgccgctgattattactgccagtcctatgacaacactgtgcgtgaatca
ccttatgtatcggaactgggaccaaggtcaccgtcctaggttctagaggt
ggtggtggtagcggcggcggcggctctggtggtggtggatccctcgagat
ggccgaggtccagctggtacagtctggggctgaggtgaagaagcctgggg
cctcagtgaaggtctcctgcaaggttccggatacaccctcactgaatta
tccatgcactgggtgcgacaggcctcctggaaaagggcttgagtggatggg
aggtttttgatcctgaagatggtgaaacaatctacgcacagaagttccagg
gcagagtcaccatgaccgaggacacatctacagacacagcctacatggag
ctgagcagcctgagatctgaggacacggccgtgtattactgtgcaacaga
```

TABLE 147-continued

ET200-121 gagtaatttagtgtcccggcactactactactacggtatggacgtctggg
gccaagggaccacggtcaccgtctcctcaactagtggccaggccggccag
caccatcaccatcaccatggcgcatacccgtacgacgttccggactacgc
ttct [SEQ ID NO: 733]

Amino Acid Sequence

QSVLTQPPSVSGAPGQRVTVSCTGSRSNIGAGYDVHWYQQLPGTAPKLLI
YGNSNRPPGVPDRFSGSKSGTSASLVITGLQAEDAADYYCQSYDNTVRES
PYVFGTGTKVTVLGSRGGGGSGGGGSGGGGSLEMAEVQLVQSGAEVKKPG
ASVKVSCKVSGYTLTELSMEIWVRQAPGKGLEWMGGFDPEDGETIYAQKF
QGRVTMTEDTSTDTAYMELSSLRSEDTAVYYCATESNLVSRHYYYYGMDV
WGQGTTVTVSSTSGQAGQHREITIHHGAYPYDVPDYAS [SEQ ID NO:
734]

TABLE 148

ET200-122

DNA Sequence ctgcctgtgctgactcagccaccctcagcgtctgggaccccgggcagag
ggtcaccatctcttgttctggaaccagctccaacatcggaagtaattctg
tagactggtaccagcagctcccaggaacggcccccaaactcctcatctat
agtaataatcagcggccctcaggggtccctgaccgaatctctggctccaa
gtctggcacctcagcctccctggccatcagtgggctccagtctgaggatg
aggctgattattactgtgcagcatgggatgacagcctgaatggttatgtc
ttcggaactgggaccaaggtcaccgtcctaggttctagaggtggtggtgg
tagcggcggcggcggctctggtggtggtggatccctcgagatggccgaag
tgcagctggtgcagtctggggctgaggtgaagaagcctggggcctcagtg
aaggtctcctgcaaggcttctggatacacccttcaccggctactatatgca
ctgggtgcgacaggcccctggacaagggcttgagtggatgggatggatca
accctaacagtggtggcacaaactatgcacagaagtttcagggcagggtc
accatgaccagggacacgtccatcagcacagcctacatggagctgagcag
gctgagatctgacgacacgccgtgtattactgtgcgagagattacggat
actatggttcggggagttattcgagcggccccctttactactactacggt
atggacgtctggggccaagggaccacggtcaccgtctcctcaactagtgg
ccaggccggccagcaccatcaccatcaccatggcgcatacccgtacgacg
ttccggactacgcttct [SEQ ID NO: 735]

Amino Acid Sequence

LPVLTQPPSASGTPGQRVTISCSGTSSNIGSNSVDWYQQLPGTAPKWYSN
NQRPSGVPDRISGSKSGTSASLAISGLQSEDEADYYCAAWDDSLNGYVFG
TGTKVTVLGSRGGGGSGGGGSGGGGSLEMAEVQLVQSGAEVKKPGASVKV
SCKASGYTFTGYYMHWVRQAPGQGLEWMGWINPNSGGTNYAQKFQGRVTM
TRDTSISTAYMELSRLRSDDTAVYYCARDYGYYGSGSYSSGPLYYYYGMD
VWGQGTTVTVSSTSGQAGQHHHHHHGAYPYDVPDYAS [SEQ ID NO:
736]

TABLE 149

ET200-123

DNA Sequence caggctgtgctgactcagccaccctcagcgtctgggaccccgggcagag
ggtcaccatctcttgttctggaagcagctccaacatcggaagtaatactg
taaactggtaccagcagctcccaggaacggcccccaaactcctcatgtat
aataatgatcagcggccctcaggggtccctgaccgattctctggctccaa
gtctggcacctcagcctccctggccatcagtgggctccagtctgaggatg
aggctgattattactgtgcagcatgggatgacagcctcaatggttatgtc
ttcggacctgggaccaaggtcaccgtcctaggttctagaggtggtggtgg
tagcggcggcggcggctctggtggtggtggatccctcgagatggcccagg
tgcagctggtggagtctggagctgaggtgaagaagcctggggcctcagtg
aaggtctcctgcaaggcttctggttacacctttaccaactatggtatcag
ctgggtgcgacaggcccctggacaagggcttgagtggatgggatggatca
gcgcttacaatggtaacacaaactatgcacatcagaagctccagggcagagtc
accatgaccacagacacatccacgagcacagcctacatggagctgaggag
cctgagatctgacgacacggccgtgtattactgtgcgagagaccctatctc TABLE 149-continued

ET200-123 ggggagctaacccgcattactactactacggtatggacgtctggggc
caagggaccacggtcaccgtctcctcaactagtggccaggccggccagca
ccatcaccatcaccatggcgcatacccgtacgacgttccggactacgctt
ct [SEQ ID NO: 737]

Amino Acid Sequence

QAVLTQPPSASGTPGQRVTISCSGSSSNIGSNTVNWYQQLPGTAPKLLMY
NNDQRPSGVPDRFSGSKSGTSASLAISGLQSEDEADYYCAAWDDSLNGYV
FGPGTKVTVLGSRGGGGSGGGGSGGGGSLEMAQVQLVESGAEVKKPGASV
KVSCKASGYTFTSYGISWVRQAPGQGLEWMGWISAYNGNTNYAQKLQGRV
TMTTDTSTSTAYMELRSLRSDDTAVYYCARDLSRGANPHYYYYYGMDVWG
QGTTVTVSSTSGQAGQHREITIHHGAYPYDVPDYAS [SEQ ID NO:
738]

TABLE 150

ET200-125

DNA Sequence aattttatgctgactcagccccacgctgtgtcggagtctccggggaagac
ggtaaccatctcctgcacccgcagcagtggcagtattgccagcaactatg
tgcagtggtaccagcagcgcccgggcagttccccccgcactgtgatttat
gaggataatcaaagaccctctgggggtcctggtcggttctctggctccat
cgacagctcctccaactctgcctccctcaccatctctggactgaagactg
aggacgaggctgactactactgtcagtcttatgattccaccagtgtgctt
ttcggcggagggaccaagctgaccgtcctaggttctagaggtggtggtgg
tagcggcggcggcggctctggtggtggtggatccctcgagatggccgagg
tccagctggtgcagtctggggctgaggtgaagaagccagggtcctcggtg
aaggtctcctgcaaggcctcggggaggcacctt cagcagcaattctctcag
ctgggtgcgacaggcccctggacaagggctgagtggatgggaaggatct
tccctatcctgggtataacaaactatgcacagaagtccagggcagagtc
acgattaccgcggacaaatccacgagcacagcctacatggagctgagcag
cctgagatctgaggacacggccgtctattactgtgcgagaggaaactacc
aatggtatgatgctttttgatatctggggccaagggacaatggtcaccgtc
tcttcaactagtggccaggccggccagcaccatcaccatcaccatggcgc
atacccgtacgacgttccggactacgcttct [SEQ ID NO: 739]

Amino Acid Sequence

NFMLTQPHAVSESPGKTVTISCTRSSGSIASNYVQWYQQRPGSSPRTVIY
EDNQRPSGVPGRFSGSIDSSSNSASLTISGLKTEDEADYYCQSYDSTSVL
FGGGTKLTVLGSRGGGGSGGGGSGGGGSLEMAEVQLVQSGAEVKKPGSSV
KVSCKASGGTFSSNSLSWVRQAPGQGLEWMGRIFPILGITNYAQKFQGRV
TITADKSTSTAYMELSSLRSEDTAVYYCARGNYQWYDAFDIWGQGTMVTV
SSTSGQAGQHFIREIHHGAYPYDVPDYAS [SEQ ID NO: 740]

TABLE 151

ET200-005

DNA Sequence cagcctgtgctgactcagccaccctcagtgtcagtggtcccaggaaagac
ggccaggattacctgtgggggaaaaaacattggaagtaaaagtgtgcact
ggtaccagcagaagccaggccaggccctgtggtggtcatccattatgat
agtgaccggccctcagggatccctgagcgattctctggctccaactctgg
gaacacggccaccctgaccatcagcagggtcgaagccggggatgaggccg
actattactgtcaggtgtgggatagtagtagtgatcatccttatgtcttc
ggaactgggaccaaggtcaccgtcctaggttctagaggtggtggtggtag
cggcggcggcggctctggtggtggtggatccctcgagatggcccaggtgc
agctggtgcagtctggggctgaggtgaagaagcctggggcctcagtgaag
gtctcctgcaaggtctcttggttacacctttaccaactatggtatcagctg
ggtgcgacaggcccctggacaagggcttgagtggatgggatggatcagcg
cttacaatggtaacacaaactatgcacatcagaagctccagggcagagtcacc
atgaccacagacacatccacgagcacagcctacatggagctgaggagc
gagacctgacgacacgccgtgtattactgtgcgcgctatacttcggttc
tcatgattactggggtcaaggtactctggtgaccgtctcctcaactagtg
gccaggccggccagcaccatcaccatcaccatggcgcatacccgtacgac
gttccggactacgcttct [SEQ ID NO: 741]

TABLE 151-continued

ET200-005

Amino Acid Sequence

QPVLTQPPSVSVVPGKTARITCGGKNIGSKSVHWYQQKPGQAPVVVIHYD
SDRPSGIPERFSGSNSGNTATLTISRVEAGDEADYYCQVWDSSSDHPYVF
GTGTKVTVLGSRGGGGSGGGGSGGGGSLEMAQVQLVQSGAEVKKPGASVK
VSCKASGYTFTNYGISWVRQAPGQGLEWMGWISAYNGNTNYAHKLQGRVT
MTTDTSTSTANMELRSLRPDDTAVYYCARSYFGSHDYWGQGTLVTVSSTS
GQAGQHHHHHHGAYPYDVPDYAS [SEQ ID NO: 742]

TABLE 152

ET200-124

DNA Sequence tcctatgtgctgactcagccaccctcggtgtcagtggcccccaggaaagac
ggccaggatttcctgtgggggaaacgacattggaagtaaaagtgttttct
ggtatcagcagaggccaggccaggcccctgtgttggtcgtctatgatgat
agcgaccggccctcagggctccctgagcgattctctggcttcaactctgg
gaacaggccaccctgaccatcagcagggtcgaagccggggatgaggccg
actattactgtcaagtgtgggatagtagtagtgatcattatgtatcggaa
ctgggaccaaggtcaccgtcctaggttctagaggtggtggtggtagcggc
ggcggcggctctggtggtggtggatccctcgagatggcccaggtcagct
ggtggagtctggggggaggcttggtacagcctggcaggtccctgagactct
cctgtgcagcctctggattcacctttgatgattatgccatgcactgggtc
cggcaagctccagggaagggcctggagtgggtctcaggtattagttggaa
tagtggtagcataggctatgcggactctgtgaaagggccgattcaccatct
ccagagacaacgccaagaactccctgtatctgcaaatgaacagtctgaga
gctgaggacacggccttgtattactgtgcaaaagatataacctatggttc
ggggagttatggtgatttgatatctgggcaagggacaatggtcaccgt
ctcttcaactagtggcaggccggccagcaccatcaccatcaccatggcg
catacccgtacgacgttccggactacgcttct [SEQ ID NO: 743]

Amino Acid Sequence

SYVLTQPPSVSVAPGKTARISCGGNDIGSKSVFWYQQRPGQAPVLVVYDD
SDRPSGLPERFSGFNSGNTATLTISRVEAGDEADYYCQVWDSSSDHYVFG
TGTKVTVLGSRGGGGSGGGGSGGGGSLEMAQVQLVESGGGLVQPGRSLRL
SCAASGFTFDDYAMHWVRQAPGKGLEWVSGISWNSGSIGYADSVKGRFTI
SRDNAKNSLYLQMNSLRAEDTALYYCAKDITYGSGSYGAFDIWGQGTMVT
VSSTSGQAGQHHHHHHGAYPYDVPDYAS [SEQ ID NO: 744]

Exemplary Anti-FcRL5 Antibodies Comprising a Heavy Chain Variable Region, a Light Chain Variable Region, a Linker Peptide and a His-Tag and HA-Tag

TABLE 153

ET200-001

DNA Sequence

Cagtctgtgttgacgcagccaccctcagcgtctgggacccccgggcagag
ggtcaccatctcttgttctggaagcagctccaacatcggaagtaatactg
taaactggtaccagcagctcccaggaacggccccaaactcctcatctat
agtaataatcagcggccctcaggggtccctgaccgattctctggctccaa
gtctggcacctcagcctccctggccatcagtgggctccagtctgaggatg
aggctgattattactgtgcagcatgggatgacagcctgaatggttatgtc
ttcggaactgggaccaaggtcaccgtcctaggttctagaggtggtggtgg
tagcggcggcggcggctctggtggtggtggatccctcgagatggcccagg
tgcagctacagcagtggggcgcaggactgttgaagcctcgggagaccctg
tccctcacctcgcctgtgtatggtgggtcttcagtggttactactggag
ctggatccgccagcccccagggaagggggctggagtggattgggaaatca
atcatagtggaagcaccaactacaacccgtccctcaagagtcgagtcacc
atatcagtagacacgtccaagaaccagttctccctgaagctgagctctgt
gaccgccgcggacacggccgtgtattactgtgcgcgcgaaggtccgtacg
acggtttcgattcttggggtcaaggtactctggtgaccgtctcctcaact
agtggcaggccggccagcaccatcaccatcaccatggcgcatacccgta
cgacgttccggactacgcttct [SEQ ID NO: 745]

TABLE 153-continued

ET200-001

Amino Acid Sequence

QSVLTQPPSASGTPGQRVTISCSGSSSNIGSNTVNWYQQLPGTAPKLLIY
SNNQRPSGVPDRFSGSKSGTSASLAISGLQSEDEADYYCAAWDDSLNGYV
FGTGTKVTVLGSRGGGGSGGGGSGGGGSLEMAQVQLQQWGAGLLKPSETL
SLTCAVYGGSFSGYYWSWIRQPPGKGLEWIGEINHSGSTNYNPSLKSRVT
ISVDTSKNQFSLKLSSVTAADTAVYYCAREGPYDGFDSWGQGTLVTVSST
SGQAGQHHHEIHHGAYPYDVPDYAS [SEQ ID NO: 746]

TABLE 154

ET200-002

DNA Sequence

Aattttatgctgactcagccccactctgtgteggagtctccggggaagac
ggtaaccatctcctgcacccgcagcagtggcagcattgccagcaactatg
tgcagtggtaccagcagcgcccgggcagtgcccccaccactgtgatctat
gaggataaccaaagaccctctggggtccctgatcggttctctggctccat
cgacagctcctccaactctgcctccctcaccatctctggactgaagactg
aggacgaggctgactactactgtcagtcttatgatagcagcaattctgtg
gtattcggcggagggaccaagctgaccgtcctaggttctagaggtggtgg
tggtagcggcggcggcggctctggtggtggtggatccctcgagatggccc
aggtccagctggtacagtctggcactgaggtgaagaagcctggggcctca
gtgagggtcgcctgcaaggcttctggttacccattaacaaatatgacatc
aactgggtgcgacaggccctggacaagggcttgagtggatgggaggcat
catccctatctttcgtacaacaaactacgcacagaagttccagggcagag
tcacgattaccgcggacgaatccacgagcacagcctacatggagctgagc
agcctgagatctgaggacacggccgtatattactgtgcgcgcgaatggtt
ctactgggatatctgggtcaaggtactctggtgaccgtctcctcaacta
gtggccaggccggccagcaccatcaccatggcgcatacccgtac
gacgttccggactacgcttct [SEQ ID NO: 747]

Amino Acid Sequence

NFMLTQPHSVSESPGKTVTISCTRSSGSIASNYVQWYQQRPGSAPTTVIY
EDNQRPSGVPDRFSGSIDSSSNSASLTISGLKTEDEADYYCQSYDSSNSV
VFGGGTKLTVLGSRGGGGSGGGGSGGGGSLEMAQVQLVQSGTEVKKPGAS
VRVACKASGYPFNKYDINWVRQAPGQGLEWMGGIIPIFRTTNYAQKFQGR
VTITADESTSTAYMELSSLRSEDTAVYYCAREWFYWDIWGQGTLVTVSST
SGQAGQHFIREIHHGAYPYDVPDYAS [SEQ ID NO: 748]

TABLE 155

ET200-003

DNA Sequence

Cagtctgtgttgactcagccaccctcagtgtccgtgtccccaggacagac
agccagcatctcctgctctggaaataaattggggactaagtatgtttact
ggtatcagaagaggccaggccagtcccctgtgttggtcatgtatgaagat
aatcagcggccctcagggatcccggagcggttctctggctccaactctgg
gaacacagccactctgaccatcagagggacccagactgtggatgaggctg
actattactgtcaggcgtgggactccgacactttcgtggtcttcggcgga
gggaccaaggtcaccgtcctaggttctagaggtggtggtggtagcggcgg
cggcggctctggtggtggtggatccctcgagatggccgaggtgcagctgg
tggagaccggggggaggcgtggtccagcctgggaggtccctgagactctcc
tgtgcagcctctggattcacctttcagtagttatggcatgcactgggtccg
ccaggctccaggcaaggggctggagtggggcagttatatcacatgatg
gaagtaataaatactacgcagactccgtgaagggccgattcaccatctcc
agagacaattccaaggacacgctgtatctgcaaatgaacagcctgagagg
tgaggacacggccgtatattactgtgcgcgctctaaccagtggtctggtt
acttctcttcgattactggggtcaaggtactctggtgaccgtctcctca
actagtggccaggccggccagcaccatcaccatcaccatggcgcataccc
gtacgacgttccggactacgcttct [SEQ ID NO: 749]

Amino Acid Sequence

QSVLTQPPSVSVSPGQTASISCSGNKLGTKYVWYQKRPGQSPVLVMYEDN
QRPSGIPERFSGSNSGNTATLTIRGTQTVDEADYYCQAWDSDTFVVFGGG
TKVTVLGSRGGGGSGGGGSGGGGSLEMAEVQLVETGGGVVQPGRSLRLSC

TABLE 155-continued

ET200-003

AASGFTFSSYGMHWVRQAPGKGLEWVAVISHDGSNKYYADSVKGRFTISR
DNSKDTLYLQMNSLRGEDTAVYYCARSNQWSGYFSFDYWGQGTLVTVSST
SGQAGQHHHHHHGAYPYDVPDYAS[SEQ ID NO: 750]

TABLE 156

ET200-006

DNA Sequence

Tcctatgtgctgactcagccaccctcagtgtcagtggccccaggaaagac
ggccaggattacctgtgggggaaacaacattggaagtaaaactgtgcact
ggtaccagcagaagccaggccaggcccctgtggtggtcatccattatgat
agcgaccggccctcagggatccctgagcgattctctggctccaactctgg
aacacggcaccctgaccatcagcagggtcgaagccggggatgaggccg
actattactgtcaggtgtgggatagtagtagtgatcatccttatgtcttc
ggaactgggaccaaggtcaccgtcctaggttctagaggtggtggtggtag
cggcggcggcggctctggtggtggtggatccctcgagatggcccaggtgc
agctggtgcagtctggagctgaggtgaagaagcctggggcctcagtgaag
gtctcctgcaaggcttctggttacacctttaccacctatggtatcagctg
ggtgcgacaggcccctggacaagggcttgagtggatgggatggatcaaca
cttacaatggtcacacaaactatgcacagaagctccagggcagagccaca
atgaccgcagacacatccacgaacacagcctacatggagctgaggagcct
gagatctgacgacactgccgtgtattactgtgcgcgcgttatctacggtt
ctggtgattactgggtcaaggtactctggtgaccgtctcctcaactagt
ggccaggccggccagcaccatcaccatcaccatggcgcatacccgtacga
cgttccggactacgcttct [SEQ ID NO: 751]

Amino Acid Sequence

SYVLTQPPSVSVAPGKTARITCGGNNIGSKSVHWYQQKPGQAPVVVIHYD
SDRPSGIPERFSGSNSGNTATLTISRVEAGDEADYYCQVWDSSSDHPYVF
GTGTKVTVLGSRGGGGSGGGGSGGGGSLEMAEVQLVQSGAEVKKPGASVK
VSCKASGYTFTTYGISWVRQAPGQGLEWMGWINTYNGHTNYAQKLQGRAT
MTADTSTNTAYMELRSLRSDDTAVYYCARVIYGSGDYWGQGTLVTVSSTS
GQAGQHHHHHHGAYPYDVPDYAS[SEQ ID NO: 752]

TABLE 157

ET200-007

DNA Sequence

Tcctatgtgctgactcagccactctcagtgtcagtggccccaggaaagac
ggccaggattacctgtgggggaaacaacattggaagtaaaactgtgcact
ggtaccagcagaagccaggccaggcccctgtgctggtcatctattatgat
agcgaccggccctcagggatccctgagcgattctctggctccaactctgg
aacacggcaccctgaccatcagcagggtcgaagccggggatgaggccg
actattactgtcaggtgtgggatagtagtagtgatcatccgggtgttcggc
ggaggaccaaggtcgaccgtcctaggttctagaggtggtggtagcgg
cggcggcggctctggtggtggtggatccctcgagatggcccaggtgcagc
tgcaggagtcgggcccaggactggtgaagccttcggagaccctgtccctc
acctgcaatgtctctggttactccatcagcagtggttacttttggggctg
gatccggcagcccccaggaagggggctggagtggattgggagtatctatc
atagtaggagcacctactacaacccgtccctcaagagtcgagtcaccata
tcagtagacacgtccaagaaccagttctccctgaagctgaactctgtgac
cgccgcagacacggccgtgtattactgtgcgcgcggttacggttacttcg
attactggggtcaaggtactctggtgaccgtctcctcaactagtggccag
gccggccagcaccatcaccatcaccatggcgcatacccgtacgacgttcc
ggactacgcttct [SEQ ID NO: 753]

Amino Acid Sequence

SYVLTQPLSVSVAPGKTARITCGGNNIGSKTVHWYQQKPGQAPVLVIYYD
SDRPSGIPERFSGSNSGNTATLTISRVEAGDEADYYCQVWDSSSDHRVFG
GGTKLTVLGSRGGGGSGGGGSGGGGSLEMAQVQLQESGPGLVKPSETLSL

TABLE 157-continued

ET200-007

TCNVSGYSISSGYFWGWIRQPPGKGLEWIGSIYHSRSTYYNPSLKSRVTI
SVDTSKNQFSLKLNSVTAADTAVYYCARGYGYFDYWGQGTLVTVSSTSGQ
AGQHHHHHHGAYPYDVPDYAS[SEQ ID NO: 754]

TABLE 158

ET200-008

DNA Sequence

Caatctgccctgactcagcctgcctccgtgtctgggtctcctggacagtc
gatcaccatctcctgcactggaaccagcagtgacgttggtggttataact
atgtctcctggtaccaacaacacccaggcaaagcccccaaactcatgatt
tatgatgtcagtaatcggccctcagggtttctaatcgcttctctggctc
caagtctggcaacacggcctccctgaccatctctgggctccaggctgagg
acgaggctgattattactgcagctcatatacaagcagcagcacttcgaag
gtgttcggcggagggaccaagctgaccgtcctaggttctagaggtggtgg
tggtagcggcggcggcggctctggtggtggtggatccctcgagatggccc
aggtgcagctggtggagtctgggggaggtggtacggcctgggggggtcc
ctgagactctcctgtgcagcctctggattcacctttggtgattatggcat
gagctgggtccgccaagctccagggaaggggctggagtgggtctctggta
ttaattggaatggtggtagcacaggttatgcagactctgtgaagggccga
ttcaccatctccagagacaacgccaagaactccctgtatctgcaaatgaa
cagtctgagagccgaggacacgccgtatattactgtgcgcgctctaaat
acaacttccatgtttactacgattactgggggtcaaggtactctggtgacc
gtctcctcaactagtggccaggccggccagcaccatcaccatcaccatgg
cgcatacccgtacgacgttccggactacgcttct [SEQ ID NO:
755]

Amino Acid Sequence

QSALTQPASVSGSPGQSITISCTGTSSDVGGYNYVSWYQQHPGKAPKLMI
YDVSNRPSGVSNRFSGSKSGNTASLTISGLQAEDEADYYCSSYTSSSTSK
VFGGGTKLTVLGSRGGGGSGGGGSGGGGSLEMAEVQLVESGGGVVRPGGS
LRLSCAASGFTFGDYGMSWVRQAPGKGLEWVSGINWNGGSTGYADSVKGR
FTISRDNAKNSLYLQMNSLRAEDTAVYYCARSKYNFHVYYDYWGQGTLVT
VSSTSGQAGQHHHHHHGAYPYDVPDYAS[SEQ ID NO: 756]

TABLE 159

ET200-009

DNA Sequence

Cagtctgtgttgacgcagccaccctcagcgtctgggaccccgggcagac
agtcaccatctcttgttctggaagcaactccaacatcggaagtaattatg
tatactggtaccagcagctcccaggaacggcccccaaactcctcatctat
aggaataatcagcggccctcaggggtccctgaccgattctcaggctccaa
gtctggcacctcagcctccctggccatcagtgggctccgctccgaggatg
aggctgattattactgtgcagctgggatgacagcctgagtggtgcttatgtc
ttcggaactgggaccaaggtcaccgtcctaggttctagaggtggtggtag
tagcggcggcggcggctctggtggtggtggatccctcgagatggcccagg
tgcagctggtgcagtctggagctgaggtgaagaagcctggggcctcagtg
aaggtctcctgcaaggcttctggttacacctttaccagctatggtatcag
ctgggtgcgacaggcccctggacaagggcttgagtggatgggatggatca
gcgcttacaatggtaacacaaactatgcacagaagctccagggcagagtc
accatgaccacagacacatccacgagcacagcctacatggagctgaggag
cctgagatctgacgacactgccgtgtattactgtgcgcgctcttctggta
acatggtttcttggaagatatgtggggtcaaggtactctggtgaccgtc
tcctcaactagtggccaggccggccagcaccatcaccatcaccatggcgc
atacccgtacgacgttccggactacgcttct [SEQ ID NO: 757]

Amino Acid Sequence

QSVLTQPPSASGTPGQTVTISCSGSNSNIGSNYVYWYQQLPGTAPKLLIY
RNNQRPSGVPDRFSGSKSGTSASLAISGLRSEDEADYYCAAWDDSLSAYV
FGTGTKVTVLGSRGGGGSGGGGSGGGGSLEMAQVQLVQSGAEVKKPGASV
KVSCKASGYTFTSYGISWVRQAPGQGLEWMGWISAYNGNTNYAQKLQGRV
TMTTDTSTSTAYMELRSLRSDDTAVYYCARSSGNMVSWKDMWGQGTLVTV
SSTSGQAGQHHHHHHGAYPYDVPDYAS[SEQ ID NO: 758]

TABLE 160

ET200-010

DNA Sequence

Caatctgccctgactcagcctgcctccgtgtctgggtctcctggacagtc
gatcaccatctcctgcactggaaccagcagtgacgttggtggttataact
ctgtctcctggtaccaacaacacccaggcaaagcccccagactcatgatt
tatgatgtcagtaatcggccctcaggggtttctaatcgcttctctggctc
caagtctggcaacacggcctccctgaccatctctgggctccaggctgagg
acgaggctgattattactgcagctcatatacaagcagcagcaccccttta
gtcttcggaactgggaccaaggtcaccgtcctaggttctagaggtggtgg
tggtagcggcggcggcggctctggtggtggtggatccctcgagatggccc
aggtgcagctggtgcagtctgggggtgaggtgaagaagcctggggcctca
gtgaaggtctcctgcaaggcttctggttacacctttaccagctatggtat
cagctgggtgcgacaggcccctggacaagggcttgagtggatgggatgga
tcagcgcttacaatggtaacacaaactatgcacagaagctccagggcaga
gtcaccatgaccacagacacatccacgagcacagcctacatggagctgag
gagcctgagatctgacgacacggccgtgtattactgtgcgcgcggtgctg
ttgcttaccatgattggggtcaaggtactctggtgaccgtctcctcaact
agtggccaggccggccagcaccatcaccatcaccatggcgcatacccgta
cgacgttccggactacgcttct [SEQ ID NO: 759]

Amino Acid Sequence

QSALTQPASVSGSPGQSITISCTGTSSDVGGYNSVSWYQQHPGKAPRLMI
YDVSNRPSGVSNRFSGSKSGNTASLTISGLQAEDEADYYCSSYTSSSTPL
VFGTGTKVTVLGSRGGGGSGGGGSGGGGSLEMAQVQLVQSGAEVKKPGAS
VKVSCKASGYTFTSYGISWVRQAPGQGLEWMGWISAYNGNTNYAQKLQGR
VTMTTDTSTSTAYMELRSLRSDDTAVYYCARGAVAYHDWGQGTLVTVSST
SGQAGQHHHHHGAYPYDVPDYAS[SEQ ID NO: 760]

TABLE 161

ET200-011

DNA Sequence

Cagtctgtcgtgacgcagccgccctcagtgtctgcggccccaggacagag
ggtcaccatctcctgctctggaagcagctccaacatttcgatttatgatg
tatcctggtatcagcagcttcccaggaacagcccccaaactcctcatttat
ggcaataataagcgaccctcggggattgctgaccgattctctggctccac
gtctggcacgtcagccaccctgggcatcaccggactccagactgggggacg
aggccgattattactgcgggaacatgggatgacagcctgggggtcgatcatcaa
ttcggcggagggaccaagctgaccgtcctaggttctagaggtggtggtgg
tagcggcggcggcggctctggtggtggtggatccctcgagatggcccaga
tgcagctggtgcaatctgggctgaggtgaagaagcctgggtcctcggtg
aaggtctcctgcgaggcttctggagcaccctcagcagctatgctatcaa
ctgggtgcgacaggcccctggacaagggcttgagtggatgggagggatca
tccctatgtttggtacagcacactacgcacagaagttccagggcagagtc
acgattaccgcggacgaatccacgaaaacagcctacatggagctgagcag
cctgagatctgaggacactgccgtgtattactgtgcgcgcggtgttcatt
acgcttctttcgatcattggggtcaaggtactctggtgaccgtctcctca
actagtggccaggccggccagcaccatcaccatcaccatggcgcataccc
gtacgacgttccggactacgcttct [SEQ ID NO: 761]

Amino Acid Sequence

QSVVTQPPSVSAAPGQRVTISCSGSSSNISIYDVSWYQQLPGTAPKLLIY
GNNKRPSGIADRFSGSTSGTSATLGITGLQTGDEADYYCGTWDDSLSGGV
FGGGTKLTVLGSRGGGGSGGGGSGGGGSLEMAQMQLVQSGAEVKKPGSSV
KVSCEASGGTLSSYAINWVRQAPGQGLEWMGGIIPMFGTAHYAQKFQGRV
TITADESTKTAYMELSSLRSEDTAVYYCARGVHYASFDHWGQGTLVTVSS
TSGQAGQHHHHHGAYPYDVPDYAS[SEQ ID NO: 762]

TABLE 162

ET200-012

DNA Sequence

Cagtctgtcgttgacgcagccgccctcagtgtctgcggccgcaggacagaa
ggtcaccatctcctgctctggaagcgactccaacattgggaataattatg
tgtcctggtatcaacacctcccagggacagcccccaaactcctcatttat
gacgttaaaaatcgaccctcagggattcctgaccggttctccggctccaa
gtctggctcgtcagccaccctaggcatcgccggactccagcctggggacg

TABLE 162-continued

ET200-012 aggccgattattactgcgggaacatgggacagtcggctggatgcctatgtc
ttcggaactgggaccaaggtcaccgtcctaggttctagaggtggtggtgg
tagcggcggcggcggctctggtggtggtggtggatccctcgagatggcccaga
tgcagctggtgcaatctggagctgaggtgaagaagcctggggcctcagtg
aaggtctcctgcaagacttctggtttcccctttaatatctcttggaatcac
ctgggtgcgacaggcccctggacaagggcttgagtggatgggatggatca
gcggttacaacggtaacacagactacccacagaagttccagggcagagtc
accatgtccacagacacatccacgagtacagcctacatggagctgaggaa
cctgaaatctgacgacacggccgtgtattactgtgcgcgcggtgatacgg
tggtatggatacttggggtcaaggtactctggtgaccgtctcctcaacta
gtggccaggccggccagcaccatcaccatcaccatggcgcatacccgtac
gacgttccggactacgcttct [SEQ ID NO: 763]

Amino Acid Sequence

QSVLTQPPSVSAAAGQKVTISCSGSDSNIGNNYVSWYQHLPGTAPKLLIY
DVKNRPSGIPDRFSGSKSGSSATLGIAGLQPGDEADYYCGTWDSRLDAYV
FGTGTKVTVLGSRGGGGSGGGGSGGGGSLEMAQMQLVQSGAEVKKPGASV
KVSCKTSGFPFNIFGITWVRQAPGQGLEWMGWISGYNGNTDYPQKFQGRV
TMSTDTSTSTAYMELRNLKSDDTAVYYCARGAYGGMDTWGQGTLVTVSST
SGQAGQHHHHHGAYPYDVPDYAS [SEQ ID NO: 764]

TABLE 163

ET200-013

DNA Sequence

Cagtctgtcgtgacgcagccgccctcagtgtctggggcccccagggcagag
ggtcaccatctcctgcactgggagcacctccaacatcggggcaggttatg
atgtacactggtatcagcagcttccaggaacagcccccaaactcctcatc
tatactaacaactttcggccctcaggggtccctgaccgattctctgcctc
caagtctggcacttcagcttccctggccatcactggtctccaggctgagg
atgaggctgattattactgcgggaacatgggatagcagcctgagtgccgtt
gtgttcggcggagggaccaagctgaccgtcctaggttctagaggtggtgg
tggtagcggcggcggcggctctggtggtggtggatccctcgagatggccg
aggtgcagctggtggagtctgggggaggtgaagaagcctggggcctcggtg
gtgaaagtctcctgcaaggcttctggttacatgtttaccagttatggtct
caactgggtgcgacaggcccctggacaagggcttgagtggatgggatgga
tcagcgctaacaatggtaagacaaattatgctaagaaattccaggacaga
gtcaccatgaccagagacacttccacgagcacagcctacatggaactgag
gagcctgagatctgacgacacggccgtatattactgtgcgcgccatatcg
gtgttcttacttcgatcgttgggtcaaggtactctggtgaccgtctcc
tcaactagtggccaggccggccagcaccatcaccatcaccatggcgcata
cccgtacgacgttccggactacgcttct [SEQ ID NO: 765]

Amino Acid Sequence

QSVVTQPPSVSGAPGQRVTISCTGSTSNIGAGYDVHWYQQLPGTAPKLLI
YTNNFRPSGVPDRFSASKSGTSASLAITGLQAEDEADYYCGTWDSSLSAV
VFGGGTKLTVLGSRGGGGSGGGGSGGGGSLEMAEVQLVESGTEVKKPGAS
VKVSCKASGYMFTSYGLNWVRQAPGQGLEWMGWISANNGKTNYAKKFQDR
VTMTRDTSTSTGYMELRSLRSDDTAVYYCARHIGGSYFDRWGQGTLVTVS
STSGQAGQHHHHHGAYPYDVPDYAS [SEQ ID NO: 766]

TABLE 164

ET200-014

DNA Sequence

Tcctatgtgctgactcagccaccctcagtgtcagtggccccaggaaagac
ggccaggattacctgtgggggaaacaacattggaagtaaaagtgtgcact
ggtaccagcagaagccaggccaggcccctgtgctggtcatctattatgat
agcgaccggccctcagggatccctgagcgattctctggctccaactctgg
gaacacggccaccctgaccatcagcagggtcgaagccggggatgaggccg
actattactgtcaggtgtgggatagtagtagtgatcattatgtcttcgga
actgggaccaaggtcaccgtcctaggttctagaggtggtggtggtagcgg
cggcggcggctctggtggtggtggatccctcgagatggcggaggtgcagc
tggtggagactggggaggcttggtacagccgggggtccctgagactc
tcctgtgcagcctctggattcacctttagcagctatgccatgagctgggt
ccgccaggctccagggaaggggctggagtgggtctcagctattagtggta
gtgatggtagcacatactacgcagactccgtgaagggccggttcaccatc

TABLE 164-continued

ET200-014

```
tccagagacaattccaagaacacgctgtatctgcaaatgaacagcctgag
agacgaggacacggccgtatattactgtgcgcgctctcatgaagctaacc
tggttggtgattggtggggtcaaggtactctggtgaccgtctcctcaact
agtggccaggccggccagcaccatcaccatcaccatggcgcatacccgta
cgacgttccggactacgcttct [SEQ ID NO: 767]
```

Amino Acid Sequence

```
SYVLTQPPSVSVAPGKTARITCGGNNIGSKSVHWYQQKPGQAPVLVIYYD
SDRPSGIPERFSGSNSGNTATLTISRVEAGDEADYYCQVWDSSSDHYVFG
TGTKVTVLGSRGGGGSGGGGSGGGGSLEMAEVQLVETGGGLVQPGGSLRL
SCAASGFTFSSYAMSWVRQAPGKGLEWVSAISGSDGSTYYADSVKGRETI
SRDNSKNTLYLQMNSLRDEDTAVYYCARSHEANLVGDWWGQGTLVTVSST
SGQAGQHHHHHHGAYPYDVPDYAS [SEQ ID NO: 768]
```

TABLE 165

ET200-015

DNA Sequence

```
Cagtctgtggtgactcagccaccctcagtgtcagtggccccaggaaagac
ggccaggattacctgtggggggaaacaacattggaagtaaaagtgtgcact
ggtaccagcagaagccaggccaggcccctgtgctggtcatctattatgat
agcgaccggccctcagggatccctgagcgattctctggctccaactctgg
gaacacggccaccctgaccatcagcagggtcgaagccgggggatgaggccg
actattactgtcaggtgtgggatagtagtagtgatgtgattcggcgga
gggaccaagctgaccgtcctaggttctagaggtggtggtggtagcggcgg
cggcggctctggtggtggtggatccctcgagatggccgaggtccagctgg
tacagtctggagctgaggtgaagaagcctggggcctcagtgaaggtctcc
tgcaaggcttctggttacacctttaccagctacgtatcagctgggtgcg
acaggcccctggacaagggcttgagtggatgggatggatcagcgcttaca
atggtaacacaaactatgcacagaagtccagggcagagtcaccatgacc
acagacacatccacgagcacagcctacatggagctgaggagcctgagatc
tgacgacaggccgtgtattactgtgcgcgctggggtggtttcggtgctg
ttgatcattggggtcaaggtactctggtgaccgtctcctcaactagtggc
caggccggccagcaccatcaccatcaccatggcgcatacccgtacgacgt
tccggactacgcttct [SEQ ID NO: 769]
```

Amino Acid Sequence

```
QSVVTQPPSVSVAPGKTARITCGGNNIGSKSVHWYQQKPGQAPVLVIYYD
SDRPSGIPERFSGSNSGNTATLTISRVEAGDEADYYCQVWDSSSDVVFG
GTKLTVLGSRGGGGSGGGGSGGGGSLEMAEVQLVQSGAEVKKPGASVKVS
CKASGYTFTSYGISWVRQAPGQGLEWMGWISAYNGNTNYAQKLQGRVTMT
TDTSTSTAYMELRSLRSDDTAVYYCARWGGFGAVDHWGQGTLVTVSSTSG
QAGQHHHHHHGAYPYDVPDYAS [SEQ ID NO: 770]
```

TABLE 166

ET200-016

DNA Sequence

```
Tcttctgagctgactcaggaccctgctgtgtctgtggccttgggacagac
agtcaagatcacgtgccaaggagacagcctcacagactaccatgcaacct
ggtaccagcagaagccaggacaggccctgtcgctgtcatctatgctaca
aacaacggccactgggatcccagaccgattctctggttccagttccgg
aaacacagcttcttgaccatcactgggctcaggcggaagatgaggcctg
actattactgtaattcccgggacagcggcacggacgaagtgttattcggc
ggagggaccaagctgaccgtcctaggttctagaggtggtggtggtagcgg
cggcggcggctctggtggtggtggatccctcgagatggccgaggtgcagc
tggtggagactggggggggcctgt caagcctgggggttccggtgctg
tcctgtgcagcctctggattcaccttcagtagctatagcatgaactgggt
ccgccaggctccagggaaggggctggagtgggtctcatccattagtagta
gtagtagttacatatactacgcagactcagtgaagggccgattcaccatc
tccagacaacgccaagaactcactgtatctgcaaatgaacagcctgag
agccgaggacacggccgtgtattactgtgcgcgcggtcagggttacgatt
actggggtcaaggtactctggtgaccgtctcctcaactagtggccaggcc
ggccagcaccatcaccatcaccatggcgcatacccgtacgacgttccgga
ctacgcttct [SEQ ID NO: 771]
```

TABLE 166-continued

ET200-016

Amino Acid Sequence

```
SSELTQDPAVSVALGQTVKITCQGDSLTDYHATWYQQKPGQAPVAVIYAT
NNRPTGIPDRFSGSSSGNTASLTITGAQAEDEADYYCNSRDSGTDEVLFG
GGTKLTVLGSRGGGGSGGGGSGGGGSLEMAEVQLVETGGGLVKPGGSLRL
SCAASGFTFSSYSMNWVRQAPGKGLEWVSSISSSSSYIYYADSVKGRFTI
SRDNAKNSLYLQMNSLRAEDTAVYYCARGQGYDYWGQGTLVTVSSTSGQA
GQHHHHHHGAYPYDVPDYAS [SEQ ID NO: 772]
```

TABLE 167

ET200-017

DNA Sequence

```
Tcctatgtgctgactcagccaccctcggtgtcagtggccccaggaaagac
ggccaggattacctgtgggggaaacaacattggaagtaaaagtgtgcact
ggtaccagcagaagccaggccaggcccctgtgctggtcgtctatgatgat
agcgaccggccctcagggatccctgagcgattctctggctccaactctgg
gaacacggccaccctgagcatcagcagggtcgaagccgggggatgaggccg
actattactgtcaggtgtgggatagtagtagtgatcatactgtcttcgga
actgggaccaaggtcaccgtcctaggttctagaggtggtggtggtagcgg
cggcggcggctctggtggtggtggatccctcgagatggcccaggtgcagc
tacagcagtggggcgcaggactgttgaagccttcggagaccctgtccctc
acctgcgctgtctatggtgggtccttcagtggttactactggagctggat
ccgccagcccccagggaagggggctggagtggattgggaaatcaatcata
gtggaagcaccaactacaaccgtccctcaagagtcgagtcaccatatca
gtagacacgtccaagaaccagttctccctgaagctgagctctgtgaccgc
cgcggacacggccgtgtattactgtgcgcgctactacccgggtatggata
tgtggggtcaaggtactctggtgaccgtctcctcaactagtggccaggcc
ggccagcaccatcaccatcaccatggcgcatacccgtacgacgttccgga
ctacgcttct [SEQ ID NO: 773]
```

Amino Acid Sequence

```
SYVLTQPPSVSVAPGKTARITCGGNNIGSKSVHWYQQKPGQAPVLVVYDD
SDRPSGIPERFSGSNSGNTATLSISRVEAGDEADYYCQVWDSSSDHTVFG
TGTKVTVLGSRGGGGSGGGGSGGGGSLEMAQVQLQQWGAGLLKPSETLSL
TCAVYGGSFSGYYWSWIRQPPGKGLEWIGEINHSGSTNYNPSLKSRVTIS
VDTSKNQFSLKLSSVTAADTAVYYCARYYPGMDMWGQGTLVTVSSTSGQA
GQHHHHHHGAYPYDVPDYAS [SEQ ID NO: 774]
```

TABLE 168

ET200-018

DNA Sequence

```
Caggctgtgctgactcagccgccctcaacgtctgggacccccgggcagag
ggtcaccatctcttgttctggaagcagctccaacatcgggagaaatggtg
taaactggtaccagcagctcccaggagcggcccccaaagtcctcatctat
aatgataatcagcgaccctcagggggtccctgaccgagtctctggctccca
gtctggctcctcaggcacctgatgggcttcggtctgaggatg
aggctgattattactgtgcgcatgggatgacagcctgcatggtggtgga
ttcggcggagggaccaagctgaccgtcctaggttctagaggtggtggtgg
tagcggcggcggcggctctggtggtggtggatccctcgagatggcccagg
tccagctggtacagtctggggctgaggtgaagaagcctggggcctcagtg
aaggtctcctgcaaggtttccggatacaccctcaatgaattatccatgca
ctgggtgcgacaggctcctggaaaagggctgagtggatgggaggttttg
atcctgaagatggtgaaacaatctacgcacagaagtccagggcagagtc
accatgaccgaggacacatctacagacacagcctacatggagctgagcag
cctgagatctgaggacactgccgtgtattactgtgcgcgcggtggttacg
gtgattcttggggtcaaggtactctggtgaccgtctcctcaactagtggc
caggccggccagcaccatcaccatcaccatggcgcatacccgtacgacgt
tccggactacgcttct [SEQ ID NO: 775]
```

Amino Acid Sequence

```
QAVLTQPPSTSGTPGQRVTISCSGSSSNIGRNGVNWYQQLPGAAPKVLIY
NDNQRPSGVPDRVSGSQSGSSGTLAIDGLRSEDEADYYCAAWDDSLHGVV
```

TABLE 168-continued

ET200-018

FGGGTKLTVLGSRGGGGSGGGGSGGGGSLEMAQVQLVQSGAEVKKPGASV
KVSCKVSGYTLNELSMHWVRQAPGKGLEWMGGFDPEDGETIYAQKFQGRV
TMTEDTSTDTAYMELSSLRSEDTAVYYCARGGYGDSWGQGTLVTVSSTSG
QAGQHHHHHHGAYPYDVPDYAS [SEQ ID NO: 776]

TABLE 169

ET200-019

DNA Sequence

Aattttatgctgactcagccccactctgtgtcggagtctccggggaagac
ggtaaccatctcctgcacccgcagcagtggcagcattgccagcaactatg
tgcagtggtaccagcagcgcccgggcagtgcccccaccactgtgatctat
gaggataaccaaagaccctctggggtccctgatcggttctctggctccat
cgacagctcctccaactctgcctccctcaccatctctggactgaagactg
aggacgaggctgactactactgtcagtctttatgatagcagcaattcttgg
gtgttcggcggagggaccaagctgaccgtcctaggttctagaggtggtgg
tggtagcggcggcggcggctctggtggtggtggatccctcgagatggccc
aggtgcagctggtgcaatctgggggctgaggtgaagaggcctgggtcctcg
gtgaaggtctcctgcacggcttctggaggcaccttcagcacgcgatgctat
cagctgggtgcgacaggcccctggacaagggcttgagtggatgggaggaa
tcatccctatgtttggtacagcaaactacgcacagaagttccagggcaga
gtcacgattaccgcggacgaatccacgagcacagcctacatggagctgag
cagcctgagatctgaggacacggccgtgtattactgtgcgcgcgcgaaggtt
actactaccgtctgcttacctggtttctgttctgaacgacatctcttct
gtttacgatgaatggggtcaaggtactctggtgaccgtctcctcaactag
tggccaggccgccagcaccatcaccatcaccatggcgcatacccgtacg
acgttccggactacgcttct [SEQ ID NO: 777]

Amino Acid Sequence

NFMLTQPHSVSESPGKTVTISCTRSSGSIASNYVQWYQQRPGSAPTTVIY
EDNQRPSGVPDRFSGSIDSSSNSASLTISGLKTEDEADYYCQSYDSSNSW
VFGGGTKLTVLGSRGGGGSGGGGSGGGGSLEMAQVQLVQSGAEVKRPGSS
VKVSCTASGGTFSSDAISWVRQAPGQGLEWMGGIIPMFGTANYAQKFQGR
VTITADESTSTAYMELSSLRSEDTAVYYCAREGYYYPSAYLGSVLNDISS
VYDEWGQGTLVTVSSTSGQAGQHHHHHHGAYPYDVPDYAS [SEQ ID
NO: 778]

TABLE 170

ET200-020

DNA Sequence

Cagtctgtcgtgacgcagccgccctcagtgtctgcggccccaggacag
aaggtcaccatctcctgctctggaagcacctccaacattggaaataat
gatgtatcctggtaccagcagctcccaggaacagcccccaaaactcctc
atttatgacaataataagcgaccctcagggattcctgaccgattctct
ggctccaagtctggcacgtcagccaccctgggcatcaccggactccag
actggggacgaggccgattattactgcggaacatgggatagcagcgtg
agtgcttcttgggtcttcggcagagggaccaagctgaccgtcctaggt
tctagaggtggtggtagcggcggcggcggctctggtggtggtgga
tccctcgagatggcccaggtgcagctggtgcagtctggagctgaggtg
aagaagcctggggcctcagtgaaggtctcctgcaaggcttctggttac
acctttaccagctatggtatcagctgggtgcgacaggcccctggacaa
gggcttgagtggatgggatggatcagcgcttacaatggtaacacaaac
tatgcacagaagctccagggcagagtcaccatgaccacagacccatcc
acgagcacagcctacatggagctgaggagcctgagatctgacgacacg
gccgtgtattactgtgcgcgcgctctatgacttctttcgattactgggt
caaggtactctggtgaccgtctcctcaactagtggccaggccggccag
caccatcaccatcaccatggcgcatacccgtacgacgttccggactac
gcttct [SEQ ID NO: 779]

Amino Acid Sequence

QSVVTQPPSVSAAPGQKVTISCSGSTSNIGNNDVSWYQQLPGTAPKLL
IYDNNKRPSGIPDRFSGSKSGTSATLGITGLQTGDEADYYCGTWDSSV
SASWVFGRGTKLTVLGSRGGGGSGGGGSGGGGSLEMAQVQLVQSGAEV

TABLE 170-continued

ET200-020

KKPGASVKVSCKASGYTFTSYGISWVRQAPGQGLEWMGWISAYNGNTN
YPQKLQGRVTMTTDPSTSTAYMELRSLRSDDTAVYYCARSMTSFDYWG
QGTLVTVSSTSGQAGQHHHHHHGAYPYDVPDYAS
[SEQ ID NO: 780]

TABLE 171

ET200-021

DNA Sequence

Cagtctgtgttgacgcagccgccctcagtgtctgcggccccaggacag
aaggtcaccatctcctgctctggaagcaactccaacattgggaataat
tatgtatcctggtatcagcaactcccagggacagcccccaaactcctc
atttatgacaataataagcgaccctcagggattcctgaccgattctct
ggctccaggtctggcacgtcagccaccctgggcatcaccggactccag
actggggacgaggccgattattactgcggaacatggaataccactgtg
actcctggctatgtcttcggaactgggaccaaggtcaccgtcctaggt
tctagaggtggtggtagcggcggcggcggctctggtggtggtgga
tccctcgagatggccgaagtgcagctggtgcagtctggagctgaggtg
aagaagcctggggcctcagtgaaggtctcctgcaaggcttctggttac
acctttaccagctatggtatcagctgggtgcgacaggcccctggacaa
gggcttgagtggatgggatggatcagcgcttacaatggtaacacaaac
tatgcacagaagctccagggcagagtcaccatgaccacagacacatcc
acgagcacagcctacatggagctgaggagcctgagatctgacgacacc
gccatgtattactgtgcgcgctctgtttacgacctggatacttgggt
caaggtactctggtgaccgtctcctcaactagtggccaggccggccag
caccatcaccatcaccatggcgcatacccgtacgacgttccggactac
gcttct [SEQ ID NO: 781]

Amino Acid Sequence

QSVLTQPPSVSAAPGQKVTISCSGSNSNIGNNYVSWYQQLPGTAPKWY
DNNKRPSGIPDRFSGSRSGTSATLGITGLQTGDEADYYCGTWNTTVTP
GYVFGTGTKVTVLGSRGGGGSGGGGSGGGGSLEMAEVQLVQSGAEVKK
PGASVKVSCKASGYTFTSYGISWVRQAPGQGLEWMGWISAYNGNTNYA
QKLQGRVTMTTDPSTSTAYMELRSLRSDDTAMYYCARSVYDLDTWGQG
TLVTVSSTSGQAGQHHHHHHGAYPYDVPDYAS
[SEQ ID NO: 782]

TABLE 172

ET200-022

DNA Sequence cagtctgtcgtgacgcagccgccctcagtgtctgcggccccaggacag
aaggtcaccatctcctgctctggaagcagctccaacattgggaataat
tatgtatcctggtaccagcagctcccaggaacagcccccaaactcctc
atttatgacaataataagcgaccctcagggattcctgaccgattctct
ggctccaagtctggcacgtcagccaccctgggcatcaccggactccag
actggggacgaggccgattattactgcggaacatgggatagcagcgtg
gggggccccttatgtcttcggaactgggaccaaggtcaccgtcctaggt
tctagaggtggtggtagcggcggcggcggctctggtggtggtgga
tccctcgagatggccgaggtgcagctggtgcagtcttggggaggctcg
gaacagcctggcaggtccctgagactctcctgtgcagcctctggattc
acctttgatgattatgccatgcactgggtccggcaagctccagggaag
ggcctggagtgggtctcaggtattagtggaatagcggtagcatagc
tatgcggactctgtgaagggccgattcaccatctccagagacaacgcc
aagaattccctgtatctgcaaatgaacagtctgagagctgaggacacc
gccatgtattactgtgcgcgctcaggttggttctgcttacgat
tcttggggtcaaggtactctggtgaccgtctcctcaactagtggccag
gccggccagcaccatcaccatcaccatggcgcatacccgtacgacgtt
ccggactacgcttct [SEQ ID NO: 783]

Amino Acid Sequence

QSVVTQPPSVSAAPGQKVTISCSGSSSNIGNNYVSWYQQLPGTAPKLL
IYDNNKRPSGIPDRFSGSKSGTSATLGITGLQTGDEADYYCGTWDSSL

TABLE 172-continued

ET200-022

GAPYVFGTGTKVTVLGSRGGGGSGGGGSGGGGSLEMAEVQLVQSWGGS
EQPGRSLRLSCAASGFTFDDYAMHWVRQAPGKGLEWVSGISWNSGSIG
YADSVKGRFTISRDNAKNSLYLQMNSLRAEDTAMYYCARYRQVGSAYD
SWGQGTLVTVSSTSGQAGQHHHHHHGAYPYDVPDYAS
[SEQ ID NO: 784]

TABLE 173

ET200-023

DNA Sequence ctgcctgtgctgactcagccaccctcggtgtcagtggcccccaggaaag
acggccaggattacctgtggggggaaacaacattggaagtaaaagtgtg
cactggtatcagcagaagccaggccaggcccctgtgctggtcgtctat
gctgatagcgaccggccctcagggatccctgagcgattctctggctcc
aactctgggaacacggccaccctgaccatcagcagggtcgaagccggg
gatgaggccgactattactgtcaggtgtgggatagtagtagttatcat
aattatgtatcggaactgggaccaaggtcaccgtcctaggttctagag
gtggtggtggtagcggcggcggcggctctggtggtggtggatccctcg
agatggccgaggtgcagctggtgcagtctggagctgaggtgaagaagc
ctgggcctcagtgaaggtctcctgcaaggcttctggttacacctta
ccagctatggtatcagctgggtgcgacaggcccctggacaagggcttg
agtggatgggatggatcagcgcttacaatggtaacacaaactatgcac
agaagctccagggcagagtcaccatgaccacagacacatccacgagca
cagcctacatggagctgagcagcctgagatctgaggacaccgccatgt
attactgtgcgcgctactgggggtttcggtgtttctgatcgttggggtc
aaggtactctggtgaccgtctcctcaactagtggccaggccggccagc
accatcaccatcaccatggcgcatacccgtacgacgttccggactacg
cttct [SEQ ID NO: 785]

Amino Acid Sequence

LPVLTQPPSVSVAPGKTARITCGGNNIGSKSVHWYQQKPGQAPVLVVY
ADSDRPSGIPERFSGSNSGNTATLTISRVEAGDEADYYCQVWDSSSYH
NYVFGTGTKVTVLGSRGGGGSGGGGSGGGGSLEMAEVQLVQSGAEVKK
PGASVKVSCKASGYTFTSYGISWVRQAPGQGLEWMGWISAYNGNTNYA
QKLQGRVTMTTDTSTSTAYMELSSLRSEDTAMYYCARYWGFGVSDRWG
QGTLVTVSSTSGQAGQHHHHHHGAYPYDVPDYAS
[SEQ ID NO: 786]

TABLE 174

ET200-024

DNA Sequence aattttatgctgactcagccccactctgtgtcggagtctccggggaag
acggtaaccatctcctgcaccggcagcagtggcagcattgccagcaac
tatgtgcagtggtaccagcagcgcccgggcagtgcccccaccactgtg
atctatgaggataaccaaagaccctctgggtcccctgatcggttctct
ggctccatcgacagctcctccaactctgcctccctcaccatctctgga
ctgaagactgaggacgaggctgactactactgtcagtcttatgacagc
agcaatctttgggtgttcggcggagggaccaagctgaccgtcctaggt
tctagaggtggtggtggtagcggcggcggcggctctggtggtggtgga
tccctcgagatggcccagatgcagctggtgcagtctggggctgaggtg
aagaagcctgggtcctcggtgaaggtctcctgcaaggcttctggaggc
accttcagcagctatgctatcagctgggtgcgacaggcccctggacaa
gggcttgagtggatgggagggatcatccctatctttggtacagcaaac
tacgcacagaagttccagggcagagtcacgattaccgcggacgaatcc
acgagcacagcctacatggagctgagcagcctgagatctgaggacact
gccgtgtattactgtgcgcgctacaactactactactacgattcttgg
ggtcaaggtactctggtgaccgtctcctcaactagtggccaggccggccag
cagcaccatcaccatcaccatggcgcatacccgtacgacgttccggac
tacgcttct [SEQ ID NO: 787]

Amino Acid Sequence

NFMLTQPHSVSESPGKTVTISCTGSSGSIASNYVQWYQQRPGSAPTTV
IYEDNQRPSGVPDRFSGSIDSSSNSASLTISGLKTEDEADYYCQSYDS
SNLWVFGGGTKLTVLGSRGGGGSGGGGSGGGGSLEMAQMQLVQSGAEV

TABLE 174-continued

ET200-024

KKPGSSVKVSCKASGGTFSSYAISWVRQAPGQGLEWMGGIIPIFGTAN
YAQKFQGRVTITADESTSTAYMELSSLRSEDTAVYYCARYNYYYYDSW
GQGTLVTVSSTSGQAGQHHHHHHGAYPYDVPDYAS
[SEQ ID NO: 788]

TABLE 175

ET200-025

DNA Sequence gacatccagatgacccagtctccatcctccctgtctgcatctgtagga
gacagagtcaccatcacttgccgggcaagtcagagcattagcagctat
ttaaattggtatcagcagaaaccagggaaagcccctaagctcctgatc
tatgctgcatccagtttgcaaagtggggtcccatcaaggttcagtggc
agtggatctgggacagatttcactctcaccatcagcagtctgcaacct
gaagattttgcaacttactactgtcaacagagttacagtacccccattc
actttcggccctgggaccaaagtggatatcaaacgttctagaggtggt
ggtggtagcggcggcggcggctctggtggtggtggatccctcgagatg
gccgaggtgcagctggtgcagtctggggctgaggtgaagaagcctggg
tcctcggtgaaggtctcctgcaaggcttctggaggcaccttcagcagc
tatgctatcagctgggtgcgacaggcccctggacaagggcttgagtgg
atgggagggatcatccctatctttggtacagcaaactacgcacagaag
ttccagggcagagtcacgattaccgcggacgaatccacgagcacagcc
tacatggagctgagcagcctgagatctgaggacaccgccatgtattac
tgtgcgcgctactggggttacgactctttacgatgaatggggtcaaggt
actctggtgaccgtctcctcaactagtggccaggccggccagccacat
caccatcaccatggcgcatacccgtacgacgttccggactacgcttct
[SEQ ID NO: 789]

Amino Acid Sequence

DIQMTQSPSSLSASVGDRVTITCRASQSISSYLNWYQQKPGKAPKLLI
YAASSLQSGVPSRFSGSGSGTDFTLTISSLQPEDFATYYCQQSYSTPF
TFGPGTKVDIKRSRGGGGSGGGGSGGGGSLEMAEVQLVQSGAEVKKPG
SSVKVSCKASGGTFSSYAISWVRQAPGQGLEWMGGIIPIFGTANYAQK
FQGRVTITADESTSTAYMELSSLRSEDTAMYYCARYWGYDSYDEWGQG
TLVTVSSTSGQAGQHHHHHHGAYPYDVPDYAS [SEQ ID NO: 790]

TABLE 176

ET200-026

DNA Sequence aattttatgctgactcagccccactctgtgtcggagtctccggggaag
acggtaaccatctcctgcaccggcagcagtggcagcattgccagcaac
tatgtgcagtggtaccagcagcgcccgggcagtgcccccaccactgtg
atctatgaggataaccaaagaccctctgggtcccctgatcggttctct
ggctccatcgacagctcctccaactctgcctccctcaccatctctgga
ctgaagactgaggacgaggctgactactactgtcagtcttatgatagc
agcaattgggtgttcggcggagggaccaagctgaccgtcctaggttct
agaggtggtggtggtagcggcggcggcggctctggtggtggtggatcc
ctcgagatggcccagatgcagctggtgcagtctggggctgaggtgaag
aagcctgggtcctcggtgaaggtctcctgcaaggcttctggaggcacc
ttcagcagctatgctatcagctgggtgcgacaggcccctggacaaggg
cttgagtggatgggagggatcatccctatctttggtacagcaaactac
gcacagaagttccagggcagagtcacgattaccgcggacgaatccacg
agcacagcctacatggagctgagcagcctgagatctgaggacacggcc
gtgtattactgtgcgcgcaacaaccattactacaacgattactgggt
caaggtactctggtgaccgtctcctcaactagtggccaggccggccag
caccatcaccatcaccatggcgcatacccgtacgacgttccggactac
gcttct [SEQ ID NO: 791]

Amino Acid Sequence

NFMLTQPHSVSESPGKTVTISCTGSSGSIASNYVQWYQQRPGSAPTTV
IYEDNQRPSGVPDRFSGSIDSSSNSASLTISGLKTEDEADYYCQSYDS
SNWVFGGGTKLTVLGSRGGGGSGGGGSGGGGSLEMAEVQLVQSGAEVK
KPGSSVKVSCKASGGTFSSYAISWVRQAPGQGLEWMGGIIPIFGTANY
AQKFQGRVTITADESTSTAYMELSSLRSEDTAVYYCARNNHYYNDYWG
QGTLVTVSSTSGQAGQHHHHHHGAYPYDVPDYAS
[SEQ ID NO: 792]

TABLE 177

ET200-027

DNA Sequence

```
cagtctgtgttgacgcagccgccctcagtgtctggggcccccagggcag
ggggtcaccatccctgcactgggagcagctccaacatcggggcaggt
tatgatgtacactggtaccagcagcttccagggacagcccccaaactc
ctcatctatggtaacaacaatcggccctcaggggtccctgaccgcttc
tctggctccaggtctggctcctcagcctccctggccatcactgggctc
caggctgaggatgaggctgattattactgccagtcctatgacagcagc
ctgagtgatgtggtattcggcggagggaccaaggtcaccgtcctaggt
tctagaggtggtggtggtagcggcggcggcggctctggtggtggtgga
tccctcgagatggccgaggtccagctggtgcagtctggggctgaggtg
aagaagcctggggctacagtgaaaatctcctgcaaggtttctggatac
accttcaccgactacatgcactgggtgcaacaggcccctggaaaa
gggcttgagtggatgggacttgttgatcctgaagatggtgaaacaata
tacgcagagaagttccagggcagagtcaccataaccgcggacacgtct
acagacacagcctacatggagctgagcagcctgagatctgaggacacg
gccgtgtattactgtgcgcgctactggtcttactctttcgactacctg
tacatgccggaaggtaacgattggtggggtcaaggtactctggtgacc
gtctcctcaactagtggccaggccggccagcaccatcaccatcaccat
ggcgcatacccgtacgacgttccggactacgcttct
[SEQ ID NO: 793]
```

Amino Acid Sequence

```
QSVLTQPPSVSGAPGQGVTIPCTGSSSNIGAGYDVHWYQQLPGTAPKL
LIYGNNNRPSGVPDRFSGSRSGSSASLAITGLQAEDEADYYCQSYDSS
LSDVVFGGGTKVTVLGSRGGGGSGGGGSGGGGSLEMAEVQLVQSGAEV
KKPGATVKISCKVSGYTFTDYYMHWVQQAPGKGLEWMGLVDPEDGETI
YAEKFQGRVTITADTSTDTAYMELSSLRSEDTAVYYCARYWSYSFDYL
YMPEGNDWWGQGTLVTVSSTSGQAGQHHHHHHGAYPYDVPDYAS
[SEQ ID NO: 794]
```

TABLE 178

ET200-028

DNA Sequence

```
cagtctgtgttgactcagccacccgcagcgtctgggaccccggacag
agagtcaccatctcttgttctggggcgtctccaacatcgggagtggt
gctctaaattggtaccagcaactcccaggaacggcccccaaactcctc
atctatagttacaatcagcggccctcaggggtctctgaccgattctct
ggctccaggtctgccacctcagcctccctggccatcagtgggctccag
tctgaggatgaggctgattattactgtgcaacctgggatgatagtgtg
aatggttgggtgttcggcggagggaccaagctgaccgtcctaggttct
agaggtggtggtggtagcggcggcggcggctctggtggtggtggatcc
ctcgagatggccaggtccagctggtacagtctggagctgaggtgaag
aagcctggggattcagtgaaggtctcctgcaaggtctggttacaat
tttctcaactatggtatcaactgggtgcgacaggcccctggacaaggg
cttgagtggatgggatggattagcacttacaccggtaacacaaactat
gcacagaagctgcagggcagagtcaccttcaccacagacacatccacg
agcacagcctacatggagctgaggagcctgacgacaccggcc
gtgtattactgtgcgcgacctgtactactacgaagtgttgattac
tggggtcaaggtactctggtgaccgtctcctcaactagtggccaggcc
ggccagcaccatcaccatcaccatggcgcatacccgtacgacgttccg
gactacgcttct [SEQ ID NO: 795]
```

Amino Acid Sequence

```
QSVLTQPPAASGTPGQRVTISCSGGVSNIGSGALNWYQQLPGTAPKLL
IYSYNQRPSGVSDRFSGSRSATSASLAISGLQSEDEADYYCATWDDSV
NGWVFGGGTKLTVLGSRGGGGSGGGGSGGGGSLEMAQVQLVQSGAEVK
KPGDSVKVSCKPSGYNFLNYGINWVRQAPGQGLEWMGWISTYTGNTNY
AQKLQGRVTFTTDTSTSTAYMEMRSLRSDDTAVYYCARDLYYYEGVDY
WGQGTLVTVSSTSGQAGQHHHHHHGAYPYDVPDYAS
[SEQ ID NO: 796]
```

TABLE 179

ET200-029

DNA Sequence

```
caggctgtgctgactcagccaccctcagtgtcagtggccccaggaaag
acggccagggttacctgtgggggaaacaacattggaagtgaaagtgtg
cactggtaccagcagaagccaggccaggcccctgtgttggtcatctat
tatgataccgaccggccctcagggatccctgagcgattctctggctcc
cactctgggaccacggccaccctgaccatcagcagggtcgaagccggg
gatgaggccgactattactgtcaggtgtgggatagtagtagggatcat
gtggtattcggcggagggaccaagctgaccgtcctaggttctagaggt
ggtggtggtagcggcggcggcggctctggtggtggtggatccctcgag
atgcccaggtgcagctggtgcagtctgggggaggcgtggtccagcct
gggaggtccctgagactctcctgtgcggcctctggattcacctttagt
agctatgctatgcactgggtccgccaggctccaggcaagggactggag
tgggtggcagttatatcatatgatggaagcaataaatactacgcagac
tccgtgaagggccgattcaccatctccagagacaattccaagaacacg
ctgtatctgcaaatgaacagcctgagagctgaggacacggccgtgtat
tactgtgcgcgctatacttcacttctggtttctacgattactggggtc
aaggtactctggtgaccgtctcctcaactagtggccaggccggccagc
accatcaccatcaccatggcgcatacccgtacgacgttccggactacg
cttct [SEQ ID NO: 797]
```

Amino Acid Sequence

```
QAVLTQPPSVSVAPGKTARVTCGGNNIGSESVHWYQQKPGQAPVLVIY
YDTDRPSGIPERFSGSHSGTTATLTISRVEAGDEADYYCQVWDSSRDH
VVFGGGTKLTVLGSRGGGGSGGGGSGGGGSLEMAQVQLVQSGGGVVQP
GRSLRLSCAASGFTFSSYAMHWVRQAPGKGLEWVAVISYDGSNKYYAD
SVKGLFTISRDNSKNTLYLQMNSLRAEDTAVYYCARSYFTSGFYDYWG
QGTLVTVSSSGQAGQHHHHHHGAYPYDVPDYAS
[SEQ ID NO: 798]
```

TABLE 180

ET200-030

DNA Sequence

```
cagtctgtcgtgacgcagccgccctcagtgtctggggcccccagggcag
agggtcaccatctcctgcactgggagcagttccaacatcggggcaggt
tatgatgtaaattggtatcagcagttccaggaacagcccccaaactc
ctcatctatggtaacagcaatcggccctcaggggtccctgaccgattc
tctggctccaagtctggcacctcagcctccctggccatcactgggctc
caggctgaggatgaggctgattattactgccagtcctatgacagcagc
ctgagtggctcttatgtcttcggaactgggaccaaggtcaccgtcctaa
ggttctagaggtggtggtggtagcggcggcggcggctctggtggtggt
ggatccctcgagatggcccagatgcagctggtgcagtctggggctgag
gtgaagaagcctggggcctcggtgaaggtctcctgcaaggatccggat
acaccctcactgaattatcatgcactgggtgcgacaggctcctggaa
aaggcttgagtggatgggaggttttgatcctgaagatggtgaaacaa
tctacgcacagaagttccagggcagagtcaccatgaccgaggacacat
ctacagacacagcctacatggagctgagcagcctgagatctgaggaca
ctgccgtgtattactgtgcgcgcatgtatctatgtactacgattgggg
tcaaggtactctggtgaccgtctcctcaactagtggccaggccggcca
gcaccatcaccatcaccatggcgcatacccgtacgacgttccggacta
cgcttct [SEQ ID NO: 799]
```

Amino Acid Sequence

```
QSVVTQPPSVSGAPGQRVTISCTGSSSNIGAGYDVNWYQQFPGTAPKL
LIYGNSNRPSGVPDRFSGSKSGTSASLAITGLQAEDEADYYCQSYDSS
LSGSYVFGTGTKVTVLGSRGGGGSGGGGSGGGGSLEMAQMQLVQSGAE
VKKPGASVKVSCKASGYTLTELSMHWVRQAPGKGLEWMGGFDPEDGET
IYAQKFQGRVTMTEDTSTDTAYMELSSLRSEDTAVYYCARMSSMYYDW
GQGTLVTVSSTSGQAGQHHHHHHGAYPYDVPDYAS
[SEQ ID NO: 800]
```

TABLE 181

ET200-031

DNA Sequence

```
tcctatgtgctgactcagccaccctcagtgtcagtggccccaggaaag
acggccaggattacctgtgggggaaacaacattggaagtaaaagtgtg
cactggtaccagcagaagccaggccaggcccctgtgctggtcatctat
tatgatagcgaccggccctcagggatccctgagcgattctctggctcc
aactctgggaacacggccaccctgaccatcagcagggtcgaagccggg
gatgaggccgactattactgtcaggtgtgggatagtagtagtgattat
gtcttcggaactgggaccaaggtcaccgtcctaggttctagaggtggt
ggtggtagcggcggcggcggctctggtggtggtggatccctcgagatg
gccgaggtgcagctggtggagactggggggaggcttggtcaagcctgga
gggtccctgagactctcctgtgcagcctctggattcaccgtcagtgac
tactacatgagctggatccgccaggctccagggaagggcctggagtgg
atttcatacattagtggtagtggtaatagcatatactacgcagactct
gtgaagggccgattcaccatctccagggacaacgccaagaactcactg
gatctgcaaatgaccagcctgagagccgaggacacggccgtatattac
tgtgcgcgctcactaaattcgattactggggtcaaggtactctggtg
accgtctcctcaactagtggccaggccggccagcaccatcaccatcac
catggcgcatacccgtacgacgttccggactacgcttct
[SEQ ID NO: 801]
```

Amino Acid Sequence

```
SYVLTQPPSVSVAPGKTARITCGGNNIGSKSVHWYQQKPGQAPVLVIY
YDSDRPSGIPERFSGSNSGNTATLTISRVEAGDEADYYCQVWDSSSDY
VFGTGTKVTVLGSRGGGGSGGGGSGGGGSLEMAEVQLVETGGGLVKPG
GSLRLSCAASGFTVSDYYMSWIRQAPGKGLEWISYISGSGNSIYYADS
VKGRFTISRDNAKNSLDLQMTSLRAEDTAVYYCARSTKFDYWGQGTLV
TVSSTSGQAGQHHHHHGAYPYDVPDYAS [SEQ ID NO: 802]
```

TABLE 182

ET200-032

DNA Sequence

```
ctgcctgtgctgactcagccaccctcagcgtctgggaccccgggcag
agggtcaccatctcttgttctggaagcagctccaacgtcggaagttac
actgtaaactggtaccggcaactcccaggaacggcccccacactcctc
atctataataataatcagcggccctcagggggtccctgaccgattctct
gactccaagtctggcacctcggcctccctgaccattagtgggctccag
cctgaggatgaggctgattattattgtgcagcatgggatgacaggctg
ggtggttatgtatcggaactgggaccaaggtcaccgtcctaggttcta
gaggtggtggtggtagcggcggcggcggctctggtggtggtggatccc
tcgagatggccgaggtgcagctggtggagactggggggaggcttgaaaa
agccgggggagtctctgaagatctcctgtaagggttctggatacagct
ttaccaactactggatcggctgggtgcgccagatgcccgggaaaggcc
tggagtggatggggatcatctatcctggtgactctgataccagataca
gcccgtccttccaaggccaggtcaccatctcagccgacaagtccatca
gcaccgcctacctacagtggagcagcctgaaggcctcggacaccgcca
tgtattactgtgcgcgctcactggttcttctcatatgtctgatgaat
ggggtcaaggtactctggtgaccgtctcctcaactagtggccaggccg
gccagcaccatcaccatcaccatggcgcatacccgtacgacgttccgg
actacgcttct [SEQ ID NO: 803]
```

Amino Acid Sequence

```
LPVLTQPPSASGTPGQRVTISCSGSSSNVGSYTVNWYRQLPGTAPTLL
IYNNNQRPSGVPDRFSDSKSGTSASLTISGLQPEDEADYYCAAWDDRL
GGYVFGTGTKVTVLGSRGGGGSGGGGSGGGGSLEMAEVQLVQSGAEVK
KPGESLKISCKGSGYSFTNYWIGWVRQMPGKGLEWMGIIYPGDSDTRY
SPSFQGQVTISADKSISTAYLQWSSLKASDTAMYYCARSTGSSHMSDE
WGQGTLVTVSSTSGQAGQHHHHHGAYPYDVPDYAS
[SEQ ID NO: 804]
```

TABLE 183

ET200-033

DNA Sequence

```
aattttatgctgactcagccccactctgtgtcggagtctccggggaag
acggtaaccatctcctgcaccggcagcagtggcagcattgccagcaac
```

TABLE 183-continued

ET200-033

```
tatgtgcagtggtaccagcagcgcccgggcagtgcccccaccactgtg
atctatgaggataaccaaagaccctctggggtccctgatcggttctct
ggctccatcgacagctcctccaactctgcctccctcaccatctctgga
ctgaagactgaggacgaggctgactactactgtcagtcttatgatagc
agcaatcattgggtgttcggcggagggaccaagctgaccgtcctaggt
tctagaggtggtggtggtagcggcggcggcggctctggtggtggtgga
tccctcgagatggccgaggtgcagctacagcagtggggcggcaggactg
ttgaagccttcggagaccctgtccctcacctgcgctgtctatggtggg
tccttcagtggttactactggagctggatccgccagccccccagggaag
gggctggagtggattgggggagatcactcatagtggaaggtccaactac
aaccgtccctcaagagtcgagtcaccatatcagtagacacgtccaag
aaccagttctccctgaagctgagctctgtgaccgccgcggacacggcc
gtgtattactgtgcgcgctcttctatcatgtctgattactggggtcaa
ggtactctggtgaccgtctcctcaactagtggccaggccggccagcac
catcaccatcaccatggcgcatacccgtacgacgttccggactacgct
tct [SEQ ID NO: 805]
```

Amino Acid Sequence

```
NFMLTQPHSVSESPGKTVTISCTGSSGSIASNYVQWYQQRPGSAPTTV
IYEDNQRPSGVPDRFSGSIDSSSNSASLTISGLKTEDEADYYCQSYDS
SNHWVFGGGTKLTVLGSRGGGGSGGGGSGGGGSLEMAQVQLQQWGAGL
LKPSETLSLTCAVYGGSFSGYYWSWIRQPPGKGLEWIGEITHSGRSNY
NPSLKSRVTISVDTSKNQFSLKLSSVTAADTAVYYCARSSIMSDYWGQ
GTLVTVSSTSGQAGQHHHHHGAYPYDVPDYAS
[SEQ ID NO: 806]
```

TABLE 184

ET200-034

DNA Sequence

```
cagtctgtgttgacgcagccgccctcagtgtctggggccccagggcag
agggtcaccatctcctgcactgggagcacctccaacatcggggcaggt
tatgatgtacactggtaccagcagatccaggaacagcccccaaactcc
tcatcaacaataacaggaatcggccctcagggggtccctgaccgattct
ctggctccaagtctggcacgtcagccaccctgggcatcaccggctcc
agactggggacgaggccgattattactgcgggaacatgggatggcagcc
tgactggtgcagtgttcggcggagggaccaagctgaccgtcctaggtt
ctagaggtggtggtggtagcggcggcggcggctctggtggtggtggat
ccctcgagatggccgaggtccagctggtggagtctgggggaggtgga
agaagcctgggtcctcggtgaaggtctcatgcaaggcttctggaggca
ccttcagcagctatgctatcagctgggtgcgacaggcccctggacaag
ggcttgagtggatgggagggatcatccctatctttggtacagcaaact
acgcacagaagttccagggcagagtcacgattaccgcggacgaatcca
cgagcacagcctacatggagctgagcagcctgagatctgaggacacgg
ccgtgtattactgtgcgcgcggttctgctctggaccattacgatcgtt
ggggtcaaggtactctggtgaccgtctcctcaactagtggccaggccg
gccagcaccatcaccatcaccatggcgcatacccgtacgacgttccgg
actacgcttct [SEQ ID NO: 807]
```

Amino Acid Sequence

```
QSVLTQPPSVSGAPGQRVTISCTGSTSNIGAGYDVHWYQQLPGTAPKL
LINNNRNRPSGVPDRFSGSKSGTSATLGITGLQTGDEADYYCGTWDGS
LTGAVFGGGTKLTVLGSRGGGGSGGGGSGGGGSLEMAEVQLVQSGAEV
KKPGSSVKVSCKASGGTFSSYAISWVRQAPGQGLEWMGGIIPIFGTAN
YAQKFQGRVTITADESTSTAYMELSSLRSEDTAVYYCARGSALDHYDR
WGQGTLVTVSSTSGQAGQHHHHHGAYPYDVPDYAS
[SEQ ID NO: 808]
```

TABLE 185

ET200-035

DNA Sequence

```
aattttatgctgactcagccccactctgtgtcggagtctccggggaa
gacggtaaccatctcctgcacccgcagcagtggcagcattgccagca
actatgtgcagtggtaccagcagcgcccgggcagtgcccccaccact
gtgatctatgaggataaccaaagaccctctggggtccctgatcggtt
ctctggctccatcgacagctcctccaactctgcctccctcaccatct
```

TABLE 185-continued

ET200-035

```
ctggactgaagactgaggacgaggctgactactactgtcagtcttat
gatagcaccaattgggtgttcggcggagggaccaagctgaccgtcct
aggttctagaggtggtggtagcggcggcggcggctctggtggtg
gtggatccctcgagatggcccaggtgcagctggtgcagtctggggct
gaggtgaagaagcctgggtcctcggtgaaggtctcctgcaaggcttc
tggaggcaccttcagcagctatgctatcagctgggtgcgacaggccc
ctggacaagggcttgagtggatggagggatcatccctatcttggt
acagcaaactacgcacagaagttccagggcagagtcacgattaccgc
ggacgaatccacgagcacagcctacatggagctgagcagcctgagat
ctgaggacactgccgtgtattactgtgcgcgctacaactactacttc
aacgattactggggtcaaggtactctggtgaccgtctcctcaactag
tggccaggccggccagcaccatcaccatcaccatggcgcatacccgt
acgacgttccggactacgcttct [SEQ ID NO: 809]
```

Amino Acid Sequence

```
NFMLTQPHSVSESPGKTVTISCTRSSGSIASNYVQWYQQRPGSAPTT
VIYEDNQRPSGVPDRFSGSIDSSSNSASLTISGLKTEDEADYYCQSY
DSTNWVFGGGTKLTVLGSRGGGGSGGGGSGGGGSLEMAQVQLVQSGA
EVKKPGSSVKVSCKASGGTFSSYAISWVRQAPGQGLEWMGGIIPIFG
TANYAQKFQGRVTITADESTSTAYMELSSLRSEDTAVYYCARYNYYF
NDYWGQGTLVTVSSTSGQAGQHHHHHHGAYPYDVPDYAS
[SEQ ID NO: 810]
```

TABLE 186

ET200-037

DNA Sequence

```
tcctatgtgctgactcagccaccctcagtgtcagtggccccaggaaa
gacggccaggattacctgtgggggaaacaacattggaagtaaaagtg
tgcactggtaccagcagaagccaggccagcccctgtgctggtcatc
tattatgatagcgaccggccctcagggatccctgagcgattctctgg
ctccaactctgggaacacggccaccctgaccatcagcagggtcgaag
ccgggggatgaggccgactattactgtcaggtgtgggatagtagtagt
gatcatccttatgtcttcggaactgggaccaaggtcaccgtcctagg
ttctagaggtggtggtggtagcggcggcggcggctctggtggtggtg
gatccctcgagatggcccagatgcagctggtgcagtctggagctgag
gtgaagaagcctgggggcctcagtgaaggtctcctgcaaggcttctgg
ttacacctttaccagctatggtatcagctgggtgcgacaggcccctg
gacaagggcttgagtggatgggatgggatcagcgcttacaatggtaac
acaaactatgcacagaagctccagggcagagtcaccatgaccacaga
cacatccacgagcacagcctacatggagctgaggagcctgagatctg
acgacactgccgtgtattactgtgcgcgctctatgttcggtgctcat
gattcttgggggtcaaggtactctggtgaccgtctcctcaactagtgg
ccaggccggccagcaccatcaccatcaccatggcgcatacccgtacg
acgttccggactacgcttct [SEQ ID NO: 811]
```

Amino Acid Sequence

```
SYVLTQPPSVSVAPGKTARITCGGNNIGSKSVHWYQQKPGQAPVLVI
YYDSDRPSGIPERFSGSNSGNTATLTISRVEAGDEADYYCQVWDSSS
DHPYVFGTGTKVTVLGSRGGGGSGGGGSGGGGSLEMAQMQLVQSGAE
VKKPGASVKVSCKASGYTFTSYGISWVRQAPGQGLEWMGWISAYNGN
TNYAQKLQGRVTMTTDTSTSTAYMELRSLRSDDTAVYYCARSMFGAH
DSWGQGTLVTVSSTSGQAGQHHHHHHGAYPYDVPDYAS
[SEQ ID NO: 812]
```

TABLE 187

ET200-038

DNA Sequence

```
cagtctgtgttgacgcagccgccctcagtgtctggggcccagggca
gagggtcaccatctcctgcactgggagcagctccaacatcggggcag
gttttgatgtacactggtaccagctacttccaggaacagcccccaaa
ctcctcatctatgctaacagcaatcggccctcaggggtccctgaccg
attctctggctccaagtctggcacctcagcctccctggccatcactg
ggctcctggctgaggatgaggctgattattactgccagtcctatgac
agcagcctgagtggtgtggtattcggcggagggaccaagctgaccgt
cctaggttctagaggtggtggtggtagcggcggcggcggctctggtg
```

TABLE 187-continued

ET200-038

```
gtggtggatccctcgagatggcccaggtgcagctggtgcaatctggg
gctgaggtgaagaagcctgggtcctcggtgaaggtctcctgcaaggc
ttctggaggcaccttcagcagctatgctatcagctgggtgcgacagg
cccctggacaagggcttgagtggatgggagggatcatccctatctttt
ggtacagcaaactacgcacagaagttccagggcagagtcacgattac
cgcggacgaatccacgagcacagcctacatggagctgagcagcctga
gatctgaggacactgccgtgtattactgtgcgcgctgcttctttc
gaccgtcatgataactggggtcaaggtactctggtgaccgtctcctc
aactagtggccaggccggccagcaccatcaccatcaccatggcgcat
acccgtacgacgttccggactacgcttct [SEQ ID NO: 813]
```

Amino Acid Sequence

```
QSVLTQPPSVSGAPGQRVTISCTGSSSNIGAGFDVHWYQLLPGTAPK
LLIYANSNRPSGVPDRFSGSKSGTSASLAITGLLAEDEADYYCQSYD
SSLSGVVFGGGTKLTVLGSRGGGGSGGGGSGGGGSLEMAQVQLVQSG
AEVKKPGSSVKVSCKASGGTFSSYAISWVRQAPGQGLEWMGGIIPIF
GTANYAQKFQGRVTITADESTSTAYMELSSLRSEDTAVYYCARGASF
DRHDNWGQGTLVTVSSTSGQAGQHHHHHHGAYPYDVPDYAS
[SEQ ID NO: 814]
```

TABLE 188

ET200-039

DNA Sequence

```
aattttatgctgactcagcccactctgtgtcggagtctccggggaa
gacggtaaccatctcctgcacccgcagcagtggcagcattgccagca
actatgtgcagtggtaccagcagcgcccgggcagttcccccaccact
gtgatctatgaggataaccaaagaccctctgggtcctgatcggtt
ctctggctccatcgacagctcctccaactctgcctccctccaccatct
ctggactgaagactgaggacgaggctgactactactgtcagtcttat
gatacagcaattgggtgttcggcggagggaccaagctgaccgtcct
aggttctagaggtggtggtggtagcggcggcggcggctctggtggtg
gtggatccctcgagatggccgaggtccagctggtgcagtctggggct
gaggtgaagaagcctggggcctcagtgaaggtctcctgcaaggcttc
tggaggcaccttcagcagctatgctatcagctgggtgcgacaggccc
ctggacaagggcttgagtggatgggagggatcatccctatctttggt
acagcaaactacgcacagaagttccagggcagagtcacgattaccgc
ggacgaatccacgagcacagcctacatggagctgagcagcctgagat
ctgaggacacggccgtgtattactgtgcgcgctctaactactactac
aacgattactggggtcaaggtactctggtgaccgtctcctcaactag
tggccaggccggccagcaccatcaccatcaccatggcgcatacccgt
acgacgttccggactacgcttct [SEQ ID NO: 815]
```

Amino Acid Sequence

```
NFMLTQPHSVSESPGKTVTISCTRSSGSIASNYVQWYQQRPGSSPTT
VIYEDNQRPSGVPDRFSGSIDSSSNSASLTISGLKTEDEADYYCQSY
DSSNWVFGGGTKLTVLGSRGGGGSGGGGSGGGGSLEMAEVQLVQSGA
EVKKPGSSVKVSCKASGGTFSSYAISWVRQAPGQGLEWMGGIIPIFG
TANYAQKFQGRVTITADESTSTAYMELSSLRSEDTAVYYCARSNYYY
NDYWGQGTLVTVSSTSGQAGQHHHHHHGAYPYDVPDYAS
[SEQ ID NO: 816]
```

TABLE 189

ET200-040

DNA Sequence

```
cagtctgtgttgacgcagccgccctcagtgtctggggcccagggca
gagggtcaccatctcctgcactgggagcagctccaacatcggggcag
gttatgatgtacactggtaccagcagatccaggaacagcccccaaac
tcctcatctatggtaacagcaatcggccctcaggggtccctgaccga
ttctctggctccaagtctggcacctcagcctccctggccatcactgg
gctcctggctgaggatgaggctgattattactgccagtcctatgaca
gcagcctgagtggtggttatgtcttcggaactgggaccaaggtcaccgtc
ctaggttctagaggtggtggtggtagcggcggcggcggctctggtgg
tggtggatccctcgagatggcccaggtgcagctggtgcagtctgggg
ctgaggtgaagaagcctgggggcctcagtgaaggtctcctgcaaggtt
tccggatacacccctcactgaattatccatgcactgggtgcgacaggc
```

TABLE 189-continued

ET200-040

```
tcctggaaaagggcttgagtggatgggaggttttgatcctgaagatg
gtgaaacaatctacgcacagaagttccagggcagagtcaccatgacc
gaggacacatctacagacacagcctacatggagctgagcagcctgag
atctgaggacacgccgtgtattactgtgcgcgctactctggtgtt
actacgattggggtcaaggtactctggtgaccgtctcctcaactagt
ggccaggccggccagcaccatcaccatcaccatggcgcatacccgta
cgacgttccggactacgcttct [SEQ ID NO: 817]
```

Amino Acid Sequence

```
QSVLTQPPSVSGAPGQRVTISCTGSSSNIGAGYDVHWYQQLPGTAPK
LLIYGNSNRPSGVPDRFSGSKSGTSASLAITGLQAEDEADYYCQSYD
SSLSGYVFGTGTKVTVLGSRGGGGSGGGGSGGGGSLEMAQVQLVQSG
AEVKKPGASVKVSCKVSGYTLTELSMHWVRQAPGKGLEWMGGFDPED
GETIYAQKFQGRVTMTEDTSTDTAYMELSSLRSEDTAVYYCARYSGV
YYDWGQGTLVTVSSTSGQAGQHHHHHGAYPYDVPDYAS
[SEQ ID NO: 818]
```

TABLE 190

ET200-041

DNA Sequence

```
aattttatgctgactcagcccactctgtgtcggggtctccggggaa
gacggtaaccatctcctgcaccggcagcagtggcagcattgccgaca
ctttgtgcagtggtaccagcagcgcccgggcggtgtccccaccact
gtgatctttaatgatgacgaaagaccctctggcgtccctgatcggtt
ctctggctccatcgacacctcctccaattctgcctccctcaccatct
ctggactgaagactgaggacgaggctgactactactgtcagtcttat
gataataataatcgaggggtgttcggcggagggaccaagctgaccgt
cctaggttctagaggtggtggtggtagcggcggcggcggctctggtg
gtggtggatccctcgagatggcccaggtacagctgcagcagtcaggt
ccaggactggtgaagccgtccaggaccctctcactctgcagtctgac
gctgaggtgaagaagcctgggtcctcggtgaaggtctcctgcaaggc
ttctggaggcaccttcagcagctatgctatcagctgggtgcgacagg
cccctggacaagggcttgagtggatgggatggatgaaccctaacagt
ggtaacacaggctatgcacagaagttccagggcagagtcaccatgac
caggaacacctccataagcacagcctacatggagctgagcaacctga
gatctgaggacacgccgtgtattactgtgcgcgctactactcttac
ggttacgattggggtcaaggtactctggtgaccgtctcctcaactag
tggccaggccggccagcaccatcaccatcaccatggcgcatacccgt
acgacgttccggactacgcttct [SEQ ID NO: 819]
```

Amino Acid Sequence

```
NFMLTQPHSVSGSPGKTVTISCTGSSSGSIADNFVQWYQQRPGGVPTT
VIFNDDERPSGVPDRFSGSIDTSSNSASLTISGLKTEDEADYYCQSY
DNNNRGVFGGGTKLTVLGSRGGGGSGGGGSGGGGSLEMAQVQLVQSG
AEVKKPGSSVKVSCKASGGTFSSYAISWVRQAPGQGLEWMGWMNPNS
GNTGYAQKFQGRVTMTRNTSISTAYMELSNLRSEDTAVYYCARYYSY
GYDWGQGTLVTVSSTSGQAGQHHHHHGAYPYDVPDYAS
[SEQ ID NO: 820]
```

TABLE 191

ET200-042

DNA Sequence

```
cagtctgtcgtgacgcagccgccctcagtgtctggggccccagggca
gacggtcaccatctcctgcactgggggcagctccaacatcgggacag
gttattttgtaaattggtaccagcaggttccaggaaaagcccccaaa
ctcctcatcctgggtaacaataatcggccctcgggggtccctgaccg
actctccggctccacgtccggcacctcagcctccctggccatcactg
ggctccaggctgaggatgaggtacttattactgccagtcctatgac
agcagcctgagtggttatgtcttcggaactgggaccaaggtcaccgt
cctaggttctagaggtggtggtggtagcggcggcggcggctctggtg
gtggtggatccctcgagatggcccaggtacagctgcagcagtcaggt
ccaggactggtgaagccgtcccagaccctctcactcacctgtgcat
ctccggggacagtgtctctaccaacagtgttgcttggcactggatca
ggcagtccccatcgagaggccttgagtggctgtgggaaggacatactac
aggtccaagtggtctaatgactatggagtatctgtgaaaagtcgaat
caccatcatcccagacacatccaagaaccagttctccctgcagctga
```

---

TABLE 191-continued

ET200-042

```
actctgtgactcccgaggacacggctgtgtattactgtgcgcgctat
cttcttggtaccagatcttcgattactgggctcaaggtactctggtg
accgtctcctcaactagtggccaggccggccagcaccatcaccatca
ccatggcgcatacccgtacgacgttccggactacgcttct
[SEQ ID NO: 821]
```

Amino Acid Sequence

```
QSVVTQPPSVSGAPGQTVTISCTGGSSNIGTGYFVNWYQQVPGKAPK
LLILGNNNRPSGVPDRLSGSTSGTSASLAITGLQAEDEGTYYCQSYD
SSLSGYVEGTGTKVTVLGSRGGGGSGGGGSGGGGSLEMAQVQLQQSG
PGLVKPSQTLSLTCGISGDSVSTNSVAWHWIRQSPSRGLEWLGRTYY
RSKWSNDYGVSVKSRITIIPDTSKNQFSLQLNSVTPEDTAVYYCARS
SSWYQIFDYWGQGTLVTVSSTSGQAGQHHHHHGAYPYDVPDYAS
[SEQ ID NO: 822]
```

TABLE 192

ET200-043

DNA Sequence

```
aattttatgctgactcagccccactctgtgtcggagtctccgggggaa
gacggtaaccatctcctgcaccggcagcagcgacagcatagcccaaca
actatgttcagtggtaccagcagcgcccgggcagtgcccccaccaat
gtgatctacgaagatgtccaaagaccctctggggtccctgatcggtt
ctctgggtccatcgacagctcctccaactctgcctccctcaccatct
ctggactgaagactgaggacgaggctgtctactattgtcagtcttat
catagcagcaatcgtttgggtgttcggcggcgggaccaagctgaccgt
cctaggttctagaggtggtggtggtagcggcggcggcggctctggtg
gtggtggatccctcgagatggcccaggtgcagctggtggagtctggg
ggaggcttggtacagcctggggggtccctgagactctcctgtgcagc
ctctggattcacctttagcagctatgccatgagctgggtccgccagg
ctccagggaaggggctggagtgggtctcagctattagtggtagtggt
ggtagcacatactacgcagactccgtgaagggccggttcaccatctc
cagagacaattccaagaacacgctgtatctgcaaatgaacagcctga
gagccgaggacacggccgtatattactgtgcgcgctctggtgatact
gggactactctgtttacgatgaatggggtcaaggtactctggtgacc
gtctcctcaactagtggccaggccggccagcaccatcaccatcacca
tggcgcatacccgtacgacgttccggactacgcttct
[SEQ ID NO: 823]
```

Amino Acid Sequence

```
NFMLTQPHSVSESPGKTVTISCTGSSDSIANNYVQWYQQRPGSAPTN
VIYEDVQRPSGVPDRFSGSIDSSSNSASLTISGLKTEDEAVYYCQSY
HSDNRWVFGGGTKLTVLGSRGGGGSGGGGSGGGGSLEMAQVQLVESG
GGLVQPGGSLRLSCAASGFTFSSYAMSWVRQAPGKGLEWVSAISGSG
GSTYYADSVKGRFTISRDNSKNTLYLQMNSLRAEDTAVYYCARSGAY
WDYSVYDEWGQGTLVTVSSTSGQAGQHHHHHGAYPYDVPDYAS
[SEQ ID NO: 824]
```

TABLE 193

ET200-044

DNA Sequence

```
cagtctgtgttgactcagccaccctcagtgtccgtgtccccaggaca
gacagccaccatcgcctgttctggacataaattggggggataaatatg
cttcctggtatcagcagaagtcgggccagtccccctgtgttgatcatc
tatcaggataataagcggccctcagggattcctgagcgattctctgg
ctccaactctgggaacacagccactctgaccatcagcgggacccagg
ctctggatgaggctgactattattgtcaggcgtgggacagtagtact
tatgtggcattcggcggagggaccaagctgaccgtcctaggttctag
aggtggtggtggtagcggcggcggcggctctggtggtggtggatccc
tcgagatggcccaggtgcagctgcaggagtccggcccaggactggtg
aagccttcggagaccctgtccctcacctgcgttgtctctggtggctc
catcagcagtagtaactggtggagctgggtccgccagcccccagggga
agggctggagtggattgggaaatctatcatagtgggagccccaac
tacaacccatccctcaagagtcgagtcaccatatcagtagacaagtc
caagaaccagttctccctgaagctgagctctgtgaccgccgcggaca
cggccgtgtattactgtgcgcgcatgactactcatactttcggttac
```

TABLE 193-continued

ET200-044 gatgcttggggtcaaggtactctggtgaccgtctcctcaactagtgg
ccaggccggccagcaccatcaccatcaccatggcgcataccgtacg
acgttccggactacgcttct [SEQ ID NO: 825]

Amino Acid Sequence

QSVLTQPPSVSVSPGQTATIACSGHKLGDKYASWYQQKSGQSPVLII
YQDNKRPSGIPERFSGSNSGNTATLTISGTQALDEADYYCQAWDSST
YVAFGGGTKLTVLGSRGGGGSGGGGSGGGGSLEMAQVQLQESGPGLV
KPSETLSLTCVVSGGSISSSNWWSWVRQPPGKGLEWIGEIYHSGSPN
YNPSLKSRVTISVDKSKNQFSLKLSSVTAADTAVYYCARMTTHTFGY
DAWGQGTLVTVSSTSGQAGQHHHHHHGAYPYDVPDYAS
[SEQ ID NO: 826]

TABLE 194

ET200-045

DNA Sequence cagcctgtgctgactcagccaccctcagtgtcagtggccccaggaaa
gacggccacgattacttgtgggggaaacaacattggaagtgaaagtg
tgcactggtaccaccagaagcaggccaggccctgtgttggtcatc
tatgatgatgccggccggccctcagggatccctgagcgattcactgg
ctccaactctgggaacacggccaccctgaccatcagcagggtcgaag
ccggggatgaggccgactattactgtcaggtgtgggacagaaatagt
gctcagtttgtatcggacctgggaccaaggtcaccgtcctaggttct
agaggtggtggtggtagcggcggcggcggctctggtggtggtggatc
cctcgagatggccgaggccagctggtgcagtctggaggtgaggtga
agaagcctggggcctcagtgaaggtctcctgcaaggcttctggttac
acctttaccagctatggtatcagctgggtgcgacaggcccctggaca
agggcttgagtggatgggatggatcagcgcttacaatggtaacaaa
actatgcacagaagctccaggggcagagtcaccatgaccacagacaca
tccacgagcacagcctacctggagtcgaggcctgagatctgacga
cacggccgtgtattactgtgcgcgcggtgttcatctggattggtggg
gtcaaggtactctggtgaccgtctcctcaactagtggccaggccggc
cagcaccatcaccatcaccatggcgcataccgtacgacgttccgga
ctacgcttct [SEQ ID NO: 827]

Amino Acid Sequence

QPVLTQPPSVSVAPGKTATITCGGNNIGSESVHWYHQKPGQAPVLVI
YDDAGRPSGIPERFTGSNSGNTATLTISRVEAGDEADYYCQVWDRNS
AQFVFGPGTKVTVLGSRGGGGSGGGGSGGGGSLEMAEVQLVQSGAEV
KKPGASVKVSCKASGYTFTSYGISWVRQAPGQGLEWMGWISAYNGNT
NYAQKLQGRVTMTTDTSTSTAYMELRSLRSDDTAVYYCARGVHLDWW
GQGTLVTVSSTSGQAGQHHHHHHGAYPYDVPDYAS
[SEQ ID NO: 828]

TABLE 195

ET200-069

DNA Sequence cagtctgtcgtgacgcagccaccctcagcgtctgggaccccgggca
gagggtcaccatctcttgttctggaagcagctccaacatcggaagta
attatgtatactggtaccagcagctcccaggaacggcccccaaactc
ctcatctatagtaataatcagcggccctcaggggtccctgaccgatt
ctctggctccaagtctggcacctcagcctccctggccatcagtgggc
tccggtccgaggatgaggctgattattactgtgcagcatgggatgac
agcctgagtggttatgtatcgggaccaaggtgaccgtccta
ggttctagaggtggtggtggtagcggcggcggcggctctggtggtgg
tggatccctcgagatggccgaggcagctacagcagtggggcgcag
gactgttgaagccttcggagaccctgtccctcacctgcgctgtctat
ggtgggtccttcagtggttactactggagctggatccgccagccc
agggaagggtctggagtggattgggaaatcaatcatagtggaagca
ccaactacaacccgtccctcaagagtcgagtcaccatatcagtagac
acgtccaagaaccagttctccctgaagctgagctctgtgaccgccgc
ggacacggccgtgtattactgtgcgcgcctgtacgaaggtggttacc TABLE 195-continued

ET200-069 atggttgggttcttggctgtatctgattcttggggtcaaggtactc
tggtgaccgtctcctcaactagtggccaggccggccagcaccatcac
catcaccatggcgcataccgtacgacgttccggactacgcttct
[SEQ ID NO: 829]

Amino Acid Sequence

QSVVTQPPSASGTPGQRVTISCSGSSSNIGSNYVYWYQQLPGTAPKL
LIYSNNQRPSGVPDRFSGSKSGTSASLAISGLRSEDEADYYCAAWDD
SLSGYVFGTGTKLTVLGSRGGGGSGGGGSGGGGSLEMAQVQLQQWGA
GLLKPSETLSLTCAVYGGSFSGYYWSWIRQPPGKGLEWIGEINHSGS
TNYNPSLKSRVTISVDTSKNQFSLKLSSVTAADTAVYYCARLYEGGY
HGWGSWLSSDSWGQGTLVTVSSTSGQAGQHHHHHHGAYPYDVPDYAS
[SEQ ID NO: 830]

TABLE 196

ET200-078

DNA Sequence cagtctgtgttgactcagccaccctcagcgtctgggaccccgggca
gagggtcaccatctcttgttctggaagcagctccaacatcggaagta
atactgtaaactggtaccagcagctcccaggaacggcccccaaactc
ctcatctatagtaataatcagcggccctcaggggtccctgaccgatt
ctctggctccaagtctggcacctcagcctccctggccatcagtgggc
tccagtctgaggatgaggctgattattactgtgcagcatgggatgac
agcctgaatggttattgggtgttcggcggagggaccaagctgaccgt
cctaggttctagaggtggtggtggtagcggcggcggcggctctggtg
gtggtggatccctcgagatggccccaggtgcagctacagcagtggggc
gcaggactgttgaagccttcggagaccctgtccctcacctgcgctgt
ctatggtgggtccttcagtggttactactggagctggatccgccagc
ccccagggaaggggctggagtggattggggaaatcaatcatagtgga
agcaccaactacaacccgtccctcaagagtcgagtcaccatatcagt
agacacgtccaagaaccagttctccctgaagctgagctctgtgaccg
ccgcggacacggctgtgtattactgtgcgcgcgaaggggcatttgat
gcttttgatatctggggccaagggacaatggtcaccgtctcttcaac
tagtggccaggccggccagcaccatcaccatcaccatggcgcatacc
cgtacgacgttccggactacgcttct [SEQ ID NO: 831]

Amino Acid Sequence

QSVLTQPPSASGTPGQRVTISCSGSSSNIGSNTVNWYQQLPGTAPKL
LIYSNNQRPSGVPDRFSGSKSGTSASLAISGLQSEDEADYYCAAWDD
SLNGYWVFGGGTKLTVLGSRGGGGSGGGGSGGGGSLEMAQVQLQQWG
AGLLKPSETLSLTCAVYGGSFSGYYWSWIRQPPGKGLEWIGEINHSG
STNYNPSLKSRVTISVDTSKNQFSLKLSSVTAADTAVYYCAREGAFD
AFDIWGQGTMVTVSSTSGQAGQHHHHHHGAYPYDVPDYAS
[SEQ ID NO: 832]

TABLE 197

ET200-079

DNA Sequence tcctatgagctgactcagccaccctcagcgtctgggaccccgggca
gagggtcaccatctcttgttctggaagcagctccaacatcggaagta
attatgtatactggtaccagcagctcccaggaacggcccccaaactc
ttcatctataggaataatcagcggccctcaggggtccctgaccgatt
ctctggctccaagtctggcacctcagcctccctggccatcagtgggc
tccggtccgaggatgaggctgattattactgtgcagcatgggatgac
agcctgagtggttatctatcggaactgggaccaagctgaccgtccta
ggttctagaggtggtggtggtagcggcggcggcggctctggtggtgg
tggatccctcgagatggccgaggcagctggtggagtctggggggag
gcttggtacagcctggggggtccctgagactctcctgtgcagcctct
ggattcacctttgatgattatgccatgcactgggtccggcaagctcc
agggaaggggctggagtgggtctcaggtattagttggaatagtggta
gcataggctatgcggactctgtgaagggccgattcaccatctccaga
gacaacgccaagaactccctgtatctgcaaatgaacagtctgagagc TABLE 197-continued

ET200-079 tgaggacacggccttgtattactgtgcaaatggcgactccaactact
actacggtatggacgtctggggccaagggaccacggtcaccgtctcc
tcaactagtggccaggccggccagcaccatcaccatcaccatggcgc
atacccgtacgacgttccggactacgcttct [SEQ ID NO: 833]

Amino Acid Sequence

SYELTQPPSASGTPGQRVTISCSGSSSNIGSNYVYWYQQLPGTAPKL
FIYRNNQRPSGVPDRFSGSKSGTSASLAISGLRSEDEADYYCAAWDD
SLSGYLFGTGTKVTVLGSRGGGGSGGGGSGGGGSLEMAEVQLVESGG
GLVQPGRSLRLSCAASGFTFDDYAMHWVRQAPGKGLEWVSGISWNSG
DVWGQGTTVTVSSTSGQAGQHHHHHHGAYPYDVPDYAS
[SEQ ID NO: 834]

TABLE 198

ET200-081

DNA Sequence cagtctgccctgactcagcctgcctccgtgtccgggtctcctggaca
gtcgatcaccatctcctgcactggaaccagcagtgacattggtggtt
ataactatgtctcctggtaccaacaacacccaggcaaagcccccaaa
ctcatgatttatgatgtcagtaatcggccctcaggggtttctaatcg
cttctctggctccaagtctggcaacacggcctccctgaccatctctg
ggctccaggctgaggacgaggctgattattactgcatctcatataca
cgcacctggaacccctatgtcttcgggagtgggaccaaggtcaccgt
cctaggttctagaggtggtggtggtagcggcggcggcggctctggtg
gtggtggatccctcgagatggccgaggtgcagctggtgcagtctggg
ggaggcgtggtacagcctgggggtccctgagactctcctgtgcagc
ctctggattcacctttgatgattatgccatgcactgggtccgtcaag
ctccagggaagggtctggagtgggtctctcttattagtggggatggt
ggtagcacatactatgcagactctgtgaagggccgattcaccatctc
cagagacaacagcaaaaactccctgtatctgcaaatgaacagtctga
gaactgaggacaccgccttgtattactgtgcaaaagatcgggcagca
gctggctactactactacggtatggacgtctggggccaagggaccac
ggtcaccgtctcctcaactagtggccaggccggccagcaccatcacc
atcaccatggcgcatacccgtacgacgttccggactacgcttct
[SEQ ID NO: 835]

Amino Acid Sequence

QSALTQPASVSGSPGQSITISCTGTSSDIGGYNYVSWYQQHPGKAPK
LMIYDVSNRPSGVSNRFSGSKSGNTASLTISGLQAEDEADYYCISYT
RTWNPYVFGSGTKVTVLGSRGGGGSGGGGSGGGGSLEMAEVQLVQSG
GGVVQPGGSLRLSCAASGFTFDDYAMHWVRQAPGKGLEWVSLISGDG
GSTYYADSVKGRFTISRDNSKNSLYLQMNSLRTEDTALYYCAKDRAA
AGYYYYGMDVWGQGTTVTVSSTSGQAGQHHHHHHGAYPYDVPDYAS
[SEQ ID NO: 836]

TABLE 199

ET200-097

DNA Sequence ctgcctgtgctgactcagccaccctcagtgtccgtgtcccaggaca
gacagccatcatcacctgctctggagataaattgggggaaaaatatg
tttcctggtatcagcagaagccaggccagtccctgtactggtcatc
gatcaagataccaggaggccctcagggatccctgagcgattctctgg
ctccaactctgggaccacagccactctgaccatcagcgggacccagg
ctatggatgaggctgactattactgtcaggcgtggacagagtgtg
gtattcggcggagggaccaagctgaccgtcctaggttctagaggtg
tggtggtagcggcggcggcggctctggtggtggtggatccctcgaga
tggccgaggtgcagctggtggagtctgggggagacttggtacagcct
ggcaggtccctgagactctcctgtgcagcctctggattcacctttaa
tgattatgccatgcactgggtccgtcaagctccagggaagggcctgg
agtgggtctcaggtattagttggagtggtaataacataggctatgcg
gactctgtgaagggccgattcaccatctcagagacaacgccaagaa
ctccctgtatctgcaaatgaacagtctgagagctgaggacacggcct TABLE 199-continued

ET200-097 tgtattactgtgcaaaagatagtatacggtatggcatcacctgggga
ggttttgactactggggccagggaaccctggtcaccgtctcctcaac
tagtggccaggccggccagcaccatcaccatcaccatggcgcatacc
cgtacgacgttccggactacgcttct [SEQ ID NO: 837]

Amino Acid Sequence

LPVLTQPPSVSVSPGQTAIITCSGDKLGEKYVSWYQQKPGQSPVLVI
DQDTRRPSGIPERFSGSNSGTTATLTISGTQAMDEADYYCQAWDRGV
VFGGGTKLTVLGSRGGGGSGGGGSGGGGSLEMAEVQLVESGGDLVQP
GRSLRLSCAASGFTFNDYAMEIWVRQAPGKGLEWVSGISWSGNNIGY
ADSVKGRFTISRDNAKNSLYLQMNSLRAEDTALYYCAKDSIRYGITW
GGFDYWGQGTLVTVSSTSGQAGQHHHHHHGAYPYDVPDYAS
[SEQ ID NO: 838]

TABLE 200

ET200-098

DNA Sequence cagcctgtgctgactcagccaccctcggtgtccaagggcttgagacaga
ccgccacactcacctgcactgggaacagcaacaatgttggcaacctagg
agtagcttggctgcagcagcaccagggccaccctcccaaactcctatcc
tacaggaataacaaccggccctcagggatctcagagagagattatctgcat
ccaggtcaggaaacacagcctccctgaccattactggactccagcctga
ggacgaggctgactattactgctcagcatgggacagtagcctcagtgct
tgggtgttcggcggagggaccaagctgaccgtcctaggttctagaggtg
gtggtggtagcggcggcggcggctctggtggtggtggatccctcgagat
ggccgaggtgcagctggtggagtctgggggagtcgtggtacagcctggg
gggtccctgagactctcctgtgcagcctctggattcacctttgatgatt
atgccatgcactgggtccgtcaagctccagggaagggctctggagtgggt
ctctcttattaattgggatggtggtagcacctactatgcagactctgtg
aagggtcgattcaccatctccagagacaacagcaaaaactccctgtatc
tgcaaatgaacagtctgagagctgaggacaccgccttgtattactgtgc
aaaaggatgggcctgggagcttttgactactggggccaggggaaccctg
gtcaccgtctcctcaactagtggccaggccggccagcaccatcaccatc
accatggcgcatacccgtacgacgttccggactacgcttct
[SEQ ID NO: 839]

Amino Acid Sequence

QPVLTQPPSVSKGLRQTATLTCTGNSNNVGNLGVAWLQQHQGHPPKLLS
YRNNNRPSGISERLSASRSGNTASLTITGLQPEDEADYYCSAWDSSLSA
WVFGGGTKLTVLGSRGGGGSGGGGSGGGGSLEMAEVQLVESGGVVVQPG
GSLRLSCAASGFTFDDYAMHWVRQAPGKGLEWVSLINWDGGSTYYADSV
KGRFTISRDNSKNSLYLQMNSLRAEDTALYYCAKGMGLRAFDYWGQGTL
VTVSSTSGQAGQHHHHHHGAYPYDVPDYAS
[SEQ ID NO: 840]

TABLE 201

ET200-099

DNA Sequence cagtctgtgttgactcagccaccctcagcgtctgggaccccgggcaga
gggtcaccatctcctgttctggaagcagctccaacatcggaagtaatac
tgtaaactggtaccagcagctcccaggaacggcccccaaactcctcatc
tatagtaatgatcagcggccctcagggtccctgaccgattctctggct
ccaagtccggcaccctcagcctccctggccatcagtgggctccagtctga
ggatgaggctgattattactgtgcttcatgggatgacagctgaatggc
cgttatgtcttcggaactgggaccaaggtcaccgtcctaggttctagag
gtggtggtagcggcggcggcggctctggtggtggtggatccctcga
gatgggccaggtgcagctggtacagtctgggggctgaggtgaggaagcct
gggggcctcagtgaaggtttcctgcaagacttctggatacacccttcagtt
ggtatgctatacattgggtgcgccaggcccccggacaaaggcttgagtg
gatgggatggatcaacgctggcaatggaaacacaaaatattcacagaaa

TABLE 201-continued

ET200-099

```
tttcagggcagagtcagtcttaccagggacacatccgcgagcacagcct
acatggagctgagcagcctgagatctgatgacacggctgtgtgattactg
tgcgagacccgataattatggttcgggtggggatgtttttgatatctg
ggccaagggacaatggtcaccgtctcttcaactagtggccaggccggc
agcaccatcaccatcaccatggcgcatacccgtacgacgttccggacta
cgcttct [SEQ ID NO: 841]
```

Amino Acid Sequence

```
QSVLTQPPSASGTPGQRVTISCSGSSSNIGSNTVNWYQQLPGTAPKLLI
YSNDQRPSGVPDRFSGSKSGTSASLAISGLQSEDEADYYCASWDDSLNG
RYVFGTGTKVTVLGSRGGGGSGGGGSGGGGSLEMAQVQLVQSGAEVRKP
GASVKVSCKTSGYTFSWYAIHWVRQAPGQRLEWMGWINAGNGNTKYSQK
FQGRVSLTRDTSASTAYMELSSLRSDDTAVYYCARPDNYGSGGDVFDIW
GQGTMVTVSSTSGQAGQHHHHHHGAYPYDVPDYAS
[SEQ ID NO: 842]
```

TABLE 202

ET200-100

DNA Sequence

```
aattttatgctgactcagcccactctgtgtcggagtctccggggaaga
cggtaaccatctcctgcacccgcagcagtggcagcattgccagcaactt
tgtgcagtggtaccagcagcgcccgggcagtgccccaccctatgatc
tatgaggataacaacagacccctggggtccctgatcggttctctgcct
ccgtcgacagctcctccaactctgcctccctcaccatctctggactgaa
gactgaggacgaggctgactactactgtcagtcttatgataccagcaat
gtggtattcggcggggggaccaagctgaccgtcctaggttctagaggtg
gtggtggtagcggcggcggcggctctggtggtggtggatccctcgagat
ggccgaggtcagctggtgagtctggggaggcttggtacagcctgga
gggtccctgagactctcctgtgcagcctctggattcaccttcagtagtt
atgaaatgaactgggtccgccaggctccaggaaggggctgtttattactgt
ttcatacattagtagtagtggtagtaccatatactacgcagactctgtg
aagggccgattcaccatctccagagacaacgccaagaactcactgtatc
tgcaaatgaacagcctgagagcgaggacacggctgtttattactgtg
acgctgggactacgtatggacgtctgggggccaagggaccacggtcacc
gtctcctcaactagtggccaggccggccagcaccatcaccatcaccatg
gcgcatacccgtacgacgttccggactacgcttct
[SEQ ID NO: 843]
```

Amino Acid Sequence

```
NFMLTQPHSVSESPGKTVTISCTRSSGSIASNFVQWYQQRPGSAPTPMI
YEDNNRPPGVPDRFSASVDSSSNSASLTISGLKTEDEADYYCQSYDTSN
VVFGGGTKLTVLGSRGGGGSGGGGSGGGGSLEMAEVQLVESGGGLVQPG
GSLRLSCAASGFTFSSYEMNWVRQAPGKGLEWVSYISSSGSTIYYADSV
KGRFTISRDNAKNSLYLQMNSLRAEDTAVYYCARWDYGMDVWGQGTTVT
VSSTSGQAGQHHHHHHGAYPYDVPDYAS
[SEQ ID NO: 844]
```

TABLE 203

ET200-101

DNA Sequence

```
caggctgtgctgactcagccaccctcagcgtctggggcccccgggcaga
gggtcaccgtctcttgttctggaagcaactccaacatcggaagtaacta
cgttaactggtaccagcagttcccaggaacggcccccaaactcctcatg
tatagtagtagtcagcggcccctcagggtccctgaccgattctctggct
ccaagtctggcacctcagcctccctggccatcagtgggctccactctga
ggatgaggctgattattactgtgctacatgggatgacagcctgaatgct
tgggtgttcggcggagggaccaagctgaccgtcctaggttctagaggtg
gtggtggtagcggcggcggcggctctggtggtggtggatccctcgagat
ggccgaggtccagctggtgcagtctggggctgaggtgaagaagcctggg
gcctcagtgaaggtttcctgcaaggacttctggatacaccttcactt ggt
atgctatacattgggtgcgccagcccccccggacaaagggcttgagtggat
gggatggatcaacgctggcagtggaaacacaaaatattcacagaaatt
cagggcagagtcaccccttaccagggacacatccgcgagcacagcgtaca
tggagctgagcagcctgagatctgatgacacggctgtgtattactgtgc
gagacccaataactatggttcgggtggggatgtttttgatatctggggc
```

TABLE 203-continued

ET200-101

```
caagggacaatggtcaccgtctcttcaactagtggccaggccggccagc
accatcaccatcaccatggcgcatacccgtacgacgttccggactacgc
ttct [SEQ ID NO: 845]
```

Amino Acid Sequence

```
QAVLTQPPSASGAPGQRVTVSCGSGSNSNIGSNYVNWYQQFPGTAPKLLM
YSSSQRPSGVPDRFSGSKSGTSASLAISGLHSEDEADYYCATWDDSLNA
WVFGGGTKLTVLGSRGGGGSGGGGSGGGGSLEMAEVQLVQSGAEVRKPG
ASVKVSCKTSGYTFTWYAIHWVRQAPGQRLEWMGWINAGSGNTKYSQKF
QGRVTLTRDTSASTAYMELSSLRSDDTAVYYCARPNNYGSGGDVFDIWG
QGTMVTVSSTSGQAGQHHHHHHGAYPYDVPDYAS
[SEQ ID NO: 846]
```

TABLE 204

ET200-102

DNA Sequence

```
cagtctgtcgtgacgcagccgccctcagtgtctgcggccccaggacaga
aggtcaccatctcctgctctggaagcagctccaacattgggaataatta
tgtatcctggtaccagcagctcccaggaacagcccccaaactcctcatt
tatgacaataataagcgaccctcagggattcctgaccgattctctggct
ccaagtctggcacgtcagccaccctgggcatcaccggactccagactgg
ggacgaggccgattattactgcggaacatgggatagcagcctgagtgct
tatgtcttcggaactgggaccaaggtcaccgtcctaggttctagaggtg
gtggtggtagcggcggcggcggctctggtggtggtggatccctcgagat
ggcccaggtccagctggtgcagtctggggctgaggtgaagaagcctggg
gcctcagtgaaagtttcctgcaaggcttctggatacacctttcacgaact
atgctctgcatttgggtgcgccaggcccccggacaagggcttgagtggat
ggcatggatcaacgctggcaatggtaacacaaaatattcacagaacttc
cagggcagagtcaccattaccagggacacatccgcgagcacagcctata
tggagctgagcagcctgagatctgaagacacggctgtgtattactgtgc
gaaaccggaggaaacagctggaacaatccactttgactactggggccag
ggaacccccggtcaccgtctcctcaactagtggccaggccggccagcacc
atcaccatcaccatggcgcatacccgtacgacgttccggactacgcttc
t [SEQ ID NO: 847]
```

Amino Acid Sequence

```
QSVVTQPPSVSAAPGQKVTISCGSGSSNIGNNYVSWYQQLPGTAPKLLI
YDNNKRPSGIPDRFSGSKSGTSATLGITGLQTGDEADYYCGTWDSSLSA
YVFGTGTKVTVLGSRGGGGSGGGGSGGGGSLEMAQVQLVQSGAEVKKPG
ASVKVSCKASGYTFTNYALHWVRQAPGQGLEWMAWINGGNGNTKYSQNF
QGRVTITRDTSASTAYMELSSLRSEDTAVYYCAKPEETAGTIHFDYWGQ
GTPVTVSSTSGQAGQHHHHHHGAYPYDVPDYAS
[SEQ ID NO: 848]
```

TABLE 205

ET200-103

DNA Sequence

```
caggctgtgctgactcagccccactctgtgtcggagtctccggggaaga
cggtaaccatctcctgcacccgcagcagtggcagcattgccagcaacta
tgtgcagtggtaccagcagcgcccgggcagtgccccaccactgtgatc
tatgaggataaccaaagaccctctggggtccctgatcggttctctggct
ccatcgacagctcctccaactctgcctccctcaccatctctggactgaa
gactgaggacgaggctgactactactgtcagtcttatgatagcaccatc
acgtgttcggcggagggaccaagctgaccgtcctaggttctagaggtg
gtggtggtagcggcggcggcggctctggtggtggtggatccctcgagat
ggcccaggtccagctggtacagtctggggctgaggtgaagaagcctggg
tcctcggtgaaggtctcctgcaaggcttctggaggcaccttcagcagct
atgctatcagctggtgcgacaggcccctggacaagggcttgagtggat
gggagggatcatccctatctttggtacagcaaactacgcacagaagttc
cagggcagagtcacgattaccgcggacgaatccacgagcacagcctaca
tggagctgagcagcctgagatctgagagacggctgtgtattactgtgc
ggggaggggttactatatagtagtggttattccaacggtgatgctttt
gatatctgggggccaagggacaatggtcaccgtctcttcaactagtggcc
aggccggccagcaccatcaccatcaccatggcgcatacccgtacgacgt
tccggactacgcttct [SEQ ID NO: 849]
```

TABLE 205-continued

ET200-103

Amino Acid Sequence

QAVLTQPHSVSESPGKTVTISCTRSSGSIASNYVQWYQQRPGSAPTTVI
YEDNQRPSGVPDRFSGSIDSSSNSASLTISGLKTEDEADYYCQSYDST
ITVFGGGTKLTVLGSRGGGGSGGGGSGGGGSLEMAQVQLVQSGAEVKK
PGSSVKVSCKASGGTFSSYAISWVRQAPGQGLEWMGGIIPIFGTANYA
QKFQGRVTITADESTSTAYMELSSLRSEDTAVYYCAGEGYYDSSGYSN
GDAFDIWGQGTMVTVSSTSGQAGQHHHHHHGAYPYDVPDYAS
[SEQ ID NO: 850]

TABLE 206

ET200-104

DNA Sequence aattttatgctgactcagcccactctgtgtcggagtctccggggaaga
cggtaaccatctcctgcacccgcagcagtggcagcattgccagcaacta
tgtgcagtggtaccagcagcgcccgggcagtgcccccaccactgtgatc
tatgaggataaccaaagaccctctggggtccctgatcggttctctggct
ccatcgacagctcctccaactctgcctccctcaccatctctggactgaa
gactgaggacgaggctgactactactgtcagtcttatgatagcagcaat
gtggtattcggcggagggaccaaggtcaccgtcctaggttctagaggtg
gtggtggtagcggcggcggcggctctggtggtggtggatccctcgagat
ggccgaggtgcagctggtggagtctgggggaggcttggtacagcctgga
gggtccctgagactctcctgtgcagcctctggattcaccttcagtagtt
atgaaatgaactgggtccgccaggctccagggaaggggctggagtgggt
ttcatacattagtagtagtggtagtatactacgcagactctgtg
aagggccgattcaccatctccagagacaacgccaagaactcactgtatc
tgcaaatgaacagcctgagagccgaggacacggctgtttattactgtgc
acgctgggactacggtatggacgtctggggccaagggaccacggtcacc
gtctcctcaactagtggccaggccggccagcaccatcaccatcaccatg
gcgcataccgtacgacgttccggactacgcttct
[SEQ ID NO: 851]

Amino Acid Sequence

NFMLTQPHSVSESPGKTVTISCTRSSGSIASNYVQWYQQRPGSAPTTVI
YEDNQRPSGVPDRFSGSIDSSSNSASLTISGLKTEDEADYYCQSYDSSN
VVFGGGTKVTVLGSRGGGGSGGGGSGGGGSLEMAEVQLVESGGGLVQPG
GSLRLSCAASGFTFSSYEMNWVRQAPGKGLEWVSYISSSGSTIYYADSV
KGRFTISRDNAKNSLYLQMNSLRAEDTAVYYCARWDYGMDVWGQGTTVT
VSSTSGQAGQHHHHHHGAYPYDVPDYAS
[SEQ ID NO: 852]

TABLE 207

ET200-105

DNA Sequence tcctatgtgctgactcagccaccctcagtgtccgtgtcccaggacaga
cagccagcatcacctgctctgagatagattgacgaataaatatgtttc
ctggtatcaacagaagccaggccagtcccctgtgttggtcatctatgag
gatgccaagcggccctcagggatccctgcgcgattctctggctccaact
ctgggaacacagccactctgaccatcagcgggacccaggctatggatga
gtctgaatattactgtcaggcgtgggacagcagtgtgtggtttttggc
ggagggaccaaggtgaccgtcctaggttctagaggtggtggtggtagcg
gcggcggcggctctggtggtggtggatccctcgagatggccgaggtgca
gctggtggagtctgggggaggcttggtacagcctggcaggtccctgaga
ctctcctgtgcagcctctggattcacctttgatgattatgccatgcact
gggtccggcaagtccaggaaggggctggagtgggtctcaggtattag
ttggaatagtggtagtataggctatgcggactctgtgaagggccgattc
accatctccagagacaacgccaagaactccctgtatctgcaaatgaaca
gtctgagagatgaggacacggccttgtattactgtgcaaaagaccgagg
ggggggagttatcgttaaggatgcttttgatatctggggccaagggaca
atggtcaccgtctcttcaactagtggccaggccggccagcaccatcacc
atcaccatggcgcatacccgtacgacgttccggactacgcttct
[SEQ ID NO: 853]

TABLE 207-continued

ET200-105

Amino Acid Sequence

SYVLTQPPSVSVSPGQTASITCSGDRLTNKYVSWYQQKPGQSPVLVIYE
DAKRPSGIPARFSGSNSGNTATLTISGTQAMDESEYYCQAWDSSVVVFG
GGTKLTVLGSRGGGGSGGGGSGGGGSLEMAEVQLVESGGGLVQPGRSLR
LSCAASGFTFDDYAMHWVRQAPGKGLEWVSGISWNSGSIGYADSVKGRF
TISRDNAKNSLYLQMNSLRDEDTALYYCAKDRGGGVIVKDAFDIWGQGT
MVTVSSTSGQAGQHHHHHHGAYPYDVPDYAS
[SEQ ID NO: 854]

TABLE 208

ET200-106

DNA Sequence tcctatgagctgactcagccacccgcagcgtctgggacccccggaca
gagagtcaccatctcttgttctggggggcgtctccaacatcgggagtg
gtgctctaaattggtaccagcaactcccaggaacggcccccaaactc
ctcatctatagttacaatcagcggccctcaggggtctctgaccgatt
ctctggctccaggtctgccacctcagcctccctggccatcagtgggc
tccagtctgaggatgaggctgattattactgtgcaacctgggatgat
agtgtgaatggtgggtgttcggcggagggaccaagctgaccgtcct
aggttctagaggtggtggtggtagcggcggcggcggctctggtggtg
gtggatccctcgagatggccgaggtgcagctggtggagtctggggct
gaggtgaagaagcctgggattcagtgaaggtctcctgcaagccttc
tggttacaattttctcaactatggtatcaactgggtgcgacaggccc
ctggacaagggcttgagtggatgggatggattagcacttacaccggt
aacacaaatatgcacagaagctgcaggcagagagtcaccttcaccac
agacacatccacgagcacagcctcacatggagatgaggagcctgagat
ctgacgacacggccgtgtattactgtgcgcgccagcaggtggtggt
tggtacgatgtttggggtcaaggtactctggtcaccgtctcctcaac
tagtggccaggccggccagcaccatcaccatcaccatggcgcatacc
cgtacgacgttccggactacgcttct [SEQ ID NO: 855]

Amino Acid Sequence

SYELTQPPAASGTPGQRVTISCSGGVSNIGSGALNWYQQLPGTAPKL
LIYSYNQRPSGVSDRFSGSRSATSASLAISGLQSEDEADYYCATWDD
SVNGWVFGGGTKLTVLGSRGGGGSGGGGSGGGGSLEMAEVQLVESGA
EVKKPGDSVKVSCKPSGYNFLNYGINWVRQAPGQGLEWMGWISTYTG
NTNYAQKLQGRVTFTTDTSTSTAYMEMRSLRSDDTAVYYCARQQGGG
WYDVWGQGTLVTVSSTSGQAGQHHHHHHGAYPYDVPDYAS
[SEQ ID NO: 856]

TABLE 209

ET200-107

DNA Sequence cagtctgtcgtgacgcagccgccctcagtgtctgcggccccaggaga
gaaggtcaccatctcctgctctggaagcaacttcaatgttggaaaata
atgatgtatcctggtatcagcaactcccaggtgcagccccaaactc
ctcatttatgacaataataagcgaccctcagggattcctgaccgatt
ctctggctccaagtctggcacgtcagccaccctggacatcaccgggc
tccacagtgacgacgaggccgattattactgcggaacatgggatagc
agcctgagtactggggggtcttcggaactggacaaggctcaccgt
cctaggttctagaggtggtggtagcggcggcggcggctctggtg
gtggtggatccctcgagatggccgaggtccagctggtgcagtctgga
gctgaggtgaagaagcctgggcctcagtgaaggtctcctgcaaggc
ttctggttcaacctttaccagctatactatcagctgggtacgacagg
ccccggacaagggcttgagtggatgggatggatcagcacttacaat
ggtctcacaaactatgcacagaacctccaggggcagagtcaccatgac
tacagacacattcacgaccacagcctacatggagctgaggagcctca
gatctgacgacacggccgtgtattactgtgcgagaggggcctgcat
gactacggtgacttcgcgtcctttgactactggggccagggaaccct
ggtcaccgtctcctcaactagtggccaggccggccagcaccatcacc
atcaccatggcgcatacccgtacgacgttccggactacgcttct
[SEQ ID NO: 857]

TABLE 209-continued

ET200-107

Amino Acid Sequence

QSVVTQPPSVSAAPGEKVTISCSGSNFNVGNNDVSWYQQLPGAAPKL
LIYDNNKRPSGIPDRFSGSKSGTSATLDITGLHSDDEADYYCGTWDS
SLNTGGVFGTGTKVTVLGSRGGGGSGGGGSGGGGSLEMAEVQLVQSG
AEVKKPGASVKVSCKASGYTFTSYTISWVRQAPGQGLEWMGWISTYN
GLTNYAQNLQGRVTMTTDTFTTTAYMELRSLRSDDTAVYYCVREGSP
DYGDFASFDYWGQGTLVTVSSTSGQAGQHHHHHHGAYPYDVPDYAS
[SEQ ID NO: 858]

TABLE 210

ET200-108

DNA Sequence cagtctgtgttgacgcagccgccctcagtgtctgcgcccccgggaca
gaaggtcaccatctcctgctctggaagcagctccaacattgggaata
attatgtatcctggtaccagcagttcccaggaacagcccccaaactc
ctcatttatgacaataataagcgaccctcagggatttctgaccgatt
ctctggctccaagtctggcacgtcagccaccctgggcatcgccggac
tccagactggggacgaggccgattattactgcggaacatgggatacc
agcctgagtggttttttatgtatcgggaagtgggaccaaggtcaccgtc
ctaggttctagaggtggtggtggtagcggcggcggcggctctggtgg
tggtggatccctcgagatggccgaggccagctggtacagtctggag
ctgaggtgaagaagcctggggcctcagtgaaggtctcctgcaaggct
tctggttacacctttaccagctatactatcagctgggtacgacaggc
ccctggacaagggcttgagtggatgggatggatcagcacttacaatg
gtctcacaaactatgcacagaacctccagggcagagtcaccatgact
acagacacattcacgaccacagcctacatggagctgaggagcctcag
atctgacgacacggccgtgtattactgtgagagaggggtccccccg
actacggtgacttcgcgtcctttgactactggggccaggggaacctg
gtcaccgtctcctcaactagtggccaggccggccagcaccatcacca
tcaccatggcgcatacccgtacgacgttccggactacgcttct
[SEQ ID NO: 859]

Amino Acid Sequence

QSVLTQPPSVSAPPGQKVTISCSGSSSNIGNNYVSWYQQFPGTAPKL
LIYDNNKRPSGISDRFSGSKSGTSATLGIAGLQTGDEADYYCGTWDT
SLSGFYVFGSGTKVTVLGSRGGGGSGGGGSGGGGSLEMAEVQLVQSG
AEVKKPGASVKVSCKASGYTFTSYTISWVRQAPGQGLEWMGWISTYN
GLTNYAQNLQGRVTMTTDTFTTTAYMELRSLRSDDTAVYYCVREGSP
DYGDFASFDYWGQGTLVTVSSTSGQAGQHHHHHHGAYPYDVPDYAS
[SEQ ID NO: 860]

TABLE 211

ET200-109

DNA Sequence ctgcctgtgctgactcagccaccctcagcgtctgcgaccccgggca
gagggtcaccatctcttgttctggaaccacctccaacatcggaagta
atactgtacactggtaccagcagctcccagggacggcccccaaactc
ctcatctataataataatcagcgggccctcaggggtccctgaccgatt
ctctggctccaagtctggcacctcagcctccctggccatcagtgggc
tccggtccgaggatgaggctacatattcctgtgcaacatgggatgac
agcctgagtggtgtggtcttcggcggagggaccaagctgaccgtcct
aggttctagaggtggtggtggtagcggcggcggcggctctggtggtg
gtggatccctcgagatggcccgaggccagctggtgcagtctgggct
gaggtgaagaagcctgggtcctcggtgaaggtctcctgcaaggcttc
tggaggcaccttcagcagctatgctatcagctgggtgcgacaggccc
ctggacaagggcttgagtggatggggagggatcatccctatctttggt
acagcaaactacgcacagaagttccaggggcagagtcacgattaccgc
ggacgaatccacgagcacagcctacatggagctgagcagcctgagat
ctgaggacacggccgtgtattactgtgcgagagatccgcctacggt
gactacggtattgctttttgatatctggggccaagggacaatggt
caccgtctcttcaactagtggccaggccggccagcaccatcaccatc
accatggcgcatacccgtacgacgttccggactacgcttct
[SEQ ID NO: 861]

TABLE 211-continued

ET200-109

Amino Acid Sequence

LPVLTQPPSASATPGQRVTISCSGTTSNIGSNTVHWYQQLPGTAPKL
LIYNNNQRPSGVPDRFSGSKSGTSASLAISGLRSEDEATYSCATWDD
SLSGVVFGGGTKLTVLGSRGGGGSGGGGSGGGGSLEMAEVQLVQSGA
EVKKPGSSVKVSCKASGGTFSSYAISWVRQAPGQGLEWMGGIIPIFG
TANYAQKFQGRVTITADESTSTAYMELSSLRSEDTAVYYCARDPAYG
DYEYDAFDIWGQGTMVTVSSTSGQAGQHHHHHHGAYPYDVPDYAS
[SEQ ID NO: 862]

TABLE 212

ET200-110

DNA Sequence cagtctgtgttgacgcagccgccctcagcgtctgggaccccgggca
gagggtcaccatctcttgttctggaagcagctccaacatcggaacta
atggtgtaaactggttccagcagttcccaggaacggcccccaaactc
ctcatctatactaatgatcagcggccctcaggggtccctgaccgatt
ctctggctccaagtctggcacctcagcctccctggccatcagtgggc
tccagtctgcggatgaggctgattattactgtgcagtgggaccac
agcctgaatggtccggtgttcggcggagggaccaagctgaccgtcct
aggttctagaggtggtggtggtagcggcggcggcggctctggtggtg
gtggatccctcgagatggcccaggtgcagctggtgcagtctggg.gct
gaggtgaagaagcctgggtcctcggtgaaggtctcctgcaaggcttc
tggaggcaccttcagcagctatgctatcagctgggtgcgacaggccc
ctggacaagggcttgagtggatgggagggatcatccctatctttggt
acagcaaactacgcacagaagttccagggcagagtcacgattaccgc
ggacgaatccacgagcacagcctacatggagctgagcagcctgagat
ctgaggacacggccgtgtattactgtgcgagaggggccggttttgat
gcttttgatatctggggccaagggacaatggtcaccgtctcttcaac
tagtggccaggccggccagcaccatcaccatggcgcatacc
cgtacgacgttccggactacgcttct [SEQ ID NO: 863]

Amino Acid Sequence

QSVLTQPPSASGTPGQRVTISCSGSSSNIGTNGVNWFQQFPGTAPKL
LIYTNDQRPSGVPDRFSGSKSGTSASLAISGLQSADEADYYCAVWDH
SLNGPVFGGGTKLTVLGSRGGGGSGGGGSGGGGSLEMAQVQLVQSGA
EVKKPGSSVKVSCKASGGTFSSYAISWVRQAPGQGLEWMGGIIPIFG
TANYAQKFQGRVTITADESTSTAYMELSSLRSEDTAVYYCARGAGFD
AFDIWGQGTMVTVSSTSGQAGQHHHHHHGAYPYDVPDYAS
[SEQ ID NO: 864]

TABLE 213

ET200-111

DNA Sequence caggctgtgctgactcagccaccctcagcgtctgggaccccgggca
gagggtcaccatctcttgttctggaagcagctccaacatcggaagta
atactgtaaactggttaccagcagctcccaggaacggcccccaaactc
ctcatctatagtaataatcagcggccctcaggggtccctgaccgatt
ctctggctccaagtctggcacctcagcctccctggccatcagtgggc
tccagtctgaggatgattattactgtgcagatgggatgac
agcctgaatggttatgtcttcggaactgggaccaagtcaccgtcct
aggttctagaggtggtggtggtagcggcggcggcggctctggtggtg
gtggatccctcgagatggcccaggtgcagctacagcagtggggcgca
ggactgttgaagccttcggagaccctgtccctcacctgcgctgtcta
tggtgggtccttcagtggttactactggagctggatccgccagccc
caggggaaggggctggagtggattggggaaatcaatcatagtggaagc
accaactacaacccgtccctcaagagtcgagtcaccatatcagtaga
cacgtccaagaaccagttctccctgaagctgagctctgtgaccgccg
cggacacggctgtgtattactgtgcgagagaggggctagatgcttttt
gatatctggggccaagggacaatggtcaccgtctcttcaactagtgg
ccaggccggccagcaccatcaccatcaccatggcgcatacccgtacg
acgttccggactacgcttct [SEQ ID NO: 865]

TABLE 213-continued

ET200-111

Amino Acid Sequence

QAVLTQPPSASGTPGQRVTISCSGSSSNIGSNTVNWYQQLPGTAPKL
LIYSNNQRPSGVPDRFSGSKSGTSASLAISGLQSEDETDYYCAAWDD
SLNGYVFGTGTKVTVLGSRGGGGSGGGGSGGGGSLEMAQVQLQQWGA
GLLKPSETLSLTCAVYGGSFSGYYWSWIRQPPGKGLEWIGEINHSGS
TNYNPSLKSRVTISVDTSKNQFSLKLSSVTAADTAVYYCAREGLDAF
DIWGQGTMVTVSSTSGQAGQHHHHHHGAYPYDVPDYAS
[SEQ ID NO: 866]

TABLE 214

ET200-112

DNA Sequence caggctgtgctgactcagccaccctcagcgtctgggaccccgggca
gagggtcaccatctcttgttctggaagcagctccaacatcggaagta
atactgtaaactggtaccagcagctcccaggaacggcccccaaactc
ctcatgtatagtaatgatcagcggccctcaggggtccctgaccgatt
ctctggctccaagtctggcacctcagcctccctggccatcagtgggc
tccagtctgaggatgaggctgattattattgtgcagcatgggatgac
agcctgaatggttatgtcttcgcagctgggacccagctcaccgtttt
aagttctagaggtggtggtggtagcggcggcggcggctctggtggtg
gtggatccctcgagatggcccaggtcagctacagcagtggggcga
ggactgttgaagccttcggagaccctgtccctcacctcgcgctgtcta
tggtgggtccttcagtggttactactggagctggatccgccagcccc
cagggaaggggctggagtggattgggaaatcaatcatagtggaagc
accaactacaacccgtccctcaagagtcgagtcaccatatcagtaga
cacgtccaagaaccagttctccctgaagctgagctctgtgaccgccg
cggacacggctgtgtattactgtgcgagagagggggctagatgcttt
gatatctggggccaagggacaatggtcaccgtctcttcaactagtgg
ccaggccggccagcaccatcaccatcaccatggcgcataccgtacg
acgttccggactacgcttct [SEQ ID NO: 867]

Amino Acid Sequence

QAVLTQPPSASGTPGQRVTISCSGSSSNIGSNTVNWYQQLPGTAPKL
LMYSNDQRPSGVPDRFSGSKSGTSASLAISGLQSEDEADYYCAAWDD
SLNGYVFAAGTQLTVLSSRGGGGSGGGGSGGGGSLEMAQVQLQQWGA
GLLKPSETLSLTCAVYGGSFSGYYWSWIRQPPGKGLEWIGEINHSGS
TNYNPSLKSRVTISVDTSKNQFSLKLSSVTAADTAVYYCAREGLDAF
DIWGQGTMVTVSSTSGQAGQHHHHHHGAYPYDVPDYAS
[SEQ ID NO: 868]

TABLE 215

ET200-113

DNA Sequence cagtctgtcgtgacgcagccgccctcagtgtctgcggccccaggaca
gaaggtcaccatctcctgctctggaagcagctccaacattgggaata
attatgtatcctggtaccagcagctcccaggaacagcccccaaactc
ctcatttatgacaataataagcgaccctcagggattcctgaccgatt
ctctggctccaagtctggcacgtcagccaccctgggcatcactggac
tccagactgggacgaggccgattattactgcggaacatgggataagc
agcctgagtgctgctttatgtcttcggaactgggaccaaggtcaccgt
cctaggttctagaggtggtggtggtagcggcggcggcggctctggtg
gtggtggatccctcgagatggcccaggtccagctggtacagtctgga
gctgaggtgaagaagcctggggcctcagtgaaggtctcctgcaagga
tctggttacagattaccagctatactatcagctggtgcgacaggcc
cctggacaaggccttgagtggatgggatgggtcagcacttacaatgg
tctcagaaactatgcacagaacctccagggcagagtcaccatgacta
cagacacactcacgaccacagcctacatggagctgaggagcctcaga
tctgacgacacggcgtgtattattgtgtgagagaggggctccccga
ctacggtgacttcgcggcctttgactactggggccagggcaccctgg
tcaccgtctcctcaactagtggccaggccggccagcaccatcaccat
caccatggcgcataccgtacgacgttccggactacgcttct
[SEQ ID NO: 869]

TABLE 215-continued

ET200-113

Amino Acid Sequence

QSVVTQPPSVSAAPGQKVTISCSGSSSNIGNNYVSWYQQLPGTAPKL
LIYDNNKRPSGIPDRFSGSKSGTSATLGITGLQTGDEADYYCGTWDS
SLSAAYVFGTGTKVTVLGSRGGGGSGGGGSGGGGSLEMAQVQLVQSG
AEVKKPGASVKVSCKASGYSFTSYTISWVRQAPGQGLEWMGWVSTYN
GLRNYAQNLQGRVTMTTDTLTTTAYMELRSLRSDDTAVYYCVREGSP
DYGDFAAFDYWGQGTLVTVSSTSGQAGQHHHHHHGAYPYDVPDYAS
[SEQ ID NO: 870]

TABLE 216

ET200-114

DNA Sequence caggctgtgctgactcagccaccctcagcgtctgagaccccgggca
gagggtcaccatctcttgttctggaagcaggtccaacatcggaacta
atattgtacactggtaccagcagcgcccaggaatggcccccaaactc
ctcacttatggtagtcggcggccctcaggggtcccgaccgattctc
tggctccaagtttggcacctcagcctccctggccatcagtgggctcc
agtctgaggatgaggctgattattattgtgcagcatgggatgacagt
ctgaatggtccggctttcggcggagggaccaagtgaccgtcctagg
ttctagaggtggtggtggtagcggcggcggcggctctggtggtggtg
gatccctcgagatggcgtcagctacagcagtggggcgcagga
ctgttgaagccttcggagaccctgtccctcacctcgcgctgtctatgg
tgggtccttcagtggttactactggagctggatccgccagcccccag
ggaaggggctggagtggattgggaaatcaatcatagtggaagcacc
aactacaacccgtccctcaagagtcgagtcaccatatcagtagacac
gtccaagaaccagttctccctgaagctgagctctgtgaccgccgcag
acacggctgtgtattactgtgcgagagacggtggggggctactttgac
tactggggccagggaaccctggtcaccgtctcctcaactagtggcca
ggccggccagcaccatcaccatcaccatggcgcataccgtacgacg
ttccggactacgcttct [SEQ ID NO: 871]

Amino Acid Sequence

QAVLTQPPSASETPGQRVTISCSGSRSNIGTNIVHWYQQRPGMAPKL
LTYGSRRPSGVPDRFSGSKFGTSASLAISGLQSEDEADYYCAAWDDS
LNGPAFGGGTKLTVLGSRGGGGSGGGGSGGGGSLEMAQVQLQQWGAG
LLKPSETLSLTCAVYGGSFSGYYWSWIRQPPGKGLEWIGEINHSGST
NYNPSLKSRVTISVDTSKNQFSLKLSSVTAADTAVYYCARDGGGYFD
YWGQGTLVTVSSTSGQAGQHHHHHHGAYPYDVPDYAS
[SEQ ID NO: 872]

TABLE 217

ET200-115

DNA Sequence cagtctgtgttgacgcagccgccctcagtgtctggggccccagggca
gagggtcaccatctcctgcactgggagcagctccaatatcgggggcac
gttatgatgtacactggtaccagcaactcccaggaacagccccccaaactc
ctcctcatctctgctaactacgatcggccctcagggtccctgaccg
attctctggctccaagtctggcacctcagcctccctggccatcactg
ggctccaggctgaggatgaggctgattattactgccagtcctatgac
agcagtgtgagtgcttggtggttcggcggagggaccaaggtcaccgt
cctaggttctagaggtggtggtagcggcggcggcggctctggtg
gtggtggatccctcgagatggccgaagtgcagctggtgcagtctggg
gctgaagtgaaggagcctggggcctcagtgaggatctcctgccaggc
atctggatacaacttcatcagttattatatgcactggtgcgccaggc
ccctgggcaaggtcttgagtggatgggcaccatcaacccaggcagt
ggtgagacagactactcacagaagttgcagggcagagtcaccatgac
cagggacccgtccacgggtacattcgacatggggctgagcagcctga
catctgggacacgggcgctattattgtgcagaggtctcatcaga
ggagctagcgatgcttttaatatctggggcgcggggacaatggtcac
cgtctcttcaactagtggccaggccggccagcaccatcaccatcacc
atggcgcataccgtacgacgttccggactacgcttct
[SEQ ID NO: 873]

TABLE 217-continued

ET200-115

UZ,1/32 Amino Acid Sequence
```
QSVLTQPPSVSGAPGQRVTISCTGSSSNIGARYDVHWYQQLPGTAPR
LLISANYDRPSGVPDRFSGSKSGTSASLAITGLQAEDEADYYCQSYD
SSVSAWVFGGGTKVTVLGSRGGGGSGGGGSGGGGSLEMAEVQLVQSG
AEVKEPGASVRISCQASGYNFISYYMHWVRQAPGQGLEWMGTINPGS
GETDYSQKLQGRVTMTRDPSTGTFDMGLSSLTSGDTAVYYCATGLIR
GASDAFNIWGRGTMVTVSSTSGQAGQHHHHHHGAYPYDVPDYAS
```
[SEQ ID NO: 874]

TABLE 218

ET200-116

DNA Sequence
```
cagcctgtgctgactcagccaccctcagtgtccgtgtccccaggaca
gacggccgccatccctgttctggagataagttgggggataaatttg
cttcctggtatcagcagaagccaggccagtccctgtgctggtcatc
tatcaagatactaagcggccctcagggatccctgagccgattctctgg
ctccaactctgggaacacagccactctgaccatcagcgggacccagg
ctatggatgaggctgactattactgtcagacgtgggccagcggcatt
gtggtgttcggcggagggaccaagctgaccgtcctaggttctagagg
tggtggtggtagcggcggcggcggctctggtggtggtggatccctcg
agatggcccaggtacagctgcagcagtcaggtccaggactggtgaag
ccctcgcagaccctctcactcacctgtgccatctccgggacagtgt
ctctagcaacagtgctgcttggaactggatcaggcagtcccatcga
gaggccttgagtggctgggaaggacatactacaggtccaagtggtat
aatgattatgcagtatctgtgaaaagtcgaataaccatcaacccaga
cacatccaagaaccagttctccctgcagctgaactctgtgactcccg
aggacacggctgtgtattactgtgcaagagagcgcagtggctggaag
ggatttgactactggggccagggaaccctggtcaccgtctcctcaac
tagtggccaggccggccagcaccatcaccatcaccatggcgcatacc
cgtacgacgttccggactacgcttct
```
[SEQ ID NO: 875]

Amino Acid Sequence
```
QPVLTQPPSVSVSPGQTAAIPCSGDKLGDKFASWYQQKPGQSPVLVI
YQDTKRPSGIPERFSGSNSGNTATLTISGTQAMDEADYYCQTWASGI
VVFGGGTKLTVLGSRGGGGSGGGGSGGGGSLEMAQVQLQQSGPGLVK
PSQTLSLTCAISGDSVSSNSAAWNWIRQSPSRGLEWLGRTYYRSKWY
NDYAVSVKSRITINPDTSKNQFSLQLNSVTPEDTAVYYCARERSGWK
GFDYWGQGTLVTVSSTSGQAGQHHHHHHGAYPYDVPDYAS
```
[SEQ ID NO: 876]

TABLE 219

ET200-117

DNA Sequence
```
gatgttgtgatgactcagtctccaccctccctgtccgtcaccctgg
agagccggcctccatcacctgcaggtctagtcagagcctcctggaaa
gaaatgcatacaactacttggattggtacctgcagaggccaggacag
tctccacagctcctgatctacttgggttctaatcgggccgccgggt
ccctgacaggttcagtggcagtggatcaggcagagattttacactga
aaatcagcagagtggagcctgaggatgttggggtttattactgcatg
caagctctacaagctccgttcactttcggcggagggaccaaggtgga
gatcaaacgttctagaggtggtggtggtagcggcggcggcggctctg
gtggtggtggatccctcgagatggccgaagtgcagctggtgcagtct
gggggaggcttggtacagcctggggggtccctgagactctcctgtgc
agcctctggattcaccttttagcagctatgccatgagctgggtccgc
caggctccagggaaggggctggagtgggtctcagctattagtggtagt
ggtggtagcacatactacgcagactccgtgaagggccggttcaccat
ctccagagacaattccaagaacacgctgtatctgcaaatgaacagcc
tgagagccgaggacacggccgtatattactgtgcgagattgggctctg
tttcaggatgctttgatatctgggccaagggacaatggtcaccg
ctcttcaactagtggccaggccggccagcaccatcaccatcaccatg
gcgcatacccgtacgacgttccggactacgcttct
```
[SEQ ID NO: 877]

TABLE 219-continued

ET200-117

Amino Acid Sequence
```
DVVMTQSPPSLSVTPGEPASITCRSSQSLLERNAYNYLDWYLQRPGQ
PQLLIYLGSNRAAGVPDRFSGSGSGRDFTLKISRVEPEDVGVYYCMQ
ALQAPFTFGGGTKVEIKRSRGGGGSGGGGSGGGGSLEMAEVQLVQSG
GGLVQPGGSLRLSCAASGFTFSSYAMSWVRQAPGKGLEWVSAISGSG
GSTYYADSVKGRFTISRDNSKNTLYLQMNSLRAEDTAVYYCAKWGPF
QDAFDIWGQGTMVTVSSTSGQAGQHHHHHHGAYPYDVPDYAS
```
[SEQ ID NO: 878]

TABLE 220

ET200-118

DNA Sequence
```
caggctgtgctgactcagcctgcctccgtgtctgggtctcctggaca
gtcgatcaccatctcctgcactgggaaccagcagtgacgttggtggtt
ataactatgtctcctggtaccaacagcacccgggcaaagcccccaaa
ctcatgatttatgaggtcagtaatcggccctcaggggffictaatcg
cttctctggctccaagtctggcaacacggcctccctgaccatctctg
ggctccaggctgaggacgaggctgattattactgcagctcatataca
agcagcagcaccccttatgtcttcggagcagggaccaaggtcaccgt
cctaggttctagaggtggtggtggtagcggcggcggcggctctggtg
gtggtggatccctcgagatggccgaggtgcagctggtggagtctggg
ggaggcttggtacagcctggcaggtccctgagactctcctgtgcagc
ctctggattcacctttgatgattatgccatgcactgggtccggcaag
ctccagggaagggcctggagtgggtctcaggtattagttggaatagt
ggtagcataggctatgcggactctgtgaagggccgattcaccatctc
cagagacaacgccaagaactccctgtatctgcaaatgaacagtctga
gagctgaggacacggccttgtattactgtgcaaaagccaggtggaca
gcagtggcatcagaccaccactttgactactggggccagggaacgct
ggtcaccgtctcctcaactagtggccaggccggccagcaccatcacc
atcaccatggcgcatacccgtacgacgttccggactacgcttct
```
[SEQ ID NO: 879]

Amino Acid Sequence
```
QAVLTQPASVSGSPGQSITISCTGTSSDVGGYNYVSWYQQHPGKAPK
LMIYEVSNRPSGVSNRFSGSKSGNTASLTISGLQAEDEADYYCSSYT
SSSTPYVFGAGTKVTVLGSRGGGGSGGGGSGGGGSLEMAEVQLVESG
GGLVQPGRSLRLSCAASGFTFDDYAMHWVRQAPGKGLEWVSGISWNS
GSIGYADSVKGRFTISRDNAKNSLYLQMNSLRAEDTALYYCAKARWT
AVASDHHFDYWGQGTLVTVSSTSGQAGQHHHHHHGAYPYDVPDYAS
```
[SEQ ID NO: 880]

TABLE 221

ET200-119

DNA Sequence
```
caggctgtgatactcagccaccctcagcgtctgggacccccgggcag
agggtcaccatctcttgttctggaagcagctccaacatcggaagtaa
tactgtaaactggtaccagcagctcccaggaacggccccccaaactcc
tcatctatagtaataatcagcggccctcaggggtccctgaccgattc
tctggctccaagtctggcacctcagcctccctggccatcagtgggct
ccagtctgaggatgaggctgattattactgtgcagcatgggatgaca
gcctgaatggttatgtcttcggaactgggaccaagctgaccgtccta
ggttctagaggtggtggtggtagcggcggcggcggctctggtggtgg
tggatccctcgagatggccgaggtgcagctggtgcagtctgggggctg
aggtgaagaagcctggagtcctcggtgaaggtctcctgcaaggcttct
ggaggcaccttcagcagctatgctatcagctgggtgcgacaggcccc
tggacaagggcttgagtggatgggagggatcatccctatctttggta
cagcaaactacgcacagaagttccagggcagagtcacgattaccgcg
gacgaatccacgagcacagcctacatggagctgagcagcctgagact
tgaggacacggccgtgtattactgtgcgagagattgggactacatgg
acgtctggggcaaagggaccacggtcaccgtctcctcaactagtggc
caggccggccagcaccatcaccatcaccatggcgcatacccgtacga
cgttccggactacgcttct
```
[SEQ ID NO: 881]

TABLE 221-continued

ET200-119

Amino Acid Sequence

QAVLTQPPSASGTPGQRVTISCSGSSSNIGSNTVNWYQQLPGTAPKL
LIYSNNQRPSGVPDRFSGSKSGTSASLAISGLQSEDEADYYCAAWDD
SLNGYVFGTGTKLTVLGSRGGGGSGGGGSGGGGSLEMAEVQLVQSGA
EVKKPGSSVKVSCKASGGTFSSYAISWVRQAPGQGLEWMGGIIPIFG
TANYAQKFQGRVTITADESTSTAYMELSSLRSEDTAVYYCARDWDYM
DVWGKGTTVTVSSTSGQAGQHHHHHHGAYPYDVPDYAS
[SEQ ID NO: 882]

TABLE 222

ET200-120

DNA Sequence tcctatgagctgactcagccaccctcagcgtctgggacccccgggca
gagggtcaccatctcttgttctggaagcagctccaacatcggaagta
atactgtaaactggtaccagcagctcccaggaacggcccccaaactc
ctcatctatagtaataatcagcggccctcaggggtccctgaccgatt
ctctggctccaagtctggcacctcagcctccctggccatcagtgggc
tccagtctgaggatgaggctgattattactgtgcagcatgggatgac
agcctgaatggttatgtcttcggaactgggaccaaggtcaccgtcct
aggttctagaggtggtggtggtagcggcggcggcggctctggtggtg
gtggatccctcgagatggccgaggtgcagctggtggagtctggagct
gaggtgaagaagcctggggcctcagtgaaggtctcctgcaaggcttc
tggttacacctttaccagctatggtatcagctgggtgcgacaggccc
ctggacaagggcttgagtggatggggatggatcagcgcttacaatggt
aacacaaactatgcacagaagctccagggcagagtcaccatgaccac
agacacatccacgagcacagcctacatggagctgaggagcctgagat
ctgacgacacggccgtgtattactgtgcgagagacctatctcgggga
gctaacccgcattactactactacggtatggacgctctgggggcca
agggaccacggtcaccgtctcctcaactagtggccaggccggccagc
accatcaccatcaccatggcgcatacccgtacgacgttccggactac
gcttct [SEQ ID NO: 883]

Amino Acid Sequence

SYELTQPPSASGTPGQRVTISCSGSSSNIGSNTVNWYQQLPGTAPKL
LIYSNNQRPSGVPDRFSGSKSGTSASLAISGLQSEDEADYYCAAWDD
SLNGYVFGTGTKVTVLGSRGGGGSGGGGSGGGGSLEMAEVQLVESGA
EVKKPGASVKVSCKASGYTFTSYGISWVRQAPGQGLEWMGWISAYNG
NTNYAQKLQGRVTMTTDTSTSTAYMELRSLRSDDTAVYYCARDLSRG
ANPHYYYYGMDVWGQGTTVTVSSTSGQAGQHHHHHHGAYPYDVPDY
AS [SEQ ID NO: 884]

TABLE 223

ET200-121

DNA Sequence cagtctgtgttgacgcagccgccctcagtgtctgggcccccagggca
gagggtcaccgtctcctgcactgggagcagatccaacatcggggcag
gatatgatgtacactggtaccagcaacttccaggaacagcccccaaa
ctcctcatctatggaaatagtaatcggcctccaggggtccctgaccg
attctctgggtctaagtctggcacctcagcctccctggtcatcactg
ggctccaggctgaggatgccgctgattattactgccagtcctatgac
aacactgtgcgtgaatcaccttatgtatcggaactgggaccaaggtc
accgtcctaggttctagaggtggtggtggtagcggcggcggcggctc
tggtggtggtggatccctcgagatggccgaggtgcagctggtacagt
ctggggctgaggtgaagaagcctggggcctcagtgaaggtctcctgc
aaggtttccggatacacccctcactgaattatccatgcactgggtgcg
acaggcctcctggaaaagggcttgagtggatgggagggttttgatcctg
aagatggtgaaacaatctacgcacagaagttccagggcagagtcacc
atgaccgaggacacatctacagacacagcctacatggagctgagcag
cctgagatctgaggacacggccgtgtattactgtgcaacagagagta
atttagtgcccggcactactactactacggtatggacgtctgggggcc
caagggaccacggtcaccgtctcctcaactagtggccaggccggccag
cgcaccatcaccatcaccatggcgcatacccgtacgacgttccggact
acgcttct [SEQ ID NO: 885]

TABLE 223-continued

ET200-121

Amino Acid Sequence

QSVLTQPPSVSGAPGQRVTVSCTGSRSNIGAGYDVHWYQQLPGTAPK
LLIYGNSNRPPGVPDRFSGSKSGTSASLVITGLQAEDAADYYCQSYD
NTVRESPYVFGTGTKVTVLGSRGGGGSGGGGSGGGGSLEMAEVQLVQ
SGAEVKKPGASVKVSCKVSGYTLTELSMEIWVRQAPGKGLEWMGGFD
PEDGETIYAQKFQGRVTMTEDTSTDTAYMELSSLRSEDTAVYYCATE
SNLVSRHYYYGMDVWGQGTTVTVSSTSGQAGQHHHHHHGAYPYDVP
DYAS [SEQ ID NO: 886]

TABLE 224

ET200-122

DNA Sequence ctgcctgtgctgactcagccaccctcagcgtctgggaccccgggca
gagggtcaccatctcttgttctggaagcagctccaacatcggaagta
attctgtagactggtaccagcagctcccaggaacggcccccaaactc
ctcatctatagtaataatcagcggccctcagggggtccctgaccgaat
ctctggctccaagtctggcacctcagcctccctggccatcagtgggc
tccagtctgaggatgaggctgattattactgtgcagcatgggatgac
agcctgaatggttatgtcttcggaactgggaccaaggtcaccgtcct
aggttctagaggtggtggtggtagcggcggcggcggctctggtggtg
gtggatccctcgagatggccgaagtgcagctggtgcagtctgggggct
gaggtgaagaagcctgggggcctcagtgaaggtctcctgcaaggcttc
tggatacaccttcaccggctactatatgcactgggtgcgacaggccc
ctggacaagggcttgagtggatgggatggatcaaccctaacagtggt
ggcacaaactatgcacagaagtttcagggcagggtcaccatgaccag
ggacacgtccatcagcacagcctacatggagctgagcaggctgagat
ctgacgacacggccgtgtattactgtgcgagagattacggatactat
ggttcggggagttattcgagcggcccccctttactactactacgtat
ggacgtctgggggccaagggaccacggtcaccgtctcctcaactagtg
gccaggccggccagcaccatcaccatcaccatggcgcatacccgtac
gacgttccggactacgcttct [SEQ ID NO: 887]

Amino Acid Sequence

LPVLTQPPSASGTPGQRVTISCSGTSSNIGSNSVDWYQQLPGTAPKL
LIYSNNQRPSGVPDRISGSKSGTSASLAISGLQSEDEADYYCAAWDD
SLNGYVFGTGTKVTVLGSRGGGGSGGGGSGGGGSLEMAEVQLVQSGA
EVKKPGASVKVSCKASGYTFTGYYMHWVRQAPGQGLEWMGWINPNSG
GTNYAQKFQGRVTMTRDTSISTAYMELSRLRSDDTAVYYCARDYGYY
GSGSYSSGPLYYYYGMDVWGQGTTVTVSSTSGQAGQHHHHHHGAYPY
DVPDYAS [SEQ ID NO: 888]

TABLE 225

ET200-123

DNA Sequence caggctgtgctgactcagccaccctcagcgtctgggaccccgggca
gagggtcaccatctcttgttctggaagcagctccaacatcggaagta
atactgtaaactggtaccagcagctcccaggaacggcccccaaactc
ctcatgtataataatgatcagcggccctcaggggtccctgaccgatt
ctctggctccaagtctggcacctcagcctccctggccatcagtgggc
tccagtctgaggatgaggctgattattactgtgcagcatgggatgac
agcctcaatggttatgtcttcggacctgggaccaaggtcaccgtcct
aggttctagaggtggtggtggtagcggcggcggcggctctggtggtg
gtggatccctcgagatggcccaggtgcagctggtggagtctggagct
gaggtgaagaagcctggggcctcagtgaaggtctcctgcaaggcttc
tggttacacctttaccagctatggtatcagctgggtgcgacaggccc
ctggacaagggcttgagtggatgggatggatcagcgcttacaatggt
aacacaaactatgcacagaagctccagggcagagtcaccatgaccac
agacacatccacgagcacagcctacatggagctgaggagcctgagat
ctgacgacacggccgtgtattactgtgcgagagacctatctcgggcca
gctaacccgcattactactactacggtatggacgtctgggggcca
agggaccacggtcaccgtctcctcaactagtggccaggccggccagc
accatcaccatcaccatggcgcatacccgtacgacgttccggactac
gcttct [SEQ ID NO: 889]

TABLE 225-continued

ET200-123

Amino Acid Sequence

```
QAVLTQPPSASGTPGQRVTISCSGSSSNIGSNTVNWYQQLPGTAPKL
LMYNNDQRPSGVPDRFSGSKSGTSASLAISGLQSEDEADYYCAAWDD
SLNGYVFGPGTKVTVLGSRGGGGSGGGGSGGGGSLEMAQVQLVESGA
EVKKPGASVKVSCKASGYTFTSYGISWVRQAPGQGLEWMGWISAYNG
NTNYAQKLQGRVTMTTDTSTSTAYMELRSLRSDDTAVYYCARDLSRG
ANPHYYYYGMDVWGQGTTVTVSSTSGQAGQHHHHHHGAYPYDVPDY
AS [SEQ ID NO: 890]
```

TABLE 226

ET200-125

DNA Sequence

```
aattttatgctgactcagccccacgctgtgtcggagtctccggggaa
gacggtaaccatctcctgcacccgcagcagtggcagtattgccagca
actatgtgcagtggtaccagcagcgcccgggcagttccccccgcact
gtgatttatgaggataatcaaagaccctctggggtccctggtcggtt
ctctggctccatcgacagctcctccaactctgcctccctcaccatct
ctggactgaagactgaggacgaggctgactactactgtcagtcttat
gattccaccagtgtgctttcggcggagggaccaaggtgaccgtcct
aggttctagaggtggtggtggtagcggcggcggcggctctggtggtg
gtggatccctcgagatggcccaggtccagctggtgcagtctggggct
gaggtgaagaagccagggtcctcggtgaaggtctcctgcaaggcctc
gggaggcaccttcagcagcaattctctcagctgggtgcgacaggcc
ctggacaagggcttgagtggatgggaaggatcttccctatcctgggt
ataacaaactatgcacagaagttccagggcagagtcacgattaccgc
ggacaaatccacgagcacagcctacatggagctgagcagcctgagat
ctgaggacacggccgtctattactgtgcgagaggaaactaccaatgg
tatgatgcttttgatatctggggccaagggacaatggtcaccgtctc
ttcaactagtggccaggccggccagcaccatcaccatcaccatggcg
cataccgtacgacgttccggactacgcttct
[SEQ ID NO: 891]
```

Amino Acid Sequence

```
NFMLTQPHAVSESPGKTVTISCTRSSGSIASNYVQWYQQRPGSSPRT
VIYEDNQRPSGVPGRFSGSIDSSSNSASLTISGLKTEDEADYYCQSY
DSTSVLFGGGTKLTVLGSRGGGGSGGGGSGGGGSLEMAEVQLVQSGA
EVKKPGSSVKVSCKASGGTFSSNSLSWVRQAPGQGLEWMGRIFPILG
ITNYAQKFQGRVTITADKSTSTAYMELSSLRSEDTAVYYCARGNYQW
YDAFDIWGQGTMVTVSSTSGQAGQHHHHHHGAYPYDVPDYAS
[SEQ ID NO: 892]
```

TABLE 227

ET200-005

DNA Sequence

```
cagcctgtgctgactcagccaccctcagtgtcagtggtcccaggaaa
gacggccaggattacctgtgggggaaaaaacattggaagtaaaagtg
tgcactggtaccagcagaagcaggccaggcccctgtggtggtcatc
cattatgatagtgaccggccctcagggatccctgagcgattctctgg
ctccaactctgggaacacggccaccctgaccatcagcagggtcgaag
ccggggatgaggccgactattactgtcaggtgtgggatagtagtagt
```

TABLE 227-continued

ET200-005

```
gatcatccttatgtcttcggaactgggaccaaggtcaccgtcctagg
ttctagaggtggtggtggtagcggcggcggcggctctggtggtggtg
gatccctcgagatggcccaggtgcagctggtgcagtctggagctgag
gtgaagaagcctggggcctcagtgaaggtctcctgcaaggcttctgg
ttacaccttttaccaactatggtatcagctgggtgcgacaggcccctg
gacaagggcttgagtggatgggatggatcagcgcttacaatggtaac
acaaactatgcacataagctccagggcagagtcaccatgaccacaga
cacatccacgagcacagccaacatggagctgaggagcctgagacctg
acgacactgccgtgtattactgtgcgcgctatacttcggttctcatg
attactggggtcaaggtactctggtgaccgtctcctcaactagtggc
caggccggccagcaccatcaccatcaccatggcgcatacccgtacga
cgttccggactacgcttct [SEQ ID NO: 893]
```

Amino Acid Sequence

```
QPVLTQPPSVSVVPGKTARITCGGKNIGSKSVHWYQQKPGQAPVVVI
HYDSDRPSGIPERFSGSNSGNTATLTISRVEAGDEADYYCQVWDSSS
DHPYVFGTGTKVTVLGSRGGGGSGGGGSGGGGSLEMAQVQLVQSGAE
VKKPGASVKVSCKASGYTFTNYGISWVRQAPGQGLEWMGWISAYNGN
TNYAHKLQGRVTMTTDTSTSTANMELRSLRPDDTAVYYCARSYFGSH
DYWGQGTLVTVSSTSGQAGQHHHHHHGAYPYDVPDYAS
[SEQ ID NO: 894]
```

TABLE 228

ET200-124

DNA Sequence

```
tcctatgtgctgactcagccaccctcggtgtcagtggcccaggaaaa
gacggccaggattcctgtggggaaacgacattggaagtaaaagtg
tifictggtatcagcagaggccaggccaggcccctgtgttggtcgtc
tatgatgatagcgaccggccctcagggctccctgagcgattctctgg
cttcaactctgggaacacggccaccctgaccatcagcagggtcgaag
ccggggatgaggccgactattactgtcaagtgtgggatagtagtagt
gatcattatgtatcggaactgggaccaaggtcaccgtcctaggttct
agaggtggtggtggtagcggcggcggcggctctggtggtggtggatc
cctcgagatggcccaggtgcagctggtggagtctggggaggaggcttg
tacagcctggcaggtccctgagactctcctgtgcagcctctggattc
acctttgatgattatgccatgcactgggtccggcaagctccagggaa
gggcctggagtgggtctcaggtattagttggaatagtggtagcatag
gctatgcggactctgtgaagggccgattcaccatctccagagacaac
gccaagaactccctgtatctgcaaatgaacagtctgagagctgagga
cacggccttgtattactgtgcaaaagatataacctatggttcgggga
gttatggtgcttttgatatctggggccaagggacaatggtcaccgtc
tcttcaactagtggccaggccggccagcaccatcaccatcaccatgg
cgcatacccgtacgacgttccggactacgcttct
[SEQ ID NO: 895]
```

Amino Acid Sequence

```
SYVLTQPPSVSVAPGKTARISCGGNDIGSKSVFWYQQRPGQAPVLVV
YDDSDRPSGLPERFSGFNSGNTATLTISRVEAGDEADYYCQVWDSSS
DHYVFGTGTKVTVLGSRGGGGSGGGGSGGGGSLEMAQVQLVQSGGGL
VQPGRSLRLSCAASGFTFDDYAMHWVRQAPGKGLEWVSGISWNSGSI
GYADSVKGRFTISRDNAKNSLYLQMNSLRAEDTALYYCAKDITYGSG
SYGAFDIWGQGTMVTVSSTSGQAGQHHHHHHGAYPYDVPDYAS
[SEQ ID NO: 896]
```

CDR Sequences of Exemplary Anti-FcRL5 Antibodies

TABLE 229

| Antibody | V$_H$CDR1 | V$_H$CDR2 | V$_H$CDR3 |
|---|---|---|---|
| ET200-001 | GGSFSGYY [SEQ ID NO: 309] | INHSGST [SEQ ID NO: 310] | AREGPYDGFDS [SEQ ID NO: 311] |
| ET200-002 | GYPFNKYD [SEQ ID NO: 315] | IIPIFRTT [SEQ ID NO: 316] | AREWFYWDI [SEQ ID NO: 317] |
| ET200-003 | GFTFSSYG [SEQ ID NO: 321] | ISHDGSNK [SEQ ID NO: 322] | ARSNQWSGYFSFDY [SEQ ID NO: 323] |

TABLE 229-continued

```
ET200-005    GYTFTNYG         ISAYNGNT       ARSYFGSHDY
             [SEQ ID NO: 326] [SEQ ID NO: 327] [SEQ ID NO: 328]

ET200-006    GYTFTTYG         INTYNGHT       ARVIYGSGDY
             [SEQ ID NO: 332] [SEQ ID NO: 333] [SEQ ID NO: 334]

ET200-007    GYSISSGYF        IYHSRST        ARGYGYFDY
             [SEQ ID NO: 335] [SEQ ID NO: 336] [SEQ ID NO: 337]

ET200-008    GFTFGDYG         INWNGGST       ARSKYNFHVYYDY
             [SEQ ID NO: 340] [SEQ ID NO: 341] [SEQ ID NO: 342]

ET200-009    GYTFTSYG         ISAYNGNT       ARSSGNMVSWKDM
             [SEQ ID NO: 346] [SEQ ID NO: 327] [SEQ ID NO: 347]

ET200-010    GYTFTSYG         ISAYNGNT       ARGAVAYHD
             [SEQ ID NO: 346] [SEQ ID NO: 327] [SEQ ID NO: 351]

ET200-011    GGTLSSYA         IIPMFGTA       ARGVHYASFDH
             [SEQ ID NO: 354] [SEQ ID NO: 355] [SEQ ID NO: 356]

ET200-012    GFPFNIFG         ISGYNGNT       ARGAYGGMDT
             [SEQ ID NO: 360] [SEQ ID NO: 361] [SEQ ID NO: 362]

ET200-013    GYMFTSYG         ISANNGKT       ARHIGGSYFDR
             [SEQ ID NO: 366] [SEQ ID NO: 367] [SEQ ID NO: 368]

ET200-014    GFTFSSYA         ISGSDGST       ARSHEANLVGDW
             [SEQ ID NO: 372] [SEQ ID NO: 373] [SEQ ID NO: 374]

ET200-015    GYTFTSYG         ISAYNGNT       ARWGGFGAVDH
             [SEQ ID NO: 346] [SEQ ID NO: 327] [SEQ ID NO: 376]

ET200-016    GFTFSSYS         ISSSSSYI       ARGQGYDY
             [SEQ ID NO: 378] [SEQ ID NO: 379] [SEQ ID NO: 380]

ET200-017    GGSFSGYY         INHSGST        ARYYPGMDM
             [SEQ ID NO: 309] [SEQ ID NO: 310] [SEQ ID NO: 384]

ET200-018    GYTLNELS         FDPEDGET       ARGGYGDS
             [SEQ ID NO: 387] [SEQ ID NO: 388] [SEQ ID NO: 389]

ET200-019    GGTFSSDA         IIPMFGTA       AREGYYYPSAYLGSVL
             [SEQ ID NO: 393] [SEQ ID NO: 355]   NDISSVYDE
                                               [SEQ ID NO: 394]

ET200-020    GYTFTSYG         ISAYNGNT       ARSMTSFDY
             [SEQ ID NO: 346] [SEQ ID NO: 327] [SEQ ID NO: 396]

ET200-021    GYTFTSYG         ISAYNGNT       ARSVYDLDT
             [SEQ ID NO: 346] [SEQ ID NO: 327] [SEQ ID NO: 400]

ET200-022    GFTFDDYA         ISWNSGSI       ARYRQVGSAYDS
             [SEQ ID NO: 403] [SEQ ID NO: 404] [SEQ ID NO: 405]

ET200-023    GYTFTSYG         ISAYNGNT       ARYWGFGVSDR
             [SEQ ID NO: 346] [SEQ ID NO: 327] [SEQ ID NO: 408]

ET200-024    GGTFSSYA         IIPIEGTA       ARYNYYYDS
             [SEQ ID NO: 411] [SEQ ID NO: 412] [SEQ ID NO: 413]

ET200-025    GGTFSSYA         IIPIEGTA       ARYWGYDSYDE
             [SEQ ID NO: 411] [SEQ ID NO: 412] [SEQ ID NO: 415]

ET200-026    GGTFSSYA         IIPIEGTA       ARNNHYYNDY
             [SEQ ID NO: 411] [SEQ ID NO: 412] [SEQ ID NO: 349]

ET200-027    GYTFTDYY         VDPEDGET       ARYWSYSFDYLYMPEG
             [SEQ ID NO: 420] [SEQ ID NO: 421]     NDW
                                               [SEQ ID NO: 422]

ET200-028    GYNFLNYG         ISTYTGNT       ARDLYYYEGVDY
             [SEQ ID NO: 425] [SEQ ID NO: 426] [SEQ ID NO: 427]

ET200-029    GFTFSSYA         ISYDGSNK       ARSYFTSGFYDY
             [SEQ ID NO: 372] [SEQ ID NO: 431] [SEQ ID NO: 432]

ET200-030    GYTLTELS         FDPEDGET       ARMSSMYYD
             [SEQ ID NO: 436] [SEQ ID NO: 388] [SEQ ID NO: 437]
```

TABLE 229-continued

```
ET200-031      GFTVSDYY         ISGSGNSI         ARSTKFDY
            [SEQ ID NO: 440] [SEQ ID NO: 441] [SEQ ID NO: 442]

ET200-032      GYSFTNYW         IYPGDSDT        ARSTGSSHMSDE
            [SEQ ID NO: 444] [SEQ ID NO: 445] [SEQ ID NO: 446]

ET200-033      GGSFSGYY          ITHSGRS         ARSSIMSDY
            [SEQ ID NO: 309] [SEQ ID NO: 450] [SEQ ID NO: 451]

ET200-034      GGTFSSYA         IIPIEGTA        ARGSALDHYDR
            [SEQ ID NO: 411] [SEQ ID NO: 412] [SEQ ID NO: 453]

ET200-035      GGTFSSYA         IIPIEGTA         ARYNYYFNDY
            [SEQ ID NO: 411] [SEQ ID NO: 412] [SEQ ID NO: 456]

ET200-037      GYTFTSYG         ISAYNGNT         ARSMFGAHDS
            [SEQ ID NO: 346] [SEQ ID NO: 327] [SEQ ID NO: 458]

ET200-038      GGTFSSYA         IIPIEGTA         ARGASFDRHDN
            [SEQ ID NO: 411] [SEQ ID NO: 412] [SEQ ID NO: 459]

ET200-039      GGTFSSYA         IIPIEGTA         ARSNYYYNDY
            [SEQ ID NO: 411] [SEQ ID NO: 412] [SEQ ID NO: 463]

ET200-040      GYTLTELS         FDPEDGET         ARYSGVYYD
            [SEQ ID NO: 436] [SEQ ID NO: 388] [SEQ ID NO: 464]

ET200-041      GGTFSSYA         MNPNSGNT         ARYYSYGYD
            [SEQ ID NO: 411] [SEQ ID NO: 466] [SEQ ID NO: 467]

ET200-042     GDSVSTNSVA        TYYRSKWSN       ARSSSWYQIEDY
            [SEQ ID NO: 471] [SEQ ID NO: 472] [SEQ ID NO: 473]

ET200-043      GFTFSSYA         ISGSGGST       ARSGAYWDYSVYDE
            [SEQ ID NO: 372] [SEQ ID NO: 475] [SEQ ID NO: 476]

ET200-044      GGSISSSNW         IYHSGSP        ARMTTHTFGYDA
            [SEQ ID NO: 480] [SEQ ID NO: 481] [SEQ ID NO: 482]

ET200-045      GYTFTSYG         ISAYNGNT         ARGVHLDW
            [SEQ ID NO: 346] [SEQ ID NO: 327] [SEQ ID NO: 486]

ET200-069      GGSFSGYY          INHSGST       ARLYEGGYHGWGSWL
            [SEQ ID NO: 309] [SEQ ID NO: 310]        SSDS
                                              [SEQ ID NO: 489]

ET200-078      GGSFSGYY          INHSGST         AREGAFDAFDI
            [SEQ ID NO: 309] [SEQ ID NO: 310] [SEQ ID NO: 492]

ET200-079      GFTFDDYA         ISWNSGSI       ANGDSNYYYGMDV
            [SEQ ID NO: 403] [SEQ ID NO: 404] [SEQ ID NO: 494]

ET200-081      GFTFDDYA         ISGDGGST      AKDRAAAGYYYYGMDV
            [SEQ ID NO: 403] [SEQ ID NO: 496] [SEQ ID NO: 497]

ET200-097      GFTFNDYA         ISWSGNNI      AKDSIRYGITWGGFDY
            [SEQ ID NO: 500] [SEQ ID NO: 501] [SEQ ID NO: 502]

ET200-098      GFTFDDYA         INWDGGST        AKGMGLRAFDY
            [SEQ ID NO: 403] [SEQ ID NO: 506] [SEQ ID NO: 507]

ET200-099      GYTFSWYA         INAGNGNT      ARPDNYGSGGDVFDI
            [SEQ ID NO: 510] [SEQ ID NO: 511] [SEQ ID NO: 512]

ET200-100      GFTFSSYE         ISSSGSTI         ARWDYGMDV
            [SEQ ID NO: 515] [SEQ ID NO: 516] [SEQ ID NO: 517]

ET200-101      GYTFTWYA         INAGSGNT      ARPNNYGSGGDVFDI
            [SEQ ID NO: 520] [SEQ ID NO: 521] [SEQ ID NO: 522]

ET200-102      GYTFTNYA         INGGNGNT      AKPEETAGTIHFDY
            [SEQ ID NO: 525] [SEQ ID NO: 526] [SEQ ID NO: 527]

ET200-103      GGTFSSYA         IIPIFGTA      AGEGYYDSSGYSNGDA
            [SEQ ID NO: 411] [SEQ ID NO: 412]        FDI
                                              [SEQ ID NO: 529]

ET200-104      GFTFSSYE         ISSSGSTI         ARWDYGMDV
            [SEQ ID NO: 515] [SEQ ID NO: 516] [SEQ ID NO: 517]
```

TABLE 229-continued

```
ET200-105      GFTFDDYA         ISWNSGSI        AKDRGGGVIVKDAFDI
            [SEQ ID NO: 403] [SEQ ID NO: 404] [SEQ ID NO: 532]

ET200-106      GYNFLNYG         ISTYTGNT         ARQQGGGWYDV
            [SEQ ID NO: 425] [SEQ ID NO: 426] [SEQ ID NO: 536]

ET200-107      GYTFTSYT         ISTYNGLT       VREGSPDYGDFASFDY
            [SEQ ID NO: 537] [SEQ ID NO: 538] [SEQ ID NO: 539]

ET200-108      GYTFTSYT         ISTYNGLT       VREGSPDYGDFASFDY
            [SEQ ID NO: 537] [SEQ ID NO: 538] [SEQ ID NO: 539]

ET200-109      GGTFSSYA         IIPIFGTA       ARDPAYGDYEYDAFDI
            [SEQ ID NO: 411] [SEQ ID NO: 412] [SEQ ID NO: 543]

ET200-110      GGTFSSYA         IIPIFGTA         ARGAGFDAFDI
            [SEQ ID NO: 411] [SEQ ID NO: 412] [SEQ ID NO: 546]

ET200-111      GGSFSGYY          INHSGST         AREGLDAFDI
            [SEQ ID NO: 309] [SEQ ID NO: 310] [SEQ ID NO: 550]

ET200-112      GGSFSGYY          INHSGST         AREGLDAFDI
            [SEQ ID NO: 309] [SEQ ID NO: 310] [SEQ ID NO: 550]

ET200-113      GYSFTSYT         VSTYNGLR       VREGSPDYGDFAAFDY
            [SEQ ID NO: 551] [SEQ ID NO: 552] [SEQ ID NO: 553]

ET200-114      GGSFSGYY          INHSGST         ARDGGGYFDY
            [SEQ ID NO: 309] [SEQ ID NO: 310] [SEQ ID NO: 555]

ET200-115      GYNFISYY         INPGSGET       ATGLIRGASDAFNI
            [SEQ ID NO: 559] [SEQ ID NO: 560] [SEQ ID NO: 561]

ET200-116     GDSVSSNSAA        TYYRSKWYN       ARERSGWKGFDY
            [SEQ ID NO: 565] [SEQ ID NO: 566] [SEQ ID NO: 567]

ET200-117      GFTFSSYA         ISGSGGST        AKWGPFQDAFDI
            [SEQ ID NO: 372] [SEQ ID NO: 475] [SEQ ID NO: 570]

ET200118       GFTFDDYA         ISWNSGSI       AKARWTAVASDHHFDY
            [SEQ ID NO: 403] [SEQ ID NO: 404] [SEQ ID NO: 574]

ET200-119      GGTFSSYA         IIPIFGTA         ARDWDYMDV
            [SEQ ID NO: 411] [SEQ ID NO: 412] [SEQ ID NO: 577]

ET200-120      GYTFTSYG         ISAYNGNT       ARDLSRGANPHYYYYY
            [SEQ ID NO: 346] [SEQ ID NO: 327]       GMDV
                                               [SEQ ID NO: 578]

ET200-121      GYTLTELS         FDPEDGET       ATESNLVSRHYYYYGM
            [SEQ ID NO: 436] [SEQ ID NO: 388]        DV
                                               [SEQ ID NO: 579]

ET200-122      GYTFTGYY         INPNSGGT       ARDYGYYGSGSYSSGP
            [SEQ ID NO: 582] [SEQ ID NO: 583]    LYYYYGMDV
                                               [SEQ ID NO: 584]

ET200-123      GYTFTSYG         ISAYNGNT       ARDLSRGANPHYYYYY
            [SEQ ID NO: 346] [SEQ ID NO: 327]       GMDV
                                               [SEQ ID NO: 578]

ET200-124      GFTFDDYA         ISWNSGSI       AKDITYGSGSYGAFDI
            [SEQ ID NO: 403] [SEQ ID NO: 404] [SEQ ID NO: 587]

ET200-125      GGTFSSNS         IFPILGIT       ARGNYQWYDAFDI
            [SEQ ID NO: 589] [SEQ ID NO: 590] [SEQ ID NO: 591]
```

| Antibody | $V_L$CDR1 | $V_L$CDR2 | $V_L$CDR3 |
|---|---|---|---|

```
ET200-001      SSNIGSNT            SNN           AAWDDSLNGYV
            [SEQ ID NO: 312] [SEQ ID NO: 313] [SEQ ID NO: 314]

ET200-002      SGSIASNY            EDN            QSYDSSNSVV
            [SEQ ID NO: 318] [SEQ ID NO: 319] [SEQ ID NO: 320]

ET200-003       KLGTKY             EDN            QAWDSDTFVV
            [SEQ ID NO: 324] [SEQ ID NO: 319] [SEQ ID NO: 325]
```

TABLE 229-continued

```
ET200-005      NIGSKS             YDS           QVWDSSSDHPYV
           [SEQ ID NO: 329] [SEQ ID NO: 330] [SEQ ID NO: 331]

ET200-006      NIGSKS             YDS           QVWDSSSDHPYV
           [SEQ ID NO: 329] [SEQ ID NO: 330] [SEQ ID NO: 331]

ET200-007      NIGSKT             YDS           QVWDSSSDHRV
           [SEQ ID NO: 338] [SEQ ID NO: 330] [SEQ ID NO: 339]

ET200-008      SSDVGGYNY          DVS           SSYTSSSTSKV
           [SEQ ID NO: 343] [SEQ ID NO: 344] [SEQ ID NO: 345]

ET200-009      NSNIGSNY           RNN           AAWDDSLSAYV
           [SEQ ID NO: 348] [SEQ ID NO: 349] [SEQ ID NO: 350]

ET200-010      SSDVGGYNS          DVS           SSYTSSSTPLV
           [SEQ ID NO: 352] [SEQ ID NO: 344] [SEQ ID NO: 353]

ET200-011      SSNISIYD           GNN           GTWDDSLSGGV
           [SEQ ID NO: 357] [SEQ ID NO: 358] [SEQ ID NO: 359]

ET200-012      DSNIGNNY           DVK           GTWDSRLDAYV
           [SEQ ID NO: 363] [SEQ ID NO: 364] [SEQ ID NO: 365]

ET200-013      TSNIGAGYD          TNN           GTWDSSLSAVV
           [SEQ ID NO: 369] [SEQ ID NO: 370] [SEQ ID NO: 371]

ET200-014      NIGSKS             YDS           QVWDSSSDHYV
           [SEQ ID NO: 329] [SEQ ID NO: 330] [SEQ ID NO: 375]

ET200-015      NIGSKS             YDS           QVWDSSSDVV
           [SEQ ID NO: 329] [SEQ ID NO: 330] [SEQ ID NO: 377]

ET200-016      SLTDYH             ATN           NSRDSGTDEVL
           [SEQ ID NO: 381] [SEQ ID NO: 382] [SEQ ID NO: 383]

ET200-017      NIGSKS             DDS           QVWDSSSDHTV
           [SEQ ID NO: 329] [SEQ ID NO: 385] [SEQ ID NO: 386]

ET200-018      SSNIGRNG           NDN           AAWDDSLHGVV
           [SEQ ID NO: 390] [SEQ ID NO: 391] [SEQ ID NO: 392]

ET200-019      SGSIASNY           EDN           QSYDSSNSWV
           [SEQ ID NO: 318] [SEQ ID NO: 319] [SEQ ID NO: 395]

ET200-020      TSNIGNND           DNN           GTWDSSVSAS
           [SEQ ID NO: 397] [SEQ ID NO: 398] [SEQ ID NO: 399]

ET200-021      NSNIGNNY           DNN           GTWNTTVTPGYV
           [SEQ ID NO: 401] [SEQ ID NO: 398] [SEQ ID NO: 402]

ET200-022      SSNIGNNY           DNN           GTWDSSLGAPYV
           [SEQ ID NO: 406] [SEQ ID NO: 398] [SEQ ID NO: 407]

ET200-023      NIGSKS             ADS           QVWDSSSYHNYV
           [SEQ ID NO: 329] [SEQ ID NO: 409] [SEQ ID NO: 410]

ET200-024      SGSIASNY           EDN           QSYDSSNLWV
           [SEQ ID NO: 318] [SEQ ID NO: 319] [SEQ ID NO: 414]

ET200-025      QSISSY             AAS           QQSYSTPFT
           [SEQ ID NO: 416] [SEQ ID NO: 417] [SEQ ID NO: 418]

ET200-026      SGSIASNY           EDN           QSYDSSNWV
           [SEQ ID NO: 318] [SEQ ID NO: 319] [SEQ ID NO: 419]

ET200-027      SSNIGAGYD          GNN           QSYDSSLSDVV
           [SEQ ID NO: 423] [SEQ ID NO: 358] [SEQ ID NO: 424]

ET200-028      VSNIGSGA           SYN           ATWDDSVNG
           [SEQ ID NO: 428] [SEQ ID NO: 429] [SEQ ID NO: 430]

ET200-029      NIGSES             YDT           QVWDSSRDHVV
           [SEQ ID NO: 433] [SEQ ID NO: 434] [SEQ ID NO: 435]

ET200-030      SSNIGAGYD          GNS           QSYDSSLSGSYV
           [SEQ ID NO: 423] [SEQ ID NO: 438] [SEQ ID NO: 439]

ET200-031      NIGSKS             YDS           QVWDSSSDYV
           [SEQ ID NO: 329] [SEQ ID NO: 330] [SEQ ID NO: 443]
```

TABLE 229-continued

```
ET200-032     SSNVGSYT           NNN           AAWDDRLGGYV
              [SEQ ID NO: 447] [SEQ ID NO: 448] [SEQ ID NO: 449]

ET200-033     SGSIASNY           EDN           QSYDSSNHWV
              [SEQ ID NO: 318] [SEQ ID NO: 319] [SEQ ID NO: 452]

ET200-034     TSNIGAGYD          NNR           GTWDGSLTGAV
              [SEQ ID NO: 369] [SEQ ID NO: 454] [SEQ ID NO: 455]

ET200-035     SGSIASNY           EDN           QSYDSTNWV
              [SEQ ID NO: 318] [SEQ ID NO: 319] [SEQ ID NO: 457]

ET200-037     NIGSKS             YDS           QVWDSSSDHPYV
              [SEQ ID NO: 329] [SEQ ID NO: 330] [SEQ ID NO: 331]

ET200-038     SSNIGAGFD          ANS           QSYDSSLSGVV
              [SEQ ID NO: 460] [SEQ ID NO: 461] [SEQ ID NO: 462]

ET200-039     SGSIASNY           EDN           QSYDSSNWV
              [SEQ ID NO: 318] [SEQ ID NO: 319] [SEQ ID NO: 419]

ET200-040     SSNIGAGYD          GNS           QSYDSSLSGYV
              [SEQ ID NO: 423] [SEQ ID NO: 438] [SEQ ID NO: 465]

ET200-041     SGSIADNF           NDD           QSYDNNNRGV
              [SEQ ID NO: 468] [SEQ ID NO: 469] [SEQ ID NO: 470]

ET200-042     SSNIGTGYF          GNN           QSYDSSLSGYV
              [SEQ ID NO: 474] [SEQ ID NO: 358] [SEQ ID NO: 465]

ET200-043     SDSIANNY           EDV           QSYHSDNRWV
              [SEQ ID NO: 477] [SEQ ID NO: 478] [SEQ ID NO: 479]

ET200-044     KLGDKY             QDN           QAWDSSTYVA
              [SEQ ID NO: 483] [SEQ ID NO: 484] [SEQ ID NO: 485]

ET200-045     NIGSES             DDA           QVWDRNSAQFV
              [SEQ ID NO: 433] [SEQ ID NO: 487] [SEQ ID NO: 488]

ET200-069     SSNIGSNY           SNN           AAWDDSLSGYV
              [SEQ ID NO: 490] [SEQ ID NO: 313] [SEQ ID NO: 491]

ET200-078     SSNIGSNT           SNN           AAWDDSLNGY
              [SEQ ID NO: 312] [SEQ ID NO: 313] [SEQ ID NO: 493]

ET200-079     SSNIGSNY           RNN           AAWDDSLSGYL
              [SEQ ID NO: 490] [SEQ ID NO: 349] [SEQ ID NO: 495]

ET200-081     SSDIGGYNY          DVS           ISYTRTWNPYV
              [SEQ ID NO: 498] [SEQ ID NO: 344] [SEQ ID NO: 499]

ET200-097     KLGEKY             QDT           QAWDRGVV
              [SEQ ID NO: 503] [SEQ ID NO: 504] [SEQ ID NO: 505]

ET200-098     SNNVGNLG           RNN           SAWDSSLSA
              [SEQ ID NO: 508] [SEQ ID NO: 349] [SEQ ID NO: 509]

ET200-099     SSNIGSNT           SND           ASWDDSLNGRYV
              [SEQ ID NO: 312] [SEQ ID NO: 513] [SEQ ID NO: 514]

ET200-100     SGSIASNF           EDN           QSYDTSNVV
              [SEQ ID NO: 518] [SEQ ID NO: 319] [SEQ ID NO: 519]

ET200-101     NSNIGSNY           SSS           ATWDDSLNA
              [SEQ ID NO: 348] [SEQ ID NO: 523] [SEQ ID NO: 524]

ET200-102     SSNIGNNY           DNN           GTWDSSLSAYV
              [SEQ ID NO: 406] [SEQ ID NO: 398] [SEQ ID NO: 528]

ET200-103     SGSIASNY           EDN           QSYDSTITV
              [SEQ ID NO: 318] [SEQ ID NO: 319] [SEQ ID NO: 530]

ET200-104     SGSIASNY           EDN           QSYDSSNVV
              [SEQ ID NO: 318] [SEQ ID NO: 319] [SEQ ID NO: 531]

ET200-105     RLTNKY             EDA           QAWDSSVVV
              [SEQ ID NO: 533] [SEQ ID NO: 534] [SEQ ID NO: 535]
```

TABLE 229-continued

| ET200-106 | VSNIGSGA | SYN | ATWDDSVNG |
| | [SEQ ID NO: 428] | [SEQ ID NO: 429] | [SEQ ID NO: 430] |
| ET200-107 | NFNVGNND | DNN | GTWDSSLNTGGV |
| | [SEQ ID NO: 540] | [SEQ ID NO: 398] | [SEQ ID NO: 541] |
| ET200-108 | SSNIGNNY | DNN | GTWDTSLSGFYV |
| | [SEQ ID NO: 406] | [SEQ ID NO: 398] | [SEQ ID NO: 542] |
| ET200-109 | TSNIGSNT | NNN | ATWDDSLSGVV |
| | [SEQ ID NO: 544] | [SEQ ID NO: 448] | [SEQ ID NO: 545] |
| ET200-110 | SSNIGTNG | TND | AVWDHSLNGPV |
| | [SEQ ID NO: 547] | [SEQ ID NO: 548] | [SEQ ID NO: 549] |
| ET200-111 | SSNIGSNT | SNN | AAWDDSLNGYV |
| | [SEQ ID NO: 312] | [SEQ ID NO: 313] | [SEQ ID NO: 314] |
| ET200-112 | SSNIGSNT | SND | AAWDDSLNGYV |
| | [SEQ ID NO: 312] | [SEQ ID NO: 513] | [SEQ ID NO: 314] |
| ET200-113 | SSNIGNNY | DNN | GTWDSSLSAAYV |
| | [SEQ ID NO: 406] | [SEQ ID NO: 398] | [SEQ ID NO: 554] |
| ET200-114 | RSNIGTNI | GS | AAWDDSLNGPA |
| | [SEQ ID NO: 556] | [SEQ ID NO: 557] | [SEQ ID NO: 558] |
| ET200-115 | SSNIGARYD | ANY | QSYDSSVSAWV |
| | [SEQ ID NO: 562] | [SEQ ID NO: 563] | [SEQ ID NO: 564] |
| ET200-116 | KLGDKF | QDT | QTWASGIVV |
| | [SEQ ID NO: 568] | [SEQ ID NO: 504] | [SEQ ID NO: 569] |
| ET200-117 | QSLLERNAYNY | LGS | MQALQAPFT |
| | [SEQ ID NO: 571] | [SEQ ID NO: 572] | [SEQ ID NO: 573] |
| ET200-118 | SSDVGGYNY | EVS | SSYTSSSTPYV |
| | [SEQ ID NO: 343] | [SEQ ID NO: 575] | [SEQ ID NO: 576] |
| ET200-119 | SSNIGSNT | SNN | AAWDDSLNGYV |
| | [SEQ ID NO: 312] | [SEQ ID NO: 313] | [SEQ ID NO: 314] |
| ET200-120 | SSNIGSNT | SNN | AAWDDSLNGYV |
| | [SEQ ID NO: 312] | [SEQ ID NO: 313] | [SEQ ID NO: 314] |
| ET200-121 | RSNIGAGYD | GNS | QSYDNTVRESPYV |
| | [SEQ ID NO: 580] | [SEQ ID NO: 438] | [SEQ ID NO: 581] |
| ET200-122 | SSNIGSNS | SNN | AAWDDSLNGYV |
| | [SEQ ID NO: 585] | [SEQ ID NO: 313] | [SEQ ID NO: 314] |
| ET200-123 | SSNIGSNT | NND | AAWDDSLNGYV |
| | [SEQ ID NO: 312] | [SEQ ID NO: 586] | [SEQ ID NO: 314] |
| ET200-124 | DIGSKS | DDS | QVWDSSSDHYV |
| | [SEQ ID NO: 588] | [SEQ ID NO: 385] | [SEQ ID NO: 375] |
| ET200-125 | SGSIASNY | EDN | QSYDSTSVL |
| | [SEQ ID NO: 318] | [SEQ ID NO: 319] | [SEQ ID NO: 592] |

EXAMPLES

The following examples are put forth so as to provide those of ordinary skill in the art with a complete disclosure and description of how to make and use the antibodies, bispecific antibodies, compositions comprising thereof, screening and therapeutic methods of the presently disclosed subject matter, and are not intended to limit the scope of what the inventors regard as their presently disclosed subject matter. It is understood that various other embodiments may be practiced, given the general description provided above.

Example 1—FcRL5 Expression in Various Tissues

The Expression of human FcRL5 was assessed and evaluated in various tissues. As shown in FIG. 1, human FcRL5 was highly expressed in lymphoma and multiple myeloma, but not in other tissues. Top panel of FIG. 1 shows differential expression of human FcRL5 in tumor cell lines from the Cancer Cell Line Encyclopedia (CCLE). The bottom panel of FIG. 1 shows differential expression of human FcRL5 in normal tissue from BioGPS. As shown in FIG. 1, human FcRL5 expression is limited to MM and lymphoma compared to other malignant cells. Normal expression appeared limited to B-cells and plasma cells.

Figure 2:
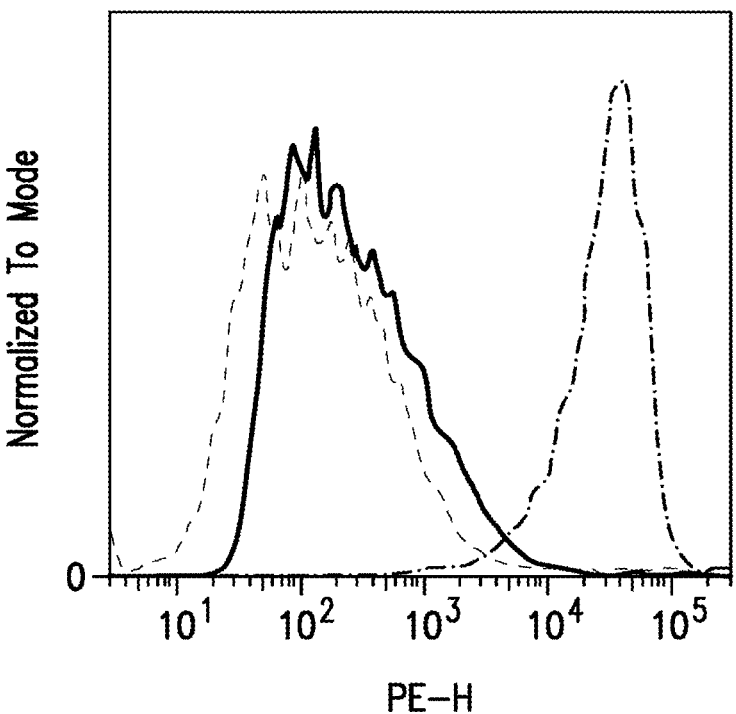
FIG. 2 depicts the screening of anti-FcRL5 scFvs using 3T3 cells expressing FcRL5 or FcRL1, 2, 3, 4 or 6.

Example 2—Selection of scFvs Specific for FcRL5 Using a Fully Human Phage Display Library Phage' display against FcRL5 was performed to enrich for scFv phage clones that bind to FcRL5 specifically. Screening was carried out on FcRL5 overexpressing 3T3 cells or 3T3 cells expressing FcRL1, 2, 3, 4 or 6 as a negative control (FIG. 2). 1080 phage clones were isolated from the enriched panning pools and screened for specific binding to FcRL5 using phage ELISA. Of the 1080 phage clones, 125 clones containing unique scFv sequences were specific to FcRL5 as determined by ELISA. Of the 125 unique clones, 76 clones showed specific binding to FcRL5-overexpressing 3T3 and Raji cells, no cross binding to FcRL1, FcRL2, FcRL3, FcRL4 and FcRL6-overexpressing 3T3 cells and no cross binding to SLAMF9 protein (another FcRL5 subfamily member, no cell line available) (see Tables 1-229 and FIG. 2).

Example 3—Selection of scFvs Specific for Domain 9 of FcRL5

FcRL5 contains 9 extracellular immunoglobulin (Ig)-like domains (domains 1-9) and can be present within a cell in a soluble isoform, a glycosyl-phosphatidyl inositol (GPI)-anchor type isoform and a transmembrane-type isoform (FIG. 3A). As shown in FIG. 3A, the transmembrane-type isoform of FcRL5 includes domain 9; whereas, the soluble isoform and the GPI-anchor type isoform do not.

To test if the scFvs were specific to domain 9 of FcRL5, the 76 clones were further screened on 3T3 cells overexpressing a vector encoding FcRL5 with a domain 9 deletion (FcRL5Δdom9) and further screened on Raji cells overexpressing full-length FcRL5 (FIG. 3B-D). Some clones showed either reduced or diminished binding towards FcRL5-domain 9 deletion-overexpressing 3T3 cells compared to binding towards FcRL5-overexpressing 3T3 cells. FIGS. 4, 5, 6, 7 and 8 shows the specificity of ET200-39, ET200-104, ET200-105, ET200-109 and ET200-117 for domain 9 of FcRL5, respectively.

Example 4—Bispecific Antibodies Specific for FcRL5 and CD3

Figure 9A:
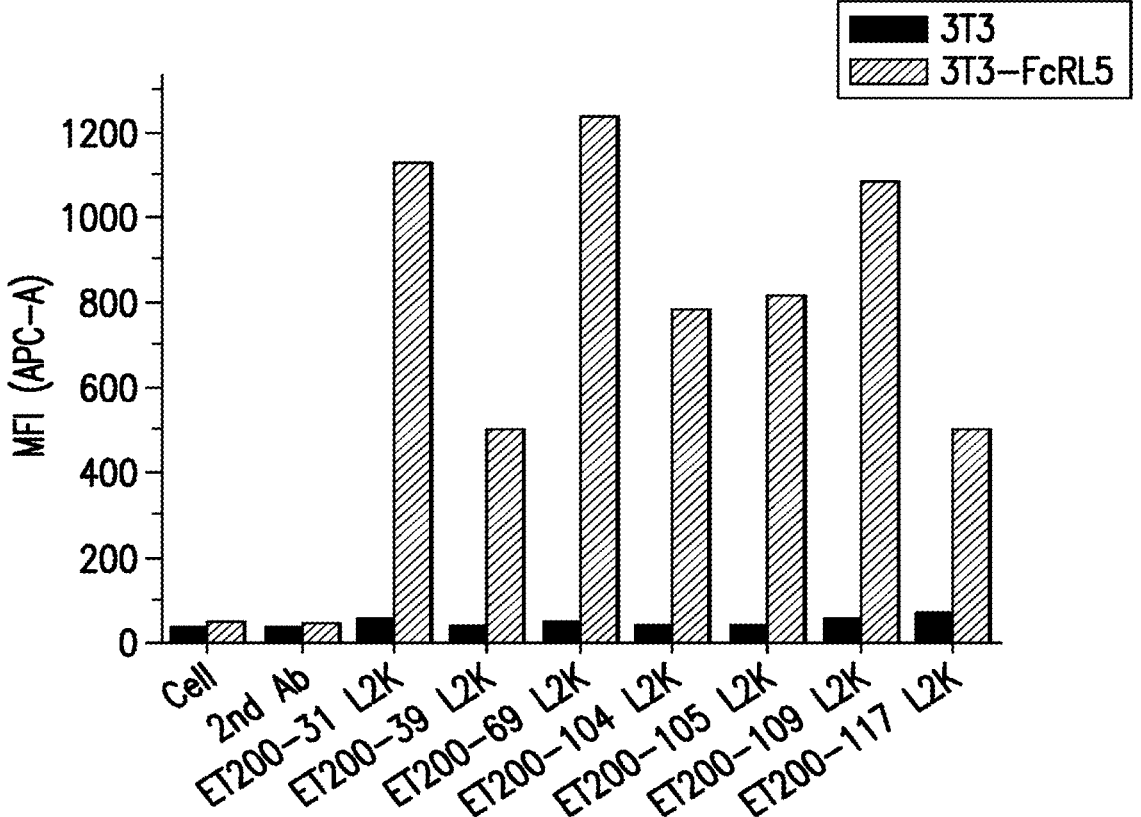
FIGS. 9A-9B depict the FACS analysis of anti-FcRL5/CD3 bispecific antibodies.
Figure 9B:
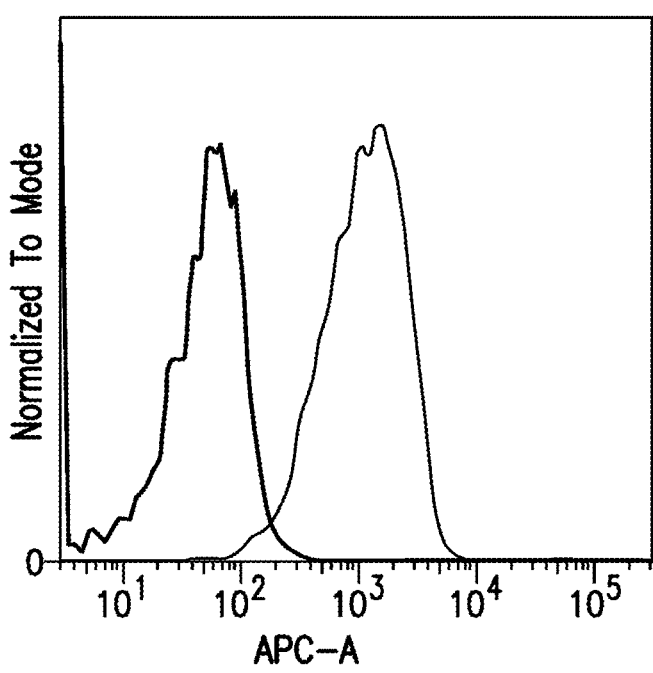
Figure 9B:
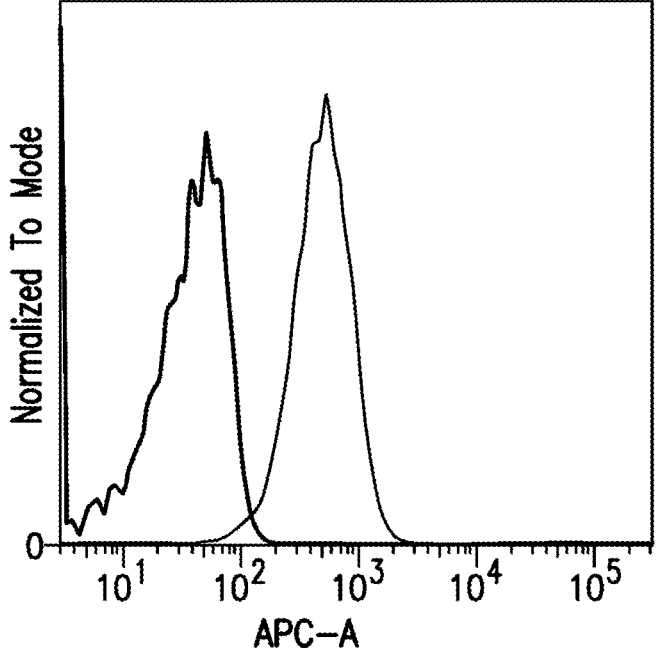
Figure 9B:
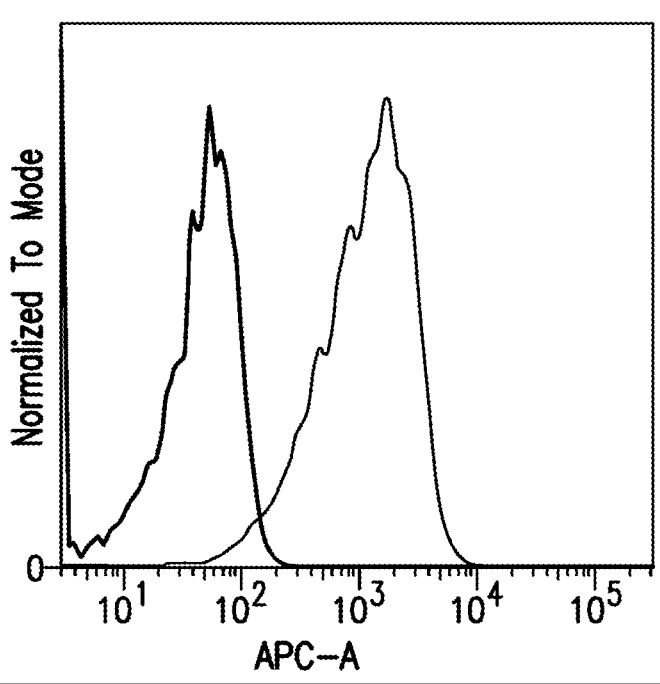
Figure 9B:
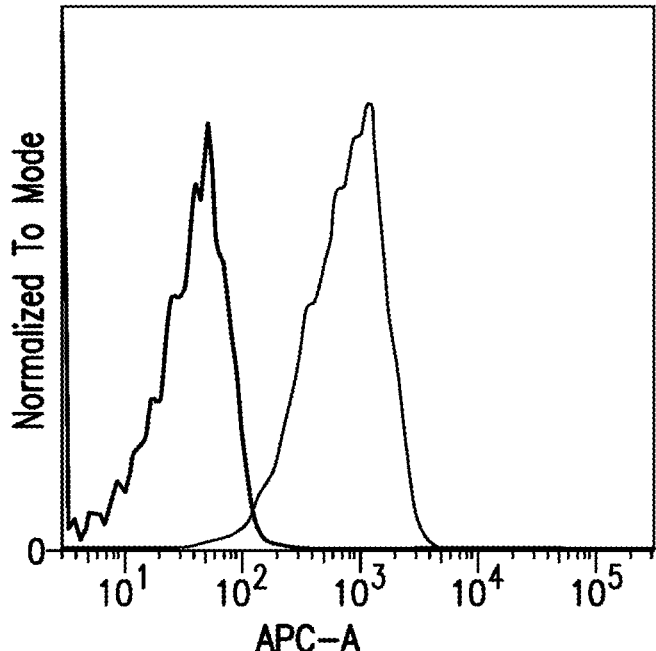
Figure 9B:
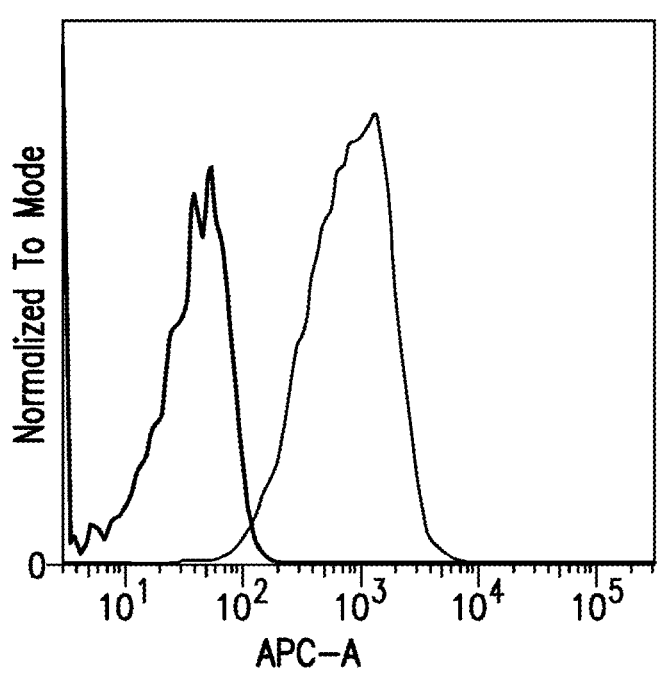
Figure 9B:
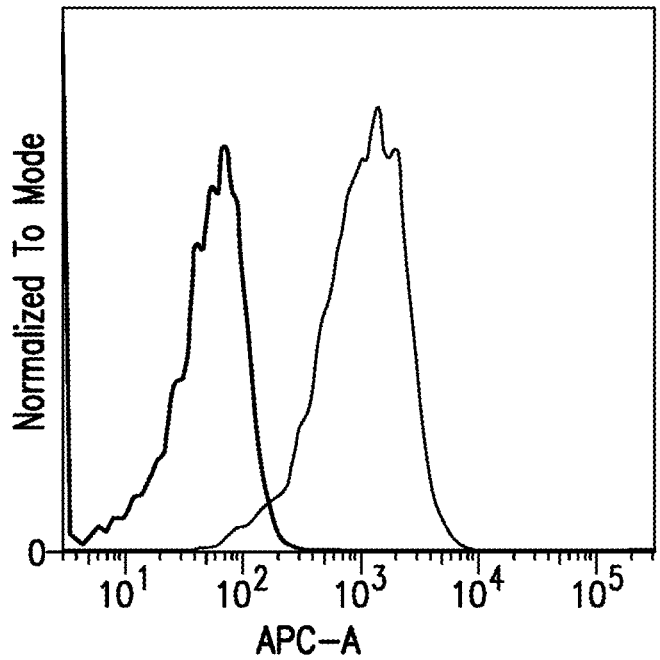
Figure 9B:
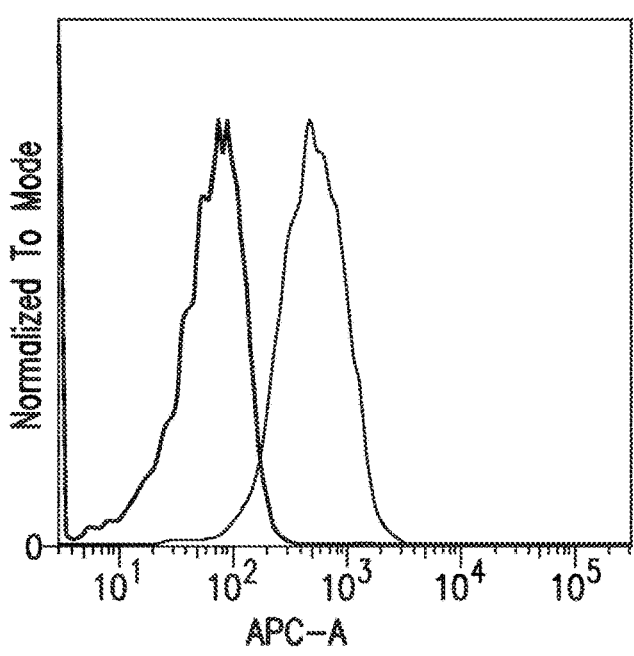
Figure 9B:
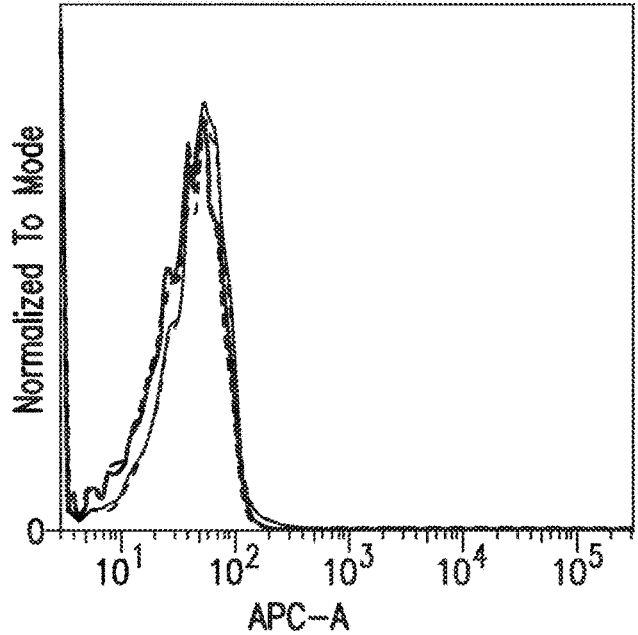

Anti-FcLR5/CD3 bispecific antibodies were generated using the ET200-31, ET200-39, ET200-69, ET200-104, ET200-105, ET200-109 and ET200-117 scFvs disclosed herein. FIGS. 9A and 9B show the FACS analysis of the anti-FcRL5/CD3 bispecific antibodies. Each antibody was incubated with 3T3 or 3T3-FcRL5 cells at 10 μg/ml, followed by the incubation with a FITC-conjugated anti-His tag antibody. The binding to FcRL5 was measured by FACS and expressed as mean fluorescence intensity (MFI). Cells incubated with the secondary antibody alone, the ET901 bispecific antibody control or the cells alone were used as negative controls. As shown in FIGS. 9A and 9B, the anti-FcRL5/CD3 bispecific antibodies generated using the disclosed scFvs specifically bound to 3T3 cells expressing FcRL5.

Example 5—Bispecific Antibodies Specific for FcRL5 and CD3

Two anti-FcRL5 bispecific antibodies, ET200-104 and ET200-117, were analyzed by Pepscan to determine epitope specificity. See Table 231. The target protein is human FcRL5 comprising amino acids 1-851 of SEQ ID NO: 899.

TABLE 231

| Name | Origin | Concentration | Location |
|---|---|---|---|
| ET200-104 bispecific scFV | human | 2.0 mg/ml | +4°C/22 |
| ET200-117 bispecific scFV | human | 1.6 mg/ml | +4°C/22 |

Methods

Figure 10:
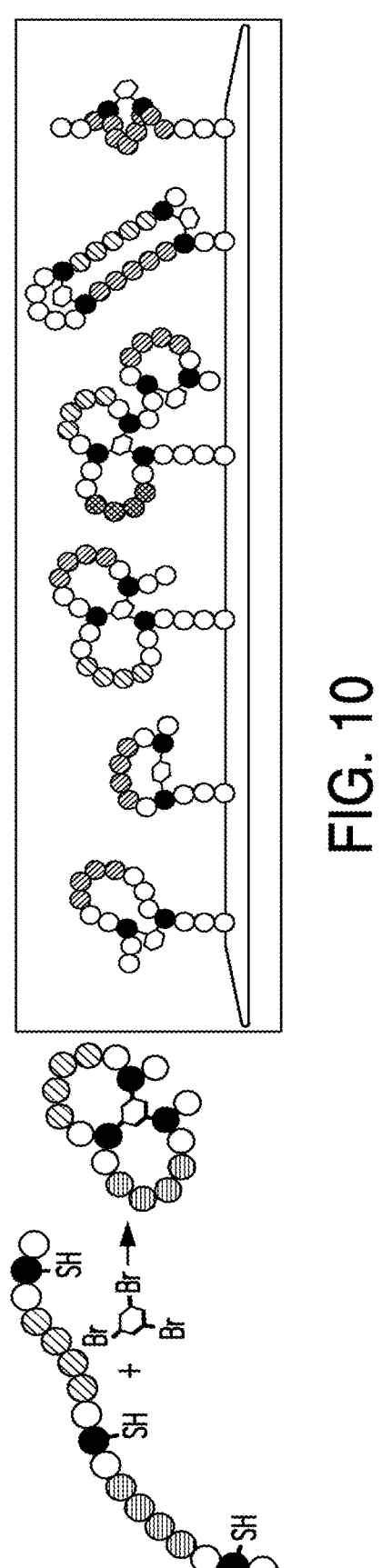
FIG. 10 illustrates the CLIPS technology. The CLIPS reaction takes place between bromo groups of the CLIPS scaffold and thiol sidechains of cysteines. The reaction is fast and specific under mild conditions. Using this elegant chemistry, native protein sequences are transformed into CLIPS constructs with a range of structures. From left to right: two different single T2 loops, T3 double loop, conjugated T2+T3 loops, stabilized beta sheet, and stabilized alpha helix (Timmerman et al., J. Mol. Recognit. 2007; 20: 283-29).

The principles of clips technology. CLIPS technology structurally fixes peptides into defined three-dimensional structures. This results in functional mimics of even the most complex binding sites. CLIPS technology is now routinely used to shape peptide libraries into single, double or triple looped structures as well as sheet- and helix-like folds (FIG. 10).

Figure 11:
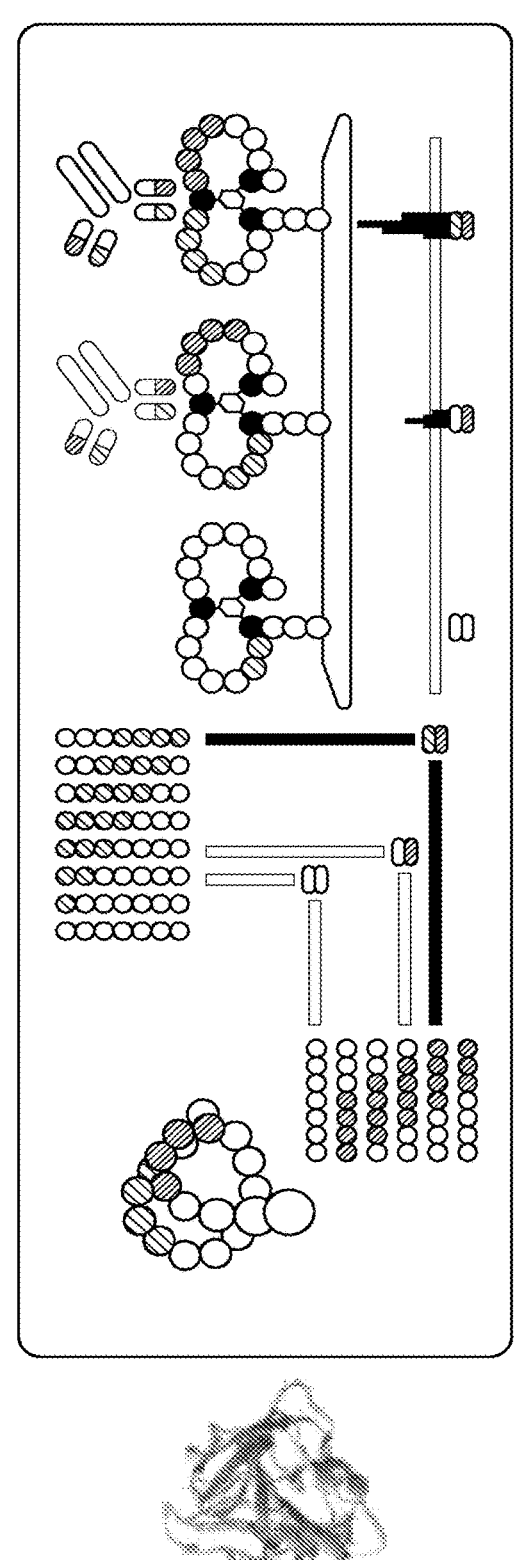
FIG. 11 illustrates combinatorial clips library screening. The target protein (left) containing a discontinuous conformational epitope is converted into a matrix library (middle). Combinatorial peptides are synthesized on a proprietary minicard and chemically converted into spatially defined CLIPS constructs (right).

Combinatorial clips library screening in detail. CLIPS library screening starts with the conversion of the target protein into a library of up to 10,000 overlapping peptide constructs, using a combinatorial matrix design. On a solid carrier, a matrix of linear peptides is synthesized, which are subsequently shaped into spatially defined CLIPS constructs (FIG. 11). Constructs representing both parts of the discontinuous epitope in the correct conformation bind the antibody with high affinity, which is detected and quantified. Constructs presenting the incomplete epitope bind the antibody with lower affinity, whereas constructs not containing the epitope do not bind at all. Affinity information is used in iterative screens to define the sequence and conformation of epitopes in detail.

Figure 12:
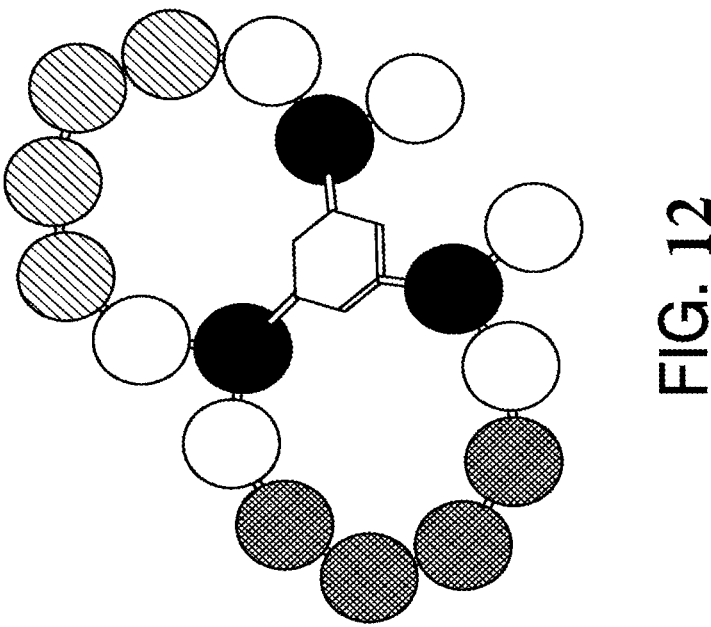
FIG. 12 depicts T3 looped CLIPS™ construct.
Figures 13A, 13B, 13C, 13D:
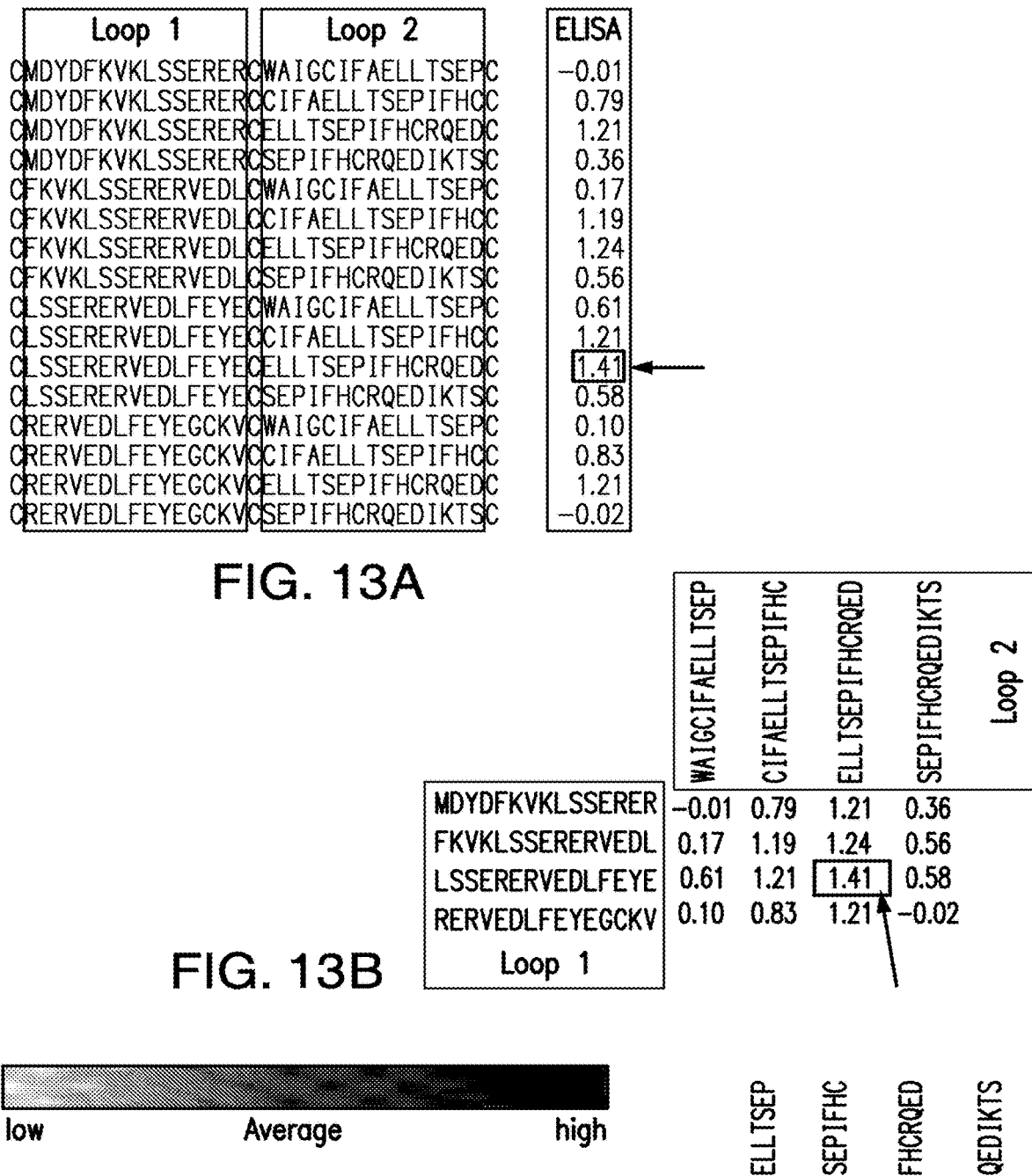
FIGS. 13A-13D illustrate heat map technology.

Heat map analysis. A heat map is a graphical representation of data where the values taken by a variable in a two-dimensional map are represented as colors. For double-looped CLIPS peptides, such a two-dimensional map can be derived from the independent sequences of the first and second loops. For example, the sequences of the 16 CLIPS peptides depicted in FIG. 13 are effectively permutations of 4 unique sub-sequences in loop 1 (colored in blue in FIG. 12) and 4 unique sub-sequences in loop 2 (colored in green in FIG. 12). Thus, the observed ELISA data (colored in red in FIG. 13A) can be plotted in a 4×4 matrix, where each X coordinate corresponds to the sequence of the first loop, and each Y coordinate corresponds to the sequence of the second loop. For instance, the ELISA value observed for CLIPS peptide CLSSERERVEDLFEYECELLTSEPIFHCRQEDC (indicated with an arrow in FIG. 12A) can be found at the third row, third column of FIG. 13B (indicated with an arrow and a red square). To further facilitate the visualization, ELISA values can be replaced with colors from a continuous gradient. In this case, extremely low values are colored in green, extremely high values are colored in red, and average values are colored in black (see FIG. 13C). For the aforementioned example, the average value is 0.71. When this color map is applied to the data matrix depicted in FIG. 13B, a color heat map is obtained (see FIG. 13D, the original data is still indicated for extra clarity).

Synthesis of peptides. To reconstruct epitopes of the target molecule a library of peptides was synthesized. An amino functionalized polypropylene support was obtained by grafting with a proprietary hydrophilic polymer formulation, followed by reaction with t-butyloxycarbonyl-hexamethyl-enediamine (BocHMDA) using dicyclohexylcarbodiimide (DCC) with Nhydroxybenzotriazole (HOBt) and subsequent cleavage of the Boc-groups using trifluoroacetic acid (TFA). Standard Fmoc-peptide synthesis was used to synthesize peptides on the amino-functionalized solid support by custom modified JANUS liquid handling stations (Perkin Elmer). Synthesis of structural mimics was done using Pepscan's proprietary Chemically Linked Peptides on Scaffolds (CLIPS) technology. CLIPS technology allows to structure peptides into single loops, doubleloops, triple loops, sheet-like folds, helix-like folds and combinations thereof. CLIPS templates are coupled to cysteine residues. The side-chains of multiple cysteines in the peptides were coupled to one or two CLIPS templates. For example, a 0.5 mM solution of the P2 CLIPS (2,6-bis(bromomethyl)pyridine) was dissolved in ammonium bicarbonate (20 mM, pH 7.8)/acetonitrile (1:3(v/v)). This solution was added onto the peptide arrays. The CLIPS template bound to side-chains of two cysteines as present in the solid-phase bound peptides of the peptide-arrays (455 wells plate with 3 μl wells). The peptide arrays were gently shaken in the solution for 30 to 60 minutes while completely covered in solution. Finally, the peptide arrays were washed extensively with excess of $H_2O$ and sonicated in disrupt-buffer containing 1% SDS/ 0.1% beta-mercaptoethanol in PBS (pH 7.2) at 70° C. for 30 minutes, followed by sonication in $H_2O$ for another 45 minutes. The T3 CLIPS carrying peptides were made in a similar way but now with three cysteines.

ELISA Screening. The binding of antibody to each of the synthesized peptides was tested in a PEPSCAN-based ELISA. The peptide arrays were incubated with primary antibody solution (overnight at 4° C.). After washing, the peptide arrays were incubated with a 1/1000 dilution of an appropriate antibody peroxidase conjugate (SBA) for one hour at 25° C. After washing, the peroxidase substrate 2,2'-azino-di-3-ethylbenzthiazoline sulfonate (ABTS) and 2 μl/ml of 3 percent $H_2O_2$ were added. After one hour, the color development was measured. The color development was quantified with a charge coupled device (CCD)— camera and an image processing system.

Data processing. The values obtained from the CCD camera ranged from 0 to 3000 mAU, similar to a standard 96-well plate ELISA-reader. The results were quantified and stored into the Peplab database. Occasionally a well contained an air-bubble resulting in a false-positive value, the cards were manually inspected and any values caused by an air-bubble were scored as 0.

Synthesis quality control. To verify the quality of the synthesized peptides, a separate set of positive and negative control peptides was synthesized in parallel. These were screened with antibody 57.9 (Posthumus et al., J. Virology, 1990, 64:3304-3309).

Results

Screening. Antibody binding depends on a combination of factors, including concentration of the antibody and the amounts and nature of competing proteins in the ELISA buffer. Also, the pre-coat conditions (the specific treatment of the peptide arrays prior to incubation with the experimental sample) affected binding. These details are summed up in Table 232. For the Pepscan Buffer and Preconditioning (SQ), the numbers indicate the relative amount of competing protein (a combination of horse serum and ovalbumin).

TABLE 232

| Screening conditions | | | |
|---|---|---|---|
| Label | Dilution | Sample Buffer | Pre-conditioning |
| ET200-104 | 8 μg/ml | PBS-Tween | PBS-Tween |
| ET200-117 | 3 μg/ml | PBS-Tween | 0.1% SQ |

Antibodies ET200-104 and ET200-117 were coated at 1 μg/ml on a Nunc Maxisorp plate for ELISA and detected with Goat Anti-Human Ig-HRP (Southern Biotech; #2010/ 05), the same conjugate that is used in minicard screenings. For ET200-104 and ET200-117 signal >1 OD was obtained for some dilutions of the secondary Ab, indicating that the secondary antibody is well suited for detection of these mAbs.

Figures 1, 14:
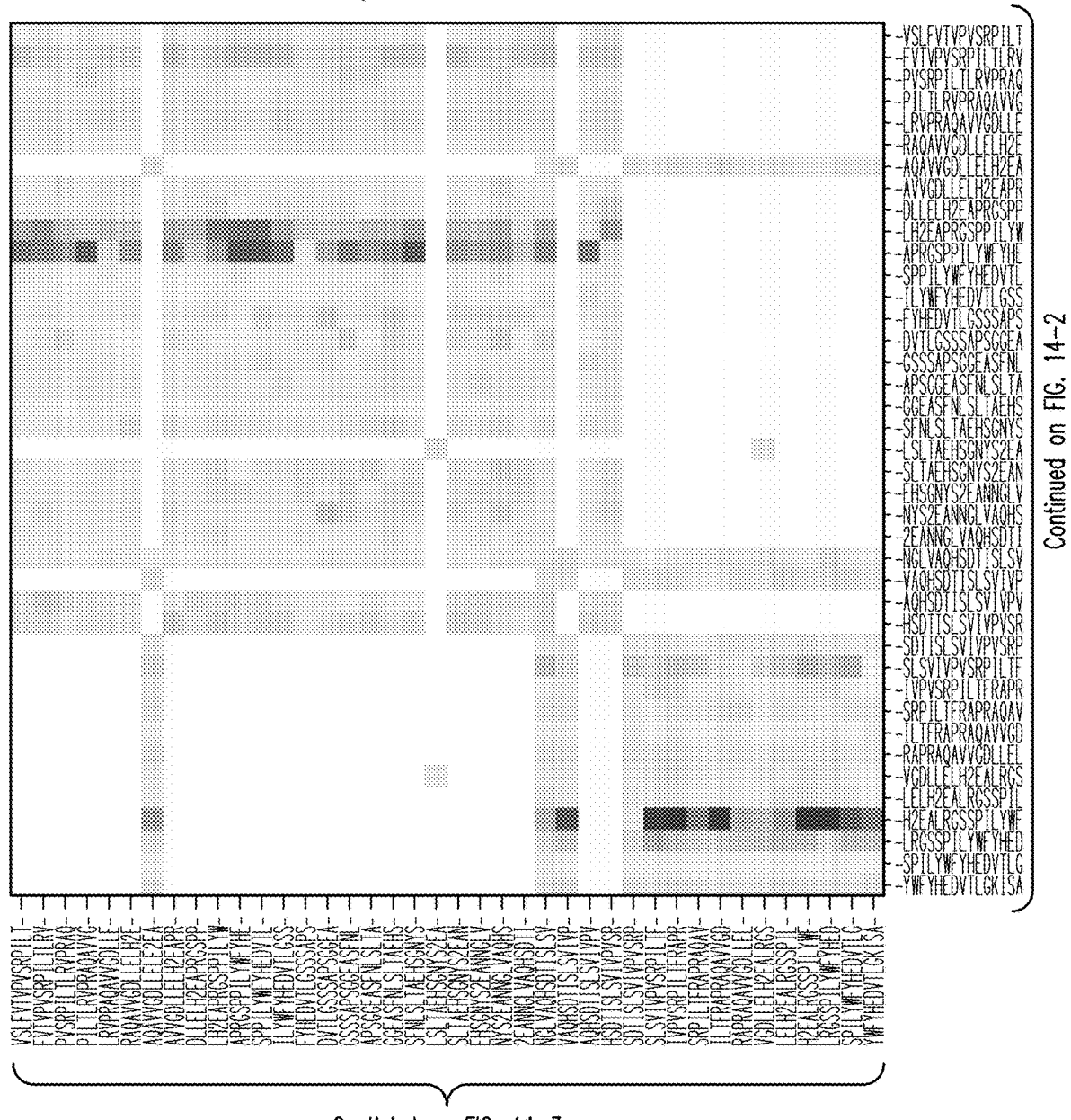
FIG. 14 shows heatmap analysis of data recorded for Herceptin.
Figures 2, 14:
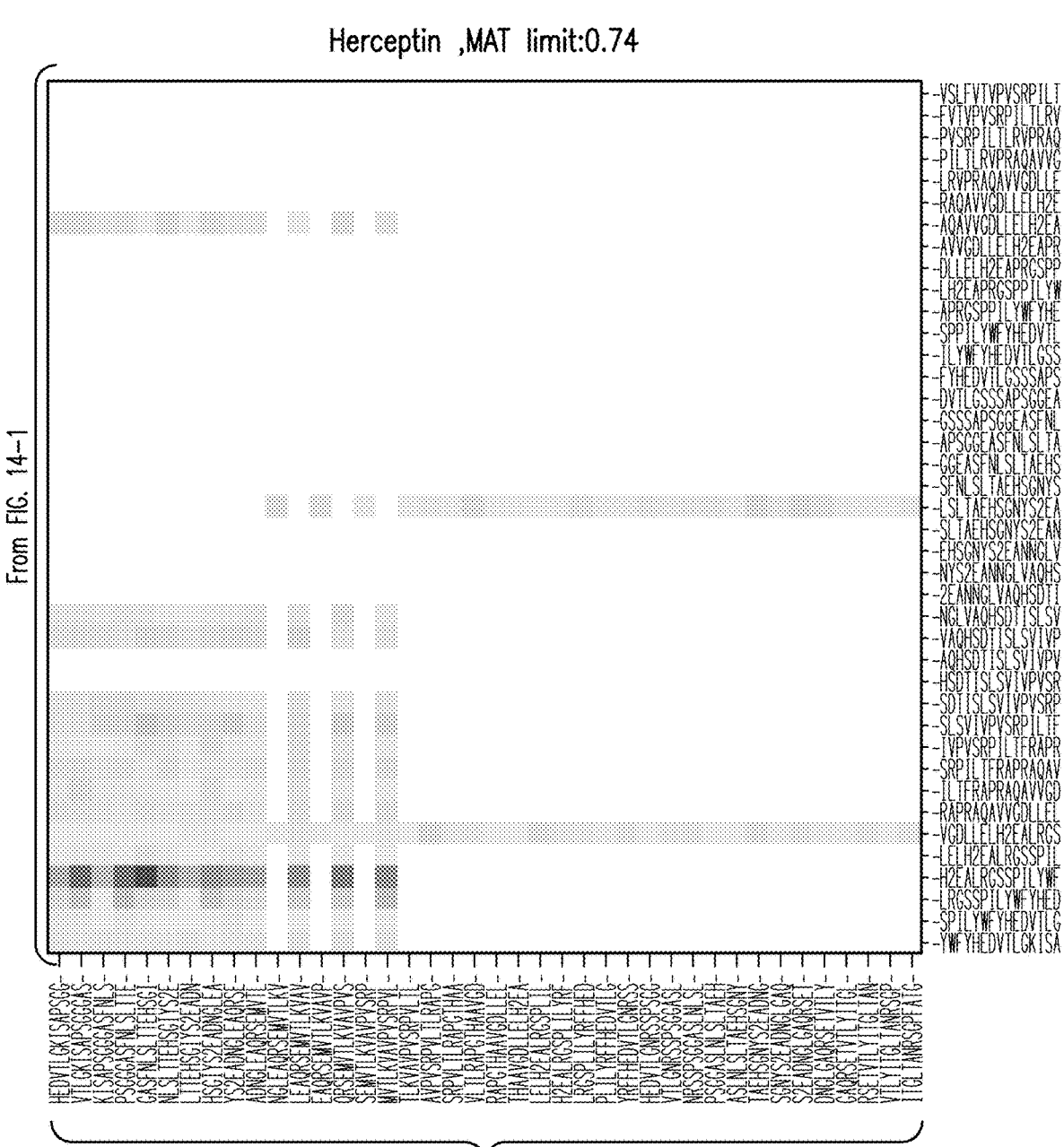
Figures 3, 14:
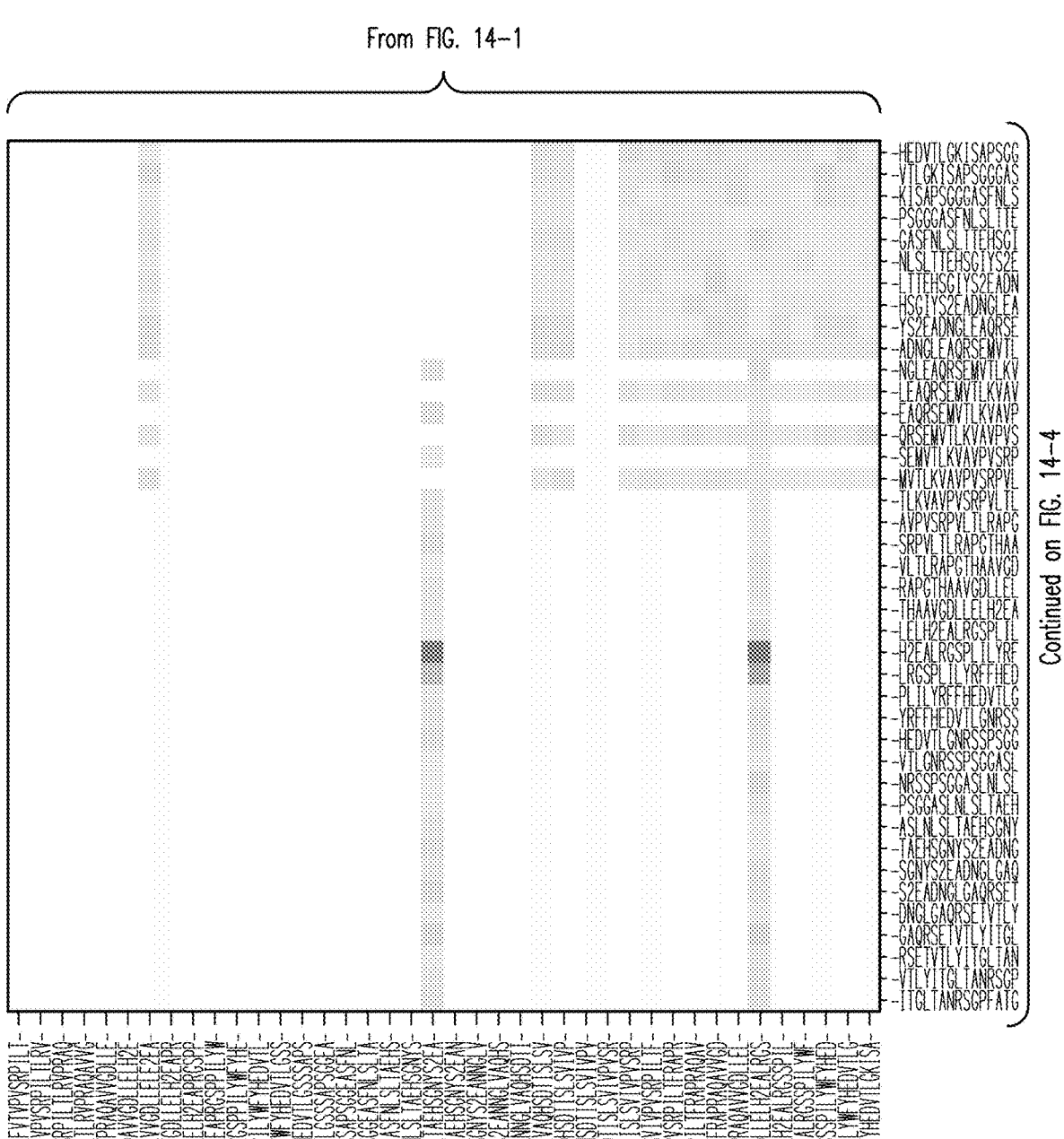
Figure 14:
Figure 4:
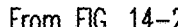

Herceptin was used as an internal negative control at high concentration in the absence of blocking buffer. Herceptin bound peptides with common sequences LRGSPLILYRF, LRGSSPILYWF and APRGSPPILYW (FIG. 14). Peptides containing aforementioned sequences were excluded from epitope candidates for test samples.

Figures 1, 15:
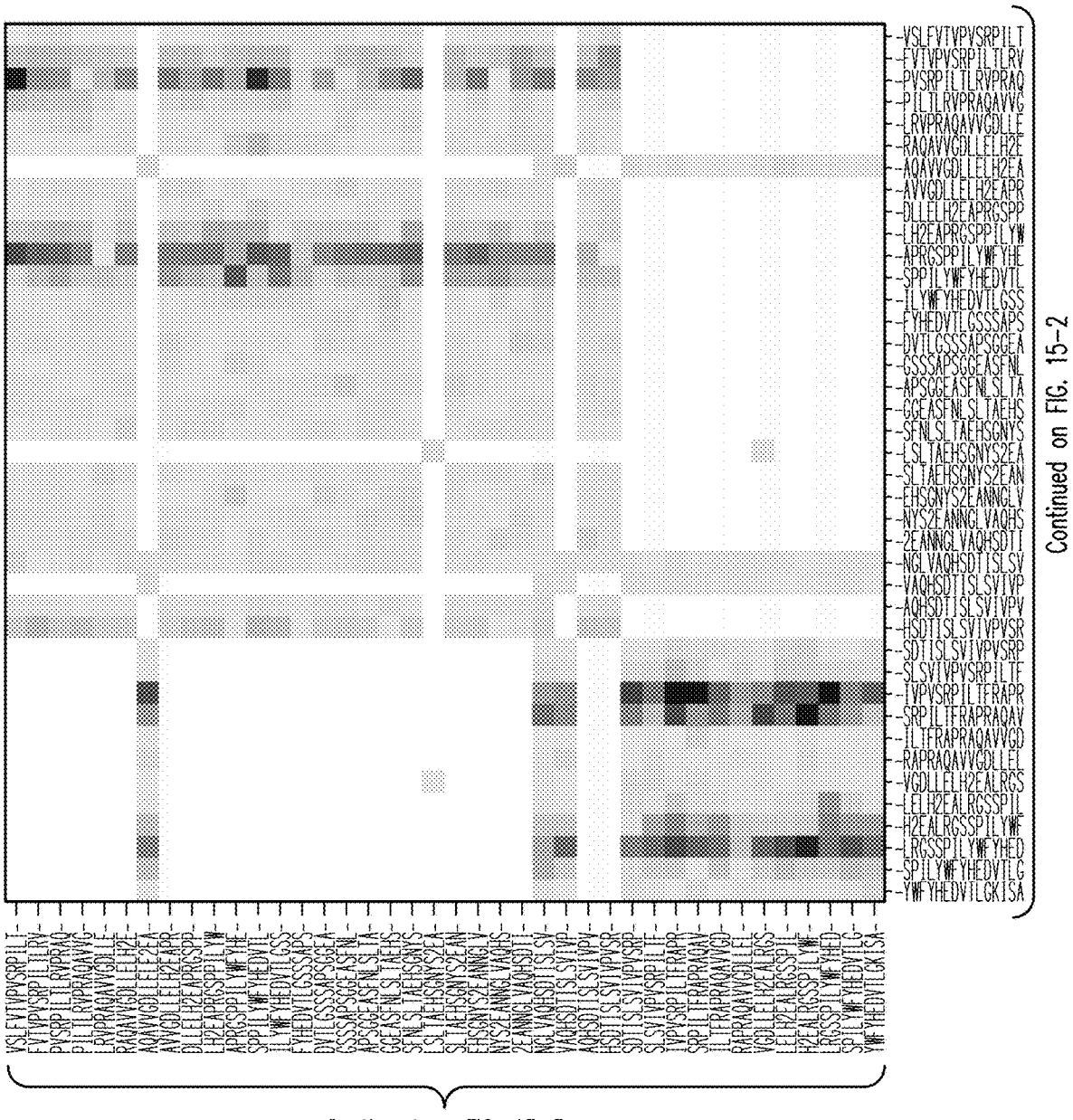
FIG. 15 shows heatmap analysis of data recorded for ET200-104.
Figures 2, 15:
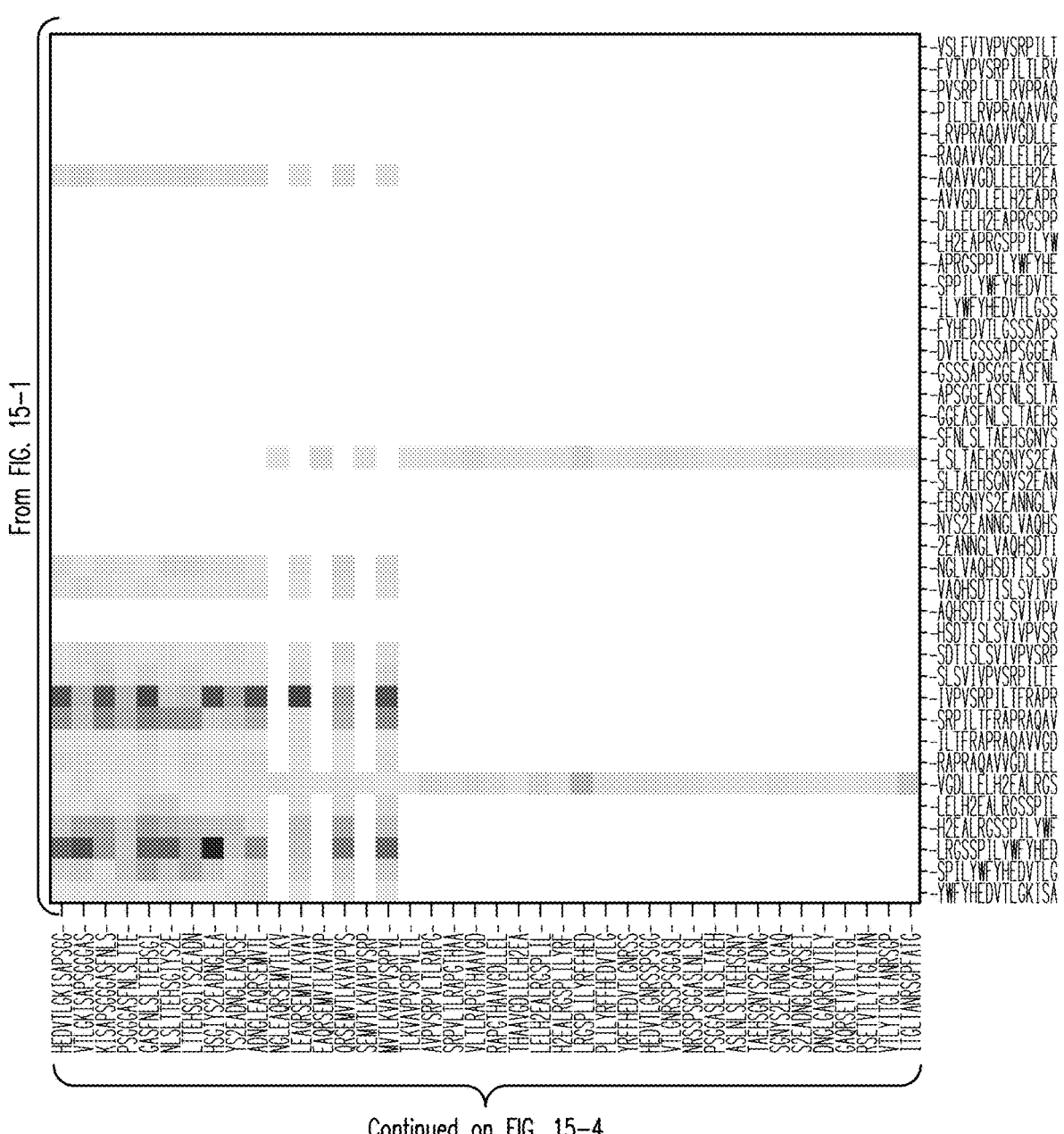
Figures 3, 15:
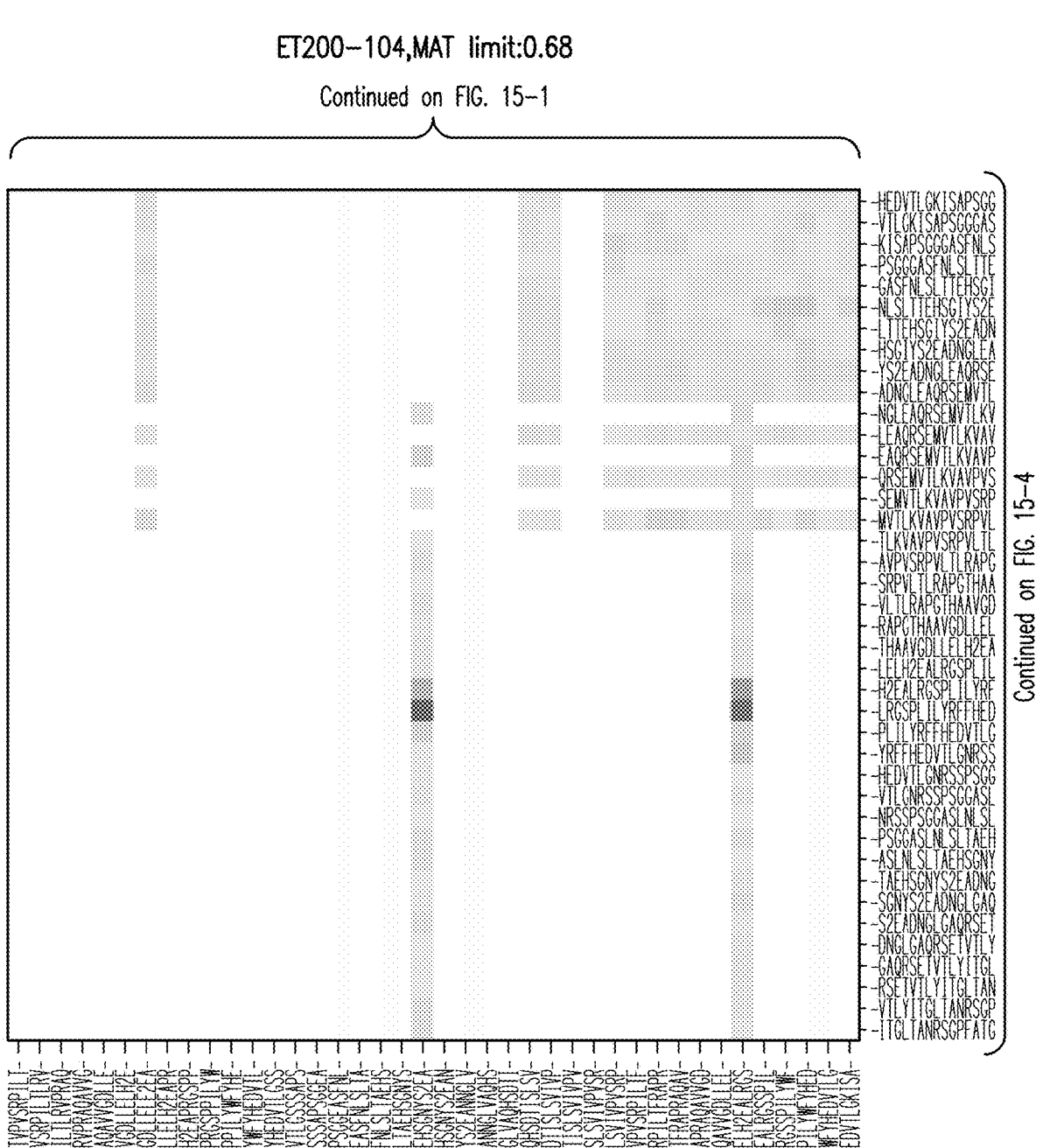
Figures 4, 15:
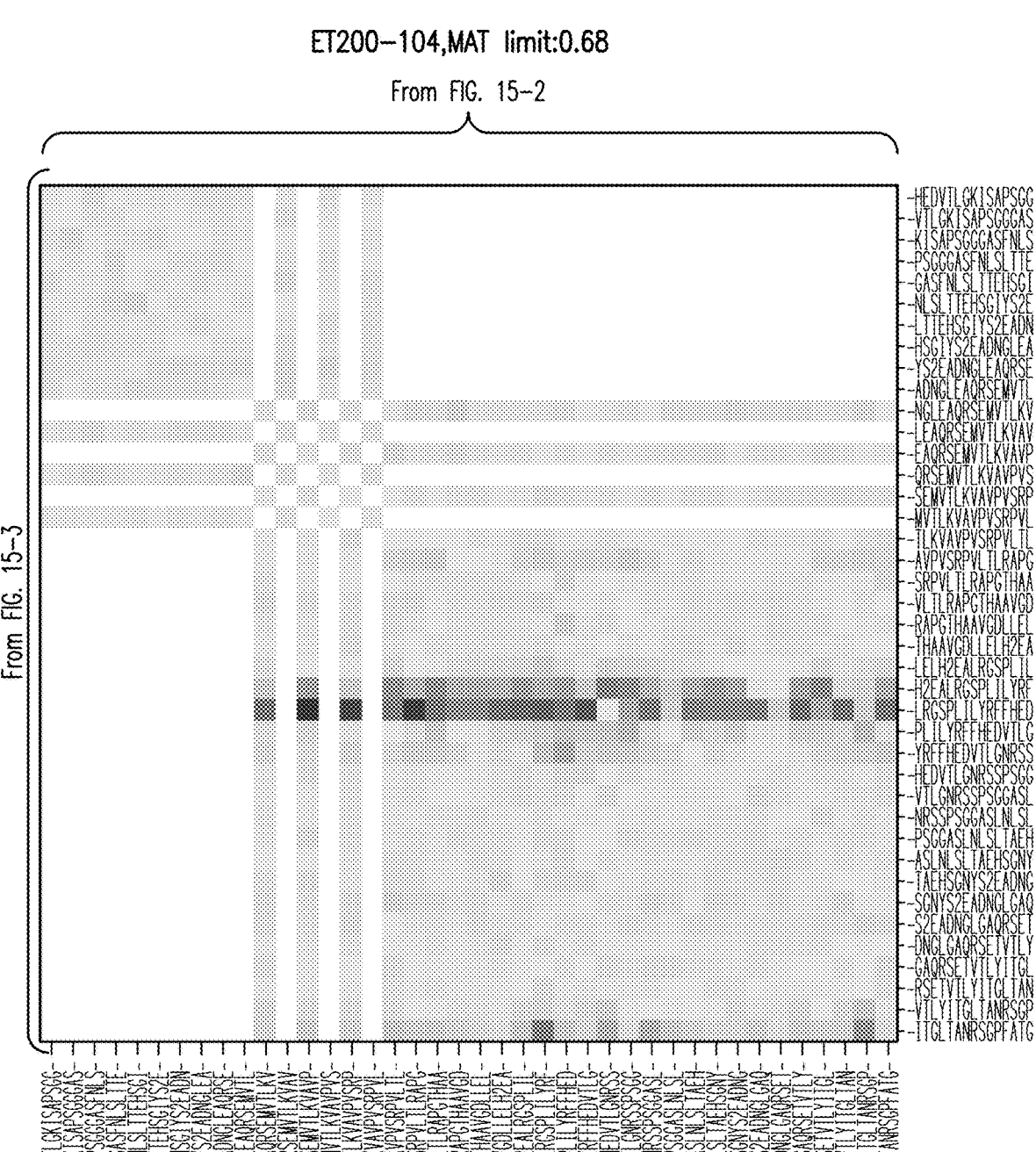

When tested under low stringency conditions and at a high concentration antibody, ET200-104 binds multiple peptide motifs in all sets (FIG. 15). The majority of peptides bound were suspected to be the result of non-specific hydrophobic interactions based on the results obtained for Herceptin (internal negative control). However, binding of peptides containing motif $_{657}$SRPILTFRAPR$_{667}$ was proposed to be specific, and was uniquely attributed to sample ET200-104.

When tested under low stringency conditions, antibody ET200-117 resulted in weak binding of multiple peptide motifs on all sets. Cumulative data analysis of data obtained for all sets suggests that the antibody uniquely recognizes a region containing peptide stretch $_{829}$RSETVTLYITGL$_{840}$ in domain 9 of Fc receptor-like protein 5 distinct from the Herceptin internal negative control and ET200-104. Again the majority of other peptides bound were suspected to be the result of unspecific hydrophic interactions that shared as the same binding pattern was recorded under low stringency conditions for antibody ET200-104.

CONCLUSIONS

Figure 16:
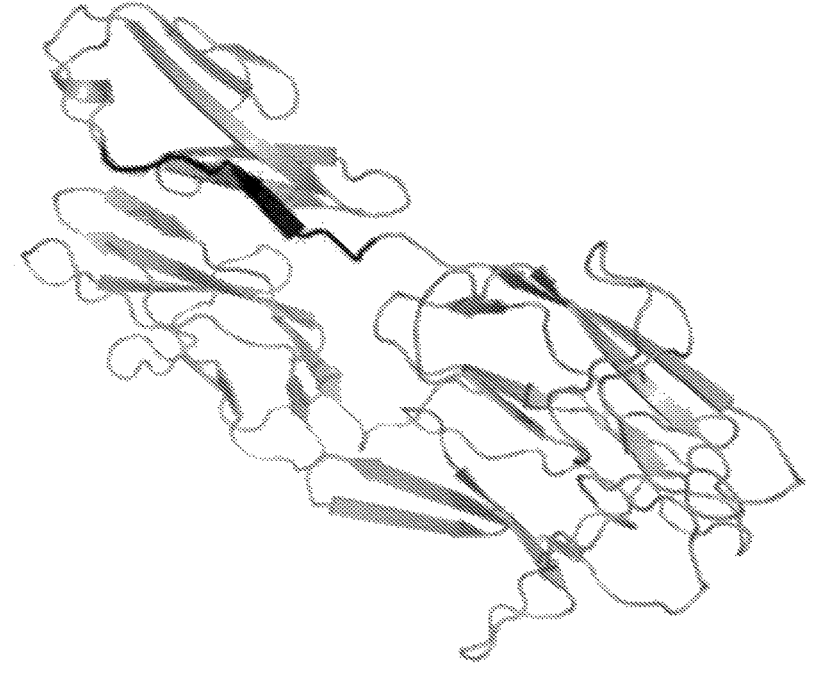
FIG. 16 illustrates a 3D model of amino acid residues 380-731 of FcRL5 with peptide stretch $_{657}$SRPILTFRAPR$_{667}$ highlighted.

Cumulative data analysis of results collected for ET200-104 and ET200-117 vs. Herceptin suggest that antibody ET200-104 targets residues $_{657}$SRPILTFRAPR$_{667}$ within domain 8 of Fc receptor-like protein 5 and antibody ET200-117 targets residues $_{829}$RSETVTLYITGL$_{840}$ within domain 9. Additionally, for both samples multiple signals were recorded with peptides non-specifically bound by Herceptin. The epitope candidate identified for ET200-104 was visualized using a publically available 3D model of Fc receptor-like protein 5 (FIG. 16). The epitope candidate for ET200-117 lies within the non-modeled part of the target and therefore cannot be visualized.

Although the foregoing presently disclosed subject matter has been described in some detail by way of illustration and example for purposes of clarity of understanding, the descriptions and examples should not be construed as limiting the scope of the presently disclosed subject matter. The disclosures of all patent and scientific literature cited herein are expressly incorporated in their entirety by reference.

SEQUENCE LISTING

The patent contains a lengthy sequence listing. A copy of the sequence listing is available in electronic form from the USPTO web site (https://seqdata.uspto.gov/docdetail?docId=US12636375B2). An electronic copy of the sequence listing will also be available from the USPTO upon request and payment of the fee set forth in 37 CFR 1.19(b)(3).

What is claimed is:

1. A nucleic acid molecule encoding an anti-Fc Receptor-Like 5 (FcRL5) antibody or an antigen-binding fragment thereof comprising a light chain variable region and a heavy chain variable region, wherein:

(aa) the encoded light chain variable region comprises a CDR1 comprising the amino acid sequence set forth in SEQ ID NO:312, a CDR2 comprising the amino acid sequence set forth in SEQ ID NO:313, and a CDR3 comprising the amino acid sequence set forth in SEQ ID NO:314; and the encoded heavy chain variable region comprises a CDR1 comprising the amino acid sequence set forth in SEQ ID NO:309, a CDR2 comprising the amino acid sequence set forth in SEQ ID NO:310, and a CDR3 comprising the amino acid sequence set forth in SEQ ID NO:311;

(ab) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:320; and the encoded heavy chain variable region comprises a CDR1 comprising the amino acid sequence set forth in SEQ ID NO:315, a CDR2 comprising the amino acid sequence set forth in SEQ ID NO:316, and a CDR3 comprising the amino acid sequence set forth in SEQ ID NO:317;

(ac) the encoded light chain variable region comprises a CDR1 comprising the amino acid sequence set forth in SEQ ID NO:324, a CDR2 comprising the amino acid sequence set forth in SEQ ID NO:319, and a CDR3 comprising the amino acid sequence set forth in SEQ ID NO:325; and the encoded heavy chain variable region comprises a CDR1 comprising the amino acid sequence set forth in SEQ ID NO:321, a CDR2 comprising the amino acid sequence set forth in SEQ ID NO:322, and a CDR3 comprising the amino acid sequence set forth in SEQ ID NO:323;

(ad) the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:331; and the encoded heavy chain variable region comprises a CDR1 comprising the amino acid sequence set forth in SEQ ID NO:326, a CDR2 comprising the amino acid sequence set forth in SEQ ID NO:327, and a CDR3 comprising the amino acid sequence set forth in SEQ ID NO:328;

(ae) the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:331; and the encoded heavy chain variable region comprises a CDR1 comprising the amino acid sequence set forth in SEQ ID NO:332, a CDR2 comprising the amino acid sequence set forth in SEQ ID NO:333, and a CDR3 comprising the amino acid sequence set forth in SEQ ID NO:334;

(af) the encoded light chain variable region comprises a CDR1 comprising the amino acid sequence set forth in SEQ ID NO:338, a CDR2 comprising the amino acid sequence set forth in SEQ ID NO:330, and a CDR3 comprising the amino acid sequence set forth in SEQ ID NO:339; and the encoded heavy chain variable region comprises a CDR1 comprising the amino acid sequence set forth in SEQ ID NO:335, a CDR2 comprising the amino acid sequence set forth in SEQ ID NO:336, and a CDR3 comprising the amino acid sequence set forth in SEQ ID NO:337;

(ag) the encoded light chain variable region comprises a CDR1 comprising the amino acid sequence set forth in SEQ ID NO:343, a CDR2 comprising the amino acid sequence set forth in SEQ ID NO:344, and a CDR3 comprising the amino acid sequence set forth in SEQ ID NO:345; and the encoded heavy chain variable region comprises a CDR1 comprising the amino acid sequence set forth in SEQ ID NO:340, a CDR2 comprising the amino acid sequence set forth in SEQ ID NO:341, and a CDR3 comprising the amino acid sequence set forth in SEQ ID NO:342;

(ah) the encoded light chain variable region comprises a CDR1 comprising the amino acid sequence set forth in SEQ ID NO:348, a CDR2 comprising the amino acid sequence set forth in SEQ ID NO:349, and a CDR3 comprising the amino acid sequence set forth in SEQ ID NO:350; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:347;

(ai) the encoded light chain variable region comprises a CDR1 comprising the amino acid sequence set forth in SEQ ID NO:352, a CDR2 comprising the amino acid sequence set forth in SEQ ID NO:344, and a CDR3 comprising the amino acid sequence set forth in SEQ ID NO:353; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:351;

(aj) the encoded light chain variable region comprises a CDR1 comprising the amino acid sequence set forth in SEQ ID NO:357, a CDR2 comprising the amino acid sequence set forth in SEQ ID NO:358, and a CDR3 comprising the amino acid sequence set forth in SEQ ID NO:359; and the encoded heavy chain variable region comprises a CDR1 comprising the amino acid sequence set forth in SEQ ID NO:354, a CDR2 comprising the amino acid sequence set forth in SEQ ID NO:355, and a CDR3 comprising the amino acid sequence set forth in SEQ ID NO:356;

(ak) the encoded light chain variable region comprises a CDR1 comprising the amino acid sequence set forth in SEQ ID NO:363, a CDR2 comprising the amino acid sequence set forth in SEQ ID NO:364, and a CDR3 comprising the amino acid sequence set forth in SEQ ID NO:365; and the encoded heavy chain variable region comprises a CDR1 comprising the amino acid sequence set forth in SEQ ID NO:360, a CDR2 comprising the amino acid sequence set forth in SEQ ID NO:361, and a CDR3 comprising the amino acid sequence set forth in SEQ ID NO:362;

(al) the encoded light chain variable region comprises a CDR1 comprising the amino acid sequence set forth in SEQ ID NO:369, a CDR2 comprising the amino acid sequence set forth in SEQ ID NO:370, and a CDR3 comprising the amino acid sequence set forth in SEQ ID NO:371; and the encoded heavy chain variable region comprises a CDR1 comprising the amino acid sequence set forth in SEQ ID NO:366, a CDR2 comprising the amino acid sequence set forth in SEQ ID NO:367, and a CDR3 comprising the amino acid sequence set forth in SEQ ID NO:368;

(am) the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:375; and the encoded heavy chain variable region comprises a CDR1 comprising the amino acid sequence set forth in SEQ ID NO:372, a CDR2 comprising the amino acid sequence set forth in SEQ ID NO:373, and a CDR3 comprising the amino acid sequence set forth in SEQ ID NO:374;

(an) the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:377; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:376;

(ao) the encoded light chain variable region comprises a CDR1 comprising the amino acid sequence set forth in SEQ ID NO:381, a CDR2 comprising the amino acid sequence set forth in SEQ ID NO:382, and a CDR3 comprising the amino acid sequence set forth in SEQ ID NO:383; and the encoded heavy chain variable region comprises a CDR1 comprising the amino acid sequence set forth in SEQ ID NO:378, a CDR2 comprising the amino acid sequence set forth in SEQ ID NO:379, and a CDR3 comprising the amino acid sequence set forth in SEQ ID NO:380;

(ap) the encoded light chain variable region comprises a CDR1 comprising the amino acid sequence set forth in SEQ ID NO:329, a CDR2 comprising the amino acid sequence set forth in SEQ ID NO:385, and a CDR3 comprising the amino acid sequence set forth in SEQ ID NO:386; and the encoded heavy chain variable region comprises a CDR1 comprising the amino acid sequence set forth in SEQ ID NO:309, a CDR2 comprising the amino acid sequence set forth in SEQ ID NO:310, and a CDR3 comprising the amino acid sequence set forth in SEQ ID NO:384;

(aq) the encoded light chain variable region comprises a CDR1 comprising the amino acid sequence set forth in SEQ ID NO:390, a CDR2 comprising the amino acid sequence set forth in SEQ ID NO:391, and a CDR3 comprising the amino acid sequence set forth in SEQ ID NO:392; and the encoded heavy chain variable region comprises a CDR1 comprising the amino acid sequence set forth in SEQ ID NO:387, a CDR2 comprising the amino acid sequence set forth in SEQ ID NO:388, and a CDR3 comprising the amino acid sequence set forth in SEQ ID NO:389;

(ar) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:395; and the encoded heavy chain variable region comprises a CDR1 comprising the amino acid sequence set forth in SEQ ID NO:393, a CDR2 comprising the amino acid sequence set forth in SEQ ID NO:355, and a CDR3 comprising the amino acid sequence set forth in SEQ ID NO:394;

(as) the encoded light chain variable region comprises a CDR1 comprising the amino acid sequence set forth in SEQ ID NO:397, a CDR2 comprising the amino acid sequence set forth in SEQ ID NO:398, and a CDR3 comprising the amino acid sequence set forth in SEQ ID NO:399; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:396;

(at) the encoded light chain variable region comprises a CDR1 comprising the amino acid sequence set forth in SEQ ID NO:401, a CDR2 comprising the amino acid sequence set forth in SEQ ID NO:398, and a CDR3 comprising the amino acid sequence set forth in SEQ ID NO:402; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:400;

(au) the encoded light chain variable region comprises a CDR1 comprising the amino acid sequence set forth in SEQ ID NO:406, a CDR2 comprising the amino acid sequence set forth in SEQ ID NO:398, and a CDR3 comprising the amino acid sequence set forth in SEQ ID NO:407; and the encoded heavy chain variable region comprises a CDR1 comprising the amino acid sequence set forth in SEQ ID NO:403, a CDR2 comprising the amino acid sequence set forth in SEQ ID NO:404, and a CDR3 comprising the amino acid sequence set forth in SEQ ID NO:405;

(av) the encoded light chain variable region comprises a CDR1 comprising the amino acid sequence set forth in SEQ ID NO:329, a CDR2 comprising the amino acid sequence set forth in SEQ ID NO:409, and a CDR3 comprising the amino acid sequence set forth in SEQ ID NO:410; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:408;

(aw) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:414; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:413;

(ax) the encoded light chain variable region comprises a CDR1 comprising the amino acid sequence set forth in SEQ ID NO:416, a CDR2 comprising the amino acid sequence set forth in SEQ ID NO:417, and a CDR3 comprising the amino acid sequence set forth in SEQ ID NO:418; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:415;

(ay) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:419; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:349;

(az) the encoded light chain variable region comprises a CDR1 comprising the amino acid sequence set forth in SEQ ID NO:423, a CDR2 comprising the amino acid sequence set forth in SEQ ID NO:358, and a CDR3 comprising the amino acid sequence set forth in SEQ ID NO:424; and the encoded heavy chain variable region comprises a CDR1 comprising the amino acid sequence set forth in SEQ ID NO:420, a CDR2 comprising the amino acid sequence set forth in SEQ ID NO:421, and a CDR3 comprising the amino acid sequence set forth in SEQ ID NO:422;

(ba) the encoded light chain variable region comprises a CDR1 comprising the amino acid sequence set forth in SEQ ID NO:428, a CDR2 comprising the amino acid sequence set forth in SEQ ID NO:429, and a CDR3 comprising the amino acid sequence set forth in SEQ ID NO:430; and the encoded heavy chain variable region comprises a CDR1 comprising the amino acid sequence set forth in SEQ ID NO:425, a CDR2 comprising the amino acid sequence set forth in SEQ ID NO:426, and a CDR3 comprising the amino acid sequence set forth in SEQ ID NO:427;

(bb) the encoded light chain variable region comprises a CDR1 comprising the amino acid sequence set forth in SEQ ID NO:433, a CDR2 comprising the amino acid sequence set forth in SEQ ID NO:434, and a CDR3 comprising the amino acid sequence set forth in SEQ ID NO:435; and the encoded heavy chain variable region comprises a CDR1 comprising the amino acid sequence set forth in SEQ ID NO:372, a CDR2 comprising the amino acid sequence set forth in SEQ ID NO:431, and a CDR3 comprising the amino acid sequence set forth in SEQ ID NO:432;

(bc) the encoded light chain variable region comprises a CDR1 comprising the amino acid sequence set forth in SEQ ID NO:423, a CDR2 comprising the amino acid sequence set forth in SEQ ID NO:438, and a CDR3 comprising the amino acid sequence set forth in SEQ ID NO:439; and the encoded heavy chain variable region comprises a CDR1 comprising the amino acid sequence set forth in SEQ ID NO:436, a CDR2 comprising the amino acid sequence set forth in SEQ ID NO:388, and a CDR3 comprising the amino acid sequence set forth in SEQ ID NO:437;

(bd) the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:443; and the encoded heavy chain variable region comprises a CDR1 comprising the amino acid sequence set forth in SEQ ID NO:440, a CDR2 comprising the amino acid sequence set forth in SEQ ID NO:441, and a CDR3 comprising the amino acid sequence set forth in SEQ ID NO:442;

(be) the encoded light chain variable region comprises a CDR1 comprising the amino acid sequence set forth in SEQ ID NO:447, a CDR2 comprising the amino acid sequence set forth in SEQ ID NO:448, and a CDR3 comprising the amino acid sequence set forth in SEQ ID NO:449; and the encoded heavy chain variable region comprises a CDR1 comprising the amino acid sequence set forth in SEQ ID NO:444, a CDR2 comprising the amino acid sequence set forth in SEQ ID NO:445, and a CDR3 comprising the amino acid sequence set forth in SEQ ID NO:446;

(bf) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:452; and the encoded heavy chain variable region comprises a CDR1 comprising the amino acid sequence set forth in SEQ ID NO:309, a CDR2 comprising the amino acid sequence set forth in SEQ ID NO:450, and a CDR3 comprising the amino acid sequence set forth in SEQ ID NO:451;

(bg) the encoded light chain variable region comprises a CDR1 comprising the amino acid sequence set forth in SEQ ID NO:369, a CDR2 comprising the amino acid sequence set forth in SEQ ID NO:454, and a CDR3 comprising the amino acid sequence set forth in SEQ ID NO:455; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:453;

(bh) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:457; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:456;

(bi) the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:331; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:458;

(bj) the encoded light chain variable region comprises a CDR1 comprising the amino acid sequence set forth in SEQ ID NO:460, a CDR2 comprising the amino acid sequence set forth in SEQ ID NO:461, and a CDR3 comprising the amino acid sequence set forth in SEQ ID NO:462; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:459;

(bl) the encoded light chain variable region comprises a CDR1 comprising the amino acid sequence set forth in SEQ ID NO:423, a CDR2 comprising the amino acid sequence set forth in SEQ ID NO:438, and a CDR3 comprising the amino acid sequence set forth in SEQ ID NO:465; and the encoded heavy chain variable region comprises a CDR1 comprising the amino acid sequence set forth in SEQ ID NO:436, a CDR2 comprising the amino acid sequence set forth in SEQ ID NO:388, and a CDR3 comprising the amino acid sequence set forth in SEQ ID NO:464;

(bm) the encoded light chain variable region comprises a CDR1 comprising the amino 479acid sequence set forth in SEQ ID NO:468, a CDR2 comprising the amino acid sequence set forth in SEQ ID NO:469, and a CDR3 comprising the amino acid sequence set forth in SEQ ID NO:470; and the encoded heavy chain variable region comprises a CDR1 comprising the amino acid sequence set forth in SEQ ID NO:411, a CDR2 comprising the amino acid sequence set forth in SEQ ID NO:466, and a CDR3 comprising the amino acid sequence set forth in SEQ ID NO:467;

(bn) the encoded light chain variable region comprises a CDR1 comprising the amino acid sequence set forth in SEQ ID NO:474, a CDR2 comprising the amino acid sequence set forth in SEQ ID NO:358, and a CDR3 comprising the amino acid sequence set forth in SEQ ID NO:465; and the encoded heavy chain variable region comprises a CDR1 comprising the amino acid sequence set forth in SEQ ID NO:471, a CDR2 comprising the amino acid sequence set forth in SEQ ID NO:472, and a CDR3 comprising the amino acid sequence set forth in SEQ ID NO:473;

(bo) the encoded light chain variable region comprises a CDR1 comprising the amino acid sequence set forth in SEQ ID NO:477, a CDR2 comprising the amino acid sequence set forth in SEQ ID NO:478, and a CDR3 comprising the amino acid sequence set forth in SEQ ID NO:479; and the encoded heavy chain variable region comprises a CDR1 comprising the amino acid sequence set forth in SEQ ID NO:372, a CDR2 comprising the amino acid sequence set forth in SEQ ID NO:475, and a CDR3 comprising the amino acid sequence set forth in SEQ ID NO:476;

(bp) the encoded light chain variable region comprises a CDR1 comprising the amino acid sequence set forth in SEQ ID NO:483, a CDR2 comprising the amino acid sequence set forth in SEQ ID NO:484, and a CDR3 comprising the amino acid sequence set forth in SEQ ID NO:485; and the encoded heavy chain variable region comprises a CDR1 comprising the amino acid sequence set forth in SEQ ID NO:480, a CDR2 comprising the amino acid sequence set forth in SEQ ID NO:481, and a CDR3 comprising the amino acid sequence set forth in SEQ ID NO:482;

(bq) the encoded light chain variable region comprises a CDR1 comprising the amino acid sequence set forth in SEQ ID NO:433, a CDR2 comprising the amino acid sequence set forth in SEQ ID NO:487, and a CDR3 comprising the amino acid sequence set forth in SEQ ID NO:488; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:486;

(bs) the encoded light chain variable region comprises a CDR1 comprising the amino acid sequence set forth in SEQ ID NO:312, a CDR2 comprising the amino acid sequence set forth in SEQ ID NO:313, and a CDR3 comprising the amino acid sequence set forth in SEQ ID NO:493; and the encoded heavy chain variable region comprises a CDR1 comprising the amino acid sequence set forth in SEQ ID NO:309, a CDR2 comprising the amino acid sequence set forth in SEQ ID NO:310, and a CDR3 comprising the amino acid sequence set forth in SEQ ID NO:492;

(bt) the encoded light chain variable region comprises a CDR1 comprising the amino acid sequence set forth in SEQ ID NO:490, a CDR2 comprising the amino acid sequence set forth in SEQ ID NO:349, and a CDR3 comprising the amino acid sequence set forth in SEQ ID NO:495; and the encoded heavy chain variable region comprises a CDR1 comprising the amino acid sequence set forth in SEQ ID NO:403, a CDR2 comprising the amino acid sequence set forth in SEQ ID NO:404, and a CDR3 comprising the amino acid sequence set forth in SEQ ID NO:494;

(bu) the encoded light chain variable region comprises a CDR1 comprising the amino acid sequence set forth in SEQ ID NO:498, a CDR2 comprising the amino acid sequence set forth in SEQ ID NO:344, and a CDR3 comprising the amino acid sequence set forth in SEQ ID NO:499; and the encoded heavy chain variable region comprises a CDR1 comprising the amino acid sequence set forth in SEQ ID NO:403, a CDR2 comprising the amino acid sequence set forth in SEQ ID NO:496, and a CDR3 comprising the amino acid sequence set forth in SEQ ID NO:497;

(bv) the encoded light chain variable region comprises a CDR1 comprising the amino acid sequence set forth in SEQ ID NO:503, a CDR2 comprising the amino acid sequence set forth in SEQ ID NO:504, and a CDR3 comprising the amino acid sequence set forth in SEQ ID NO:505; and the encoded heavy chain variable region comprises a CDR1 comprising the amino acid sequence set forth in SEQ ID NO:500, a CDR2 comprising the amino acid sequence set forth in SEQ ID NO:501, and a CDR3 comprising the amino acid sequence set forth in SEQ ID NO:502;

(bw) the encoded light chain variable region comprises a CDR1 comprising the amino acid sequence set forth in SEQ ID NO:508, a CDR2 comprising the amino acid sequence set forth in SEQ ID NO:349, and a CDR3 comprising the amino acid sequence set forth in SEQ ID NO:509; and the encoded heavy chain variable region comprises a CDR1 comprising the amino acid sequence set forth in SEQ ID NO:403, a CDR2 comprising the amino acid sequence set forth in SEQ ID NO:506, and a CDR3 comprising the amino acid sequence set forth in SEQ ID NO:507;

(bx) the encoded light chain variable region comprises a CDR1 comprising the amino acid sequence set forth in SEQ ID NO:312, a CDR2 comprising the amino acid sequence set forth in SEQ ID NO:513, and a CDR3 comprising the amino acid sequence set forth in SEQ ID NO:514; and the encoded heavy chain variable region comprises a CDR1 comprising the amino acid sequence set forth in SEQ ID NO:510, a CDR2 comprising the amino acid sequence set forth in SEQ ID NO:511, and a CDR3 comprising the amino acid sequence set forth in SEQ ID NO:512;

(by) the encoded light chain variable region comprises a CDR1 comprising the amino acid sequence set forth in SEQ ID NO:518, a CDR2 comprising the amino acid sequence set forth in SEQ ID NO:319, and a CDR3 comprising the amino acid sequence set forth in SEQ ID NO:519; and the encoded heavy chain variable region comprises a CDR1 comprising the amino acid sequence set forth in SEQ ID NO:515, a CDR2 comprising the amino acid sequence set forth in SEQ ID NO:516, and a CDR3 comprising the amino acid sequence set forth in SEQ ID NO:517;

(bz) the encoded light chain variable region comprises a CDR1 comprising the amino acid sequence set forth in SEQ ID NO:348, a CDR2 comprising the amino acid sequence set forth in SEQ ID NO:523, and a CDR3 comprising the amino acid sequence set forth in SEQ ID NO:524; and the encoded heavy chain variable region comprises a CDR1 comprising the amino acid sequence set forth in SEQ ID NO:520, a CDR2 comprising the amino acid sequence set forth in SEQ ID NO:521, and a CDR3 comprising the amino acid sequence set forth in SEQ ID NO:522;

(ca) the encoded light chain variable region comprises a CDR1 comprising the amino acid sequence set forth in SEQ ID NO:406, a CDR2 comprising the amino acid sequence set forth in SEQ ID NO:398, and a CDR3 comprising the amino acid sequence set forth in SEQ ID NO:528; and the encoded heavy chain variable region comprises a CDR1 comprising the amino acid sequence set forth in SEQ ID NO:525, a CDR2 comprising the amino acid sequence set forth in SEQ ID NO:526, and a CDR3 comprising the amino acid sequence set forth in SEQ ID NO:527;

(cb) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:530; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:529;

(cd) the encoded light chain variable region comprises a CDR1 comprising the amino acid sequence set forth in SEQ ID NO:533, a CDR2 comprising the amino acid sequence set forth in SEQ ID NO:534, and a CDR3 comprising the amino acid sequence set forth in SEQ ID NO:535; and the encoded heavy chain variable region comprises a CDR1 comprising the amino acid sequence set forth in SEQ ID NO:403, a CDR2 comprising the amino acid sequence set forth in SEQ ID NO:404, and a CDR3 comprising the amino acid sequence set forth in SEQ ID NO:532;

(ce) the encoded light chain variable region comprises a CDR1 comprising the amino acid sequence set forth in SEQ ID NO:428, a CDR2 comprising the amino acid sequence set forth in SEQ ID NO:429, and a CDR3 comprising the amino acid sequence set forth in SEQ ID NO:430; and the encoded heavy chain variable region comprises a CDR1 comprising the amino acid sequence set forth in SEQ ID NO:425, a CDR2 comprising the amino acid sequence set forth in SEQ ID NO:426, and a CDR3 comprising the amino acid sequence set forth in SEQ ID NO:536;

(cf) the encoded light chain variable region comprises a CDR1 comprising the amino acid sequence set forth in SEQ ID NO:540, a CDR2 comprising the amino acid sequence set forth in SEQ ID NO:398, and a CDR3 comprising the amino acid sequence set forth in SEQ ID NO:541; and the encoded heavy chain variable region comprises a CDR1 comprising the amino acid sequence set forth in SEQ ID NO:537, a CDR2 comprising the amino acid sequence set forth in SEQ ID NO:538, and a CDR3 comprising the amino acid sequence set forth in SEQ ID NO:539;

(cg) the encoded light chain variable region comprises a CDR1 comprising the amino acid sequence set forth in SEQ ID NO:406, a CDR2 comprising the amino acid sequence set forth in SEQ ID NO:398, and a CDR3 comprising the amino acid sequence set forth in SEQ ID NO:542; and the encoded heavy chain variable region comprises a CDR1 comprising the amino acid sequence set forth in SEQ ID NO:537, a CDR2 comprising the amino acid sequence set forth in SEQ ID NO:538, and a CDR3 comprising the amino acid sequence set forth in SEQ ID NO:539;

(ch) the encoded light chain variable region comprises a CDR1 comprising the amino acid sequence set forth in SEQ ID NO:544, a CDR2 comprising the amino acid sequence set forth in SEQ ID NO:448, and a CDR3 comprising the amino acid sequence set forth in SEQ ID NO:545; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:543;

(ci) the encoded light chain variable region comprises a CDR1 comprising the amino acid sequence set forth in SEQ ID NO:547, a CDR2 comprising the amino acid sequence set forth in SEQ ID NO:548, and a CDR3 comprising the amino acid sequence set forth in SEQ ID NO:549; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:546;

(cj) the encoded light chain variable region comprises a CDR1 comprising the amino acid sequence set forth in SEQ ID NO:312, a CDR2 comprising the amino acid sequence set forth in SEQ ID NO:313, and a CDR3 comprising the amino acid sequence set forth in SEQ ID NO:314; and the encoded heavy chain variable region comprises a CDR1 comprising the amino acid sequence set forth in SEQ ID NO:309, a CDR2 comprising the amino acid sequence set forth in SEQ ID NO:310, and a CDR3 comprising the amino acid sequence set forth in SEQ ID NO:550;

(ck) the encoded light chain variable region comprises a CDR1 comprising the amino acid sequence set forth in SEQ ID NO:312, a CDR2 comprising the amino acid sequence set forth in SEQ ID NO:513, and a CDR3 comprising the amino acid sequence set forth in SEQ ID NO:314; and the encoded heavy chain variable region comprises a CDR1 comprising the amino acid sequence set forth in SEQ ID NO:309, a CDR2 comprising the amino acid sequence set forth in SEQ ID NO:310, and a CDR3 comprising the amino acid sequence set forth in SEQ ID NO:550;

(cl) the encoded light chain variable region comprises a CDR1 comprising the amino acid sequence set forth in SEQ ID NO:406, a CDR2 comprising the amino acid sequence set forth in SEQ ID NO:398, and a CDR3 comprising the amino acid sequence set forth in SEQ ID NO:554; and the encoded heavy chain variable region comprises a CDR1 comprising the amino acid sequence set forth in SEQ ID NO:551, a CDR2 comprising the amino acid sequence set forth in SEQ ID NO:552, and a CDR3 comprising the amino acid sequence set forth in SEQ ID NO:553;

(cm) the encoded light chain variable region comprises a CDR1 comprising the amino acid sequence set forth in SEQ ID NO:556, a CDR2 comprising the amino acid sequence set forth in SEQ ID NO:557, and a CDR3 comprising the amino acid sequence set forth in SEQ ID NO:558; and the encoded heavy chain variable region comprises a CDR1 comprising the amino acid sequence set forth in SEQ ID NO:309, a CDR2 comprising the amino acid sequence set forth in SEQ ID NO:310, and a CDR3 comprising the amino acid sequence set forth in SEQ ID NO:555;

(cn) the encoded light chain variable region comprises a CDR1 comprising the amino acid sequence set forth in SEQ ID NO:562, a CDR2 comprising the amino acid sequence set forth in SEQ ID NO:563, and a CDR3 comprising the amino acid sequence set forth in SEQ ID NO:564; and the encoded heavy chain variable region comprises a CDR1 comprising the amino acid sequence set forth in SEQ ID NO:559, a CDR2 comprising the amino acid sequence set forth in SEQ ID NO:560, and a CDR3 comprising the amino acid sequence set forth in SEQ ID NO:561;

(co) the encoded light chain variable region comprises a CDR1 comprising the amino acid sequence set forth in SEQ ID NO:568, a CDR2 comprising the amino acid sequence set forth in SEQ ID NO:504, and a CDR3 comprising the amino acid sequence set forth in SEQ ID NO:569; and the encoded heavy chain variable region comprises a CDR1 comprising the amino acid sequence set forth in SEQ ID NO:565, a CDR2 comprising the amino acid sequence set forth in SEQ ID NO:566, and a CDR3 comprising the amino acid sequence set forth in SEQ ID NO:567;

(cq) the encoded light chain variable region comprises a CDR1 comprising the amino acid sequence set forth in SEQ ID NO:343, a CDR2 comprising the amino acid sequence set forth in SEQ ID NO:575, and a CDR3 comprising the amino acid sequence set forth in SEQ ID NO:576; and the encoded heavy chain variable region comprises a CDR1 comprising the amino acid sequence set forth in SEQ ID NO:403, a CDR2 comprising the amino acid sequence set forth in SEQ ID NO:404, and a CDR3 comprising the amino acid sequence set forth in SEQ ID NO:574;

(cr) the encoded light chain variable region comprises a CDR1 comprising the amino acid sequence set forth in SEQ ID NO:312, a CDR2 comprising the amino acid sequence set forth in SEQ ID NO:313, and a CDR3 comprising the amino acid sequence set forth in SEQ ID NO:314; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:577;

(cs) the encoded light chain variable region comprises a CDR1 comprising the amino acid sequence set forth in SEQ ID NO:312, a CDR2 comprising the amino acid sequence set forth in SEQ ID NO:313, and a CDR3 comprising the amino acid sequence set forth in SEQ ID NO:314; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:578;

(ct) the encoded light chain variable region comprises a CDR1 comprising the amino acid sequence set forth in SEQ ID NO:580, a CDR2 comprising the amino acid sequence set forth in SEQ ID NO:438, and a CDR3 comprising the amino acid sequence set forth in SEQ ID NO:581; and the encoded heavy chain variable region comprises a CDR1 comprising the amino acid sequence set forth in SEQ ID NO:436, a CDR2 comprising the amino acid sequence set forth in SEQ ID NO:388, and a CDR3 comprising the amino acid sequence set forth in SEQ ID NO:579;

(cu) the encoded light chain variable region comprises a CDR1 comprising the amino acid sequence set forth in SEQ ID NO:585, a CDR2 comprising the amino acid sequence set forth in SEQ ID NO:313, and a CDR3 comprising the amino acid sequence set forth in SEQ ID NO:314; and the encoded heavy chain variable region comprises a CDR1 comprising the amino acid sequence set forth in SEQ ID NO:582, a CDR2 comprising the amino acid sequence set forth in SEQ ID NO:583, and a CDR3 comprising the amino acid sequence set forth in SEQ ID NO:584;

(cv) the encoded light chain variable region comprises a CDR1 comprising the amino acid sequence set forth in SEQ ID NO:312, a CDR2 comprising the amino acid sequence set forth in SEQ ID NO:586, and a CDR3 comprising the amino acid sequence set forth in SEQ ID NO:314; and the encoded heavy chain variable region comprises a CDR1 comprising the amino acid sequence set forth in SEQ ID NO:346, a CDR2 comprising the amino acid sequence set forth in SEQ ID NO:327, and a CDR3 comprising the amino acid sequence set forth in SEQ ID NO:578;

(cw) the encoded light chain variable region comprises a CDR1 comprising the amino acid sequence set forth in SEQ ID NO:588, a CDR2 comprising the amino acid sequence set forth in SEQ ID NO:385, and a CDR3 comprising the amino acid sequence set forth in SEQ ID NO:375; and the encoded heavy chain variable region comprises a CDR1 comprising the amino acid sequence set forth in SEQ ID NO:403, a CDR2 comprising the amino acid sequence set forth in SEQ ID NO:404, and a CDR3 comprising the amino acid sequence set forth in SEQ ID NO:587; or (cx) the encoded light chain variable region comprises a CDR1 comprising the amino acid sequence set forth in SEQ ID NO:318, a CDR2 comprising the amino acid sequence set forth in SEQ ID NO:319, and a CDR3 comprising the amino acid sequence set forth in SEQ ID NO:592; and the encoded heavy chain variable region comprises a CDR1 comprising the amino acid sequence set forth in SEQ ID NO:589, a CDR2 comprising the amino acid sequence set forth in SEQ ID NO:590, and a CDR3 comprising the amino acid sequence set forth in SEQ ID NO:591.

2. The nucleic acid molecule of claim 1, wherein:

(aa) the encoded light chain variable region comprises an amino acid sequence that has at least about 90% sequence identity to the sequence set forth in SEQ ID NO:3, and the encoded heavy chain variable region comprises an amino acid sequence that has at least about 90% sequence identity to the sequence set forth in SEQ ID NO:4;

(ab) the encoded light chain variable region comprises an amino acid sequence that has at least about 90% sequence identity to the sequence set forth in SEQ ID NO:7, and the encoded heavy chain variable region comprises an amino acid sequence that has at least about 90% sequence identity to the sequence set forth in SEQ ID NO:8;

(ac) the encoded light chain variable region comprises an amino acid sequence that has at least about 90% sequence identity to the sequence set forth in SEQ ID NO:11, and the encoded heavy chain variable region comprises an amino acid sequence that has at least about 90% sequence identity to the sequence set forth in SEQ ID NO:12;

(ad) the encoded light chain variable region comprises an amino acid sequence that has at least about 90% sequence identity to the sequence set forth in SEQ ID NO:299, and the encoded heavy chain variable region comprises an amino acid sequence that has at least about 90% sequence identity to the sequence set forth in SEQ ID NO:300;

(ae) the encoded light chain variable region comprises an amino acid sequence that has at least about 90% sequence identity to the sequence set forth in SEQ ID NO:15, and the encoded heavy chain variable region comprises an amino acid sequence that has at least about 90% sequence identity to the sequence set forth in SEQ ID NO:16;

(af) the encoded light chain variable region comprises an amino acid sequence that has at least about 90% sequence identity to the sequence set forth in SEQ ID NO:19, and the encoded heavy chain variable region comprises an amino acid sequence that has at least about 90% sequence identity to the sequence set forth in SEQ ID NO:20;

(ag) the encoded light chain variable region comprises an amino acid sequence that has at least about 90% sequence identity to the sequence set forth in SEQ ID NO:23, and the encoded heavy chain variable region comprises an amino acid sequence that has at least about 90% sequence identity to the sequence set forth in SEQ ID NO:24;

(ah) the encoded light chain variable region comprises an amino acid sequence that has at least about 90% sequence identity to the sequence set forth in SEQ ID NO:27, and the encoded heavy chain variable region comprises an amino acid sequence that has at least about 90% sequence identity to the sequence set forth in SEQ ID NO:28;

(ai) the encoded light chain variable region comprises an amino acid sequence that has at least about 90% sequence identity to the sequence set forth in SEQ ID NO:31, and the encoded heavy chain variable region comprises an amino acid sequence that has at least about 90% sequence identity to the sequence set forth in SEQ ID NO:32;

(aj) the encoded light chain variable region comprises an amino acid sequence that has at least about 90% sequence identity to the sequence set forth in SEQ ID NO:35, and the encoded heavy chain variable region comprises an amino acid sequence that has at least about 90% sequence identity to the sequence set forth in SEQ ID NO:36;

(ak) the encoded light chain variable region comprises an amino acid sequence that has at least about 90% sequence identity to the sequence set forth in SEQ ID NO:39, and the encoded heavy chain variable region comprises an amino acid sequence that has at least about 90% sequence identity to the sequence set forth in SEQ ID NO:40;

(al) the encoded light chain variable region comprises an amino acid sequence that has at least about 90% sequence identity to the sequence set forth in SEQ ID NO:43, and the encoded heavy chain variable region comprises an amino acid sequence that has at least about 90% sequence identity to the sequence set forth in SEQ ID NO:44;

(am) the encoded light chain variable region comprises an amino acid sequence that has at least about 90% sequence identity to the sequence set forth in SEQ ID NO:47, and the encoded heavy chain variable region comprises an amino acid sequence that has at least about 90% sequence identity to the sequence set forth in SEQ ID NO:48;

(an) the encoded light chain variable region comprises an amino acid sequence that has at least about 90% sequence identity to the sequence set forth in SEQ ID NO:51, and the encoded heavy chain variable region comprises an amino acid sequence that has at least about 90% sequence identity to the sequence set forth in SEQ ID NO:52;

(ao) the encoded light chain variable region comprises an amino acid sequence that has at least about 90% sequence identity to the sequence set forth in SEQ ID NO:55, and the encoded heavy chain variable region comprises an amino acid sequence that has at least about 90% sequence identity to the sequence set forth in SEQ ID NO:56;

(ap) the encoded light chain variable region comprises an amino acid sequence that has at least about 90% sequence identity to the sequence set forth in SEQ ID NO:59, and the encoded heavy chain variable region comprises an amino acid sequence that has at least about 90% sequence identity to the sequence set forth in SEQ ID NO:60;

(aq) the encoded light chain variable region comprises an amino acid sequence that has at least about 90% sequence identity to the sequence set forth in SEQ ID NO:63, and the encoded heavy chain variable region comprises an amino acid sequence that has at least about 90% sequence identity to the sequence set forth in SEQ ID NO:64;

(ar) the encoded light chain variable region comprises an amino acid sequence that has at least about 90% sequence identity to the sequence set forth in SEQ ID NO:67, and the encoded heavy chain variable region comprises an amino acid sequence that has at least about 90% sequence identity to the sequence set forth in SEQ ID NO:68;

(as) the encoded light chain variable region comprises an amino acid sequence that has at least about 90% sequence identity to the sequence set forth in SEQ ID NO:71, and the encoded heavy chain variable region comprises an amino acid sequence that has at least about 90% sequence identity to the sequence set forth in SEQ ID NO:72;

(at) the encoded light chain variable region comprises an amino acid sequence that has at least about 90% sequence identity to the sequence set forth in SEQ ID NO:75, and the encoded heavy chain variable region comprises an amino acid sequence that has at least about 90% sequence identity to the sequence set forth in SEQ ID NO:76;

(au) the encoded light chain variable region comprises an amino acid sequence that has at least about 90% sequence identity to the sequence set forth in SEQ ID NO:79, and the encoded heavy chain variable region comprises an amino acid sequence that has at least about 90% sequence identity to the sequence set forth in SEQ ID NO:80;

(av) the encoded light chain variable region comprises an amino acid sequence that has at least about 90% sequence identity to the sequence set forth in SEQ ID NO:83, and the encoded heavy chain variable region comprises an amino acid sequence that has at least about 90% sequence identity to the sequence set forth in SEQ ID NO:84;

(aw) the encoded light chain variable region comprises an amino acid sequence that has at least about 90% sequence identity to the sequence set forth in SEQ ID NO:87, and the encoded heavy chain variable region comprises an amino acid sequence that has at least about 90% sequence identity to the sequence set forth in SEQ ID NO:88;

(ax) the encoded light chain variable region comprises an amino acid sequence that has at least about 90% sequence identity to the sequence set forth in SEQ ID NO:91, and the encoded heavy chain variable region comprises an amino acid sequence that has at least about 90% sequence identity to the sequence set forth in SEQ ID NO:92;

(ay) the encoded light chain variable region comprises an amino acid sequence that has at least about 90% sequence identity to the sequence set forth in SEQ ID NO:95, and the encoded heavy chain variable region comprises an amino acid sequence that has at least about 90% sequence identity to the sequence set forth in SEQ ID NO:96;

(az) the encoded light chain variable region comprises an amino acid sequence that has at least about 90% sequence identity to the sequence set forth in SEQ ID NO:99, and the encoded heavy chain variable region comprises an amino acid sequence that has at least about 90% sequence identity to the sequence set forth in SEQ ID NO:100;

(ba) the encoded light chain variable region comprises an amino acid sequence that has at least about 90% sequence identity to the sequence set forth in SEQ ID NO:103, and the encoded heavy chain variable region comprises an amino acid sequence that has at least about 90% sequence identity to the sequence set forth in SEQ ID NO:104;

(bb) the encoded light chain variable region comprises an amino acid sequence that has at least about 90% sequence identity to the sequence set forth in SEQ ID NO:107, and the encoded heavy chain variable region comprises an amino acid sequence that has at least about 90% sequence identity to the sequence set forth in SEQ ID NO:108;

(bc) the encoded light chain variable region comprises an amino acid sequence that has at least about 90% sequence identity to the sequence set forth in SEQ ID NO:111, and the encoded heavy chain variable region comprises an amino acid sequence that has at least about 90% sequence identity to the sequence set forth in SEQ ID NO:112;

(bd) the encoded light chain variable region comprises an amino acid sequence that has at least about 90% sequence identity to the sequence set forth in SEQ ID NO:115, and the encoded heavy chain variable region comprises an amino acid sequence that has at least about 90% sequence identity to the sequence set forth in SEQ ID NO:116;

(be) the encoded light chain variable region comprises an amino acid sequence that has at least about 90% sequence identity to the sequence set forth in SEQ ID NO:119, and the encoded heavy chain variable region comprises an amino acid sequence that has at least about 90% sequence identity to the sequence set forth in SEQ ID NO:120;

(bf) the encoded light chain variable region comprises an amino acid sequence that has at least about 90% sequence identity to the sequence set forth in SEQ ID NO:123, and the encoded heavy chain variable region comprises an amino acid sequence that has at least about 90% sequence identity to the sequence set forth in SEQ ID NO:124;

(bg) the encoded light chain variable region comprises an amino acid sequence that has at least about 90% sequence identity to the sequence set forth in SEQ ID NO:127, and the encoded heavy chain variable region comprises an amino acid sequence that has at least about 90% sequence identity to the sequence set forth in SEQ ID NO:128;

(bh) the encoded light chain variable region comprises an amino acid sequence that has at least about 90% sequence identity to the sequence set forth in SEQ ID NO:131, and the encoded heavy chain variable region comprises an amino acid sequence that has at least about 90% sequence identity to the sequence set forth in SEQ ID NO:132;

(bi) the encoded light chain variable region comprises an amino acid sequence that has at least about 90% sequence identity to the sequence set forth in SEQ ID NO:135, and the encoded heavy chain variable region comprises an amino acid sequence that has at least about 90% sequence identity to the sequence set forth in SEQ ID NO:136;

(bj) the encoded light chain variable region comprises an amino acid sequence that has at least about 90% sequence identity to the sequence set forth in SEQ ID NO:139, and the encoded heavy chain variable region comprises an amino acid sequence that has at least about 90% sequence identity to the sequence set forth in SEQ ID NO:140;

(bl) the encoded light chain variable region comprises an amino acid sequence that has at least about 90% sequence identity to the sequence set forth in SEQ ID NO:147, and the encoded heavy chain variable region comprises an amino acid sequence that has at least about 90% sequence identity to the sequence set forth in SEQ ID NO:148;

(bm) the encoded light chain variable region comprises an amino acid sequence that has at least about 90% sequence identity to the sequence set forth in SEQ ID NO:151, and the encoded heavy chain variable region comprises an amino acid sequence that has at least about 90% sequence identity to the sequence set forth in SEQ ID NO:152;

(bn) the encoded light chain variable region comprises an amino acid sequence that has at least about 90% sequence identity to the sequence set forth in SEQ ID NO:155, and the encoded heavy chain variable region comprises an amino acid sequence that has at least about 90% sequence identity to the sequence set forth in SEQ ID NO:156;

(bo) the encoded light chain variable region comprises an amino acid sequence that has at least about 90% sequence identity to the sequence set forth in SEQ ID NO:159, and the encoded heavy chain variable region comprises an amino acid sequence that has at least about 90% sequence identity to the sequence set forth in SEQ ID NO:160;

(bp) the encoded light chain variable region comprises an amino acid sequence that has at least about 90% sequence identity to the sequence set forth in SEQ ID NO:163, and the encoded heavy chain variable region comprises an amino acid sequence that has at least about 90% sequence identity to the sequence set forth in SEQ ID NO:164;

(bq) the encoded light chain variable region comprises an amino acid sequence that has at least about 90% sequence identity to the sequence set forth in SEQ ID NO:167, and the encoded heavy chain variable region comprises an amino acid sequence that has at least about 90% sequence identity to the sequence set forth in SEQ ID NO:168;

(bs) the encoded light chain variable region comprises an amino acid sequence that has at least about 90% sequence identity to the sequence set forth in SEQ ID NO:175, and the encoded heavy chain variable region comprises an amino acid sequence that has at least about 90% sequence identity to the sequence set forth in SEQ ID NO:176;

(bt) the encoded light chain variable region comprises an amino acid sequence that has at least about 90% sequence identity to the sequence set forth in SEQ ID NO:179, and the encoded heavy chain variable region comprises an amino acid sequence that has at least about 90% sequence identity to the sequence set forth in SEQ ID NO:180;

(bu) the encoded light chain variable region comprises an amino acid sequence that has at least about 90% sequence identity to the sequence set forth in SEQ ID NO:183, and the encoded heavy chain variable region comprises an amino acid sequence that has at least about 90% sequence identity to the sequence set forth in SEQ ID NO:184;

(bv) the encoded light chain variable region comprises an amino acid sequence that has at least about 90% sequence identity to the sequence set forth in SEQ ID NO:187, and the encoded heavy chain variable region comprises an amino acid sequence that has at least about 90% sequence identity to the sequence set forth in SEQ ID NO:188;

(bw) the encoded light chain variable region comprises an amino acid sequence that has at least about 90% sequence identity to the sequence set forth in SEQ ID NO:191, and the encoded heavy chain variable region comprises an amino acid sequence that has at least about 90% sequence identity to the sequence set forth in SEQ ID NO:192;

(bx) the encoded light chain variable region comprises an amino acid sequence that has at least about 90% sequence identity to the sequence set forth in SEQ ID NO:195, and the encoded heavy chain variable region comprises an amino acid sequence that has at least about 90% sequence identity to the sequence set forth in SEQ ID NO:196;

(by) the encoded light chain variable region comprises an amino acid sequence that has at least about 90% sequence identity to the sequence set forth in SEQ ID NO:199, and the encoded heavy chain variable region comprises an amino acid sequence that has at least about 90% sequence identity to the sequence set forth in SEQ ID NO:200;

(bz) the encoded light chain variable region comprises an amino acid sequence that has at least about 90% sequence identity to the sequence set forth in SEQ ID NO:203, and the encoded heavy chain variable region comprises an amino acid sequence that has at least about 90% sequence identity to the sequence set forth in SEQ ID NO:204;

(ca) the encoded light chain variable region comprises an amino acid sequence that has at least about 90% sequence identity to the sequence set forth in SEQ ID NO:207, and the encoded heavy chain variable region comprises an amino acid sequence that has at least about 90% sequence identity to the sequence set forth in SEQ ID NO:208;

(cb) the encoded light chain variable region comprises an amino acid sequence that has at least about 90% sequence identity to the sequence set forth in SEQ ID NO:211, and the encoded heavy chain variable region comprises an amino acid sequence that has at least about 90% sequence identity to the sequence set forth in SEQ ID NO:212;

(cd) the encoded light chain variable region comprises an amino acid sequence that has at least about 90% sequence identity to the sequence set forth in SEQ ID NO:219, and the encoded heavy chain variable region comprises an amino acid sequence that has at least about 90% sequence identity to the sequence set forth in SEQ ID NO:220;

(ce) the encoded light chain variable region comprises an amino acid sequence that has at least about 90% sequence identity to the sequence set forth in SEQ ID NO:223, and the encoded heavy chain variable region comprises an amino acid sequence that has at least about 90% sequence identity to the sequence set forth in SEQ ID NO:224;

(cf) the encoded light chain variable region comprises an amino acid sequence that has at least about 90% sequence identity to the sequence set forth in SEQ ID NO:227, and the encoded heavy chain variable region comprises an amino acid sequence that has at least about 90% sequence identity to the sequence set forth in SEQ ID NO:228;

(cg) the encoded light chain variable region comprises an amino acid sequence that has at least about 90% sequence identity to the sequence set forth in SEQ ID NO:231, and the encoded heavy chain variable region comprises an amino acid sequence that has at least about 90% sequence identity to the sequence set forth in SEQ ID NO:232;

(ch) the encoded light chain variable region comprises an amino acid sequence that has at least about 90% sequence identity to the sequence set forth in SEQ ID NO:235, and the encoded heavy chain variable region comprises an amino acid sequence that has at least about 90% sequence identity to the sequence set forth in SEQ ID NO:236;

(ci) the encoded light chain variable region comprises an amino acid sequence that has at least about 90% sequence identity to the sequence set forth in SEQ ID NO:239, and the encoded heavy chain variable region comprises an amino acid sequence that has at least about 90% sequence identity to the sequence set forth in SEQ ID NO:240;

(cj) the encoded light chain variable region comprises an amino acid sequence that has at least about 90% sequence identity to the sequence set forth in SEQ ID NO:243, and the encoded heavy chain variable region comprises an amino acid sequence that has at least about 90% sequence identity to the sequence set forth in SEQ ID NO:244;

(ck) the encoded light chain variable region comprises an amino acid sequence that has at least about 90% sequence identity to the sequence set forth in SEQ ID NO:247, and the encoded heavy chain variable region comprises an amino acid sequence that has at least about 90% sequence identity to the sequence set forth in SEQ ID NO:248;

(cl) the encoded light chain variable region comprises an amino acid sequence that has at least about 90% sequence identity to the sequence set forth in SEQ ID NO:251, and the encoded heavy chain variable region comprises an amino acid sequence that has at least about 90% sequence identity to the sequence set forth in SEQ ID NO:252;

(cm) the encoded light chain variable region comprises an amino acid sequence that has at least about 90% sequence identity to the sequence set forth in SEQ ID NO:255, and the encoded heavy chain variable region comprises an amino acid sequence that has at least about 90% sequence identity to the sequence set forth in SEQ ID NO:256;

(cn) the encoded light chain variable region comprises an amino acid sequence that has at least about 90% sequence identity to the sequence set forth in SEQ ID NO:259, and the encoded heavy chain variable region comprises an amino acid sequence that has at least about 90% sequence identity to the sequence set forth in SEQ ID NO:260;

(co) the encoded light chain variable region comprises an amino acid sequence that has at least about 90% sequence identity to the sequence set forth in SEQ ID NO:263, and the encoded heavy chain variable region comprises an amino acid sequence that has at least about 90% sequence identity to the sequence set forth in SEQ ID NO:264;

(cq) the encoded light chain variable region comprises an amino acid sequence that has at least about 90% sequence identity to the sequence set forth in SEQ ID NO:271, and the encoded heavy chain variable region comprises an amino acid sequence that has at least about 90% sequence identity to the sequence set forth in SEQ ID NO:272;

(cr) the encoded light chain variable region comprises an amino acid sequence that has at least about 90% sequence identity to the sequence set forth in SEQ ID NO:275, and the encoded heavy chain variable region comprises an amino acid sequence that has at least about 90% sequence identity to the sequence set forth in SEQ ID NO:276;

(cs) the encoded light chain variable region comprises an amino acid sequence that has at least about 90% sequence identity to the sequence set forth in SEQ ID NO:279, and the encoded heavy chain variable region comprises an amino acid sequence that has at least about 90% sequence identity to the sequence set forth in SEQ ID NO:280;

(ct) the encoded light chain variable region comprises an amino acid sequence that has at least about 90% sequence identity to the sequence set forth in SEQ ID NO:283, and the encoded heavy chain variable region comprises an amino acid sequence that has at least about 90% sequence identity to the sequence set forth in SEQ ID NO:284;

(cu) the encoded light chain variable region comprises an amino acid sequence that has at least about 90% sequence identity to the sequence set forth in SEQ ID NO:287, and the encoded heavy chain variable region comprises an amino acid sequence that has at least about 90% sequence identity to the sequence set forth in SEQ ID NO:288;

(cv) the encoded light chain variable region comprises an amino acid sequence that has at least about 90% sequence identity to the sequence set forth in SEQ ID NO:291, and the encoded heavy chain variable region comprises an amino acid sequence that has at least about 90% sequence identity to the sequence set forth in SEQ ID NO:292;

(cw) the encoded light chain variable region comprises an amino acid sequence that has at least about 90% sequence identity to the sequence set forth in SEQ ID NO:303, and the encoded heavy chain variable region comprises an amino acid sequence that has at least about 90% sequence identity to the sequence set forth in SEQ ID NO:304; or (cx) the encoded light chain variable region comprises an amino acid sequence that has at least about 90% sequence identity to the sequence set forth in SEQ ID NO:295, and the encoded heavy chain variable region comprises an amino acid sequence that has at least about 90% sequence identity to the sequence set forth in SEQ ID NO:296.

3. The nucleic acid molecule of claim 1, wherein:

(aa) the encoded light chain variable region comprises the amino acid sequence set forth in SEQ ID NO:3, and the encoded heavy chain variable region comprises the amino acid sequence set forth in SEQ ID NO:4;

(ab) the encoded light chain variable region comprises the amino acid sequence set forth in SEQ ID NO:7, and the encoded heavy chain variable region comprises the amino acid sequence set forth in SEQ ID NO:8;

(ac) the encoded light chain variable region comprises the amino acid sequence set forth in SEQ ID NO:11, and the encoded heavy chain variable region comprises the amino acid sequence set forth in SEQ ID NO:12;

(ad) the encoded light chain variable region comprises the amino acid sequence set forth in SEQ ID NO:299, and the encoded heavy chain variable region comprises the amino acid sequence set forth in SEQ ID NO:300;

(ae) the encoded light chain variable region comprises the amino acid sequence set forth in SEQ ID NO:15, and the encoded heavy chain variable region comprises the amino acid sequence set forth in SEQ ID NO:16;

(af) the encoded light chain variable region comprises the amino acid sequence set forth in SEQ ID NO:19, and the encoded heavy chain variable region comprises the amino acid sequence set forth in SEQ ID NO:20;

(ag) the encoded light chain variable region comprises the amino acid sequence set forth in SEQ ID NO:23, and the encoded heavy chain variable region comprises the amino acid sequence set forth in SEQ ID NO:24;

(ah) the encoded light chain variable region comprises the amino acid sequence set forth in SEQ ID NO:27, and the encoded heavy chain variable region comprises the amino acid sequence set forth in SEQ ID NO:28;

(ai) the encoded light chain variable region comprises the amino acid sequence set forth in SEQ ID NO:31, and the encoded heavy chain variable region comprises the amino acid sequence set forth in SEQ ID NO:32;

(aj) the encoded light chain variable region comprises the amino acid sequence set forth in SEQ ID NO:35, and the encoded heavy chain variable region comprises the amino acid sequence set forth in SEQ ID NO:36;

(ak) the encoded light chain variable region comprises the amino acid sequence set forth in SEQ ID NO:39, and the encoded heavy chain variable region comprises the amino acid sequence set forth in SEQ ID NO:40;

(al) the encoded light chain variable region comprises the amino acid sequence set forth in SEQ ID NO:43, and the encoded heavy chain variable region comprises the amino acid sequence set forth in SEQ ID NO:44;

(am) the encoded light chain variable region comprises the amino acid sequence set forth in SEQ ID NO:47, and the encoded heavy chain variable region comprises the amino acid sequence set forth in SEQ ID NO:48;

(an) the encoded light chain variable region comprises the amino acid sequence set forth in SEQ ID NO:51, and the encoded heavy chain variable region comprises the amino acid sequence set forth in SEQ ID NO:52;

(ao) the encoded light chain variable region comprises the amino acid sequence set forth in SEQ ID NO:55, and the encoded heavy chain variable region comprises the amino acid sequence set forth in SEQ ID NO:56;

(ap) the encoded light chain variable region comprises the amino acid sequence set forth in SEQ ID NO:59, and the encoded heavy chain variable region comprises the amino acid sequence set forth in SEQ ID NO:60;

(aq) the encoded light chain variable region comprises the amino acid sequence set forth in SEQ ID NO:63, and the encoded heavy chain variable region comprises the amino acid sequence set forth in SEQ ID NO:64;

(ar) the encoded light chain variable region comprises the amino acid sequence set forth in SEQ ID NO:67, and the encoded heavy chain variable region comprises the amino acid sequence set forth in SEQ ID NO:68;

(as) the encoded light chain variable region comprises the amino acid sequence set forth in SEQ ID NO:71, and the encoded heavy chain variable region comprises the amino acid sequence set forth in SEQ ID NO:72;

(at) the encoded light chain variable region comprises the amino acid sequence set forth in SEQ ID NO:75, and the encoded heavy chain variable region comprises the amino acid sequence set forth in SEQ ID NO:76;

(au) the encoded light chain variable region comprises the amino acid sequence set forth in SEQ ID NO:79, and the encoded heavy chain variable region comprises the amino acid sequence set forth in SEQ ID NO:80;

(av) the encoded light chain variable region comprises the amino acid sequence set forth in SEQ ID NO:83, and the encoded heavy chain variable region comprises the amino acid sequence set forth in SEQ ID NO:84;

(aw) the encoded light chain variable region comprises the amino acid sequence set forth in SEQ ID NO:87, and the encoded heavy chain variable region comprises the amino acid sequence set forth in SEQ ID NO:88;

(ax) the encoded light chain variable region comprises the amino acid sequence set forth in SEQ ID NO:91, and the encoded heavy chain variable region comprises the amino acid sequence set forth in SEQ ID NO:92;

(ay) the encoded light chain variable region comprises the amino acid sequence set forth in SEQ ID NO:95, and the encoded heavy chain variable region comprises the amino acid sequence set forth in SEQ ID NO:96;

(az) the encoded light chain variable region comprises the amino acid sequence set forth in SEQ ID NO:99, and the encoded heavy chain variable region comprises the amino acid sequence set forth in SEQ ID NO:100;

(ba) the encoded light chain variable region comprises the amino acid sequence set forth in SEQ ID NO:103, and the encoded heavy chain variable region comprises the amino acid sequence set forth in SEQ ID NO:104;

(bb) the encoded light chain variable region comprises the amino acid sequence set forth in SEQ ID NO:107, and the encoded heavy chain variable region comprises the amino acid sequence set forth in SEQ ID NO:108;

(bc) the encoded light chain variable region comprises the amino acid sequence set forth in SEQ ID NO:111, and the encoded heavy chain variable region comprises the amino acid sequence set forth in SEQ ID NO:112;

(bd) the encoded light chain variable region comprises the amino acid sequence set forth in SEQ ID NO:115, and the encoded heavy chain variable region comprises the amino acid sequence set forth in SEQ ID NO:116;

(be) the encoded light chain variable region comprises the amino acid sequence set forth in SEQ ID NO:119, and the encoded heavy chain variable region comprises the amino acid sequence set forth in SEQ ID NO:120;

(bf) the encoded light chain variable region comprises the amino acid sequence set forth in SEQ ID NO:123, and the encoded heavy chain variable region comprises the amino acid sequence set forth in SEQ ID NO:124;

(bg) the encoded light chain variable region comprises the amino acid sequence set forth in SEQ ID NO:127, and the encoded heavy chain variable region comprises the amino acid sequence set forth in SEQ ID NO:128;

(bh) the encoded light chain variable region comprises the amino acid sequence set forth in SEQ ID NO:131, and the encoded heavy chain variable region comprises the amino acid sequence set forth in SEQ ID NO:132;

(bi) the encoded light chain variable region comprises the amino acid sequence set forth in SEQ ID NO:135, and the encoded heavy chain variable region comprises the amino acid sequence set forth in SEQ ID NO:136;

(bj) the encoded light chain variable region comprises the amino acid sequence set forth in SEQ ID NO:139, and the encoded heavy chain variable region comprises the amino acid sequence set forth in SEQ ID NO:140;

(bl) the encoded light chain variable region comprises the amino acid sequence set forth in SEQ ID NO:147, and the encoded heavy chain variable region comprises the amino acid sequence set forth in SEQ ID NO:148;

(bm) the encoded light chain variable region comprises the amino acid sequence set forth in SEQ ID NO:151, and the encoded heavy chain variable region comprises the amino acid sequence set forth in SEQ ID NO:152;

(bn) the encoded light chain variable region comprises the amino acid sequence set forth in SEQ ID NO:155, and the encoded heavy chain variable region comprises the amino acid sequence set forth in SEQ ID NO:156;

(bo) the encoded light chain variable region comprises the amino acid sequence set forth in SEQ ID NO:159, and the encoded heavy chain variable region comprises the amino acid sequence set forth in SEQ ID NO:160;

(bp) the encoded light chain variable region comprises the amino acid sequence set forth in SEQ ID NO:163, and the encoded heavy chain variable region comprises the amino acid sequence set forth in SEQ ID NO:164;

(bq) the encoded light chain variable region comprises the amino acid sequence set forth in SEQ ID NO:167, and the encoded heavy chain variable region comprises the amino acid sequence set forth in SEQ ID NO:168;

(bs) the encoded light chain variable region comprises the amino acid sequence set forth in SEQ ID NO:175, and the encoded heavy chain variable region comprises the amino acid sequence set forth in SEQ ID NO:176;

(bt) the encoded light chain variable region comprises the amino acid sequence set forth in SEQ ID NO:179, and the encoded heavy chain variable region comprises the amino acid sequence set forth in SEQ ID NO:180;

(bu) the encoded light chain variable region comprises the amino acid sequence set forth in SEQ ID NO:183, and the encoded heavy chain variable region comprises the amino acid sequence set forth in SEQ ID NO:184;

(bv) the encoded light chain variable region comprises the amino acid sequence set forth in SEQ ID NO:187, and the encoded heavy chain variable region comprises the amino acid sequence set forth in SEQ ID NO:188;

(bw) the encoded light chain variable region comprises the amino acid sequence set forth in SEQ ID NO:191, and the encoded heavy chain variable region comprises the amino acid sequence set forth in SEQ ID NO:192;

(bx) the encoded light chain variable region comprises the amino acid sequence set forth in SEQ ID NO:195, and the encoded heavy chain variable region comprises the amino acid sequence set forth in SEQ ID NO:196;

(by) the encoded light chain variable region comprises the amino acid sequence set forth in SEQ ID NO:199, and the encoded heavy chain variable region comprises the amino acid sequence set forth in SEQ ID NO:200;

(bz) the encoded light chain variable region comprises the amino acid sequence set forth in SEQ ID NO:203, and the encoded heavy chain variable region comprises the amino acid sequence set forth in SEQ ID NO:204;

(ca) the encoded light chain variable region comprises the amino acid sequence set forth in SEQ ID NO:207, and the encoded heavy chain variable region comprises the amino acid sequence set forth in SEQ ID NO:208;

(cb) the encoded light chain variable region comprises the amino acid sequence set forth in SEQ ID NO:211, and the encoded heavy chain variable region comprises the amino acid sequence set forth in SEQ ID NO:212;

(cd) the encoded light chain variable region comprises the amino acid sequence set forth in SEQ ID NO:219, and the encoded heavy chain variable region comprises the amino acid sequence set forth in SEQ ID NO:220;

(ce) the encoded light chain variable region comprises the amino acid sequence set forth in SEQ ID NO:223, and the encoded heavy chain variable region comprises the amino acid sequence set forth in SEQ ID NO:224;

(cf) the encoded light chain variable region comprises the amino acid sequence set forth in SEQ ID NO:227, and the encoded heavy chain variable region comprises the amino acid sequence set forth in SEQ ID NO:228;

(cg) the encoded light chain variable region comprises the amino acid sequence set forth in SEQ ID NO:231, and the encoded heavy chain variable region comprises the amino acid sequence set forth in SEQ ID NO:232;

(ch) the encoded light chain variable region comprises the amino acid sequence set forth in SEQ ID NO:235, and the encoded heavy chain variable region comprises the amino acid sequence set forth in SEQ ID NO:236;

(ci) the encoded light chain variable region comprises the amino acid sequence set forth in SEQ ID NO:239, and the encoded heavy chain variable region comprises the amino acid sequence set forth in SEQ ID NO:240;

(cj) the encoded light chain variable region comprises the amino acid sequence set forth in SEQ ID NO:243, and the encoded heavy chain variable region comprises the amino acid sequence set forth in SEQ ID NO:244;

(ck) the encoded light chain variable region comprises the amino acid sequence set forth in SEQ ID NO:247, and the encoded heavy chain variable region comprises the amino acid sequence set forth in SEQ ID NO:248;

(cl) the encoded light chain variable region comprises the amino acid sequence set forth in SEQ ID NO:251, and the encoded heavy chain variable region comprises the amino acid sequence set forth in SEQ ID NO:252;

(cm) the encoded light chain variable region comprises the amino acid sequence set forth in SEQ ID NO:255, and the encoded heavy chain variable region comprises the amino acid sequence set forth in SEQ ID NO:256;

(cn) the encoded light chain variable region comprises the amino acid sequence set forth in SEQ ID NO:259, and the encoded heavy chain variable region comprises the amino acid sequence set forth in SEQ ID NO:260;

(co) the encoded light chain variable region comprises the amino acid sequence set forth in SEQ ID NO:263, and the encoded heavy chain variable region comprises the amino acid sequence set forth in SEQ ID NO:264;

(cq) the encoded light chain variable region comprises the amino acid sequence set forth in SEQ ID NO:271, and the encoded heavy chain variable region comprises the amino acid sequence set forth in SEQ ID NO:272;

(cr) the encoded light chain variable region comprises the amino acid sequence set forth in SEQ ID NO:275, and the encoded heavy chain variable region comprises the amino acid sequence set forth in SEQ ID NO:276;

(cs) the encoded light chain variable region comprises the amino acid sequence set forth in SEQ ID NO:279, and the encoded heavy chain variable region comprises the amino acid sequence set forth in SEQ ID NO:280;

(ct) the encoded light chain variable region comprises the amino acid sequence set forth in SEQ ID NO:283, and the encoded heavy chain variable region comprises the amino acid sequence set forth in SEQ ID NO:284;

(cu) the encoded light chain variable region comprises the amino acid sequence set forth in SEQ ID NO:287, and the encoded heavy chain variable region comprises the amino acid sequence set forth in SEQ ID NO:288;

(cv) the encoded light chain variable region comprises the amino acid sequence set forth in SEQ ID NO:291, and the encoded heavy chain variable region comprises the amino acid sequence set forth in SEQ ID NO:292;

(cw) the encoded light chain variable region comprises the amino acid sequence set forth in SEQ ID NO:303, and the encoded heavy chain variable region comprises the amino acid sequence set forth in SEQ ID NO:304; or (cx) the encoded light chain variable region comprises the amino acid sequence set forth in SEQ ID NO:295, and the encoded heavy chain variable region comprises the amino acid sequence set forth in SEQ ID NO:296.

4. The nucleic acid molecule of claim 1, wherein the nucleic acid comprises a first nucleotide sequence encoding the light chain variable region and a second nucleotide sequence encoding the heavy chain variable region, wherein:

(aa) the first nucleotide sequence is set forth in SEQ ID NO: 1, and the second nucleotide sequence is set forth in SEQ ID NO: 2;

(ab) the first nucleotide sequence is set forth in SEQ ID NO: 5, and the second nucleotide sequence is set forth in SEQ ID NO: 6;

(ac) the first nucleotide sequence is set forth in SEQ ID NO: 9, and the second nucleotide sequence is set forth in SEQ ID NO: 10;

(ad) the first nucleotide sequence is set forth in SEQ ID NO: 13, and the second nucleotide sequence is set forth in SEQ ID NO: 14;

(ae) the first nucleotide sequence is set forth in SEQ ID NO: 17, and the second nucleotide sequence is set forth in SEQ ID NO: 18;

(af) the first nucleotide sequence is set forth in SEQ ID NO: 21, and the second nucleotide sequence is set forth in SEQ ID NO: 22;

(ag) the first nucleotide sequence is set forth in SEQ ID NO: 25, and the second nucleotide sequence is set forth in SEQ ID NO: 26;

(ah) the first nucleotide sequence is set forth in SEQ ID NO: 29, and the second nucleotide sequence is set forth in SEQ ID NO: 30;

(ai) the first nucleotide sequence is set forth in SEQ ID NO: 33, and the second nucleotide sequence is set forth in SEQ ID NO: 34;

(aj) the first nucleotide sequence is set forth in SEQ ID NO: 37, and the second nucleotide sequence is set forth in SEQ ID NO: 38;

(ak) the first nucleotide sequence is set forth in SEQ ID NO: 41, and the second nucleotide sequence is set forth in SEQ ID NO: 42;

(al) the first nucleotide sequence is set forth in SEQ ID NO: 45, and the second nucleotide sequence is set forth in SEQ ID NO: 46;

(am) the first nucleotide sequence is set forth in SEQ ID NO: 49, and the second nucleotide sequence is set forth in SEQ ID NO: 50;

(an) the first nucleotide sequence is set forth in SEQ ID NO: 53, and the second nucleotide sequence is set forth in SEQ ID NO: 54;

(ao) the first nucleotide sequence is set forth in SEQ ID NO: 57, and the second nucleotide sequence is set forth in SEQ ID NO: 58;

(ap) the first nucleotide sequence is set forth in SEQ ID NO: 61, and the second nucleotide sequence is set forth in SEQ ID NO: 62;

(aq) the first nucleotide sequence is set forth in SEQ ID NO: 65, and the second nucleotide sequence is set forth in SEQ ID NO: 66;

(ar) the first nucleotide sequence is set forth in SEQ ID NO: 69, and the second nucleotide sequence is set forth in SEQ ID NO: 70;

(as) the first nucleotide sequence is set forth in SEQ ID NO: 73, and the second nucleotide sequence is set forth in SEQ ID NO: 74;

(at) the first nucleotide sequence is set forth in SEQ ID NO: 77, and the second nucleotide sequence is set forth in SEQ ID NO: 78;

(au) the first nucleotide sequence is set forth in SEQ ID NO: 81, and the second nucleotide sequence is set forth in SEQ ID NO: 82;

(av) the first nucleotide sequence is set forth in SEQ ID NO: 85, and the second nucleotide sequence is set forth in SEQ ID NO: 86;

(aw) the first nucleotide sequence is set forth in SEQ ID NO: 89, and the second nucleotide sequence is set forth in SEQ ID NO: 90;

(ax) the first nucleotide sequence is set forth in SEQ ID NO: 93, and the second nucleotide sequence is set forth in SEQ ID NO: 94;

(ay) the first nucleotide sequence is set forth in SEQ ID NO: 97, and the second nucleotide sequence is set forth in SEQ ID NO: 98;

(az) the first nucleotide sequence is set forth in SEQ ID NO: 101, and the second nucleotide sequence is set forth in SEQ ID NO: 102;

(ba) the first nucleotide sequence is set forth in SEQ ID NO: 105, and the second nucleotide sequence is set forth in SEQ ID NO: 106;

(bb) the first nucleotide sequence is set forth in SEQ ID NO: 109, and the second nucleotide sequence is set forth in SEQ ID NO: 110;

(bc) the first nucleotide sequence is set forth in SEQ ID NO: 113, and the second nucleotide sequence is set forth in SEQ ID NO: 114;

(bd) the first nucleotide sequence is set forth in SEQ ID NO: 117, and the second nucleotide sequence is set forth in SEQ ID NO: 118;

(be) the first nucleotide sequence is set forth in SEQ ID NO: 121, and the second nucleotide sequence is set forth in SEQ ID NO: 122;

(bf) the first nucleotide sequence is set forth in SEQ ID NO: 125, and the second nucleotide sequence is set forth in SEQ ID NO: 126;

(bg) the first nucleotide sequence is set forth in SEQ ID NO: 129, and the second nucleotide sequence is set forth in SEQ ID NO: 130;

(bh) the first nucleotide sequence is set forth in SEQ ID NO: 133, and the second nucleotide sequence is set forth in SEQ ID NO: 134;

(bi) the first nucleotide sequence is set forth in SEQ ID NO: 137, and the second nucleotide sequence is set forth in SEQ ID NO: 138;

(bj) the first nucleotide sequence is set forth in SEQ ID NO: 141, and the second nucleotide sequence is set forth in SEQ ID NO: 142;

(bl) the first nucleotide sequence is set forth in SEQ ID NO: 149, and the second nucleotide sequence is set forth in SEQ ID NO: 150;

(bm) the first nucleotide sequence is set forth in SEQ ID NO: 153, and the second nucleotide sequence is set forth in SEQ ID NO: 154;

(bn) the first nucleotide sequence is set forth in SEQ ID NO: 157, and the second nucleotide sequence is set forth in SEQ ID NO: 158;

(bo) the first nucleotide sequence is set forth in SEQ ID NO: 161, and the second nucleotide sequence is set forth in SEQ ID NO: 162;

(bp) the first nucleotide sequence is set forth in SEQ ID NO: 165, and the second nucleotide sequence is set forth in SEQ ID NO: 166;

(bq) the first nucleotide sequence is set forth in SEQ ID NO: 169, and the second nucleotide sequence is set forth in SEQ ID NO: 170;

(bs) the first nucleotide sequence is set forth in SEQ ID NO: 177, and the second nucleotide sequence is set forth in SEQ ID NO: 178;

(bt) the first nucleotide sequence is set forth in SEQ ID NO: 181, and the second nucleotide sequence is set forth in SEQ ID NO: 182;

(bu) the first nucleotide sequence is set forth in SEQ ID NO: 185, and the second nucleotide sequence is set forth in SEQ ID NO: 186;

(bv) the first nucleotide sequence is set forth in SEQ ID NO: 189, and the second nucleotide sequence is set forth in SEQ ID NO: 190;

(bw) the first nucleotide sequence is set forth in SEQ ID NO: 193, and the second nucleotide sequence is set forth in SEQ ID NO: 194;

(bx) the first nucleotide sequence is set forth in SEQ ID NO: 197, and the second nucleotide sequence is set forth in SEQ ID NO: 198;

(by) the first nucleotide sequence is set forth in SEQ ID NO: 201, and the second nucleotide sequence is set forth in SEQ ID NO: 202;

(bz) the first nucleotide sequence is set forth in SEQ ID NO: 205, and the second nucleotide sequence is set forth in SEQ ID NO: 206;

(ca) the first nucleotide sequence is set forth in SEQ ID NO: 209, and the second nucleotide sequence is set forth in SEQ ID NO: 210;

(cb) the first nucleotide sequence is set forth in SEQ ID NO: 213, and the second nucleotide sequence is set forth in SEQ ID NO: 214;

(cd) the first nucleotide sequence is set forth in SEQ ID NO: 221, and the second nucleotide sequence is set forth in SEQ ID NO: 222;

(ce) the first nucleotide sequence is set forth in SEQ ID NO: 225, and the second nucleotide sequence is set forth in SEQ ID NO: 226;

(cf) the first nucleotide sequence is set forth in SEQ ID NO: 229, and the second nucleotide sequence is set forth in SEQ ID NO: 230;

(cg) the first nucleotide sequence is set forth in SEQ ID NO: 233, and the second nucleotide sequence is set forth in SEQ ID NO: 234;

(ch) the first nucleotide sequence is set forth in SEQ ID NO: 237, and the second nucleotide sequence is set forth in SEQ ID NO: 238;

(ci) the first nucleotide sequence is set forth in SEQ ID NO: 241, and the second nucleotide sequence is set forth in SEQ ID NO: 242;

(cj) the first nucleotide sequence is set forth in SEQ ID NO: 245, and the second nucleotide sequence is set forth in SEQ ID NO: 246;

(ck) the first nucleotide sequence is set forth in SEQ ID NO: 249, and the second nucleotide sequence is set forth in SEQ ID NO: 250;

(cl) the first nucleotide sequence is set forth in SEQ ID NO: 253, and the second nucleotide sequence is set forth in SEQ ID NO: 254;

(cm) the first nucleotide sequence is set forth in SEQ ID NO: 257, and the second nucleotide sequence is set forth in SEQ ID NO: 258;

(cn) the first nucleotide sequence is set forth in SEQ ID NO: 261, and the second nucleotide sequence is set forth in SEQ ID NO: 262;

(co) the first nucleotide sequence is set forth in SEQ ID NO: 265, and the second nucleotide sequence is set forth in SEQ ID NO: 266;

(cq) the first nucleotide sequence is set forth in SEQ ID NO: 273, and the second nucleotide sequence is set forth in SEQ ID NO: 274;

(cr) the first nucleotide sequence is set forth in SEQ ID NO: 277, and the second nucleotide sequence is set forth in SEQ ID NO: 278;

(cs) the first nucleotide sequence is set forth in SEQ ID NO: 281, and the second nucleotide sequence is set forth in SEQ ID NO: 282;

(ct) the first nucleotide sequence is set forth in SEQ ID NO: 285, and the second nucleotide sequence is set forth in SEQ ID NO: 286;

(cu) the first nucleotide sequence is set forth in SEQ ID NO: 289, and the second nucleotide sequence is set forth in SEQ ID NO: 290;

(cv) the first nucleotide sequence is set forth in SEQ ID NO: 293, and the second nucleotide sequence is set forth in SEQ ID NO: 294;

(cw) the first nucleotide sequence is set forth in SEQ ID NO: 297, and the second nucleotide sequence is set forth in SEQ ID NO: 298; or (cx) the first nucleotide sequence is set forth in SEQ ID NO: 301, and the second nucleotide sequence is set forth in SEQ ID NO: 302.

5. The nucleic acid molecule of claim 1, wherein the encoded light chain variable region comprises a CDR1 comprising the amino acid sequence set forth in SEQ ID NO:533, a CDR2 comprising the amino acid sequence set forth in SEQ ID NO:534, and a CDR3 comprising the amino acid sequence set forth in SEQ ID NO:535; and the encoded heavy chain variable region comprises a CDR1 comprising the amino acid sequence set forth in SEQ ID NO:403, a CDR2 comprising the amino acid sequence set forth in SEQ ID NO:404, and a CDR3 comprising the amino acid sequence set forth in SEQ ID NO:532.

6. The nucleic acid molecule of claim 1, wherein the encoded light chain variable region comprises a CDR1 comprising the amino acid sequence set forth in SEQ ID NO:544, a CDR2 comprising the amino acid sequence set forth in SEQ ID NO:448, and a CDR3 comprising the amino acid sequence set forth in SEQ ID NO:545; and the encoded heavy chain variable region comprises a CDR1 comprising the amino acid sequence set forth in SEQ ID NO:411, a CDR2 comprising the amino acid sequence set forth in SEQ ID NO:412, and a CDR3 comprising the amino acid sequence set forth in SEQ ID NO:543.

7. The nucleic acid molecule of claim 1, wherein the encoded light chain variable region comprises a CDR1 comprising the amino acid sequence set forth in SEQ ID NO:329, a CDR2 comprising the amino acid sequence set forth in SEQ ID NO:330, and a CDR3 comprising the amino acid sequence set forth in SEQ ID NO:443; and the encoded heavy chain variable region comprises a CDR1 comprising the amino acid sequence set forth in SEQ ID NO:440, a CDR2 comprising the amino acid sequence set forth in SEQ ID NO:441, and a CDR3 comprising the amino acid sequence set forth in SEQ ID NO:442.

8. The nucleic acid molecule of claim 1, wherein the encoded antigen-binding fragment is a single chain variable fragment (scFv).

9. The nucleic acid molecule of claim 8, wherein the encoded antibody or antigen-binding fragment thereof further comprises a peptide linker; and comprises the amino acid sequence set forth in SEQ ID NO:594, SEQ ID NO:596, SEQ ID NO:598, SEQ ID NO:600, SEQ ID NO:602, SEQ ID NO:604, SEQ ID NO:606, SEQ ID NO:608, SEQ ID NO:610, SEQ ID NO:612, SEQ ID NO:614, SEQ ID NO:616, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:644, SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:666, SEQ ID NO:668, SEQ ID NO:670, SEQ ID NO:672, SEQ ID NO:674, SEQ ID NO:676, SEQ ID NO:680, SEQ ID NO:682, SEQ ID NO:684, SEQ ID NO:686, SEQ ID NO:688, SEQ ID NO:690, SEQ ID NO:692, SEQ ID NO:694, SEQ ID NO:696, SEQ ID NO:698, SEQ ID NO:702, SEQ ID NO:704, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:722, SEQ ID NO:724, SEQ ID NO:728, SEQ ID NO:730, SEQ ID NO:732, SEQ ID NO:734, SEQ ID NO:736, SEQ ID NO:738, SEQ ID NO:740, SEQ ID NO:742, or SEQ ID NO:744.

10. The nucleic acid molecule of claim 9, wherein the nucleic acid molecule comprises the nucleotide sequence set forth in SEQ ID NO:593, SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:611, SEQ ID NO:613, SEQ ID NO:615, SEQ ID NO:617, SEQ ID NO:619, SEQ ID NO:621, SEQ ID NO:623, SEQ ID NO:625, SEQ ID NO:627, SEQ ID NO:629, SEQ ID NO:631, SEQ ID NO:633, SEQ ID NO:635, SEQ ID NO:637, SEQ ID NO:639, SEQ ID NO:641, SEQ ID NO:643, SEQ ID NO:645, SEQ ID NO:647, SEQ ID NO:649, SEQ ID NO:651, SEQ ID NO:653, SEQ ID NO:655, SEQ ID NO:657, SEQ ID NO:659, SEQ ID NO:661, SEQ ID NO:665, SEQ ID NO:667, SEQ ID NO:669, SEQ ID NO:671, SEQ ID NO:673, SEQ ID NO:675, SEQ ID NO:679, SEQ ID NO:681, SEQ ID NO:683, SEQ ID NO:685, SEQ ID NO:687, SEQ ID NO:689, SEQ ID NO:691, SEQ ID NO:693, SEQ ID NO:695, SEQ ID NO:697, SEQ ID NO:701, SEQ ID NO:703, SEQ ID NO:705, SEQ ID NO:707, SEQ ID NO:709, SEQ ID NO:711, SEQ ID NO:713, SEQ ID NO:715, SEQ ID NO:717, SEQ ID NO:719, SEQ ID NO:721, SEQ ID NO:723, SEQ ID NO:727, SEQ ID NO:729, SEQ ID NO:731, SEQ ID NO:733, SEQ ID NO:735, SEQ ID NO:737, SEQ ID NO:739, SEQ ID NO:741, or SEQ ID NO:743.

11. The nucleic acid molecule of claim 3, wherein the encoded light chain variable region comprises the amino acid sequence set forth in SEQ ID NO:219; and the encoded heavy chain variable region comprises the amino acid sequence set forth in SEQ ID NO:220.

12. The nucleic acid molecule of claim 3, wherein the encoded light chain variable region comprises the amino acid sequence set forth in SEQ ID NO:235; and the encoded heavy chain variable region comprises the amino acid sequence set forth in SEQ ID NO:236.

13. The nucleic acid molecule of claim 3, wherein the encoded light chain variable region comprises the amino acid sequence set forth in SEQ ID NO:115; and the encoded heavy chain variable region comprises the amino acid sequence set forth in SEQ ID NO:116.

14. An expression vector comprising the nucleic acid molecule of claim 1.

15. A host cell comprising the expression vector of claim 14.

* * * * *